US007282723B2

(12) United States Patent
Schomacker et al.

(10) Patent No.: US 7,282,723 B2
(45) Date of Patent: Oct. 16, 2007

(54) METHODS AND APPARATUS FOR PROCESSING SPECTRAL DATA FOR USE IN TISSUE CHARACTERIZATION

(75) Inventors: Kevin T. Schomacker, Maynard, MA (US); Thomas M. Meese, Brookline, MA (US); Ross F. Flewelling, Oakland, CA (US); Chunsheng Jiang, Reading, MA (US); Christopher E. Griffin, West Groton, MA (US); Alex Zelenchuk, Stoughton, MA (US)

(73) Assignee: MediSpectra, Inc., Lexington, MA (US)

( * ) Notice: Subject to any disclaimer, the term of this patent is extended or adjusted under 35 U.S.C. 154(b) by 509 days.

(21) Appl. No.: 10/418,415

(22) Filed: Apr. 18, 2003

(65) Prior Publication Data

US 2004/0010375 A1    Jan. 15, 2004

Related U.S. Application Data

(63) Continuation-in-part of application No. 10/295,794, filed on Nov. 15, 2002, now Pat. No. 6,933,154, which is a continuation-in-part of application No. 10/243,535, filed on Sep. 13, 2002, now Pat. No. 6,818,903.

(60) Provisional application No. 60/394,696, filed on Jul. 9, 2002.

(51) Int. Cl.
    *A61B 5/04* (2006.01)

(52) U.S. Cl. .................. 250/458.1; 250/458.1; 250/461.1; 600/476; 600/477; 600/478; 600/317

(58) Field of Classification Search ............. 250/458.1, 250/459.1, 461.1; 600/476, 477, 478, 317
See application file for complete search history.

(56) References Cited

U.S. PATENT DOCUMENTS

| 3,013,467 A | 12/1961 | Minsky ..................... 88/14 |
| 3,632,865 A | 1/1972 | Haskell et al. ................. 178/6 |
| 3,809,072 A | 5/1974 | Ersek et al. .................. 128/23 |

(Continued)

FOREIGN PATENT DOCUMENTS

DE         19629646          1/1998

(Continued)

OTHER PUBLICATIONS

Noble et al., "Automated, Nonrigid Alignment of Clinical Myocardial Contrast Echocardiography Image Sequences: Comparison with Manual Alignment," *Ultrasound in Medicine and Biology*, vol. 28, No. 1 (2002), pp. 115-123.

(Continued)

*Primary Examiner*—David Porta
*Assistant Examiner*—Christine Sung
(74) *Attorney, Agent, or Firm*—Goodwin Procter LLP

(57) ABSTRACT

The invention provides methods for processing tissue-derived spectral data for use in a tissue classification algorithm. Methods of the invention comprise application of spectral and/or image masks for automatically separating ambiguous or unclassifiable spectral data from valid spectral data. The invention improves the accuracy of tissue classification, in part, by properly identifying and accounting for spectral data from tissue regions that are affected by an obstruction and/or regions that lie outside a diagnostic zone of interest.

95 Claims, 112 Drawing Sheets
(30 of 112 Drawing Sheet(s) Filed in Color)

U.S. PATENT DOCUMENTS

| | | | | |
|---|---|---|---|---|
| 3,890,462 A | 6/1975 | Limb et al. ............... 178/6.8 |
| 3,945,371 A | 3/1976 | Adelman |
| 3,963,019 A | 6/1976 | Quandt et al. ............... 128/2 |
| D242,393 S | 11/1976 | Bauman ............... D83/12 R |
| D242,396 S | 11/1976 | Bauman ............... D83/12 R |
| D242,397 S | 11/1976 | Bauman ............... D83/12 R |
| D242,398 S | 11/1976 | Bauman ............... D83/12 R |
| 4,017,192 A | 4/1977 | Rosenthal et al. ......... 356/201 |
| 4,071,020 A | 1/1978 | Puglise et al. ............... 128/2 |
| 4,198,571 A | 4/1980 | Sheppard ............... 250/571 |
| 4,218,703 A | 8/1980 | Netravali et al. ......... 358/136 |
| 4,254,421 A | 3/1981 | Kreutel, Jr. ............... 343/754 |
| 4,273,110 A | 6/1981 | Groux ............... 128/6 |
| 4,349,510 A | 9/1982 | Kolehmainen et al. |
| 4,357,075 A | 11/1982 | Hunter ............... 350/294 |
| 4,396,579 A | 8/1983 | Schroeder et al. |
| 4,397,557 A | 8/1983 | Herwig et al. ............... 356/342 |
| 4,515,165 A | 5/1985 | Carroll ............... 128/664 |
| 4,549,229 A | 10/1985 | Nakano et al. ............... 360/8 |
| 4,558,462 A | 12/1985 | Horiba et al. ............... 382/42 |
| 4,641,352 A | 2/1987 | Fenster et al. ............... 382/6 |
| 4,646,722 A | 3/1987 | Silverstein et al. ............... 128/4 |
| 4,662,360 A | 5/1987 | O'Hara et al. ............... 128/9 |
| 4,733,063 A | 3/1988 | Kimura et al. ............... 250/201 |
| 4,741,326 A | 5/1988 | Sidall et al. ............... 128/4 |
| 4,753,530 A | 6/1988 | Knight et al. ............... 356/73 |
| 4,755,055 A | 7/1988 | Johnson et al. |
| 4,768,513 A | 9/1988 | Suzuki ............... 128/634 |
| 4,800,571 A | 1/1989 | Konishi ............... 375/10 |
| 4,803,049 A | 2/1989 | Hirschfeld et al. |
| 4,844,617 A | 7/1989 | Kelderman et al. ......... 356/372 |
| 4,845,352 A | 7/1989 | Benschop ............... 250/201 |
| 4,852,955 A | 8/1989 | Doyle et al. ............... 350/1.2 |
| 4,877,033 A | 10/1989 | Seitz, Jr. ............... 128/660.05 |
| 4,878,485 A | 11/1989 | Adair ............... 128/6 |
| 4,891,829 A | 1/1990 | Deckman et al. ............... 378/4 |
| 4,930,516 A | 6/1990 | Alfano et al. ............... 128/665 |
| 4,945,478 A | 7/1990 | Merickel et al. ........ 364/413.22 |
| 4,965,441 A | 10/1990 | Picard ............... 250/201.3 |
| 4,972,258 A | 11/1990 | Wolf et al. ............... 358/93 |
| 4,974,580 A | 12/1990 | Anapliotis ............... 128/4 |
| 4,979,498 A | 12/1990 | Oneda et al. ............... 128/6 |
| 4,997,242 A | 3/1991 | Amos ............... 350/6.91 |
| 5,003,979 A | 4/1991 | Merickel et al. ........ 364/413.22 |
| 5,011,243 A | 4/1991 | Doyle et al. ............... 350/1.2 |
| 5,022,757 A | 6/1991 | Modell ............... 356/318 |
| 5,028,802 A | 7/1991 | Webb et al. ............... 250/571 |
| 5,032,720 A | 7/1991 | White ............... 250/236 |
| 5,034,613 A | 7/1991 | Denk et al. ............... 250/458.1 |
| 5,036,853 A | 8/1991 | Jeffcoat et al. ............... 128/634 |
| 5,042,494 A | 8/1991 | Alfano ............... 128/665 |
| 5,048,946 A | 9/1991 | Sklar et al. ............... 351/206 |
| 5,054,926 A | 10/1991 | Dabbs et al. ............... 356/345 |
| 5,065,008 A | 11/1991 | Hakamata et al. ......... 250/216 |
| 5,071,246 A | 12/1991 | Blaha et al. ............... 351/221 |
| 5,074,306 A | 12/1991 | Green et al. ............... 128/664 |
| 5,083,220 A | 1/1992 | Hill ............... 359/234 |
| 5,091,652 A | 2/1992 | Mathies et al. ......... 250/458.1 |
| 5,101,825 A | 4/1992 | Gravenstein et al. ........ 128/633 |
| 5,120,953 A | 6/1992 | Harris ............... 250/227.2 |
| 5,122,653 A | 6/1992 | Ohki ............... 250/216 |
| 5,131,398 A | 7/1992 | Alfano et al. ............... 600/476 |
| 5,132,526 A | 7/1992 | Iwasaki ............... 250/201.3 |
| 5,139,025 A | 8/1992 | Lewis et al. ............... 128/665 |
| 5,154,166 A | 10/1992 | Chikama ............... 128/4 |
| 5,159,919 A | 11/1992 | Chikama ............... 128/4 |
| 5,161,053 A | 11/1992 | Dabbs ............... 359/384 |
| 5,162,641 A | 11/1992 | Fountain ............... 250/201.2 |
| 5,162,941 A | 11/1992 | Favro et al. ............... 359/386 |
| 5,168,157 A | 12/1992 | Kimura ............... 250/234 |
| 5,192,980 A | 3/1993 | Dixon et al. ............... 356/326 |
| 5,193,525 A | 3/1993 | Silverstein et al. ............. 128/4 |
| RE34,214 E | 4/1993 | Carlsson et al. ............... 358/93 |
| 5,199,431 A | 4/1993 | Kittrell et al. ............... 128/634 |
| 5,201,318 A | 4/1993 | Rava et al. ............... 128/665 |
| 5,201,908 A | 4/1993 | Jones ............... 128/4 |
| 5,203,328 A | 4/1993 | Samuels et al. ............. 128/633 |
| 5,205,291 A | 4/1993 | Potter |
| 5,225,671 A | 7/1993 | Fukuyama ............... 250/216 |
| 5,235,457 A | 8/1993 | Lichtman et al. ............ 359/368 |
| 5,237,984 A | 8/1993 | Williams, III et al. ........... 128/4 |
| 5,239,178 A | 8/1993 | Derndinger et al. ........ 250/234 |
| 5,248,876 A | 9/1993 | Kerstens et al. ............. 250/561 |
| 5,253,071 A | 10/1993 | MacKay ............... 358/222 |
| 5,257,617 A | 11/1993 | Takahashi ............... 128/4 |
| 5,260,569 A | 11/1993 | Kimura ............... 250/234 |
| 5,260,578 A | 11/1993 | Bliton et al. ............... 250/461.1 |
| 5,261,410 A | 11/1993 | Alfano et al. ............... 128/664 |
| 5,262,646 A | 11/1993 | Booker et al. ............... 250/341 |
| 5,267,179 A | 11/1993 | Butler et al. |
| 5,274,240 A | 12/1993 | Mathies et al. ........... 250/458.1 |
| 5,284,149 A | 2/1994 | Dhadwal et al. ............. 128/665 |
| 5,285,490 A | 2/1994 | Bunch et al. |
| 5,286,964 A | 2/1994 | Fountain ............... 250/201.2 |
| 5,289,274 A | 2/1994 | Kondo ............... 348/208 |
| 5,294,799 A | 3/1994 | Aslund et al. ............. 250/458.1 |
| 5,296,700 A | 3/1994 | Kumagai ............... 250/216 |
| 5,303,026 A | 4/1994 | Strobl et al. ............... 356/318 |
| 5,306,902 A | 4/1994 | Goodman ............... 250/201.3 |
| 5,313,567 A | 5/1994 | Civanlar et al. ............. 395/124 |
| 5,319,200 A | 6/1994 | Rosenthal et al. .......... 250/341 |
| 5,321,501 A | 6/1994 | Swanson et al. ............ 356/345 |
| 5,324,979 A | 6/1994 | Rosenthal ............... 250/504 R |
| 5,325,846 A | 7/1994 | Szabo ............... 128/4 |
| 5,329,352 A | 7/1994 | Jacobsen ............... 356/301 |
| 5,337,734 A | 8/1994 | Saab ............... 128/4 |
| 5,343,038 A | 8/1994 | Nishiwaki et al. .......... 250/234 |
| 5,345,306 A | 9/1994 | Ichimura et al. ............ 356/346 |
| 5,345,941 A | 9/1994 | Rava et al. ............... 128/665 |
| 5,347,590 A | 9/1994 | Nonnweiler et al. |
| 5,349,961 A | 9/1994 | Stoddart et al. ............. 128/665 |
| 5,383,874 A | 1/1995 | Jackson et al. |
| 5,398,685 A | 3/1995 | Wilk et al. ............... 128/653.1 |
| 5,402,768 A | 4/1995 | Adair ............... 128/4 |
| 5,406,939 A | 4/1995 | Bala ............... 128/4 |
| 5,412,563 A | 5/1995 | Cline et al. ............... 345/420 |
| 5,413,092 A | 5/1995 | Williams, III et al. .......... 128/4 |
| 5,413,108 A | 5/1995 | Alfano ............... 128/665 |
| 5,415,157 A | 5/1995 | Welcome ............... 128/4 |
| 5,418,797 A | 5/1995 | Bashkansky et al. ........... 372/3 |
| 5,419,311 A | 5/1995 | Yabe et al. ............... 128/4 |
| 5,419,323 A | 5/1995 | Kittrell et al. ............... 128/653 |
| 5,421,337 A | 6/1995 | Richards-Kortum et al. ............... 128/665 |
| 5,421,339 A | 6/1995 | Ramanujam et al. ........ 128/665 |
| 5,424,543 A | 6/1995 | Dombrowski et al. ....... 250/330 |
| 5,441,053 A | 8/1995 | Lodder et al. |
| 5,450,857 A | 9/1995 | Garfield et al. ............. 128/778 |
| 5,451,931 A | 9/1995 | Miller et al. ............... 340/630 |
| 5,452,723 A | 9/1995 | Wu |
| 5,458,132 A | 10/1995 | Yabe et al. ............... 128/4 |
| 5,458,133 A | 10/1995 | Yabe et al. ............... 600/121 |
| 5,467,767 A | 11/1995 | Alfano et al. ............... 128/665 |
| 5,469,853 A | 11/1995 | Law et al. ............... 128/662.06 |
| 5,477,382 A | 12/1995 | Pernick ............... 359/559 |
| 5,480,775 A | 1/1996 | Ito et al. ............... 435/7.2 |
| 5,493,444 A | 2/1996 | Khoury et al. ............... 359/559 |
| 5,496,259 A | 3/1996 | Perkins ............... 600/124 |
| 5,507,295 A | 4/1996 | Skidmore ............... 600/121 |
| 5,516,010 A | 5/1996 | O'Hara et al. ............... 600/122 |
| 5,519,545 A | 5/1996 | Kawahara ............... 360/46 |
| 5,529,235 A | 6/1996 | Bolarski et al. .......... 227/175.1 |
| 5,536,236 A | 7/1996 | Yabe et al. ............... 600/125 |
| 5,545,121 A | 8/1996 | Yabe et al. ............... 600/121 |

| Patent | Date | Inventor | Class |
|---|---|---|---|
| 5,551,945 A | 9/1996 | Yabe et al. | 600/122 |
| 5,556,367 A | 9/1996 | Yabe et al. | 600/124 |
| 5,562,100 A | 10/1996 | Kittrell et al. | 128/665 |
| 5,579,773 A | 12/1996 | Vo-Dinh et al. | 128/665 |
| 5,582,168 A | 12/1996 | Samuels et al. | 128/633 |
| 5,587,832 A | 12/1996 | Krause | 359/385 |
| 5,596,992 A | 1/1997 | Haaland et al. | 128/664 |
| 5,599,717 A | 2/1997 | Vo-Dinh | 436/63 |
| 5,609,560 A | 3/1997 | Ichikawa et al. | 600/101 |
| 5,612,540 A | 3/1997 | Richards-Kortum et al. | 250/461.2 |
| 5,623,932 A | 4/1997 | Ramanujam et al. | 128/665 |
| 5,643,175 A | 7/1997 | Adair | 600/133 |
| 5,647,368 A | 7/1997 | Zeng et al. | 128/665 |
| 5,659,384 A | 8/1997 | Ina | 355/53 |
| 5,662,588 A | 9/1997 | Lida | 600/121 |
| 5,685,822 A | 11/1997 | Harhen | 600/125 |
| 5,690,106 A | 11/1997 | Bani-Hashemi et al. | 128/653.1 |
| 5,693,043 A | 12/1997 | Kittrell et al. | 606/15 |
| 5,695,448 A | 12/1997 | Kimura et al. | 600/121 |
| 5,697,373 A | 12/1997 | Richards-Kortum et al. | 128/664 |
| 5,699,795 A | 12/1997 | Richards-Kortum | 128/634 |
| 5,704,892 A | 1/1998 | Adair | 600/121 |
| 5,707,343 A | 1/1998 | O'Hara et al. | 600/121 |
| 5,713,364 A | 2/1998 | DeBaryshe et al. | 128/664 |
| 5,717,209 A | 2/1998 | Bigman et al. | 250/339.12 |
| 5,720,293 A | 2/1998 | Quinn et al. | |
| 5,730,701 A | 3/1998 | Furukawa et al. | 600/127 |
| 5,733,244 A | 3/1998 | Yasui et al. | 600/127 |
| 5,735,276 A | 4/1998 | Lemelson | 128/653.1 |
| 5,746,695 A | 5/1998 | Yasui et al. | 600/127 |
| 5,768,333 A | 6/1998 | Abdel-Mottaleb | 378/37 |
| 5,769,792 A | 6/1998 | Palcic et al. | 600/477 |
| 5,773,835 A | 6/1998 | Sinofsky et al. | 250/462.1 |
| 5,784,162 A | 7/1998 | Cabib et al. | |
| 5,791,346 A | 8/1998 | Craine et al. | 128/653 |
| 5,792,049 A | 8/1998 | Eppstein et al. | 600/306 |
| 5,795,632 A | 8/1998 | Buchalter | 428/35.2 |
| 5,800,350 A | 9/1998 | Coppleson et al. | 600/372 |
| 5,807,248 A | 9/1998 | Mills | 600/322 |
| 5,813,987 A | 9/1998 | Modell et al. | 600/473 |
| 5,817,015 A | 10/1998 | Adair | 600/121 |
| 5,830,146 A | 11/1998 | Skladnev et al. | 600/478 |
| 5,832,931 A | 11/1998 | Wachter et al. | |
| 5,833,617 A | 11/1998 | Hayashi | 600/476 |
| 5,838,435 A | 11/1998 | Sandison | |
| 5,840,035 A | 11/1998 | Heusmann et al. | 600/47 |
| 5,842,995 A | 12/1998 | Mahadevan-Jansen et al. | 600/473 |
| 5,845,639 A | 12/1998 | Hochman et al. | 600/407 |
| 5,850,486 A | 12/1998 | Maas, III et al. | 382/294 |
| 5,855,551 A | 1/1999 | Sklandnev et al. | 600/372 |
| 5,860,913 A | 1/1999 | Yamaya et al. | 600/127 |
| 5,863,287 A | 1/1999 | Segawa | 600/121 |
| 5,865,726 A | 2/1999 | Katsurada et al. | 600/127 |
| 5,871,439 A | 2/1999 | Takahashi et al. | |
| 5,876,329 A | 3/1999 | Harhen | 600/125 |
| 5,894,340 A | 4/1999 | Loree et al. | |
| 5,902,246 A | 5/1999 | McHenry et al. | |
| 5,912,257 A | 6/1999 | Prasad et al. | |
| 5,920,399 A | 7/1999 | Sandison et al. | 356/418 |
| 5,921,926 A | 7/1999 | Rolland et al. | 600/407 |
| 5,929,985 A | 7/1999 | Sandison et al. | 365/318 |
| 5,931,779 A | 8/1999 | Arakaki et al. | 600/310 |
| 5,938,617 A | 8/1999 | Vo-Dinh | 600/476 |
| 5,941,834 A | 8/1999 | Skladnev et al. | 600/587 |
| 5,983,125 A | 11/1999 | Alfano et al. | 600/473 |
| 5,987,343 A | 11/1999 | Kinast | |
| 5,989,184 A | 11/1999 | Blair et al. | 600/167 |
| 5,991,653 A | 11/1999 | Richards-Kortum et al. | 660/475 |
| 5,994,690 A | 11/1999 | Kulkarni et al. | 250/216 |
| 5,995,645 A | 11/1999 | Soenksen et al. | 382/133 |
| 5,999,844 A | 12/1999 | Gombrich et al. | |
| 6,011,596 A | 1/2000 | Burl et al. | |
| 6,021,344 A | 2/2000 | Lui et al. | 600/476 |
| 6,026,319 A | 2/2000 | Hayashi | |
| 6,040,139 A | 3/2000 | Bova | |
| 6,058,322 A | 5/2000 | Nishikawa et al. | 600/408 |
| 6,067,371 A | 5/2000 | Gouge et al. | 382/128 |
| 6,069,689 A | 5/2000 | Zeng et al. | 356/773 |
| 6,083,487 A | 7/2000 | Biel | 424/9.6 |
| 6,091,985 A | 7/2000 | Alfano et al. | 600/476 |
| 6,092,722 A | 7/2000 | Heinrichs et al. | |
| 6,095,982 A | 8/2000 | Richards-Kortum et al. | 600/476 |
| 6,096,065 A | 8/2000 | Crowley | 607/88 |
| 6,099,464 A | 8/2000 | Shimizu et al. | 600/104 |
| 6,101,408 A | 8/2000 | Craine et al. | |
| 6,104,945 A | 8/2000 | Modell et al. | 600/473 |
| 6,119,031 A | 9/2000 | Crowley | 600/407 |
| 6,123,454 A | 9/2000 | Canfield et al. | |
| 6,124,597 A | 9/2000 | Shehada et al. | 250/461.2 |
| 6,126,899 A | 10/2000 | Woudenberg et al. | |
| 6,135,965 A | 10/2000 | Tumor et al. | |
| 6,146,897 A | 11/2000 | Cohenford et al. | 436/63 |
| 6,166,079 A | 12/2000 | Follen et al. | |
| 6,169,817 B1 | 1/2001 | Parker et al. | 382/131 |
| 6,181,810 B1 | 1/2001 | Zhang et al. | 382/128 |
| 6,187,289 B1 | 2/2001 | Richards-Kortum et al. | 424/9.8 |
| 6,208,887 B1 | 3/2001 | Clarke et al. | 600/476 |
| 6,210,331 B1 | 4/2001 | Raz | |
| 6,224,256 B1 | 5/2001 | Bala | |
| 6,236,751 B1 | 5/2001 | Farrell | 382/168 |
| 6,241,662 B1 | 6/2001 | Richards-Kortum et al. | 600/310 |
| 6,243,601 B1 | 6/2001 | Wist | 600/473 |
| 6,246,471 B1 | 6/2001 | Jung et al. | 356/73 |
| 6,246,479 B1 | 6/2001 | Jung et al. | 356/419 |
| 6,258,576 B1 | 7/2001 | Richards-Kortum et al. | 435/172 |
| 6,277,067 B1 | 8/2001 | Blair | |
| 6,285,639 B1 | 9/2001 | Maenza et al. | 369/47.28 |
| 6,289,236 B1* | 9/2001 | Koenig et al. | 600/477 |
| 6,312,385 B1 | 11/2001 | Mo et al. | 600/443 |
| 6,317,617 B1 | 11/2001 | Gilhuijs et al. | 600/408 |
| 6,332,092 B1 | 12/2001 | Deckert et al. | |
| D453,832 S | 2/2002 | Morrell et al. | D24/138 |
| D453,962 S | 2/2002 | Morrell et al. | D24/138 |
| D453,963 S | 2/2002 | Morrell et al. | D24/138 |
| D453,964 S | 2/2002 | Morrell et al. | D24/138 |
| 6,370,422 B1 | 4/2002 | Richards-Kortum et al. | |
| 6,373,998 B2 | 4/2002 | Thirion et al. | |
| 6,377,842 B1 | 4/2002 | Pogue et al. | 600/478 |
| 6,385,484 B2 | 5/2002 | Nordstrom et al. | 600/476 |
| 6,389,157 B2 | 5/2002 | Rogers et al. | 382/132 |
| 6,390,671 B1 | 5/2002 | Tseng | |
| 6,405,070 B1 | 6/2002 | Banerjee | |
| 6,411,835 B1 | 6/2002 | Modell et al. | 600/407 |
| 6,411,838 B1 | 6/2002 | Nordstrom et al. | 600/476 |
| D460,821 S | 7/2002 | Morrell et al. | D24/138 |
| 6,421,553 B1 | 7/2002 | Costa et al. | 600/476 |
| 6,424,852 B1 | 7/2002 | Zavislan | |
| 6,427,082 B1 | 7/2002 | Nordstrom et al. | 600/476 |
| 6,465,968 B1 | 10/2002 | Sendai | |
| 6,466,687 B1 | 10/2002 | Uppaluri et al. | 382/128 |
| 6,487,440 B2 | 11/2002 | Deckert et al. | |
| 6,497,659 B1 | 12/2002 | Rafert | |
| 6,556,720 B1 | 4/2003 | Avinash | 382/260 |
| 6,571,118 B1 | 5/2003 | Utzinger et al. | 600/476 |
| 6,571,119 B2* | 5/2003 | Hayashi | 600/477 |
| 6,574,502 B2 | 6/2003 | Hayashi | 600/476 |
| 6,593,101 B2 | 7/2003 | Richards-Kortum et al. | |
| 6,593,102 B2 | 7/2003 | Zahniser | |
| 6,633,657 B1 | 10/2003 | Kump et al. | |

| | | | |
|---|---|---|---|
| 6,639,674 B2 | 10/2003 | Sokolov et al. | |
| 6,640,000 B1 | 10/2003 | Fey et al. | |
| 6,671,540 B1 | 12/2003 | Hochman | |
| 6,697,666 B1 | 2/2004 | Richards-Kortum et al. | |
| 6,717,668 B2 | 4/2004 | Treado et al. | |
| 6,718,055 B1 | 4/2004 | Suri | 382/128 |
| 6,757,414 B1 | 6/2004 | Turek et al. | 382/128 |
| 6,760,613 B2 | 7/2004 | Nordstrom et al. | |
| 6,766,184 B2 | 7/2004 | Utzinger et al. | |
| 6,768,918 B2 | 7/2004 | Zelenchuk | 600/476 |
| 6,794,431 B1 | 9/2004 | Rosania et al. | |
| 6,818,903 B2 | 11/2004 | Schomacker et al. | |
| 6,826,422 B1 | 11/2004 | Modell et al. | |
| D500,134 S | 12/2004 | Banks et al. | |
| 6,834,238 B1 | 12/2004 | Hochman | 702/21 |
| 6,839,661 B2 | 1/2005 | Costa et al. | |
| 6,847,490 B1 | 1/2005 | Nordstrom et al. | |
| 6,885,763 B2 | 4/2005 | Ogino | 382/131 |
| 6,902,935 B2 | 6/2005 | Kaufman et al. | |
| D507,349 S | 7/2005 | Banks et al. | |
| 6,933,154 B2 | 8/2005 | Schomacker et al. | |
| 6,940,998 B2 | 9/2005 | Garoutte | 382/103 |
| 6,975,899 B2 * | 12/2005 | Faupel et al. | 600/476 |
| 7,015,310 B2 | 3/2006 | Remington et al. | 530/350 |
| 7,103,401 B2 | 9/2006 | Schomacker et al. | 600/476 |
| 7,127,282 B2 | 10/2006 | Nordstrom et al. | 600/477 |
| 7,136,518 B2 | 11/2006 | Griffin et al. | 382/133 |
| 2001/0031076 A1 | 10/2001 | Campanini et al. | 382/128 |
| 2001/0041843 A1 | 11/2001 | Modell et al. | |
| 2002/0007122 A1 | 1/2002 | Kaufman et al. | 600/476 |
| 2002/0007123 A1 | 1/2002 | Balas et al. | 600/476 |
| 2002/0107668 A1 | 8/2002 | Costa et al. | 702/189 |
| 2002/0127735 A1 | 9/2002 | Kaufman et al. | 600/436 |
| 2002/0133073 A1 | 9/2002 | Nordstrom et al. | |
| 2002/0177777 A1 | 11/2002 | Nordstrom et al. | 600/475 |
| 2002/0183626 A1 | 12/2002 | Nordstrom et al. | 600/476 |
| 2002/0197728 A1 | 12/2002 | Kaufman et al. | |
| 2003/0095721 A1 | 5/2003 | Clune et al. | 382/294 |
| 2003/0114762 A1 | 6/2003 | Balas | |
| 2003/0144585 A1 | 7/2003 | Kaufman et al. | 600/407 |
| 2003/0163049 A1 | 8/2003 | Balas | |
| 2003/0207250 A1 | 11/2003 | Kaufman et al. | |
| 2003/0218780 A1 | 11/2003 | Braun et al. | 358/3.12 |
| 2004/0007674 A1 | 1/2004 | Schomacker et al. | 250/458.1 |
| 2004/0010187 A1 | 1/2004 | Schomacker et al. | 600/317 |
| 2004/0010195 A1 | 1/2004 | Zelenchuk | |
| 2004/0010375 A1 | 1/2004 | Schomacker et al. | |
| 2004/0023406 A1 | 2/2004 | Schomacker et al. | 436/164 |
| 2004/0066960 A1 | 4/2004 | McLaren et al. | 382/128 |
| 2004/0206882 A1 | 10/2004 | Banks et al. | |
| 2004/0206913 A1 | 10/2004 | Costa et al. | |
| 2004/0206914 A1 | 10/2004 | Schomacker et al. | |
| 2004/0207625 A1 | 10/2004 | Griffin et al. | |
| 2004/0208385 A1 | 10/2004 | Jiang | |
| 2004/0208390 A1 | 10/2004 | Jiang et al. | |
| 2004/0209237 A1 | 10/2004 | Flewelling et al. | |
| 2004/0264749 A1 | 12/2004 | Skladnev et al. | 382/128 |
| 2005/0054936 A1 | 3/2005 | Balas | |
| 2005/0090751 A1 | 4/2005 | Balas | |

FOREIGN PATENT DOCUMENTS

| | | |
|---|---|---|
| EP | 0 135 134 | 3/1985 |
| EP | 0 280 418 | 8/1988 |
| EP | 0 335 725 | 10/1989 |
| EP | 0 444 689 A2 | 9/1991 |
| EP | 0 474 264 | 3/1992 |
| EP | 0 641 542 | 3/1995 |
| EP | 0 689 045 A1 | 12/1995 |
| EP | 0 737 849 A2 | 10/1996 |
| EP | 1246124 A2 | 10/2002 |
| JP | 1-245215 | 9/1989 |
| JP | 02-017429 | 1/1990 |
| JP | 05-256772 | 5/1993 |
| JP | 08-280602 | 10/1996 |
| SU | 1 223 092 A | 4/1986 |
| WO | WO 92/19148 | 11/1992 |
| WO | WO 93/14688 | 8/1993 |
| WO | WO 94/26168 | 11/1994 |
| WO | WO 95/00067 | 1/1995 |
| WO | WO 95/04385 | 2/1995 |
| WO | 96/41152 | 12/1996 |
| WO | WO 97/05473 | 2/1997 |
| WO | WO 98/30889 | 2/1997 |
| WO | WO 97/48331 | 12/1997 |
| WO | WO 98/05253 | 2/1998 |
| WO | WO 98/24369 | 6/1998 |
| WO | WO 98/41176 | 9/1998 |
| WO | WO 99/18847 | 4/1999 |
| WO | WO 99/20313 | 4/1999 |
| WO | WO 99/20314 | 4/1999 |
| WO | WO 99/47041 | 9/1999 |
| WO | WO 99/57507 | 11/1999 |
| WO | WO 99/57529 | 11/1999 |
| WO | WO 00/15101 | 3/2000 |
| WO | WO 00/41615 | 7/2000 |
| WO | WO 00/57361 | 9/2000 |
| WO | WO 00/59366 | 10/2000 |
| WO | WO 00/74556 | 12/2000 |
| WO | 04/005885 | 1/2004 |

OTHER PUBLICATIONS

Ko et al., "Multiresolution Registration of Coronary Artery Image Sequences," *International Journal of Medical Informatics*, vol. 44 (1997), pp. 93-104.

Agrawal et al. (1999), "Fluorescence Spectroscopy of the Cervix: Influence of Acetic Acid, Cervical Mucus, and Vaginal Medications," *Lasers in Surgery and Medicine*, 25:237-249.

Althof et al. (1997), "A rapid and automatic image registration algorithm with subpixel accuracy," *IEEE Transactions on Medical Imaging*, 16(3):308-316.

Anderson (1994), "Confocal Laser Microscopes See A Wider Field of Application", *Laser Focus World*, pp. 83-86.

Aström et al. (1999), "Motion estimation in image sequences using the deformation of apparent contours," *IEEE Transactions on Pattern Analysis and Machine Intelligence*, 21(2):114-127.

Balakrishnama et al, "Linear Discriminant Analysis—A Brief Tutorial," *Institute for Signal and Information Processing Department of Electrical and Computer Engineering*, 8 pages.

Balas (1997), "An Imaging Colorimeter for Noncontact Tissue Color Mapping," *IEEE Transactions on Biomedical Engineering*, 44(6):468-474.

Balas (2001), "A Novel Optical Imaging Method for the Early Detection, Quantitative Grading, and Mapping of Cancerous and Precancerous Lesions of Cervix," *IEEE Transactions on Biomedical Engineering*, 48(1):96-104.

Balas et al. (1997), "A modular diffuse reflection and fluorescence emission imaging colorimeter for the in-vivo study of parameters related with the phototoxic effect in PDT," *SPIE*, 3191:50-57.

Balas et al. (1998), "In Vivo Assessment of Acetic Acid-Cervical Tissue Interaction Using Quantitative Imaging of Back-Scattered Light: Its Potential Use for the In Vivo Cervical Cancer Detection Grading and Mapping," Part of EUROPTO Conference on Optical Biopsy, Stockholm, Sweden, *SPIE*, vol. 3568:31-37.

Balas et al. (1999), "In Vivo Detection and Staging of Epithelial Dysplasias and Malignancies Based on the Quantitative Assessment of Acetic Acid-Tissue Interaction Kinetics," *Journal of Photochemistry and Photobiology B: Biology*, 53:153-157.

Bessey et al. (1949), "The Fluorometric measurement of the nucleotides of riboflavin and their concentration in tissues," *J. Biol.-Chem.*; 180:755-769.

Bors et al. (1998), "Optical flow estimation and moving object segmentation based on median radial basis function network," *IEEE Transactions on Image Processing*, 7(5):693-702.

Bouthemy et al. (1999), "A unified approach to shot change detection and camera motion characterization," *IEEE Transactions on Circuits and Systems for Video Technology*, 9(7):1030-1044.

Braichotte et al. (1995), "Clinical Pharmacokinetic Studies of Photofrin by Fluorescence Spectroscopy in the Oral Cavity, the Esophagus, and the Bronchi," *Cancer* 75(11):2760-2778.

Brown (1990), "Chemometrics," *Anal. Chem.*, 62:84R-101R.

Camus et al. (1997), "Real-time quantized optical flow," *Real-Time Imaging*, 3:71-86.

Caplier et al. (1998), "Real-time implementation of a MRF-based motion detection algorithm," *Real-Time Imaging*, 4:41-54.

Contini et al. (1989), "Colposcopy and Computer Graphics: a New Method?" *Amer. J. Obstet. Gynecol.*, 160(3):535-538.

Craine et al. (1993), "Digital Imaging Colposcopy: basic concepts and applications," *Amer. J. Obstet. Gynecol.*, 82(5):869-873.

Craine et al. (1998), "Digital imaging colposcopy: Corrected area measurements using shape-from-shading," *IEEE Transactions on Medical Imaging*, 17(6):1003-1010.

Crisp et al. (1990), "The Computerized Digital Imaging Colposcope: Future Directions," *Amer. J. Obstet. Gynecol.*, 162(6):1491-1497.

Cronjé et al. (1997), "Effects of Dilute Acetic Acid on the Cervical Smear," *Acta. Cytol.*, 41:1091-1094.

Davidovits et al. (1971), "Scanning Laser Microscope for Biological Investigations", *Applied Optics*, 10(7):1615-1619.

Dickman et al. (2001), "Identification of Cervical Neoplasia Using a Simulation of Human Vision," *Journal of Lower Genital Tract Disease*, 5(3):144-152.

Drezek et al. (1999), "Light scattering from cells: finite-difference time-domain simulations and goniometric measurements," *Applied Optics* 38(16):3651-3661.

Drezek et al. (2000), "Laser Scanning Confocal Microscopy of Cervical Tissue Before and After Application of Acetic Acid," *Am. J. Obstet. Gynecol.*, 182(5):1135-1139.

Dumontier et al. (1999), "Real-time DSP implementation for MRF-based video motion detection," *IEEE Transactions on Image Processing*, 8(10):1341-1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence*, 18(9):927-932.

Edebiri, A.A. (1990), "The relative significance of colposcopic discriptive appearances in the dianosis of cervical intraepithelial neoplasia," *Int. J. Gynecol. Obstet.*, 33:23-29.

Eisner et al. (1987), "Use of Cross-Correlation Function to Detect Patient Motion During Spectral Imaging," *Journal of Nuclear Medicine*, 28(1):97-101.

Ferris et al. (1998), "Colposcopy Quality Control: Establishing Colposcopy Criterion Standards for the NCI ALTS Trial Using Cervigrams," *J. Lower Genital Tract Disease*, 2(4):195-203.

Fleet et al. (1995), "Recursive Filters for Optical Flow," *IEEE Transactions on Pattern Analysis and Machine Intelligence*, 17(1):61-67.

Gao et al. (1998), "A work minimization approach to image morphing," *The Visual Computer*, 14:390-400.

Gauch (1999), "Image Segmentation and Analysis Via Multiscale Gradient Watershed Hierarchies," *IEEE Transactions on Image Processing*, 8(1):69-79.

Hall et al. (1992), "Near-Infrared Spectrophotometry: A New Dimension in Clinical Chemistry", *Clin. Chem.* 38(9):1623-1631.

Haralick (1984), "Digital Step Edges from Zero Crossing of Second Directional Derivatives," *IEEE Transactions on Pattern Analysis and Machine Intelligence*, 6(1):58-68.

Haris et al. (1998), "Hybrid Image Segmentation Using Watersheds and Fast Region Merging," *IEEE Transactions on Image Processing*, 7(12):1684-1699.

Helmerhorst et al. (1987), "The accuracy of colposcopically directed biopsy in diagnosis of CIN 2/3." *Eur. J. Obstet. Gyn. Reprod. Biol.*, 24, 221-229.

Horn et al. (1981), "Determining Optical Flow," *Artificial Intelligence*, 17(1-3):185-203.

Horn et al. (1993), "Determining Optical Flow": a retrospective, *Artificial Intelligence*, 59:81-87.

Huang et al. (1979), "A fast two-dimensional median filtering algorithm," *IEEE Transactions on Acoustics, Speech, and Signal Processing*, 27(1):13-18.

Jackway (1996), "Gradient Watersheds in Morphological Scale-Space," *IEEE Transactions on Image Processing*, 5(6):913-921.

Ji et al. (2000), "Texture Analysis for Classification of Cervix Lesions," *IEEE Transactions on Medical Imaging*, 19(11):1144-1149.

Kierkegaard et al. (1995), "Association between Colposcopic Findings and Histology in Cervical Lesions: The Significance of the Size of the Lesion" *Gynecologic Oncology*, 57:66-71.

Koester (1980), "Scanning Mirror Microscope with Optical Sectioning Characteristics: Applications in Ophthalmology", *Applied Optics*, 19(11):1749-1757.

Koester, "Comparison of Optical Sectioning Methods: The Scanning Slit Confocal Microscope", *Confocal Microscope Handbook*, pp. 189-194.

Kumar et al. (1996), "Optical Flow: A Curve Evolution Approach," *IEEE Transactions on Image Processing*, 5(4):598-610.

Linde et al. (1980), An algorithm for vector quantizer design,: *IEEE Transactions on Communications*, 28(1):84-95.

MacAulay et al. (2002), "Variation of fluorescence spectroscopy during the menstrual cycle," *Optics Express*, 10(12):493-504.

MacLean A.B. (1999), "What is Acetowhite Epithelium," *Abstract Book: 10th World Congress of Cervical Pathology and Colposcopy*, Nov. 7-11, Buenos Aires, Argentina 41.

Marzetta et al. (1999), "A surprising radon transform result and its application to motion detection," *IEEE Transactions on Image Processing*, 8(8):1039-1049.

Miike et al. (1999), "Motion enhancement for preprocessing of optical flow and scientific visualization," *Pattern Recognition Letters*, 20:451-461.

Mikhail et al. (1995), "Computerized colposcopy and conservative management of cervical intraepithelial neoplasia in pregnancy," *Acta Obstet. Gynecol. Scand.*, 74:376-378.

Milanfar (1999), "Two-dimensional matched filtering for motion estimation," *IEEE Transactions on Image Processing*, 8(3):438-444.

Mitchell et al. (1998), "Colposcopy for the diagnosis of squamous intraepithelial lesions: a meta-analysis," *Obstet. Gynecol.*, 91(4):626-631.

Mycek et al. (1998), "Colonic polyp differentiation using time-resolved autofluorescence spectroscopy," *Gastrointestinal Endoscopy*, 48(4):390-394.

Nanda et al. (2000), "Accuracy of the Papanicolaou test in screening for and follow-up of cervical cytologic abnormalities: a systematic review," *Ann Intern Med.*, 132(10):810-819.

Nesi et al. (1998), "RETIMAC REalTime Motion Analysis Chip," *IEEE Transactions on Circuits and Systems-II: Analog and Digital Signal Processing*, 45(3):361-375.

Noumeir et al. (1996), "Detection of Motion During Tomographic Acquisition by an Optical Flow Algorithm," *Computers and Biomedical Research*, 29(1):1-15.

O'Sullivan et al. (1994), "Interobserver variation in the diagnosis and grading of dyskaryosis in cervical smears: specialist cytopathologists compared with non-specialists," *J. Clin. Pathol.*, 47(6):515-518.

Ogura et al. (1995), "A cost effective motion estimation processor LSI using a simple and efficient algorithm," *IEEE Transactions on Consumer Electronics*, 41(3):690-698.

Okatani et al. (1997), "Shape reconstruction from an endoscope image by shape from shading technique for a point light source at the projection center," *Computer Vision and Image Understanding*, 66(2):119-131.

Pan et al. (1998), "Correlation-feedback Technique in Optical Flow Determination," *IEEE Transactions on Image Processing*, 7(7):1061-1067.

Perona et al. (1990), "Scale-space and edge detection using anisotropic diffusion," *IEEE Transactions on Pattern Analysis and Machine Intelligence*, 12(7):629-639.

Pogue et al. (2001), "Analysis of Acetic Acid-Induced Whitening of High-Grade Squamous Intraepithelial Lesions," *Journal of Biomedical Optics*, 6(4):397-403.

Radjadhyaksha et al. (2000), "Confocal microscopy of excised human skin using acetic acid and crossed polarization: rapid detection of non-melanoma skin cancers," *Proceedings of SPIE*, 3907:84-88.

Rakshit et al. (1997), "Computation of Optical Flow Using Basis Functions," *IEEE Transactions on Image Processing*, 6(9):1246-1254.

Ramanujam et al. (1994) "In vivo diagnosis of cervical intraepithelial neoplasia using 337-nm-exited laser-induced fluorescence", *Pro. Natl. Acad. Sci. USA*, 91:10193-10197.

Ramanujam et al. (1994), "Fluorescence Spectroscopy: A Diagnostic Tool for Cervical Intraepithelial Neoplasia (CIN)," *Gynecologic Oncology*, 52:31-38.

Reid et al. (1985), "Genital warts and cervical cancer. VII. An improved colposcopic index for differentiating benign papillomaviral infections from high-grade CIN," *Am. J. Obstet. Gynecol.*, 153(6):611-618.

Richards-Kortum et al. (1994), "Description and Performance of a Fiber-optic Confocal Fluorescence Spectrometer," *Applied Spectroscopy*, 48(3):350-355.

Romano et al. (1997), "Spectroscopic study of human leukocytes," *Physica Medica*, 13:291-295.

Ruprecht et al. (1995), "Image warping with scattered data interpolation methods," *IEEE Computer Graphics and Applications*, 37-43.

Sakuma (1985), "Quantitative Analysis of the Whiteness of the Atypical Cervical Transformation Zone", *The Journal of Reproductive Medicine*, 30(10):773-776.

Schmid (1999), "Lesion Detection in Dermatoscopic Images Using Anisotropic Diffusion and Morphological Flooding," *Proceedings of the International Conference on Image Processing (ICIP-99)*, 3:449-453.

Schmid (1999), "Segmentation and Symmetry Measure for Image Analysis: Application to Digital Dermatoscopy," *Ph.D. Thesis, Swiss Federal Institute of Technology (EPFL), Signal Processing Laboratory (LTS)*.

Schmid (1999), "Segmentation of Digitized Dermatoscopic Images by 2D Color Clustering," *IEEE Transactions on Medical Imaging*, 18(2):164-171.

Schmitt et al. (1994), "Confocal Microscopy in Turbid Media", *J. Opt. Soc. Am. A*, 11(8):2225-2235.

Schmitt et al. (1994), "Interferometric Versus Confocal Techniques for Imaging Microstructures in Turbid Biological Media", *Proc. SPIE*, 2135:1-12.

Schomacker et al. (1992), "Ultraviolet Laser-Induced Fluorescence of Colonic Polyps," *Gastroenterology*, 102:1155-1160.

Schomacker et al. (1992), "Ultraviolet Laser-Induced Fluorescence of Colonic Tissue; Basic Biology and Diagnostic Potential", *Lasers in Surgery and Medicine*, 12:63-78.

Schwartz (1993), "Real-time laser-scanning Confocal ratio imaging", *American Laboratory*, pp. 53-62.

Shafarenko et al. (1997), "Automatic Watershed Segmentation of Randomly Textured Color Images," *IEEE Transactions on Image Processing*, 6(11):1530-1544.

Shafi et al. (1995), "Modern image capture and data collection technology," *Clin. Obstet. Gynecol.*, 38(3):640-643.

Sheppard et al. (1978), "Depth of Field in the Scanning Microscope", *Optics Letters*, 3(3):115-117.

Szarewski et al., (1996), "Effect of smoking cessation on cervical lesions size," *Lancet*, 347:941-943.

Szeliski et al. (1997), "Spline-based image registration," *International Journal of Computer Vision*, 22(3):199-218.

Tadrous (2000), "Methods for Imaging the Structure and Function of Living Tissues and Cells: 2. Fluorescence Lifetime Imaging," *Journal of Pathology*, 191(3):229-234.

Thirion et al. (1999), "Deformation analysis to detect and quantify active lesions in three-dimensional medical image sequences," *IEEE Transactions on Medial Imaging*, 18(5):429-441.

Toglia et al. (1997), "Evaluation of colposcopic skills in an obstetrics and gynecology residency training program," *J. Lower Gen. Tract. Dis.*, 1(1):5-8.

Treameau et al. (1997), "A Region Growing and Merging Algorithm to Color Segmentation," *Pattern Recognition*, 30(7):1191-1203.

Van den Elsen et al. (1995), "Automatic registration of ct and mr brain images using correlation of geometrical features," *IEEE Transactions on medical imaging*, 14(2):384-396.

Vernon (1999), "Computation of Instantaneous Optical Flow Using the Phase of Fourier Components," *Image and Vision Computing*, 17:189-199.

Vincent et al. (1991), "Watersheds in Digital Spaces: An Efficient Algorithm Based on Immersion Simulations," *IEEE Transactions on Patterns Analysis and Machine Intelligence*, 13(6):583-598.

Vincent et al. (1993), "Morphological grayscale reconstruction in image analysis: Applications and efficient algorithms," *IEEE Transactions on Image Processing*, 2(2):176-201.

Wang et al. (1999), "Fast algorithms for the estimation of motion vectors," *IEEE Transactions on Image Processing*, 8(3):435-438.

Weng et al. (1997), "Three-Dimensional Surface Reconstruction Using Optical Flow for Medical Imaging," *IEEE Transactions on Medical Imaging*, 16(5):630-641.

Wilson, "The Role of the Pinhold in Confocal Imaging Systems", *Confocal Microscopy Handbook*, Chapter 11, 113-126.

Wolberg et al. (1998) "Image morphing: a survey," *The Visual Computer*, 14:360-372.

You et al. (1996), "Behavioral analysis of anisotropic diffusion in image processing," *IEEE Transactions on Image Processing*, 5(11):1539-1553.

Zahm et al. (1998), "Colposcopic appearance of cervical intraepithelial neoplasia is age dependent," *Am. J. Obstet. Gynecol.*, 179(5):1298-1304.

Zeger et al. (1992), "Globally optimal vector quantizer design by stochastic relaxation," *IEEE Transactions on Signal Processing*, 40(2):310-322.

Zeng et al. (1993), "A computerized autofluorescence and diffuse reflectance spectroanalyser system for in vivo skin studies," *Phys. Med. Biol.*, 38:231-240.

Zeng et al. (1997), "Optimization of fast block motion estimation algorithms," *IEEE Transactions on Circuits and Systems for Video Technology*, 7(6):833-844.

Zhang et al. (1999), "Shape from shading: a survey," *IEEE Transactions on Pattern Analysis and Machine Intelligence*, 21(8):690-706.

Zheng et al. (1991), "Estimation of illumination direction, albedo, and shape from shading," *IEEE Transactions on Pattern Analysis and Machine Intelligence*, 13(7):680-702.

Zhengfang et al. (1998), "Identification of Colonic Dysplasia and Neoplasia by Diffuse Reflectance Spectroscopy and Pattern Recognition Techniques," *Applied Spectroscopy*, 52(6):833-839.

European Search Report for Pending European Patent Application No. 02019837-0, Jan. 14, 2004 (4 pgs.).

European Search Report for Pending European Patent Application No. 00938257, Jun. 14, 2005 (3 pgs.).

International Search Report for International Application No. PCT/US04/11820 dated Sep. 3, 2004 (3 pages).

Written Opinion for International Application No. PCT/US04/11820 dated Sep. 29, 2004 (5 pages).

International Search Report for International Application No. PCT/US03/21347 dated Nov. 3, 2003 (2 pgs.).

Fielding et al., "Prediction of Outcome After Curative Resection for Large Bowel Cancer," *The Lancet*, Oct. 18, 1986, pp. 904-907.

Lin et al., "Evidence of possible carcinogenesis during conformational changes in bladder mucosa induced by bladder outlet obstruction," Cancer Letters, 79 (1994), 221-226.

Zhao, Project Abstract, "Integration of 3-D Imaging Technology and Feature Extraction Algorithm Designs," Center for Engineering Education and Practice, University of Michigan—Dearborn, Feb. 1999.

Frank et al., "Classification: Oldtimers and Newcomers," Journal of Chemometrics, vol. 3, 463-475 (1989).

Frayne et al., "3D MR DSA: Effects of Injection Protocol and Image Masking," Journal of Magnetic Resonance Imaging, 12:476-487 (2000).

Farzaneh et al., "MR Fluoroscopy: Initial Clinical Studies," Radiology, vol. 171, pp. 545-549 (1989).

Sergeev et al., "In vivo endoscopic OCT imaging of precancer and cancer states of human mucosa," Optics Express, vol. 1, pp. 432-440 (1997).

* cited by examiner

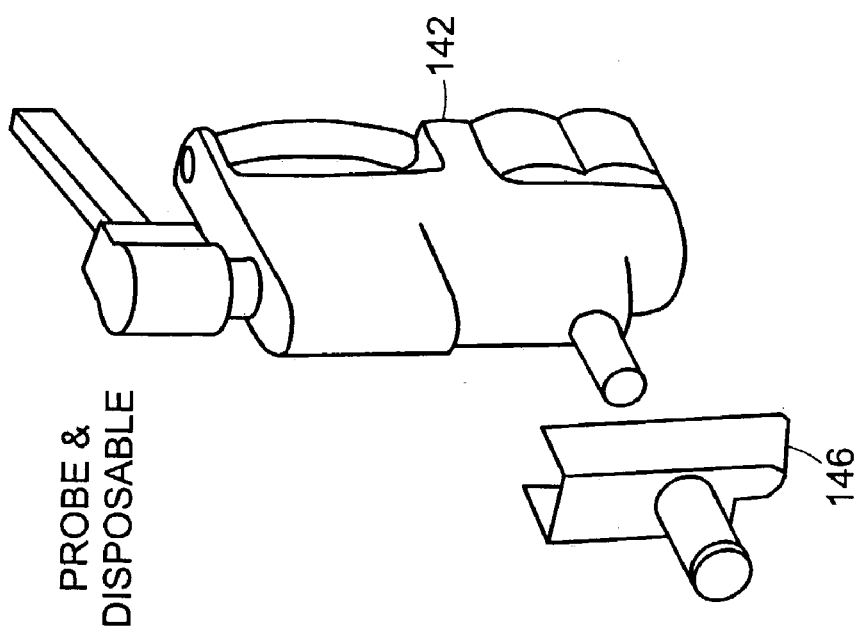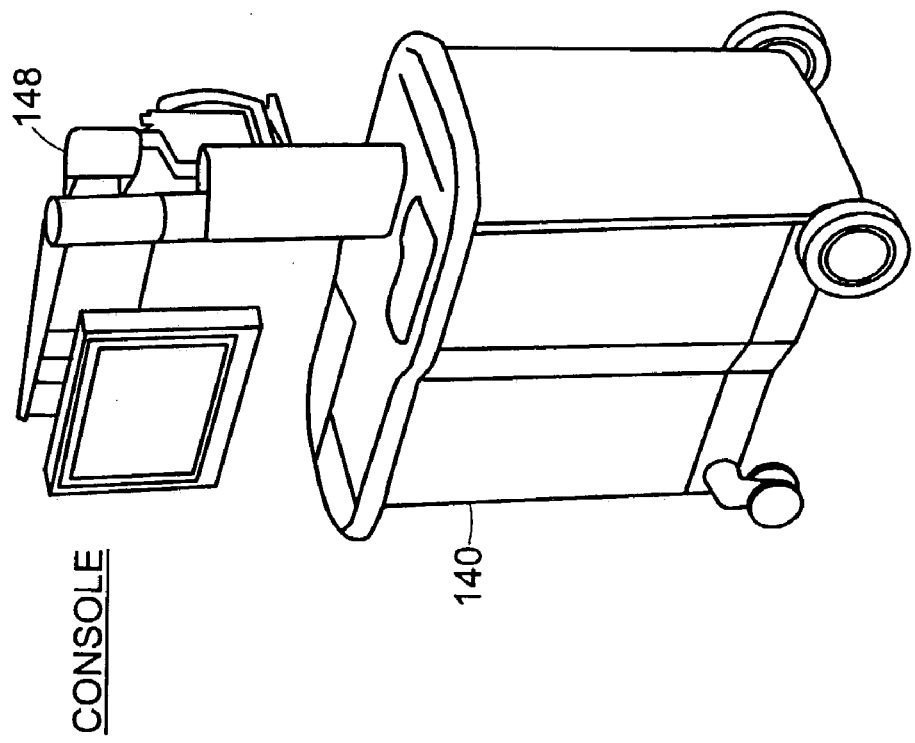
FIG. 2

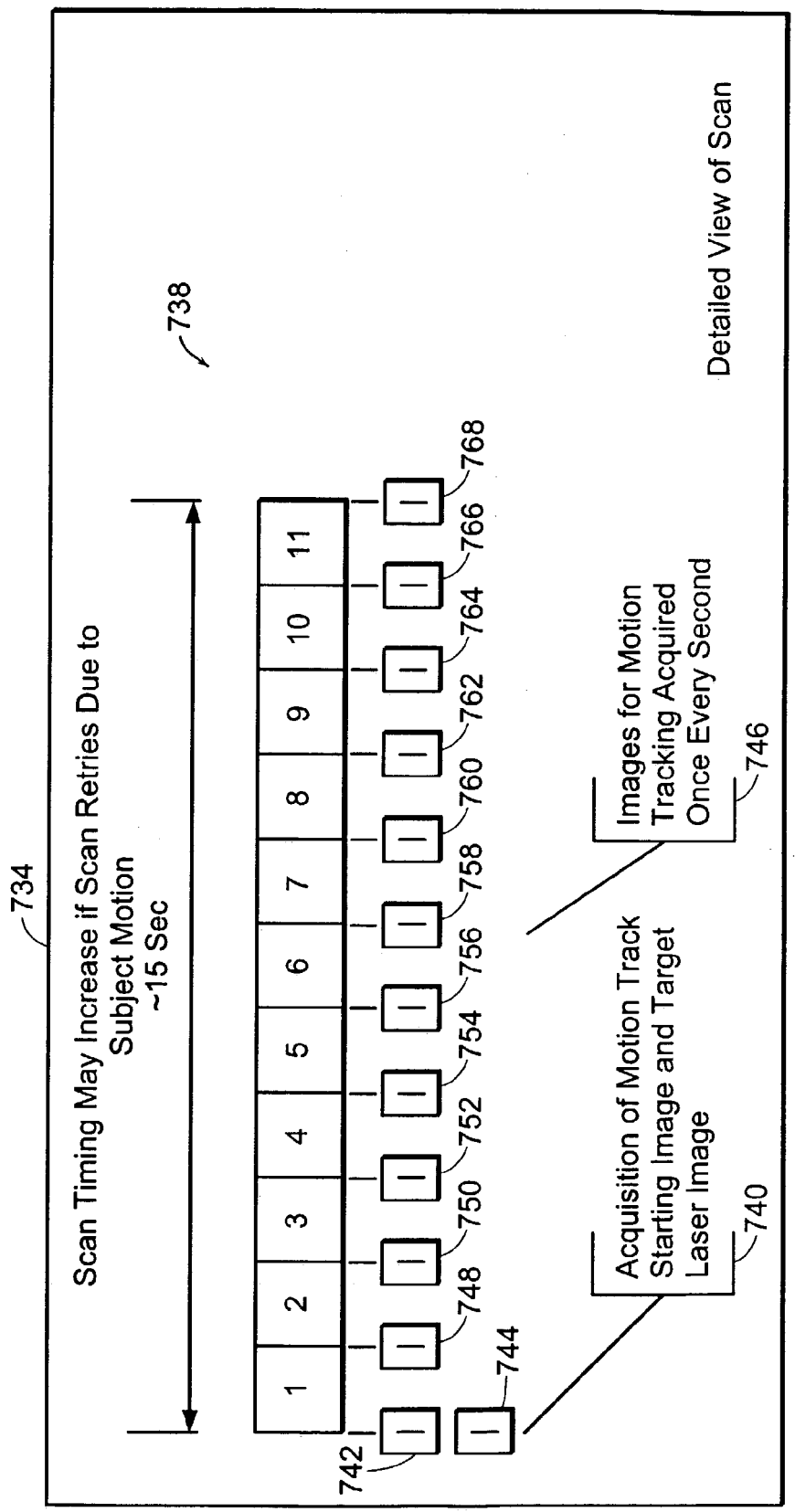

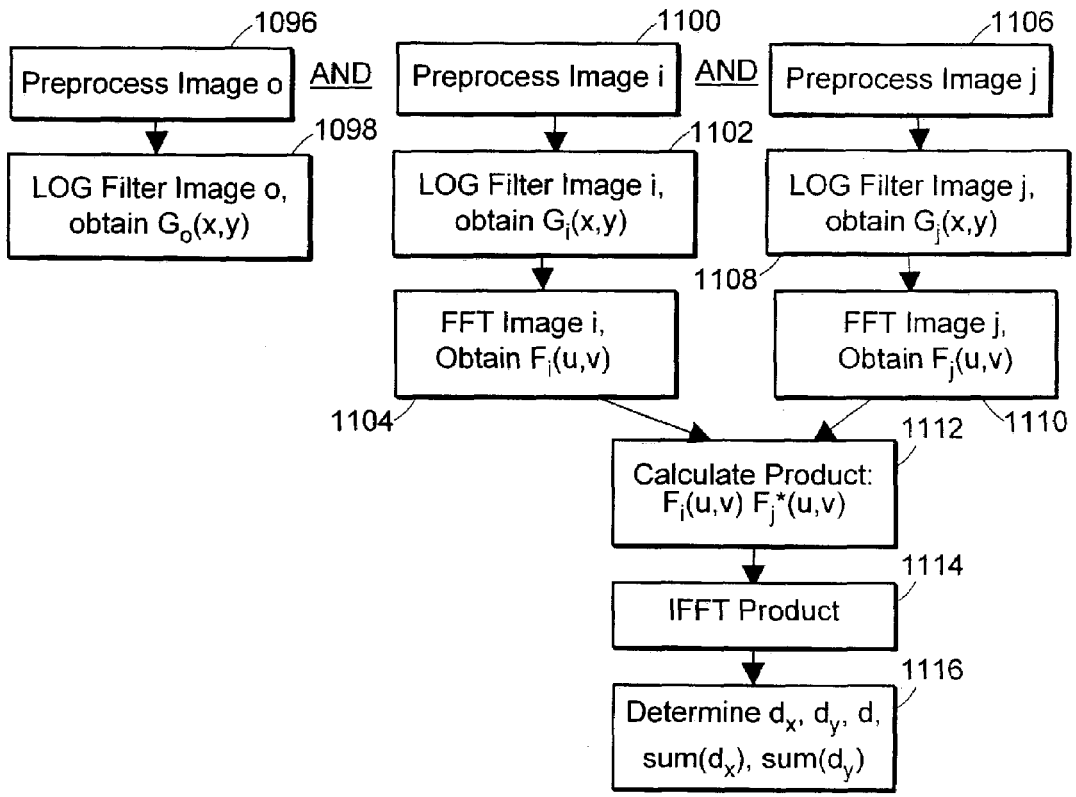
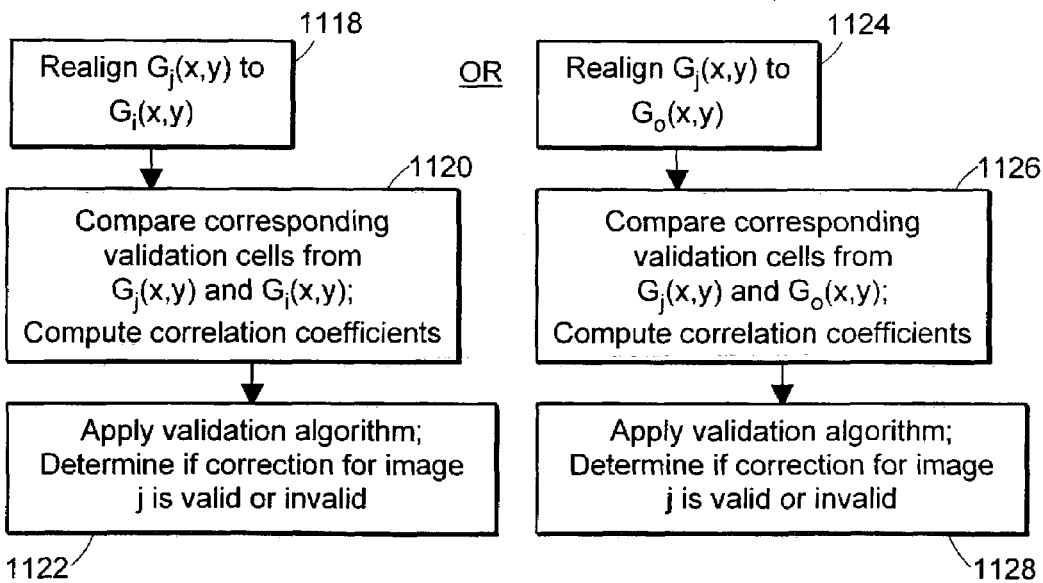
FIG. 45

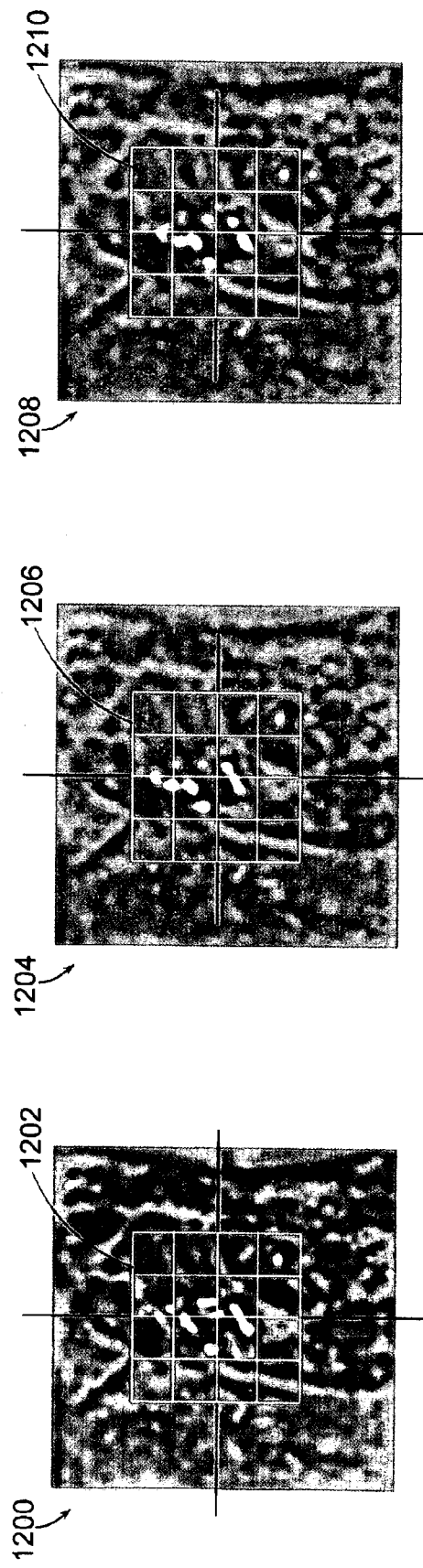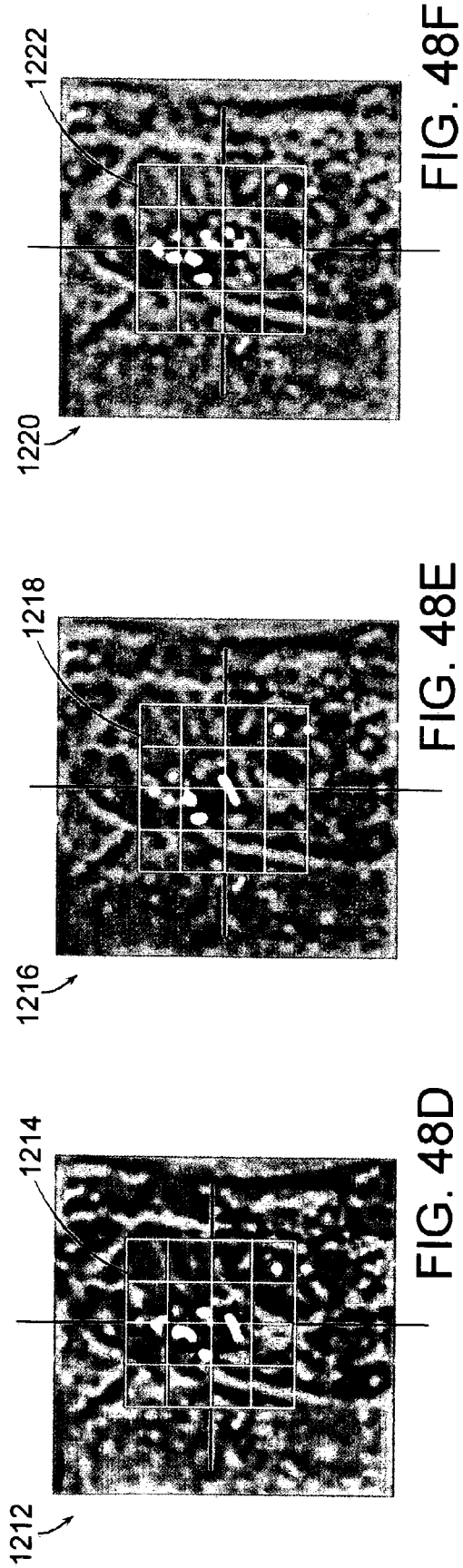

Hamming + LOG 9

Feathering + LOG 9

Feathering + LOG 21

Feathering + LOG 31

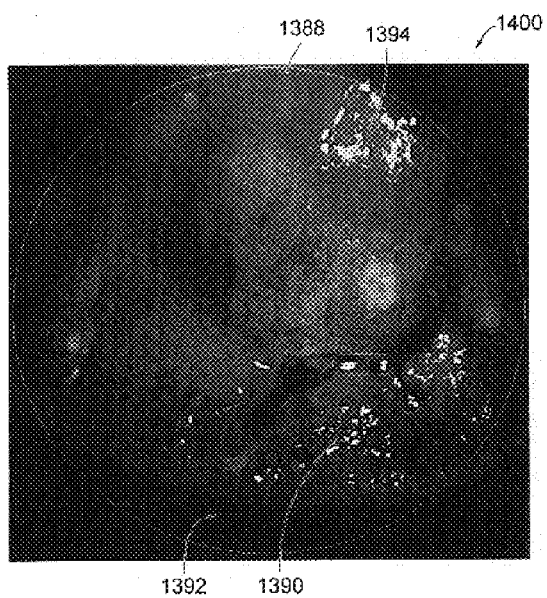
FIG. 70A
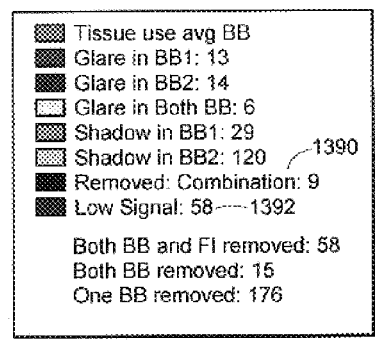
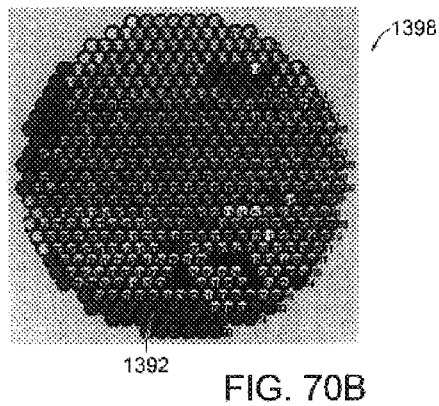
FIG. 70B

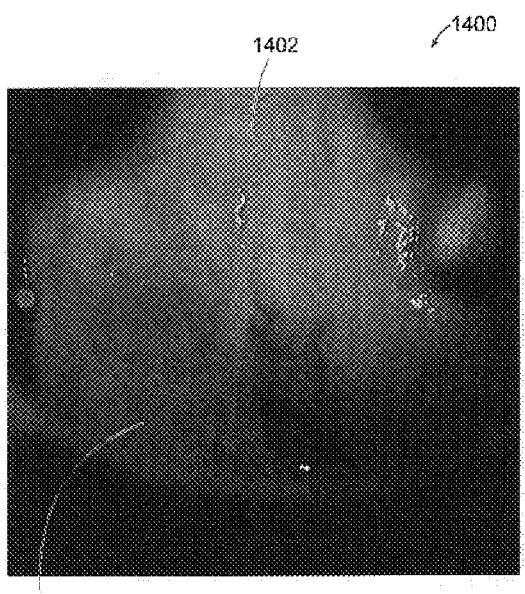
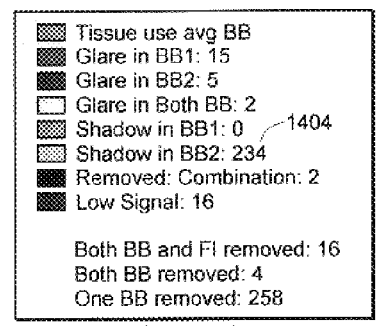
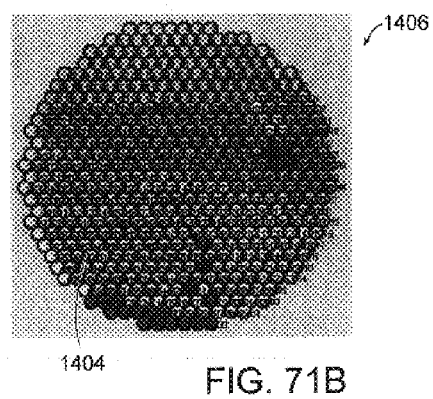
FIG. 71A
FIG. 71B

Data V.1.4x

- · Scan Position — 1624
- ○ Porphyrin — 1626
- ✱ FAD — 1628
- ◦ Classifier — 1630
- ✽ Filtered — 1632

$r_{disco} = [0.2, 0.11, 0.3, 0.22, 0.17]$ $r_{date} = [0.2, 0.14, 0.25, 0.23, 0.18]$ FIG. 92A
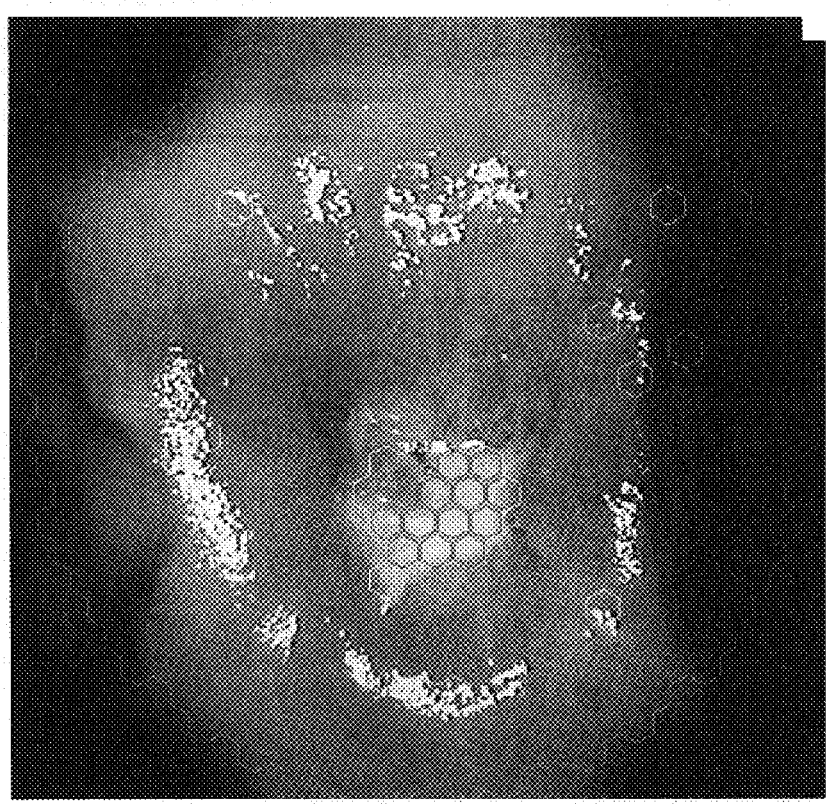
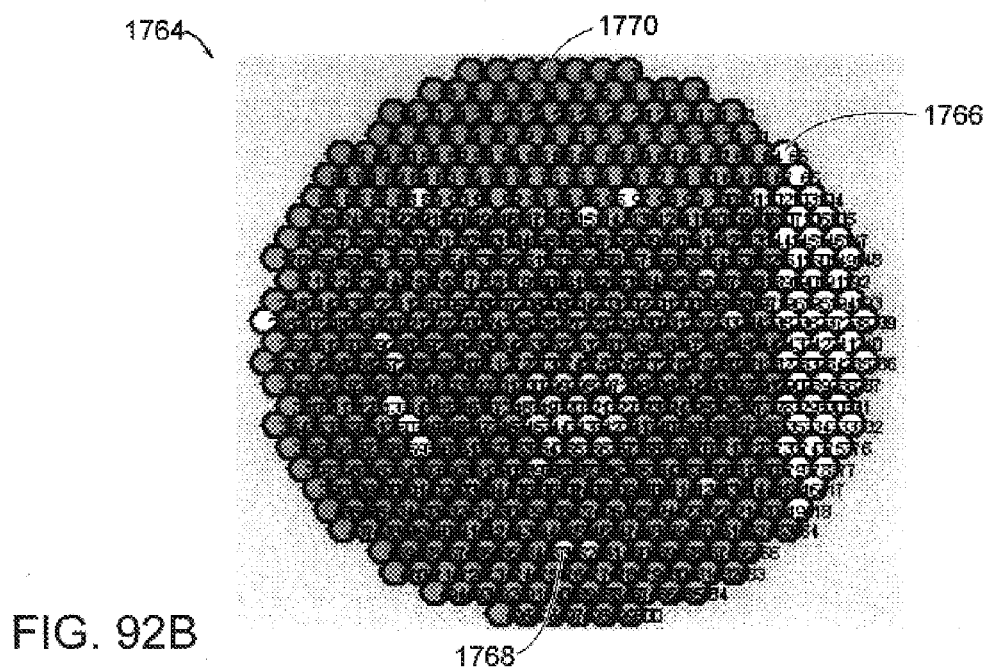
FIG. 92B

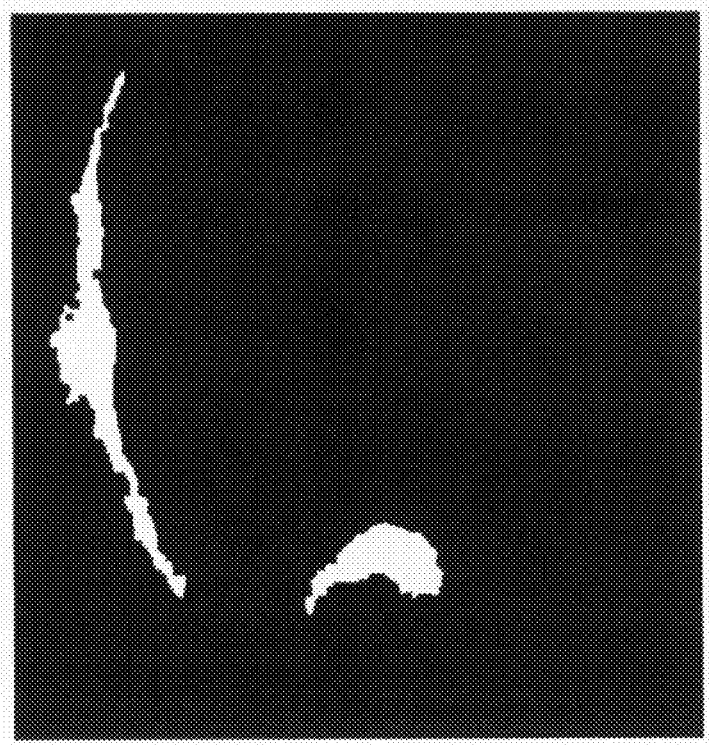

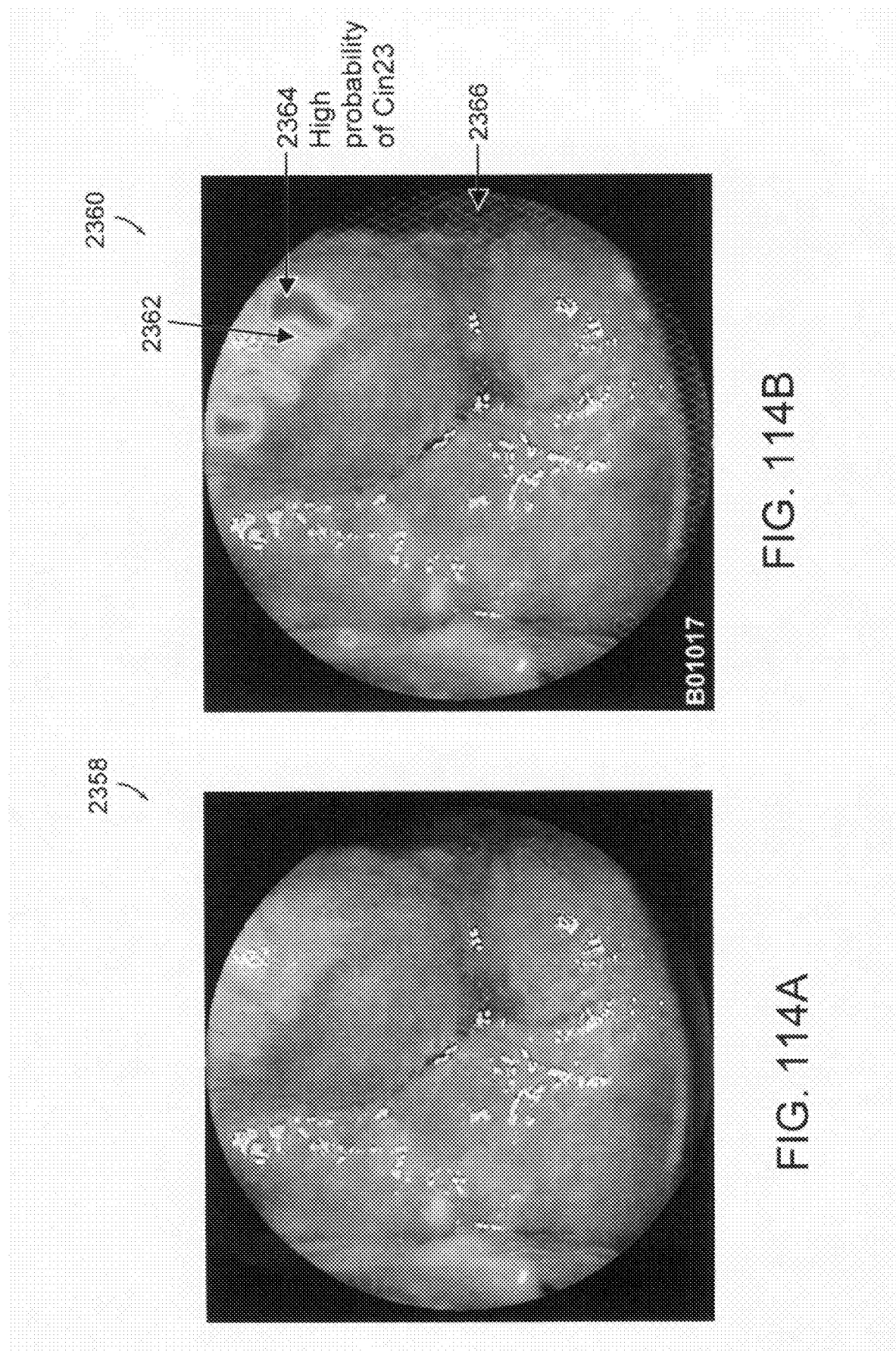

US 7,282,723 B2

METHODS AND APPARATUS FOR PROCESSING SPECTRAL DATA FOR USE IN TISSUE CHARACTERIZATION

RELATED APPLICATIONS

The present application is a continuation-in-part of U.S. patent application Ser. No. 10/243,535, filed Sep. 13, 2002, now U.S. Pat. No. 6,818,903 which claims priority to and the benefit of U.S. Provisional Patent Application Ser. No. 60/394,696, filed Jul. 9, 2002. The present application is also a continuation-in-part of U.S. patent application Ser. No. 10/295,794, filed Nov. 15, 2002, now U.S. Pat. No. 6,933,154 which claims priority to and the benefit of U.S. Provisional Patent Application Ser. No. 60/394,696, filed Jul. 9, 2002. Additionally, the present application is related to the following commonly-owned applications: U.S. patent application Ser. Nos. 10/418,922, 10/418,902, 10/418,974, 10/418,668, 10/418,975, 10/419,181, and 10/418,973, all of which are filed on even date herewith.

FIELD OF THE INVENTION

This invention relates generally to spectroscopic methods. More particularly, in certain embodiments, the invention relates to methods of processing spectral data for use in a tissue classification scheme.

BACKGROUND OF THE INVENTION

It is common in the field of medicine to perform visual examination to diagnose disease. For example, visual examination of the cervix can discern areas where there is a suspicion of pathology. However, direct visual observation alone may be inadequate for proper identification of an abnormal tissue sample, particularly in the early stages of disease.

In some procedures, such as colposcopic examinations, a chemical agent, such as acetic acid, is applied to enhance the differences in appearance between normal and pathological tissue. Such acetowhitening techniques may aid a colposcopist in the determination of areas in which there is a suspicion of pathology.

Colposcopic techniques are not perfect. They generally require analysis by a highly-trained physician. Colposcopic images may contain complex and confusing patterns and may be affected by glare, shadow, or the presence of blood or other obstruction, rendering an indeterminate diagnosis.

Spectral analysis has increasingly been used to diagnose disease in tissue. Spectral analysis is based on the principle that the intensity of light that is transmitted from an illuminated tissue sample may indicate the state of health of the tissue. As in colposcopic examination, spectral analysis of tissue may be conducted using a contrast agent such as acetic acid. In spectral analysis, the contrast agent is used to enhance differences in the light that is transmitted from normal and pathological tissues.

Spectral analysis offers the prospect of at least partially-automated diagnosis of tissue using a classification algorithm. However, examinations using spectral analysis may be adversely affected by glare, shadow, or the presence of blood or other obstruction, rendering an indeterminate diagnosis. Some artifacts may not be detectable by analysis of the spectral data alone; hence, erroneous spectral data may be inseparable from valid spectral data.

There exists a general need for more accurate spectral analysis methods for diagnosing tissue. More specifically, there is a need to reduce the inaccuracy of tissue classification algorithms due to erroneous spectral data.

SUMMARY OF THE INVENTION

The invention provides methods for processing tissue-derived spectral data for use in a classification algorithm. Methods of the invention comprise application of spectral and/or image masks for separating ambiguous or unclassifiable spectral data from valid spectral data.

More specifically, the invention improves the accuracy of tissue classification, in part, by properly identifying and accounting for spectral data that are non-representative of a zone of interest of a tissue sample, for example, spectral data from tissue regions that are affected by an obstruction and/or regions that lie outside a diagnostic zone of interest. During examination of tissue, a portion of the tissue may be obstructed, for example, by mucus, fluid, foam, a medical instrument, glare, shadow, and/or blood. Moreover, tissue examination may include data from portions of the tissue that lie outside an identified zone of interest. Regions that lie outside a zone of interest include, for example, a tissue wall (e.g., a vaginal wall), an os, an edge surface of a tissue (e.g., a cervical edge), and tissue in the vicinity of a smoke tube. Once data from the obstructed regions and regions outside a zone of interest are identified, they are processed by either elimination (hard masking) or by weighting (soft masking) in a tissue classification algorithm.

Therefore, a preferred method of the invention comprises applying spectral masks to automatically identify data from regions of a tissue sample that are obstructed or lie outside a zone of interest. Regions from which such data are obtained are then identified and characterized as being indeterminate. Data from these regions may then be eliminated from further processing in the tissue classification algorithm.

In some cases, data from a region that is only partially obstructed or which lies only partially outside a zone of interest are still used in a tissue classification scheme, for example, to determine tissue-class probabilities. Those probabilities may be "soft masked"—that is, weighted according to a likelihood the region (or a point within the region) is affected by an obstruction and/or lies outside a zone of interest.

The invention also provides methods of processing spectral data by applying spectral masks in conjunction with image masks. Image masks are similar to spectral masks, except that image masks are based on image data from the tissue sample—for example, luminescence or RGB intensities. Methods of the invention comprise determining an overlap between regions identified by a spectral mask and those identified by an image mask. Data from the area of overlap are classified as indeterminate or are appropriately weighted, according to the tissue classification algorithm.

A spectral mask as applied in the present invention may take the form of a metric. A metric may include a series of logical statements, each comparing a single spectral measurement or a combination of spectral measurements obtained from a given region of a tissue sample to a threshold value. If the metric is satisfied, the corresponding region is considered to be "masked."

In addition to filtering erroneous data, spectral masks can be used to identify regions of tissue having a predetermined condition (e.g., disease state, response to treatment, cell type, etc). For example, the invention provides a method of identifying healthy tissue by evaluating a metric based at least in part on two ratios of spectral data obtained from a tissue sample. The invention also provides a method of identifying necrotic tissue by evaluating a metric based on fluorescence data obtained from the tissue sample.

In addition, the invention provides methods of obtaining and arbitrating between redundant sets of spectral data obtained from the same region of tissue. For example, one embodiment comprises obtaining two sets of reflectance spectral data from the same region, wherein each set is obtained using light incident to the region at a different angle. In this way, if one set of data is affected by an artifact, such as glare, shadow, or other obstruction, the other set of data provides a back-up that may not be affected by the artifact. The invention comprises methods of automatically determining whether one or more data sets is/are affected by an artifact, and provides methods of arbitrating between the multiple data sets in order to select a representative set of data for the region. The representative set of data may then be processed according to the various embodiments of the invention, as introduced above.

Accordingly, the invention comprises obtaining spectral data from one or more regions of a tissue sample, arbitrating between redundant data sets obtained from each region, automatically masking the data to identify regions that are outside a zone of interest or are affected by an obstruction, and processing spectral data from the identified regions in a tissue classification scheme. Methods of the invention also comprise identifying healthy tissue and necrotic tissue by evaluating metrics based on spectral data obtained from a tissue sample.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views. The patent or application file contains at least one drawing executed in color. Copies of this patent or patent application publication with color drawing(s) will be provided by the U.S. Patent and Trademark Office upon request and payment of the necessary fee.

While the invention is particularly shown and described herein with reference to specific examples and specific embodiments, it should be understood by those skilled in the art that various changes in form and detail may be made therein without departing from the spirit and scope of the invention.

FIG. 2 is a schematic representation of components of the instrument used in the tissue characterization system of FIG. 1 to obtain spectral data and image data from a tissue sample according to an illustrative embodiment of the invention.

FIG. 27B is a block diagram featuring steps that the system of FIG. 1 performs during acquisition of spectral data in a patient scan to detect and compensate for movement of the sample during the scan.

FIG. 45 is a schematic flow diagram depicting steps in a method of determining a correction for image misalignment in the tissue characterization system of FIG. 1, according to an illustrative embodiment of the invention.

FIGS. 48A-F depict a subset of adjusted images from a sequence of images of a tissue with an overlay of gridlines showing the validation cells used in validating the determinations of misalignment correction between the images according to an illustrative embodiment of the invention.

FIG. 70A depicts an exemplary image of cervical tissue divided into regions for which two types of reflectance spectral data and one type of fluorescence spectral data are obtained, according to an illustrative embodiment of the invention.

FIG. 70B is a representation of the regions depicted in FIG. 70A and shows the categorization of each region using the metrics in the arbitration step 128 of FIG. 1, according to an illustrative embodiment of the invention.

FIG. 71A depicts an exemplary image of cervical tissue divided into regions for which two types of reflectance spectral data and one type of fluorescence spectral data are obtained, according to an illustrative embodiment of the invention.

FIG. 71B is a representation of the regions depicted in FIG. 71A and shows the categorization of each region using the metrics in the arbitration step 128 of FIG. 1, according to an illustrative embodiment of the invention.

FIG. 92A depicts an exemplary reference image of cervical tissue from a patient scan in which spectral data is used in arbitration and fluids/mucus ($[MU]_{spec}$) spectral masking, according to an illustrative embodiment of the invention.

FIG. 92B is a representation (obgram) of the interrogation points (regions) of the tissue sample depicted in FIG. 92A and shows points classified as "filtered" following arbitration and "masked" following fluids/mucus ($[MU]_{spec}$) spectral masking, according to an illustrative embodiment of the invention.

FIG. 99B represents a smoke tube image mask, $[ST]_{vid}$, corresponding to the exemplary image in FIG. 99A, according to an illustrative embodiment of the invention.

FIG. 100 is a block diagram depicting steps in a method of determining a smoke tube image mask, $[ST]_{vid}$, for an image of cervical tissue, according to an illustrative embodiment of the invention.

FIG. 101A depicts an exemplary image of cervical tissue obtained during a patient examination and used in determining a corresponding os image mask, $Os_{vid}$, according to an illustrative embodiment of the invention.

FIG. 101B represents an os image mask, $Os_{vid}$, corresponding to the exemplary image in FIG. 101A, according to an illustrative embodiment of the invention.

FIG. 102 is a block diagram depicting steps in a method of determining an os image mask, $Os_{vid}$, for an image of cervical tissue, according to an illustrative embodiment of the invention.

FIG. 103A depicts an exemplary image of cervical tissue obtained during a patient examination and used in determining a corresponding blood image mask, $Blood_{vid}$, according to an illustrative embodiment of the invention.

FIG. 103B represents a blood image mask, $Blood_{vid}$, corresponding to the exemplary image in FIG. 103A, according to an illustrative embodiment of the invention.

FIG. 104 is a block diagram depicting steps in a method of determining a blood image mask, $Blood_{vid}$, for an image of cervical tissue, according to an illustrative embodiment of the invention.

FIG. 105A depicts an exemplary image of cervical tissue obtained during a patient examination and used in determining a corresponding mucus image mask, $Mucus_{vid}$, according to an illustrative embodiment of the invention.

FIG. 105B represents a mucus image mask, $Mucus_{vid}$, corresponding to the exemplary reference image in FIG. 105A, according to an illustrative embodiment of the invention.

FIG. 106 is a block diagram depicting steps in a method of determining a mucus image mask, $Mucus_{vid}$, for an image of cervical tissue, according to an illustrative embodiment of the invention.

FIG. 107A depicts an exemplary reference image of cervical tissue obtained during a patient examination and used in determining a corresponding speculum image mask, $[SP]_{vid}$, according to an illustrative embodiment of the invention.

Figure 107:
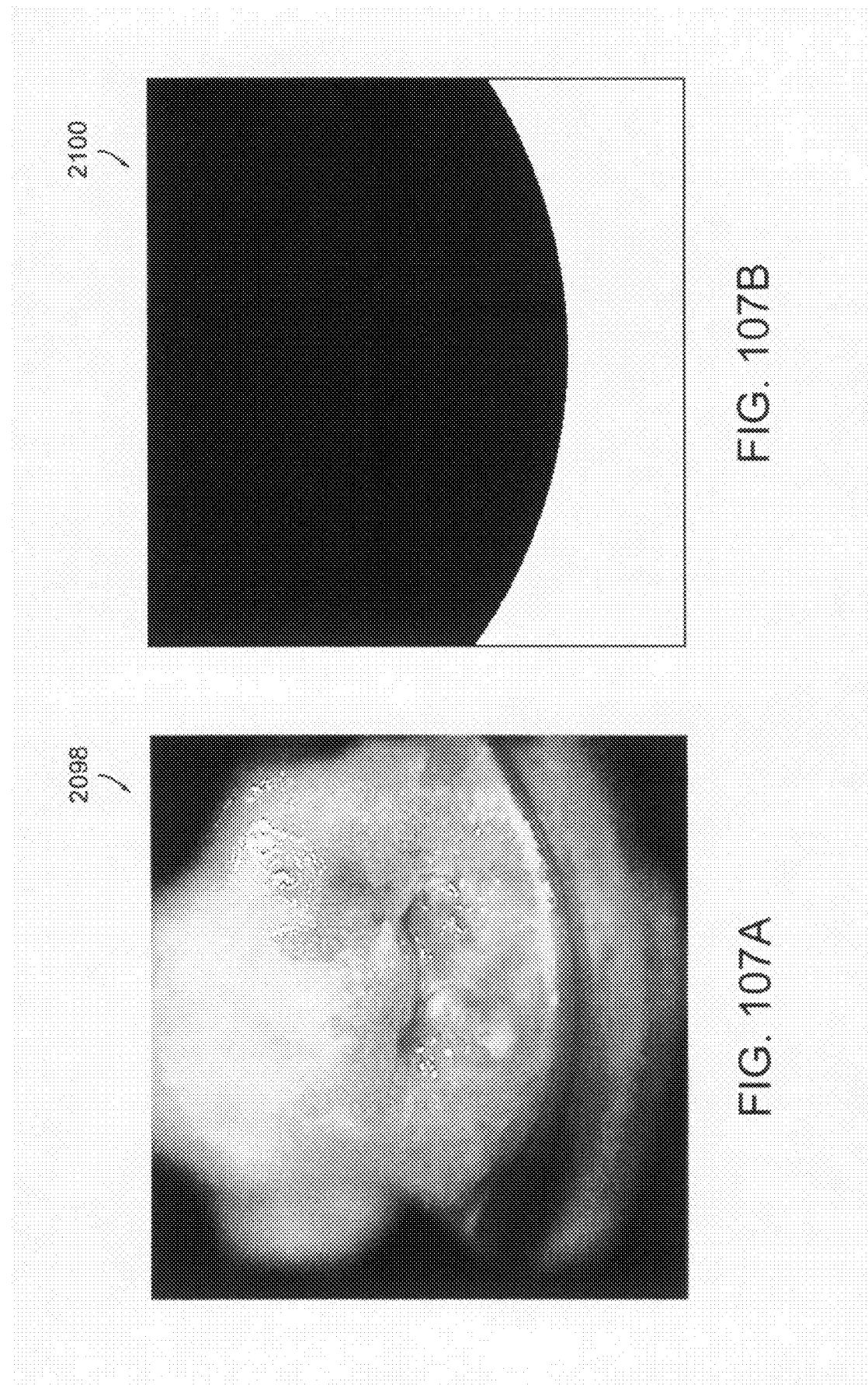

FIG. 107B represents a speculum image mask, $[SP]_{vid}$, corresponding to the exemplary image in FIG. 107A, according to an illustrative embodiment of the invention.

Figure 108:
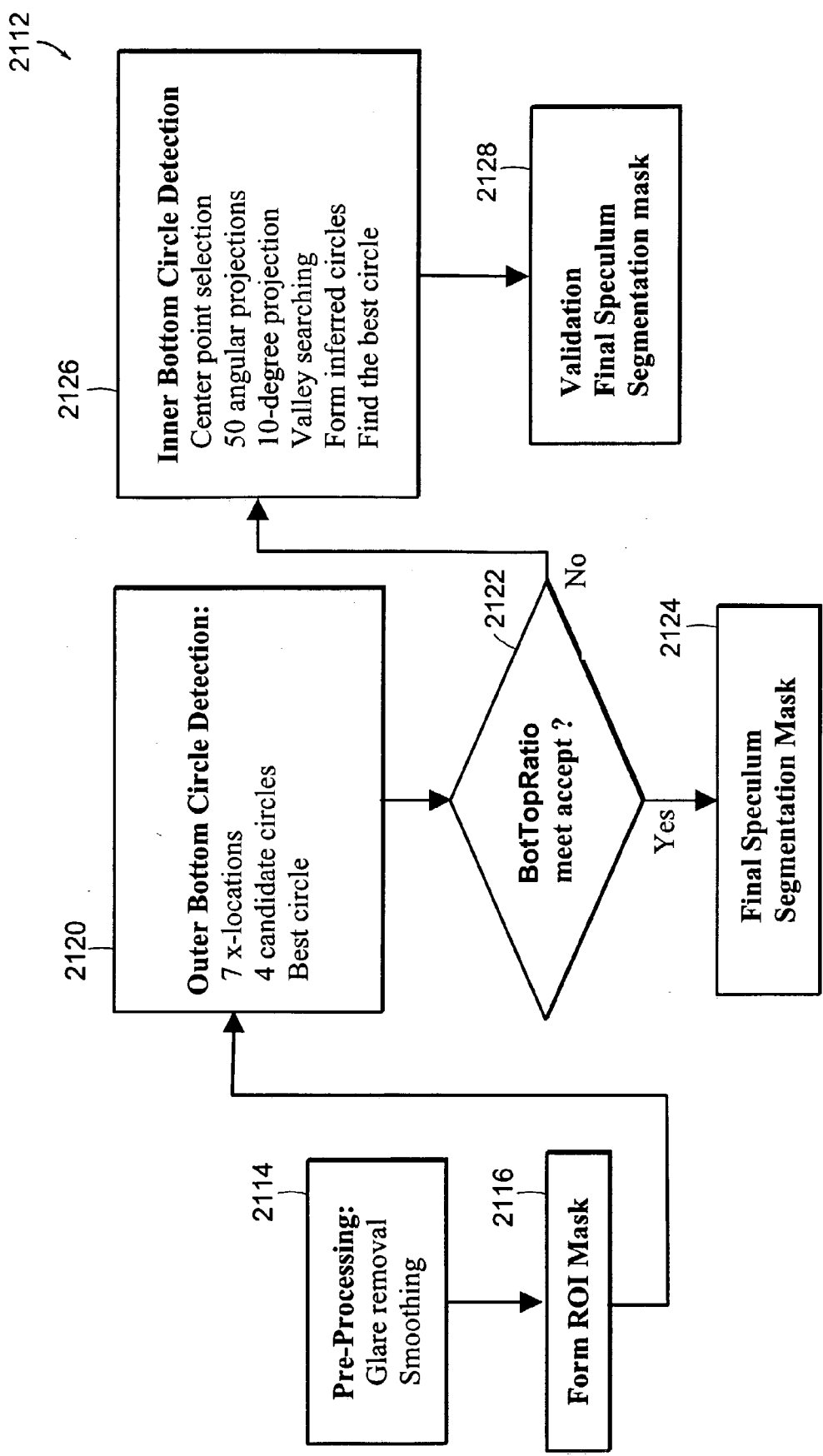

FIG. 108 is a block diagram depicting steps in a method of determining a speculum image mask, $[SP]_{vid}$, for an image of cervical tissue, according to an illustrative embodiment of the invention.

Figure 109:
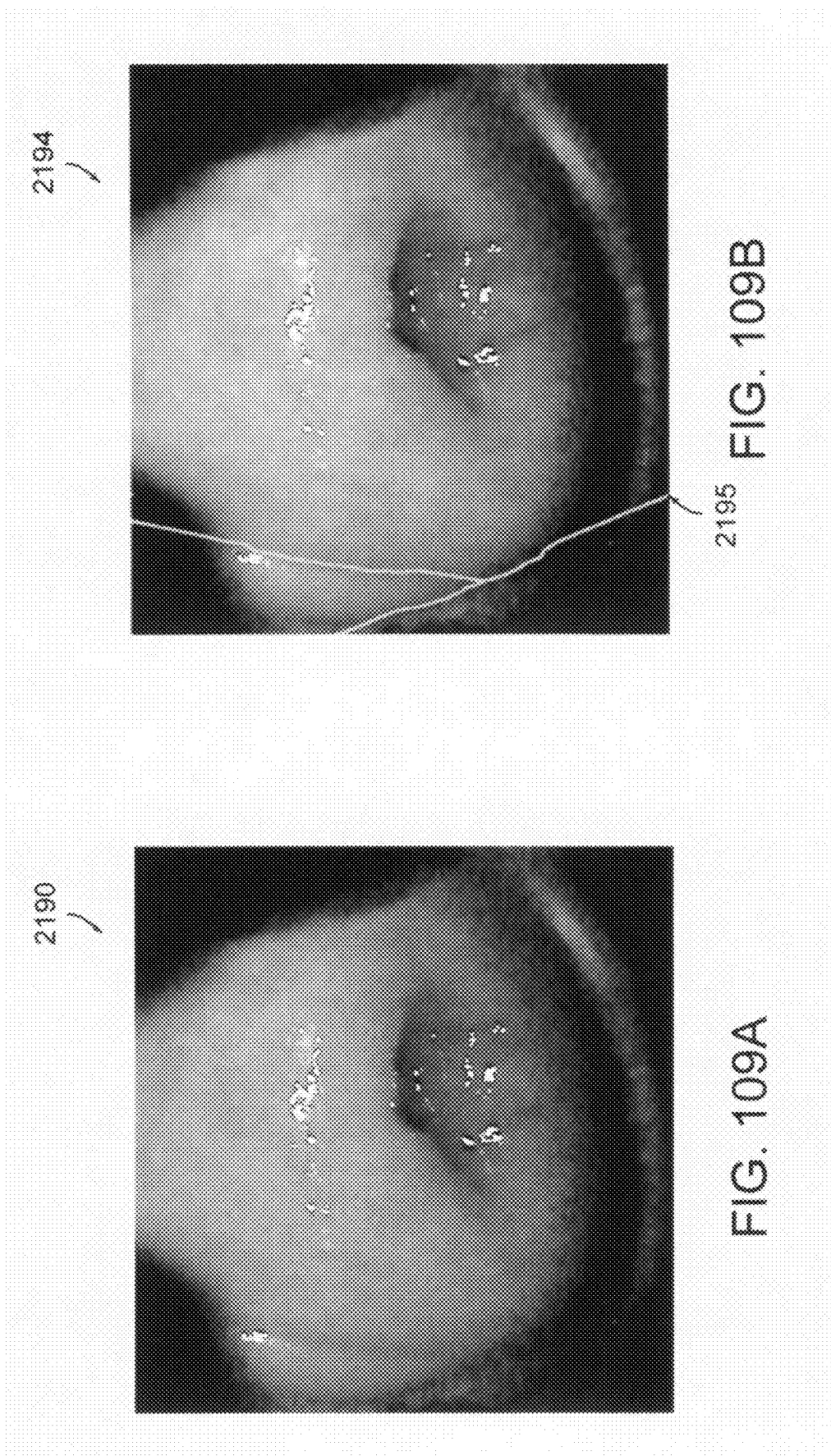

FIG. 109A depicts an exemplary image of cervical tissue obtained during a patient examination and used in determining a vaginal wall image mask, $[VW]_{vid}$, according to an illustrative embodiment of the invention.

FIG. 109B represents the image of FIG. 109A overlaid with a vaginal wall image mask, $[VW]_{vid}$, following extension, determined according to an illustrative embodiment of the invention.

Figure 110:
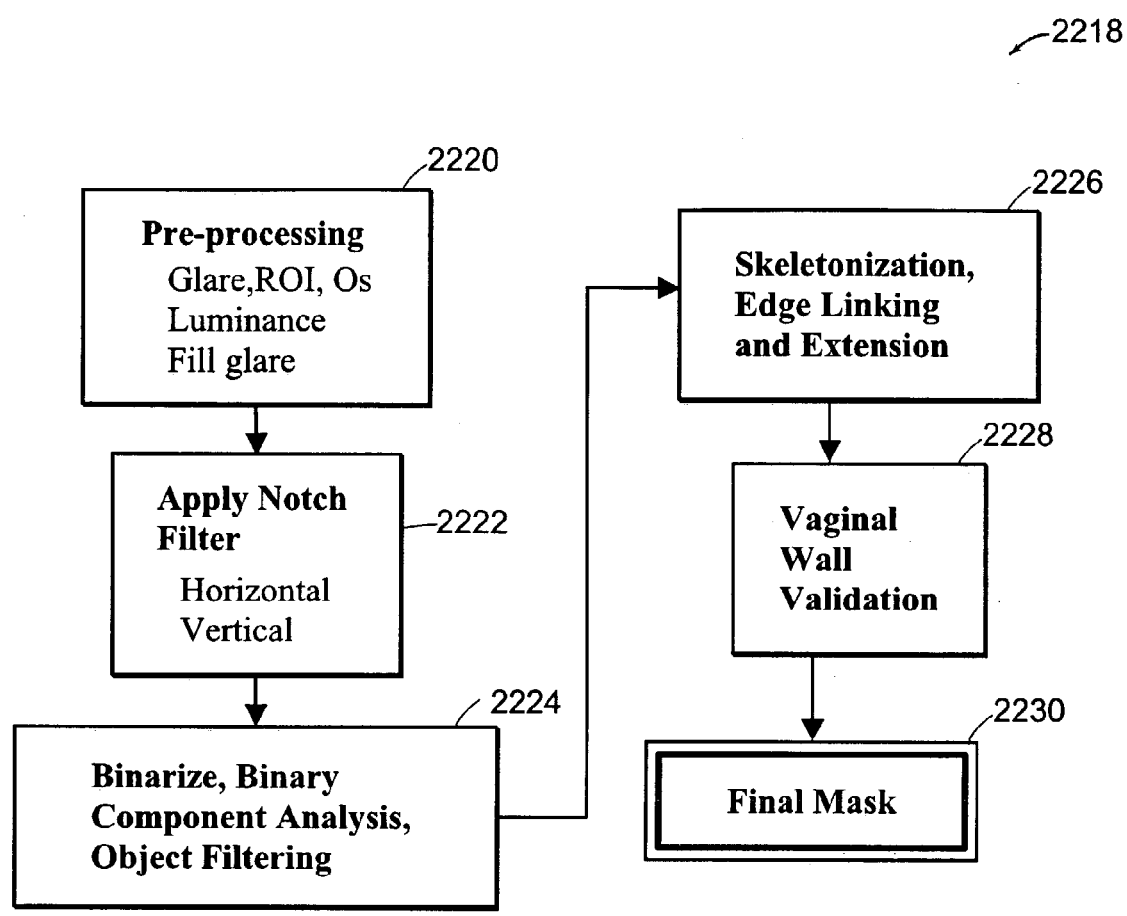

FIG. 110 is a block diagram depicting steps in a method of determining a vaginal wall image mask, $[VW]_{vid}$, for an image of cervical tissue, according to an illustrative embodiment of the invention.

FIG. 111A depicts an exemplary image of cervical tissue obtained during a patient examination and used in determining a corresponding fluid-and-foam image mask, $[FL]_{vid}$, according to an illustrative embodiment of the invention.

FIG. 111B represents a fluid-and-foam image mask, $[FL]_{vid}$, corresponding to the exemplary image in FIG. 111A, according to an illustrative embodiment of the invention.

Figure 112:
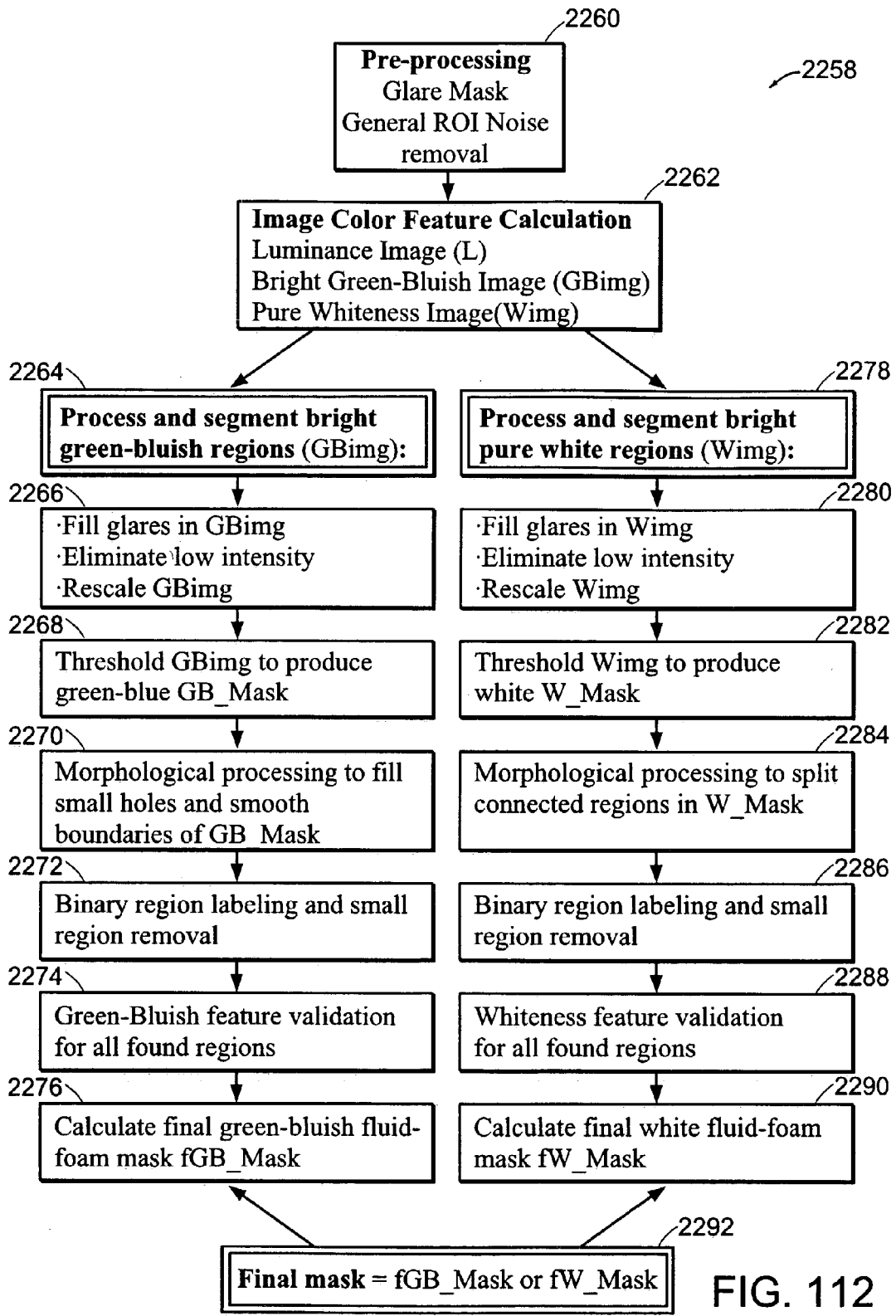

FIG. 112 is a block diagram depicting steps in a method of determining a fluid-and-foam image mask, $[FL]_{vid}$, for an image of cervical tissue, according to an illustrative embodiment of the invention.

Figures 113A, 113B, 113C:
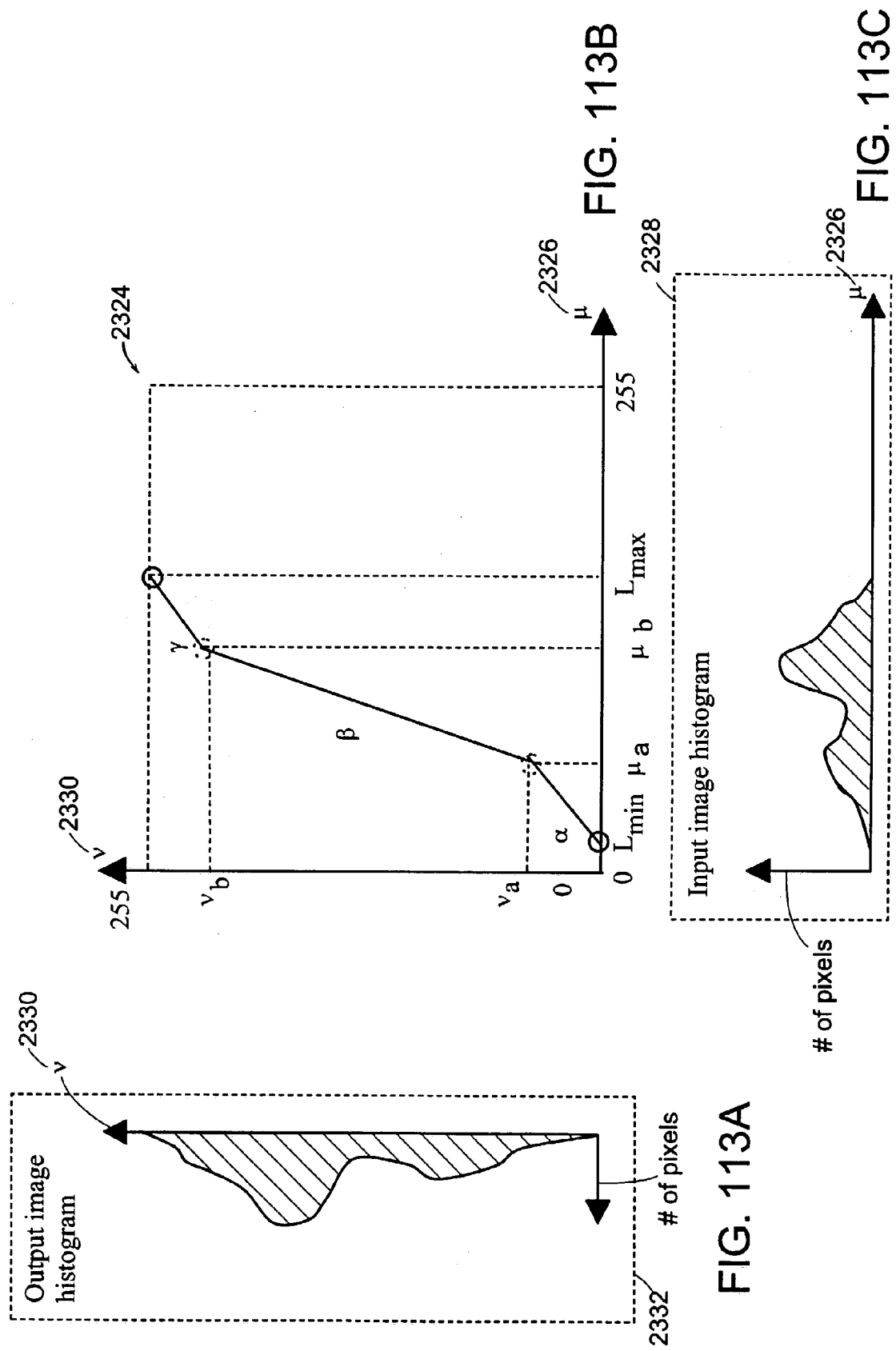

FIGS. 113A-C show graphs representing a step in a method of image visual enhancement in which a piecewise linear transformation of an input image produces an output image with enhanced image brightness and contrast, according to one embodiment of the invention.

FIG. 114A depicts an exemplary image of cervical tissue obtained during a patient examination and used as a reference (base) image in a method of disease probability display, according to one embodiment of the invention.

FIG. 114B depicts the output overlay image corresponding to the reference image in FIG. 114A, produced using a method of disease probability display according to one embodiment of the invention.

Figure 115B:
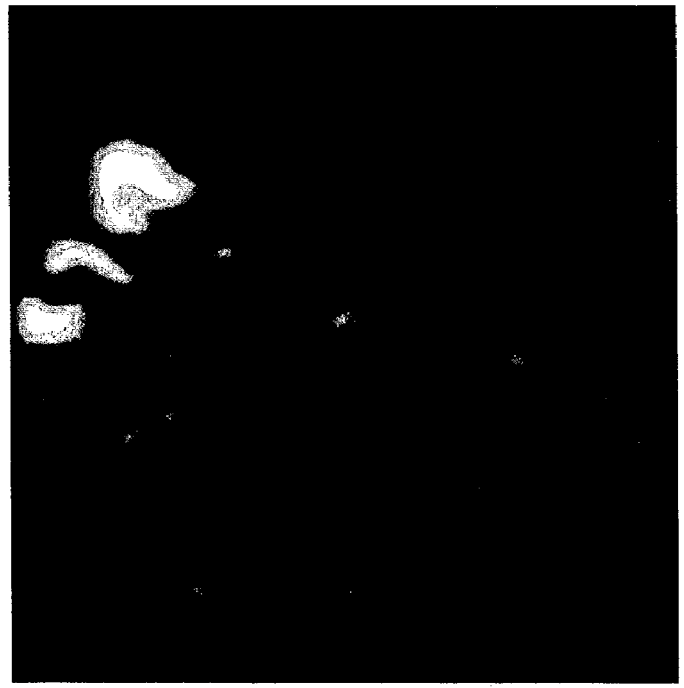
Figure 115A:
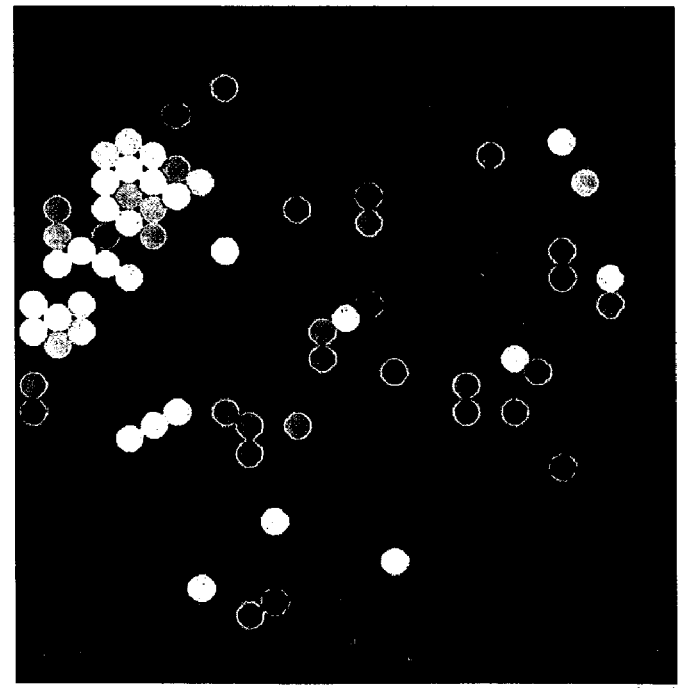

FIG. 115A represents a disease display layer produced in a method of disease probability display for the reference image in FIG. 114A, wherein CIN 2/3 probabilities at interrogation points are represented by circles with intensities scaled by CIN 2/3 probability, according to one embodiment of the invention.

FIG. 115B represents the disease display layer of FIG. 114B following filtering using a Hamming filter, according to one embodiment of the invention.

Figure 116:
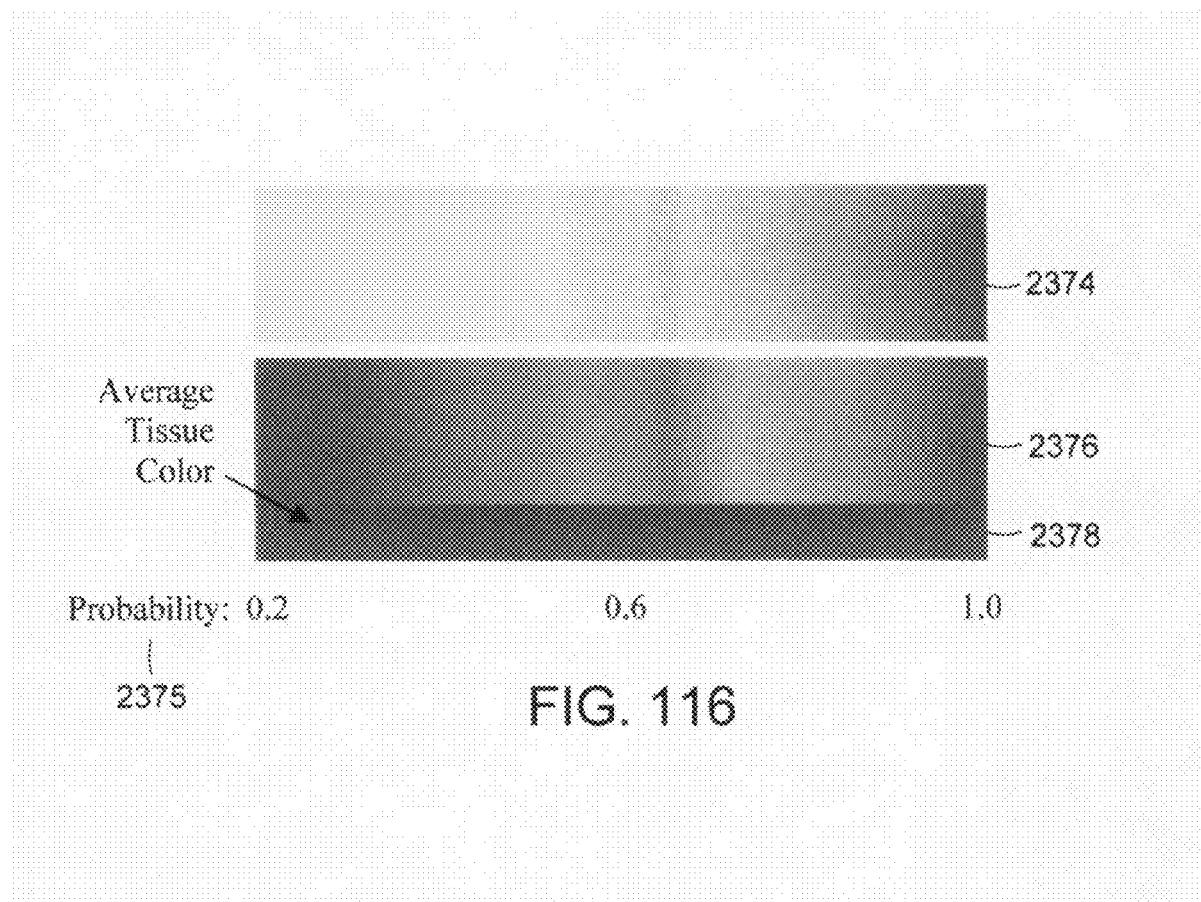

FIG. 116 represents the color transformation used to determine the disease display layer image in a disease probability display method, according to one embodiment of the invention.

Figure 117B:
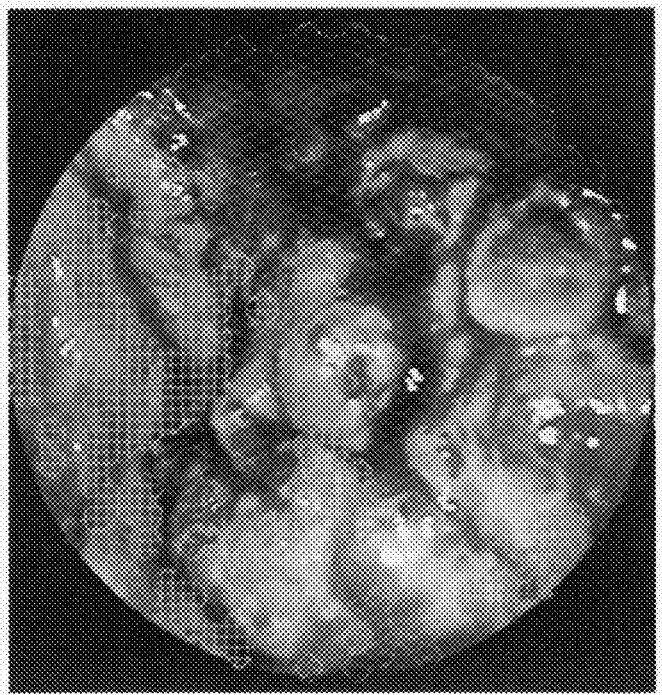
Figure 117A:

FIG. 117A depicts an exemplary reference image of cervical tissue having necrotic regions, obtained during a patient examination and used as a reference (base) image in a method of disease probability display, according to one embodiment of the invention.

FIG. 117B depicts the output overlay image corresponding to the reference image in FIG. 117A, including necrotic regions, indeterminate regions, and CIN 2/3 regions, and produced using a method of disease probability display according to one embodiment of the invention.

DESCRIPTION OF THE ILLUSTRATIVE EMBODIMENT

Table of Contents

System overview
Instrument
Spectral calibration
Patient scan procedure
Video calibration and focusing
Determining optimal data acquisition window
Motion tracking
Broadband reflectance arbitration and low-signal masking
Classification system overview
Spectral masking
Image masking
   $Glare_{vid}$
   $[ROI]_{vid}$
   $[ST]_{vid}$
   $Os_{vid}$
   $Blood_{vid}$
   $Mucus_{vid}$
   $[SP]_{vid}$
   $[VW]_{vid}$
   $[FL]_{vid}$
Classifiers
Combining spectral and image data
Image enhancement
Diagnostic display The Table of Contents above is provided as a general organizational guide to the Description of the Illustrative Embodiment. Entries in the Table do not serve to limit support for any given element of the invention to a particular section of the Description.

System 100 Overview

The invention provides systems and methods for obtaining spectral data and image data from a tissue sample, for processing the data, and for using the data to diagnose the tissue sample. As used herein, "spectral data" from a tissue sample includes data corresponding to any wavelength of the electromagnetic spectrum, not just the visible spectrum. Where exact wavelengths are specified, alternate embodiments comprise using wavelengths within a ±5 nm range of the given value, within a ±10 nm range of the given value, and within a ±25 nm range of the given value. As used herein, "image data" from a tissue sample includes data from a visual representation, such as a photo, a video frame, streaming video, and/or an electronic, digital or mathematical analogue of a photo, video frame, or streaming video. As used herein, a "tissue sample" may comprise, for example, animal tissue, human tissue, living tissue, and/or dead tissue. A tissue sample may be in vivo, in situ, ex vivo, or ex situ, for example. A tissue sample may comprise material in the vacinity of tissue, such as non-biological materials including dressings, chemical agents, and/or medical instruments, for example.

Embodiments of the invention include obtaining data from a tissue sample, determining which data are of diagnostic value, processing the useful data to obtain a prediction of disease state, and displaying the results in a meaningful way. In one embodiment, spectral data and image data are obtained from a tissue sample and are used to create a diagnostic map of the tissue sample showing regions in which there is a high probability of disease.

The systems and methods of the invention can be used to perform an examination of in situ tissue without the need for excision or biopsy. In an illustrative embodiment, the systems and methods are used to perform in-situ examination of the cervical tissue of a patient in a non-surgical setting, such as in a doctor's office or examination room. The examination may be preceded or accompanied by a routine pap smear and/or colposcopic examination, and may be followed-up by treatment or biopsy of suspect tissue regions.

Figure 1:
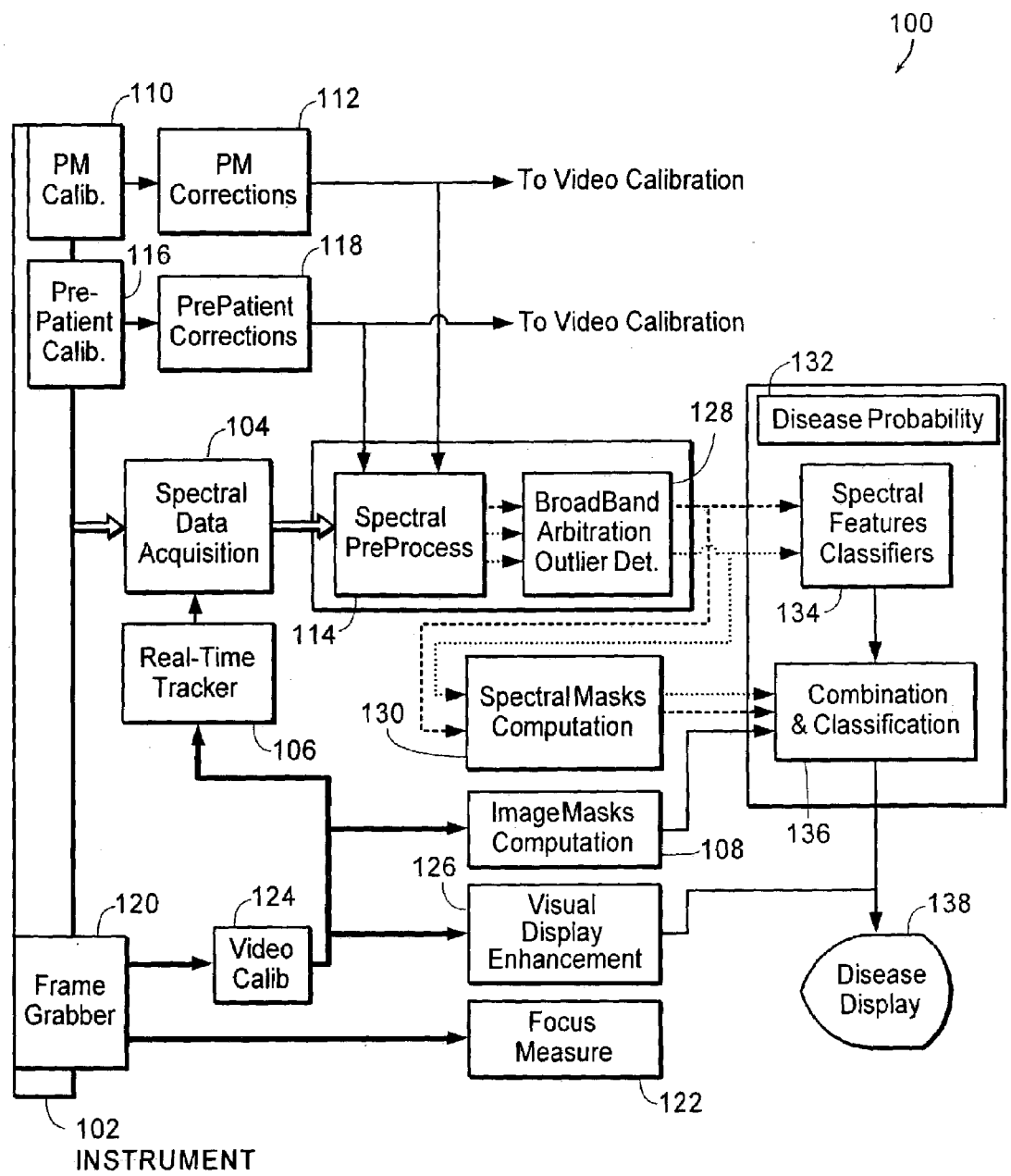
FIG. 1 is a block diagram featuring components of a tissue characterization system according to an illustrative embodiment of the invention.

FIG. 1 depicts a block diagram featuring components of a tissue characterization system 100 according to an illustrative embodiment of the invention. Each component of the system 100 is discussed in more detail herein. The system includes components for acquiring data, processing data, calculating disease probabilities, and displaying results.

In the illustrative system 100 of FIG. 1, an instrument 102 obtains spectral data and image data from a tissue sample. The instrument 102 obtains spectral data from each of a plurality of regions of the sample during a spectroscopic scan of the tissue 104. During a scan, video images of the tissue are also obtained by the instrument 102. Illustratively, one or more complete spectroscopic spectra are obtained for each of 500 discrete regions of a tissue sample during a scan lasting about 12 seconds. However, in other illustrative embodiments any number of discrete regions may be scanned and the duration of each scan may vary. Since in-situ tissue may shift due to involuntary or voluntary patient movement during a scan, video images are used to detect shifts of the tissue, and to account for the shifts in the diagnostic analysis of the tissue. Preferably, a detected shift is compensated for in real time 106. For example, as described below in further detail, one or more components of the instrument 102 may be automatically adjusted during the examination of a patient while spectral data are obtained in order to compensate for a detected shift caused by patient movement. Additionally or alternatively, the real-time tracker 106 provides a correction for patient movement that is used to process the spectral data before calculating disease probabilities. In addition to using image data to track movement, the illustrative system 100 of FIG. 1 uses image data to identify regions that are obstructed or are outside the areas of interest of a tissue sample 108. This feature of the system 100 of FIG. 1 is discussed herein in more detail.

The system 100 shown in FIG. 1 includes components for performing factory tests and periodic preventive maintenance procedures 110, the results of which 112 are used to preprocess patient spectral data 114. In addition, reference spectral calibration data are obtained 116 in an examination setting prior to each patient examination, and the results 118 of the pre-patient calibration are used along with the factory and preventive maintenance results 112 to preprocess patient spectral data 114.

The instrument 102 of FIG. 1 includes a frame grabber 120 for obtaining a video image of the tissue sample. A focusing method 122 is applied and video calibration is performed 124. The corrected video data may then be used to compensate for patient movement during the spectroscopic data acquisition 104. The corrected video data is also used in image masking 108, which includes identifying obstructed regions of the tissue sample, as well as regions of tissue that lie outside an area of diagnostic interest. In one illustrative embodiment, during a patient scan, a single image is used to compute image masks 108 and to determine a brightness and contrast correction 126 for displaying diagnostic results. In illustrative alternative embodiments, more than one image is used to create image masks and/or to determine a visual display correction.

In the system of FIG. 1, spectral data are acquired 104 within a predetermined period of time following the application of a contrast agent, such as acetic acid, to the tissue sample. According to the illustrative embodiment, four raw spectra are obtained for each of approximately 500 regions of the tissue sample and are processed. A fluorescence spectrum, two broadband reflectance (backscatter) spectra, and a reference spectrum are obtained at each of the regions over a range from about 360 nm to about 720 nm wavelength. The period of time within which a scan is acquired is chosen so that the accuracy of the resulting diagnosis is maximized. In one illustrative embodiment, a spectral data scan of a cervical tissue sample is performed over an approximately 12-second period of time within a range between about 30 seconds and about 130 seconds following application of acetic acid to the tissue sample.

The illustrative system 100 includes data processing components for identifying data that are potentially non-representative of the tissue sample. Preferably, potentially non-representative data are either hard-masked or soft-masked. Hard-masking of data includes eliminating the identified, potentially non-representative data from further consideration. This results in an indeterminate diagnosis in the corresponding region. Hard masks are determined in components 128, 130, and 108 of the system 100. Soft masking includes applying a weighting function or weighting factor to the identified, potentially non-representative data. The weighting is taken into account during calculation of disease probability 132, and may or may not result in an indeterminate diagnosis in the corresponding region. Soft masks are determined in component 130 of the system 100.

Soft masking provides a means of weighting spectral data according to the likelihood that the data is representative of clear, unobstructed tissue in a region of interest. For example, if the system 100 determines there is a possibility that one kind of data from a given region is affected by an obstruction, such as blood or mucus, that data is "penalized" by attributing a reduced weighting to that data during calculation of disease probability 132. Another kind of data from the same region that is determined by the system 100 not to be affected by the obstruction is more heavily weighted in the diagnostic step than the possibly-affected data, since the unaffected data is attributed a greater weighting in the calculation of disease probability 132.

In the illustrative system 100, soft masking is performed in addition to arbitration of two or more redundant data sets. Arbitration of data sets is performed in component 128. In the illustrative embodiment, this type of arbitration employs the following steps: obtaining two sets of broadband reflectance (backscatter) data from each region of the tissue sample using light incident to the region at two different angles; determining if one of the data sets is affected by an artifact such as shadow, glare, or obstruction; eliminating one of the redundant reflectance data sets so affected; and using the other data set in the diagnosis of the tissue at the region. If both of the data sets are unaffected by an artifact, a mean of the two sets is used.

According to the illustrative embodiment, the instrument 102 obtains both video images and spectral data from a tissue sample. The spectral data may include fluorescence data and broadband reflectance (backscatter) data. The raw spectral data are processed and then used in a diagnostic algorithm to determine disease probability for regions of the tissue sample. According to the illustrative embodiment, both image data and spectral data are used to mask data that is potentially non-representative of unobstructed regions of interest of the tissue. In another illustrative embodiment, both the image data and the spectral data are alternatively or additionally used in the diagnostic algorithm.

The system 100 also includes a component 132 for determining a disease probability at each of a plurality of the approximately 500 interrogation points using spectral data processed in the components 128 and 130 and using the image masks determined in component 108. Illustratively, the disease probability component 132 processes spectral data with statistical and/or heuristics-based (non-statistically-derived) spectral classifiers 134, incorporates image and/or spectral mask information 136, and assigns a probability of high grade disease, such as CIN 2+, to each examined region of the tissue sample. The classifiers use stored, accumulated training data from samples of known disease state. The disease display component 138 graphically presents regions of the tissue sample having the highest probability of high grade disease by employing a color map overlay of the cervical tissue sample. The disease display component 138 also displays regions of the tissue that are necrotic and/or regions at which a disease probability could not be determined.

Each of the components of the illustrative system 100 is described in more detail below.

Instrument—102

FIG. 2 is a schematic representation of components of the instrument 102 used in the tissue characterization system 100 of FIG. 1 to obtain spectral data and image data from a tissue sample according to an illustrative embodiment of the invention. The instrument of FIG. 2 includes a console 140 connected to a probe 142 by way of a cable 144. The cable 144 carries electrical and optical signals between the console 140 and the probe 142. In an alternative embodiment, signals are transmitted between the console 140 and the probe 142 wirelessly, obviating the need for the cable 144. The probe 142 accommodates a disposable component 146 that comes into contact with tissue and may be discarded after one use. The console 140 and the probe 142 are mechanically connected by an articulating arm 148, which can also support the cable 144. The console 140 contains much of the hardware and the software of the system, and the probe 142 contains the necessary hardware for making suitable spectroscopic observations. The details of the instrument 100 are further explained in conjunction with FIG. 3.

Figure 3:
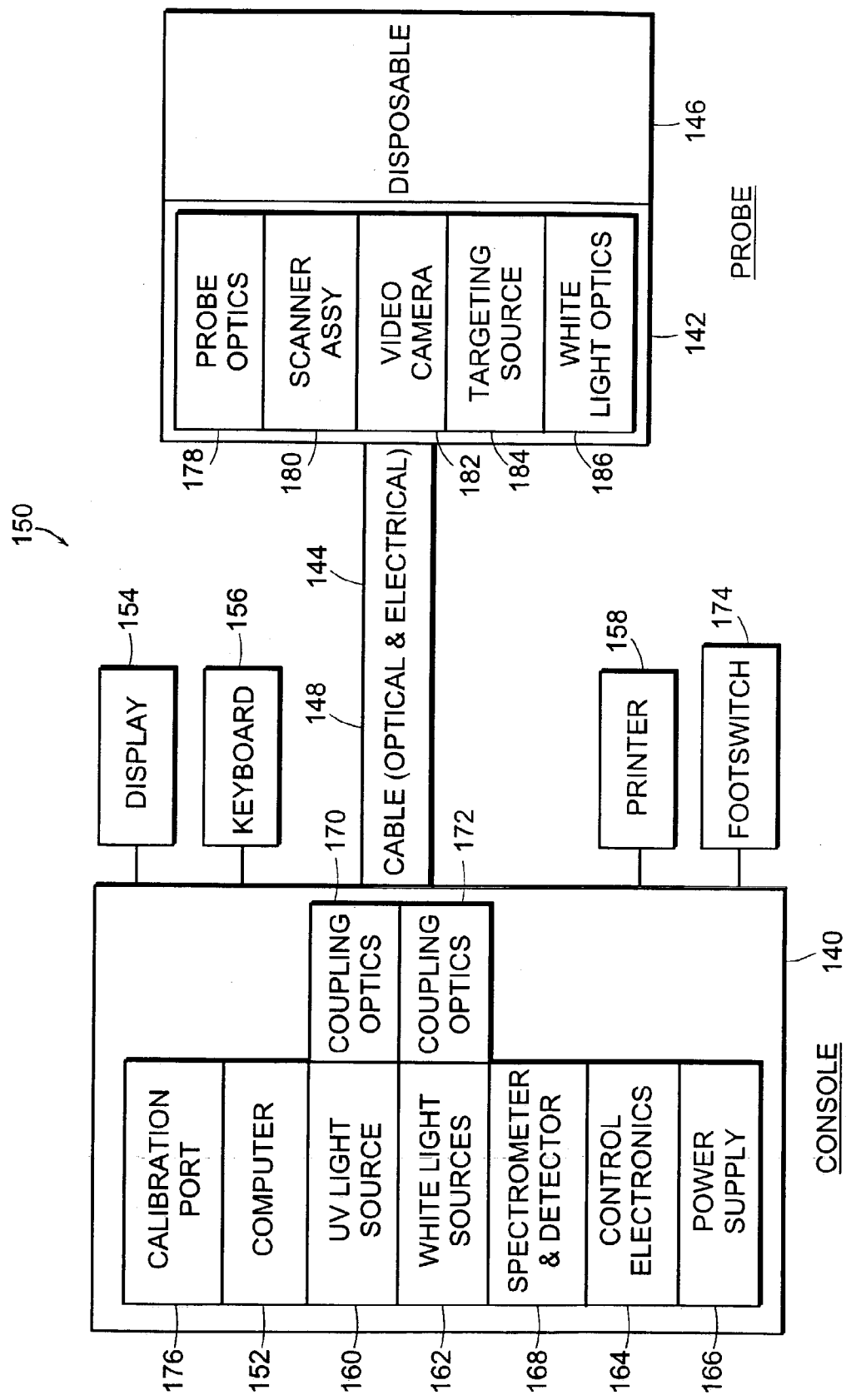
FIG. 3 is a block diagram of the instrument used in the tissue characterization system of FIG. 1 according to an illustrative embodiment of the invention.

FIG. 3 shows an exemplary operational block diagram 150 of an instrument 102 of the type depicted in FIG. 2. Referring to FIGS. 1 and 2, in some illustrative embodiments the instrument 102 includes features of single-beam spectrometer devices, but is adapted to include other features of the invention. In other illustrative embodiments, the instrument 102 is substantially the same as double-beam spectrometer devices, adapted to include other features of the invention. In still other illustrative embodiments the instrument 102 employs other types of spectroscopic devices. In the depicted embodiment, the console 140 includes a computer 152, which executes software that controls the operation of the instrument 102. The software includes one or more modules recorded on machine-readable media such as magnetic disks, magnetic tape, CD-ROM, and semiconductor memory, for example. Preferably, the machine-readable medium is resident within the computer 152. In alternative embodiments, the machine-readable medium can be connected to the computer 152 by a communication link. However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like.

The computer 152 of the instrument 102 is preferably a general purpose computer. The computer 152 can be, for example, an embedded computer, a personal computer such as a laptop or desktop computer, or another type of computer, that is capable of running the software, issuing suitable control commands, and recording information in real-time. The illustrative computer 152 includes a display 154 for reporting information to an operator of the instrument 102, a keyboard 156 for enabling the operator to enter information and commands, and a printer 158 for providing a print-out, or permanent record, of measurements made by the instrument 102 and for printing diagnostic results, for example, for inclusion in the chart of a patient. According to the illustrative embodiment of the invention, some commands entered at the keyboard 156 enable a user to perform certain data processing tasks, such as selecting a particular spectrum for analysis, rejecting a spectrum, and/or selecting particular segments of a spectrum for normalization. Other commands enable a user to select the wavelength range for each particular segment and/or to specify both wavelength contiguous and non-contiguous segments. In one illustrative embodiment, data acquisition and data processing are automated and require little or no user input after initializing a scan.

The illustrative console 140 also includes an ultraviolet (UV) source 160 such as a nitrogen laser or a frequency-tripled Nd:YAG laser, one or more white light sources 162 such as one, two, three, four, or more Xenon flash lamps, and control electronics 164 for controlling the light sources both as to intensity and as to the time of onset of operation and the duration of operation. One or more power supplies 166 are included in the illustrative console 140 to provide regulated power for the operation of all of the components of the instrument 102. The illustrative console 140 of FIG. 3 also includes at least one spectrometer and at least one detector (spectrometer and detector 168) suitable for use with each of the light sources. In some illustrative embodiments, a single spectrometer operates with both the UV light source 160 and the white light source(s) 162. The same detector may record both UV and white light signals. However, in other illustrative embodiments, different detectors are used for each light source.

The illustrative console 140 further includes coupling optics 170 to couple the UV illumination from the UV light source 160 to one or more optical fibers in the cable 144 for transmission to the probe 142, and coupling optics 172 for coupling the white light illumination from the white light source(s) 162 to one or more optical fibers in the cable 144 for transmission to the probe 142. The spectral response of a specimen to UV illumination from the UV light source 160 observed by the probe 142 is carried by one or more optical fibers in the cable 144 for transmission to the spectrometer and detector 168 in the console 140. The spectral response of a specimen to the white light illumination from the white light source(s) 162 observed by the probe 142 is carried by one or more optical fibers in the cable 144 for transmission to the spectrometer and detector 168 in the console 140. As shown in FIG. 3, the console 140 includes a footswitch 174 to enable an operator of the instrument 102 to signal when it is appropriate to commence a spectral scan by stepping on the switch. In this manner, the operator has his or her hands free to perform other tasks, for example, aligning the probe 142.

The console 140 additionally includes a calibration port 176 into which a calibration target may be placed for calibrating the optical components of the instrument 102. Illustratively, an operator places the probe 142 in registry with the calibration port 176 and issues a command that starts the calibration operation. In illustrative calibration operation, a calibrated light source provides a calibration signal in the form of an illumination of known intensity over a range of wavelengths, and/or at a number of discrete wavelengths. The probe 142 detects the calibration signal, and transmits the detected signal through the optical fiber in the cable 144 to the spectrometer and detector 168. A test spectral result is obtained. A calibration of the spectral system can be computed as the ratio of the amplitude of the known illumination at a particular wavelength divided by the test spectral result at the same wavelength. Calibration may include factory calibration 110, preventive maintenance calibration 110, and/or pre-patient calibration 116, as shown in the system 100 of FIG. 1. Pre-patient calibration 116 may be performed to account for patient-to-patient variation, for example.

Figure 4:
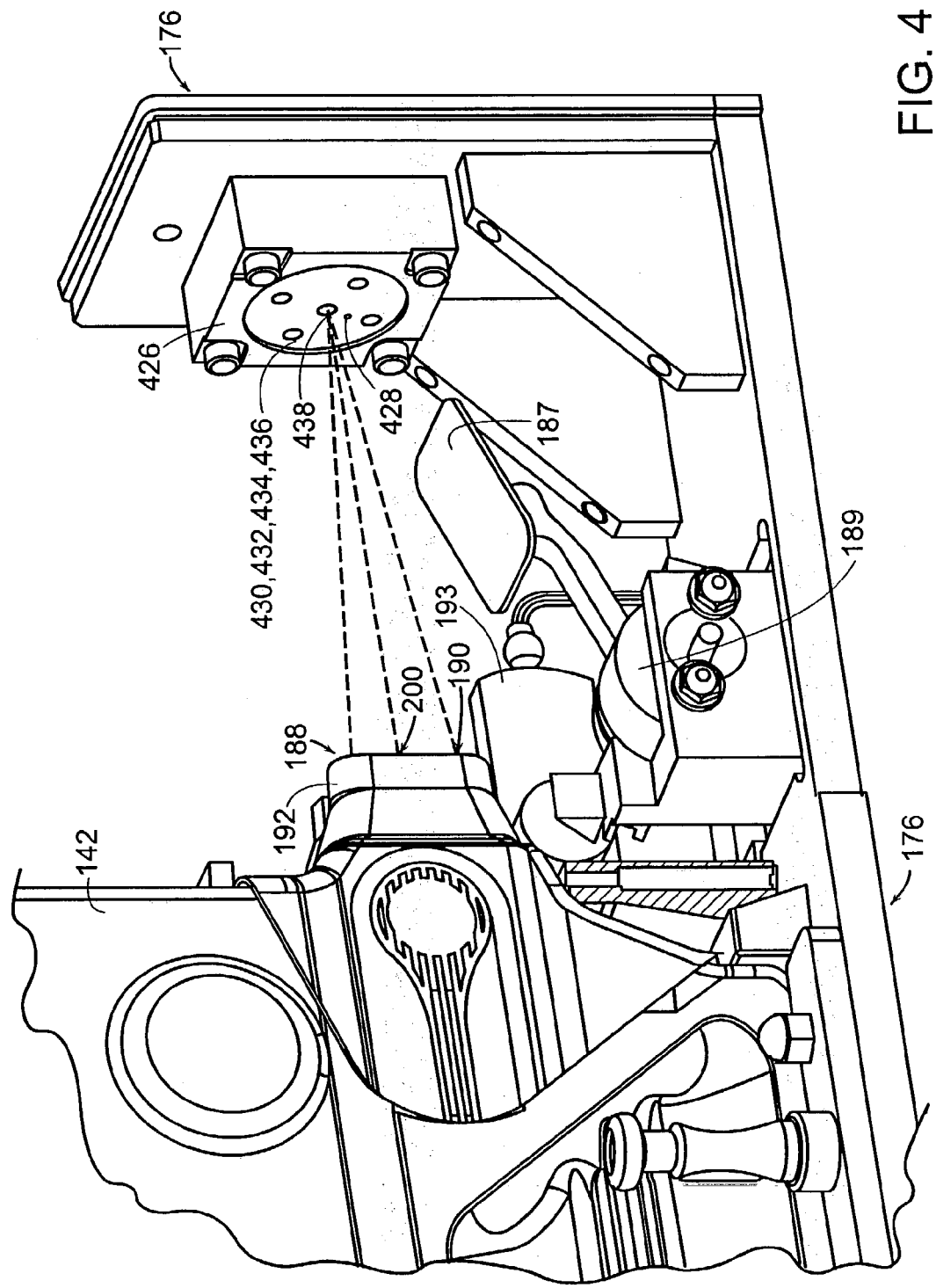
FIG. 4 depicts a probe within a calibration port according to an illustrative embodiment of the invention.

FIG. 4 depicts the illustrative probe 142 of FIG. 2 resting within a calibration port 176 according to an illustrative embodiment of the invention. Referring to FIGS. 2-4, the illustrative calibration port 176 is adjustably attached to the probe 142 or the console 140 to allow an operator to perform pre-patient calibration without assembling detachable parts. The pre-patient calibration port may contain one or more pre-positioned calibration targets, such as a customized target 426 (see also FIG. 19) and a null target 187, both described in more detail below.

According to the illustrative embodiment, factory and/or preventive maintenance calibration includes using a portable, detachable calibration port to calibrate any number of individual units, allowing for a standardized calibration procedure among various instruments. Preferably, the calibration port 176 is designed to prevent stray room light or other external light from affecting a calibration measurement when a calibration target is in place in the calibration port 176. For example, as shown in FIG. 4, the null target 187 can be positioned up against the probe head 192 by way of an actuator 189 such that the effect of external stray light is minimized. When not in use, the null target 187 is positioned out of the path of light between the customized target 426 and the collection optics 200, as depicted in FIG. 4. An additional fitting may be placed over the probe head 192 to further reduce the effect of external stray light. According to one illustrative embodiment, the target 187 in the calibration port 176 is located approximately 100 mm from the probe head 192; and the distance light travels from the target 187 to the first optical component of the probe 142 is approximately 130 mm. The location of the target (in relation to the probe head 192) during calibration may approximate the location of tissue during a patient scan.

The illustrative probe 142 includes probe optics 178 for illuminating a specimen to be analyzed with UV light from the UV source 160 and for collecting the fluorescent and broadband reflectance (backscatter) illumination from the specimen being analyzed. The illustrative probe 142 of FIGS. 2 and 3 includes a scanner assembly 180 that provides illumination from the UV source 160, for example, in a raster pattern over a target area of the specimen of cervical tissue to be analyzed. The probe 142 also includes a video camera 182 for observing and recording visual images of the specimen under analysis. The probe 142 also includes a targeting source 184 for determining where on the surface of the specimen to be analyzed the probe 142 is pointing. The probe 142 also includes white light optics 186 to deliver white light from the white light source(s) 162 for recording the reflectance data and to assist the operator in visualizing the specimen to be analyzed. Once the operator aligns the instrument 102 and depresses the footswitch 174, the computer 152 controls the actions of the light sources 160, 162, the coupling optics 170, 172, the transmission of light signals and electrical signals through the cable 144, the operation of the probe optics 178 and the scanner assembly 180, the retrieval of observed spectra, the coupling of the observed spectra into the spectrometer and detector 168 via the cable 144, the operation of the spectrometer and detector 168, and the subsequent signal processing and analysis of the recorded spectra.

FIG. 4 depicts the probe 142 having top and bottom illumination sources 188, 190 according to an illustrative embodiment of the invention. In this embodiment, the illumination sources 188, 190 are situated at an upper and a lower location about the perimeter of a probe head 192 such that there is illuminating light incident to a target area at each of two different angles. In one embodiment, the target area is a tissue sample. The probe head 192 contains probe optics 178 for illuminating regions of tissue and for collecting illumination reflected or otherwise emitted from regions of tissue. Illustratively, the probe optics for collecting the illumination 200 are located between the top and bottom illumination sources 188, 190. In other illustrative embodiments, other arrangements of the illuminating and collecting probe optics 178 are used that allow the illumination of a given region of tissue with light incident to the region at more than one angle. One such arrangement includes the collecting optics 200 positioned around the illuminating optics.

In one illustrative embodiment, the top and bottom illumination sources 188, 190 are alternately turned on and off in order to sequentially illuminate the tissue at equal and opposite angles relative to the collection axis. For example, the top illumination source 188 is turned on while the bottom illumination source 190 is turned off, such that spectral measurements may be obtained for light reflected from a region of the tissue sample 194 illuminated with light incident to the region at a first angle. This angle is relative to the surface of the tissue sample at a point on the region, for example. Then, the top illumination source 188 is turned off while the bottom illumination source 190 is turned on, such that spectral measurements may be obtained using light incident to the region at a second angle. If data obtained using one of the illumination sources is adversely affected by an artifact, such as glare or shadow, then data obtained using another illumination source, with light incident to the region at a different angle, may be unaffected by the artifact and may still be useful. The spectral measurements can include reflectance and/or fluorescence data obtained over a range of wavelengths.

According to the various illustrative embodiments, the top and the bottom illumination sources 188, 190 may be alternately cycled on and off more than once while obtaining data for a given region. Also, cycles of the illumination sources 188, 190 may overlap, such that more than one illumination source is on at one time for at least part of the illumination collection procedure. Other illumination alternation schemes are possible, depending at least in part on the arrangement of illumination sources 188, 190 in relation to the probe head 192.

After data are obtained from one region of the tissue using light incident to the region at more than one angle, data may likewise be obtained from another region of the tissue. In the illustrative embodiment of FIG. 4, the scanner assembly 180 illuminates a target area of the tissue sample region-by-region. Illustratively, a first region is illuminated using light incident to the region at more than one angle as described above, then the probe optics 178 are automatically adjusted to repeat the illumination sequence at a different region within the target area of the tissue sample. The illustrative process is repeated until a desired subset of the target area has been scanned. As mentioned above, preferably about five hundred regions are scanned within a target area having a diameter of about 25-mm. Using the instrument 102, the scan of the aforementioned five hundred regions takes about 12 seconds. In other illustrative embodiments, the number of regions scanned, the size of the target area, and/or the duration of the scan vary from the above.

Figure 5:
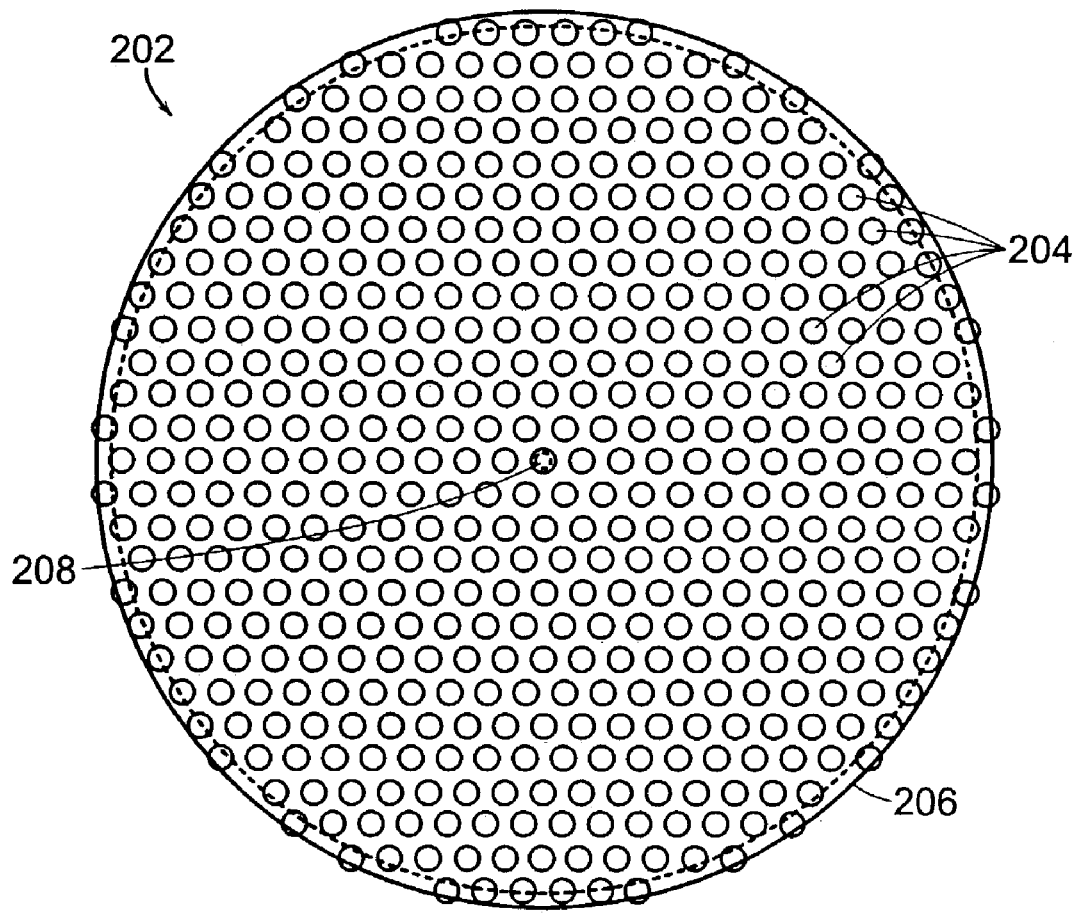
FIG. 5 depicts an exemplary scan pattern used by the instrument of FIG. 1 to obtain spatially-correlated spectral data and image data from a tissue sample according to an illustrative embodiment of the invention.

FIG. 5 depicts an exemplary scan pattern 202 used by the instrument 102 to obtain spatially-correlated spectral data and image data from a tissue sample according to an illustrative embodiment of the invention. Illustratively, spectral data are obtained at 499 regions of the tissue sample, plus one region out of the field of view of the cervix obtained, for example, for calibration purposes. The exemplary scan pattern 202 of FIG. 5 includes 499 regions 204 whose centers are inside a circle 206 that measures about 25.8 mm in diameter. The center of each region is about 1.1 mm away from each of the nearest surrounding regions. This may be achieved by offsetting each scan line by about 0.9527 mm in the y-direction and by staggering each scan line in the x-direction by about 0.55 mm. Each of the 499 regions is about 0.7 mm in diameter. In other illustrative embodiments, other geometries are used.

According to the illustrative embodiment, the spectral data acquisition component 104 of the system 100 depicted in FIG. 1 is performed using the scan pattern 202 shown in FIG. 5. A fluorescence spectrum, two broadband reflectance spectra, and a reference spectrum are obtained at each region 204. The two broadband reflectance spectra use light incident to the sample at two different angles. A scan preferably begins at the center region 208, which corresponds to a pixel in a 500×480 pixel video image of the tissue sample at location 250, 240. As discussed in more detail below, a sequence of video images of the tissue sample may be taken during a scan of the 499 regions shown in FIG. 5 and may be used to detect and compensate for movement of the tissue sample during the scan. The real-time tracker component 106 of the system 100 shown in FIG. 1 performs this motion detection and compensation function. Preferably, the scanner assembly 180 of FIG. 3 includes controls for keeping track of the data obtained, detecting a stalled scan process, aborting the scan if the tissue is exposed to temperature or light outside of acceptable ranges, and/or monitoring and reporting errors detected by the spectral data acquisition component 104 of the system of FIG. 1.

Figure 6:
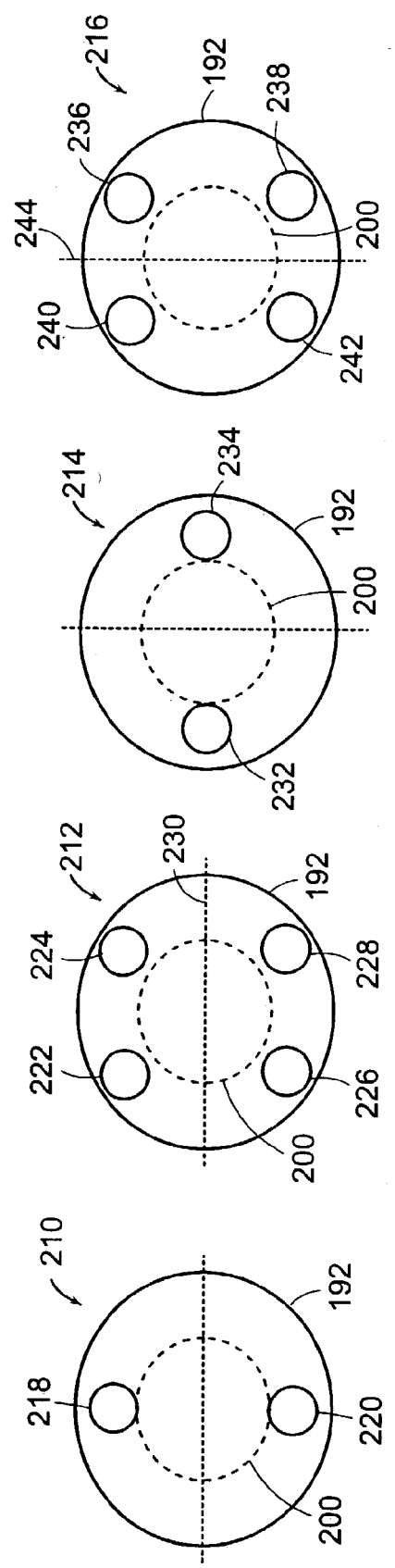
FIG. 6 depicts front views of four exemplary arrangements of illumination sources about a probe head according to various illustrative embodiments of the invention.

FIG. 6 depicts front views of four exemplary arrangements 210, 212, 214, 216 of illumination sources about a probe head 192 according to various illustrative embodiments of the invention. The drawings are not to scale; they serve to illustrate exemplary relative arrangements of illumination sources about the perimeter of a probe head 192. Other arrangements include positioning collecting optics 200 around the perimeter of the probe head 192, about the illumination sources, or in any other suitable location relative to the illumination sources. The first arrangement 210 of FIG. 6 has one top illumination source 218 and one bottom illumination source 220, which are alternately cycled on and off as described above. The illumination sources are arranged about the collecting optics 200, which are located in the center of the probe head 192. Light from an illumination source is reflected from the tissue and captured by the collecting optics 200.

The second arrangement 212 of FIG. 6 is similar to the first arrangement 210, except that there are two illumination sources 222, 224 in the top half of the probe head 192 and two illumination sources 226, 228 in the bottom half of the probe head 192. In one embodiment, the two lights above the midline 230 are turned on and the two lights below the midline 230 are turned off while obtaining a first set of spectral data; then the lights above the midline 230 are turned off and the lights below the midline 230 are turned on while obtaining a second set of spectral data. In an alternate illustrative embodiment, only one of the four illumination sources are turned on at a time to obtain four sets of spectral data for a given region. Other illustrative embodiments include turning the illumination sources on and off in other patterns. Other alternative embodiments include using non-circular or otherwise differently shaped illumination sources, and/or using a different number of illumination sources.

The third arrangement 214 of FIG. 6 includes each illumination source 232, 234 positioned on either side of the probe head 192. The sources 232, 234 may be alternated in a manner analogous to those described for the first arrangement 210.

The fourth arrangement 216 of FIG. 6 is similar to the second arrangement 212, except that the illumination sources 236, 238 on the right side of the probe head 192 are turned off and on together, alternately with the illumination sources 240, 242 on the left side of the probe head 192. Thus, two sets of spectral data may be obtained for a given region, one set using the illumination sources 236, 238 on the right of the midline 244, and the other set using the illumination sources 240, 242 on the left of the midline 244.

Figure 7:
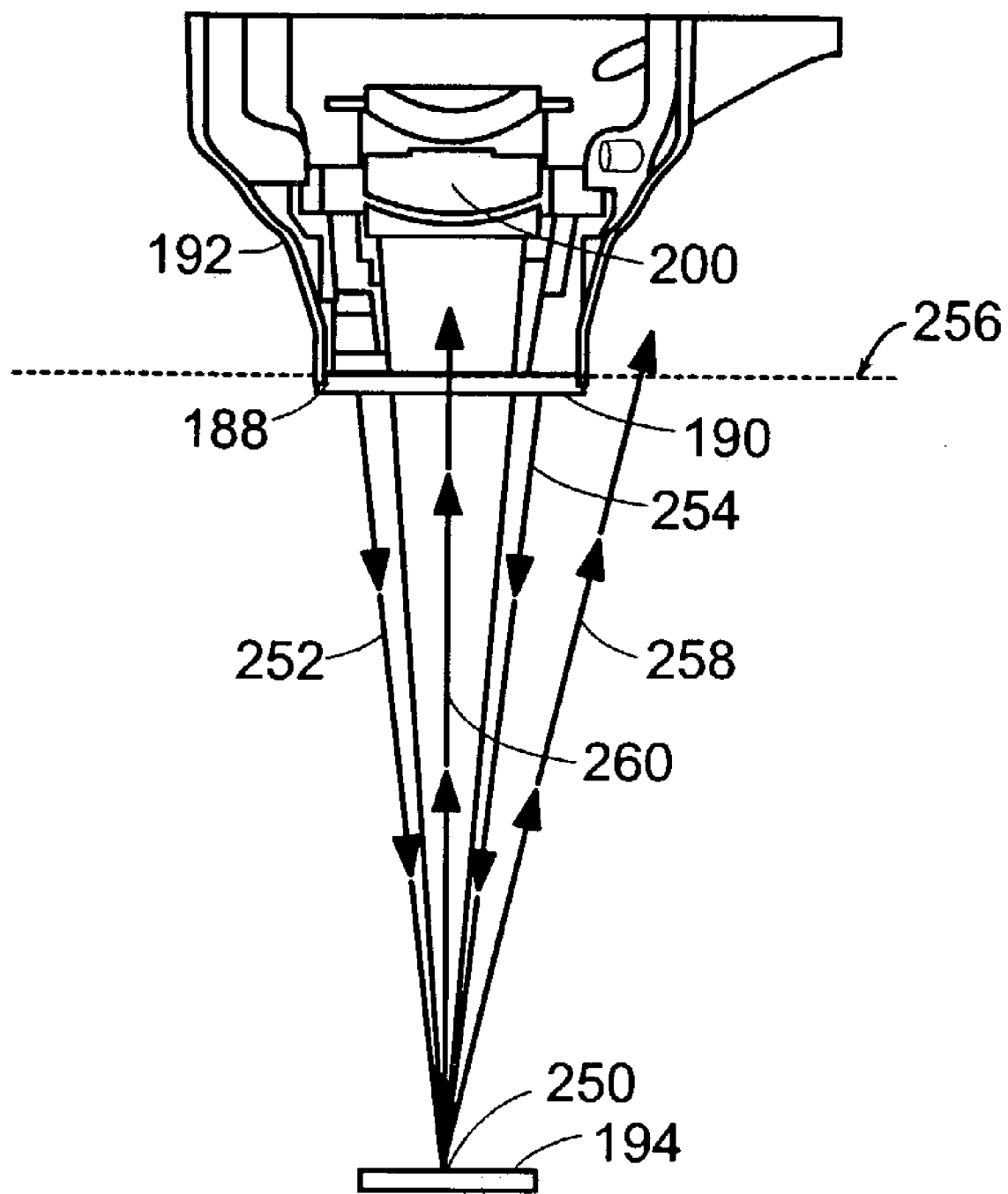
FIG. 7 depicts exemplary illumination of a region of a tissue sample using light incident to the region at two different angles according to an illustrative embodiment of the invention.

FIG. 7 depicts exemplary illumination of a region 250 of a tissue sample 194 using light incident to the region 250 at two different angles 252, 254 according to an illustrative embodiment of the invention. FIG. 7 demonstrates that source light position may affect whether data is affected by glare. The probe head 192 of FIG. 7 is depicted in a cut-away view for illustrative purposes. In this illustrative embodiment, the top illumination source 188 and bottom illumination source 190 are turned on sequentially and illuminate the surface of a tissue sample 194 at equal and opposite angles relative to the collection axis 256. Arrows represent the light emitted 252 from the top illumination source 188, and the light specularly reflected 258 from the surface of the region 250 of the tissue sample 194. In preferred embodiments, it is desired to collect diffusely reflected light, as opposed to specularly reflected light 258 (glare). Since the specularly reflected light 258 from the top illumination source 188 does not enter the collecting optics 200 in the example illustrated in FIG. 7, a set of data obtained using the top illumination source 188 would not be affected by glare.

However, in the example illustrated in FIG. 7, the emitted light 254 from the bottom illumination source 190 reaches the surface of the region 250 of the tissue 194 and is specularly reflected into the collecting optics 200, shown by the arrow 260. Data obtained using the bottom illumination source 190 in the example pictured in FIG. 7 would be affected by glare. This data may not be useful, for example, in determining a characteristic or a condition of the region 250 of the tissue 194. In this example, it would be advantageous to instead use the set of data obtained using the top illumination source 188 since it is not affected by glare.

The position of the collection optics 200 may affect whether or not data is affected by glare. For example, light 252 with illumination intensity $I_o(\lambda)$ strikes a tissue surface at a given region 250. A fraction of the initial illumination intensity, $\alpha I_o(\lambda)$, is specularly reflected from the surface 258, where a is a real number between 0 and 1. An acceptance cone 268 is the space through which light is diffusely reflected from the tissue 194 into the collecting optics 200, in this embodiment. Light may also be emitted or otherwise transmitted from the surface of the tissue. The diffusely reflected light is of interest, since spectral data obtained from diffusely reflected light can be used to determine the condition of the region of the sample. If there is no specular reflection within the acceptance cone 268, only diffusely reflected light is collected, and the collected signal corresponds to $I_r(\lambda)$, where $I_r(\lambda)$ is the intensity of light diffusely reflected from the region 250 on the surface of the tissue.

If the collection optics 200 are off-center, light incident to the tissue surface may specularly reflect within the acceptance cone 268. For example, light with illumination intensity $I_o(\lambda)$ strikes the surface of the tissue. Light with a fraction of the initial illumination intensity, $\alpha I_o(\lambda)$, from a given source is specularly reflected from the surface 266, where $\alpha$ is a real number between 0 and 1. Where there is specular reflection of light within the acceptance cone 268, both diffusely reflected light and specularly reflected light reach the collecting optics 200. Thus, the collected signal corresponds to an intensity represented by the sum $I_r(\lambda)+\alpha I_o(\lambda)$. It may be difficult or impossible to separate the two components of the measured intensity, thus, the data may not be helpful in determining the condition of the region of the tissue sample due to the glare effect.

Figure 8:
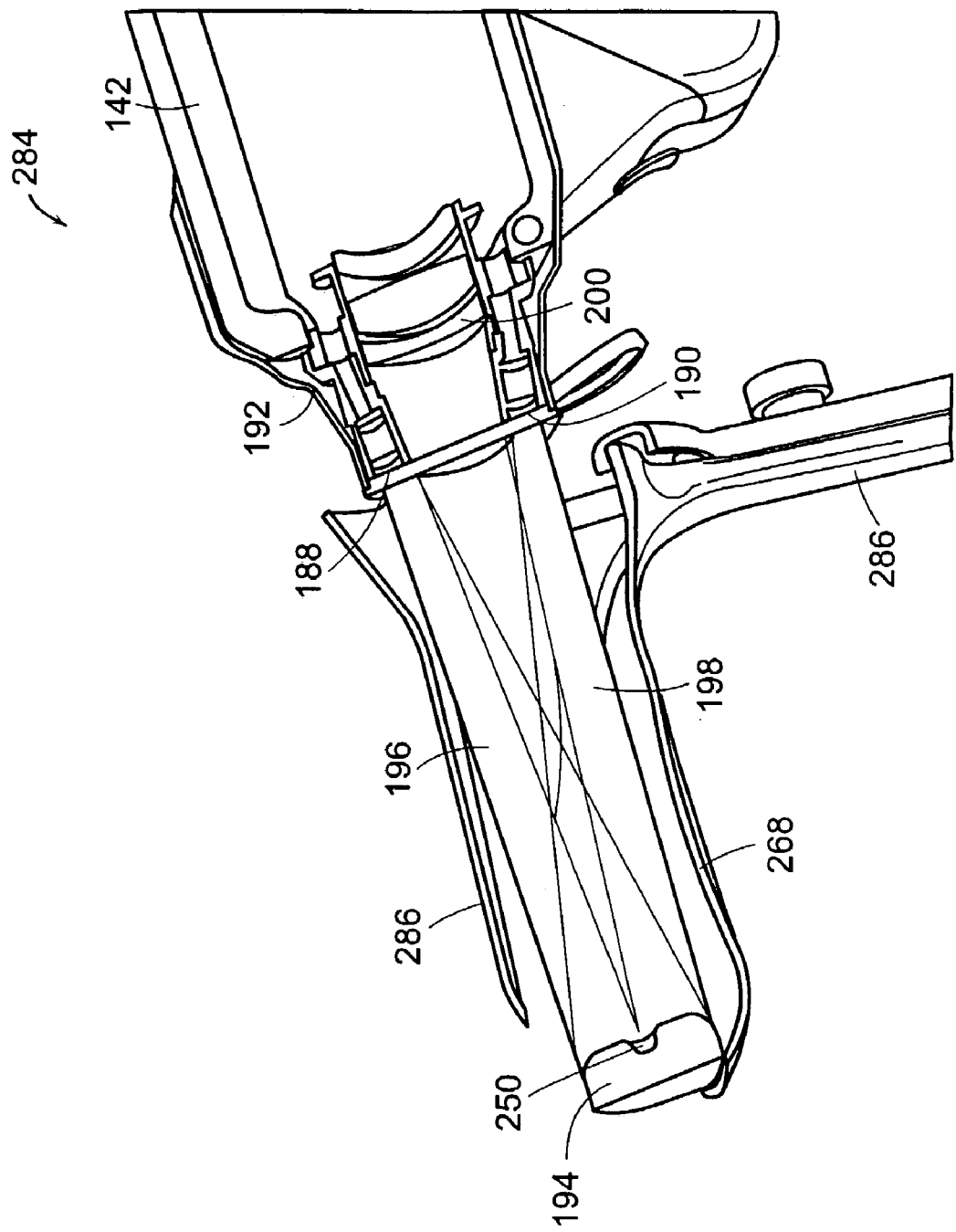
FIG. 8 depicts illumination of a cervical tissue sample using a probe and a speculum according to an illustrative embodiment of the invention.
Figure 9:
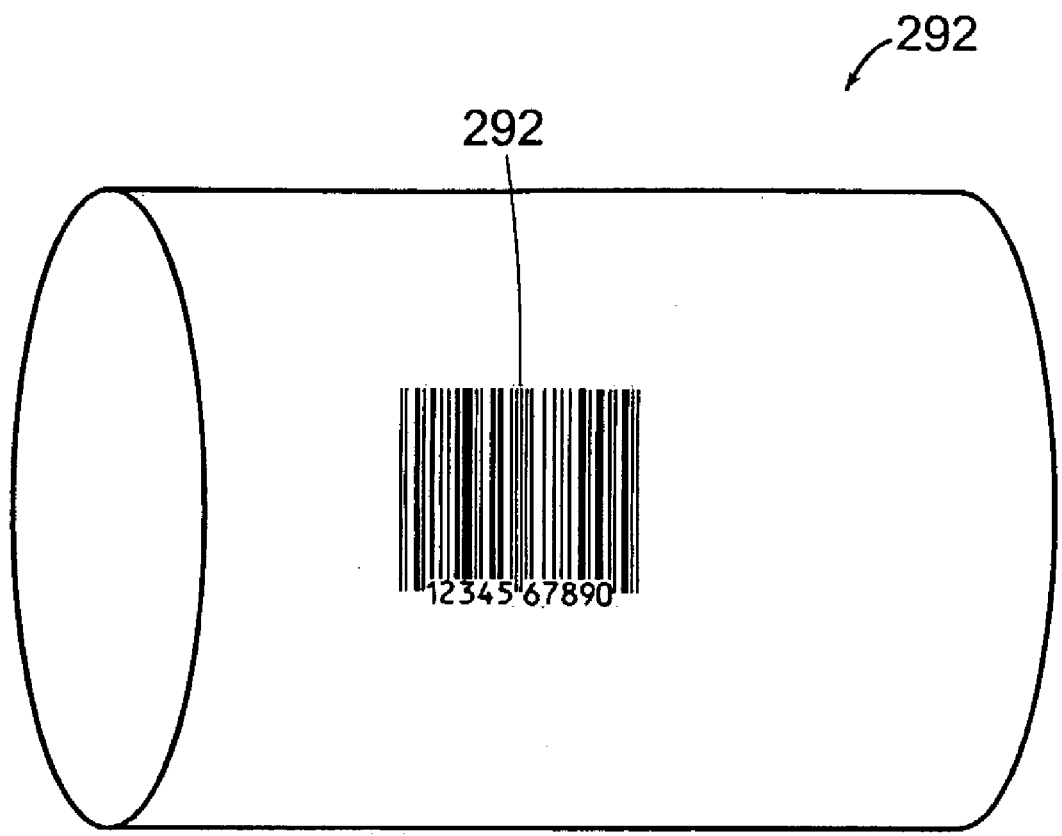
FIG. 9 is a schematic representation of an accessory device for a probe marked with identifying information in the form of a bar code according to an illustrative embodiment of the invention.

FIG. 8 is a diagram 284 depicting illumination of a region 250 of a cervical tissue sample 194 using a probe 142 and a vaginal speculum 286 according to an illustrative embodiment of the invention. Here, the illuminating light incident to the tissue sample 194, is depicted by the upper and lower intersecting cones 196, 198. In a preferred embodiment, the probe 142 operates without physically contacting the tissue being analyzed. In one embodiment, a disposable sheath 146 is used to cover the probe head 192, for example, in case of incidental contact of the probe head 192 with the patient's body. FIG. 9 is a schematic representation of an accessory device 290 that forms at least part of the disposable sheath 146 for a probe head 192 according to an illustrative embodiment of the invention. In one illustrative embodiment, the entire sheath 146, including the accessory device 290, if present, is disposed of after a single use on a patient. As shown in FIG. 8, in one illustrative embodiment, the disposable sheath 146 and/or the accessory device 290 have a unique identifier, such as a two-dimensional bar code 292.

According to an illustrative feature, the accessory device 290 is configured to provide an optimal light path between the optical probe 142 and the target tissue 194. Optional optical elements in the accessory device 290 may be used to enhance the light transmitting and light receiving functions of the probe 142.

Although an illustrative embodiment of the invention is described herein with respect to analysis of vaginal tissue, other tissue types may be analyzed using these methods, including, for example, colorectal, gastroesophageal, urinary bladder, lung, skin tissue, and/or any tissue comprising epithelial cells.

Spectral Calibration—110, 112, 116

Figure 10:
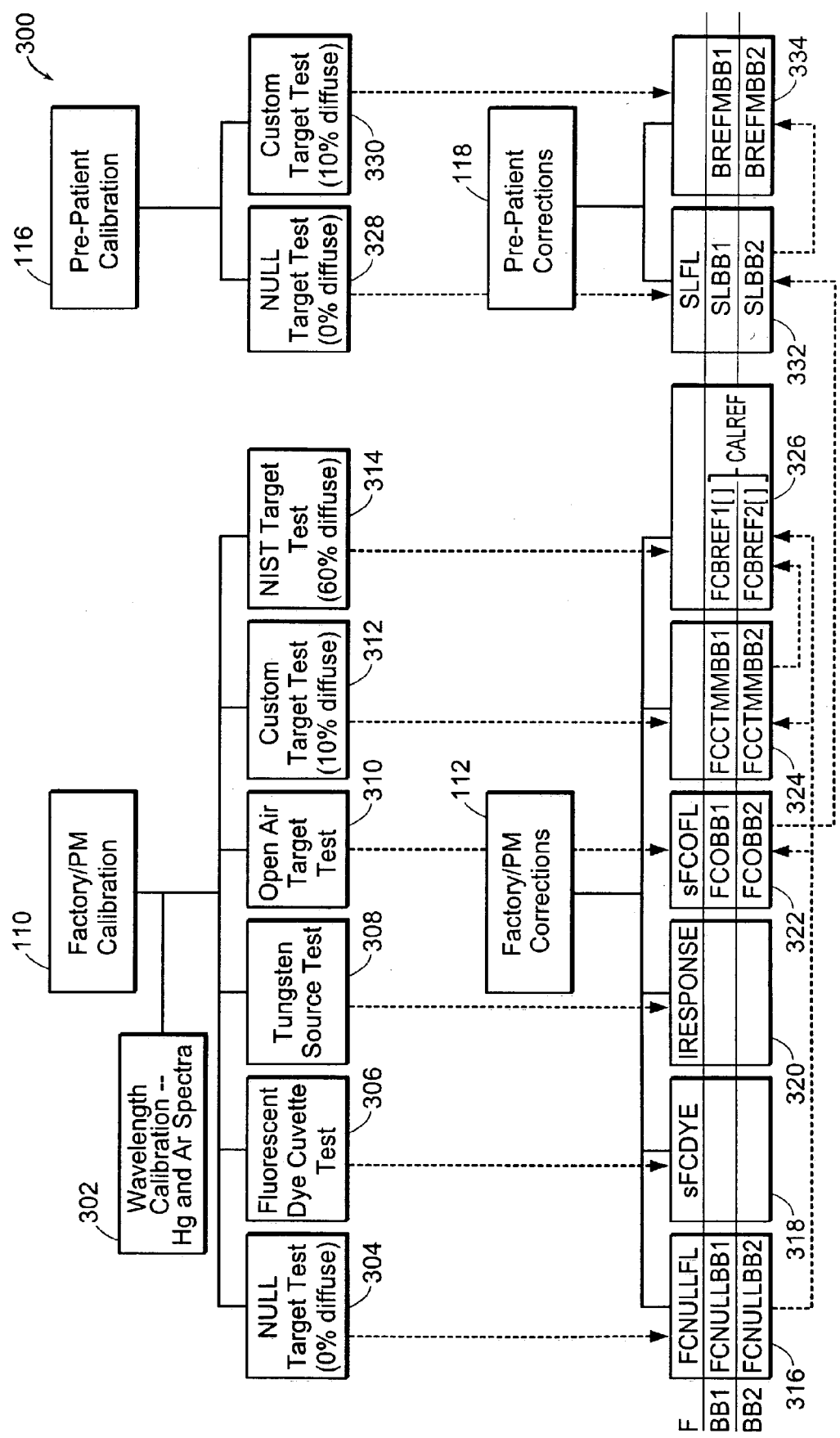
FIG. 10 is a block diagram featuring spectral data calibration and correction components of the tissue characterization system of FIG. 1 according to an illustrative embodiment of the invention.

FIG. 10 is a block diagram 300 featuring components of the tissue characterization system 100 of FIG. 1 that involve spectral data calibration and correction, according to an illustrative embodiment of the invention. The instrument 102 of FIG. 1 is calibrated at the factory, prior to field use, and may also be calibrated at regular intervals via routine preventive maintenance (PM). This is referred to as factory and/or preventive maintenance calibration 110. Additionally, calibration is performed immediately prior to each patient scan to account for temporal and/or intra-patient sources of variability. This is referred to as pre-patient calibration 116. The illustrative embodiment includes calibrating one or more elements of the instrument 102, such as the spectrometer and detector 168 depicted in FIG. 3.

Calibration includes performing tests to adjust individual instrument response and/or to provide corrections accounting for individual instrument variability and/or individual test (temporal) variability. During calibration procedures, data is obtained for the pre-processing of raw spectral data from a patient scan. The tissue classification system 100 of FIG. 1 includes determining corrections based on the factory and/or preventive maintenance calibration tests, indicated by block 112 in FIG. 10 and in FIG. 1. Where multiple sets of factory and/or preventive maintenance (PM) data exists, the most recent set of data is generally used to determine correction factors and to pre-process spectral data from a patient scan. Corrections are also determined based on pre-patient calibration tests, indicated by block 118 of FIG. 10. The correction factors are used, at least indirectly, in the pre-processing (114, FIG. 1) of fluorescence and reflectance spectral data obtained using a UV light source and two white light sources. Block 114 of FIG. 11 corresponds to the preprocessing of spectral data in the overall tissue classification system 100 of FIG. 1, and is further discussed herein.

Calibration accounts for sources of individual instrument variability and individual test variability in the preprocessing of raw spectral data from a patient scan. Sources of instrument and individual test variability include, for example, external light (light originating outside the instrument 102, such as room light) and internal stray light. Internal stray light is due at least in part to internal "cross talk," or interaction between transmitted light and the collection optics 200. Calibration also accounts for the electronic background signal read by the instrument 102 when no light sources, internal or external, are in use. Additionally, calibration accounts for variations in the amount of light energy delivered to a tissue sample during a scan, spatial inhomogeneities of the illumination source(s), chromatic aberration due to the scanning optics, variation in the wavelength response of the collection optics 200, and/or the efficiency of the collection optics 200, for example, as well as other effects.

In the illustrative embodiment of FIG. 10, factory and preventive maintenance calibration tests are performed to determine correction factors 112 to apply to raw fluorescence and reflectance spectral data obtained during patient scans. The factory/preventive maintenance calibration tests 110 include a wavelength calibration test 302, a "null" target test 304, a fluorescent dye cuvette test 306, a tungsten source test 308, an "open air" target test 310, a customized target test 312, and a NIST standard target test 314.

The wavelength calibration test 302 uses mercury and argon spectra to convert a CCD pixel index to wavelengths (nm). A wavelength calibration and interpolation method using data from the mercury and argon calibration test 302 is described below.

The null target test 304 employs a target having about 0% diffuse reflectivity and is used along with other test results to account for internal stray light. Data from the factory/PM null target test 304 are used to determine the three correction factors shown in block 316 for fluorescence spectral measurements (F) obtained using a UV light source, and broadband reflectance measurements (BB1, BB2) obtained using each of two white light sources. In one embodiment, these three correction factors 316 are used in determining correction factors for other tests, including the factory/PM fluorescent dye cuvette test 306, the factory/PM open air target test 310, the factory/PM customized target test 312, and the factory/PM NIST standard target test 314. The open air target test 310, the customized target test 312, and the NIST standard target test 314 are used along with the null target test 304 to correct for internal stray light in spectral measurements obtained using a UV light source and one or more white light sources.

The open air target test 310 is performed without a target and in the absence of external light (all room lights turned off). The customized target test 312 employs a custom-designed target including a material of approximately 10% diffuse reflectivity and is performed in the absence of external light. The custom-designed target also contains phosphorescent and fluorescent plugs that are used during instrument focusing and target focus validation 122. In one embodiment, the custom-designed target is also used during pre-patient calibration testing (116, 330) to monitor the stability of fluorescence readings between preventive maintenance procedures and/or to align an ultraviolet (UV) light source 160—for example, a nitrogen laser or a frequency-tripled Nd:YAG laser. The NIST (U.S. National Institute of Standards and Technology) standard target test 314 employs a NIST-standard target comprising a material of approximately 60% diffuse reflectivity and is performed in the absence of external light. Correction factors determined from the "open air" target test 310, the custom target test 312, and the NIST-standard target test 314 are shown in blocks 322, 324, and 326 of FIG. 10, respectively. The correction factors are discussed in more detail below.

The fluorescent dye cuvette test 306 accounts for the efficiency of the collection optics 200 of a given unit. The illustrative embodiment uses data from the fluorescent dye cuvette test 306 to determine a scalar correction factor 318 for fluorescence measurements (F) obtained using a UV light source. The tungsten source test 308 uses a quartz-tungsten-halogen lamp to account for the wavelength response of the fluorescence collection optics 200, and data from this test are used to determine a correction factor 320 for fluorescence measurements (F) obtained using a UV light source.

In addition to factory and preventive maintenance calibration 110, pre-patient calibration 116 is performed immediately before each patient scan. The pre-patient calibration 116 includes performing a null target test 328 and a customized target test 330 before each patient scan. These tests are similar to the factory/PM null target test 304 and the factory/PM custom target test 312, except that they are each performed under exam room conditions immediately before a patient scan is conducted. The correction factors shown in blocks 332 and 334 of FIG. 10 are determined from the results of the pre-patient calibration tests. Here, correction factors (316, 322) from the factory/PM null target test 304 and the factory/PM open air test 310 are used along with pre-patient calibration data to determine the pre-patient correction factors 118, which are used, in turn, to pre-process raw spectral data from a patient scan, as shown, for example, in FIG. 11.

Figure 11:
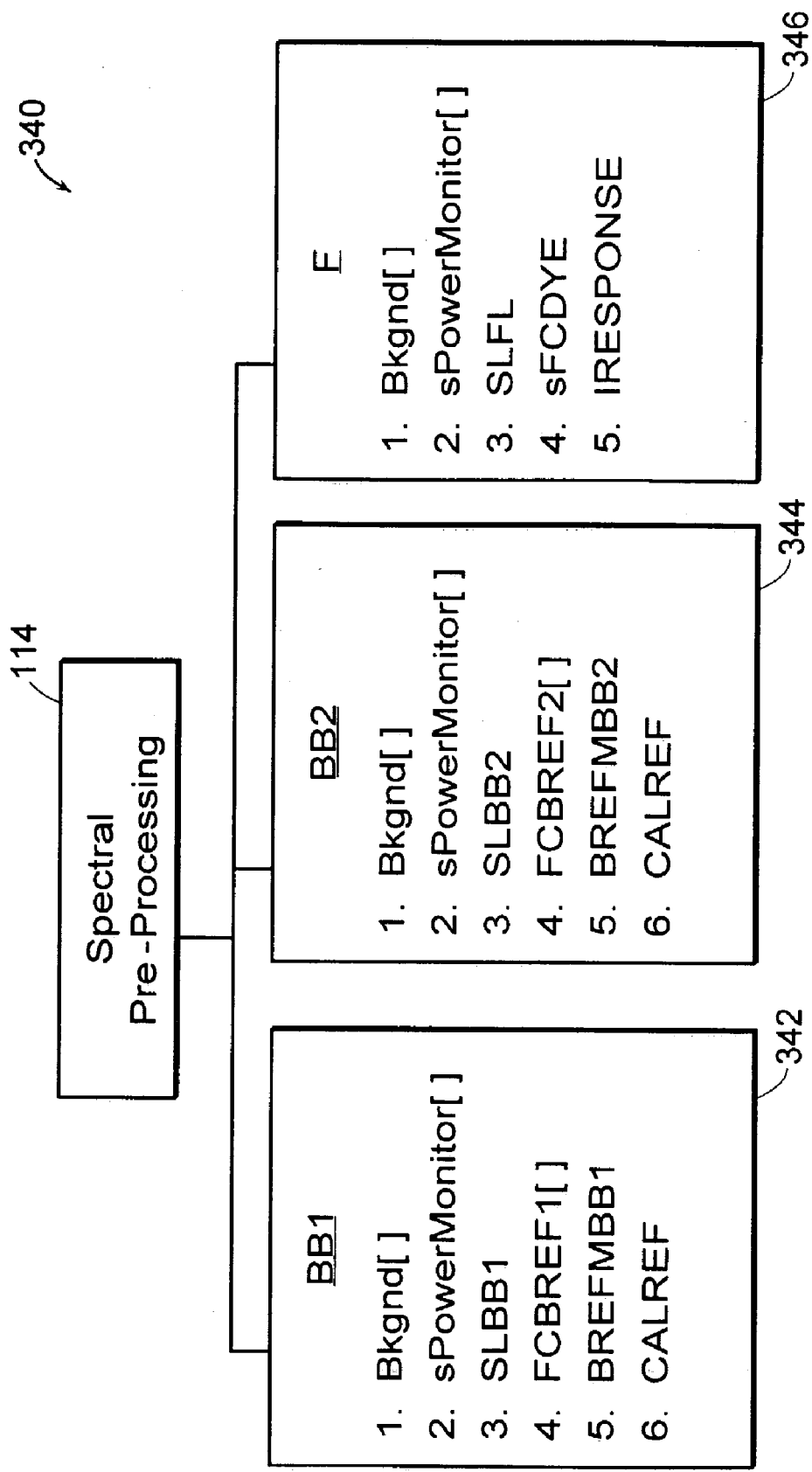
FIG. 11 is a block diagram featuring the spectral data pre-processing component of the tissue characterization system of FIG. 1 according to an illustrative embodiment of the invention.

FIG. 11 is a block diagram 340 featuring the spectral data pre-processing component 114 of the tissue characterization system 100 of FIG. 1 according to an illustrative embodiment of the invention. In FIG. 11, "F" represents the fluorescence data obtained using the UV light source 160, "BB1" represents the broadband reflectance data obtained using the first 188 of the two white light sources 162 and "BB2" represents the broadband reflectance data obtained using the second 190 of the two white light sources 162. Blocks 342 and 344 indicate steps undertaken in pre-processing raw reflectance data obtained from the tissue using each of the two white light sources 188, 190, respectively. Block 346 indicates steps undertaken in pre-processing raw fluorescence data obtained from the tissue using the UV light source 160. These steps are discussed in more detail below.

The instrument 102 detailed in FIG. 3 features a scanner assembly 180 which includes a CCD (charge couple device) detector and spectrograph for collecting fluorescence and reflectance spectra from tissue samples. Because a CCD detector is used, the system employs a calibration procedure to convert a pixel index into wavelength units. Referring to FIG. 10, the pixel-to-wavelength calibration 302 is performed as part of factory and/or preventive maintenance calibration procedures 110.

In the illustrative embodiment, the tissue classification system 100 uses spectral data obtained at wavelengths within a range from about 360 nm to about 720 nm. Thus, the pixel-to-wavelength calibration procedure 302 uses source light that produces peaks near and/or within the 360 nm to 720 nm range. A mercury lamp produces distinct, usable peaks between about 365 nm and about 578 nm, and an argon lamp produces distinct, usable peaks between about 697 nm and about 740 nm. Thus, the illustrative embodiment uses mercury and argon emission spectra to convert a pixel index from a CCD detector into units of wavelength (nm).

First, a low-pressure pen-lamp style mercury lamp is used as source light, and intensity is plotted as a function of pixel index. The pixel indices of the five largest peaks are correlated to ideal, standard Hg peak positions in units of nanometers. Second, a pen-lamp style argon lamp is used as source light and intensity is plotted as a function of pixel index. The two largest peaks are correlated to ideal, standard Ar peak positions in units of nanometers.

The seven total peaks provide a set of representative peaks well-distributed within a range from about 365 nm to about 738 nm—comparable to the range from about 360 nm to about 720 nm that is used for data analysis in the tissue classification system 100. The calibration procedure in block 302 of FIG. 10 includes retrieving the following spectra: a spectrum using a mercury lamp as light source, a mercury background spectrum (a spectrum obtained with the mercury source light turned off), a spectrum using an argon lamp as light source, and an argon background spectrum. The respective Hg and Ar background spectra are subtracted from the Hg and Ar spectra, producing the background-corrected Hg and Ar spectra. The spectra are essentially noise-free and require no smoothing. Each of the seven pixel values corresponding to the seven peaks above are determined by finding the centroid of the curve of each peak over a +/−5 pixel range of the maximum as shown in Equation 1:

$$\text{centroid} = \frac{\int_{p_{\max}-5}^{p_{\max}+5} p I_p \, dp}{\int_{p_{\max}-5}^{p_{\max}+5} I_p \, dp}, \quad (1)$$

where p is pixel value, $I_p$ is the intensity at pixel p, and $p_{max}$ is the pixel value corresponding to each peak maximum. From the $p_{max}$ determinations, a polynomial function correlating pixel value to wavelength value is determined by performing a least-squares fit of the peak data. In one embodiment, the polynomial function is of fourth order. In alternative embodiments, the polynomial is of first order, second order, third order, fifth order, or higher order.

Alternatively to finding $p_{max}$ by determining the centroid as discussed above, in another illustrative embodiment the pixel-to-wavelength calibration procedure 302 includes fitting a second order polynomial to the signal intensity versus pixel index data for each of the seven peaks around the maximum +/−3 pixels (range including 7 pixels); taking the derivative of the second order polynomial; and finding the y-intercept to determine each $p_{max}$.

The resulting polynomial function correlating pixel value to wavelength value is validated, for example, by specifying that the maximum argon peak be located within a given pixel range, such as [300:340] and/or that the intensity count at the peak be within a reasonable range, such as between 3000 and 32,000 counts. Additionally, the maximum mercury peak is validated to be between pixel 150 and 225 and to produce an intensity count between 3000 and 32,000 counts. Next, the maximum difference between any peak wavelength predicted by the polynomial function and its corresponding ideal (reference) peak is required to be within about 1.0 nm. Alternatively, other validation criteria may be set.

Additional validation procedures may be performed to compare calibration results obtained for different units, as well as stability of calibration results over time. In one illustrative embodiment, the pixel-to-wavelength calibration 302 and/or validation is performed as part of routine preventive maintenance procedures.

Since fluorescence and reflectance spectral data that are used as reference data in the classification system 100 may be obtained at multiple clinical sites with different individual instruments, the illustrative system 100 standardizes spectral data in step 302 of FIG. 10 by determining and using values of spectral intensity only at designated values of wavelength. Spectral intensity values are standardized by interpolating pixel-based intensities such that they correspond to wavelengths that are spaced every 1 nm between about 360 nm and about 720 nm. This may be done by linear interpolation of the pixel-based fluorescence and/or reflectance values. Other illustrative embodiments use, for example, a cubic spline interpolation procedure instead of linear interpolation.

In some illustrative embodiments, spectral data acquisition during patient scans and during the calibration procedures of FIG. 10 includes the use of a CCD array as part of the scanner assembly 180 depicted in FIG. 3. The CCD array may contain any number of pixels corresponding to data obtained at a given time and at a given interrogation point. In one embodiment, the CCD array contains about 532 pixels, including unused leading pixels from index 0 to 9, relevant data from index 10 to 400, a power monitor region from index 401 to 521, and unused trailing pixels from index 522 to 531. One embodiment includes "power correcting" or "power monitor correcting" by scaling raw reflectance and/or fluorescence intensity measurements received from a region of a tissue sample with a measure of the intensity of light transmitted to the region of the tissue sample. In order to provide the scaling factor, the instrument 102 directs a portion of a light beam onto the CCD array, for example, at pixel indices 401 to 521, and integrates intensity readings over this portion of the array.

In one preferred embodiment, both factory/PM 110 and pre-patient 116 calibration accounts for chromatic, spatial, and temporal variability caused by system interference due to external stray light, internal stray light, and electronic background signals. External stray light originates from sources external to the instrument 102, for example, examination room lights and/or a colposcope light. The occurrence and intensity of the effect of external stray light on spectral data is variable and depends on patient parameters and the operator's use of the instrument 102. For example, as shown in FIG. 8, the farther the probe head 192 rests from the speculum 286 in the examination of cervical tissue, the greater the opportunity for room light to be present on the cervix. The configuration and location of a disposable component 146 on the probe head 192 also affects external stray light that reaches a tissue sample. Additionally, if the operator forgets to turn off the colposcope light before taking a spectral scan, there is a chance that light will be incident on the cervix and affect spectral data obtained.

Electronic background signals are signals read from the CCD array when no light sources, internal or external, are in use. According to the illustrative embodiment, for all components of the tissue characterization system 100 that involve obtaining and/or using spectral data, including components 110, 116, 104, and 114 of FIG. 1, both external stray light and electronic background signals are taken into account by means of a background reading. For each interrogation point in a spectral scan in which one or more internal light sources are used, a background reading is obtained in which all internal light sources (for example, the Xenon lamps and the UV laser) are turned off. According to one feature, the background reading immediately precedes the fluorescence and broadband reflectance measurements at each scan location, and the system 100 corrects for external stray light and electronic background by subtracting the background reading from the corresponding spectral reading at a given interrogation point. In FIG. 10, each calibration test—including 304, 306, 308, 310, 312, 314, 328, and 330—includes obtaining a background reading at each interrogation point and subtracting it from the test reading to account for external stray light and electronic background signals. Also, background subtraction is a step in the spectral data preprocessing 114 methods in FIG. 11, for the pre-processing of raw BB1 and BB2 reflectance data 342, 344 as well as the pre-processing of raw fluorescence data 346.

Equation 2 shows the background correction for a generic spectral measurement from a tissue sample, $S_{tissue+ISL+ESL+EB}(i,\lambda)$:

$$S_{tissue+ISL}(i,\lambda) = S_{tissue+ISL+ESL+EB}(i,\lambda) - Bk_{EB+ESL}(i,\lambda) \qquad (2)$$

where i corresponds to a scan location; λ is wavelength or its pixel index equivalent; and subscripts denote influences on the spectral measurement—where "tissue" represents the tissue sample, "ISL" represents internal stray light (internal to the instrument 102), "ESL" represents external stray light, and "EB" represents electronic background. $S_{tissue+ISL+ESL+EB}(i,\lambda)$ is a two-dimensional array (which may be power-monitor corrected) of spectral data obtained from the tissue at each interrogation point (region) i as a function of wavelength λ; and $Bk_{EB+ESL}(i,\lambda)$ is a two-dimensional array representing values of the corresponding background spectral readings at each point i as a function of wavelength λ. $S_{tissue+ISL}(i,\lambda)$ is the background-subtracted spectral array that is thereby corrected for effects of electronic background (EB) and external stray light (ESL) on the spectral data from the tissue sample. The electronic background reading is subtracted on a wavelength-by-wavelength, location-by-location basis. Subtracting the background reading generally does not correct for internal stray light (ISL), as denoted in the subscript of $S_{tissue+ISL}(i,\lambda)$.

Internal stray light includes internal cross talk and interaction between the transmitted light within the system and the collection optics. For fluorescence measurements, a primary source of internal stray light is low-level fluorescence of optics internal to the probe 142 and the disposable component 146. For reflectance measurements, a primary source of internal stray light is light reflected off of the disposable 146 and surfaces in the probe 142 that is collected through the collection optics 200. The positioning of the disposable 146 can contribute to the effect of internal stray light on reflectance measurements. For example, the internal stray light effect may vary over interrogation points of a tissue sample scan in a non-random, identifiable pattern due to the position of the disposable during the test.

According to the illustrative embodiment of FIG. 10, the factory/PM null target test 304, the factory/PM open air target test 306, the factory/PM custom target test 312, the factory/PM NIST target test 314, the pre-patient null target test 328, and the pre-patient custom target test 330 provide correction factors to account for internal stray light effects on fluorescence and reflectance spectral measurements. In an alternative illustrative embodiment, a subset of these tests is used to account for internal stray light effects.

The null target test 304, 328, performed in factory/preventive maintenance 110, and pre-patient 116 calibration procedures, uses a target that has a theoretical diffuse reflectance of 0%, although the actual value may be higher. Since, at least theoretically, no light is reflected by the target, the contribution of internal stray light can be measured for a given internal light source by obtaining a spectrum from a region or series of regions of the null target with the internal light source turned on, obtaining a background spectrum from the null target with the internal light source turned off, and background-subtracting to remove any effect of electronic background signal or external stray light. The background-subtracted reading is then a measure of internal stray light. The pre-patient null target test 328 takes into account spatially-dependent internal stray light artifacts induced by the position of a disposable 146, as well as temporal variability induced, for example, by the aging of the instrument and/or dust accumulation. In one embodiment, the factory/PM null target test 304 is used in calculating correction factors from other factory and/or preventive maintenance calibration procedures. The null target tests 304, 328 are not perfect, and improved measurements of the effect of internal stray light on spectral data can be achieved by performing additional tests.

The open air target test 310 is part of the factory preventive maintenance (PM) calibration procedure 110 of FIG. 10 and provides a complement to the null target tests 304, 328. The open air target test 310 obtains data in the absence of a target with the internal light sources turned on and all light sources external to the device turned off, for example, in a darkroom. The null target test 304, by contrast, does not have to be performed in a darkroom since it uses a target in place in the calibration port, thereby sealing the instrument such that measurements of light from the target are not affected by external light. Although a disposable 146 is in place during open air test measurements, the factory/PM open air target test 310 does not account for any differences due to different disposables used in each patient run. The open air measurements are important in some embodiments, however, since they are performed under more controlled conditions than pre-patient calibration tests 116, for example, the open air tests may be performed in a darkroom. Also, the factory/PM calibration 110 measurements account for differences between individual instruments 102, as well as the effects of machine aging—both important factors since reference data obtained by any number of individual instruments 102 are standardized for use in a tissue classification algorithm, such as the one depicted in block 132 of FIG. 1.

Figure 12:
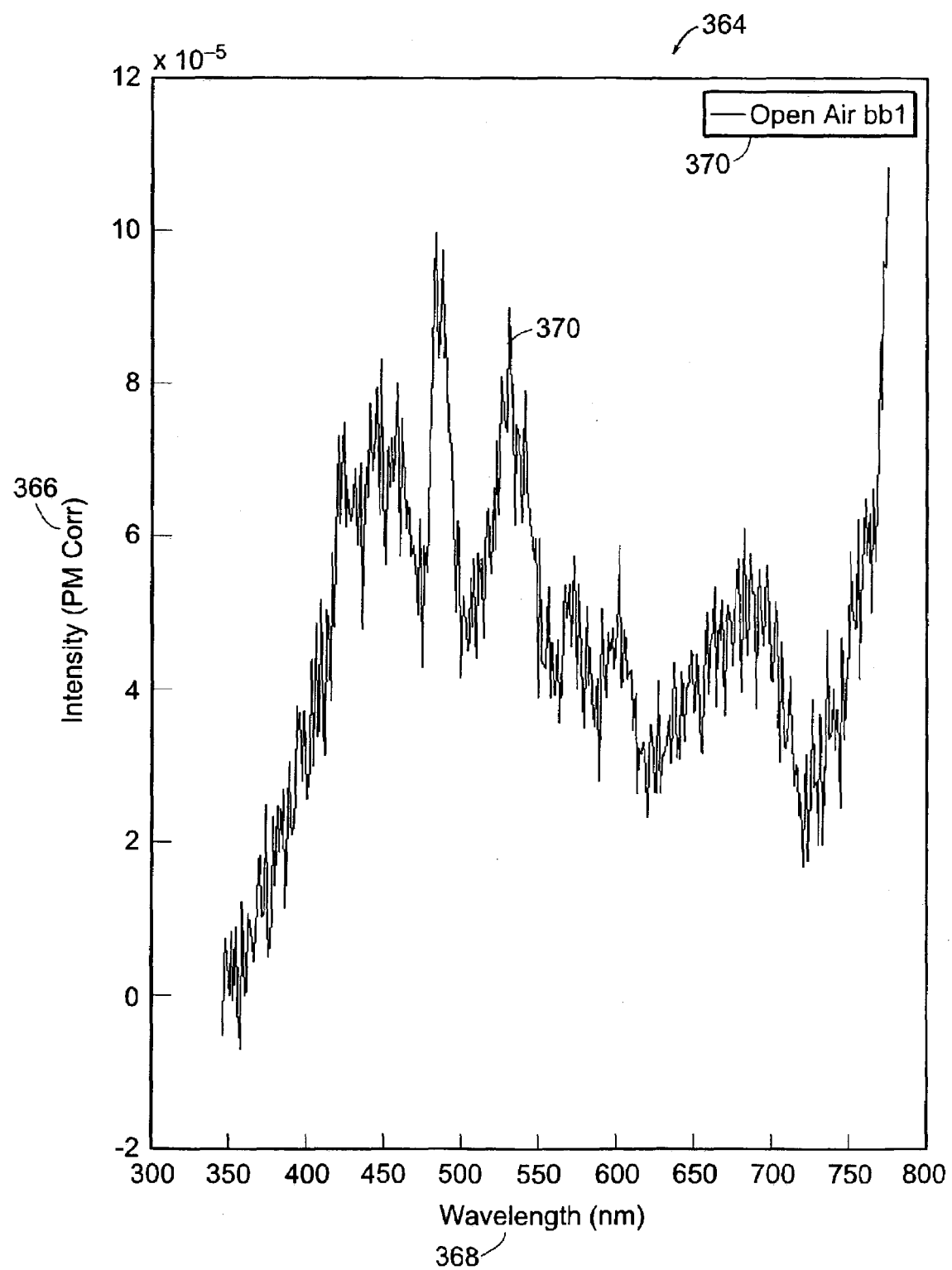
FIG. 12 shows a graph depicting reflectance spectral intensity as a function of wavelength using an open air target according to an illustrative embodiment of the invention.
Figure 13:
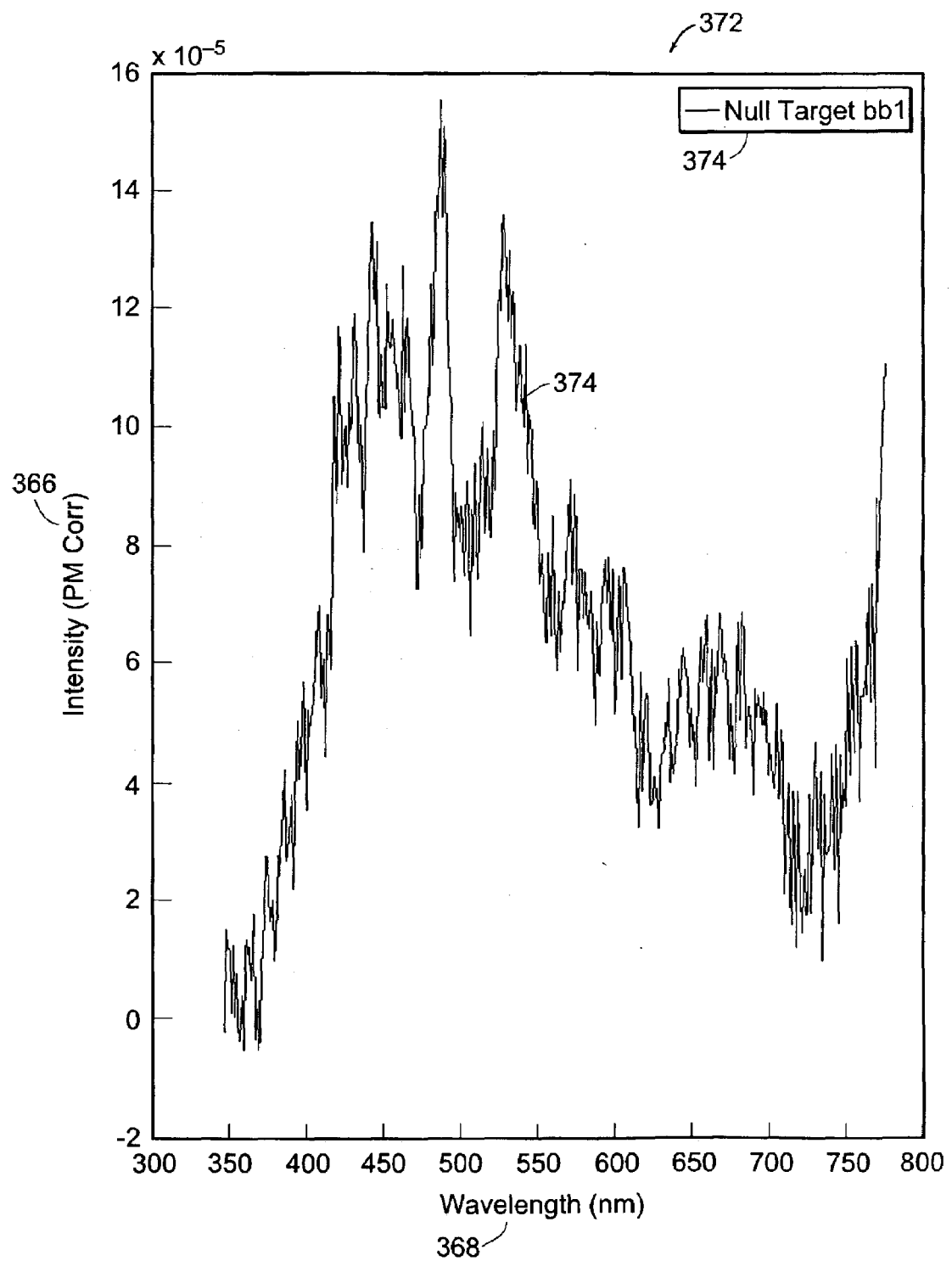
FIG. 13 shows a graph depicting reflectance spectral intensity as a function of wavelength using a null target according to an illustrative embodiment of the invention.

FIGS. 12, 13, 14, and 15 show graphs demonstrating mean background-subtracted, power-monitor-corrected intensity readings from a factory open air target test 310 and a null target test 304 using a BB1 reflectance white light source and a UV light source (laser). FIG. 12 shows a graph 364 of mean intensity 366 from an open air target test over a set of regions as a function of wavelength 368 using a BB1 reflectance white light source 188—the "top" source 188 as depicted in FIGS. 4, 7, and 8. FIG. 13 shows a graph 372 of mean intensity 366 from a null target test over the set of regions as a function of wavelength 368 using the same BB1 light source. Curves 370 and 374 are comparable but there are some differences.

Figure 14:
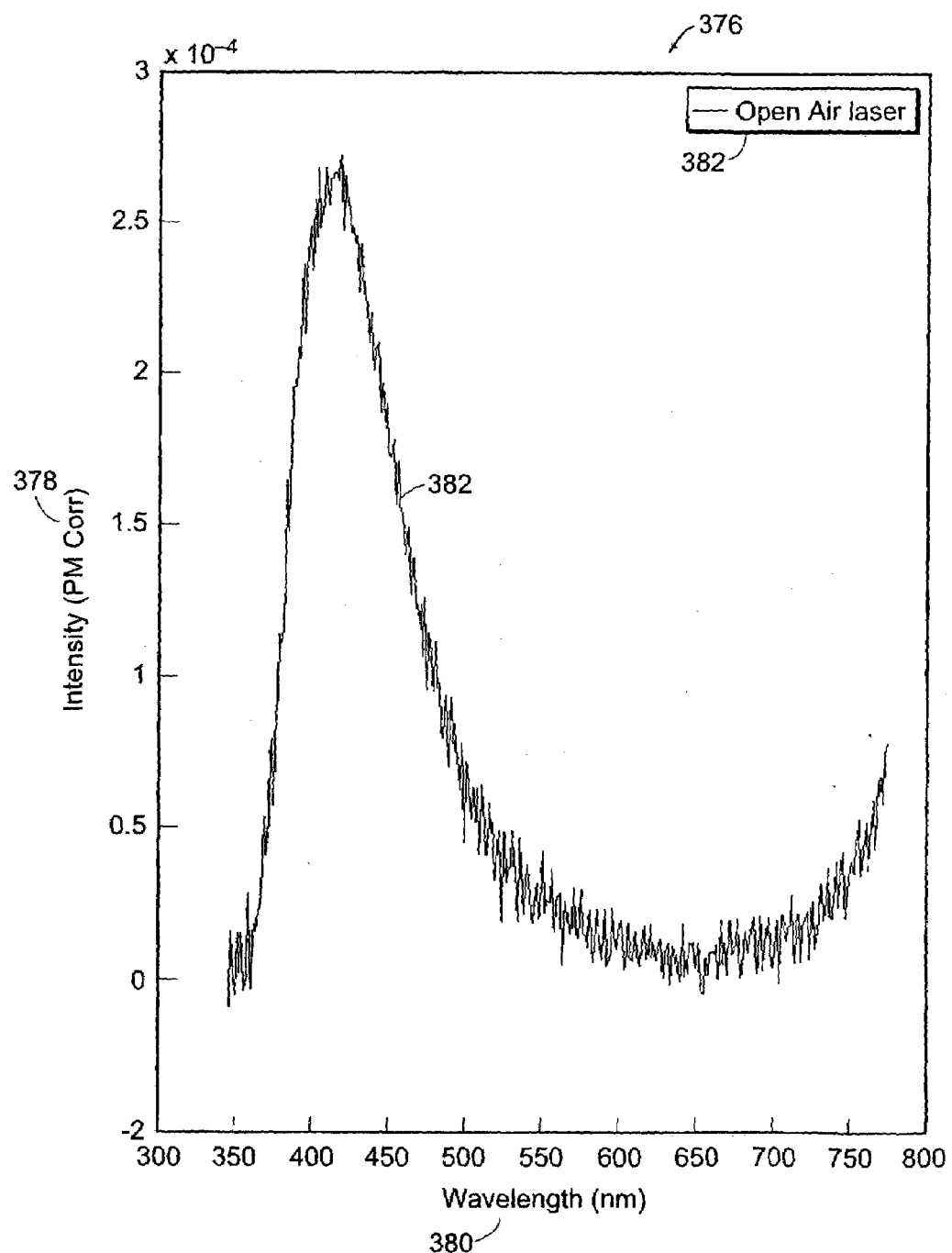
FIG. 14 shows a graph depicting fluorescence spectral intensity as a function of wavelength using an open air target according to an illustrative embodiment of the invention.
Figure 15:
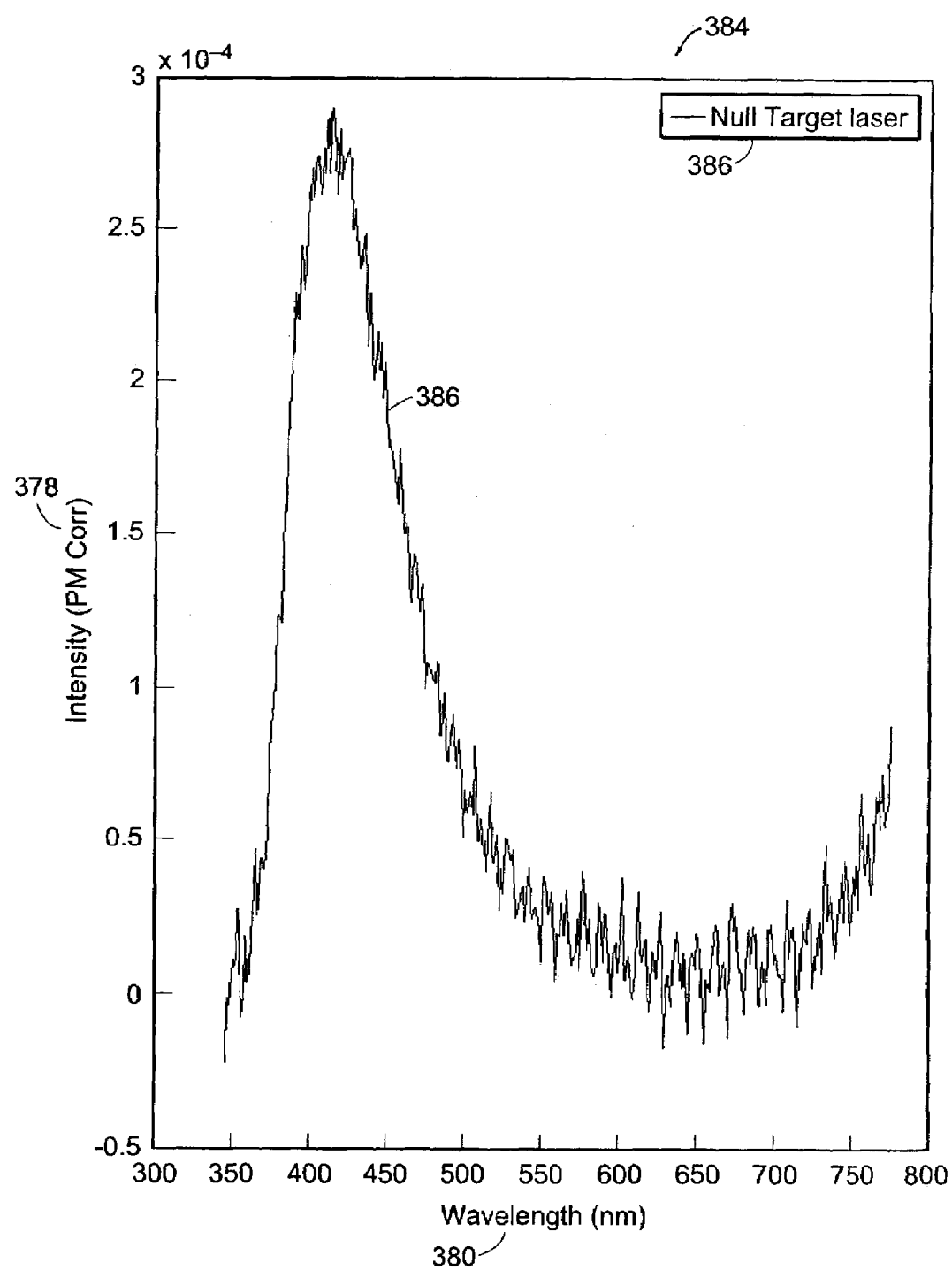
FIG. 15 shows a graph depicting fluorescence spectral intensity as a function of wavelength using a null target according to an illustrative embodiment of the invention.

FIG. 14 shows a graph 376 of mean intensity 378 from an open air target test over a set of regions as a function of wavelength 380 using a UV light source, while FIG. 15 shows a graph 384 of mean intensity 378 from a null target test over the set of regions as a function of wavelength 380 using the UV light source. Again, curves 382 and 386 are comparable, but there are some differences between them. Differences between the open air test intensity and null target test intensity are generally less than 0.1% for reflectance data and under 1 count/μJ for fluorescence data.

Accounting for internal stray light is more complicated for reflectance measurements than for fluorescence measurements due to an increased spatial dependence. The open air target test measurement, in particular, has a spatial profile that is dependent on the position of the disposable.

Figure 16:
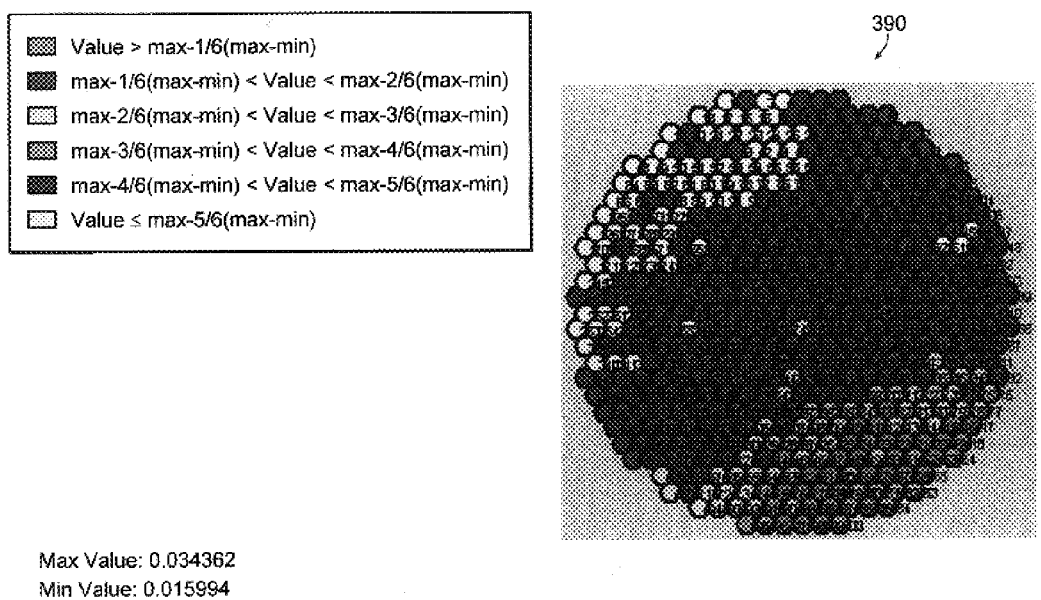
FIG. 16 is a representation of regions of a scan pattern and shows values of broadband reflectance intensity at each region using an open air target according to an illustrative embodiment of the invention.

FIG. 16 shows a representation 390 of regions of an exemplary scan performed in a factory open air target test. The representation 390, shows that broadband intensity readings can vary in a non-random, spatially-dependent manner. Other exemplary scans performed in factory open air target tests show a more randomized, less spatially-dependent variation of intensity readings than the scan shown in FIG. 16.

Figure 17:
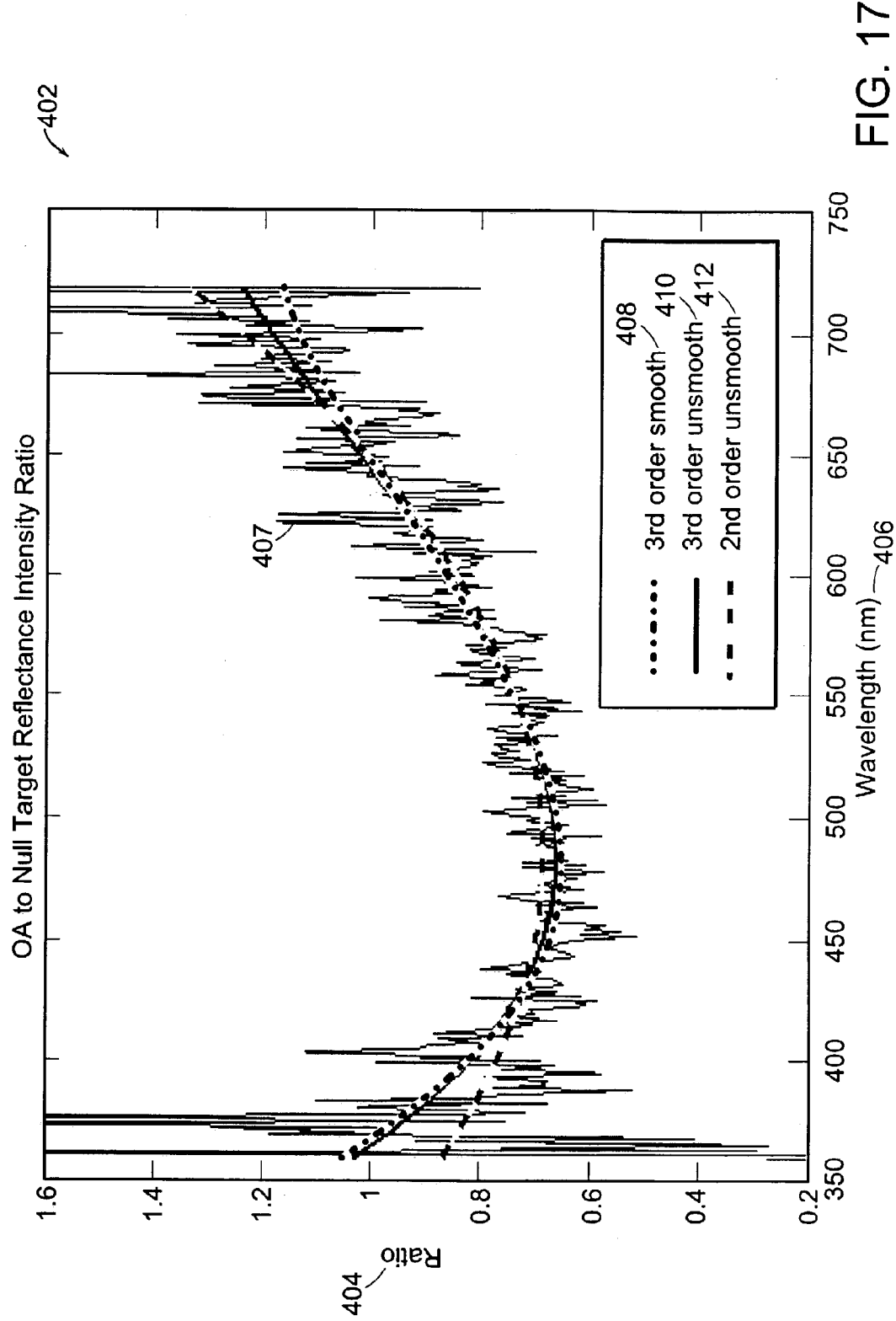
FIG. 17 shows a graph depicting as a function of wavelength the ratio of reflectance spectral intensity using an open air target to the reflectance spectral intensity using a null target according to an illustrative embodiment of the invention.

According to the illustrative embodiment, the system 100 of FIG. 1 accounts for internal stray light by using a combination of the results of one or more open air target tests 310 with one or more null target tests 304, 328. In an alternative embodiment, open air target test data is not used at all to correct for internal stray light, pre-patient null target test data being used instead.

Where open air and null target test results are combined, it is helpful to avoid compounding noise effects from the tests. FIG. 17 shows a graph 402 depicting as a function of wavelength 406 the ratio 404 of the background-corrected, power-monitor-corrected reflectance spectral intensity at a given region using an open air target to the reflectance spectral intensity at the region using a null target according to an illustrative embodiment of the invention. The raw data 407 is shown in FIG. 17 fit with a second-order polynomial 412, and fit with a third-order polynomial without filtering 410, and with filtering 408. As seen by the differences between curve 407 and curves 408, 410, and 412, where a ratio of open air target data and null target data are used to correct for internal stray light in reflectance measurements, a curve fit of the raw data reduces the effect of noise. This is shown in more detail herein with respect to the calculation of pre-patient corrections 118 in FIG. 10. Also evident in FIG. 17 is that the open air measurement generally differs from the null target measurement, since the ratio 404 is not equal to 1, and since the ratio 404 has a distinct wavelength dependence.

Figure 18:
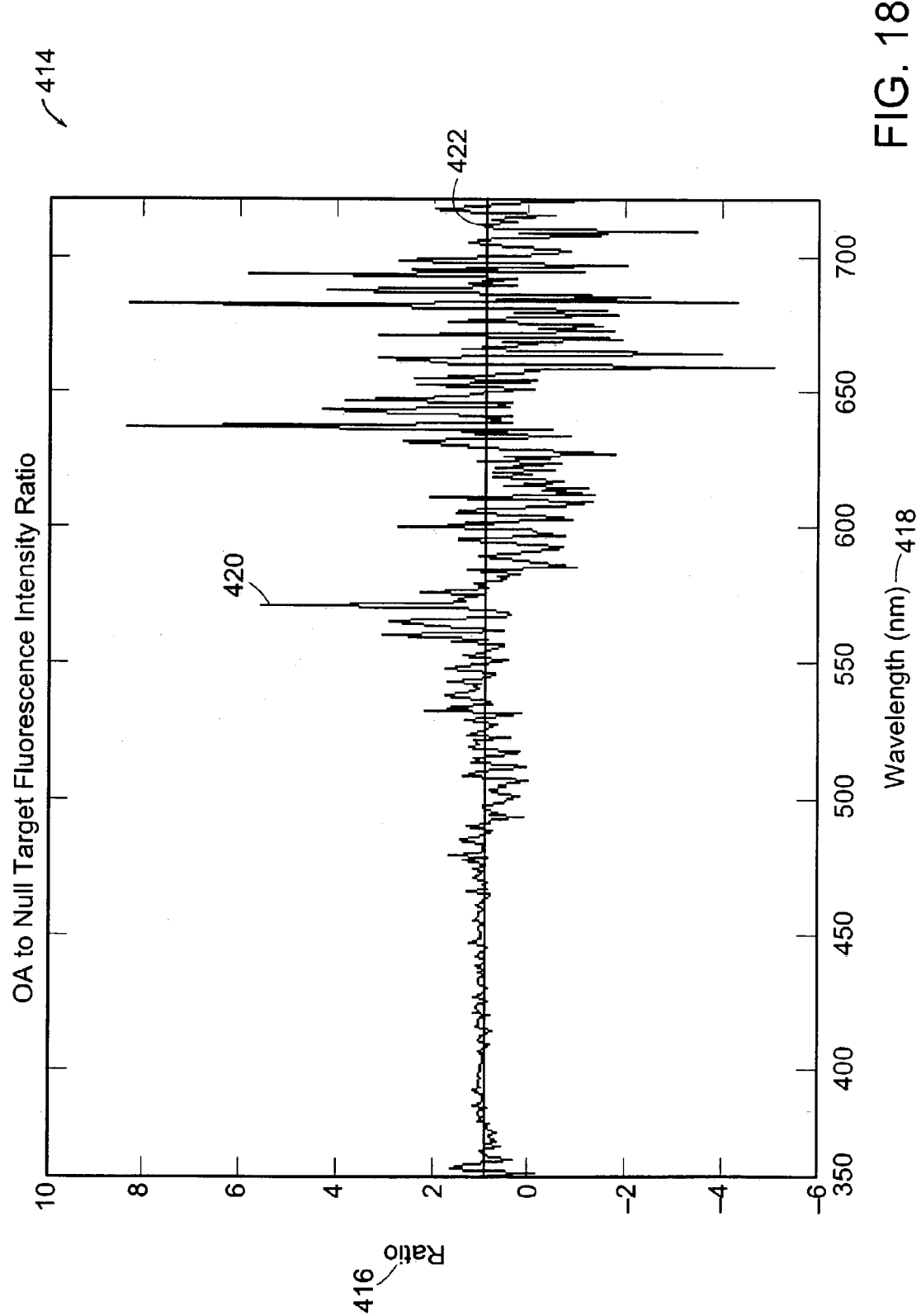
FIG. 18 shows a graph depicting as a function of wavelength the ratio of fluorescence spectral intensity using an open air target to the fluorescence spectral intensity using a null target according to an illustrative embodiment of the invention.

FIG. 18 shows a graph 414 depicting as a function of wavelength 418 the ratio 416 of fluorescence spectral intensity using an open air target to the fluorescence spectral intensity using a null target according to an illustrative embodiment of the invention. The raw data 420 does not display a clear wavelength dependence, except that noise increases at higher wavelengths. A mean 422 based on the ratio data 420 over a range of wavelengths is plotted in FIG. 18. Where a ratio of open air target to null target data is used to correct for internal stray light in fluorescence measurements, using a mean value calculated from raw data over a stable range of wavelength reduces noise and does not ignore any clear wavelength dependence.

FIG. 10 shows correction factors corresponding to open air 310 and null target 304, 328 calibration tests in one embodiment that compensates spectral measurements for internal stray light effects. There are three types of spectral measurements in FIG. 10—fluorescence (F) measurements and two reflectance measurements (BB1, BB2) corresponding to data obtained using a UV light source and two different white light sources, respectively. The corrections in blocks 316, 322, and 332 come from the results of the factory/PM null target test 304, the factory/PM open air target test 310, and the pre-patient null target test 328, respectively, and these correction factors are applied in spectral data pre-processing (FIG. 11) to compensate for the effects of internal stray light. These correction factors are described below in terms of this embodiment.

Block 316 in FIG. 10 contains correction factors computed from the results of the null target test 304, performed during factory and/or preventive maintenance (PM) calibration. The null target test includes obtaining a one-dimensional array of mean values of spectral data from each channel—F, BB1, and BB2—corresponding to the three different light sources, as shown in Equations 3, 4, and 5:

$$FCNULLFL = <I_{nt,F}(i,\lambda,t_o)>_i \quad (3)$$

$$FCNULLBB1 = <I_{nt,BB1}(i,\lambda,t_o)>_i \quad (4)$$

$$FCNULLBB2 = <I_{nt,BB2}(i,\lambda,t_o)>_i \quad (5)$$

where $I_{nt}$ refers to a background-subtracted, power-monitor-corrected two-dimensional array of spectral intensity values; subscript F refers to intensity data obtained using the fluorescence UV light source; subscripts BB1 and BB2 refer to intensity data obtained using the reflectance BB1 and BB2 white light sources, respectively; i refers to interrogation point "i" on the calibration target; $\lambda$ refers to a wavelength at which an intensity measurement corresponds or its approximate pixel index equivalent; $t_o$ refers to the fact the measurement is obtained from a factory or preventive maintenance test, the "time" the measurement is made; and $<>_i$ represents a one-dimensional array (spectrum) of mean values computed on a pixel-by-pixel basis for each interrogation point, i. In this embodiment, a one-dimensional array (spectrum) of fluorescence values corresponding to wavelengths from $\lambda=370$ nm to $\lambda=720$ nm is obtained at each of 499 interrogation points, i. An exemplary scan pattern 202 of 499 interrogation points appears in FIG. 5. In the illustrative embodiment, data from an additional interrogation point is obtained from a region outside the target 206. Each of the reflectance intensity spectra is obtained over the same wavelength range as the fluorescence intensity spectra, but the BB1 data is obtained at each of 250 interrogation points over the bottom half of the target and the BB2 data is obtained at each of 249 interrogation points over the top half of the target. This avoids a shadowing effect due to the angle at which the light from each source strikes the target during the null target test 304. Values of the most recent factory or preventive maintenance calibration test, including the factory/PM null target test 304, are used in spectral data pre-processing (FIG. 11) for each patient scan.

The pre-patient null target test, shown in block 328 of FIG. 10, is similar to the factory/PM null target test 304, except that it is performed just prior to each patient test scan. Each pre-patient null target test 328 produces three arrays of spectral data as shown below:

$$I_{nt,F}(i,\lambda,t') \quad (6)$$

$$I_{nt,BB1}(i,\lambda,t') \quad (7)$$

$$I_{nt,BB2}(i,\lambda,t') \quad (8)$$

where t' refers to the fact the measurements are obtained just prior to the test patient scan, as opposed to during factory/PM testing ($t_o$).

Block 332 in FIG. 10 contains correction factors from the open air target test 310, preformed during factory and/or preventive maintenance (PM) calibration 110. The open air target test is performed with the disposable in place, in the absence of a target, with the internal light sources turned on, and with all light sources external to the device turned off. The open air target test 310 includes obtaining an array of spectral data values from each of the three channels—F, BB1, and BB2—as shown below:

$$I_{oa,F}(i,\lambda,t_o) \quad (9)$$

$$I_{ao,BB1}(i,\lambda,t_o) \quad (10)$$

$$I_{oa,BB2}(i,\lambda,t_o) \quad (11)$$

In each of items 9, 10, and 11 above, $I_{oa}$ refers to a background-subtracted, power-monitor-corrected array of spectral intensity values; i runs from interrogation points 1 to 499; and $\lambda$ runs from 370 nm to 720 nm (or the approximate pixel index equivalent).

According to the illustrative embodiment, correction for internal stray light makes use of both null target test results and open air target test results. Correction factors in block 322 of FIG. 10 use results from the factory/PM null target test 304 and factory/PM open air target test 310. The correction factors in block 322 are computed as follows:

$$sFCOFL = [<I_{oa,F}(i,\lambda,t_o)>_i / (I_{nt,F}(i,\lambda,t_o)>_i]_{mean, \lambda=375 \text{ nm to } 470 \text{ nm}} \quad (12)$$

$$FCOBB1 = \text{fitted form of } <I_{oa,BB1}(i,\lambda,t_o)>_i / (I_{nt,BB1}(i,\lambda,t_o)>_i \quad (13)$$

$$FCOBB2 = \text{fitted form of } <I_{oa,BB2}(i,\lambda,t_o)>_i / <I_{nt,BB2}(i,\lambda,t_o)>_i \quad (14)$$

where $<>_i$ represents a spectrum (1-dimensional array) of mean values computed on a pixel-by-pixel basis for each interrogation point i, and where $<>_i / <>_i$ represents a spectrum (1-dimensional array) of quotients (ratios of means) computed on a pixel-by-pixel basis for each interrogation point i. The correction factor sFCOFL in Equation 12 is a scalar quantity representing the mean value of the 1-dimensional array in brackets [] across pixel indices corresponding to the wavelength range of about 375 nm to about 470 nm.

FIG. 18 shows an example value of sFCOFL 422 evaluated using a set of mean open air spectral data and mean null target spectral data. Large oscillations are damped by using the mean in Equation 12. Other wavelength ranges can be chosen instead of the wavelength range of about 375 nm to about 470 nm.

The one-dimensional arrays, FCOBB1 and FCOBB2, are obtained by curve-fitting the spectra of quotients in Equations 13 and 14 with second-order polynomials and determining values of the curve fit corresponding to each pixel. FIG. 17 shows an example curve fit for FCOBB1 (412). Unlike the fluorescence measurements, there is wavelength dependence of this ratio, and a curve fit is used to properly reflect this wavelength dependence without introducing excessive noise in following computations.

Block 332 in FIG. 10 contains correction factors using results from the pre-patient null target test 328, as well as the most recent factory/PM null target test 304 and open air target test 310. The correction factors in block 332 are computed as follows:

$$SLFL = sFCOFL \cdot <I_{nt,F}(i,\lambda,t')>_i \quad (15)$$

$$SLBB1 = FCOBB1 \cdot <I_{nt,BB1}(i,\lambda,t')>_i \quad (16)$$

$$SLBB2 = FCOBB2 \cdot <I_{nt,BB2}(i,\lambda,t')>_i \quad (17)$$

where Equation 15 represents multiplying each value in the fluorescence mean pre-patient null target spectrum by the scalar quantity sFCOFL from Equation 12; Equation 16 represents multiplying corresponding elements of the mean pre-patient null target BB1 spectrum and the one-dimensional array FCOBB1 from Equation 13; and Equation 17 represents multiplying corresponding elements of the mean pre-patient null target BB2 spectrum and the one-dimensional array FCOBB2 from Equation 14. Each of SLFL, SLBB1, and SLBB2 is a one-dimensional array.

The correction factors in block 332 of FIG. 10 represent the contribution due to internal stray light (ISL) for a given set of spectral data obtained from a given patient scan. Combining equations above:

$$SLFL = [<I_{oa,F}(i,\lambda,t_o)>_i / >I_{nt,F}(i,\lambda,t_o)>_i]_{mean, \lambda=375 \text{ nm to } 470 \text{ nm}} \cdot <I_{nt,F}(i,\lambda,t')>_i \quad (18)$$

$$SLBB1 = [<I_{oa,BB1}(i,\lambda,t_o)>_i / <I_{nt,BB1}(i,\lambda,t_o)>_i]_{fitted} \cdot <I_{nt,BB1}(i,\lambda,t')>_i \quad (19)$$

$$SLBB2 = [<I_{oa,BB2}(i,\lambda,t_o)>_i / <I_{nt,BB2}(i,\lambda,t_o)>_i]_{fitted} \cdot <I_{nt,BB2}(i,\lambda,t')>_i \quad (20)$$

Alternative internal stray light correction factors are possible. For example, in one alternative embodiment, the scalar quantity in Equation 18 is replaced with the value 1.0. In one alternative embodiment, the first term on the right side of either or both of Equation 19 and Equation 20 is replaced with a scalar quantity, for example, a mean value or the value 1.0.

Spectral data preprocessing 114 as detailed in FIG. 11 includes compensating for internal stray light effects as measured by SLFL, SLBB1 and SLBB2. In one embodiment, a patient scan includes the acquisition at each interrogation point in a scan pattern (for example, the 499-point scan pattern 202 shown in FIG. 5) of a set of raw fluorescence intensity data using the UV light source 160, a first set of raw broadband reflectance intensity data using a first white light source (162, 188), a second set of raw broadband reflectance intensity data using a second white light source (162, 192), and a set of raw background intensity data using no internal light source, where each set of raw data spans a CCD pixel index corresponding to a wavelength range between about 370 nm and 720 nm. In another embodiment, the wavelength range is from about 370 nm to about 700 nm. In another embodiment, the wavelength range is from about 300 nm to about 900 nm. Other embodiments include the use of different wavelength ranges.

The raw background intensity data set is represented as the two-dimensional array Bkgnd[] in FIG. 11. Spectral data processing 114 includes subtracting the background array, Bkgnd[], from each of the raw BB1, BB2, and F arrays on a pixel-by-pixel and location-by-location basis. This accounts at least for electronic background and external stray light effects, and is shown as item #1 in each of blocks 342, 344, and 346 in FIG. 11.

Also, each CCD array containing spectral data includes a portion for monitoring the power output by the light source used to obtain the spectral data. In one embodiment, the intensity values in this portion of each array are added or integrated to provide a one-dimensional array of scalar values, sPowerMonitor[], shown in FIG. 11. Spectral data pre-processing 114 further includes dividing each element of the background-subtracted arrays at a given interrogation point by the power monitor scalar correction factor in sPowerMonitor[] corresponding to the given interrogation point. This allows the expression of spectral data at a given wavelength as a ratio of received light intensity to transmitted light intensity.

Spectral data pre-processing 114 further includes subtracting each of the stray light background arrays—SLBB1, SLBB2, and SLFL—from its corresponding background-corrected, power-monitor-corrected spectral data array—BB1, BB2, and F—on a pixel-by-pixel, location-by-location basis. This accounts for chromatic, temporal, and spatial variability effects of internal stray light on the spectral data.

The remaining steps in blocks 342 and 344 of the spectral data pre-processing block diagram 340 of FIG. 11 include further factory, preventive maintenance (PM) and/or pre-patient calibration of reflectance (BB1, BB2) measurements using one or more targets of known, non-zero diffuse reflectance. In the embodiment shown in FIG. 10, this calibration uses results from the factory/PM custom target test 312, the factory/PM NIST-standard target test 314, and the pre-patient custom target test 330. These calibration tests provide correction factors as shown in blocks 324, 326, and 334 of FIG. 10, that account for chromatic, temporal, and spatial sources of variation in broadband reflectance spectral measurements. These sources of variation include temporal fluctuations in the illumination source, spatial inhomogeneities in the illumination source, and chromatic aberration due to the scanning optics. The broadband reflectance calibration tests (312, 314, 330) also account for system artifacts attributable to both transmitted and received light, since these artifacts exist in both test reflectance measurements and known reference measurements.

According to the illustrative embodiment, reflectance, R, computed from a set of regions of a test sample (a test scan) is expressed as in Equation 21:

$$R = [\text{Measurement/Reference Target}] \cdot \text{Reflectivity of Reference Target} \quad (21)$$

where R, Measurement, and Reference Target refer to two-dimensional (wavelength, position) arrays of background-corrected, power-corrected and/or internal-stray-light-corrected reflectance data; Measurement contains data obtained from the test sample; Reference Target contains data obtained from the reference target; Reflectivity of Reference Target is a known scalar value; and division of the arrays is performed in a pixel-by-pixel, location-by-location manner.

The factory/PM NIST target test 314 uses a 60%, NIST-traceable, spectrally flat diffuse reflectance target in the focal plane, aligned in the instrument 102 represented in FIG. 3. The NIST target test 314 includes performing four scans, each of which proceed with the target at different rotational orientations, perpendicular to the optical axis of the system. For example, the target is rotated 90° from one scan to the next. The results of the four scans are averaged on a location-by-location, pixel-by-pixel basis to remove spatially-dependent target artifacts (speckling) and to reduce system noise. The goal is to create a spectrally clean (low noise) and spatially-flat data set for application to patient scan data. In one embodiment, the NIST target test 314 is performed only once, prior to instrument 102 use in the field (factory test), and thus, ideally, is temporally invariant.

Figure 19:
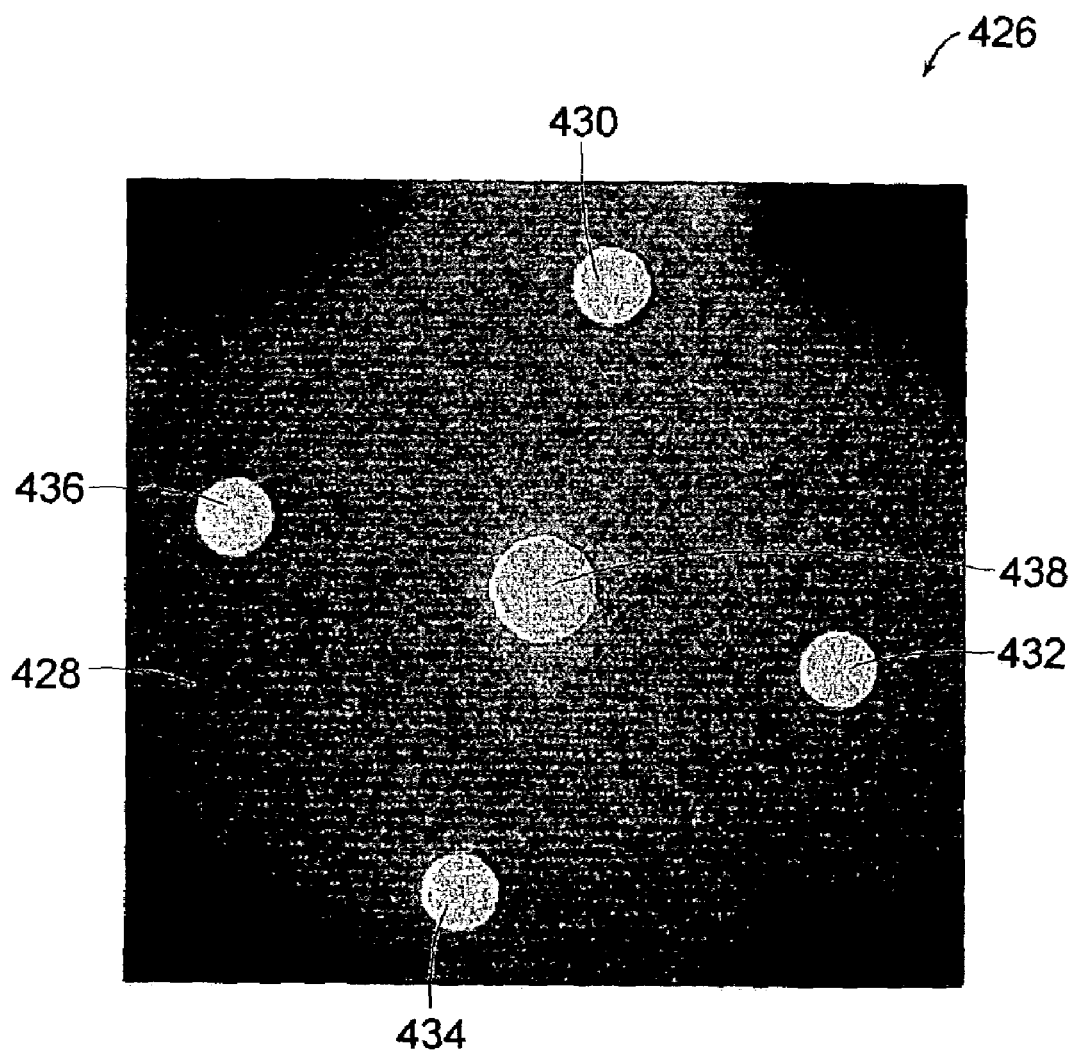
FIG. 19 is a photograph of a customized target for factory/preventive maintenance calibration and for pre-patient calibration of the instrument used in the tissue characterization system of FIG. 1 according to an illustrative embodiment of the invention.

The custom target tests 312, 330 use a custom-made target for both factory and/or preventive maintenance calibration, as well as pre-patient calibration of reflectance data. The custom target is a 10% diffuse reflective target with phosphorescent and/or fluorescent portions used, for example, to align the ultraviolet (UV) light source and/or to monitor the stability of fluorescence readings between preventive maintenance procedures. FIG. 19 is a photograph of the custom target 426 according to an illustrative embodiment. In FIG. 19, the target 426 includes a portion 428 that is about 10% diffuse reflective material, with four phosphorescent plugs 430, 432, 434, 436 equally-spaced at the periphery and a single fluorescent plug 438 at the center. As a result of the plugs, not all scan locations in the scan pattern 202 of FIG. 5, as applied to the custom target test 426, accurately measure the 10% reflective portion. Thus, a mask provides a means of filtering out the plug-influenced portions of the custom target 426 during a custom target calibration scan 312, 330.

Figure 20:
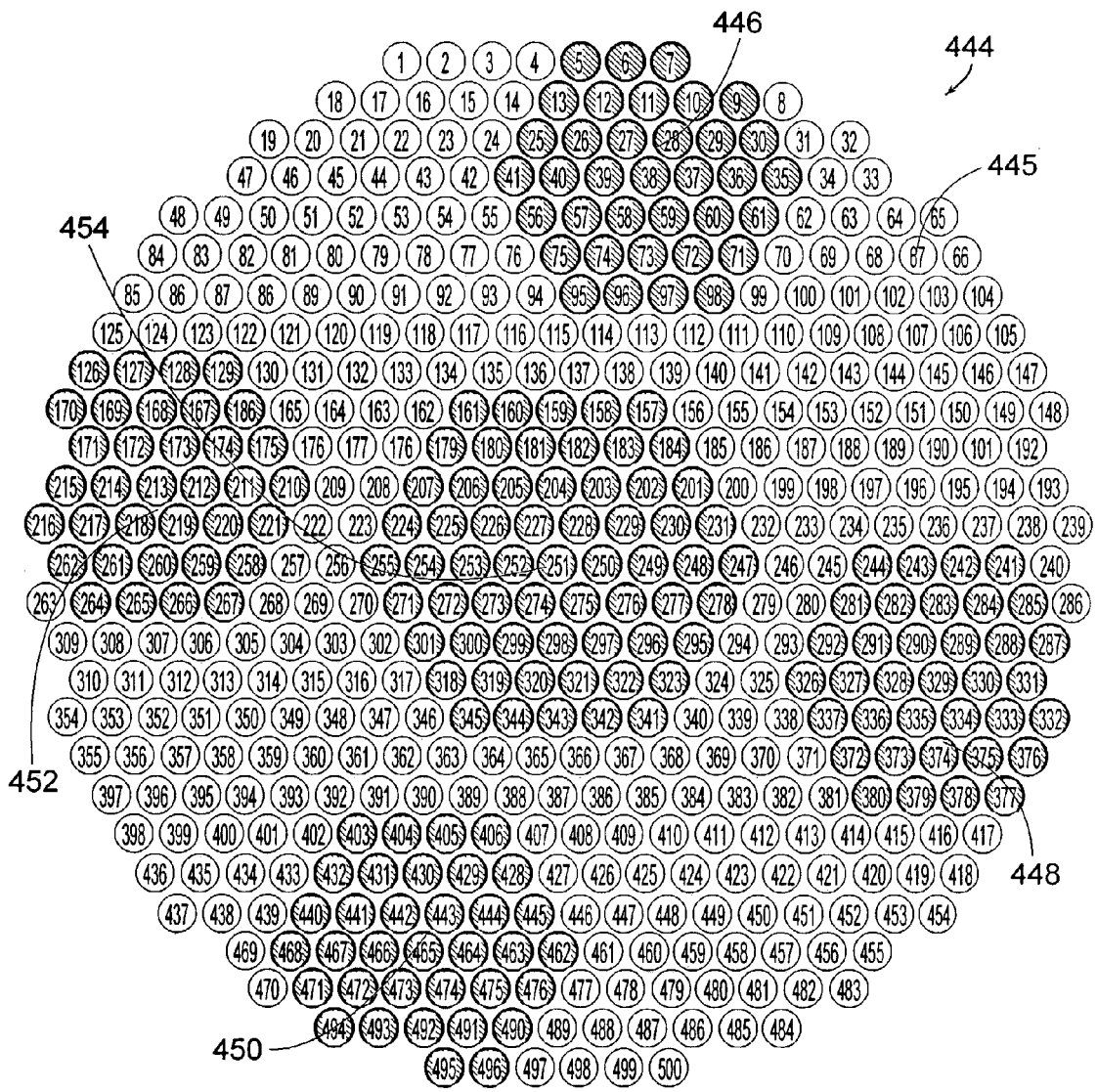
FIG. 20 is a representation of the regions of the customized target of FIG. 19 that are used to calibrate broadband reflectance spectral data according to an illustrative embodiment of the invention.

FIG. 20 is a representation of such a mask 444 for the custom target reflectance calibration tests 312, 330. Area 445 in FIG. 20 corresponds to regions of the custom target 426 of FIG. 19 that are not affected by the plugs 430, 432, 434, 436, and which, therefore, are usable in the custom target reflectance calibration tests 312, 330. Areas 446, 448, 450, 452, and 454 of FIG. 20 correspond to regions of the custom target 426 that are affected by the plugs, and which are masked out in the custom target calibration scan results.

In the illustrative embodiment, the factory/PM NIST target test 314 provides reflectance calibration data for a measured signal from a test sample (patient scan), and the test sample signal is processed according to Equation 22:

$$R(i,\lambda,t') = [I_m(i,\lambda,t')/I_{fc}(i,\lambda,t_o)] \cdot 0.6 \quad (22)$$

Where R, $I_m$, and $I_{fc}$ are two-dimensional arrays of background-corrected, power-corrected reflectance data; R contains reflectance intensity data from the test sample adjusted according to the reflectance calibration data; $I_m$ contains reflectance intensity data from the sample, $I_{fc}$ contains reflectance intensity data from the factory/PM NIST-standard target test 314, and 0.6 is the known reflectivity of the NIST-standard target. Equation 22 presumes the spectral response of the illumination source is temporally invariant such that the factory calibration data from a given unit does not change with time, as shown in Equation 23 below:

$$I_{fc}(t') = I_{fc}(t_o) \quad (23)$$

However, the spectral lamp function of a xenon flash lamp, as used in the illustrative embodiment as the white light source 162 in the instrument 102 of FIG. 3, is not invariant over time.

The illustrative reflectance data spectral preprocessing 114 accounts for temporal variance by obtaining pre-patient custom target test (330) reflectance calibration data and using the data to adjust data from a test sample, $I_m$, to produce adjusted reflectance R, as follows:

$$R(i,\lambda,t') = [I_m(i,\lambda,t')/<I_{cp}(i,\lambda,t')>_i] \cdot 0.1 \quad (24)$$

where masked, mean reflectance intensity data from the pre-patient custom target test 330 with 10% diffuse reflectivity, $<I_{cp}(i,\lambda,t')>_i$, replaces $I_{fc}(i,\lambda,t')$ in Equation 22. Since the pre-patient custom target test data is updated before every patient exam, the temporal variance effect is diminished or eliminated. In other illustrative embodiments, various other reference targets may be used in place of the custom target 426 shown in FIG. 19.

The system 100 also accounts for spatial variability in the target reference tests of FIG. 10 in pre-processing reflectance spectral data. Illustratively, spatial variability in reflectance calibration target intensity is dependent on wavelength, suggesting chromatic aberrations due to wavelength-dependence of transmission and/or collection optic efficiency.

The illustrative reflectance data spectral preprocessing 114 accounts for these chromatic and spatial variability effects by obtaining reflectance calibration data and using the data to adjust data from a test sample, $I_m$, to produce adjusted reflectance R, as follows:

$$R(i,\lambda,t') = [I_m(i,\lambda,t')/<I_{cp}(i,\lambda,t')>_i] \cdot [<I_{fc}(i,\lambda,t_o)>_i/I_{fc}(i,\lambda,t_o)] \cdot 0.1 \quad (25)$$

Equation 25 accounts for variations of the intensity response of the lamp by applying the pre-patient custom-target measurements—which are less dependent on differences caused by the disposable—in correcting patient test sample measurements. Equation 25 also accounts for the spatial response of the illumination source by applying the factory NIST-target measurements in correcting patient test sample measurements.

In an alternative illustrative embodiment, the NIST-target test 314 is performed as part of pre-patient calibration 116 to produce calibration data, $I_{fc}(i,\lambda,t')$, and Equation 22 is used in processing test reflectance data, where the quantity $I_{fc}(i,\lambda,t')$ replaces the quantity $I_{fc}(i,\lambda,t_o)$ in Equation 22. According to this illustrative embodiment, the test data pre-processing procedure 114 includes both factory/PM calibration 110 results and pre-patient calibration 116 results in order to maintain a more consistent basis for the accumulation and use of reference data from various individual units obtained at various times from various patients in a tissue characterization system. Thus, this illustrative embodiment uses Equation 26 below to adjust data from a test sample, $I_m$, to produce adjusted reflectance R, as follows:

$$R(i,\lambda,t') = [I_m(i,\lambda,t')/(I_{fc}(i,\lambda,t')>_i] \cdot [<I_{fc}(i,\lambda,t_o)>_i/I_{fc}(i,\lambda,t_o)] \cdot 0.6 \quad (26)$$

where the NIST-standard target test 314 is performed both as a factory/PM test 110 ($t_o$) and as a pre-patient test 116 (t').

According to the illustrative embodiment, it is preferable to combine calibration standards with more than one target, each having a different diffuse reflectance, since calibration is not then tied to a single reference value. Here, processing using Equation 25 is preferable to Equation 26. Also, processing via Equation 25 may allow for an easier pre-patient procedure, since the custom target combines functions for both fluorescence and reflectance system set-up, avoiding the need for an additional target test procedure.

Figure 21:
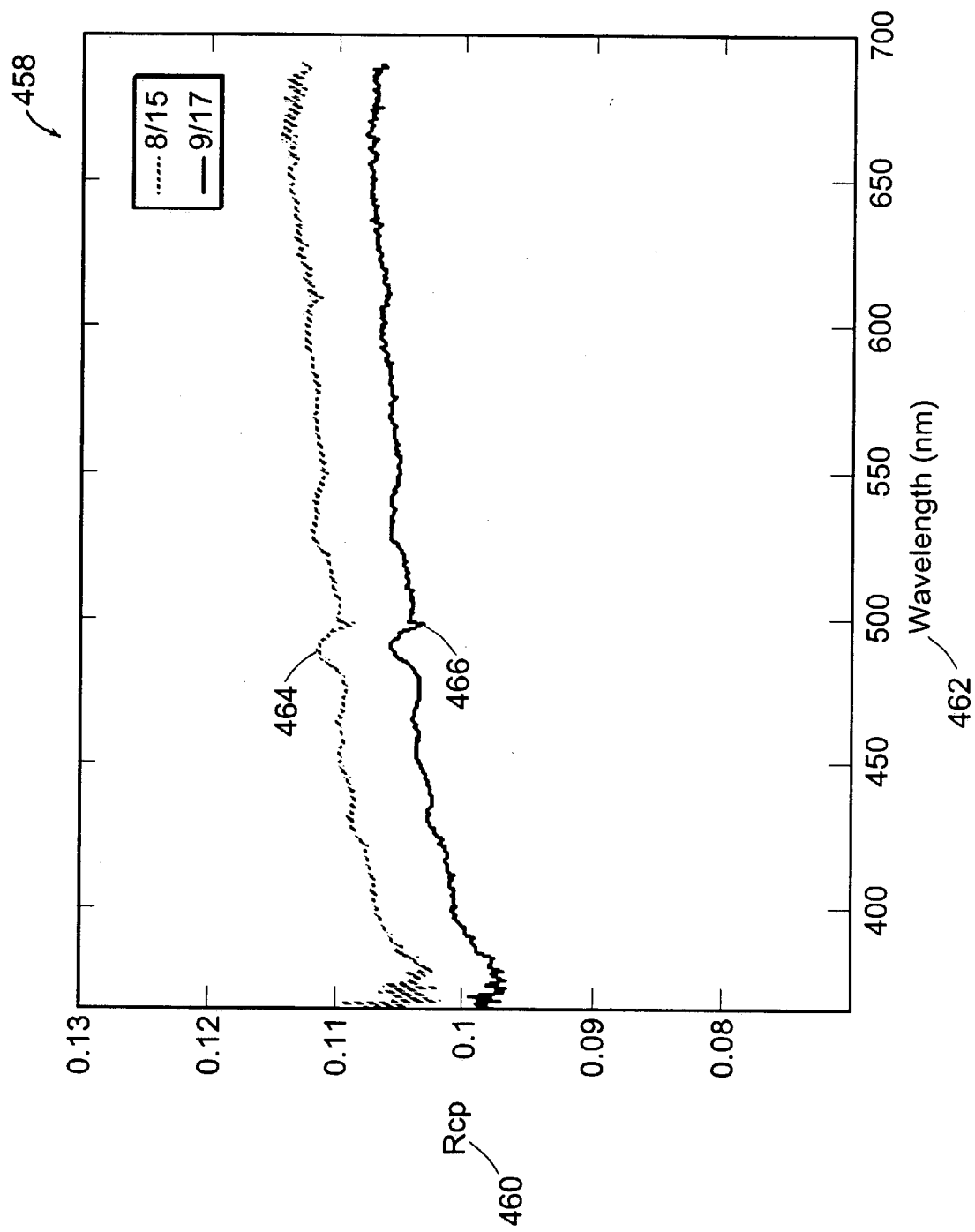
FIG. 21 shows a graph depicting as a function of wavelength the mean reflectivity of the 10% diffuse target of FIG. 19 over the non-masked regions shown in FIG. 20, measured using the same instrument on two different days according to an illustrative embodiment of the invention.

Values of the custom target reflectance in a given individual instrument 102 vary over time and as a function of wavelength. For example, FIG. 21 shows a graph 458 depicting as a function of wavelength 462 a measure of the mean reflectivity 460, $R_{cp}$, of the 10% diffuse target 426 of FIG. 19 over the non-masked regions 445 shown in FIG. 20, obtained using the same instrument on two different days. $R_{cp}$ is calculated as shown in Equation 27:

$$R_{cp}(\lambda) = [<I_{cp}(i,\lambda,t_o)>_i/<I_{fc}(i,\lambda,t_o)>_i] \cdot R_{fc} \quad (27)$$

where $R_{fc}=0.6$, the diffuse reflectance of the NIST-traceable standard target. Values of $R_{cp}$ vary as a function of wavelength 462, as seen in each of curves 464 and 466 of FIG. 21. Also, there is a shift from curve 464 to curve 466, each obtained on a different day. Similarly, values of $R_{cp}$ vary among different instrument units. Curves 464 and 466 show that $R_{cp}$ varies with wavelength and varies from 0.1; thus, assuming $R_{cp}=0.1$ as in Equation 25 may introduce inaccuracy.

Figure 22A:
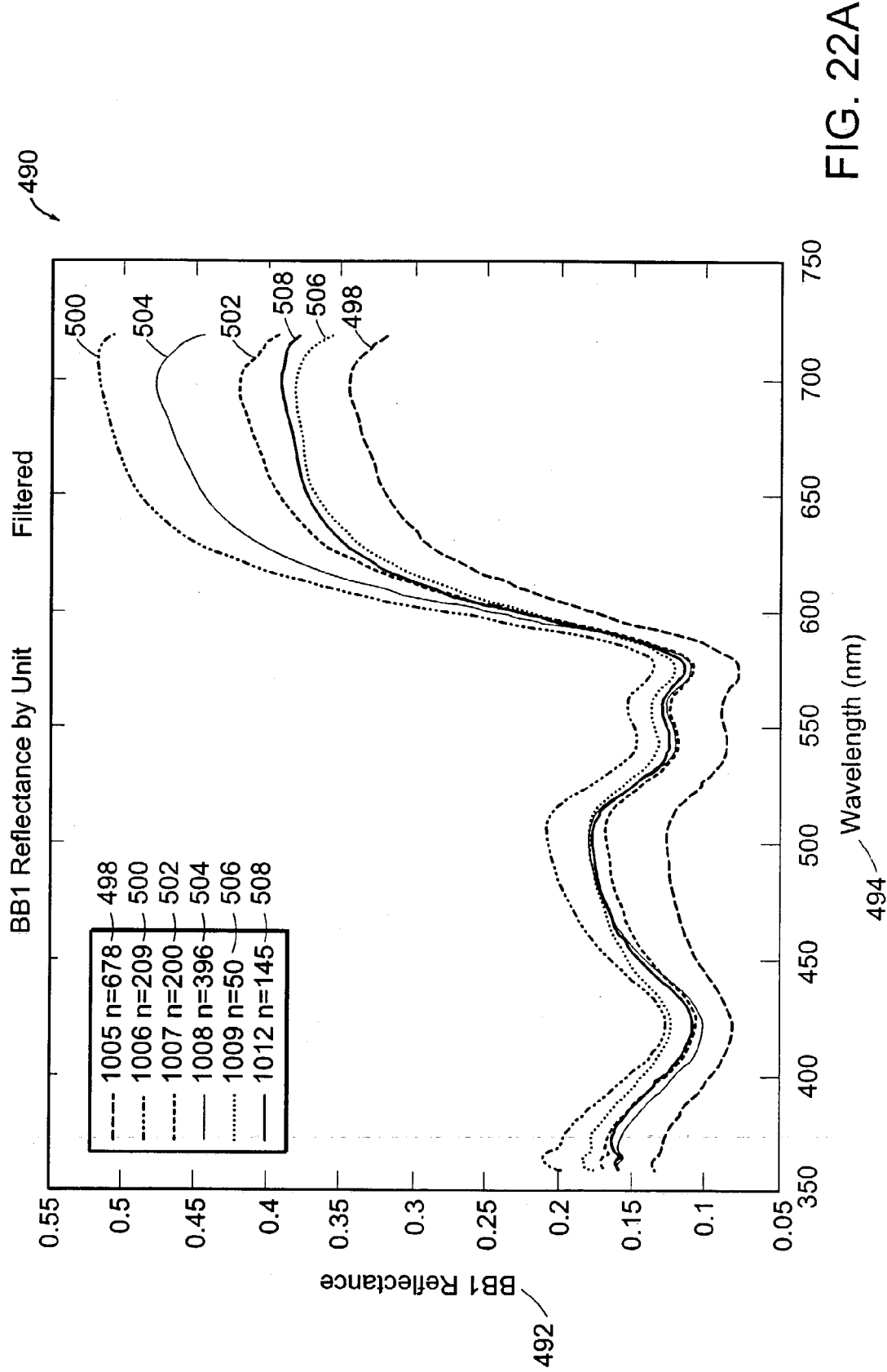
FIG. 22A shows a graph depicting, for various individual instruments, curves of reflectance intensity (using the BB1 light source), each instrument curve representing a mean of reflectance intensity values for regions confirmed as metaplasia by impression and filtered according to an illustrative embodiment of the invention.
Figure 22B:
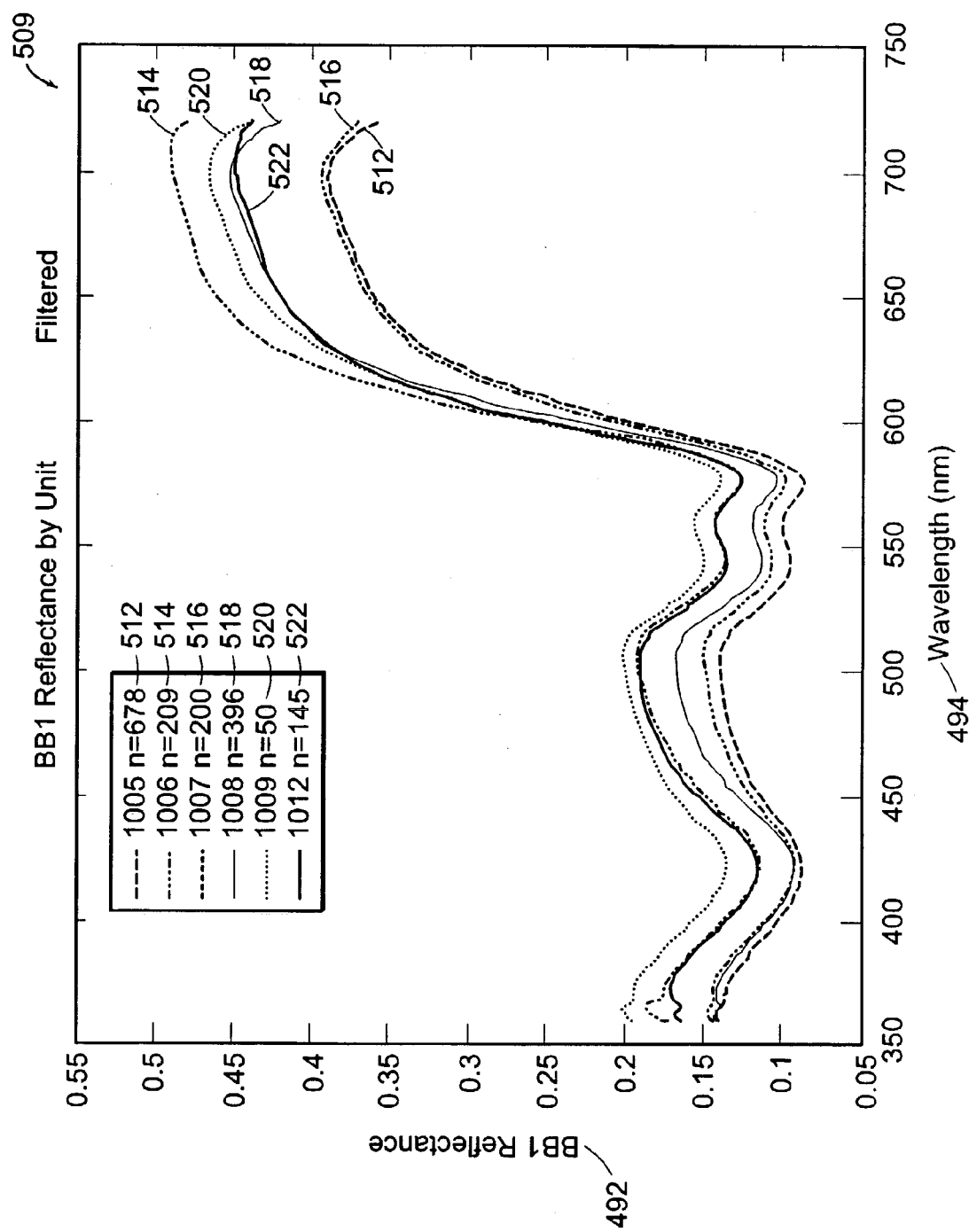
FIG. 22B shows a graph depicting, for various individual instruments, curves of reflectance intensity of the metaplasia-by-impression regions of FIG. 22A, after adjustment according to an illustrative embodiment of the invention.

Equation 25 can be modified to account for this temporal and wavelength dependence, as shown in Equation 28:

$$R(i,\lambda,t') = [I_m(i,\lambda,t')/<I_{cp}(i,\lambda,t')>_i] \cdot [<I_{fc}(i,\lambda,t_o)>_i/I_{fc}(i,\lambda,t_o)] \cdot R_{cp,fitted} \quad (28)$$

where $R_{cp,fitted}$ is an array of values of a second-order polynomial curve fit of $R_{cp}$ shown in Equation 27. The polynomial curve fit reduces the noise in the $R_{cp}$ array. Other curve fits may be used alternatively. For example, FIG. 22A shows a graph 490 depicting, for seven individual instruments, curves 496, 498, 500, 502, 504, 506, 508 of sample reflectance intensity using the BB1 white light source 188 as depicted in FIGS. 4, 7 and 8 graphed as functions of wavelength 494. Each of the seven curves represents a mean of reflectance intensity at each wavelength, calculated using Equation 25 for regions confirmed as metaplasia by impression. FIG. 22B shows a graph 509 depicting corresponding curves 510, 512, 514, 516, 518, 520, 522 of test sample reflectance intensity calculated using Equation 28, where $R_{cp}$ varies with time and wavelength. The variability between individual instrument units decreases when using measured values for $R_{cp}$ as in Equation 28 rather than as a constant value. The variability between reflectance spectra obtained from samples having a common tissue-class/state-of-health classification, but using different instrument units decreases when using measured values for $R_{cp}$ as in Equation 28 rather than a constant value as in Equation 25.

In an alternative embodiment, processing of reflectance data includes applying Equation 28 without first fitting $R_{cp}$ values to a quadratic polynomial. Thus, processing is performed in accordance with Equation 29 to adjust data from a test sample, $I_m$, to produce adjusted reflectance R, as follows:

$$R(i,\lambda,t') = [I_m(i,\lambda,t')/(I_{cp}(i,\lambda,t')>_i] \cdot [<I_{fc}(i,\lambda,t_o)>_i/I_{fc}(i,\lambda,t_o)] \cdot R_{cp} \quad (29)$$

Applying Equation 29, however, introduces an inconsistency in the reflectance spectra at about 490 nm, caused, for example, by the intensity from the 60% reflectivity factory calibration target exceeding the linear range of the CCD array. This can be avoided by using a darker factory calibration target in the factory NIST target test 314, for example, a target having a known diffuse reflectance from about 10% to about 30%.

Results from the factory/PM custom target test 312, the factory/PM NIST target test 314, and the pre-patient custom target test 330 provide the correction factors shown in blocks 324, 326, and 334, respectively used in preprocessing reflectance data from a patient scan using the BB1 white light source 188 and the BB2 white light source 190 shown in FIGS. 4, 7, and 8. Correction factors in block 324 represent background-subtracted, power-monitor-corrected (power-corrected), and null-target-subtracted reflectance data from a given factory/PM custom target test 312 (cp) and are shown in Equations 30 and 31:

$$FCCTMMBB1 = <I_{cp,BB1}(i,\lambda,t_o)>_{i,masked} - FC\text{-}NULLBB1 \quad (30)$$

$$FCCTMMBB2 = <I_{cp,BB2}(i,\lambda,t_o)>_{i,masked} - FC\text{-}NULLBB2 \quad (31)$$

where FCNULLBB1 and FCNULLBB2 are given by Equations 4 and 5, and $<>_{i,masked}$ represents a one-dimensional array of mean data computed on a pixel-by-pixel basis in regions of area 445 of the scan pattern 444 of FIG. 20.

Correction factors in block 326 of FIG. 10 represent ratios of background-subtracted, power-corrected, and null-target-subtracted reflectance data from a factory/PM custom target test 312 (cp) and a factory/PM NIST standard target test 314 (fc) and are shown in Equations 32, 33, and 34:

$$FCBREF1[] = \frac{\langle I_{fc,BB1}(i,\lambda,t_o)_{\text{avg of 4}} - FCNULLBB1\rangle_i}{I_{fc,BB1}(i,\lambda,t_o)_{\text{avg of 4}} - FCNULLBB1} \quad (32)$$

$$FCBREF2[] = \frac{\langle I_{fc,BB2}(i,\lambda,t_o)_{\text{avg of 4}} - FCNULLBB2\rangle_i}{I_{fc,BB2}(i,\lambda,t_o)_{\text{avg of 4}} - FCNULLBB2} \quad (33)$$

$$CALREF = [0.5 \cdot (FCCTMMBB1/<FCBREF1[]>_i) + (FCCTMBB2/<FCBREF2[]>_i)]_{interp,fit} \quad (34)$$

where values of the two-dimensional arrays $I_{fc,BB1}$ and $I_{fc,BB2}$ are averages of data using the target at each of four positions, rotated 90° between each position; and all divisions, subtractions, and multiplications are on a location-by-location, pixel-by-pixel basis. The correction factor, CALREF, is a one-dimensional array of values of the quantity in brackets [] on the right side of Equation 34, interpolated such that they correspond to wavelengths at 1-nm intervals between λ=360 nm and λ=720 nm. The interpolated values are then fit with a quadratic or other polynomial to reduce noise.

Correction factors in block 334 of FIG. 10 represent background-subtracted, power-corrected, internal-stray-light-corrected reflectance data from a pre-patient custom target test 330 (cp) and are given in Equations 35 and 36 as follows:

$$BREFMBB1 = \langle I_{cp,BB1}(i,\lambda,t') - SLBB1 \rangle_i \quad (35)$$

$$BREFMBB2 = \langle I_{cp,BB2}(i,\lambda,t') - SLBB2 \rangle_i \quad (36)$$

where SLBB1 and SLBB2 are as shown in Equations 19 and 20.

Steps #4, 5, and 6 in each of blocks 342 and 344 of the spectral data pre-processing block diagram 340 of FIG. 11 include processing patient reflectance data using the correction factors from blocks 324, 326, and 334 of FIG. 10 computed using results of the factory/PM custom target test 312, the factory/PM NIST standard target test 314, and the pre-patient custom target test 330.

In step #4 of block 342 in FIG. 11, the array of background-subtracted, power-corrected, internal-stray-light-subtracted patient reflectance data obtained using the BB1 light source is multiplied by the two-dimensional array correction factor, FCBREF1[], and then in step #5, is divided by the correction factor BREFMBB1. After filtering using, for example, a 5-point median filter and a second-order 27-point Savitsky-Golay filter, the resulting array is linearly interpolated using results of the wavelength calibration step 302 in FIG. 10 to produce a two-dimensional array of spectral data corresponding to wavelengths ranging from 360 nm to 720 nm in 1-nm increments at each of 499 interrogation points of the scan pattern 202 shown in FIG. 5. This array is multiplied by CALREF in step #6 of block 342 in FIG. 11, and pre-processing of the BB1 spectral data in this embodiment is complete.

Steps #4, 5, and 6 in block 344 of FIG. 11 concern processing of BB2 data and is directly analogous to the processing of BB1 data discussed above.

Steps #4 and in block 346 of FIG. 1 include processing fluorescence data using factory/PM-level correction factors, applied after background correction (step #1), power monitor correction (step #2), and stray light correction (step #3) of fluorescence data from a test sample. Steps #4 and include application of correction factors sFCDYE and IRESPONSE, which come from the factory/PM fluorescent dye cuvette test 306 and the factory/PM tungsten source test 308 in FIG. 10.

The factory/PM tungsten source test 308 accounts for the wavelength response of the collection optics for a given instrument unit. The test uses a quartz tungsten halogen lamp as a light source. Emission from the tungsten filament approximates a blackbody emitter. Planck's radiation law describes the radiation emitted into a hemisphere by a blackbody (BB) emitter:

$$W_{BB}(\lambda) = [a \cdot (CE)]/[\lambda^5 \cdot \{\exp(b/\lambda T) - 1\}] \quad (37)$$

where $a = 2\pi hc^2 = 3.742 \times 10^{16}$ [W(nm)$^4$/cm$^2$]; $b = hc/k = 1.439 \times 10^7$ [(nm)K]; T is source temperature; CE is a fitted parameter to account for collection efficiency; and both T and CE are treated as variables determined for a given tungsten lamp by curve-fitting emission data to Equation 37.

Figure 23:
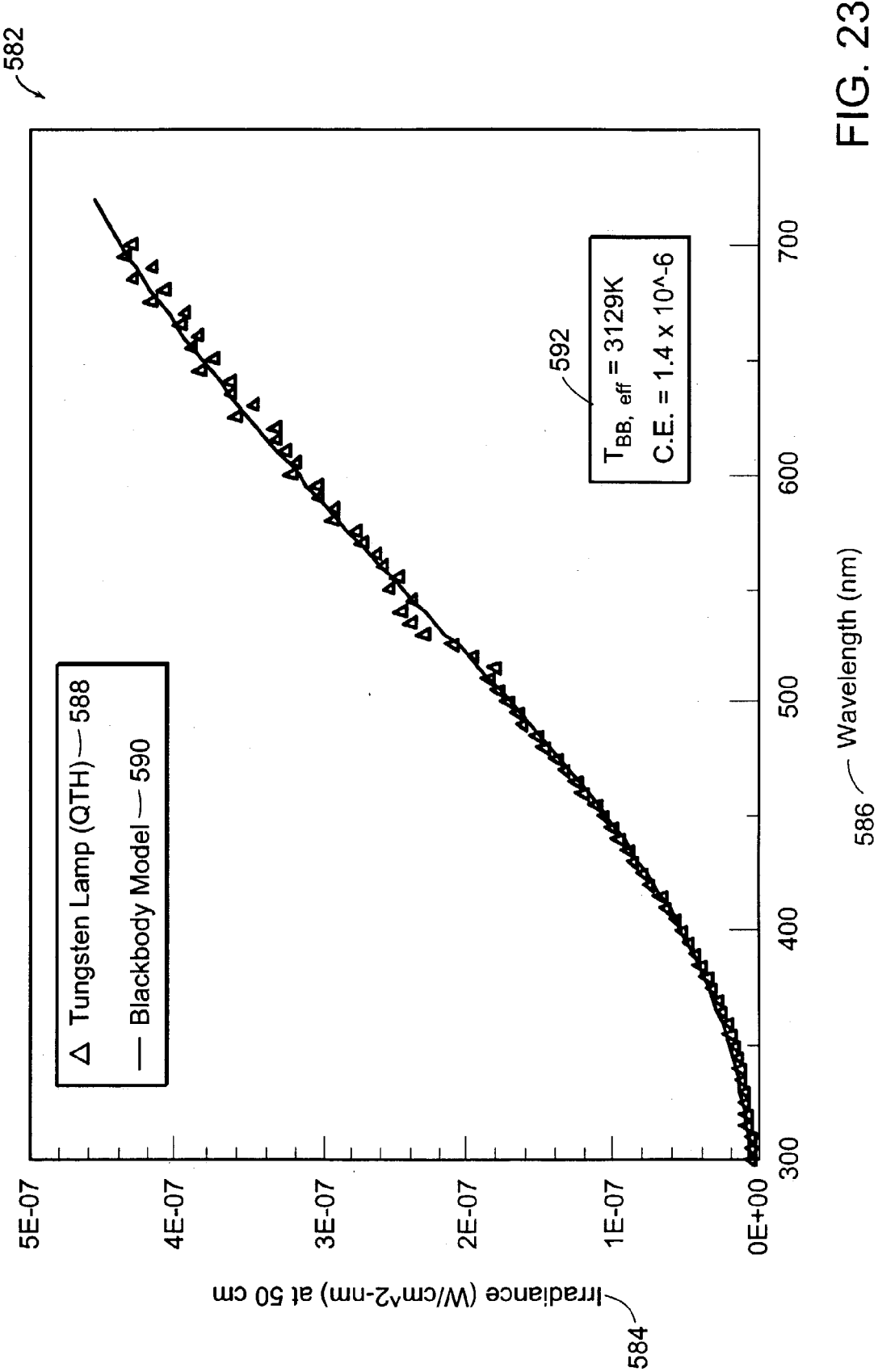
FIG. 23 shows a graph depicting the spectral irradiance of a NIST traceable Quartz-Tungsten-Halogen lamp, along with a model of a blackbody emitter, used for determining an instrument response correction for fluorescence intensity data according to an illustrative embodiment of the invention.

The lamp temperature, T, is determined by fitting NIST-traceable source data to Equation 37. FIG. 23 shows a graph 582 depicting the spectral irradiance 584, $W_{NIST\ lamp}$, of a NIST-traceable quartz-tungsten-halogen lamp, along with a curve fit 590 of the data to the model in Equation 37 for blackbody irradiance, $W_{BB}$. Since the lamp is a gray-body and not a perfect blackbody, Equation 37 includes a proportionality constant, CE. This proportionality constant also accounts for the "collection efficiency" of the setup in an instrument 102 as depicted in the tissue characterization system 100 of FIG. 1. In the illustrative embodiment, the target from which measurements are obtained is about 50-cm away from the lamp and has a finite collection cone that subtends a portion of the emission hemisphere of the lamp. Thus, while $W_{BB}(\lambda)$ in Equation 37 has units of [W/nm], calibration values for a given lamp used in the instrument 102 in FIG. 1 has units of [W/cm$^2$-nm at 50 cm distance]. The two calibration constants, CE and T, are obtained for a given lamp by measuring the intensity of the given lamp relative to the intensity of a NIST-calibrated lamp using Equation 38:

$$W_{lamp} = [I_{lamp}/I_{NIST\ lamp}] \cdot W_{NIST\ lamp} \quad (38)$$

Then, values of T and CE are determined by plotting $W_{lamp}$ versus wavelength and curve-fitting using Equation 37. The curve fit provides a calibrated lamp response, $I_{lamp}(\lambda)$, to which the tungsten lamp response measured during factory/PM testing 308 at a given interrogation point and using a given instrument, $S_{lamp}(i,\lambda)$, is compared. This provides a measure of "instrument response", IR(i,λ), for the given point and the given instrument, as shown in Equation 39:

$$IR(i,\lambda) = S_{lamp}(i,\lambda)/I_{lamp}(\lambda) \quad (39)$$

The factory/PM tungsten source test 308 in FIG. 10 includes collecting an intensity signal from the tungsten lamp as its light reflects off an approximately 99% reflective target. The test avoids shadowing effects by alternately positioning the tungsten source at each of two locations—for example, on either side of the probe head 192 at locations corresponding to the white light source locations 188, 190 shown in FIG. 8—and using the data for each given interrogation point corresponding to the source position where the given point is not in shadow.

Once the instrument response measure, IR(i,λ), is obtained, a correction factor is determined such that its value is normalized to unity at a given wavelength, for example, at λ=500 nm. Thus, the distance between the lamp and the detecting aperture, the photoelectron quantum efficiency of the detector, and the reflectivity of the target do not need to be measured.

According to the illustrative embodiment, the fluorescence component of the spectral data pre-processing 114 of the system 100 of FIG. 1 corrects a test fluorescence intensity signal, $S_F(i,\lambda)$, for individual instrument response by applying Equation 40 to produce $I_F(i,\lambda)$, the instrument-response-corrected fluorescence signal:

$$I_F(i,\lambda) = S_F(i,\lambda) \div [\{500 \cdot IR(i,\lambda)\}/\{\lambda \cdot IR(i,500)\}] \quad (40)$$

where IR(i,500) is the value of the instrument response measure IR at point i and at wavelength λ=500 nm; and where the term λ/500 converts the fluorescence intensity from energetic to photometric units, proportional to fluorophore concentration. In one embodiment, the differences between values of IR at different interrogation points is small, and a mean of IR(λ) over all interrogation points is used in place of IR(i,λ) in Equation 40.

The fluorescent dye cuvette test 306 accounts for variations in the efficiency of the collection optics 200 of a given instrument 102. Fluorescence collection efficiency depends on a number of factors, including the spectral response of the optics and detector used. In one embodiment, for example, the collection efficiency tends to decrease when a scan approaches the edge of the optics. A fluorescent dye cuvette test 306, performed as part of factory and/or preventive maintenance (PM) calibration, provides a means of accounting for efficiency differences.

An about 50-mm-diameter cuvette filled with a dye solution serves as a target for the fluorescent dye cuvette test 306 to account for collection optic efficiency variation with interrogation point position and variation between different units. The factory/PM dye-filled cuvette test 306 includes obtaining the peak intensity of the fluorescence intensity signal at each interrogation point of the dye-filled cuvette, placed in the calibration target port of the instrument 102, and comparing it to a mean peak intensity of the dye calculated for a plurality of units.

Illustratively, a calibrated dye cuvette can be prepared as follows. First, the fluorescence emission of a 10-mm-pathlength quartz cuvette filled with ethylene glycol is obtained. The ethylene glycol is of 99+% spectrophotometric quality, such as that provided by Aldrich Chemical Company. The fluorescence emission reading is verified to be less than about 3000 counts, particularly at wavelengths near the dye peak intensity. An approximately $2.5 \times 10^{-4}$ moles/L solution of coumarin-515 in ethylene glycol is prepared. Coumarin-515 is a powdered dye of molecular weight 347, produced, for example, by Exciton Chemical Company. The solution is diluted with ethylene glycol to a final concentration of about $1.2 \times 10^{-5}$ moles/L. Then, a second 10-mm-pathlength quartz cuvette is filled with the coumarin-515 solution, and an emission spectrum is obtained. The fluorescence emission reading is verified to have a maximum between about 210,000 counts and about 250,000 counts. The solution is titrated with either ethylene glycol or concentrated coumarin-515 solution until the peak lies in this range; Once achieved, 50-mm-diameter quartz cuvettes are filled with the titrated standard solution and flame-sealed.

A correction factor for fluorescence collection efficiency can be determined as follows. First, the value of fluorescence intensity of an instrument-response-corrected signal, $I_F(i,\lambda)$, is normalized by a measure of the UV light energy delivered to the tissue as in Equation 41:

$$F_T(i,\lambda) = [I_F(i,\lambda)/P_m(i)] \cdot [P_m/E_{\mu J}]_{FC/PM} \tag{41}$$

where $F_T(i,\lambda)$ is the instrument-response-corrected, power-monitor-corrected fluorescence intensity signal; $P_m(i)$ is a power-monitor reading that serves as an indirect measure of laser energy, determined by integrating or adding intensity readings from pixels on a CCD array corresponding to a portion on which a beam of the output laser light is directed; and $[P_m/E_{\mu J}]_{FC/PM}$ is the ratio of power monitor reading to output laser energy determined during factory calibration and/or preventive maintenance (FC/PM).

Figure 31:
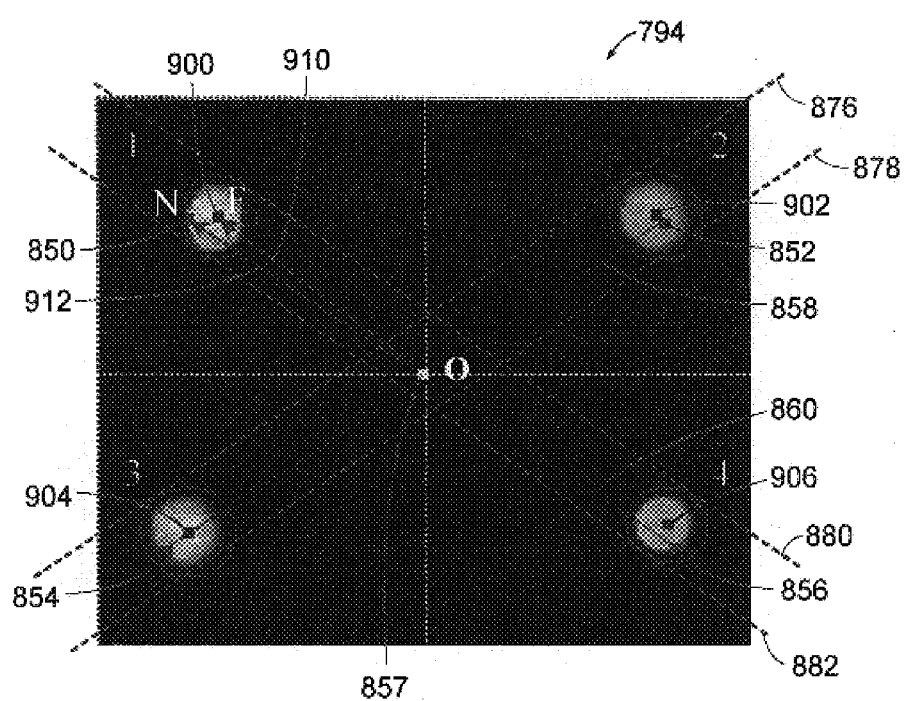
FIG. 31 illustrates some of the steps of the target focus validation procedure of FIG. 30 as applied to the target in FIG. 29A.

Next, the illustrative embodiment includes obtaining the fluorescence intensity response of a specific unit at a specific interrogation point (region) in its scan pattern using a cuvette of the titrated coumarin-515 dye solution as the target, and comparing that response to a mean fluorescence intensity response calculated for a set of units, after accounting for laser energy variations as in Equation 41. Equation 42 shows a fluorescence collection efficiency correction factor for a given unit applied to an instrument-response-corrected fluorescence signal, $I_F(i,\lambda)$, along with the energy correction of Equation 41:

$$F_T(i,\lambda) = \frac{I_F(i,\lambda)}{P_m(i)} \cdot \left(\frac{P_m}{E_{\mu J}}\right)_{PM} \cdot \left(\frac{\left\langle \frac{I_{Dye}(251,\lambda_p)}{P_m(251)} \cdot \frac{P_m}{E_{\mu J}} \right\rangle_{Instruments}}{\frac{I_{Dye}(i,\lambda_p)}{P_m(i)} \cdot \frac{P_m}{E_{\mu J}}}\right)_{PM} \tag{42}$$

where $I_{Dye}(i,\lambda_p)$ is the peak measured fluorescence intensity at interrogation position i using the dye-filled cuvette, as shown in FIG. 31; $\lambda_p$ is the wavelength (or its approximate pixel index equivalent) corresponding to the peak intensity; and the quantity in brackets $\langle\rangle_{Instruments}$ is the mean power-corrected intensity at interrogation point 251, corresponding to the center of the exemplary scan pattern of FIG. 5, calculated for a plurality of units.

Figure 24:
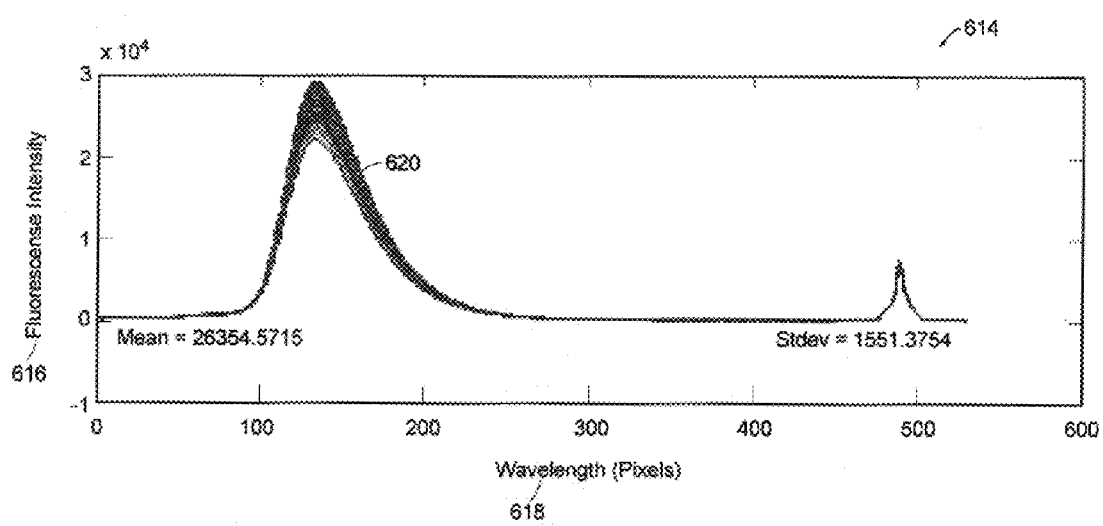
FIG. 24 shows a graph depicting as a function of wavelength the fluorescence intensity of a dye solution at each region of a 499-point scan pattern according to an illustrative embodiment of the invention.

The fluorescence collection efficiency tends to decrease when the scans approach the edge of the optics. FIG. 24 shows typical fluorescence spectra from the dye test 306. The graph 614 in FIG. 24 depicts as a function of wavelength 618 the fluorescence intensity 616 of the dye solution at each region of a 499-point scan pattern. The curves 620 all have approximately the same peak wavelength, $\lambda_p$, but the maximum fluorescence intensity values vary.

Figure 25:
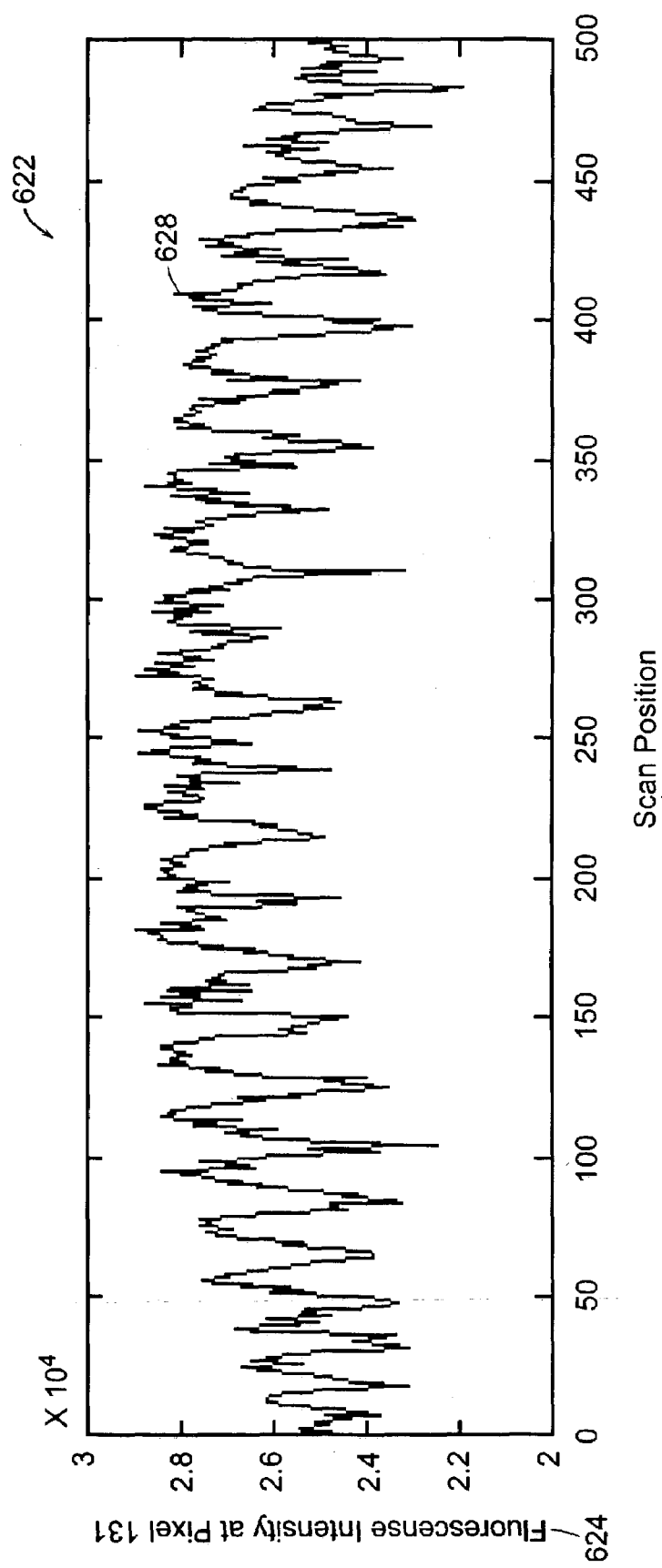
FIG. 25 shows a graph depicting as a function of scan position the fluorescence intensity of a dye solution at a wavelength corresponding to a peak intensity seen in FIG. 24 according to an illustrative embodiment of the invention.

FIG. 25 shows how the peak fluorescence intensity (intensity measured at pixel 131 corresponding approximately to $\lambda_p$) 624, determined in FIG. 24, varies as a function of scan position (interrogation point) 626. Oscillations are due at least in part to optic scanning in the horizontal plane, while the lower frequency frown pattern is due to scan stepping in the vertical plane. According to the illustrative embodiment, curves of the fluorescence intensity of the dye cuvette at approximate peak wavelength are averaged to improve on the signal-to-noise ratio.

Equation 42 simplifies to Equations 43 and 44 as follows:

$$F_T(i,\lambda) = \frac{I_F(i,\lambda)}{P_m(i)} \cdot \left(\frac{\left\langle \frac{I_{Dye}(251,\lambda_p)}{P_m(251)} \cdot \frac{P_m}{E_{\mu J}} \right\rangle_{Instruments}}{\frac{I_{Dye}(i,\lambda_p)}{P_m(i)}}\right)_{PM} \tag{43}$$

$$= \frac{I_F(i,\lambda)}{P_m(i)} \cdot FCDYE(i) \tag{44}$$

The term, $[P_m/E_{\mu J}]_{PM}$, drops out of equation 42. Variations in laser energy measurements become less important as the energy is averaged over multiple measurements made on many instruments.

In FIG. 10, the correction factor sFCDYE in block 318 is a one-dimensional scalar array and is calculated using Equation 45:

$$sFCDYE = \left(\frac{\left\langle \frac{I_{Dye}(251,\lambda_p)}{P_m(251)} \cdot \frac{P_m}{E_{\mu J}} \right\rangle_{Instruments}}{\frac{I_{Dye}(i,\lambda_p)}{P_m(i)}}\right) \tag{45}$$

Here, values of $I_{Dye}(i,\lambda_p)$ are background-subtracted, power-corrected, and null-target-subtracted.

In FIG. 10, the correction factor IRESPONSE in block 320 is a one-dimensional array and is calculated using the results of the factory/PM tungsten source test 308, as in Equation 46:

$$IRESPONSE = [\{500 \cdot IR(i,\lambda)\}/\{\lambda \cdot IR(i,500)\}] \quad (46)$$

where IR(i,500) is the value of the instrument response measure IR given in Equation 39 at point i and at wavelength $\lambda = 500$ nm.

Steps #4 and 5 in block 346 of the fluorescence spectral data pre-processing block diagram 340 of FIG. 11 include processing fluorescence data using sFCDYE and IRESPONSE as defined in Equations 45 and 46. The fluorescence data pre-processing proceeds by background-subtracting, power-correcting, and stray-light-subtracting fluorescence data from a test sample using Bkgnd[], sPowerMonitor[], and SLFL as shown in Steps #1, 2, and 3 in block 346 of FIG. 11. Then, the result is multiplied by sFCDYE and divided by IRESPONSE on a pixel-by-pixel, location-by-location-basis. Next, the resulting two-dimensional array is smoothed using a 5-point median filter, then a second-order, 27-point Savitsky-Golay filter, and interpolated using the pixel-to-wavelength conversion determined in block 302 of FIG. 10 to produce an array of data corresponding to a spectrum covering a range from 360 nm to 720 nm at 1-nm intervals, for each of 499 interrogation points of the scan pattern.

As a further feature, the stability of fluorescence intensity readings are monitored between preventive maintenance procedures. This may be performed prior to each patient scan by measuring the fluorescence intensity of the center plug 438 of the custom target 426 shown in FIG. 19 and comparing the result to the expected value from the most recent preventive maintenance test. If the variance from the expected value is significant, and/or if the time between successive preventive maintenance testing is greater than about a month, the following correction factor may be added to those in block 346 of FIG. 11:

$$FSTAB = \frac{\left[\frac{I_{ct}(251, \lambda_p)}{P_m(251)}\right]_{PM}}{\left[\frac{I_{ct}(251, \lambda_p)}{P_m(251)}\right]_{PP}} \quad (47)$$

where PM denotes preventive maintenance test results; PP denotes pre-patient test results; $I_{ct}(251, \lambda_p)$ is the fluorescence peak intensity reading at scan position 251 (center of the custom target) at peak wavelength $\lambda_p$; and $P_m$ is the power monitor reading at scan position 251.

The spectral data pre-processing 114 in FIG. 11 further includes a procedure for characterizing noise and/or applying a threshold specification for acceptable noise performance. Noise may be a significant factor in fluorescence spectral data measurements, particularly where the peak fluorescence intensity is below about counts/µJ (here, and elsewhere in this specification, values expressed in terms of counts/µJ are interpretable in relation to the mean fluorescence of normal squamous tissue being 70 ct/µJ at about 450 nm).

The procedure for characterizing noise includes calculating a power spectrum for a null target background measurement. The null target background measurement uses a null target having about 0% reflectivity, and the measurement is obtained with internal lights off and optionally with all external lights turned off so that room lights and other sources of stray light do not affect the measurement. Preferably, the procedure includes calculating a mean null target background spectrum of the individual null target background spectra at all interrogation points on the target—for example, at all 499 points of the scan pattern 202 of FIG. 5. Then, the procedure subtracts the mean spectrum from each of the individual null target background spectra and calculates the Fast Fourier Transform (FFT) of each mean-subtracted spectrum. Then, a power spectrum is calculated for each FFT spectrum and a mean power spectrum is obtained.

Figure 26:
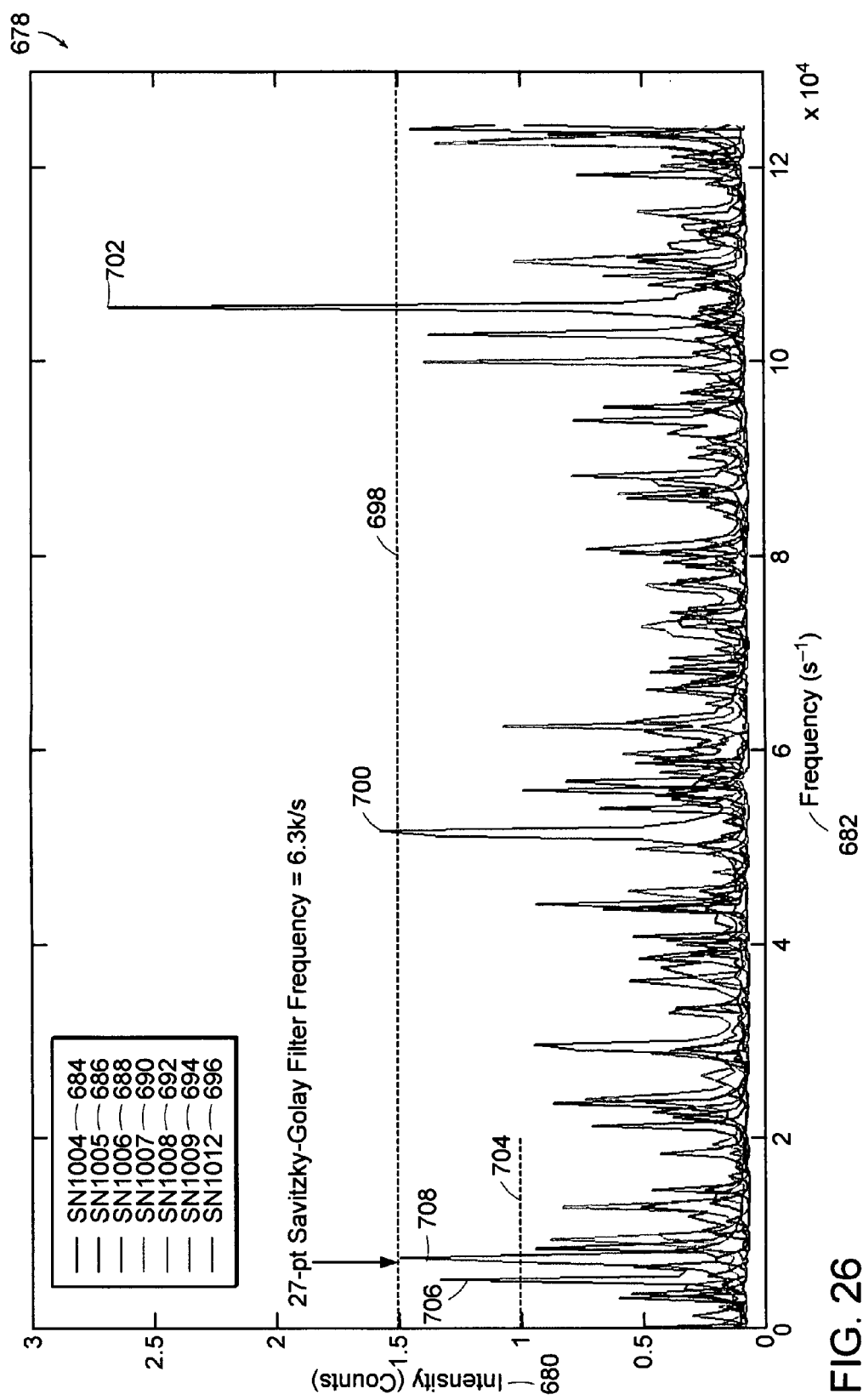
FIG. 26 shows a graph depicting exemplary mean power spectra for various individual instruments subject to a noise performance criterion according to an illustrative embodiment of the invention.

FIG. 26 shows a graph 678 depicting exemplary mean power spectra for various individual instruments 684, 686, 688, 690, 692, 694, 696. A 27-point Savitzky-Golay filter has an approximate corresponding frequency of about 6300 s$^{-1}$ and frequencies above about 20,000 s$^{-1}$ are rapidly damped by applying this filter. In the case of a 27-point Savistzky-Golay filter, spectral data pre-processing in FIG. 11 further includes applying a threshold maximum criterion of 1 count in the power spectrum for frequencies below 20,000 s$^{-1}$. Here, data from an individual unit must not exhibit noise greater than 1 count at frequencies below 20,000 s$^{-1}$ in order to satisfy the criterion. In FIG. 26, the criterion is not met for units with curves 692 and 696, since their power spectra contain points 706 and 708, each exceeding 1 count at frequencies below 20,000 s$^{-1}$. The criterion is met for all other units.

According to an alternative illustrative embodiment, a second noise criterion is applied instead of or in addition to the aforementioned criterion. The second criterion specifies that the mean power spectral intensity for a given unit be below 1.5 counts at all frequencies. In FIG. 26, the criterion is not met for units with curves 692 and 696, since their power spectra contain points 700 and 702, each exceeding 1.5 counts.

The illustrative spectral data pre-processing 114 in FIG. 11 and/or the factory/PM 110 and pre-patient calibration 116 and correction in FIG. 10 further includes applying one or more validation criteria to data from the factory/PM 110 and pre-patient 114 calibration tests. The validation criteria identify possibly-corrupted calibration data so that the data are not incorporated in the core classifier algorithms and/or the spectral masks of steps 132 and 130 in the system 100 of FIG. 1. The validation criteria determine thresholds for acceptance of the results of the calibration tests. According to the illustrative embodiment, the system 100 of FIG. 1 signals if validation criteria are not met and/or prompts retaking of the data.

Validation includes validating the results of the factory/PM NIST 60% diffuse reflectance target test 314 in FIG. 10. Validation may be necessary, for example, because the intensity of the xenon lamp used in the test 314 oscillates during a scan over the 25-mm scan pattern 202 of FIG. 5. The depth of modulation of measured reflected light intensity depends, for example, on the homogeneity of the illumination source at the target, as well as the collection efficiency over the scan field. The depth of modulation also depends on how well the target is aligned relative to the optical axis. In general, inhomogeneities of the illumination source are less important than inhomogeneities due to target misalignment, since illumination source inhomogeneities are generally accounted for by taking the ratio of reflected light intensity to incident light intensity. Thus, the calibration 110, 116 methods use one or two metrics to sense off-center targets and prompt retaking of data.

One such metric includes calculating a coefficient of variation, $CV_i(\lambda)$, of measured reflected light intensity across the scan field according to Equation 48:

$$CV_i(\lambda) = \frac{\text{std}(I(\lambda, i))_i}{\text{mean}(I(\lambda, i))_i} \quad (48)$$

where $I(\lambda,i) = \text{mean } [\{I_{target}(\lambda,i) - I_{bkg}(\lambda,i)\}/P_m(i)]_{4 \text{ rotations}}$; "std" represents standard deviation; i represents an interrogation point; $\lambda$ represents wavelength (in one embodiment, between 370 nm and 700 nm); and $P_m(i)$ represents the power monitor value for interrogation point i. $I(\lambda,i)$ is the mean of the background-subtracted (bkg), power-monitor-corrected reflectance intensity values from the NIST target measured 4 times, rotating the target 90° between each measurement. Validation according to the metric of Equation 48 requires the value of $CV_i(\lambda)$ be less than an experimentally-determined, fixed value.

Another metric from the 60% diffuse target test 314 includes calculating the relative difference, RD, between the minimum and maximum measured intensity over the scan field according to Equation 49:

$$RD(\lambda) = \frac{2 \cdot [\max(I'(\lambda, i))_i - \min(I'(\lambda, i))_i]}{[\max(I'(\lambda, i))_i + \min(I'(\lambda, i))_i]} \quad (49)$$

where $I'(\lambda, i) =$ $$\text{mean}\left(\left(\frac{I_{traget}(\lambda, i) - I_{bkg}(\lambda, i)}{P_m(i)}\right) \cdot \text{mean}(P_m(i))_i\right)_{4 \text{ rotations}}$$

Here, $I'$ is scaled by the mean of the power monitor values. In one embodiment, the relative difference, RD, between the minimum and maximum computed in Equation 49 is more sensitive to off-centered targets than the coefficient of variation, $CV_i$, computed in Equation 48. Here, validation requires the value of $RD(\lambda)$ be less than an experimentally-determined, fixed value. In the illustrative embodiment, validation requires that Equation 50 be satisfied as follows:

$RD(\lambda) < 0.7$ for $\lambda$ between 370 nm and 700 nm (50)

where $RD(\lambda)$ is given by Equation 49.

Validation also includes validating the results of the tungsten source test 308 from FIG. 11 using the approximately 99% diffuse reflectivity target. This test includes obtaining two sets of data, each set corresponding to a different position of the external tungsten source lamp. Data from each set that are not affected by shadow are merged into one set of data. Since the power monitor correction is not applicable for this external source, a separate background measurement is obtained.

The illustrative calibration methods 110, 116 use one or two metrics to validate data from the tungsten source test 308. One metric includes calculating a coefficient of variation, $CV_i(\lambda)$, of the mean foreground minus the mean background data, $W(\lambda,i)$, of the merged set of data, as in Equation 51:

$$CV_i(\lambda) = \frac{\text{std}(W(\lambda, i))_i}{\text{mean}(W(\lambda, i))_i} \quad (51)$$

where the coefficient of variation, $CV_i(\lambda)$, is calculated using the mean instrument spectral response curve, IR, averaging over all interrogation points of the scan pattern. Validation requires the value of $CV_i(\lambda)$ be less than an experimentally-determined, fixed value. In the illustrative embodiment, validation requires that Equation 52 be satisfied for all interrogation points i:

$CV_i(\lambda) < 0.5$ for $\lambda$ between 370 nm and 700 nm (52)

where $CV_i(\lambda)$ is given by Equation 51.

A second metric includes calculating a mean absolute difference spectrum, $MAD(\lambda)$, comparing the current spectral response curve to the last one measured, as in Equation 53:

$MAD(\lambda) = \text{mean}(|IR_t(i,\lambda) - IR_{t-1}(i,\lambda)|)_i$ (53)

where the instrument spectral response curve, IR, is given by Equation 39. Validation requires the value of $MAD(\lambda)$ be less than an experimentally-determined, fixed value. In one embodiment, validation requires that Equation 54 be satisfied:

$MAD(\lambda) < 0.2$ for $\lambda$ between 370 nm and 700 nm (54)

where $MAD(\lambda)$ is given by Equation 53.

Validation can further include validating the results of the fluorescent dye cuvette test 306 in FIG. 10, used to standardize fluorescence measurements between individual units and to correcting for variation in collection efficiency as a unit collects data at interrogation points of a scan pattern. The illustrative calibration methods 110, 116 use one or more metrics to validate data from the fluorescent dye cuvette test 306 using a coefficient of variation, $CV_i(\lambda)$, of dye cuvette intensity, $I_{Dye}$, as in Equation 55:

$$CV_i(\lambda) = \frac{\text{std}(I_{Dye}(\lambda, i))_i}{\text{mean}(I_{Dye}(\lambda, i))_i} \quad (55)$$

The coefficient of variation, $CV_i(\lambda)$, in Equation 55 between about 470 nm and about 600 nm is generally representative of fluorescence efficiency variations over the scan pattern. The coefficient of variation at about 674 nm is a measure of how well the collection system blocks the 337-nm excitation light. As the excitation light passes over the surface of the cuvette, the incidence and collection angles go in and out of phase, causing modulation around 574 nm. The coefficient of variation at about 425 nm is a measure of the cleanliness of the cuvette surface and is affected by the presence of fingerprints, for example. The coefficient of variation below about 400 nm and above about 700 nm is caused by a combination of the influence of 337-nm stray excitation light and reduced signal-to-noise ratio due to limited fluorescence from the dye solution at these wavelengths.

One metric includes calculating a mean coefficient of variation, $CV_i(\lambda)$, according to Equation 55, between about 500 nm and about 550 nm, and comparing the mean coefficient of variation to an experimentally-determined, fixed value. According to the illustrative embodiment, validation requires that Equation 56 be satisfied:

$$\text{mean } CV_i(\lambda) < 0.06 \text{ for } \lambda \text{ between 500 nm and 550 nm} \quad (56)$$

A second metric includes requiring the coefficient of variation at about 674 nm be less than an experimentally-determined, fixed value. In one embodiment, validation requires that Equation 57 be satisfied for all interrogation points i:

$$CV_i(674) < 0.5 \quad (57)$$

where $CV_i(\lambda)$ is calculated as in Equation 55.

Validation can also include validating results of the fluorescent dye cuvette test 306 using both Equations 56 and 57. Here, applying Equation 56 prevents use of data from tests where the scan axis is significantly shifted relative to the center of the optical axis, as well as tests where the cuvette is not full or is off-center. Applying Equation 57 prevents use of data from tests where a faulty UV emission filter is installed or where the UV filter degrades over time, for example.

Validation can also include validating the results of the 10% diffuse reflectivity custom target tests 312, 330 in FIG. 10. Here, an off-center target may result in a faulty test due to interference at regions near the edge of the target, as well as regions near the fluorescent and phosphorescent plugs that are improperly masked. According to the illustrative embodiment, validation of the custom target tests 312, 330 requires that the relative difference between the minimum and maximum intensity, $RD(\lambda)$, is below a pre-determined value, where $RD(\lambda)$ is calculated as in Equation 58:

$$RD(\lambda) = \frac{2 \cdot [\max(I'(\lambda, i))_{i=mask} - \min(I'(\lambda, i))_{i=mask}]}{[\max(I'(\lambda, i))_{i=mask} + \min(I'(\lambda, i))_{i=mask}]} \quad (58)$$

where $(I'(\lambda,i))_{i=mask}$ refers to all scan positions except those masked to avoid the plugs, as shown in FIGS. 19 and 20. In one embodiment, validation requires that Equation 59 be satisfied:

$$RD(\lambda) < 1.2 \text{ for } \lambda \text{ between 370 nm and 700 nm} \quad (59)$$

where $RD(\lambda)$ is calculated as in Equation 58.

The invention can also validate the results of the null target test 304, 328 in FIG. 10. The null target test is used, for example, to account for internal stray light in a given instrument. According to the illustrative embodiment, a maximum allowable overall amount of stray light is imposed. For example, in one preferred embodiment, validation of a null target test 304, 328 requires the integrated energy, IE, be below a predetermined value, where IE is calculated from background-subtracted, power-monitor-corrected null target reflectance intensity measurements, as in Equation 60:

$$IE = \int_{370}^{700} \text{mean}\left(\frac{null(\lambda, i) - bkg(\lambda, i)}{P_m(i)}\right)_i \cdot \text{mean}(P_m(i))_i \, d\lambda \quad (60)$$

$$\approx \sum_{370}^{700} \text{mean}\left(\frac{null(\lambda, i) - bkg(\lambda, i)}{P_m(i)}\right)_i \cdot \text{mean}(P_m(i))_i$$

where $\Delta\lambda$ in the summation above is about 1-nm. In one embodiment, validation requires that Equation 61 be satisfied:

$$IE < 4000 \text{ counts} \quad (61)$$

where IE is calculated as in Equation 60.

The invention may also employ validation of the open air target test 310 in FIG. 10. Like the null target test 304, 328, the open air target test is used in accounting for internal stray light in a given instrument. According to the illustrative embodiment, validation of an open air target test 310 requires the integrated energy, IE, be below a predetermined value, where IE is calculated as in Equation 60, except using open air reflectance intensity measurements in place of null target measurements, null($\lambda$,i). By way of-example, in one case validation requires that the value of integrated energy for the open air test be below 1.2 times the integrated energy from the null target test, calculated as in Equation 60.

According to another feature, the invention validates the power monitor corrections used in the calibration tests in FIG. 10. Patient and calibration data that use a power monitor correction may be erroneous if the illumination source misfires. According to one approach, validation of a power monitor correction requires that the maximum raw power monitor intensity reading, $P_{m,max}(i)$, be greater than a predetermined minimum value and/or be less than a predetermined maximum value at each interrogation point i. In the illustrative embodiment, validation requires that Equation 62 be satisfied:

$$6000 \text{ counts} < P_{m\,max}(i) < 30{,}000 \text{ counts for all } i \quad (62)$$

According to the illustrative embodiment, spectral data pre-processing 114 in FIG. 11 includes accounting for the result of the real-time motion tracker 106 in the system 100 of FIG. 1 when applying the correction factors in block diagram 340 of FIG. 11. As discussed herein, the system 100 of FIG. 1 applies the calibration-based corrections in FIG. 11 to spectral data acquired from a patient scan. These corrections are applied by matching spectral data from each interrogation point in a patient scan to calibration data from a corresponding interrogation point. However, a patient scan of the 499 interrogation points shown in the scan pattern 202 of FIG. 5 takes approximately 12 seconds. During those 12 seconds, it is possible that the tissue will shift slightly, due to patient movement. Thus, spectral data obtained during a scan may not correspond to an initial index location, since the tissue has moved from its original position in relation to the scan pattern 202. The real-time motion tracker 106 of FIG. 1 accounts for this movement by using data from video images of the tissue to calculate, as a function of scan time, a translational shift in terms of an x-displacement and a y-displacement. The motion tracker 106 also validates the result by determining whether the calculated x,y translational shift accurately accounts for movement of the tissue in relation to the scan pattern or some other fixed standard such as the initial position of component(s) of the data acquisition system (the camera and/or spectroscope). The motion tracker 106 is discussed in more detail below.

Illustratively, the spectral data pre-processing 114 in FIG. 11 accounts for the result of the real-time motion tracker 106 by applying a calibration spectra lookup method. The lookup method includes obtaining the motion-corrected x,y coordinates corresponding to the position of the center of an interrogation point from which patient spectral data is obtained during a patient scan. Then the lookup method includes using the x,y coordinates to find the calibration data obtained from an interrogation point whose center is closest to the x,y coordinates.

The scan pattern 202 of FIG. 5 is a regular hexagonal sampling grid with a pitch (center-to-center distance) of 1.1 mm and a maximum interrogation point spot size of 1 mm. This center-to-center geometry indicates a horizontal pitch of 1.1 mm, a vertical pitch of about 0.9527 mm, and a maximum corner distance of the circumscribed regular hexagon to the center of 0.635 mm. Thus, the illustrative lookup method finds the calibration interrogation point whose center is closest to the motion-corrected x,y coordinates of a patient scan interrogation point by finding coordinates of a calibration point that is less than 0.635 mm from x,y.

The background spectra, Bkgnd[], in FIG. 11, are obtained at nearly the same time patient spectral data are obtained and no motion correction factor is needed to background-subtract patient spectral data. For example, at a given interrogation point during a patient scan, the system 100 of FIG. 1 pulses the UV light source on only while obtaining fluorescence data, then pulses the BB1 light source on only while obtaining the first set of reflectance data, then pulses the BB2 light source on only while obtaining the second set of reflectance data, then obtains the background data, Bkgnd[], at the interrogation point with all internal light sources off. All of this data is considered to be approximately simultaneous and no motion correction factor is needed for the Bkgnd[] calibration data.

The real-time motion tracker 106 of FIG. 1 uses video data obtained from the tissue contemporaneously with the spectral data. In addition to motion correction, the system of FIG. 1 uses video (image) data to determine image masks for disease probability computation, to focus the probe 142 through which spectral and/or image data is acquired, and to compute a brightness and contrast correction and/or image enhancement for use in disease overlay display.

Patient Scan Procedure

Figure 27A:
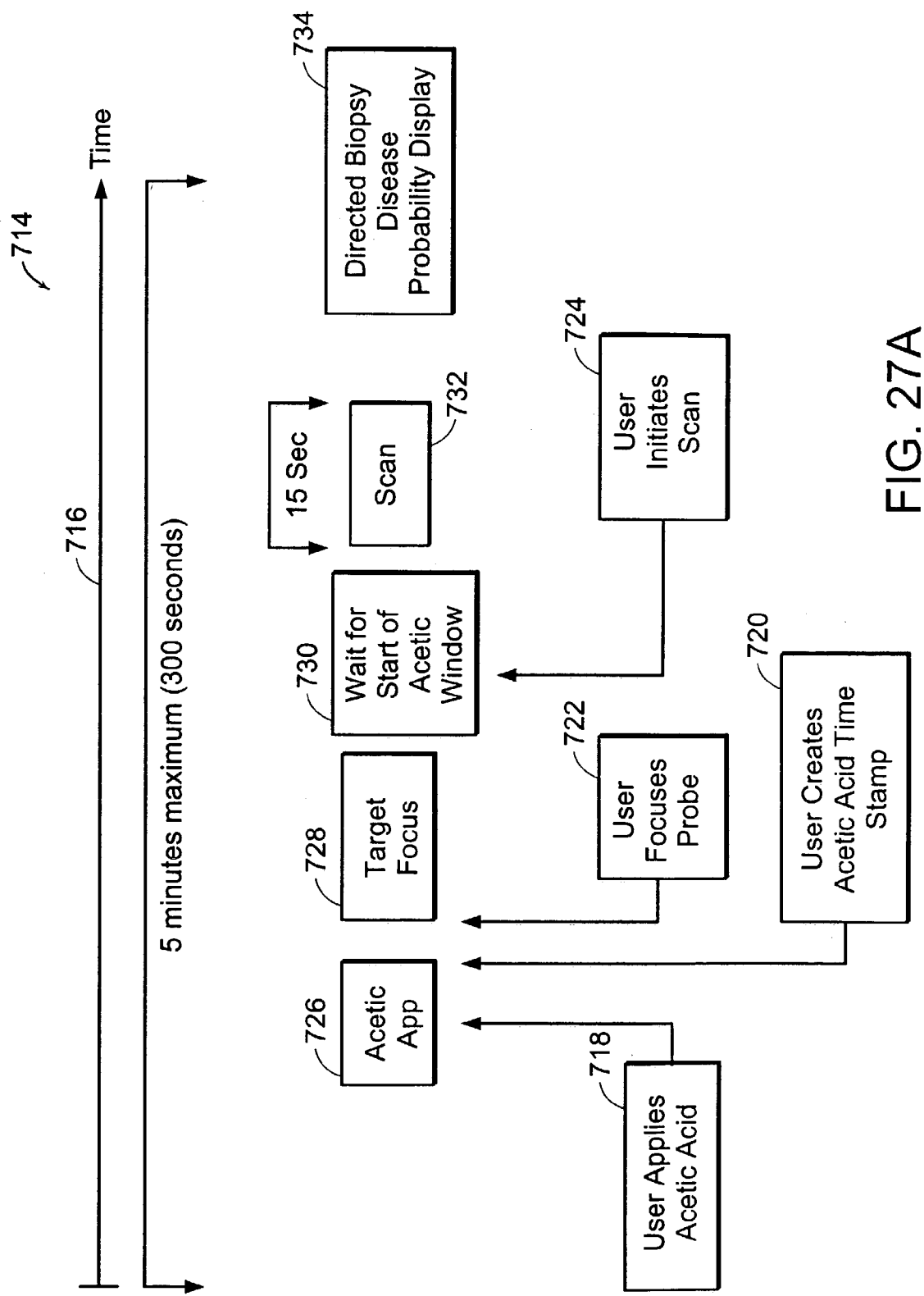
FIG. 27A is a block diagram featuring steps an operator performs in relation to a patient scan using the system of FIG. 1 according to an illustrative embodiment of the invention.

FIG. 27A is a block diagram 714 showing steps an operator performs before a patient scan as part of spectral data acquisition 104 in the system 100 of FIG. 1, according to an illustrative embodiment of the invention. The steps in FIG. 27A are arranged sequentially with respect to a time axis 716. As shown, an operator applies a contrast agent to the tissue sample 718, marks the time application is complete 720, focuses the probe 142 through which spectral and/or image data will be obtained 722, then initiates the spectral scan of the tissue 724 within a pre-determined window of time.

According to the illustrative embodiment, the window of time is an optimum range of time following application of contrast agent to tissue within which an approximately 12 to 15 second scan can be performed to obtain spectral data that are used to classify tissue samples with a high degree of sensitivity and selectivity. The optimum window should be long enough to adequately allow for restarts indicated by focusing problems or patient movement, but short enough so that the data obtained is consistent. Consistency of test data is needed so that tissue classification results for the test data are accurate and so that the test data may be added to a bank of reference data used by the tissue classification scheme. In one illustrative embodiment, the optimum window is expressed in terms of a fixed quantity of time following application of contrast agent. In another illustrative embodiment, the optimum window is expressed in terms of a threshold or range of a trigger signal from the tissue, such as a reflectance intensity indicative of degree of tissue whiteness.

The contrast agent in FIG. 27A is a solution of acetic acid. According to one exemplary embodiment, the contrast agent is a solution between about 3 volume percent and about 6 volume percent acetic acid in water. More particularly, in one preferred embodiment, the contrast agent is an about 5 volume percent solution of acetic acid in water. Other contrast agents may be used, including, for example, formic acid, propionic acid, butyric acid, Lugol's iodine, Shiller's iodine, methylene blue, toluidine blue, indigo carmine, indocyanine green, fluorescein, and combinations of these agents.

According to the illustrative embodiment, the time required to obtain results from a patient scan, following pre-patient calibration procedures, is a maximum of about 5 minutes. Thus, in FIG. 27A, the five-minute-or-less procedure includes applying acetic acid to the tissue sample 726; focusing the probe (142) 728; waiting, if necessary, for the beginning of the optimum pre-determined window of time for obtaining spectral data 730; obtaining spectral data at all interrogation points of the tissue sample 732; and processing the data using a tissue classification scheme to obtain a diagnostic display 734. The display shows, for example, a reference image of the tissue sample with an overlay indicating regions that are classified as necrotic tissue, indeterminate regions, healthy tissue (no evidence of disease, NED), and CIN 2/3 tissue, thereby indicating where biopsy may be needed.

The times indicated in FIG. 27A may vary. For example, if the real-time motion tracker 106 in the system of FIG. 1 indicates too much movement occurred during a scan 732, the scan 732 may be repeated if there is sufficient time left in the optimum window.

FIG. 27B is a block diagram 738 showing a time line for the spectral scan 732 indicated in FIG. 27A. In the embodiment shown in FIG. 27B, a scan of all interrogation points of the scan pattern (for example, the scan pattern 202 of FIG. 5) takes from about 12 seconds to about 15 seconds, during which time a sequence of images is obtained for motion tracking, as performed in step 106 of the system 100 of FIG. 1. By the time a scan begins, a motion-tracking starting image 742 and a target laser image 744 have been obtained 740. The target laser image 744 may be used for purposes of off-line focus evaluation, for example. During the acquisition of spectral data during the scan, a frame grabber 120 (FIG. 1) obtains a single image about once every second 746 for use in monitoring and/or correcting for movement of the tissue from one frame to the next. In FIG. 27B, a frame grabber acquires images 748, 750, 752, 754, 756, 758, 760, 762, 764, 766, 768 that are used to track motion that occurs during the scan.

Image data from a video subsystem is used, for example, in target focusing 728 in FIG. 27A and in motion tracking 106, 746 in FIG. 27B. Image data is also used in detecting the proper alignment of a target in a calibration procedure, as well as detecting whether a disposable is in place prior to contact of the probe with a patient. Additionally, in one embodiment, colposcopic video allows a user to monitor the tissue sample throughout the procedure.

Video Calibration and Focusing

Figure 28:
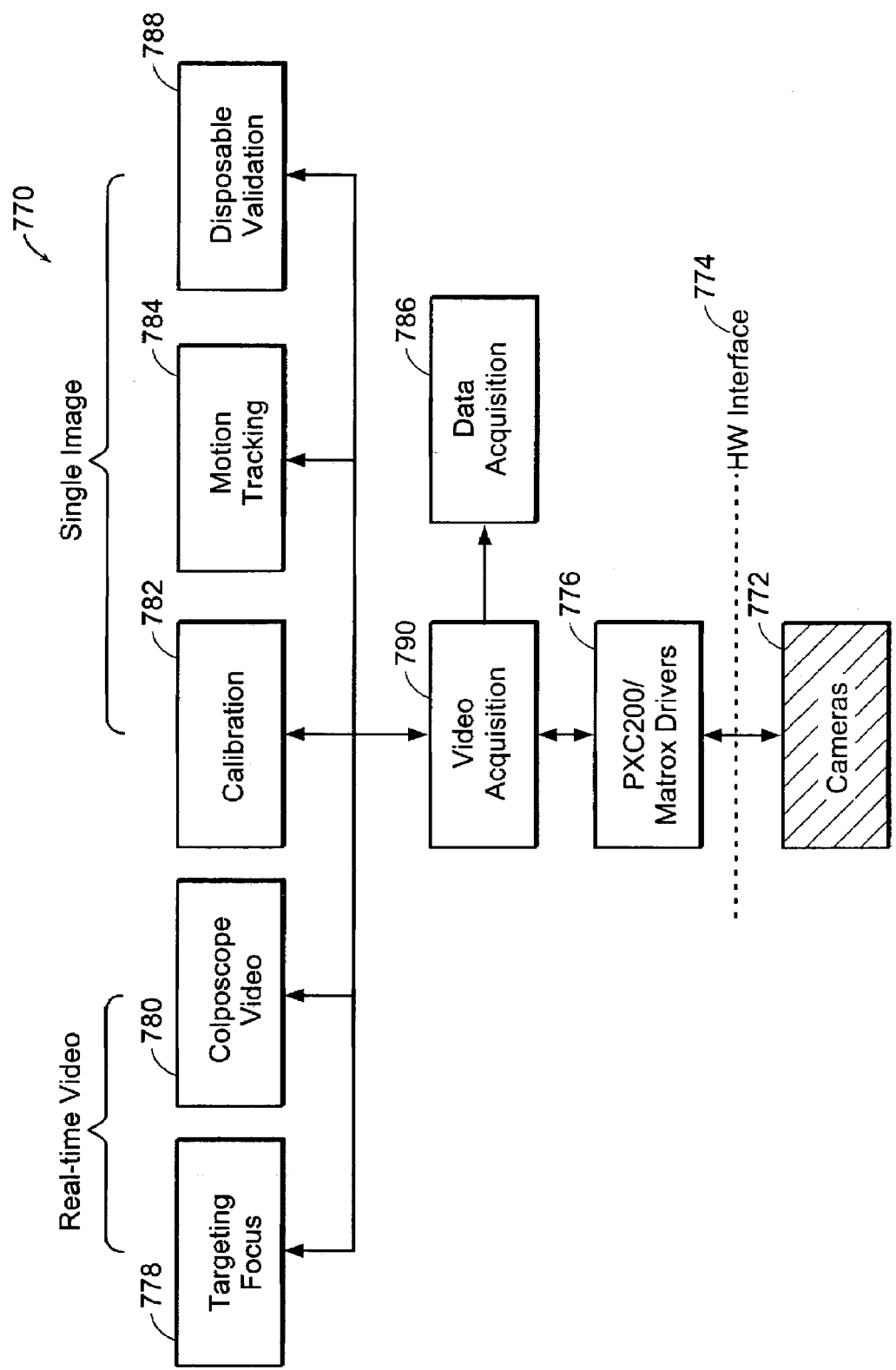
FIG. 28 is a block diagram showing the architecture of a video system used in the system of FIG. 1 and how it relates to other components of the system of FIG. 1 according to an illustrative embodiment of the invention.

FIG. 28 is a block diagram 770 that shows the architecture of an illustrative video subsystem used in the system 100 of FIG. 1. FIG. 28 shows elements of the video subsystem in relation to components of the system 100 of FIG. 1. The video subsystem 770 acquires single video images and real-time (streaming) video images. The video subsystem 770 can post-process acquired image data by applying a mask overlay and/or by adding other graphical annotations to the acquired image data. Illustratively, image data is acquired in two frame buffers during real-time video acquisition so that data acquisition and data processing can be alternated between buffers. The camera(s) 772 in the video subsystem 770 of FIG. 28 include a camera located in or near the probe head 192 shown in FIG. 4, and optionally includes a colposcope camera external to the probe 142 for visual monitoring of the tissue sample during testing. In one illustrative embodiment, only the probe head camera is used. FIG. 28 shows a hardware interface 774 between the cameras 772 and the rest of the video subsystem 770. The frame grabber 120 shown in FIG. 1 acquires video data for processing in other components of the tissue characterization system 100. In one embodiment, the frame grabber 120 uses a card for video data digitization (video capture) and a card for broadband illumination (for example, flash lamps) control. For example, one embodiment uses a Matrox Meteor 2 card for digitization and an Imagenation PXC-200F card for illumination control, as shown in block 776 of FIG. 28.

Real-time (streaming) video images are used for focusing the probe optics 778 as well as for visual colposcopic monitoring of the patient 780. Single video images provide data for calibration 782, motion tracking 784, image mask computation (used in tissue classification) 786, and, optionally, detection of the presence of a disposable 788. In some illustrative embodiments, a single reference video image of the tissue sample is used to compute the image masks 108 in the system 100 of FIG. 1. This reference image is also used in determining a brightness and contrast correction and/or other visual enhancement 126, and is used in the disease overlay display 138 in FIG. 1.

The illustrative video subsystem 770 acquires video data 790 from a single video image within about 0.5 seconds. The video subsystem 770 acquires single images in 24-bit RGB format and is able to convert them to grayscale images. For example, image mask computation 108 in FIG. 1 converts the RGB color triplet data into a single luminance value, Y, (grayscale intensity value) at each pixel, where Y is given by Equation 63:

$$Y=0.299R+0.587G+0.114B \quad (63)$$

where the grayscale intensity component, Y, is expressed in terms of red (R), green (G), and blue (B) intensities; and where R, G, and B range from 0 to 255 for a 24-bit RGB image.

Laser target focusing 728 is part of the scan procedure in FIG. 27A. An operator uses a targeting laser in conjunction with real-time video to quickly align and focus the probe 142 prior to starting a patient scan. In the illustrative embodiment, an operator performs a laser "spot" focusing procedure in step 728 of FIG. 27A where the operator adjusts the probe 142 to align laser spots projected onto the tissue sample. The user adjusts the probe while looking at a viewfinder with an overlay indicating the proper position of the laser spots. In one alternative embodiment, an operator instead performs a thin-line laser focusing method, where the operator adjusts the probe until the laser lines become sufficiently thin. The spot focus method allows for faster, more accurate focusing than a line-width-based focusing procedure, since thin laser lines can be difficult to detect on tissue, particularly dark tissue or tissue obscured by blood. Quick focusing is needed in order to obtain a scan within the optimal time window following application of contrast agent to the tissue; thus, a spot-based laser focusing method is preferable to a thin line method, although a thin line focus method may be used in alternative embodiments.

A target focus validation procedure 122 is part of the tissue characterization system 100 of FIG. 1, and determines whether the optical system of the instrument 102 is in focus prior to a patient scan. If the system is not in proper focus, the acquired fluorescence and reflectance spectra may be erroneous. Achieving proper focus is important to the integrity of the image masking 108, real-time tracking 106, and overall tissue classification 132 components of the system 100 of FIG. 1.

The focus system includes one or more target laser(s) that project laser light onto the patient sample prior to a scan. In one embodiment, the targeting laser(s) project laser light from the probe head 192 toward the sample at a slight angle with respect to the optical axis of the probe 142 so that the laser light that strikes the sample moves within the image frame when the probe is moved with respect to the focal plane. For example, in one illustrative embodiment, four laser spots are directed onto a target such that when the probe 142 moves toward the target during focusing, the spots move closer together, toward the center of the image. Similarly, when the probe 142 moves away from the target, the spots move further apart within the image frame, toward the corners of the image.

Figure 29A:
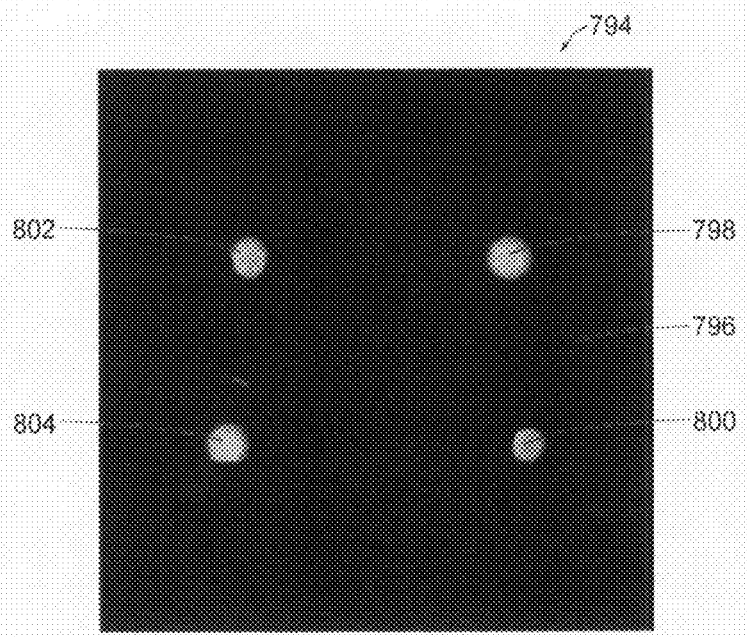
FIG. 29A is a single video image of a target of 10% diffuse reflectivity upon which an arrangement of four laser spots is projected in a target focus validation procedure according to an illustrative embodiment of the invention.
Figure 29B:
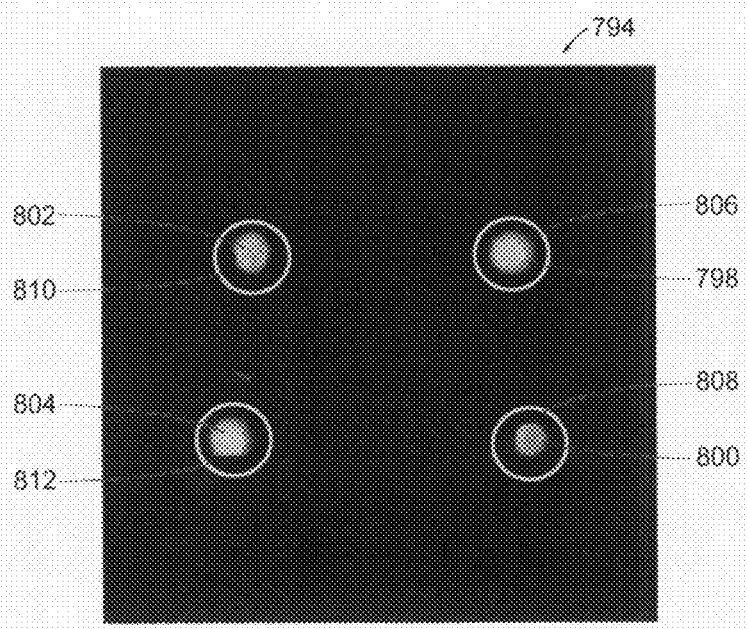
FIG. 29B depicts the focusing image on the target in FIG. 29A with superimposed focus rings viewed by an operator through a viewfinder according to an illustrative embodiment of the invention.

FIG. 29A is a single video image 794 of a target 796 of 10% diffuse reflectivity upon which a target laser projects a focusing pattern of four laser spots 798, 800, 802, 804. During laser target focusing 728 (FIG. 27A), an operator views four focus rings that are displayed at predetermined locations, superimposed on the target focusing image. FIG. 29B depicts the focusing image 794 on the target 796 in FIG. 29A with superimposed focus rings 806, 808, 810, 812. The operator visually examines the relative positions of the laser spots 798, 800, 802, 804 in relation to the corresponding focus rings 806, 808, 810, 812 while moving the probe head 192 along the optical axis toward or away from the target/tissue sample. When the laser spots lie within the focus rings as shown in FIG. 29B, the system is within its required focus range. The best focus is achieved by aligning the centers of all the laser spots with the corresponding centers of the focus rings. Alternatively, spot patterns of one, two, three, five, or more laser spots may be used for focus alignment.

It is generally more difficult to align laser spots that strike a non-flat tissue sample target than to align the spots on a flat, uniform target as shown in FIG. 29B. In some instances, a laser spot projected onto tissue is unclear, indistinct, or invisible. Visual evaluation of focus may be subjective and qualitative. Thus, a target focus validation procedure is useful to insure proper focus of a tissue target is achieved. Proper focus allows the comparison of both image data and spectral data from different instrument units and different operators.

In one illustrative embodiment, the system 100 of FIG. 1 performs an automatic target focus validation procedure using a single focus image. The focus image is a 24-bit RGB color image that is obtained before acquisition of spectral data in a patient scan. The focus image is obtained with the targeting laser turned on and the broadband lights (white lights) turned off. Automatic target focus validation includes detecting the locations of the centers of visible laser spots and measuring their positions relative to stored, calibrated positions ("nominal" center positions). Then, the validation procedure applies a decision rule based on the number of visible laser spots and their positions and decides whether the system is in focus and a spectral scan can be started.

Figure 30:
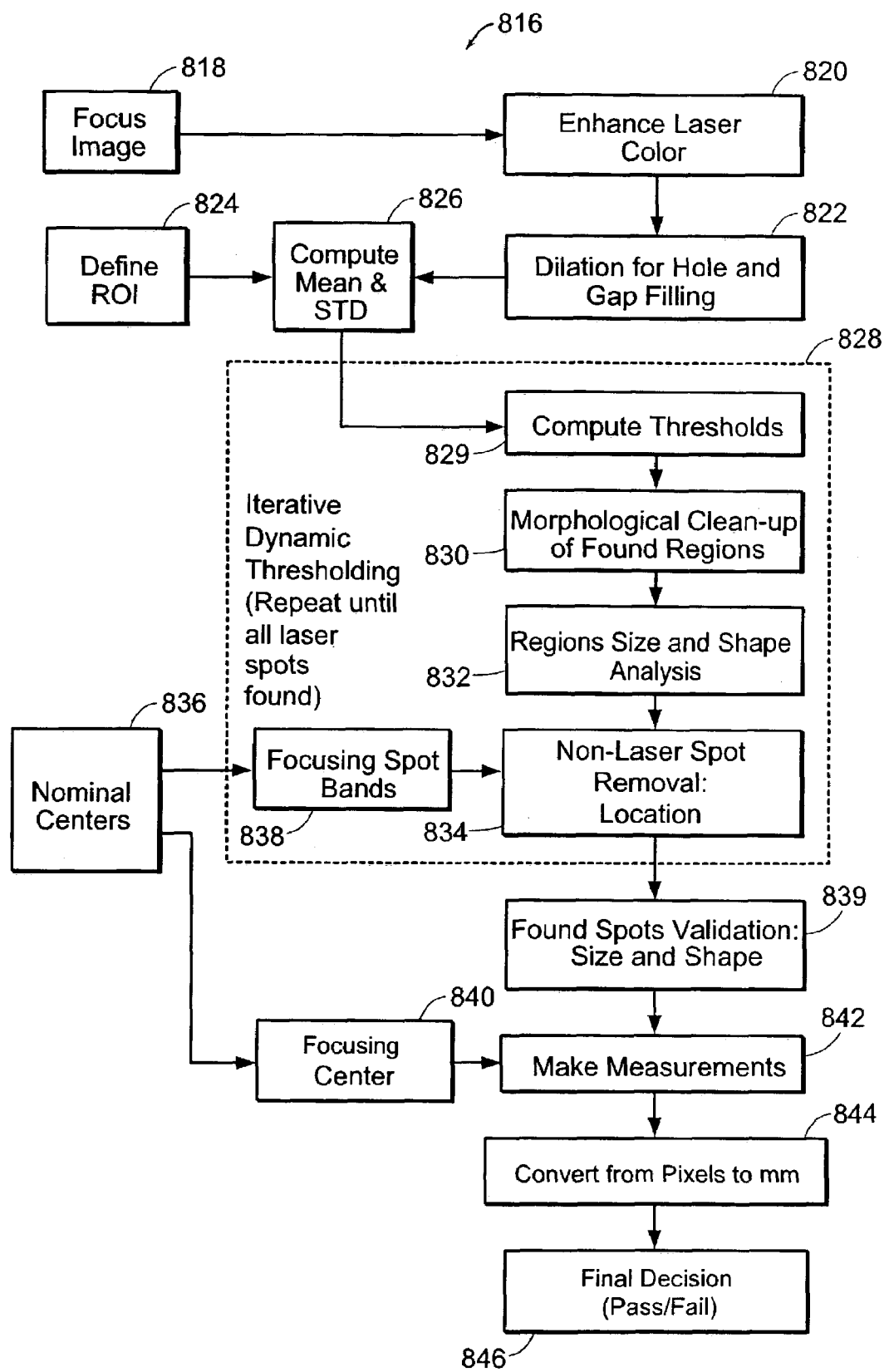
FIG. 30 is a block diagram of a target focus validation procedure according to an illustrative embodiment of the invention.

FIG. 30 is a block diagram 816 of a target focus validation procedure according to an illustrative embodiment of the invention. The steps include obtaining a 24-bit RGB focus image 818, performing image enhancement 820 to highlight the coloration of the laser spots, performing morphological image processing (dilation) to fill holes and gaps within the spots 822, defining a region of interest (ROI) of the image 824, and computing a mean and standard deviation 826 of the luminance values (brightness) of pixels within the region of interest. Next, the focus validation procedure iteratively and dynamically thresholds 828 the enhanced focus image using the computed mean and standard deviation to extract the laser spots. Between thresholding iterations, morphological processing 830 disconnects differentiated image objects and removes small image objects from the thresholded binary image, while a region analysis procedure 832 identifies and removes image objects located outside the bounds of the target laser spot pathways 838 and objects whose size and/or shape do not correspond to a target laser spot. After all thresholding iterations, the found "spots" are either verified as true target laser spots or are removed from the image 834, based on size, shape, and/or location. Next, in step 842, the focus validation procedure computes how far the centers of the found spots are from the nominal focus centers and converts the difference from pixels to millimeters in step 844. The validation procedure then applies a decision rule based on the number of found spots and their positions and decides whether the system is in focus such that a spectral scan of the patient can begin.

The focus validation procedure of FIG. 30 begins with obtaining the 24-bit RGB focus image and splitting it into R, G, and B channels. Each channel has a value in the range of 0 to 255. FIG. 31 depicts the RGB focus image 794 from FIG. 29A with certain illustrative geometry superimposed. FIG. 31 shows the four nominal spot focus centers 850, 852, 854, 856 as red dots, one of which is the red dot labeled "N" in quadrant 1. The nominal spot focus centers represent the ideal location of centers of the projected laser spots, achieved when the probe optics are in optimum focus. The nominal spot focus centers 850, 852, 854, 856 correspond to the centers of the rings 806, 808, 810, 812 in FIG. 29B. An (x,y) position is determined for each nominal focus center. A nominal image focus center (857), O, is defined by the intersection of the two red diagonal lines 858, 860 in FIG. 31. The red diagonal lines 858, 860 connect the two pairs of nominal spot focus centers 852, 854 in quadrants 2 and 3 and 850, 856 in quadrants 1 and 4, respectively. Also, the slopes of the two lines 858, 860 are computed for later use.

Step 820 in the procedure of FIG. 30 is image enhancement to highlight the coloration of the laser spots in contrast to the surrounding tissue. In one embodiment, the R value of saturated spots is "red clipped" such that if R is greater than 180 at any pixel, the R value is reduced by 50. Then, a measure of greenness, $G_E$, of each pixel is computed as in Equation 64:

$$G_E = G - R - 15 \tag{64}$$

where G is the green value of a pixel, R is the red value of the pixel, and 15 is a correction factor to remove low intensity noise, experimentally-determined here to be 15 gray levels.

Figure 32:
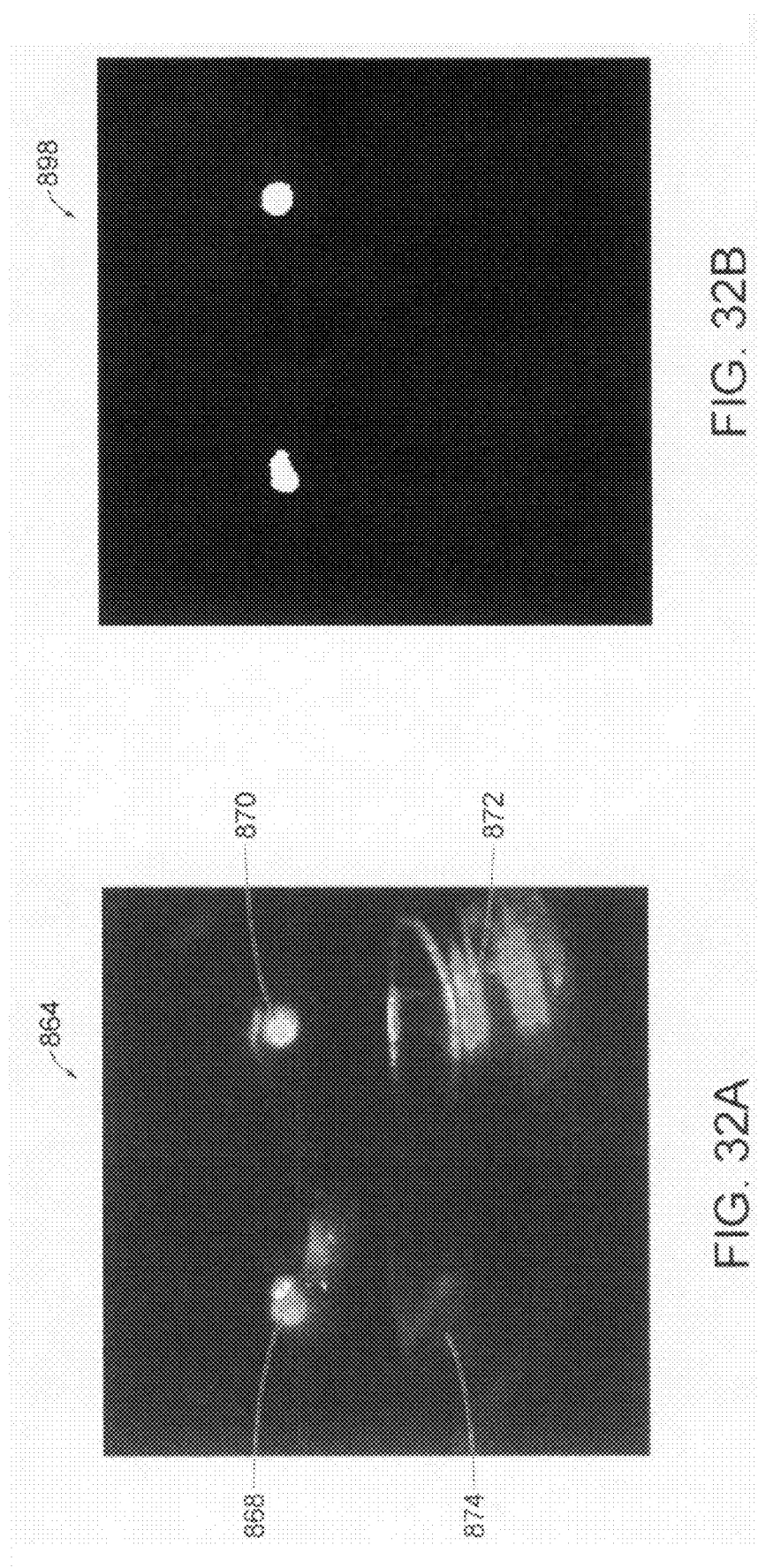
FIG. 32A represents the green channel of an RGB image of a cervical tissue sample, used in a target focus validation procedure according to an illustrative embodiment of the invention.
FIG. 32B represents an image of the final verified laser spots on the cervical tissue sample of FIG. 32A, verified during application of the target focus validation procedure of FIG. 30 according to an illustrative embodiment of the invention.

FIG. 32A represents the green channel of an RGB image 864 of a cervical tissue sample, used in an exemplary target focus validation procedure. In this image, only two top focus laser spots 868, 870 are clear. The lower right spot 872 is blurred/diffused while the lower left spot 874 is obscured. The green-channel luminance (brightness), $G_E$, of the green-enhanced RGB image 864 of FIG. 32A may be computed using Equation 64 and may be displayed, for example, as grayscale luminance values between 0 and 255 at each pixel.

In step 822 of FIG. 30, the focus validation procedure performs morphological dilation using a 3×3 square structuring element to fill holes and gaps within the found spots. Then in step 824, the procedure uses a pre-defined, circular region of interest (ROI) for computing a mean, M, and a standard deviation, STD, 826 of the greenness value, $G_E$, of the pixels within the ROI, which are used in iterative dynamic thresholding 828. According to the illustrative embodiment, the ROI is a substantially circular region with a 460-pixel diameter whose center coincides with the nominal image focus center, O.

Before iterative dynamic thresholding begins, $G_E$ is set equal to zero at a 50-pixel diameter border about the ROI. Then, iterative dynamic thresholding 828 begins by setting an iteration variable, p, to zero, then computing a threshold value, Th, as follows:

$$Th = M + p \cdot STD \tag{65}$$

where M and STD are defined from the ROI. Since p=0 in the first iteration, the threshold, Th, is a "mean" greenness value over the entire ROI in the first iteration. In this embodiment, image thresholding is a subclass of image segmentation that divides an image into two segments. The result is a binary image made up of pixels, each pixel having a value of either 0 (off) or 1 (on). In step 828 of the focus validation procedure of FIG. 30, the enhanced greenness value of a pixel corresponding to point (x,y), within the ROI, $G_E(x,y)$, is compared to the threshold value, Th. The threshold is applied as in Equation 66:

$$\text{IF } G_E(x,y) > Th, \text{ THEN the binary pixel value at } (x,y), B_T = 1, \text{ else } B_T = 0. \tag{66}$$

Iterative dynamic thresholding 828 proceeds by performing morphological opening 830 to separate nearby distinguishable image objects and to remove small objects of the newly thresholded binary image. According to the illustrative embodiment, the morphological opening 830 includes performing an erosion, followed by a dilation, each using a 3×3 square structuring element. The procedure then determines the centroid of each of the thresholded objects and removes each object whose center is outside the diagonal bands bounded by two lines that are 40 pixels above and below the diagonal lines 858, 860 in FIG. 31. These diagonal bands include the region between lines 876, 878 and the region between lines 880, 882 in FIG. 31, determined in step 838 of FIG. 30. An image object whose center lies outside these bands does not correspond to a target focus spot, since the centers of the focus laser spots should appear within these bands at any position of the probe along the optical axis. The spots move closer together, within the bands, as the probe moves closer to the tissue sample, and the spots move farther apart, within the bands, as the probe moves away from the tissue sample.

Next, step 832 of the thresholding iteration 828 computes an area (A), eccentricity (E), and equivalent diameter (ED) of the found image objects, and removes an object whose size and/or shape—described here by A, E, and ED—does not correspond to that of a focus laser spot. E and ED are defined as follows:

$$E=(1-b^2/a^2)^{0.5} \quad (67)$$

$$ED=2(A/\pi)^{0.5} \quad (68)$$

where a is the minor axis length and b is the major axis length in units of pixels. For example, step 832 applies Equation 69 as follows:

IF A>5000 OR IF E>0.99 OR IF ED>110, THEN
remove object (set $B_T=0$ for all pixels in
object). (69)

Other criteria may be applied. For example, Equation 70 may be applied in place of Equation 69:

IF A>2500 OR IF E>0.99 OR IF ED>80, THEN
remove object (set $B_r=0$ for all pixels in object). (70)

Next, the iteration variable, p, is increased by a fixed value, for example, by 0.8, and a new threshold is calculated using Equation 65. The iteration proceeds by applying the new threshold, performing a morphological opening, computing centroids of the newly thresholded regions, removing regions whose center position, size, and/or shape do not correspond to those of a target focus spot, and stepping up the value of the iteration variable p. Iterative dynamic thresholding proceeds until a pre-determined condition is satisfied. For example, the thresholding ends when the following condition is satisfied:

IF p>6 OR IF the number of qualified spots (image
objects)≦4, THEN STOP. (71)

Step 834 of the focus validation procedure eliminates any image object remaining after dynamic thresholding that does not meet certain laser spot size and shape criteria. For example, according to the illustrative embodiment, step 834 applies the condition in Equation 72 for each remaining image object:

IF A<80 OR IF E>0.85 OR IF ED<10, THEN
remove object. (72)

In an alternative embodiment, one or more additional criteria based on the position of each image object (found spot) are applied to eliminate objects that are still within the focus bands of FIG. 31, but are too far from the nominal centers 850, 852, 854, 856 to be valid focus spots.

FIG. 32B shows an image 898 of the cervical tissue sample of FIG. 32A following step 834, wherein the top two image objects were verified as target laser spots, while the bottom objects were eliminated.

Step 842 of the focus validation procedure assigns each of the found spots to its respective quadrant and computes the centroid of each found spot. FIG. 31 shows the found spots as blue dots 900, 902, 904, 906. Then for each found spot, step 842 computes the distance between the center of the spot to the nominal image focus center 857, O. For the focus spot center 900 labeled "F" in FIG. 31, this distance is $L_{OF}$, the length of the blue line 910 from point O to point F. The distance, between the nominal focus center, N, 850 corresponding to the quadrant containing the found spot, and the nominal image focus center 857, O, is $L_{ON}$, the length of the red line 912 from point O to point N. Step 842 of the focus validation procedure then determines a focus value for verified focus spot 900 equal to the difference between the lengths $L_{OF}$ and $L_{ON}$. The focus value of each of the verified focus spots is computed in this manner, and the focus values are converted from pixels to millimeters along the focus axis (z-axis) in step 844 of FIG. 30 using an empirically-determined conversion ratio—for example, 0.34 mm per pixel.

Next, the focus validation procedure of FIG. 30 applies a decision rule in step 846 based on the number of found spots and their positions. The decision rule is a quantitative means of deciding whether the system is in focus and a spectral scan of the tissue can begin. According to the illustrative embodiment, step 846 applies a decision rule given by Equations 73, 74, and 75:

IF 3 or more spots are found, THEN IF the focus
value determined in step 842 is ≦6 mm for any
3 spots OR IF the focus value is ≦4 mm for
any 2 spots, THEN "Pass", ELSE "Fail" (re-
quire refocus). (73)

IF only 2 spots are found, THEN IF the focus value
of any spot is ≧4 mm, THEN "Fail" (require
refocus), ELSE "Pass". (74)

IF ≦1 spot is found, THEN "Fail" (require refocus). (75)

Other decision rules may be used alternatively.

Figure 33:
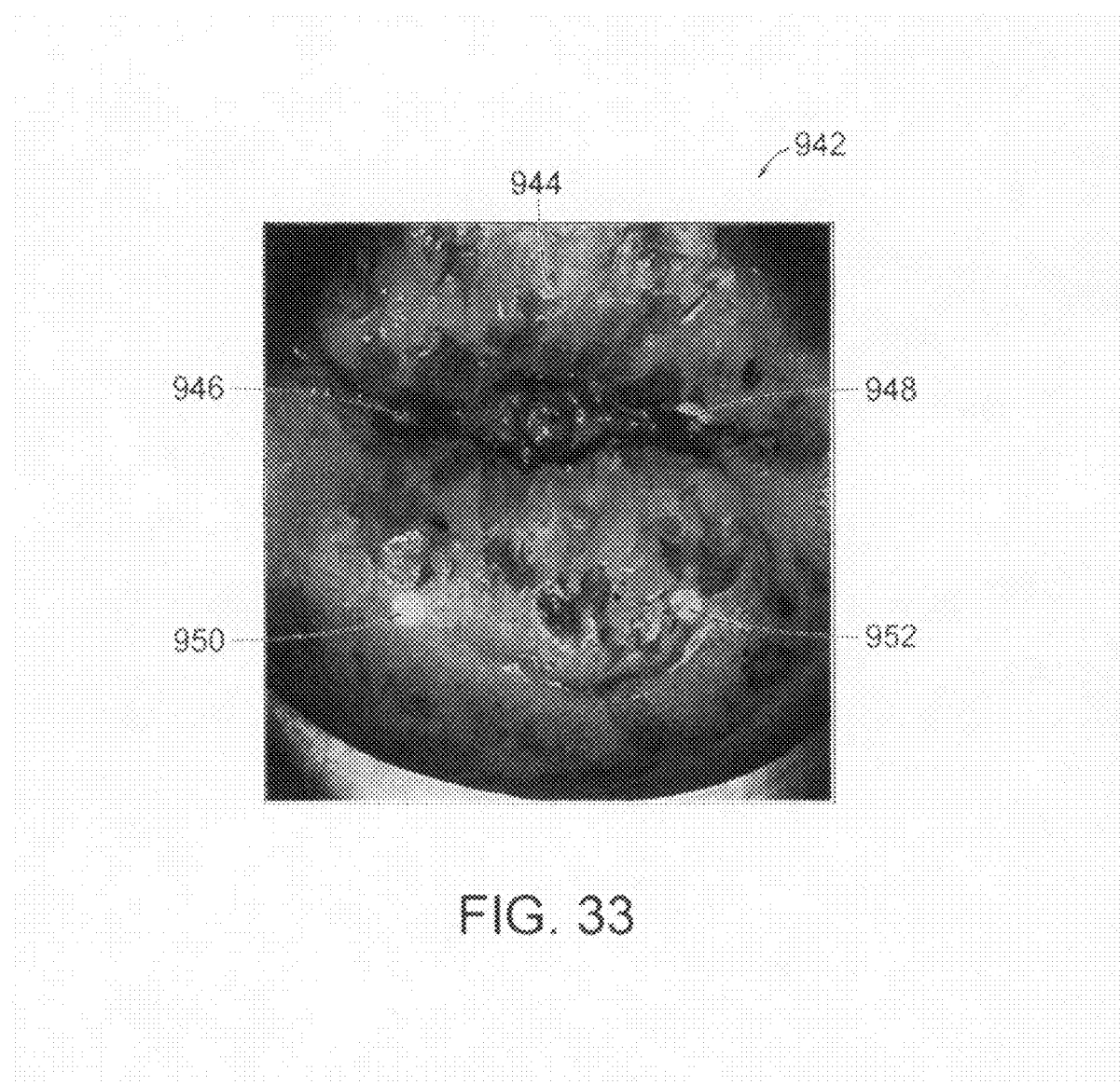
FIG. 33 depicts a cervix model onto which laser spots are projected during an exemplary application of the target focus validation procedure of FIG. 30, where the cervix model is off-center such that the upper two laser spots fall within the os region of the cervix model, according to an illustrative embodiment of the invention.
Figure 34:
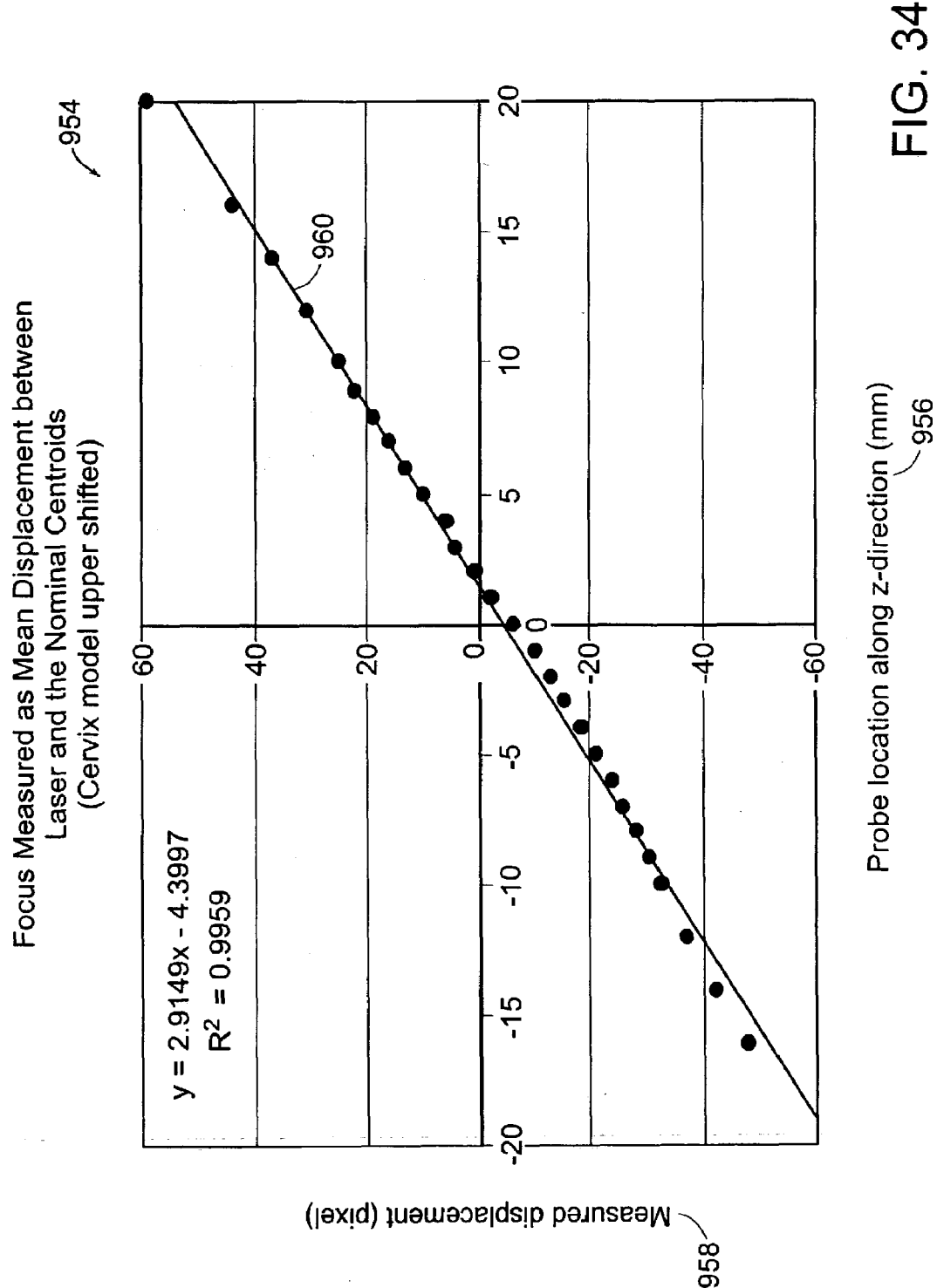
FIG. 34 shows a graph depicting, as a function of probe position, the mean of a measure of focus of each of the four laser spots projected onto the off-center cervix model of FIG. 33 in the target focus validation procedure of FIG. 30, according to an illustrative embodiment of the invention.

FIGS. 33 and 34 show the application of the focus validation procedure of FIG. 30 using a rubber cervix model placed so that the two upper laser spots are within the os region. For this example, the distance between the edge of the probe head 192 and the target (or target tissue) is approximately 100 mm at optimum focus, and the distance light travels between the target (or target tissue) and the first optic within the probe 142 is approximately 130 mm at optimum focus.

FIG. 33 is a 24-bit RGB target laser focus image 942 of a rubber cervix model 944 onto which four laser spots 946, 948, 950, 952 are projected. The cervix model 944 is off-center in the image 942 such that the two upper laser spots 946, 948 lie within the os region. FIG. 34 shows a graph 954 depicting as a function of probe position relative to the target tissue 956, the mean of a focus value 958 (in pixels) of each of the four laser spots 946, 948, 950, 952 projected onto the rubber cervix model 944. The curve fit 960 of the data indicates the relationship between measured focus, f, 958 and probe location, $z_p$, 956 (in mm) is substantially linear. However, the curve is shifted down and is not centered at (0,0). This indicates a focus error introduced by the manual alignment used to obtain the z=0 focus position. Such an error may prompt a "Fail" determination in step 846 of the focus validation procedure of FIG. 30, depending on the chosen decision rule. FIG. 34 indicates the difficulty in making a visual focus judgment to balance the focus of the four spots, particularly where the target surface (tissue sample) is not flat and perpendicular to the optical axis (z-axis) of the probe system.

The focus validation procedure illustrated in FIG. 30 provides an automatic, quantitative check of the quality of focus. Additionally, in the illustrative embodiment, the focus validation procedure predicts the position of optimum focus and/or automatically focuses the optical system accordingly by, for example, triggering a galvanometer subsystem to move the probe to the predicted position of optimum focus.

The focus validation procedure in FIG. 30 produces a final decision in step 846 of "Pass" or "Fail" for a given focus image, based on the decision rule given by Equations 73-75. This indicates whether the focus achieved for this tissue sample is satisfactory and whether a spectral data scan may proceed as shown in step 732 of FIGS. 27A and 27B.

Determining Optimal Data Acquisition Window

After application of contrast agent 726 and target focusing 728, step 730 of FIG. 27A indicates that the operator waits for the beginning of the optimum window for obtaining spectral data unless the elapsed time already exceeds the start of the window. The optimum window indicates the best time period for obtaining spectral data, following application of contrast agent to the tissue, considering the general time constraints of the entire scan process in a given embodiment. For example, according to the illustrative embodiment, it takes from about 12 to about 15 seconds to perform a spectral scan of 499 interrogation points of a tissue sample. An optimum window is determined such that data may be obtained over a span of time within this window from a sufficient number of tissue regions to provide an adequately detailed indication of disease state with sufficient sensitivity and selectivity. The optimum window preferably, also allows the test data to be used, in turn, as reference data in a subsequently developed tissue classification module. According to another feature, the optimum window is wide enough to allow for restarts necessitated, for example, by focusing problems or patient movement. Data obtained within the optimum window can be added to a bank of reference data used by a tissue classification scheme, such as component 132 of the system 100 of FIG. 1. Thus, the optimum window is preferably narrow enough so that data from a given region is sufficiently consistent regardless of when, within the optimum window, it is obtained.

According to the illustrative embodiment, the optimal window for obtaining spectral data in step 104 of FIG. 1 is a period of time from about 30 seconds following application of the contrast agent to about 130 seconds following application of the contrast agent. The time it takes an operator to apply contrast agent to the tissue sample may vary, but is preferably between about 5 seconds and about 10 seconds. The operator creates a time stamp in the illustrative scan procedure of FIG. 27A after completing application of the contrast agent, and then waits 30 seconds before a scan may begin, where the optimum window is between about 30 seconds and about 130 seconds following application of contrast agent. If the scan takes from about 12 seconds to about 15 seconds to complete (where no retake is required), the start of the scan procedure must begin soon enough to allow all the data to be obtained within the optimum window. In other words, in this embodiment, the scan must begin at least before 115 (assuming a worst case of 15 seconds to complete the scan) seconds following the time stamp (115 seconds after application of contrast agent) so that the scan is completed by 130 seconds following application of contrast agent. Other optimum windows may be used. In one embodiment, the optimum window is between about 30 seconds and about 110 seconds following application of contrast agent. One alternative embodiment has an optimal window with a "start" time from about 10 to about 60 seconds following application of acetic acid, and an "end" time from about 110 to about 180 seconds following application of acetic acid. Other optimum windows may be used.

In one illustrative embodiment, the tissue characterization system 100 of FIG. 1 includes identifying an optimal window for a given application, and/or subsequently using spectral data obtained within the pre-determined window in a tissue classification module, such as step 132 of FIG. 1. According to one feature, optimal windows are determined by obtaining optical signals from reference tissue samples with known states of health at various times following application of a contrast agent.

Determining an optimal window illustratively includes the steps of obtaining a first set of optical signals from tissue samples having a known disease state, such as CIN 2/3 (grades 2 and/or 3 cervical intraepithelial neoplasia); obtaining a second set of optical signals from tissue samples having a different state of health, such as non-CIN 2/3; and categorizing each optical signal into "bins" according to the time it was obtained in relation to the time of application of contrast agent. The optical signal may include, for example, a reflectance spectrum, a fluorescence spectrum, a video image intensity signal, or any combination of these.

A measure of the difference between the optical signals associated with the two types of tissue is then obtained, for example, by determining a mean signal as a function of wavelength for each of the two types of tissue samples for each time bin, and using a discrimination function to determine a weighted measure of difference between the two mean optical signals obtained within a given time bin. This provides a measure of the difference between the mean optical signals of the two categories of tissue samples—diseased and healthy—weighted by the variance between optical signals of samples within each of the two categories.

According to the illustrative embodiment, the invention further includes developing a classification model for each time bin for the purpose of determining an optimal window for obtaining spectral data in step 104 of FIG. 1. After determining a measure of difference between the tissue types in each bin, an optimal window of time for differentiating between tissue types is determined by identifying at least one bin in which the measure of difference between the two tissue types is substantially maximized. For example, an optimal window of time may be chosen to include every time bin in which a respective classification model provides an accuracy of 70% or greater. Here, the optimal window describes a period of time following application of a contrast agent in which an optical signal can be obtained for purposes of classifying the state of health of the tissue sample with an accuracy of at least 70%. Models distinguishing between three or more categories of tissue may also be used in determining an optimal window for obtaining spectral data. As discussed below, other factors may also be considered in determining the optimal window.

An analogous embodiment includes determining an optimal threshold or range of a measure of change of an optical signal to use in obtaining (or triggering the acquisition of) the same or a different signal for predicting the state of health of the sample. Instead of determining a specific, fixed window of time, this embodiment includes determining an optimal threshold of change in a signal, such as a video image whiteness intensity signal, after which an optical signal, such as a diffuse reflectance spectrum and/or a fluorescence spectrum, can be obtained to accurately characterize the state of health or other characteristic of the sample. This illustrative embodiment includes monitoring reflectance and/or fluorescence at a single or multiple wavelength(s), and upon reaching a threshold change from the initial condition, obtaining a full reflectance and/or fluorescence spectrum for use in diagnosing the region of tissue. This method allows for reduced data retrieval and monitoring, since it involves continuous tracking of a single, partial-spectrum or discrete-wavelength "trigger" signal (instead of multiple, full-spectrum scans), followed by the acquisition of spectral data in a spectral scan for use in tissue characterization, for example, the tissue classification module 132 of FIG. 1. Alternatively, the trigger may include more than one discrete-wavelength or partial-spectrum signal. The measure of change used to trigger obtaining one or more optical signals for tissue classification may be a weighted measure, and/or it may be a combination of measures of change of more than one signal.

In a further illustrative embodiment, instead of determining an optimal threshold or range of a measure of change of an optical signal, an optimal threshold or range of a measure of the rate of change of an optical signal is determined. For example, the rate of change of reflectance and/or fluorescence is monitored at a single or multiple wavelength(s), and upon reaching a threshold rate of change, a spectral scan is performed to provide spectral data for use in diagnosing the region of tissue. The measure of rate of change used to trigger obtaining one or more optical signals for tissue classification may be a weighted measure, and/or it may be a combination of measures of change of more than one signal. For example, the measured rate of change may be weighted by an initial signal intensity.

According to the illustrative embodiment, the optimum time window includes a time window in which spectra from cervical tissue may be obtained such that sites indicative of grades 2 and 3 cervical intraepithelial neoplasia (CIN 2/3) can be separated from non-CIN 2/3 sites. Non-CIN 2/3 sites include sites with grade 1 cervical intraepithelial neoplasia (CIN 1), as well as NED sites, normal columnar and normal squamous epithelia, and mature and immature metaplasia. Alternately, sites indicative of high grade disease, CIN 2+, which includes CIN 2/3 categories, carcinoma in situ (CIS), and cancer, may be separated from non-high-grade-disease sites. In general, for any embodiment discussed herein in which CIN 2/3 is used as a category for classification or characterization of tissue, the more expansive category CIN 2+ may be used alternatively. Preferably, the system 100 can differentiate amongst three or more classification categories. Exemplary embodiments are described below and include analysis of the time response of diffuse reflectance and/or 337-nm fluorescence spectra of a set of reference tissue samples with regions having known states of health to determine temporal characteristics indicative of the respective states of health. These characteristics are then used in building a model to determine a state of health of an unknown tissue sample. Other illustrative embodiments include analysis of fluorescence spectra using other excitation wavelengths, such as 380 nm and 460 nm, for example.

According to one illustrative embodiment, an optimum window is determined by tracking the difference between spectral data of two tissue types using a discrimination function.

According to the illustrative embodiment, the discrimination function shown below in Equation 76 may be used to extract differences between tissue types:

$$D(\lambda) = \frac{\mu(\text{test}(\lambda))_{non-CIN2/3} - \mu(\text{test}(\lambda))_{CIN2/3}}{\sqrt{\sigma^2(\text{test}(\lambda))_{non-CIN2/3} + \sigma^2(\text{test}(\lambda))_{CIN2/3}}} \quad (76)$$

where $\mu$ corresponds to the mean optical signal for the tissue type indicated in the subscript; and $\sigma$ corresponds to the standard deviation. The categories CIN 2/3 and non-CIN 2/3 are used in this embodiment because spectral data is particularly well-suited for differentiating between these two categories of tissue, and because spectral data is prominently used in one embodiment of the classification schema in the tissue classification module in step 132 of FIG. 1 to identify CIN 2/3 tissue. Thus, in this way, it is possible to tailor the choice of an optimal scan window such that spectral data obtained within that window are well-adapted for use in identifying CIN 2/3 tissue in the tissue classification scheme 132. In one illustrative embodiment, the optical signal in Equation 76 includes diffuse reflectance. In another illustrative embodiment, the optical signal includes 337-nm fluorescence emission spectra. Other illustrative embodiments use fluorescence emission spectra at another excitation wavelength such as 380 nm and 460 nm. In still other illustrative embodiments, the optical signal is a video signal, Raman signal, or infrared signal. Some illustrative embodiments include using difference spectra calculated between different phases of acetowhitening, using various normalization schema, and/or using various combinations of spectral data and/or image data as discussed above.

In one preferred embodiment, determining an optimal window for obtaining spectral data in step 104 of FIG. 1 includes developing linear discriminant analysis models using spectra from each time bin shown in Table 1 below.

TABLE 1

Time bins for which means spectra are obtained in an exemplary embodiment

| Bin | Time after application of Acetic Acid (s) |
|---|---|
| 1 | t ≦ 0 |
| 2 | 0 < t ≦ 40 |
| 3 | 40 < t ≦ 60 |
| 4 | 60 < t ≦ 80 |
| 5 | 80 < t ≦ 100 |
| 6 | 100 < t ≦ 120 |
| 7 | 120 < t ≦ 140 |
| 8 | 140 < t ≦ 160 |
| 9 | 160 < t ≦ 180 |
| 10 | t > 180 |

Alternatively, nonlinear discriminant analysis models may be developed. Generally, models for the determination of an optimal window are trained using reflectance and fluorescence data separately, although some embodiments include using both data types to train a model. The discriminant analysis models discussed herein for exemplary embodiments of the determination of an optimal window are generally less sophisticated than the schema used in the tissue classification schema in the module 132 in FIG. 1. Alternatively, a model based on the tissue classification schema in the module 132 in FIG. 1 can be used to determine an optimal window for obtaining spectral data in step 104 of FIG. 1.

In exemplary embodiments for determining an optimal window discussed herein, reflectance and fluorescence intensities are down-sampled to one value every 10 nm between 360 and 720 nm. A model is trained by adding and removing intensities in a forward manner, continuously repeating the process until the model converges such that additional intensities do not appreciably improve tissue classification. Testing is performed by a leave-one-spectrum-out jack-knife process.

Figure 35:
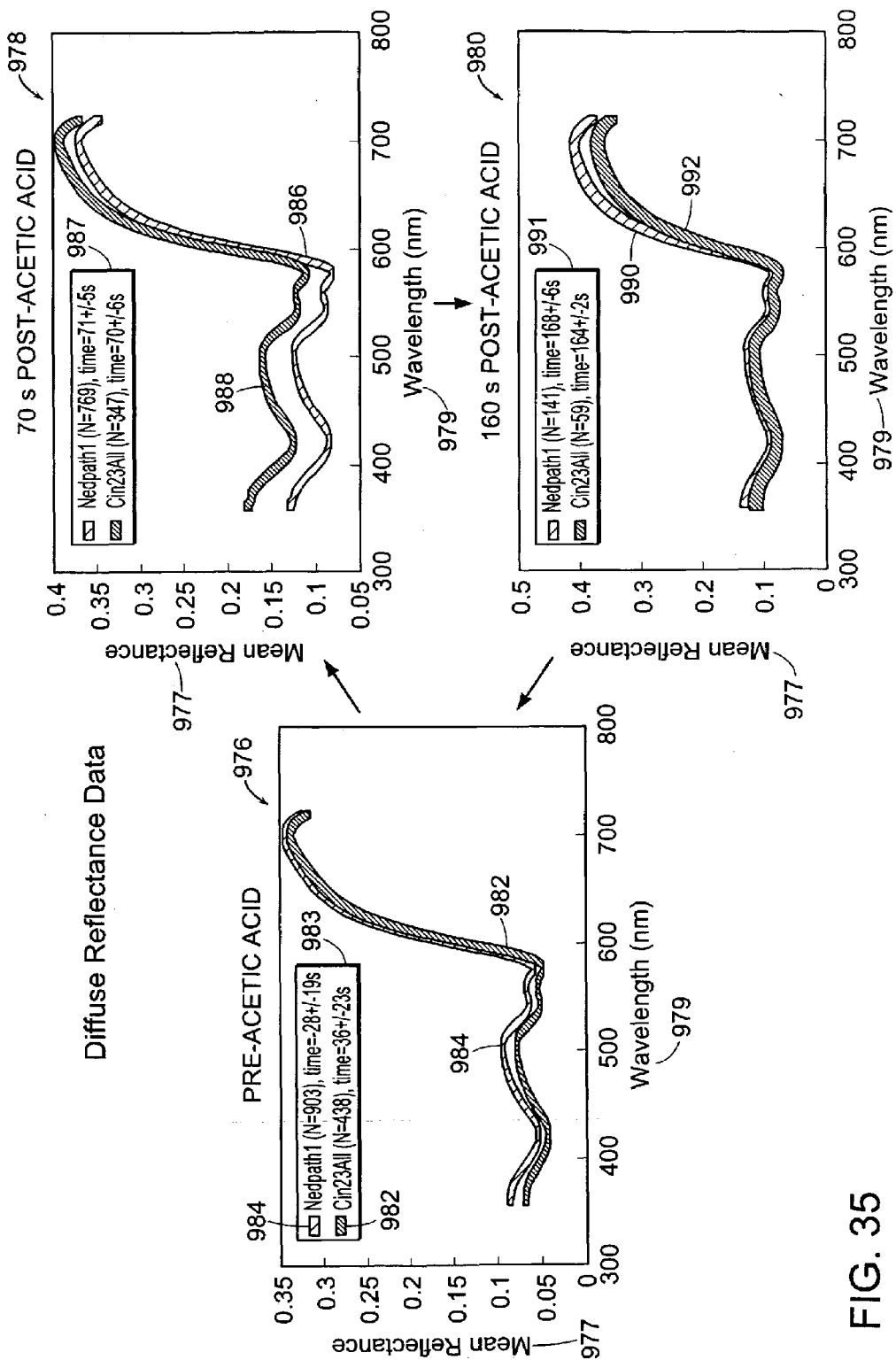
FIG. 35 shows a series of graphs depicting mean reflectance spectra for CIN 2/3 and non-CIN 2/3 tissues at a time prior to application of acetic acid, at a time corresponding to maximum whitening, and at a time corresponding to the latest time at which data was obtained—used in determining an optimal window for obtaining spectral data according to an illustrative embodiment of the invention.

FIG. 35 shows the difference between the mean reflectance spectra for non-CIN 2/3 tissues and CIN 2/3 tissues at three times (prior to the application of acetic acid (graph 976), maximum whitening (graph 978, about 60-80 seconds post-AA), and the last time data were obtained (graph 980, about 160-180 seconds post-AA)). The time corresponding to maximum whitening was determined from reflectance data, and occurs between about 60 seconds and 80 seconds following application of acetic acid. In the absence of acetic acid, the reflectance spectra for CIN 2/3 (curve 982 of graph 976 in FIG. 35) are on average lower than non-CIN 2/3 tissue (curve 984 of graph 976 in FIG. 35). Following the application of acetic acid, a reversal is noted—CIN 2/3 tissues have higher reflectance than the non-CIN 2/3 tissues. The reflectance of CIN 2/3 and non-CIN 2/3 tissues increase with acetic acid, with CIN 2/3 showing a larger relative percent change (compare curves 986 and 988 of graph 978 in FIG. 35). From about 160 s to about 180 s following acetic acid, the reflectance of CIN 2/3 tissue begins to return to the pre-acetic acid state, while the reflectance of the non-CIN 2/3 group continues to increase (compare curves 990 and 992 of graph 980 in FIG. 35).

Figure 36:
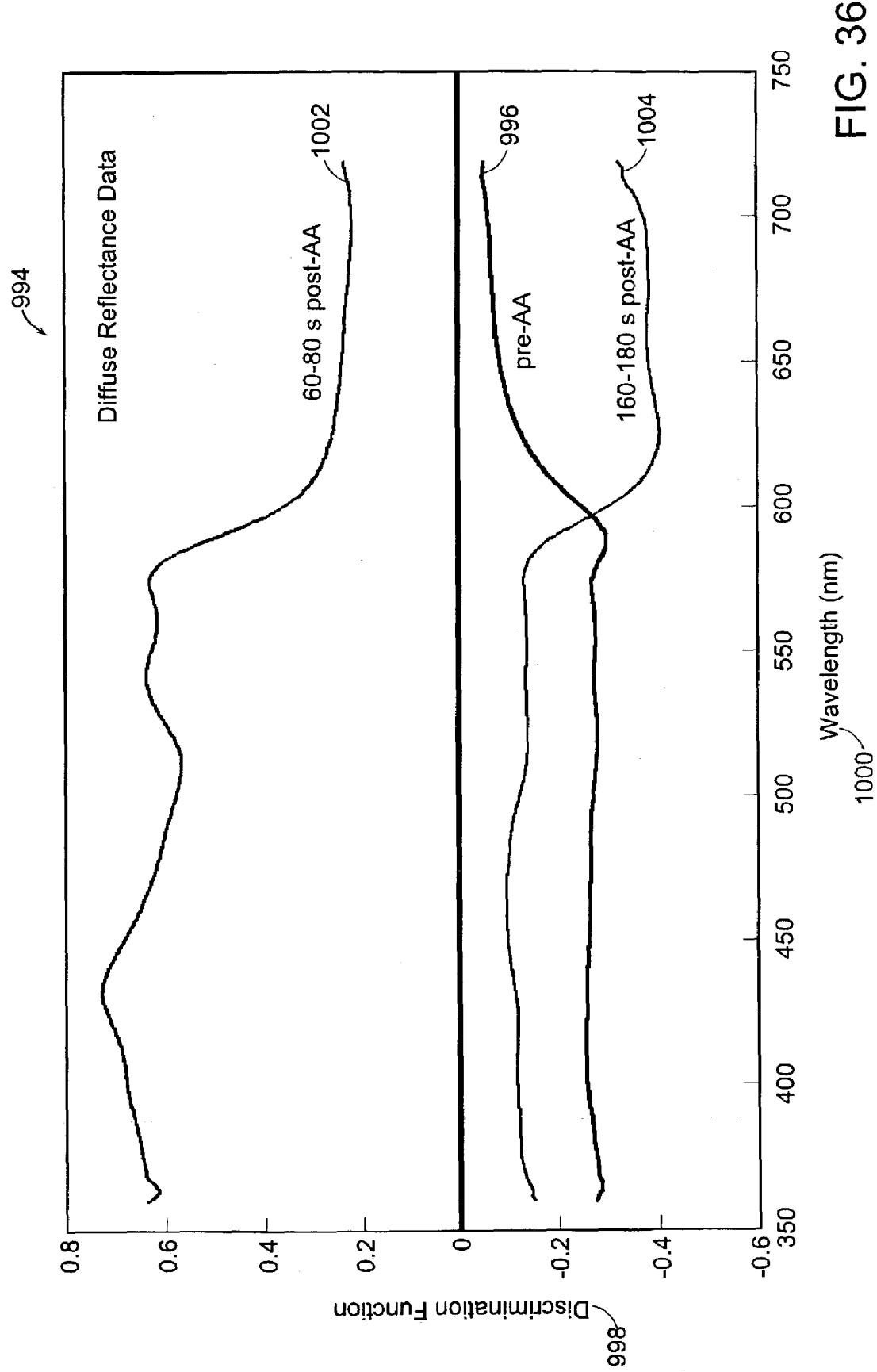
FIG. 36 shows a graph depicting the reflectance discrimination function spectra useful for differentiating between CIN 2/3 and non-CIN 2/3 tissues, used in determining an optimal window for obtaining spectral data according to an illustrative embodiment of the invention.

Discrimination function 'spectra' are calculated from the reflectance spectra of CIN 2/3 and non-CIN 2/3 tissues shown in FIG. 35 as one way to determine an optimal window for obtaining spectral data. Discrimination function spectra comprise values of the discrimination function in Equation 76 determined as a function of wavelength for sets of spectral data obtained at various times. As shown in FIG. 36, the largest differences (measured by the largest absolute values of discrimination function) are found about 60 s to about 80 s post-acetic acid (curve 1002), and these data agree with the differences seen in the mean reflectance spectra of FIG. 35 (curves 986 and 988 of graph 978 in FIG. 35).

Multivariate linear regression analysis takes into account wavelength interdependencies in determining an optimal data acquisition window. One way to do this is to classify spectral data shown in FIG. 35 using a model developed from the reflectance data for each of the bins in Table 1. Then, the accuracy of the models for each bin is computed and compared. Reflectance intensities are down-sampled to one about every 10 nm between about 360 nm and about 720 nm. The model is trained by adding intensities in a forward-stepped manner. Testing is performed with a leave-one-spectrum-out jack-knife process. The results of the linear regression show which wavelengths best separate CIN 2/3 from non-CIN 2/3, as shown in Table 2.

TABLE 2

Forwarded selected best-reflectance wavelengths for classifying CIN 2/3 from non-CIN 2/3 spectra obtained at different times pre and post-AA.

| Time from AA (s) | LDA Model Input Wavelengths (nm) | Accuracy |
|---|---|---|
| −30 | 370 400 420 440 530 570 590 610 | 66 |
| 30 | 420 430 450 600 | 74 |
| 50 | 360 400 420 430 580 600 | 74 |
| 70 | 360 370 420 430 560 580 600 | 77 |
| 90 | 360 420 430 540 590 | 73 |
| 110 | 360 440 530 540 590 | 71 |
| 130 | 360 420 430 540 590 | 71 |
| 150 | 370 400 430 440 540 620 660 690 720 | 72 |
| 170 | 490 530 570 630 650 | 75 |

As shown in Table 2, the two best models for separating CIN 2/3 and non-CIN 2/3, taking into account wavelength interdependence, use reflectance data obtained at peak CIN 2/3 whitening (from about 60 s to about 80 s) and reflectance data obtained from about 160 s to about 180 s post acetic acid. The first model uses input wavelengths between about 360 and about 600 nm, while the second model uses more red-shifted wavelengths between about 490 and about 650 nm. This analysis shows that the optimal windows are about 60 s-80 s post AA and about 160-180 post AA (the latest time bin). This is consistent with the behavior of the discrimination function spectra shown in FIG. 6.

Figure 37:
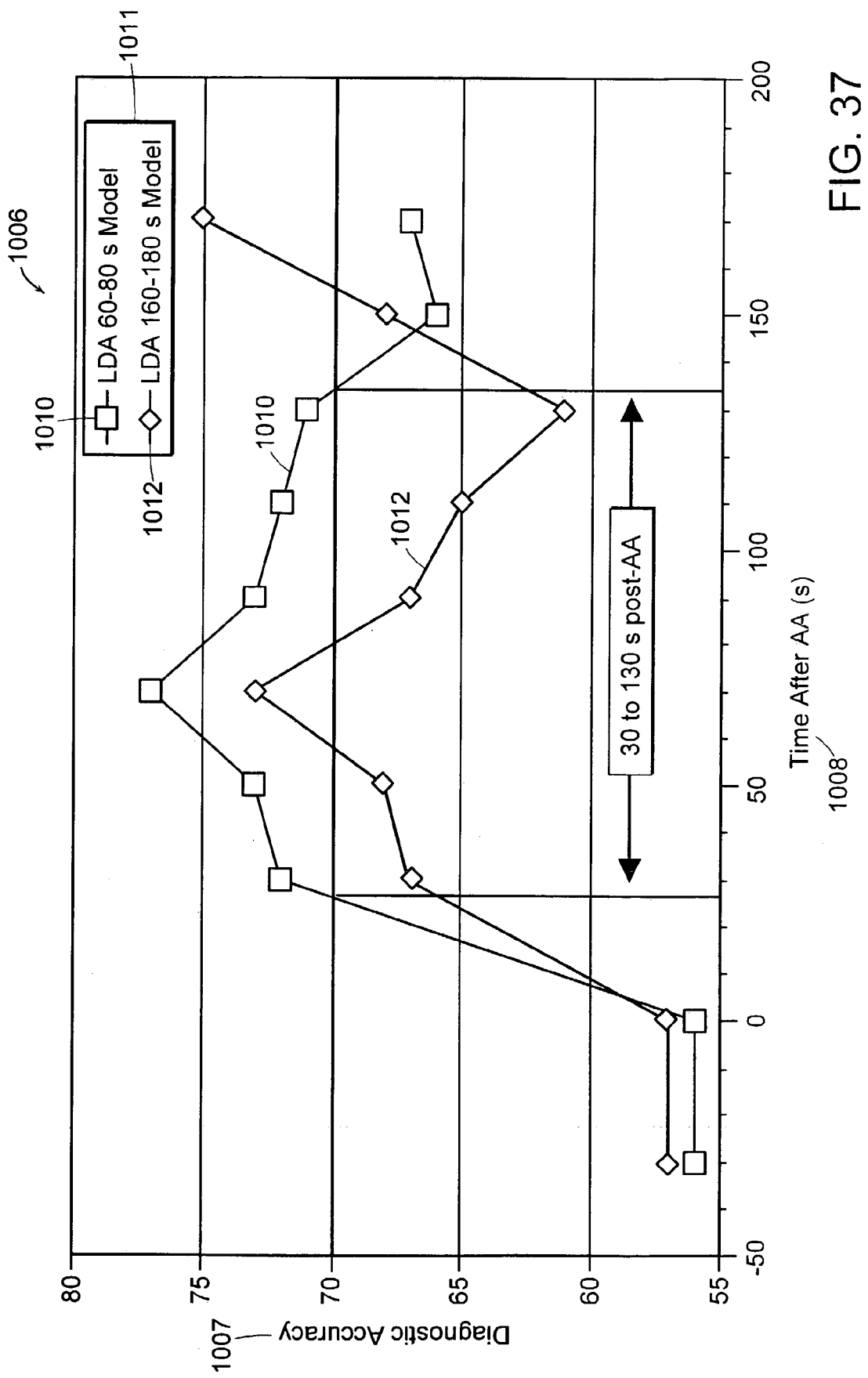
FIG. 37 shows a graph depicting the performance of two LDA (linear discriminant analysis) models as applied to reflectance data obtained at various times following application of acetic acid, used in determining an optimal window for obtaining spectral data according to an illustrative embodiment of the invention.

FIG. 37 demonstrates one step in determining an optimal window for obtaining spectral data, for purposes of discriminating between CIN 2/3 and non-CIN 2/3 tissue. FIG. 37 shows a graph 1006 depicting the performance of the two LDA models described in Table 2 above as applied to reflectance spectral data obtained at various times following application of acetic acid 1008. Curve 1010 in FIG. 37 is a plot of the diagnostic accuracy of the LDA model based on reflectance spectral data obtained between about 60 and about 80 seconds ("peak whitening model") as applied to reflectance spectra from the bins of Table 1, and curve 1012 in FIG. 37 is a plot of the diagnostic accuracy of the LDA model based on reflectance spectral data obtained between about 160 and about 180 seconds, as applied to reflectance spectra from the bins of Table 1. For the peak-whitening model, the highest accuracy was obtained at about 70 s, while accuracies greater than 70% were obtained with spectra collected in a window between about 30 s and about 130 s. The 160-180 s model had a narrower window around 70 s, but performs better at longer times.

Figure 38:
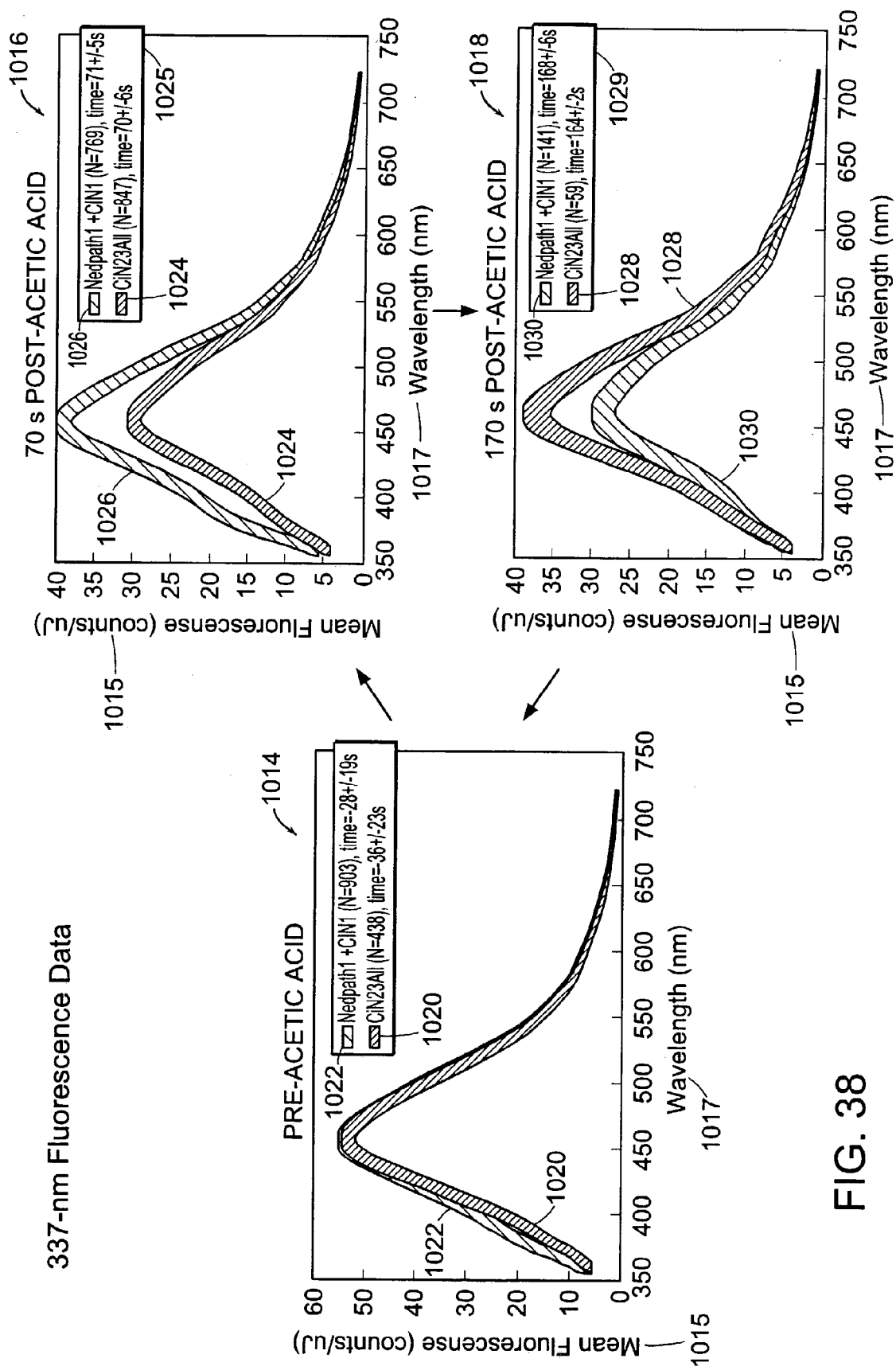
FIG. 38 shows a series of graphs depicting mean fluorescence spectra for CIN 2/3 and non-CIN 2/3 tissues at a time prior to application of acetic acid, at a time corresponding to maximum whitening, and at a time corresponding to the latest time at which data was obtained, used in determining an optimal window for obtaining spectral data according to an illustrative embodiment of the invention.

FIG. 38 shows the difference between the mean 337-nm fluorescence spectra for non-CIN 2/3 tissues and CIN 2/3 tissues at three times (prior to application of acetic acid (graph 1014), maximum whitening (graph 1016, about 60 to about 80 seconds post-AA), and at a time corresponding to the latest time period in which data was obtained (graph 1018, about 160 to about 180 seconds post-AA)). The time corresponding to maximum whitening was determined from reflectance data, and occurs between about 60 seconds and 80 seconds following application of acetic acid. In the absence of acetic acid, the fluorescence spectra for CIN 2/3 tissue (curve 1020 of graph 1014 in FIG. 38) and for non-CIN 2/3 tissue (curve 1022 of graph 1014 in FIG. 38) are essentially equivalent with a slightly lower fluorescence noted around 390 nm for CIN 2/3 sites. Following the application of acetic acid, the fluorescence of CIN 2/3 and non-CIN 2/3 tissues decrease, with CIN 2/3 showing a larger relative percent change (compare curves 1024 and 1026 of graph 1016 in FIG. 38). From about 160 s to about 180 s following acetic acid application, the fluorescence of CIN 2/3 tissue shows signs of returning to the pre-acetic acid state while the fluorescence of the non-CIN 2/3 group continues to decrease (compare curves 1028 and 1030 of graph 1018 in FIG. 38).

Figure 39:
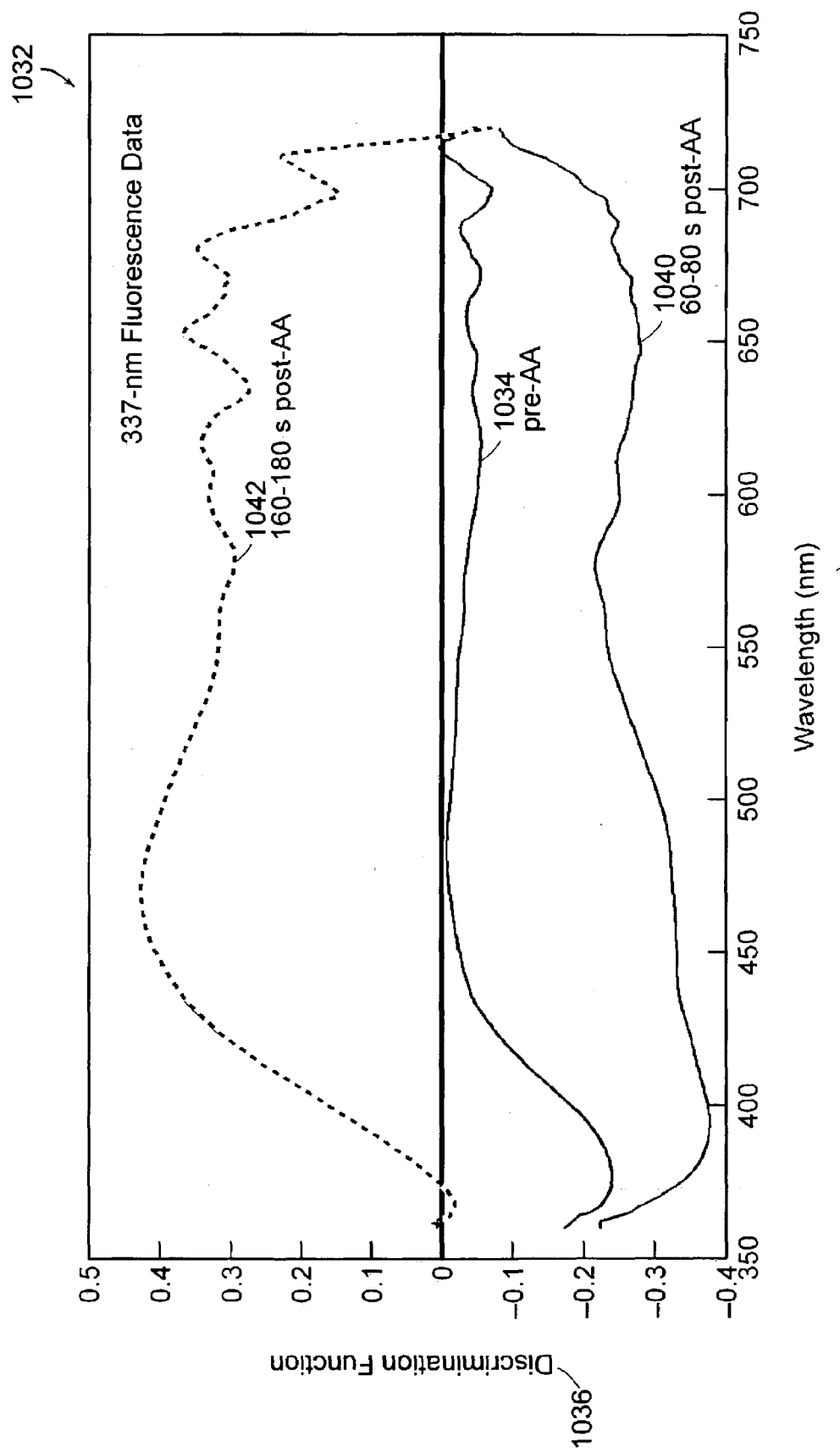
FIG. 39 shows a graph depicting the fluorescence discrimination function spectra useful for differentiating between CIN 2/3 and non-CIN 2/3 tissues in determining an optimal window for obtaining spectral data according to an illustrative embodiment of the invention.

An optimal data acquisition window may also be obtained using a discrimination function calculated from fluorescence spectra of CIN 2/3 and non-CIN 2/3 tissues shown in FIG. 38. In one example, discrimination function spectra include values of the discrimination function in Equation 76 determined as a function of wavelength for sets of spectral data obtained at various times. FIG. 39 shows a graph 1032 depicting the discrimination function spectra evaluated using the fluorescence data of FIG. 38 obtained prior to application of acetic acid, and at two times post-AA. As shown in FIG. 39, applications of acetic acid improves that distinction between CIN 2/3 and non-CIN 2/3 tissues using fluorescence data. The largest absolute values are found using data measured within the range of about 160-180 s post-acetic acid (curve 1042), and these agree with the differences seen in the mean fluorescence spectra of FIG. 38 (curves 1030 and 1028 of graph 1018 in FIG. 38).

Multivariate linear regression takes into account wavelength interdependencies in determining an optimal data acquisition window. An application of one method of determining an optimal window includes classifying data represented in the CIN 2/3, CIN 1, and NED categories in the Appendix Table into CIN 2/3 and non-CIN 2/3 categories by using classification models developed from the fluorescence data shown in FIG. 38. Fluorescence intensities are downsampled to one about every 10 nm between about 360 and about 720 nm. The model is trained by adding intensities in a forward manner. Testing is performed by a leave-one-spectrum-out jack-knife process. The result of this analysis shows which wavelengths best separate CIN 2/3 from non-CIN 2/3, as shown in Table 3.

TABLE 3

Forwarded selected best 337-nm fluorescence wavelengths for classifying CIN 2/3 from non-CIN 2/3 spectra obtained at different times pre and post-AA.

| Time from AA (s) | LDA Model Input Wavelengths (nm) | Accuracy |
| --- | --- | --- |
| −30 | 380, 430, 440, 610, 660, 700, 710 | 61 |
| 30 | 370, 380, 390, 640 | 61 |
| 50 | 410 | 54 |
| 70 | 360, 390, 490, 580, 590, 670 | 63 |
| 90 | 370, 380, 420, 460, 500, 560, 660 | 64 |
| 110 | 360, 390, 400, 710 | 51 |
| 130 | 370 | 53 |
| 150 | 370, 380, 440, 620, 640, 700 | 65 |
| 170 | 370, 480, 510, 570, 600, 700, 720 | 76 |

As shown in Table 3, the two best models for separating CIN 2/3 and non-CIN 2/3, taking into account wavelength interdependencies, use data obtained at peak CIN 2/3 whitening (60-80 s) and data obtained at the latest time measured (from about 160 s to about 180 s post acetic acid). The first model uses input wavelengths between about 360 and about 670 nm, while the second model uses wavelengths between about 370 and about 720 nm.

Figure 40:
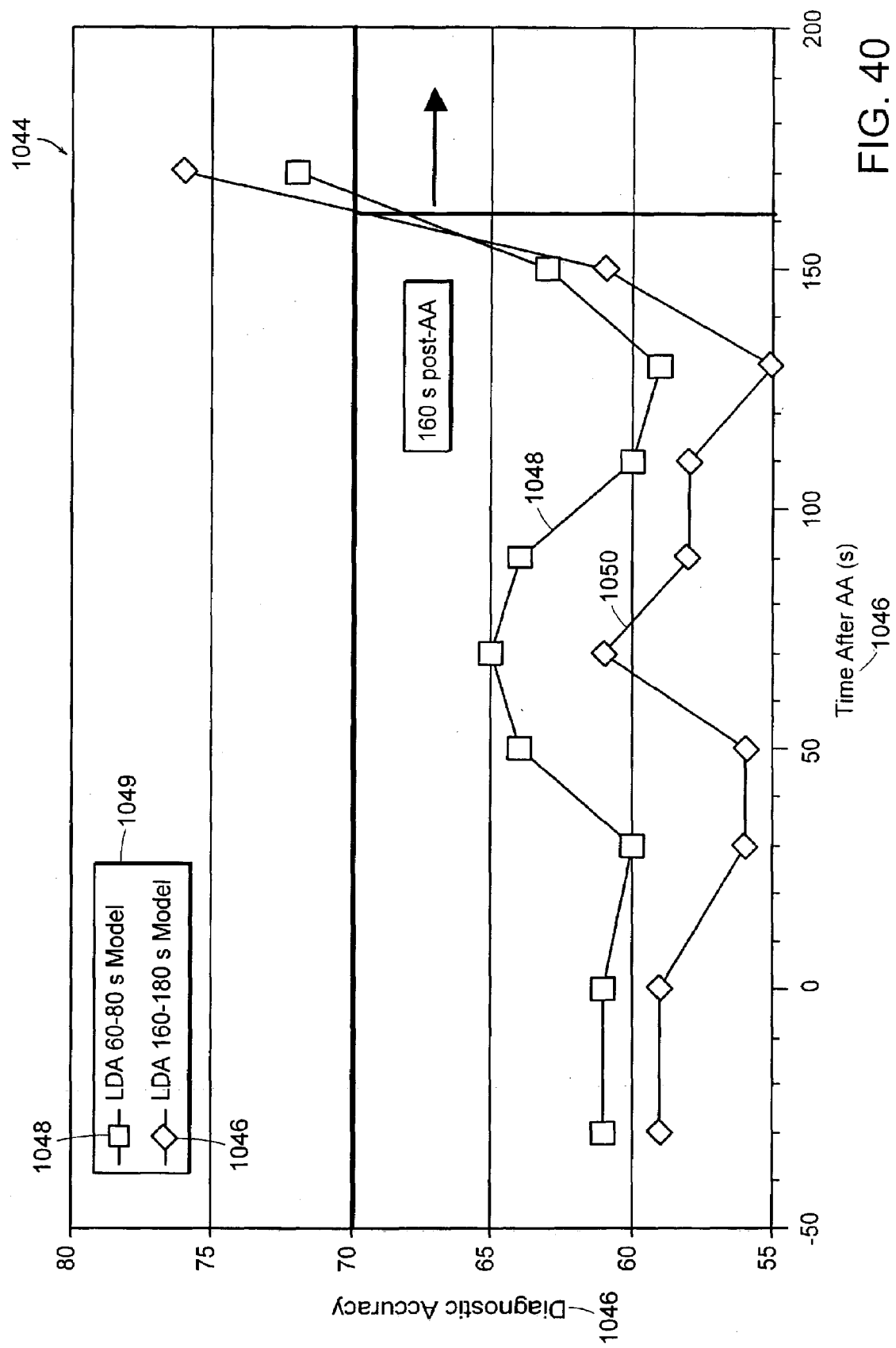
FIG. 40 shows a graph depicting the performance of two LDA (linear discriminant analysis) models as applied to fluorescence data obtained at various times following application of acetic acid, used in determining an optimal window for obtaining spectral data according to an illustrative embodiment of the invention.

FIG. 40 demonstrates one step in determining an optimal window. FIG. 40 shows a graph 1044 depicting the performance of the two LDA models described in Table 3 above as applied to fluorescence spectral data obtained at various times following application of acetic acid 1046. Curve 1048 in FIG. 40 is a plot of the diagnostic accuracy of the LDA model based on fluorescence spectral data obtained between about 60 and about 80 seconds ("peak whitening model") as applied to fluorescence spectra from the bins of Table 1, and curve 1050 in FIG. 40 is a plot of the diagnostic accuracy of the LDA model based on fluorescence spectral data obtained between about 160 and about 180 seconds, as applied to fluorescence spectra from the bins of Table 1. The accuracies of these models vary depending on when the fluorescence spectra are recorded relative to the application of acetic acid, as shown in FIG. 40. The predictive ability of the fluorescence models in FIG. 40 tend to be less than that of the reflectance models in FIG. 37. Accuracies greater than 70% are obtained with spectra collected after about 160 seconds post-AA.

One embodiment includes classifying spectral data shown in FIG. 38 from known reference tissue samples into CIN 2/3 and non-CIN 2/3 categories by using classification models developed from the fluorescence data for each of the bins in Table 1. Models are developed based on time post acetic acid. Ratios of fluorescence to reflectance are downsampled to one every 10 nm between about 360 and about 720 nm. The model is trained by adding intensities in a forward manner. Testing is performed by a leave-one-spectrum-out jack-knife process. For this analysis, the model is based on intensities at about 360, 400, 420, 430, 560, 610, and 630 nm. In general, the results are slightly better than a model based on fluorescence alone. Improved performance is noted from spectra acquired at about 160 s post acetic acid.

Figure 41:
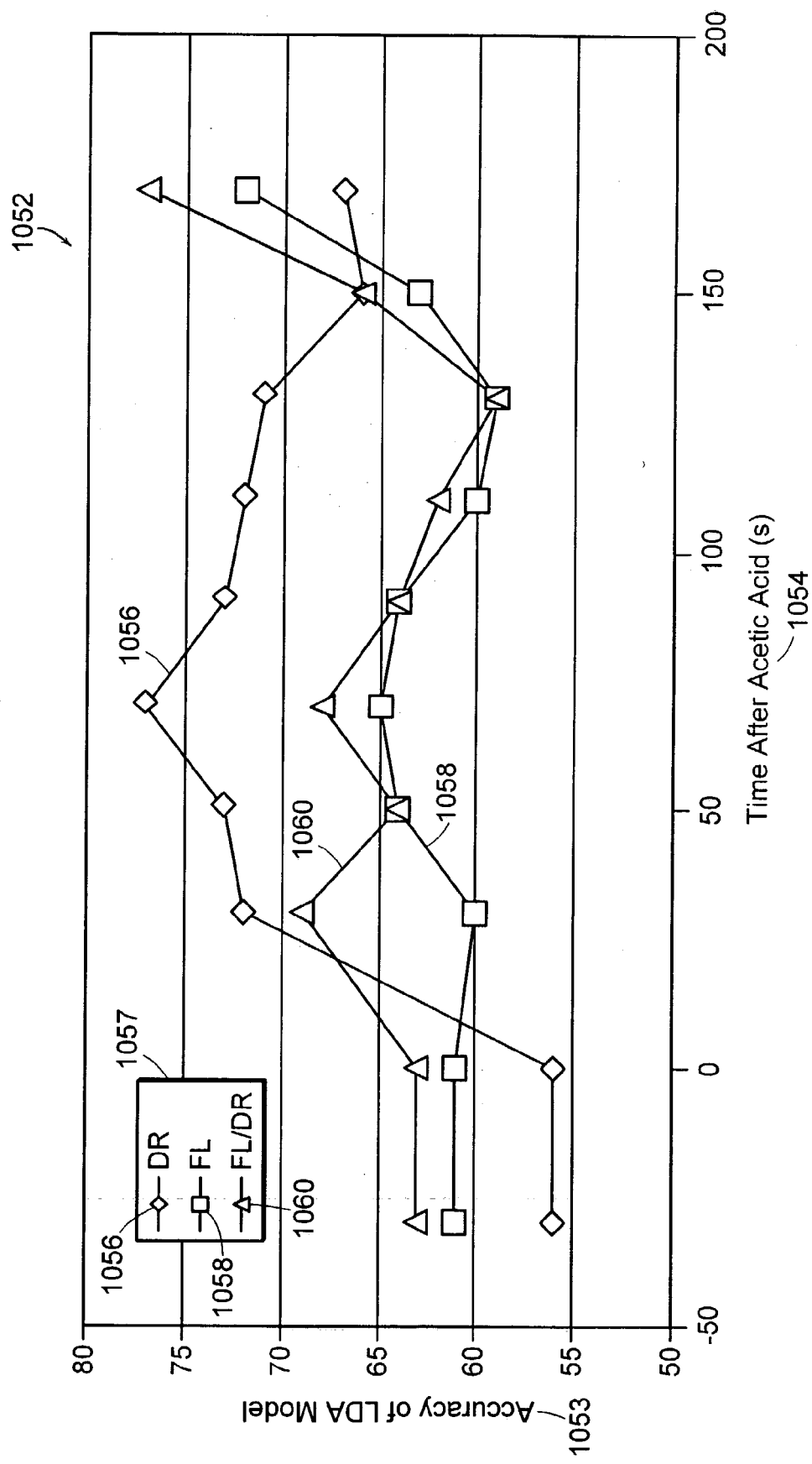
FIG. 41 shows a graph depicting the performance of three LDA models as applied to data obtained at various times following application of acetic acid, used in determining an optimal window for obtaining spectral data according to an illustrative embodiment of the invention.

FIG. 41 shows a graph 1052 depicting the accuracy of three LDA models as applied to spectral data obtained at various times following application of acetic acid 1054, used in determining an optimal window for obtaining spectral data. Curve 1056 in FIG. 41 is a plot of the diagnostic accuracy of the LDA model based on reflectance spectral data obtained between about 60 and about 80 seconds ("peak whitening model"), also shown as curve 1010 in FIG. 37. Curve 1058 in FIG. 41 is a plot of the diagnostic accuracy of the LDA model based on fluorescence spectral data obtained between about 60 and about 80 seconds ("peak whitening model"), also shown as curve 1048 in FIG. 40. Curve 1060 in FIG. 41 is a plot of the diagnostic accuracy of the LDA model based on fluorescence intensity divided by reflectance, as described in the immediately preceding paragraph.

The exemplary embodiments discussed above and illustrated in FIGS. 35 to 41 provide a basis for selecting an optimum window for obtaining spectral data upon application of acetic acid. Other factors to be considered include the time required to apply the contrast agent and to perform target focusing as shown in FIG. 27A. Another factor is the time required to perform a scan over a sufficient number of regions of a tissue sample to provide an adequate indication of disease state with sufficient sensitivity and selectivity. Also, a consideration may be made for the likelihood of the need for and time required for retakes due to patient motion.

The factors and analysis discussed above indicate that an optimal data acquisition window is a period of time from about 30 seconds following application of a contrast agent (for example, a 5 volume percent acetic acid solution) to about 130 seconds following application of the contrast agent. Other optimal windows are possible. For example, one alternative embodiment uses an optimal window with a "start" time from about 10 to about 60 seconds following application of acetic acid, and an "end" time from about 110 to about 180 seconds following application of acetic acid.

An alternative manner for determining an optimal window comprises determining and using a relative amplitude change and/or rate of amplitude change as a trigger for obtaining spectral data from a sample. By using statistical and/or heuristic methods such as those discussed herein, it is possible to relate more easily-monitored relative changes or rates-of-change of one or more optical signals from a tissue sample to corresponding full spectrum signals that can be used in characterizing the state of health of a given sample. For example, by performing a discrimination function analysis, it may be found for a given tissue type that when the relative change in reflectance at a particular wavelength exceeds a threshold value, the corresponding full-spectrum reflectance can be obtained and then used to accurately classify the state of health of the tissue. In addition, the triggers determined above may be converted into optimal time windows for obtaining diagnostic optical data from a sample.

Figure 42:
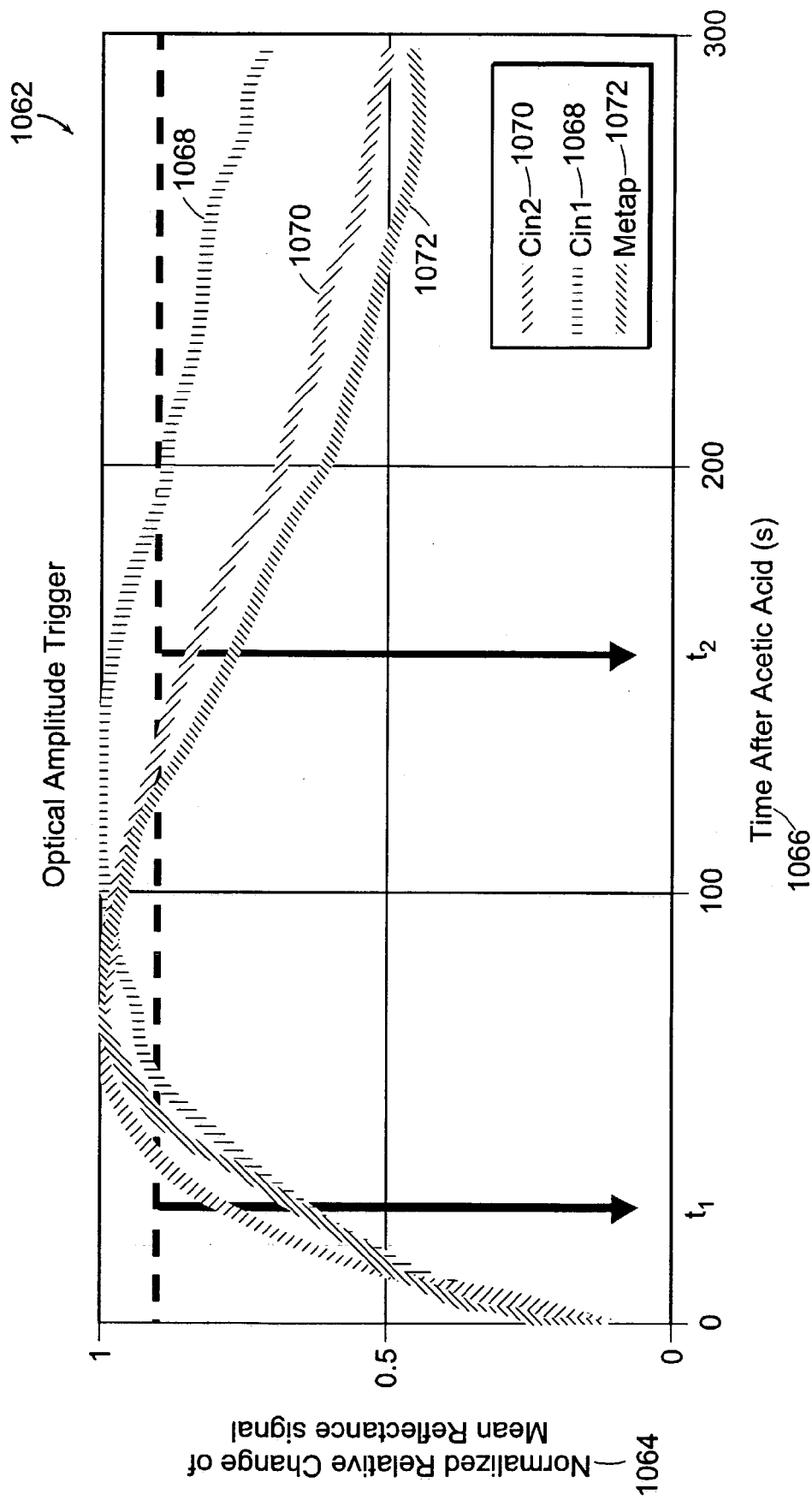
FIG. 42 shows a graph depicting the determination of an optimal time window for obtaining diagnostic optical data using an optical amplitude trigger, according to an illustrative embodiment of the invention.

FIG. 42 shows how an optical amplitude trigger is used to determine an optimal time window for obtaining diagnostic optical data. The graph 1062 in FIG. 42 plots the normalized relative change of mean reflectance signal 1064 from tissue samples with a given state of health as a function of time following application of acetic acid 1066. The mean reflectance signal determined from CIN 1, CIN 2, and Metaplasia samples are depicted in FIG. 42 by curves 1068, 1070, and 1072, respectively. FIG. 42 shows that when the normalized relative change of mean reflectance reaches or exceeds 0.75 in this example, the image intensity data and/or the full reflectance and/or fluorescence spectrum is most indicative of a given state of health of a sample. Thus, for CIN 2 samples, for example, this corresponds to a time period between $t_1$ and $t_2$, as shown in the graph 1062 of FIG. 42. Therefore, spectral and/or image data obtained from a tissue sample between $t_1$ and $t_2$ following application of acetic-acid are used in accurately determining whether or not CIN 2 is indicated for that sample. In one embodiment, the relative change of reflectance of a tissue sample at one or more given wavelengths is monitored. When that relative change is greater than or equal to the 0.75 threshold, for example, more comprehensive spectral and/or image data are obtained to characterize whether the sample is indicative of CIN 2. In another embodiment, a predetermined range of values of the relative optical signal change is used such that when the relative signal change falls within the predetermined range of values, additional spectral and/or image data is captured in order to characterize the sample.

Figure 43:
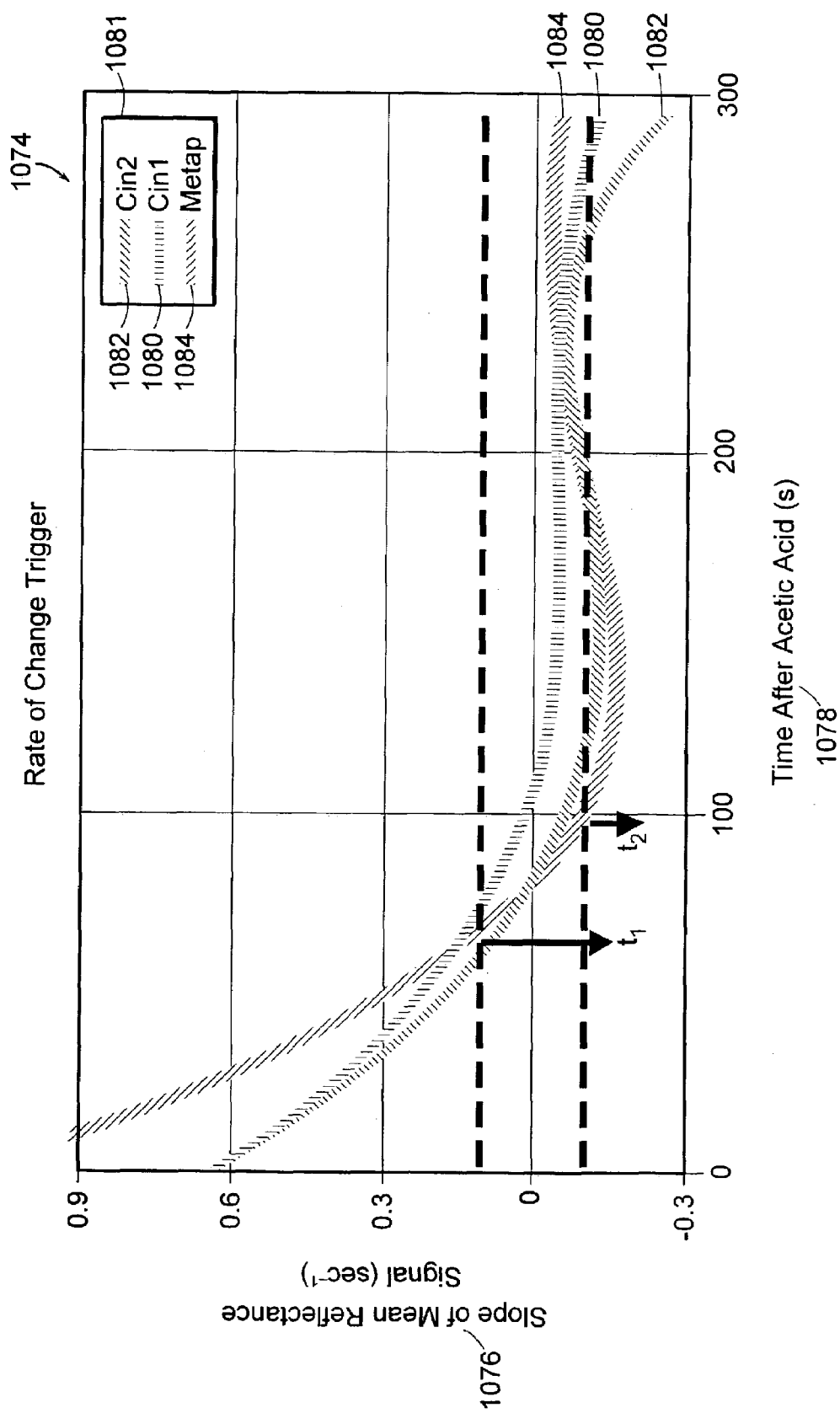
FIG. 43 shows a graph depicting the determination of an optimal time window for obtaining diagnostic data using a rate of change of mean reflectance signal trigger, according to an illustrative embodiment of the invention.

FIG. 43 shows how a rate-of-change of an optical amplitude trigger is used to determine an optimal time window for obtaining diagnostic optical data. The graph 1074 of FIG. 43 plots the slope of an exemplary mean reflectance signal 1076 from tissue samples with a given state of health as a function of time following application of acetic acid 1078. The slope of mean reflectance is a measure of the rate of change of the mean reflectance signal. The rate of change of mean reflectance determined from CIN 1, CIN 2, and metaplasia samples are depicted in FIG. 43 by curves 1080, 1082, and 1084, respectively. Those curves show that when the absolute value of the slope is less than or equal to 0.1, for example, in the vicinity of maximum reflectance, the image intensity data and/or the full reflectance and/or fluorescence spectrum is most indicative of a given state of health of a sample. Thus, for CIN 2 samples, for example, this corresponds to a time period between $t_1$ and $t_2$ as shown in the graph 1074 of FIG. 43. Therefore, spectral and/or image data obtained from a tissue sample between $t_1$ and $t_2$ following application of acetic acid is used in accurately determining whether or not CIN 2 is indicated for that sample. In the example, the rate of change of reflectance of a tissue sample is monitored at one or more wavelengths. When that rate of change has an absolute value less than or equal to 0.1, more comprehensive spectral and/or image data are obtained from the sample for purposes of characterizing whether or not the sample is indicative of CIN 2. FIG. 43 demonstrates use of a range of values of rate of optical signal change. Other embodiments use a single threshold value.

Motion Tracking

In one embodiment, the tissue characterization system shown in FIG. 1 comprises real-time motion tracking (step 106 in FIG. 1). Real-time tracking determines a correction for and/or compensates for a misalignment between two images of the tissue sample obtained during a spectral data scan (i.e. step 732 in FIG. 27A and 27B), where the misalignment is caused by a shift in the position of the sample with respect to the instrument 102 in FIG. 1 (or, more particularly, the probe optics 178). The misalignment may be caused by unavoidable patient motion, such as motion due to breathing during the spectral data scan 732.

In one embodiment, the correction factor determined by the real-time tracker is used to automatically compensate for patient motion, for example, by adjusting the instrument 102 (FIG. 1) so that spectral data obtained from indexed regions of the tissue sample during the scan correspond to their originally-indexed locations. Alternatively or additionally, the motion correction factor can be used in spectral data pre-processing, step 114 in FIG. 1 and FIG. 11, to correct spectral data obtained during a scan according to an applicable correction factor. For example, the spectral data lookup method in step 114 of FIG. 1 as discussed herein may compensate for patient motion by using a correction determined by the real-time tracker 106 to correlate a set of spectral data obtained during a scan with its true, motion-corrected position (x,y) on the tissue sample. In one embodiment, the motion correction factor determined in step 106 of FIG. 1 is updated about once every second during the scan using successive images of the tissue, as shown in FIG. 27B. Step 106 determines and validates a motion correction factor about once every second during the spectral scan, corresponding to each successive image in FIG. 27B. Then, the pre-processing component 114 of FIG. 1 corrects the spectral data obtained at an interrogation point during the spectral scan using the correction factor corresponding to the time at which the spectral data were obtained.

A typical misalignment between two images obtained about 1 second apart is less than about 0.55-mm within a two-dimensional, 480×500 pixel image frame field covering a tissue area of approximately 25-mm×25-mm. These dimensions provide an example of the relative scale of misalignment versus image size. In some instances it is only necessary to compensate for misalignments of less than about one millimeter within the exemplary image frame field defined above. In other cases, it is necessary to compensate for misalignments of less than about 0.3-mm within the exemplary image frame field above. Also, the dimensions represented by the image frame field, the number of pixels of the image frame field, and/or the pixel resolution may differ from the values shown above.

A misalignment correction determination may be inaccurate, for example, due to any one or a combination of the following: non-translational sample motion such as rotational motion, local deformation, and/or warping; changing features of a sample such as whitening of tissue; and image recording problems such as focus adjustment, missing images, blurred or distorted images, low signal-to-noise ratio, and computational artifacts. Validation procedures of the invention identify such inaccuracies. The methods of validation may be conducted "on-the-fly" in concert with the methods of determining misalignment corrections in order to improve accuracy and to reduce the time required to conduct a given test.

In order to facilitate the automatic analysis in the tissue classification system 100 of FIG. 1, it is often necessary to adjust for misalignments caused by tissue sample movement that occurs during the diagnostic procedure. For example, during a given procedure, in vivo tissue may spatially shift within the image frame field from one image to the next due to movement of the patient. Accurate tissue characterization requires that this movement be taken into account in the automated analysis of the tissue sample. In one embodiment, spatial shift correction made throughout a spectral data scan is more accurate than a correction made after the scan is complete, since "on-the-fly" corrections compensate for smaller shifts occurring over shorter periods of time and since spectral data is being continuously obtained throughout the approximately 12 to 15 second scan in the embodiment of FIG. 27B.

If a sample moves while a sequence of images is obtained, the procedure may have to be repeated. For example, this may be because the shift between consecutive images is too large to be accurately compensated for, or because a region of interest moves outside of a usable portion of the frame captured by the optical signal detection device. Stepwise motion correction of spectral data reduces the cumulative effect of sample movement. If correction is made only after an entire sequence is obtained, it may not be possible to accurately compensate for some types of sample movement. On-the-fly, stepwise compensation for misalignment reduces the need for retakes.

On-the-fly compensation may also obviate the need to obtain an entire sequence of images before making the decision to abort a failed procedure, particularly when coupled with on-the-fly, stepwise validation of the misalignment correction determination. For example, if the validation procedure detects that a misalignment correction determination is either too large for adequate compensation to be made or is invalid, the procedure may be aborted before obtaining the entire sequence of images. It can be immediately determined whether or not the obtained data is useable. Retakes may be performed during the same patient visit; no follow-up visit to repeat an erroneous test is required. A diagnostic test invalidated by excessive movement of the patient may be aborted before obtaining the entire sequence of images, and a new scan may be completed, as long as there is enough remaining time in the optimal time window for obtaining spectral data.

In preferred embodiments, a determination of misalignment correction is expressed as a translational displacement in two dimensions, x and y. Here, x and y represent Cartesian coordinates indicating displacement on the image frame field plane. In other embodiments, corrections for misalignment are expressed in terms of non-Cartesian coordinate systems, such as biradical, spherical, and cylindrical coordinate systems, among others. Alternatives to Cartesian-coordinate systems may be useful, for example, where the image frame field is non-planar.

Some types of sample motion—including rotational motion, warping, and local deformation—may result in an invalid misalignment correction determination, since it may be impossible to express certain instances of these types of sample motion in terms of a translational displacement, for example, in the two Cartesian coordinates x and y. It is noted, however, that in some embodiments, rotational motion, warping, local deformation, and/or other kinds of non-translational motion are acceptably accounted for by a correction expressed in terms of a translational displacement. The changing features of the tissue, as in acetowhitening, may also affect the determination of a misalignment correction. Image recording problems such as focus adjustment, missing images, blurred or distorted images, low signal-to-noise ratio (i.e. caused by glare), and computational artifacts may affect the correction determination as well. Therefore, validation of a determined correction is often required. In some embodiments, a validation step includes determining whether an individual correction for misalignment is erroneous, as well as determining whether to abort or continue the test in progress. Generally, validation comprises splitting at least a portion of each of a pair of images into smaller, corresponding units (subimages), determining for each of these smaller units a measure of the displacement that occurs within the unit between the two images, and comparing the unit displacements to the overall displacement between the two images.

In certain embodiments, the method of validation takes into account the fact that features of a tissue sample may change during the capture of a sequence of images. For example, the optical intensity of certain regions of tissue change during the approximately 12 to 15 seconds of a scan, due to acetowhitening of the tissue. Therefore, in one embodiment, validation of a misalignment correction determination is performed using a pair of consecutive images. In this way, the difference between the corresponding validation cells of the two consecutive images is less affected by gradual tissue whitening changes, as compared with images obtained further apart in time. In an alternative embodiment, validation is performed using pairs of nonconsecutive images taken within a relatively short period of time, compared with the time in which the overall sequence of images is obtained. In other embodiments, validation comprises the use of any two images in the sequence of images.

A determination of misalignment correction between two images is inadequate if significant portions of the images are featureless or have low signal-to-noise ratio (i.e. are affected by glare). Similarly, validation using cells containing significant portions that are featureless or that have low signal-to-noise ratio may result in the erroneous invalidation of valid misalignment correction determinations. This may occur in cases where the featureless portion of the overall image is small enough so that it does not adversely affect the misalignment correction determination. For example, analysis of featureless validation cells may produce meaningless correlation coefficients. One embodiment includes identifying one or more featureless cells and eliminating them from consideration in the validation of a misalignment correction determination, thereby preventing rejection of a good misalignment correction.

A determination of misalignment correction may be erroneous due to a computational artifact of data filtering at the image borders. For example, in one exemplary embodiment, an image with large intensity differences between the upper and lower borders and/or the left and right borders of the image frame field undergoes Laplacian of Gaussian frequency domain filtering. Since Laplacian of Gaussian frequency domain filtering corresponds to cyclic convolution in the space-time domain, these intensity differences (discontinuities) yield a large gradient value at the image border, and cause the overall misalignment correction determination to be erroneous, since changes between the two images due to spatial shift are dwarfed by the edge effects. One alternative embodiment employs pre-multiplication of image data by a Hamming window to remove or reduce this "wraparound error." However, one preferred embodiment employs an image-blending technique such as feathering, to smooth any border discontinuity, while requiring only a minimal amount of additional processing time.

Figure 44B:
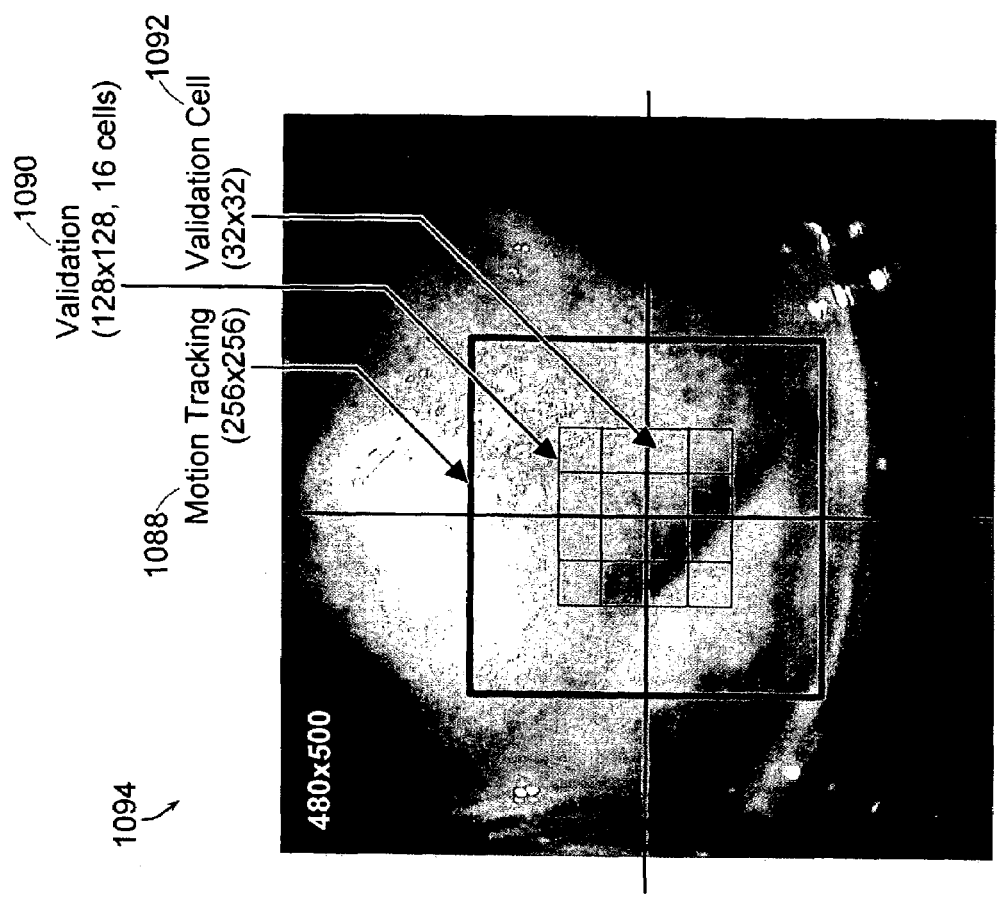
FIG. 44B depicts the image represented in FIG. 44A and shows a 128×128 pixel portion of the image, made up of 16 individual 32×32 pixel validation cells, from which data is used in performing a validation of the misalignment correction determination according to an illustrative embodiment of the invention.
Figure 44A:
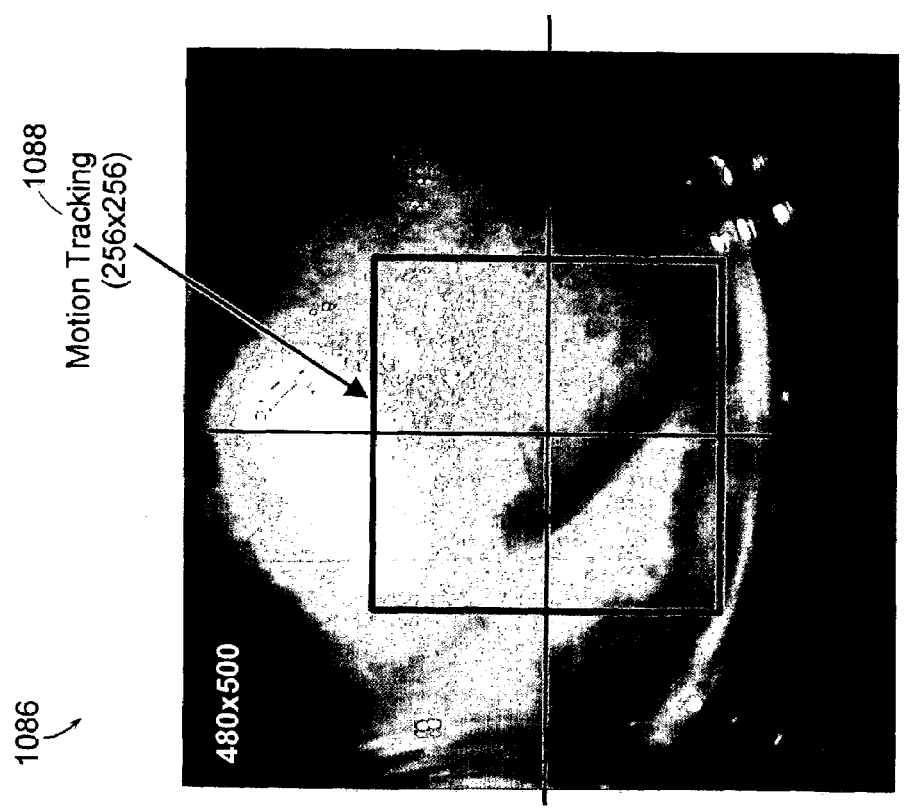
FIG. 44A represents a 480×500 pixel image from a sequence of images of in vivo human cervix tissue and shows a 256×256 pixel portion of the image from which data is used in determining a correction for a misalignment between two images from a sequence of images of the tissue in the tissue characterization system of FIG. 1, according to an illustrative embodiment of the invention.

FIG. 44A represents a 480×500 pixel image 1086 from a sequence of images of in vivo human cervix tissue and shows a 256×256 pixel portion 1088 of the image that the motion correction step 106 in FIG. 1 uses in identifying a misalignment correction between two images from a sequence of images of the tissue, according to one embodiment. The image 1086 of FIG. 44A has a pixel resolution of about 0.054-mm. The embodiments described herein show images with pixel resolutions of about 0.0547-mm to about 0.0537-mm. Other embodiments have pixel resolutions outside this range. In some embodiments, the images of a sequence have an average pixel resolution of between about 0.044-mm and about 0.064-mm. In the embodiment of FIG. 44A, step 106 of the system of FIG. 1 uses the central 256×256 pixels 1088 of the image 1086 for motion tracking. An alternative embodiment uses a region of different size for motion tracking, which may or may not be located in the center of the image frame field. In the embodiment of FIG. 44A, the motion tracking step 106 of FIG. 1 determines an x-displacement and a y-displacement corresponding to the translational shift (misalignment) between the 256×256 central portions 1088 of two images in the sequence of images obtained during a patient spectral scan.

The determination of misalignment correction may be erroneous for any number of various reasons, including but not limited to non-translational sample motion (i.e. rotational motion, local deformation, and/or warping), changing features of a sample (i.e. whitening of tissue), and image recording problems such as focus adjustment, missing images, blurred or distorted images, low signal-to-noise ratio, and computational artifacts. Therefore, in preferred embodiments, validation comprises splitting an image into smaller units (called cells), determining displacements of these cells, and comparing the cell displacements to the overall displacement. FIG. 44B depicts the image represented in FIG. 44A and shows a 128×128 pixel portion 1090 of the image, made up of 16 individual 32×32 pixel validation cells 1092, from which data is used to validate the misalignment correction.

Figure 46A:
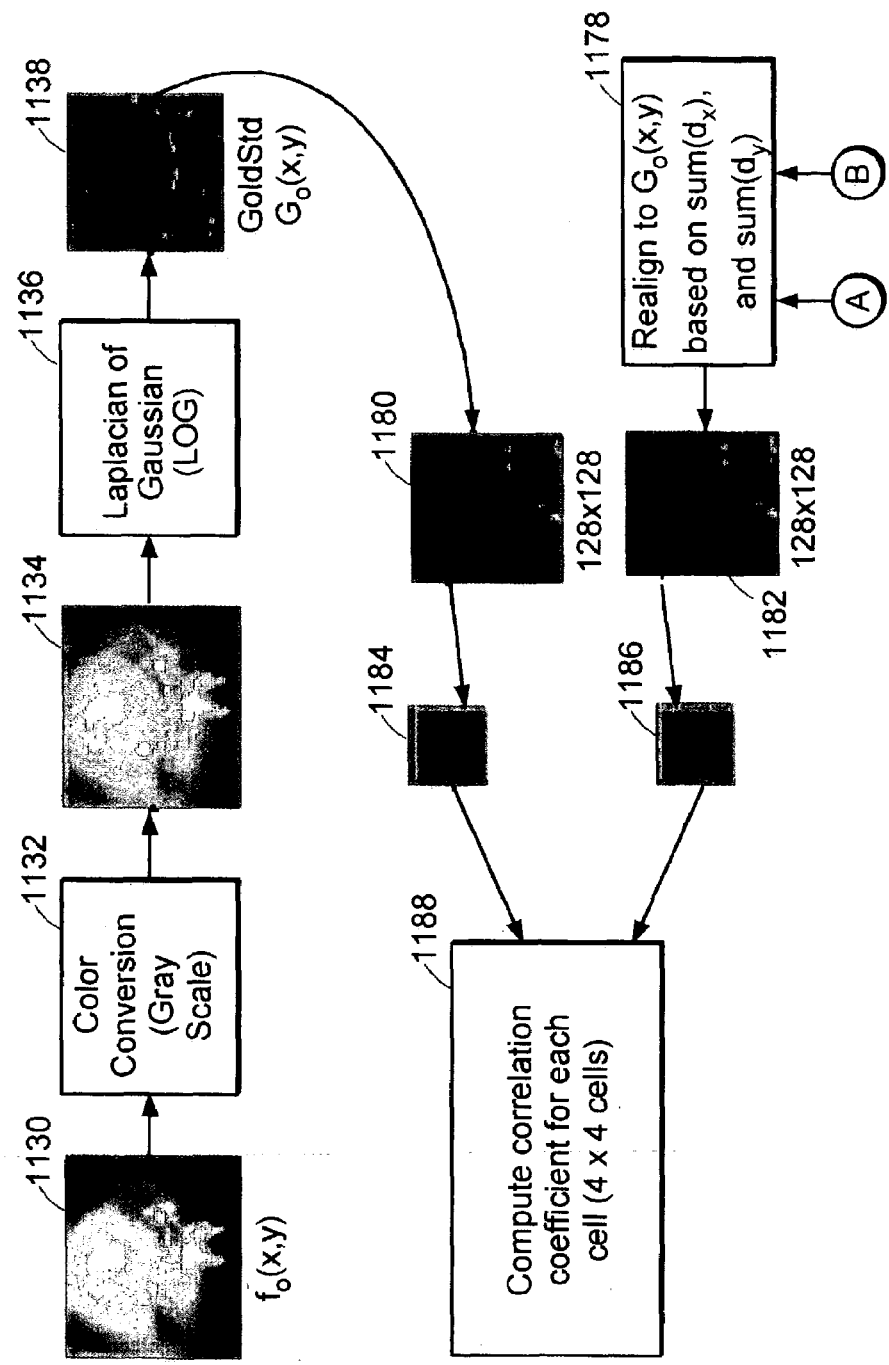
FIGS. 46A and 46B show a schematic flow diagram depicting steps in a version of the method shown in FIG. 45 of determining a correction for image misalignment according to an illustrative embodiment of the invention.
Figure 46B:
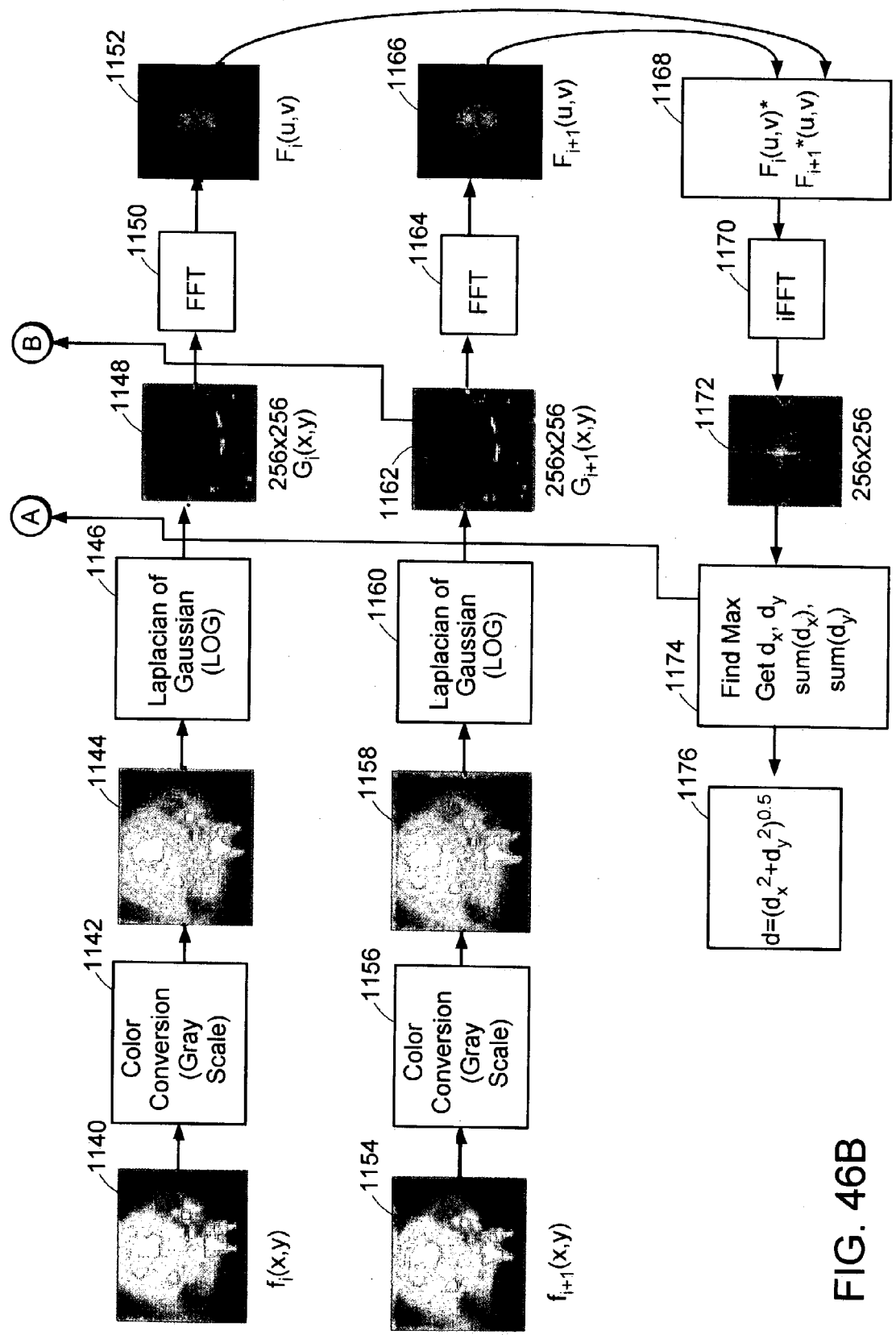
Figure 47A:
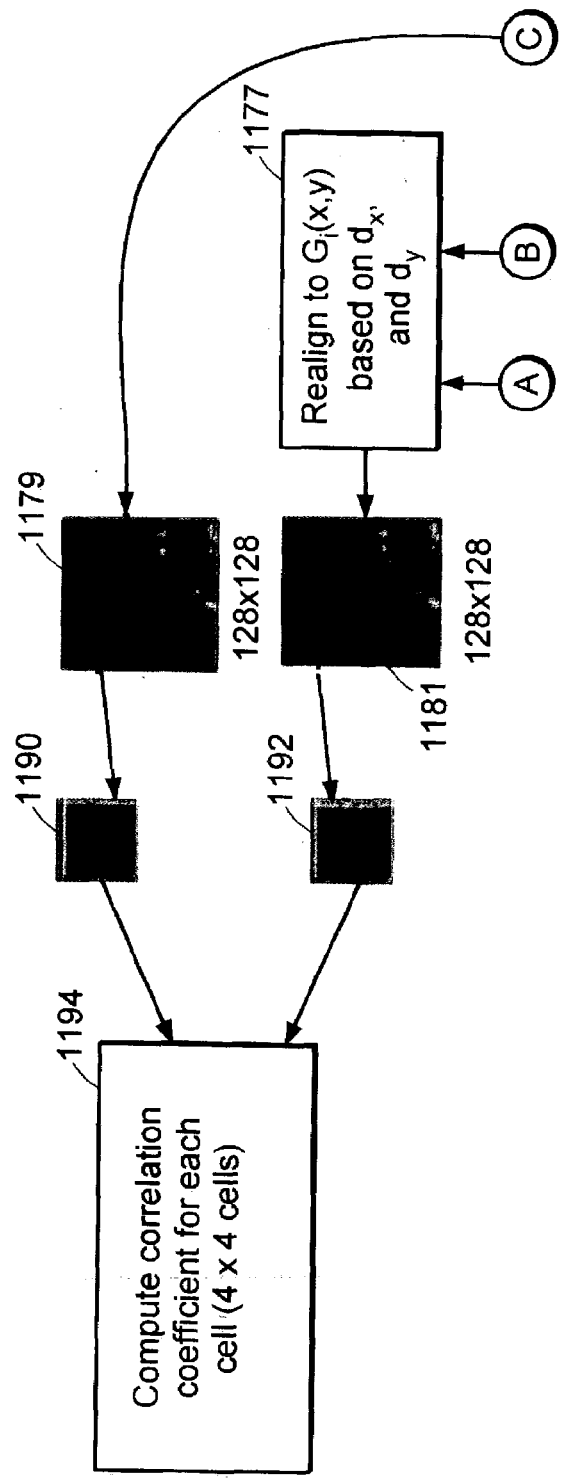
FIGS. 47A and 47B show a schematic flow diagram depicting steps in a version of the method shown in FIG. 45 of determining a correction for image misalignment according to an illustrative embodiment of the invention.

FIG. 45, FIGS. 46A and B, and FIGS. 47A and B depict steps in illustrative embodiment methods of determining a misalignment correction between two images of a sequence, and methods of validating that determination. Steps 1096 and 1098 of FIG. 45 show development of data from an initial image with which data from a subsequent image are compared in order to determine a misalignment correction between the subsequent image and the initial image. An initial image "o" is preprocessed, then filtered to obtain a matrix of values, for example, optical luminance (brightness, intensity), representing a portion of the initial image. In one embodiment, preprocessing comprises transforming the three RGB color components corresponding to a given pixel into a single luminance value. An exemplary luminance is CCIR 601, shown in Equation 63. CCIR 601 luminance may be used, for example, as a measure of the "whiteness" of a particular pixel in an image from an acetowhitening test. Different expressions for grayscale luminance may be used, and the choice may be geared to the specific type of diagnostic test conducted. The details of step 1096 of FIG. 45 is illustrated in blocks 1130, 1132, and 1134 of FIG. 46A, where block 1130 represents the initial color image, "o", in the sequence, block 1132 represents conversion of color data to grayscale using Equation 63, and block 1134 represents the image of block 240 after conversion to grayscale. Referring now to FIGS. 46A and 46B, FIG. 46B is a continuation of FIG. 46A, linked, for example, by the circled connectors labeled A and B. Accordingly, going forward, FIGS. 46A and 46B are referred to as FIG. 46.

Step 1098 of FIG. 45 represents filtering a 256×256 portion of the initial image, for example, a portion analogous to the 256×256 central portion 1088 of the image 1086 of FIG. 44A, using Laplacian of Gaussian filtering. Other filtering techniques are used in other embodiments. Preferred embodiments employ Laplacian of Gaussian filtering, which combines the Laplacian second derivative approximation with the Gaussian smoothing filter to reduce the high frequency noise components prior to differentiation. This filtering step may be performed by discrete convolution in the space domain, or by frequency domain filtering. The Laplacian of Gaussian (LoG) filter may be expressed in terms of x and y coordinates (centered on zero) as shown in Equation 77:

$$LoG(x, y) = -\frac{1}{\pi\sigma^4}\left[1 - \frac{x^2 + y^2}{2\sigma^2}\right]e^{-\frac{x^2+y^2}{2\sigma^2}} \quad (77)$$

where x and y are space coordinates and a is the Gaussian standard deviation. In one preferred embodiment, an approximation to the LoG function is used. Illustrative embodiments described herein include use of an approximation kernel(s) of size 9×9, 21×21, and/or 31×31. The Gaussian standard deviation, a, is chosen in certain preferred embodiments using Equation 78:

$$\sigma = \text{LoG filter size}/8.49 \quad (78)$$

where LoG filter size corresponds to the size of the discrete kernel approximation to the LoG function (i.e. 9, 21, and 31 for the approximation kernels used herein). Other embodiments employ different kernel approximations and/or different values of Gaussian standard deviation.

The LoG filter size may be chosen so that invalid scans are failed and valid scans are passed with a minimum of error. Generally, use of a larger filter size is better at reducing large structured noise and is more sensitive to larger image features and larger motion, while use of a smaller filter size is more sensitive to smaller features and smaller motion. One embodiment of the invention comprises adjusting filter size to coordinate with the kind of motion being tracked and the features being imaged.

Figure 47B:
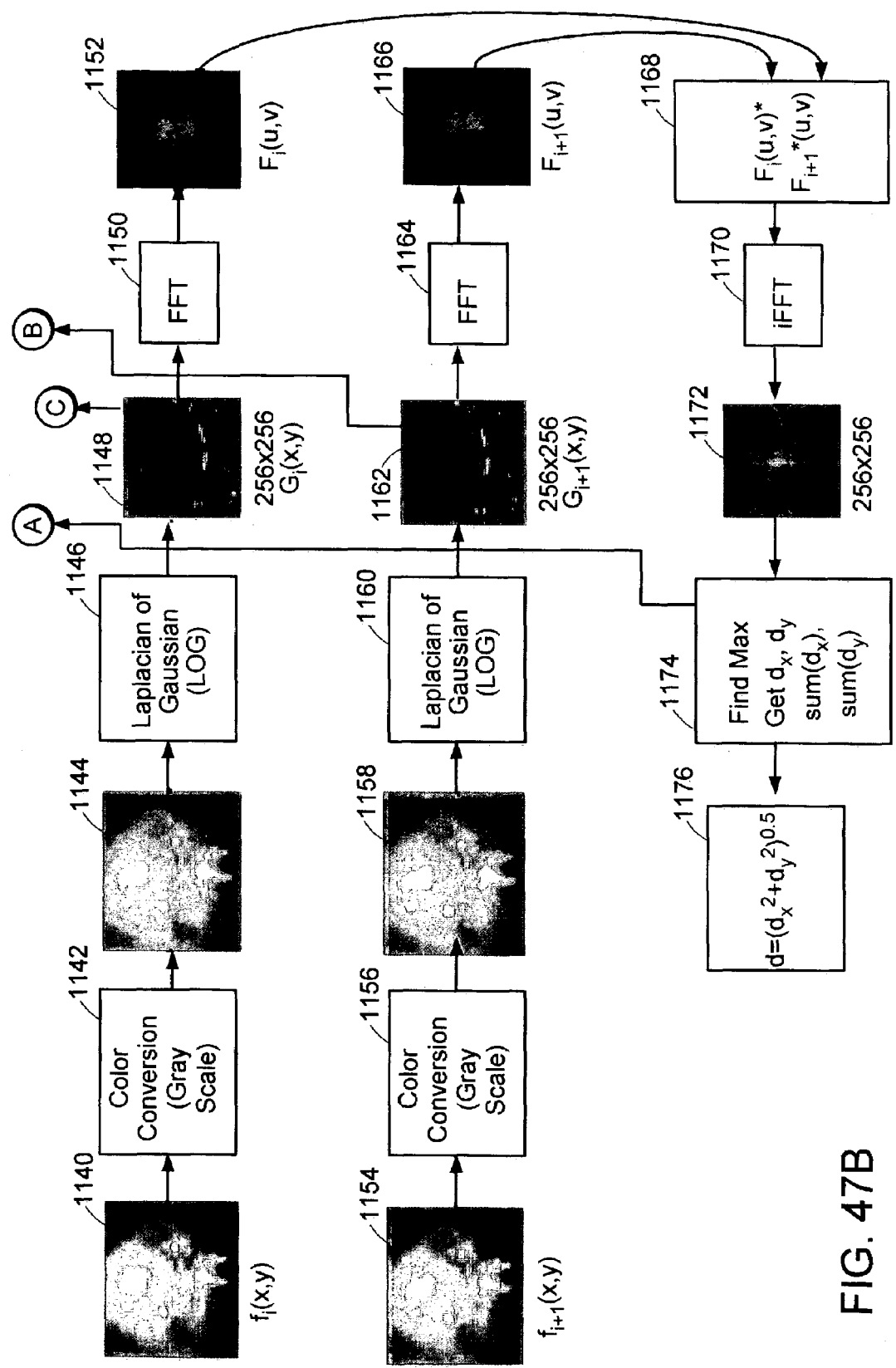

The details of step 1098 of FIG. 45 is illustrated in FIG. 46 in blocks 1134, 1136, and 1138 where block 1134 represents data from the initial image in the sequence after conversion to grayscale luminance, block 1136 represents the application of the LoG filter, and block 1138 represents the 256×256 matrix of data values, $G_o(x,y)$, which is the "gold standard" by which other images are compared in validating misalignment correction determinations in this embodiment. As detailed in FIGS. 47A and 47B, one embodiment validates a misalignment correction determination by comparing a given image to its preceding image in the sequence, not by comparing a given image to the initial image in the sequence as shown in FIG. 46. (Referring now to FIGS. 47A and 47B, FIG. 47B is a continuation of FIG. 47A, linked, for example, by the circled connectors labeled A, B, and C. Accordingly, going forward, FIGS. 47A and 47B are referred to as FIG. 47.) Although FIG. 45, FIG. 46, and FIG. 47 show application of the LoG filter as a discrete convolution in the space domain, resulting in a standard expressed in space coordinates, other embodiments comprise applying the LoG filter in the frequency domain. In either case, the LoG filter is preferably zero padded to the image size.

The details of steps 1100 and 1102 of FIG. 45 represent preprocessing an image "i" by converting RGB values to grayscale luminance as discussed above, and performing LoG filtering to obtain $G_i(x,y)$, a matrix of values from image "i" which is compared with that of another image in the sequence in order to determine a misalignment correction between the two images. The details of steps 1100 and 1102 of FIG. 45 are illustrated in FIG. 46 in blocks 1140, 1142, 1144, 1146, and 1148, where $f_i(x,y)$ in block 1140 is the raw image data from image "i", block 1142 represents conversion of the $f_i(x,y)$ data to gray scale intensities as shown in block 1144, and block 1146 represents application of the LoG filter on the data of block 1144 to produce the data of block 1148, $G_i(x,y)$.

Similarly, steps 1106 and 1108 of FIG. 45 represent preprocessing an image "j" by converting RGB values to grayscale luminance as discussed above, and performing LoG filtering to obtain $G_j(x,y)$, a matrix of values from image "j" which is compared with image "i" in order to determine a measure of misalignment between the two images. In some preferred embodiments, image "j" is subsequent to image "i" in the sequence. In some preferred embodiments, "i" and "j" are consecutive images. Steps 1106 and 1108 of FIG. 45 are illustrated in FIG. 46 in blocks 1154, 1156, 1158, 1160, and 1162, where "j" is "i+1", the image consecutive to image "i" in the sequence. In FIG. 46, block 1154 is the raw "i+1" image data, block 1156 represents conversion of the "i+1" data to gray scale intensities as shown in block 1158, and block 1160 represents application of the LoG filter on the data of block 1158 to produce the data of block 1162, $G_{i+1}(x,y)$.

Steps 1104 and 1110 of FIG. 45 represent applying a Fourier transform, for example, a Fast Fourier Transform (FFT), using $G_i(x,y)$ and $G_j(x,y)$, respectively, to obtain $F_i(u,v)$ and $F_j(u,v)$, which are matrices of values in the frequency domain corresponding to data from images "i" and "j", respectively. Details of steps 1104 and 1110 of FIG. 45 are illustrated in FIG. 46 by blocks 1148, 1150, 1152, 1162, 1164, and 1166, where "j" is "i+1", the image consecutive to image "i" in the sequence. In FIG. 46, block 1148 represents the LoG filtered data, $G_i(x,y)$, corresponding to image "i", and block 1150 represents taking the Fast Fourier Transform of $G_i(x,y)$ to obtain $F_i(u,v)$, shown in block 1152. Similarly, in FIG. 46 block 1162 is the LoG filtered data, $G_{i+1}(x,y)$, corresponding to image "i+1" and block 1164 represents taking the Fast Fourier Transform of $G_{i+1}(x,y)$ to obtain $F_{i+1}(u,v)$, shown in block 1166.

Step 1112 of FIG. 45 represents computing the cross correlation $F_i(u,v) \ F^*_j(u,v)$, where $F_i(u,v)$ is the Fourier transform of data from image "i", $F^*_j(u,v)$ is the complex conjugate of the Fourier transform of data from image "j", and u and v are frequency domain variables. The cross-correlation of two signals of length $N_1$ and $N_2$ provides $N_1+N_2-1$ values; thus avoiding aliasing problems due to under-sampling, the two signals should be padded with zeros up to $N_1+N_2-1$ samples. Details of step 1112 of FIG. 45 are represented in FIG. 46 by blocks 1152, 1166, and 1168. Block 1168 of FIG. 46 represents computing the cross correlation, $F_i(u,v) \ F^*_{i+1}(u,v)$, using $F_i(u,v)$, the Fourier transform of data from image "i", and $F^*_{i+1}(u,v)$, the complex conjugate of the Fourier transform of data from image "i+1". The cross-correlation may also be expressed as c(k,l) in Equation 79:

$$c(k,l) = \Sigma\Sigma I_1(p,q) I_2(p-k, q-l) \qquad (79)$$

where variables (k,l) can be thought of as the shifts in each of the x- and y-directions which are being tested in a variety of combinations to determine the best measure of misalignment between two images $I_1$ and $I_2$, and where p and q are matrix element markers.

Step 1114 of FIG. 45 represents computing the inverse Fourier transform of the cross-correlation computed in step 1112. Step 1114 of FIG. 45 is represented in FIG. 46 by block 1170. The resulting inverse Fourier transform maps how well the 256×256 portions of images "i" and "j" match up with each other given various combinations of x- and y-shifts. Generally, the normalized correlation coefficient closest to 1.0 corresponds to the x-shift and y-shift position providing the best match, and is determined from the resulting inverse Fourier transform. In a preferred embodiment, correlation coefficients are normalized by dividing matrix values by a scalar computed as the product of the square root of the (0,0) value of the auto-correlation of each image. In this way, variations in overall brightness between the two images have a more limited effect on the correlation coefficient, so that the actual movement within the image frame field between the two images is better reflected in the misalignment determination.

Step 1116 of FIG. 45 represents determining misalignment values $d_x$, $d_y$, d, sum($d_x$), sum($d_y$), and Sum($d_j$), where $d_x$ is the computed displacement between the two images "i" and "j" in the x-direction, $d_y$ is the computed displacement between the two images in the y-direction, d is the square root of the sum $d_x^2 + d_y^2$ and represents an overall displacement between the two images, sum($d_x$) is the cumulative x-displacement between the current image "j" and the first image in the sequence "o", sum($d_y$) is the cumulative y-displacement between the current image "j" and the first image in the sequence "o", and Sum($d_j$) is the cumulative displacement, d, between the current image "j" and the first image in the sequence "o". Step 1116 of FIG. 45 is represented in FIG. 46 by blocks 1172, 1174, and 1176. Blocks 1174 and 1176 represent finding the maximum value in the data of block 1172 in order to calculate $d_x$, $d_y$, d, sum($d_x$), sum($d_y$), and Sum($d_{i+1}$) as described above, where image "j" in FIG. 45 is "i+1" in FIG. 46, the image consecutive to image "i". For example, in the scan illustrated by block 732 in FIG. 27B, if image "i" is the image at block 750, then image "j" is the next consecutive image (the image at block 752).

Steps 1118, 1120, and 1122 of FIG. 45 represent one method of validating the misalignment correction determined for image "j" in step 1116 of FIG. 45. This method of validating misalignment correction is represented in blocks 1177, 1179, 1181, 1190, 1192, and 1194 of FIG. 47. Another method of validating a misalignment correction is represented in steps 1124, 1126, and 1128 of FIG. 45; and this method is represented in blocks 1178, 1180, 1182, 1184, 1186, and 1188 of FIG. 46. FIG. 47 is a schematic flow diagram depicting steps in a version of the methods shown in FIG. 45 of determining a correction for a misalignment between two images in which validation is performed using data from two consecutive images. One embodiment includes using consecutive or near-consecutive images to validate a misalignment correction determination, as in FIG. 47. Other embodiments comprise using the initial image to validate a misalignment correction determination for a given image, as in FIG. 46.

In FIG. 45, step 1118 represents realigning $G_j(x,y)$, the LoG-filtered data from image "j", to match up with $G_i(x,y)$, the LoG-filtered data from image "i", using the misalignment values $d_x$ and $d_y$ determined in step 1116. In preferred embodiments, image "j" is consecutive to image "i" in the sequence of images. Here, image "j" is image "i+1" such that $G_i(x,y)$ is aligned with $G_{i+1}(x,y)$ as shown in block 1177 of FIG. 47. Similarly, in FIG. 45, step 1124 represents realigning $G_j(x,y)$, the LoG-filtered data from image "j", to match up with $G_o(x,y)$, the LoG-filtered "gold standard" data from the initial image "o", using the displacement values sum($d_x$) and sum($d_y$) determined in step 1116. Step 1124 of FIG. 45 is represented in block 1178 of FIG. 46.

Step 1120 of FIG. 45 represents comparing corresponding validation cells from $G_j(x,y)$ and $G_i(x,y)$ by computing correlation coefficients for each cell. This is represented schematically in FIG. 47 by blocks 1179, 1181, 1190, 1192, and 1194 for the case where j=i+1. First, a 128×128 pixel central portion of the realigned $G_{i+1}(x,y)$ is selected, and the corresponding 128×128 pixel central portion of $G_i(x,y)$ is selected, as shown in blocks 1179 and 1181 of FIG. 47. An exemplary 128×128 pixel validation region 1090 is shown in FIG. 44B. Then, one embodiment comprises computing a correlation coefficient for each of 16 validation cells. An exemplary validation cell from each of the realigned $G_{i+1}(x,y)$ matrix 1181 and $G_j(x,y)$ matrix 1179 is shown in blocks 1192 and 1190 of FIG. 47. The validation cells are as depicted in the 32×32 pixel divisions 1092 of the 128×128 pixel validation region 1090 of FIG. 44B. Different embodiments use different numbers and/or different sizes of validation cells. Correlation coefficients are computed for each of the 16 cells, as shown in block 1194 of FIG. 47. Each correlation coefficient is a normalized cross-correlation coefficient as shown in Equation 80:

$$c'(m,n) = \frac{\sum\sum I_1[p,q] \times I_2[p,q]}{\sqrt{\sum\sum I_1^2[p,q]} \sqrt{\sum\sum I_2^2[p,q]}} \quad (80)$$

where c'(m,n) is the normalized cross-correlation coefficient for the validation cell (m,n), m is an integer 1 to 4 corresponding to the column of the validation cell whose correlation coefficient is being calculated, n is an integer 1 to 4 corresponding to the row of the validation cell whose correlation coefficient is being calculated, p and q are matrix element markers, $I_1[p,q]$ are elements of the cell in column m and row n of the 128×128 portion of the realigned image shown in block 1181 of FIG. 47, and $I_2[p,q]$ are elements of the cell in column m and row n of the 128×128 portion of $G_j(x,y)$ shown in block 1179 of FIG. 47. In that figure, p=1 to 32 and q=1 to 32, and the sums shown in Equation 80 are performed over p and q. The cross-correlation coefficient of Equation 80 is similar to an auto-correlation in the sense that a subsequent image is realigned with a prior image based on the determined misalignment correction so that, ideally, the aligned images appear to be identical. A low value of c'(m,n) indicates a mismatching between two corresponding cells. The misalignment correction determination is then either validated or rejected based on the values of the 16 correlation coefficients computed in step 1194 of FIG. 47. For example, each correlation coefficient may be compared against a threshold maximum value. This corresponds to step 1122 of FIG. 45.

Step 1126 of FIG. 45 represents comparing corresponding validation cells from $G_j(x,y)$ and $G_o(x,y)$ by computing correlation coefficients for each cell. This is represented schematically in FIG. 46 by blocks 1180, 1182, 1184, 1186, and 1188 for the case where j=i+1. First, a 128×128 pixel central portion of the realigned $G_{i+1}(x,y)$ is selected, and the corresponding 128×128 pixel central portion of $G_o(x,y)$ is selected, as shown in blocks 1182 and 1180 of FIG. 46. An exemplary 128×128 pixel validation region 1090 is shown in FIG. 44B. Then, one embodiment comprises computing a correlation coefficient for each of the 16 validation cells. An exemplary validation cell from each of the realigned $G_{i+1}(x,y)$ matrix 1182 and $G_o(x,y)$ matrix 1180 is shown in blocks 1186 and 1184 of FIG. 46. The validation cells are as depicted in the 32×32 pixel divisions 1092 of the 128×128 pixel validation region 1090 of FIG. 44B. Other embodiments use different numbers of and/or different sizes of validation cells. Correlation coefficients are computed for each of the 16 cells, as shown in block 1188 of FIG. 46. Each correlation coefficient is a normalized "auto"-correlation coefficient as shown in Equation 80 above, where $I_1[p,q]$ are elements of the cell in column m and row n of the 128×128 portion of the realigned subsequent image shown in block 1182 of FIG. 46, and $I_2[p,q]$ are elements of the cell in column m and row n of the 128×128 portion of $G_o(x,y)$ shown in block 1180 of FIG. 46. A low value of c'(m,n) indicates a mismatching between two corresponding cells. The misalignment determination is then either validated or rejected based on the values of the 16 correlation coefficients computed in step 1188 of FIG. 46. This corresponds to step 1128 of FIG. 45.

In one embodiment, determinations of misalignment correction and validation of these determinations as shown in each of FIG. 45, FIG. 46, and FIG. 47 are performed using a plurality of the images in sequence. In one embodiment, determinations of misalignment correction and validations thereof are performed while images are being obtained, so that an examination in which a given sequence of images is obtained may be aborted before all the images are obtained. In some embodiments, a misalignment correction is determined, validated, and compensated for by adjusting the optical signal detection device obtaining the images. In certain embodiments, an adjustment of the optical signal detection device is made after each of a plurality of images are obtained. In certain embodiments, an adjustment, if required by the misalignment correction determination, is made after every image subsequent to the first image (except the last image), and prior to the next consecutive image. In one embodiment, a cervical tissue scan comprising a sequence of 13 images is performed using on-the-fly misalignment correction determination, validation, and camera adjustment, such that the scan is completed in about 12 seconds. Other embodiments comprise obtaining sequences of any number of images in more or less time than indicated here.

Each of steps 1122 and 1128 of the embodiment of FIG. 45 represents applying a validation algorithm to determine at least the following: (1) whether the misalignment correction can be made, for example, by adjusting the optical signal detection device, and (2) whether the misalignment correction determined is valid. In an exemplary embodiment, the validation algorithm determines that a misalignment correction cannot be executed during an acetowhitening exam conducted on cervical tissue in time to provide sufficiently aligned subsequent images, if either of conditions (a) or (b) is met, as follows: (a) di, the displacement between the current image "i" and the immediately preceding image "i−1" is greater than 0.55-mm or (b) Sum($d_i$), the total displacement between the current image and the first image in the sequence, "o", is greater than 2.5-mm. If either of these conditions is met, the spectral scan in progress is aborted, and another scan must be performed. If sufficient time remains within the optimal time window for obtaining spectral data, a fresh scan may begin immediately after a previous scan is aborted. Other embodiments may comprise the use of different validation rules. In one embodiment, if only condition (a) is met, the system retakes image "i" while continuing the spectral scan, and if condition (b) is met, the spectral scan is aborted and must be restarted if sufficient time remains within the optimal window.

In one embodiment, validation is performed for each determination of misalignment correction by counting how many of the correlation coefficients c'$_r$(m,n) shown in Equation 80 (corresponding to the 16 validation cells) is less than 0.5. If this number is greater than 1, the scan in progress is aborted. In one embodiment, if there are more than three correlation coefficients c'$_r$(m,n) less than 0.35, then the scan is aborted. Other embodiments comprise the use of different validation rules. Gradual changes in image features, such as acetowhitening of tissue or changes in glare, cause discrepancies which are reflected in the correlation coefficients of the validation cells, but which do not represent a spatial shift. Thus, in preferred embodiments, the validation is performed as shown in FIG. 47, where validation cells of consecutive images are used to calculate the correlation coefficients. In other embodiments, the validation is performed as shown in FIG. 46, where validation cells of a current image, "i", and an initial image of the sequence, "o", are used to calculate the correlation coefficients of Equation 80.

FIGS. 48A-F depict a subset of adjusted, filtered images 1200, 1204, 1208, 1212, 1216, and 1220 from a sequence of images of a tissue with an overlay of gridlines showing the validation cells used in validating the determinations of misalignment correction between the images, according to an illustrative embodiment of the invention. By performing validation according to FIG. 47, using consecutive images to calculate the correlation coefficients of Equation 80, the number of validation cells with correlation coefficient below 0.5 for the misalignment-corrected images of FIG. 48A-F is 0, 1, 0, 0, and 1 for images 1204, 1208, 1212, 1216, and 1220, respectively. Since none of the images have more than one coefficient below 0.5, this sequence is successful and is not aborted. There is only a gradually changing glare, seen to move within the validation region 1202, 1206, 1210, 1214, 1218, 1222 of each image. In an embodiment in which validation is performed as in FIG. 46, the number of validation cells with correlation coefficient below 0.5 for the misalignment-corrected images of FIG. 48A-F is 3, 4, 5, 5, and 6 for images 1204, 1208, 1212, 1216, and 1220, respectively. This is not a good result in this example, since the exam would be erroneously aborted, due only to gradual changes in glare or whitening of tissue, not uncompensated movement of the tissue sample.

Alternatively, validation cells that are featureless or have low signal-to-noise ratio are eliminated from consideration. Those cells can produce meaningless correlation coefficients. Featureless cells in a preferred embodiment are identified and eliminated from consideration by examining the deviation of the sum squared gradient of a given validation cell from the mean of the sum squared gradient of all cells as shown in Equation 81:

IF $ssg_1(m,n) < \text{Mean}[ssg(m,n)] - \text{STD}[ssg(m,n)]$, THEN
set $c'_1(m,n) = 1.0$ (81)

where $c'_1(m,n)$ is the correlation of the given validation cell "1", $ssg_1(m,n) = \Sigma\Sigma I_1^2[p,q]$, m=1 to 4, n=1 to 4, $I_1[p,q]$ is the matrix of values of the given validation cell "1", p=1 to 32, q=1 to 32, the summations $\Sigma\Sigma$ are performed over pixel markers p and q, Mean[ssg(m,n)] is the mean of the sum squared gradient of all 16 validation cells, and STD[ssg(m,n)] is the standard deviation of the sum squared gradient of the given validation cell "1" from the mean sum squared gradient. By setting $c'_1(m,n) = 1.0$ for the given validation cell, the cell does not count against validation of the misalignment correction determination in the rubrics of either step 1122 or step 1128 of FIG. 45, since a correlation coefficient of 1.0 represents a perfect match.

If an image has large intensity differences between the upper and lower borders and/or the left and right borders of the image frame field, LoG filtering may result in "wraparound error." A preferred embodiment employs an image blending technique such as "feathering" to smooth border discontinuities, while requiring only a minimal amount of additional processing time.

Figures 49A, 49B:
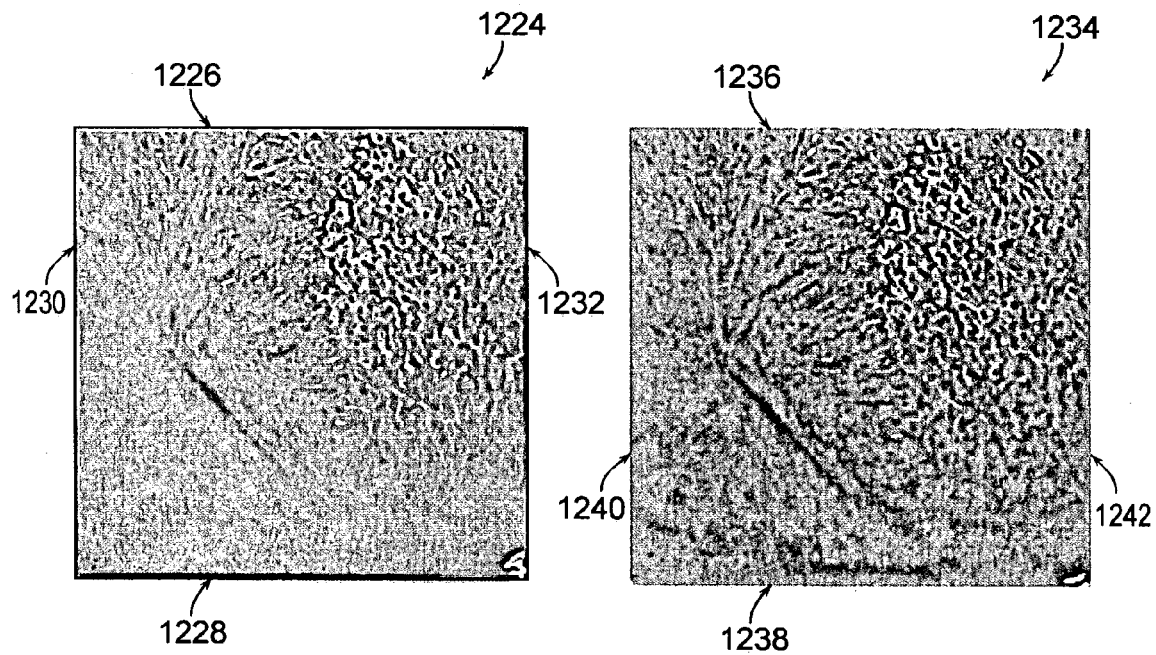
FIG. 49A depicts a sample image after application of a 9-pixel size (9×9) is Laplacian of Gaussian filter (LoG 9 filter) on an exemplary image from a sequence of images of tissue, used in determining a correction for image misalignment, according to an illustrative embodiment of the invention.
FIG. 49B depicts the application of both a feathering technique and a Laplacian of Gaussian filter on the exemplary image used in FIG. 49A to account for border processing effects, used in determining a correction for image misalignment according to an illustrative embodiment of the invention.

FIG. 49A depicts a sample image 1224 after application of a 9-pixel size [9×9] Laplacian of Gaussian filter (LoG 9 filter) on an exemplary image from a sequence of images of tissue, according to an illustrative embodiment of the invention. The filtered intensity values are erroneous at the top edge 1226, the bottom edge 1228, the right edge 1232, and the left edge 1230 of the image 1224. Since LoG frequency domain filtering corresponds to cyclic convolution in the space-time domain, intensity discontinuities between the top and bottom edges of an image and between the right and left edges of an image result in erroneous gradient approximations. These erroneous gradient approximations can be seen in the dark stripe on the right edge 1232 and bottom edge 1228 of the image 1224, as well as the light stripe on the top edge 1226 and the left edge 1230 of the image 1224. This often results in a misalignment correction determination that is too small, since changes between the images due to spatial shift are dwarfed by the edge effects. A preferred embodiment uses a "feathering" technique to smooth border discontinuities and reduce "wraparound error."

Feathering comprises removal of border discontinuities prior to application of a filter. In preferred embodiments, feathering is performed on an image before LoG filtering, for example, between steps 1100 and 1102 in FIG. 45. In embodiments where LoG filtering is performed in the frequency domain (subsequent to Fourier transformation), feathering is preferably performed prior to both Fourier transformation and LoG filtering. For two-dimensional image intensity (luminance) functions $I_1(x,y)$ and $I_2(x,y)$ that are discontinuous at $x=x_0$, an illustrative feathering algorithm is as follows:

$$I'_1(x, y) = I_1(x, y) \cdot f\left(\frac{x - x_0}{d} + 0.5\right) \text{ and} \quad (82)$$

$$I'_2(x, y) = I_2(x, y) \cdot \left(1 - f\left(\frac{x - x_0}{d} + 0.5\right)\right),$$

$$f(x) = \begin{cases} 0 & x < 0 \\ 3x^2 - 2x^3 & 0 \leq x \leq 1, \\ 0 & x > 1 \end{cases}$$

where $I_1'(x,y)$ and $I_2'(x,y)$ are the intensity (luminance) functions $I_1(x,y)$ and $I_2(x,y)$ after applying the feathering algorithm of Equation 82, and d is the feathering distance chosen. The feathering distance, d, adjusts the tradeoff between removing wraparound error and suppressing image content.

FIG. 49B depicts the application of both a feathering technique and a LoG filter on the same unfiltered image used in FIG. 49A. The feathering is performed to account for border processing effects, according to an illustrative embodiment of the invention. Here, a feathering distance, d, of 20 pixels was used. Other embodiments use other values of d. The filtered image 1234 of FIG. 49B does not display uncharacteristically large or small gradient intensity values at the top edge 1236, bottom edge 1238, right edge 1242, or left edge 1240, since discontinuities are smoothed prior to LoG filtering. Also, there is minimal contrast suppression of image detail at the borders. Pixels outside the feathering distance, d, are not affected. The use of feathering here results in more accurate determinations of misalignment correction between two images in a sequence of images.

Another method of border smoothing is multiplication of unfiltered image data by a Hamming window. In some embodiments, a Hamming window function is multiplied to image data before Fourier transformation so that the border pixels are gradually modified to remove discontinuities. However, application of the Hamming window suppresses image intensity as well as gradient information near the border of an image.

Figures 50A, 50B:
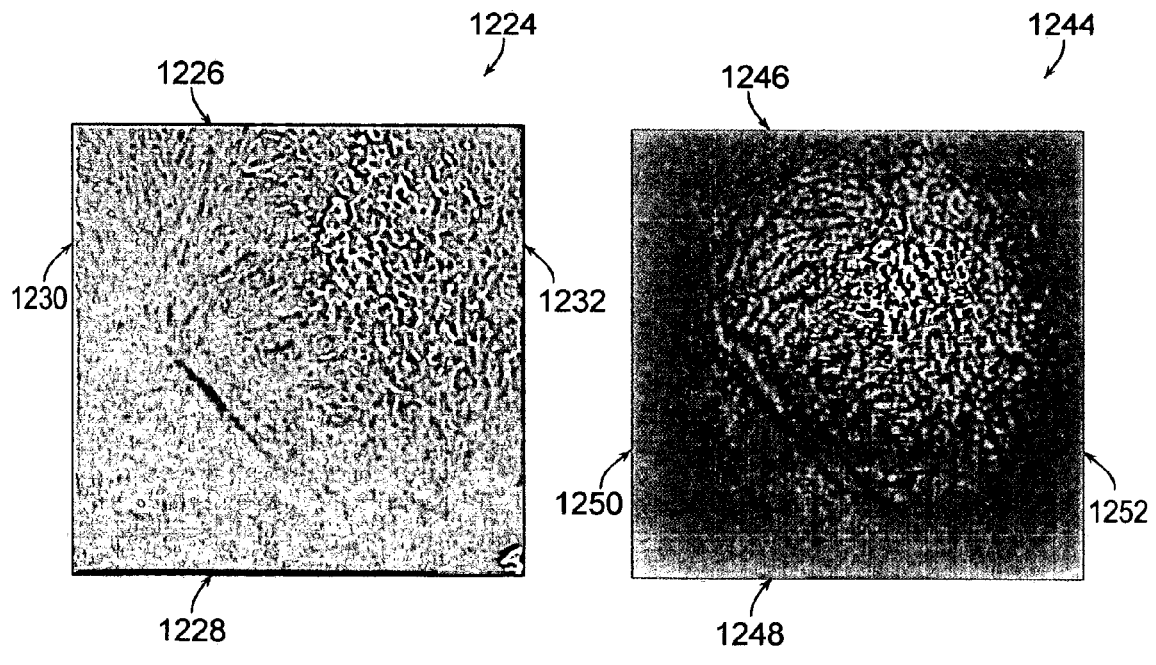
FIG. 50A depicts a sample image after application of a LoG 9 filter on an exemplary image from a sequence of images of tissue, used in determining a correction for image misalignment according to an illustrative embodiment of the invention.
FIG. 50B depicts the application of both a Hamming window technique and a LoG 9 filter on the exemplary image in FIG. 50A to account for border processing effects in the determination of a correction for image misalignment according to an illustrative embodiment of the invention.

FIG. 50A is identical to FIG. 49A and depicts the application of a LoG 9 filter on an exemplary image from a sequence of images of tissue according to an illustrative embodiment of the invention. The filtered intensity values are erroneous at the top edge 1226, the bottom edge 1228, the right edge 1232, and the left edge 1230 of the image 1224.

FIG. 50B depicts the application of both a Hamming window and a LoG 9 filter on the same unfiltered image used in FIG. 50A. Hamming windowing is performed to account for border processing effects, according to an illustrative embodiment of the invention. Each of the edges 1246, 1248, 1250, 1252 of the image 1244 of FIG. 50B no longer show the extreme filtered intensity values seen at the edges 1226, 1228, 1230, 1232 of the image 1224 of FIG. 50A. However, there is a greater suppression of image detail in FIG. 50B than in FIG. 49B. Thus, for this particular embodiment, application of the feathering technique is preferred over application of Hamming windowing.

One embodiment includes removing cyclic convolution artifacts by zero padding the image prior to frequency domain filtering to assure image data at an edge would not affect filtering output at the opposite edge. This technique adds computational complexity and may increase processing time.

Figure 51A:
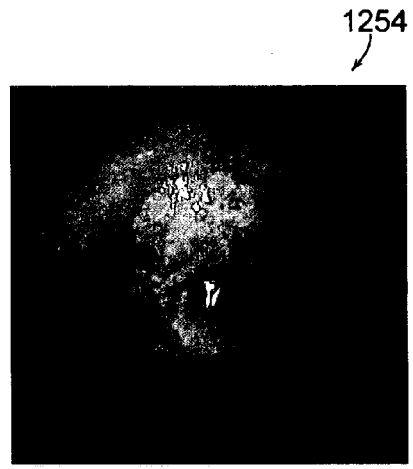
FIGS. 51A-F depict the determination of a correction for image misalignment using methods including the application of LoG filters of various sizes, as well as the application of a Hamming window technique and a feathering technique according to illustrative embodiments of the invention.
Figure 51B:
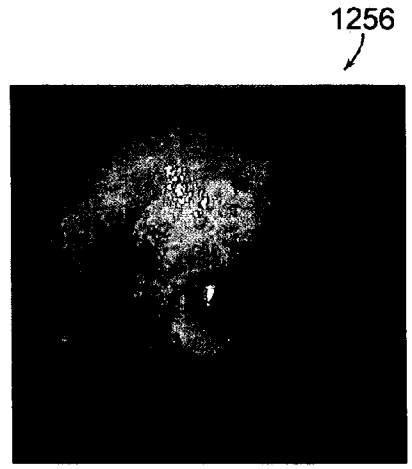
Figure 51C:
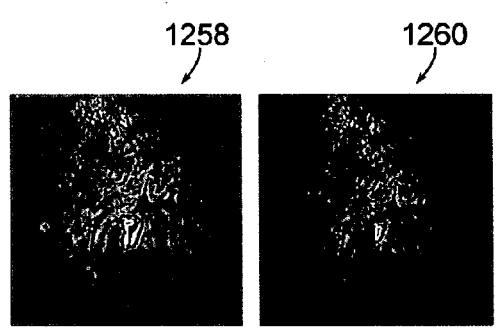
Figure 51D:
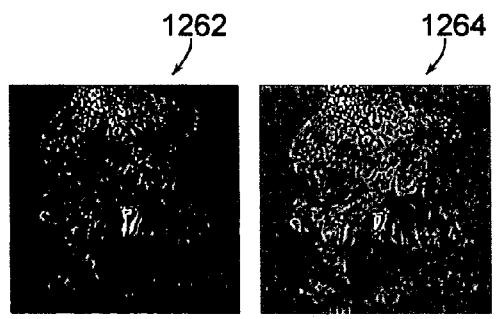
Figure 51E:
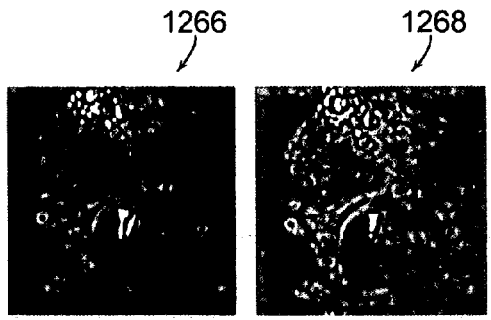
Figure 51F:
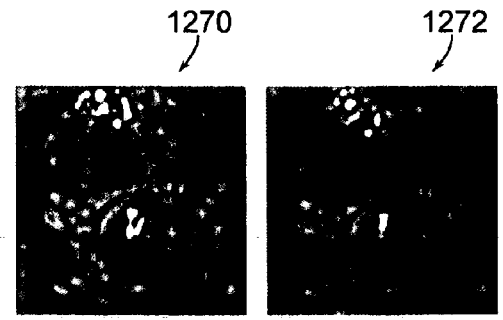

FIGS. 51A-F depict the determination of a misalignment correction between two images using methods including the application of LoG filters of various sizes, as well as the application of a Hamming window technique and a feathering technique, according to illustrative embodiments of the invention. Image 1254 and image 1256 of FIGS. 51A-B are consecutive images from a sequence of images of cervix tissue obtained during a diagnostic exam, each with a pixel resolution of about 0.054-mm. FIGS. 51C-F depict the application of four different image filtering algorithms: (1) Hamming window with LoG 9 filtering, (2) feathering with LoG 9 filtering, (3) feathering with LoG 21 filtering, and (4) feathering with LoG 31 filtering. Each of these algorithms are implemented as part of a misalignment correction determination and validation technique as illustrated in FIG. 45 and FIG. 47, and values of $d_x$ and $d_y$ between images 1254 and 1256 of FIGS. 51A-B are determined using each of the four filtering algorithms. For image 1254, each of the four different image filtering algorithms (1)-(4) listed above are applied, resulting in images 1258, 1262, 1266, and 1270, respectively, each having 256×256 pixels. The four different image filtering algorithms are also applied for image 1256, resulting in images 1260, 1264, 1268, and 1272, respectively, each having 256×256 pixels. Values of $(d_x, d_y)$ determined using Hamming+LoG 9 filtering are (−7, 0), expressed in pixels. Values of $(d_x, d_y)$ determined using feathering+LoG 9 filtering are (−2, −10). Values of $(d_x, d_y)$ determined using feathering+LoG 21 filtering are (−1, −9). Values of $(d_x, d_y)$ determined using feathering+LoG 31 filtering are (0, −8). All of the displacement values determined using feathering are close in this embodiment, and agree well with visually-verified displacement. However, in this example, the displacement values determined using Hamming windowing are different from those obtained using the other three filtering methods, and result in a misalignment correction that does not agree well with visually-verified displacement. Thus, for this example, feathering works best since it does not suppress as much useful image data.

The effect of the filtering algorithm employed, as well as the choice of validation rules are examined by applying combinations of the various filtering algorithms and validation rules to pairs of sequential images of tissue and determining the number of "true positives" and "false positives" identified. A true positive occurs when a bad misalignment correction determination is properly rejected by a given validation rule. A false positive occurs when a good misalignment correction determination is improperly rejected as a failure by a given validation rule. The classification of a validation result as a "true positive" or a "false positive" is made by visual inspection of the pair of sequential images. In preferred embodiments, whenever true failures occur, the scan should be aborted. Some examples of situations where true failures occur in certain embodiments include image pairs between which there is one or more of the following: a large non-translational deformation such as warping or tilting; a large jump for which motion tracking cannot compute a correct translational displacement; rotation greater than about 3 degrees; situations in which a target laser is left on; video system failure such as blur, dark scan lines, or frame shifting; cases where the image is too dark and noisy, in shadow; cases where a vaginal speculum (or other obstruction) blocks about half the image; other obstructions such as sudden bleeding.

In one embodiment, a set of validation rules is chosen such that true positives are maximized and false positives are minimized. Sensitivity and specificity can be adjusted by adjusting choice of filtering algorithms and/or choice of validation rules. Table 4 shows the number of true positives (true failures) and false positives (false failures) determined by a validation rule as depicted in FIG. 45 and FIG. 47 where validation is determined using consecutive images. Table 4 shows various combinations of filtering algorithms and validation rules. The four filtering algorithms used are (1) Hamming windowing with LoG 9 filtering, (2) feathering with LoG 9 filtering, (3) feathering with LoG 21 filtering, and (4) feathering with LoG 31 filtering. The values, c'(m,n), correspond to the normalized "auto"-correlation coefficient of Equation 80 whose value must be met or exceeded in order for a validation cell to "pass" in an embodiment. The "Number Threshold" column indicates the maximum number of "failed" validation cells, out of the 16 total cells, that are allowed for a misalignment correction determination to be accepted in an embodiment. If more than this number of validation cells fail, then the misalignment correction determination is rejected.

TABLE 4

True positives and false positives of validation determinations for embodiments using various combinations of filtering algorithms and validation rules.

| | c'(m, n) | Number Threshold | TP | FP |
|---|---|---|---|---|
| Hamming LoG 9 | −0.1 | 1 | 34 | 28 |
| Feathering LoG 9 | −0.1 | 3 | 19 | 17 |
| | 0.3 | 2 | 46 | 10 |
| Feathering LoG 21 | 0.35 | 3 | 52 | 4 |
| Feathering LoG 31 | 0.5 | 3 | 48 | 3 |

For the given set of cervical image pairs on which the methods shown in Table 4 were applied, feathering performs better than Hamming windowing, since there are more true positives and fewer false positives. Among different LoG filter sizes, LoG 21 and LoG 31 performs better than LoG 9 for both tracking and validation here. The LoG 21 filter is more sensitive to rotation and deformation than the LoG 31 filter for these examples. One embodiment of the determination and validation of misalignment corrections between 256×256 pixel portions of images of cervical tissue with pixel resolution of about 0.054-mm employs one or more of the following: (1) use of feathering for image border processing, (2) application of LoG 21 filter, (3) elimination of validation cells with low signal-to-noise ratio, and (4) use of consecutive images for validation.

Broadband Reflectance Arbitration and Low-Signal Masking

A tissue characterization system as shown in FIG. 1 also may comprise arbitrating between two or more redundant sets of spectral data as depicted in step 128 of FIG. 1. In one embodiment shown in FIG. 1, step 128 includes arbitrating between two sets of broadband reflectance data obtained in step 104 during a spectral scan for each interrogation point of a tissue sample. Data are obtained at each interrogation point using light incident to the interrogation point at two different angles, as depicted in FIG. 8. In this way, if only one set of reflectance data is affected by an artifact such as glare or shadow, the other set can be used in tissue classification, for example, in step 132 of FIG. 1. The arbitration step 128 in FIG. 1 determines whether either of the two sets of reflectance spectral data at each point is affected by an artifact. Step 128 also determines a single set of reflectance data from each interrogation point to be used in tissue classification if at least one of the two sets is acceptably unaffected by an artifact. As used here, artifacts identified in the arbitration step 128 of FIG. 1 include, for example, both lighting artifacts and obstruction artifacts—such as glare, shadow, blood, mucus, a speculum, smoke tube tissue, and/or os tissue.

In the embodiment shown in FIG. 1, step 128 additionally includes a first-level "hard masking" of certain interrogation points. For example, interrogation points are considered "indeterminate" where values of both sets of reflectance spectral data and/or values of the set of fluorescence data are low due to shadow or an obstruction. Additional spectral masks, both hard masks and soft masks, are determined in one embodiment in step 130 of FIG. 1. As discussed herein, hard-masking of data includes eliminating identified, potentially non-representative data from further consideration and identifying the corresponding tissue region as "indeterminate", while soft-masking includes applying a weighting function or weighting factor to identified, potentially non-representative data so that the importance of the data as a diagnostic indicator of a tissue region in a tissue classification algorithm is thereby reduced. A point that is soft-masked is not necessarily identified as "indeterminate".

The diagram 284 of FIG. 8 shows that a misalignment of the probe 142 may create conditions where either or both of the top and bottom speculum blades 286 block part or all of the illumination path from either or both of the intersecting upper and lower cones of illuminating light 196,198, thereby affecting the spectral data obtained for the region 250 of the tissue sample 194. The speculum blades, or other obstructions present during a spectral scan, may physically obstruct the region 250 being analyzed, or may partially obstruct the light illuminating the region 250 causing a shadow. In either case, the spectral data obtained may be adversely affected and rendered unusable for characterizing the region of the tissue sample. Obtaining multiple sets of spectral data using illumination from sources at various positions and angles improves the chances of obtaining at least one set of spectral data that is not affected by glare, shadow, and/or obstructions.

Figure 52:
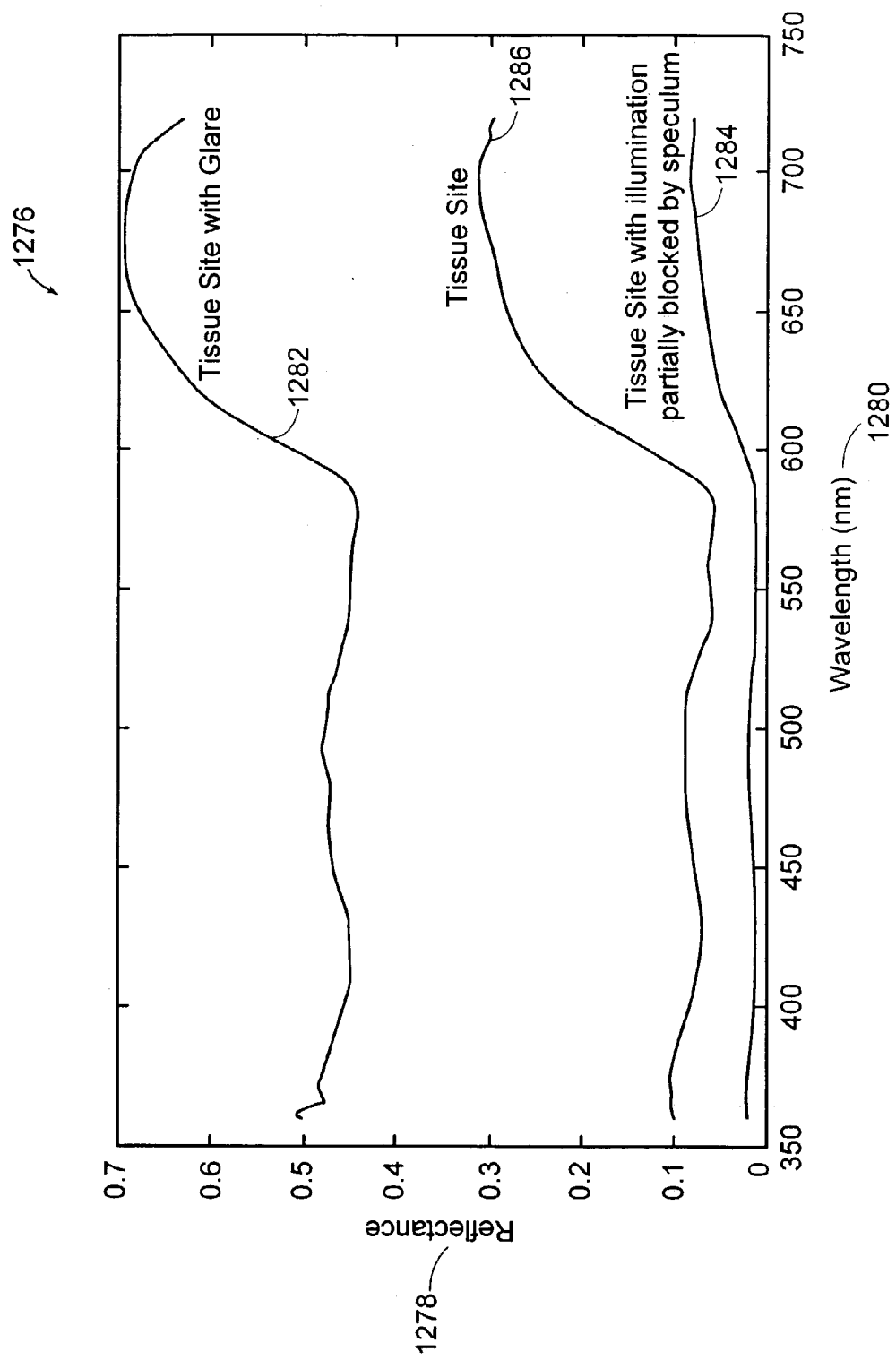
FIG. 52 shows a graph depicting exemplary mean values of reflectance spectral data as a function of wavelength for tissue regions affected by glare, tissue regions affected by shadow, and tissue regions affected by neither glare nor shadow according to an illustrative embodiment of the invention.

FIG. 52 shows a graph 1276 depicting exemplary mean values of reflectance spectral data 1278 as a function of wavelength 1280 for tissue regions affected by glare 1282, tissue regions affected by shadow 1284, and tissue regions affected by neither glare nor shadow 1286 according to an illustrative embodiment of the invention. The reflectance spectral data 1278 represent the fraction of incident light that is reflected from the sample. The graph 1276 shows that the reflectance values of a region of tissue affected by glare 1282 are higher at all measured wavelengths than the reflectance of a region of tissue not affected by glare 1286. The graph 1276 also shows that the reflectance values of a region of tissue with illumination partially blocked by a speculum blade such that the region is in shadow 1284, are lower at all measured wavelengths than the reflectance of a region of tissue not affected by shadow 1286. The shapes of all three curves 1282, 1284, 1286 are different. In this example, the data affected by glare or shadow may not be usable to determine a condition or characteristic of the region of the sample, if the data are not representative of the region of the tissue sample. Hence, glare and shadow may adversely affect spectral data obtained for a region of a tissue sample.

In one embodiment, step 104 of FIG. 1 comprises obtaining one fluorescence spectrum and two broadband reflectance spectra at each of a plurality of scan locations of the sample tissue (interrogation points). Here, a spectrum refers to a collection of spectral data over a range of wavelengths. In one embodiment method, spectral data are collected over a range of wavelengths between 360 and 720 nm in 1 nm increments. In other embodiments, the range of wavelengths lies anywhere between about 190 nm and 1100 nm. Here, the two reflectance spectra are referred to as the BB1 (broadband one) and BB2 (broadband two) spectra. BB1 and BB2 differ in the way that the tissue is illuminated at the time the spectral data are obtained as described below. In the embodiment shown in FIG. 6, the probe head 192 has 4 illumination sources 222, 224, 226, 228 located circumferentially about the collection optics 200. Two sources are above 222, 224 and two are below the horizontal plane 226, 228, as illustrated in the second arrangement 212 of FIG. 6. The two upper sources are used to obtain BB1 spectra and the two lower sources are used to obtain BB2 spectra. Since the upper and lower sources illuminate a region of the tissue sample using light incident to the region at different angles, an artifact—for example, or shadow—may affect one of the two reflectance spectra obtained for the region, while the other reflectance spectrum is unaffected. For example, during acquisition of spectral data, the BB1 spectrum may be unaffected by an artifact even if the BB2 spectrum is adversely affected by the artifact. In such a case, BB1 spectral data may be used to characterize the condition of the region of tissue, for example, in step 132 of FIG. 1, even though the BB2 data is not representative of the region. In other embodiments, the BB1 and BB2 spectra comprise one or more other types of spectral data, such as absorbance spectra, adsorption spectra, transmission spectra, fluorescence spectra, and/or other types of optical and atomic emission spectra.

Figure 53:
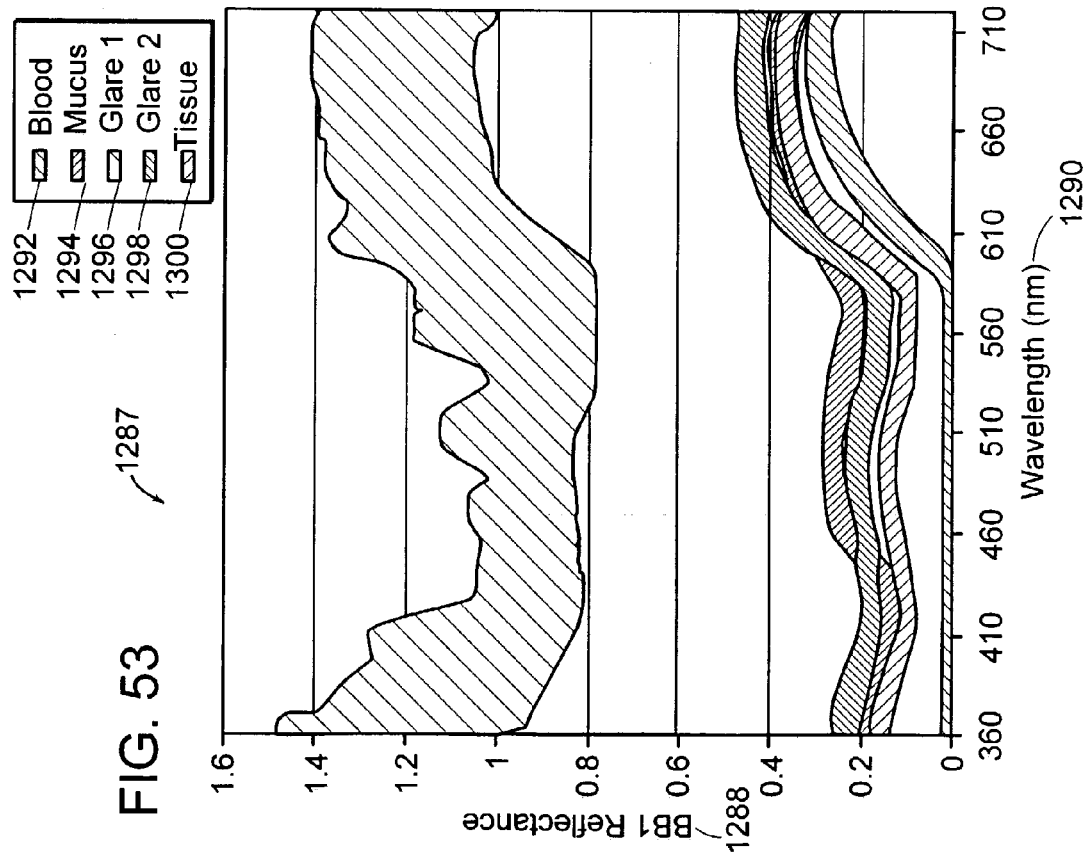
FIG. 53 shows a graph depicting mean values and standard deviations of broadband reflectance spectral data using the BB1 channel light source for regions confirmed as being obscured by blood, obscured by mucus, obscured by glare from the BB1 source, obscured by glare from the BB2 source, or unobscured, according to an illustrative embodiment of the invention.

FIG. 53 shows a graph 1287 depicting mean values and standard deviations of broadband reflectance spectral data using the BB1 channel light source for regions confirmed as being obscured by blood, obscured by mucus, obscured by glare from the BB1 source, obscured by glare from the BB2 source, or unobscured, according to an illustrative embodiment of the invention. Various sample test points corresponding to regions of tissue from patient scans were visually identified as having blood, mucus, or glare present. A sample point was identified as having blood present if it was completely covered by blood and if there was no glare. A sample point was identified as having mucus present if it was completely covered by mucus and if there was no glare. A sample point was identified as having glare based on visual evidence of glare and large reflectance values in at least one of the two sets of reflectance spectral data (the BB1 spectrum or the BB2 spectrum). FIG. 53 shows the range of BB1 reflectance values 1288 for a given category of the sample test points which lie within one standard deviation of the mean for the category, plotted as a function of wavelength 1290. FIG. 53 shows ranges of BB1 reflectance values 1288 for each of the following categories of sample test points: those identified as having blood present 1292, those identified as having mucus present 1294, those identified as having glare from the BB1 illumination source 1296, those identified as having glare from the BB2 illumination source 1298, and those identified as unobstructed tissue 1300.

Figure 54:
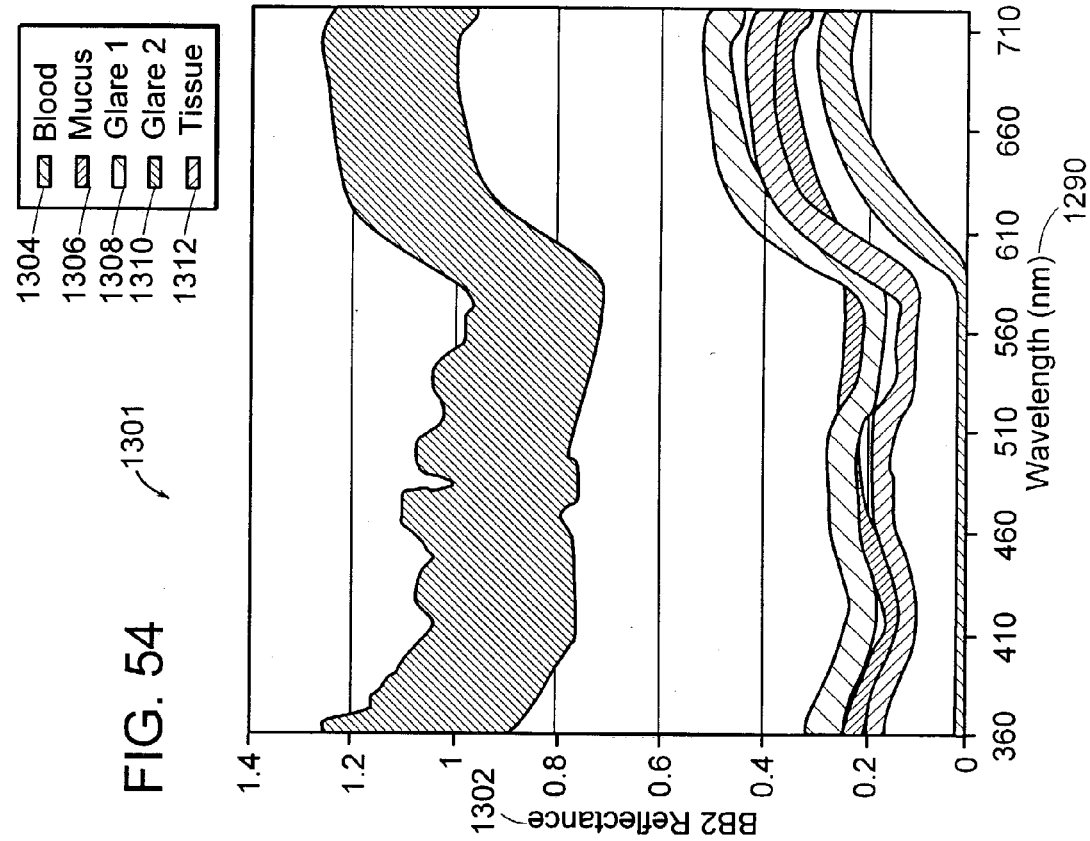
FIG. 54 shows a graph depicting mean values and standard deviations of broadband reflectance spectral data using the BB2 channel light source for regions confirmed as being obscured by blood, obscured by mucus, obscured by glare from the BB1 source, obscured by glare from the BB2 source, or unobscured, according to an illustrative embodiment of the invention.

Similarly, FIG. 54 shows a graph 1301 depicting mean values and standard deviations of broadband reflectance spectral data using the BB2 channel light source for to regions confirmed as being obscured by blood 1304, obscured by mucus 1306, obscured by glare from the BB1 source 1308, obscured by glare from the BB2 source 1310, or unobscured 1312, according to an illustrative embodiment of the invention. FIG. 54 shows the range of BB2 reflectance values 1302 for a given category of the sample test points which lie within one standard deviation of the mean for the category, plotted as a function of wavelength 1290. FIG. 54 shows ranges of BB2 reflectance values 1302 for each of the following categories of sample test points: those identified as having blood present 1304, those identified as having mucus present 1306, those identified as having glare from the BB1 illumination source 1308, those identified as having glare from the BB2 illumination source 1310, and those identified as unobstructed tissue 1312.

FIGS. 53 and 54 show that a region with glare from one illumination source does not necessarily have high reflectance values corresponding to data obtained using the other illumination source. For example, in FIG. 53, the range of BB1 reflectance values 1288 of points with visual evidence of glare from the BB2 source 1298 is similar to the range of BB1 reflectance values 1288 of unobstructed tissue 1300. Similarly, in FIG. 54, the range of BB2 reflectance values 1302 of points demonstrating glare from the BB1 source 1308 is similar to the range of BB2 reflectance values 1302 of unobstructed tissue 1312. Therefore, one of the two sets of reflectance spectral data may be useful in characterizing the tissue even if the other of the two sets is corrupted by an artifact, such as glare.

It may also be desirable to determine spectral characteristics caused by various artifacts so that data corresponding to a region affected by a given artifact may be identified or to determine a spectral characteristic of an artifact based on the spectral data itself, without having to rely on other visual evidence of a given artifact. In order to determine these spectral characteristics, an embodiment of the invention comprises using spectral data known to be affected by a given artifact based on visual evidence, as well as spectral data known not to be affected by an artifact. Techniques that may be used to identify spectral characteristics and/or to develop classification rules determining whether given data are affected by an artifact include, for example, discriminant analysis (linear, nonlinear, multivariate), neural networks, principal component analysis, and decision tree analysis. One embodiment comprises determining a particular wavelength that gives the greatest difference between the artifact-affected spectral data (the outlier) and spectral data from corresponding nearby tissue that is known to be unaffected by the artifact (the tissue). Alternatively, the embodiment comprises determining a wavelength that gives the largest difference between the outlier and the tissue, as weighted by a measure of variability of the data. In one embodiment, this method locates where the difference between the mean reflectance for the outlier and the tissue is at a maximum relative to the difference between the standard deviations for the outlier data and the tissue data. In one embodiment, the method determines a maximum value of D as a function of wavelength, where D is the difference given in Equation 83 below:

$$D(\lambda) = \frac{|\mu(BB(\lambda))_{Outlier} - \mu(BB(\lambda))_{Tissue}|}{\sqrt{\sigma^2(BB(\lambda))_{Outlier} + \sigma^2(BB(\lambda))_{Tissue}}}, \quad (83)$$

where $\mu(BB(\lambda))_{Outlier}$ is the mean of a set of reflectance spectral data at wavelength $\lambda$ known to be affected by a given artifact, $\mu(BB(\lambda))_{Tissue}$ is the mean of a set of reflectance spectral data at wavelength $\lambda$ that is known not to be affected by the artifact, $\sigma(BB(\lambda))_{Outlier}$ is the standard deviation of the set of reflectance spectral data at wavelength $\lambda$ known to be affected by the given artifact, and $\sigma(BB(\lambda))_{Tissue}$ is the standard deviation of the set of reflectance spectral data at wavelength $\lambda$ known not to be affected by the given artifact.

Figure 55:
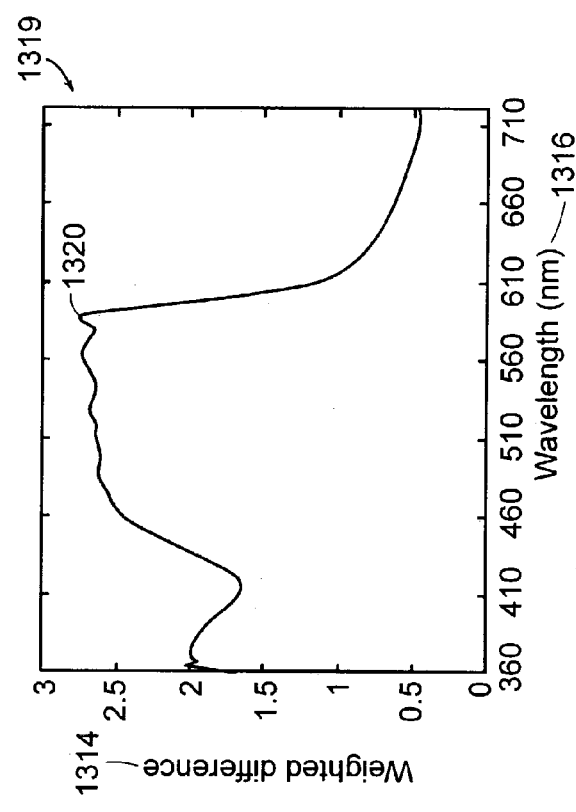
FIG. 55 shows a graph depicting the weighted difference between the mean reflectance values of glare-obscured regions and unobscured regions of tissue as a function of wavelength used in determining metrics for application in the arbitration step in FIG. 1, according to an illustrative embodiment of the invention.

FIG. 55 shows a graph 1313 depicting the weighted difference 1314 between the mean reflectance values of glare-obscured regions and unobscured regions of tissue as a function of wavelength 1316, according to an illustrative embodiment of the invention. The weighted difference 1314 is as given in Equation 83. For the data sets used in FIG. 55, the wavelength providing the maximum value 1318 of D in Equation 83 is about 420 nm. Thus, exemplary spectral characteristics identifiable with this set of glare-obscured "outlier" data include the reflectance spectral data at around 420 nm, and any deviation of this data from reflectance spectral "tissue" data for unobscured regions of correspondingly similar tissue at around 420 nm. This embodiment uses reflectance spectral data. Other embodiments may use other types of spectral data, including fluorescence data.

Figure 56:
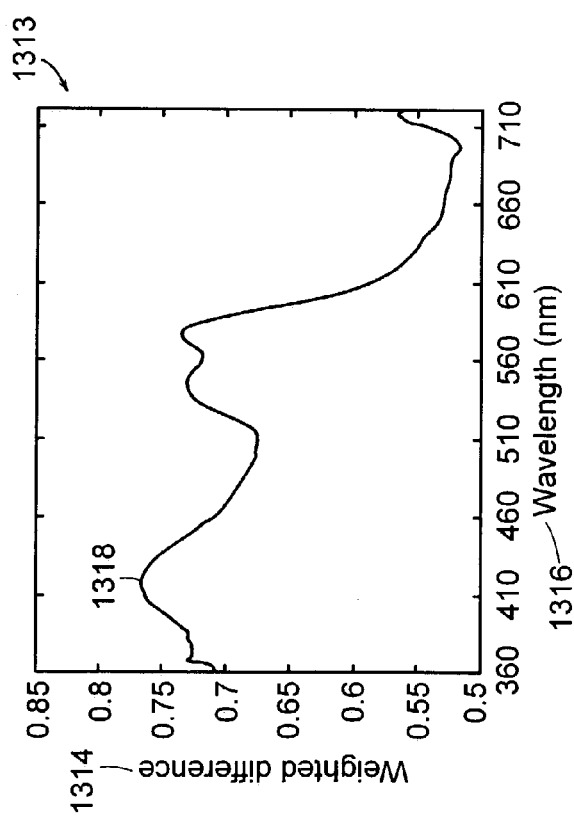
FIG. 56 shows a graph depicting the weighted difference between the mean reflectance values of blood-obscured regions and unobscured regions of tissue as a function of wavelength used in determining metrics for application in the arbitration step in FIG. 1, according to an illustrative embodiment of the invention.

FIG. 56 shows a graph 1319 depicting the weighted difference 1314 between the mean reflectance values of blood-obscured regions and unobscured regions of tissue as a function of wavelength 1316, according to an illustrative embodiment of the invention. The weighted difference is as given in Equation 83. For the data sets used in FIG. 56, the wavelength providing the maximum value 1320 of D in Equation 83 is about 585 nm.

Thus, exemplary spectral characteristics identifiable with this set of blood-obscured "outlier" data include the reflectance spectral data at about 585 nm, and any deviation of this data from reflectance spectral "tissue" data for unobscured regions of correspondingly similar tissue at about 585 nm. This embodiment uses reflectance spectral data. Other embodiments may use other types of spectral data, including fluorescence spectral data.

Figure 57:
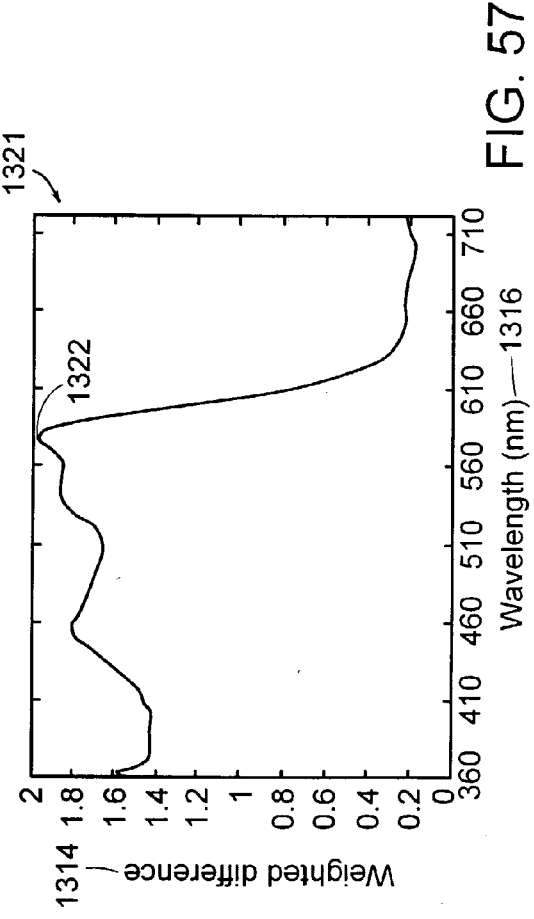
FIG. 57 shows a graph depicting the weighted difference between the mean reflectance values of mucus-obscured regions and unobscured regions of tissue as a function of wavelength, used in determining metrics for application in the arbitration step in FIG. 1 according to an illustrative embodiment of the invention.

FIG. 57 shows a graph 1321 depicting the weighted difference 1314 between the mean reflectance values of mucus-obscured regions and unobscured regions of tissue as a function of wavelength 1316, according to an illustrative embodiment of the invention. The weighted difference is as given in Equation 83. For the data sets used in FIG. 57, the wavelength providing the maximum value 1322 of D in Equation 83 is about 577 nm. Thus, exemplary spectral characteristics identifiable with this set of mucus-obscured "outlier" data include the reflectance spectral data at about 577 nm, and any deviation of this data from reflectance spectral "tissue" data for unobscured regions of correspondingly similar tissue at about 577 nm. This embodiment uses reflectance spectral data. Other embodiments may use other types of spectral data, including fluorescence spectral data.

One illustrative embodiment comprises determining two wavelengths where the ratio of spectral data at the two wavelengths is most different for the artifact-affected spectral data (the "outlier") and spectral data from corresponding nearby tissue that is known to be unaffected by the artifact (the "tissue"). Alternatively, the method comprises determining two wavelengths where the ratio of spectral data at the two wavelengths weighted by a measure of variability is most different for the outlier data and the tissue data. In one embodiment, the method comprises determining a maximum value of D as a function of wavelength, where D is the difference given in Equation 84 below:

$$D = \frac{|\mu(BB(\lambda)/BB(\lambda'))_{Outlier} - \mu(BB(\lambda)/BB(\lambda'))_{Tissue}|}{\sqrt{\sigma^2(BB(\lambda)/BB(\lambda'))_{Outlier} + \sigma^2(BB(\lambda)/BB(\lambda'))_{Tissue}}}, \quad (84)$$

where $\mu(BB(\lambda)/BB(\lambda'))_{Outlier}$ is the mean of the ratios of reflectance at wavelength $\lambda$ and reflectance at wavelength $\lambda'$ for a set of reflectance spectral data known to be affected by a given artifact, $\mu(BB(\lambda)/BB(\lambda'))_{Tissue}$ is the mean of the ratios of reflectance at wavelength $\lambda$ and reflectance at wavelength $\lambda'$ for a set of reflectance spectral data that is known not to be affected by the given artifact, $\sigma(BB(\lambda)/BB(\lambda'))_{Outlier}$ is the standard deviation of the ratios of reflectance at wavelength $\lambda$ and reflectance at wavelength $\lambda'$ for a set of reflectance spectral data known to be affected by the given artifact, and $\sigma(BB(\lambda)/BB(\lambda'))_{Tissue}$ is the standard deviation of the ratios of reflectance at wavelength $\lambda$ and reflectance at wavelength $\lambda'$ for a set of reflectance spectral data known not to be affected by the given artifact.

Figure 58:
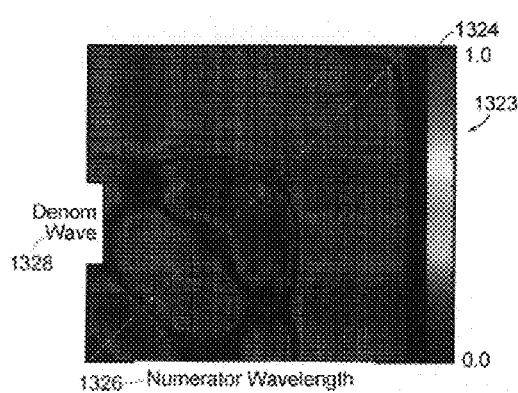
FIG. 58 shows a graph depicting a ratio of the weighted differences between the mean reflectance values of glare-obscured regions and unobscured regions of tissue at two wavelengths, used in determining metrics for application in the arbitration step in FIG. 1 according to an illustrative embodiment of the invention.

FIG. 58 shows a graph 1323 depicting a ratio of the weighted differences 1324 between the mean reflectance values of glare-obscured regions and unobscured regions of tissue at two wavelengths, a numerator wavelength 1326 and a denominator wavelength 1328, according to an illustrative embodiment of the invention. The weighted difference 1324 is as given in Equation 84. For the data sets used in FIG. 58, the two wavelengths providing the maximum value of D in Equation 84 are about 401 nm (numerator) and about 404 nm (denominator). Thus, exemplary spectral characteristics identifiable with this set of glare-obscured "outlier" data include the ratio of reflectance spectral data at about 401 nm and the reflectance spectral data at about 404 nm, as well as any deviation of this ratio from those of corresponding regions of similar but unobscured tissue. This embodiment uses reflectance spectral data. Other embodiments may use other types of spectral data, including fluorescence data.

Figure 59:
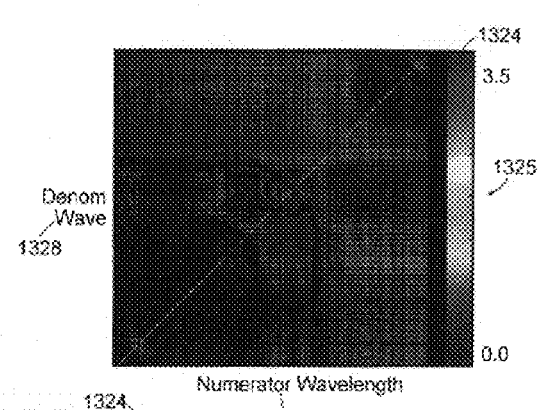
FIG. 59 shows a graph depicting a ratio of the weighted differences between the mean reflectance values of blood-obscured regions and unobscured regions of tissue at two wavelengths, used in determining metrics for application in the arbitration step in FIG. 1 according to an illustrative embodiment of the invention.

FIG. 59 shows a graph 1325 depicting a ratio of the weighted differences 1324 between the mean reflectance values of blood-obscured regions and unobscured regions of tissue at two wavelengths, a numerator wavelength 1326 and a denominator wavelength 1328, according to an illustrative embodiment of the invention. The weighted difference is as given in Equation 84. For the data sets used in FIG. 59, the two wavelengths providing the maximum value of D in Equation 84 are about 595 nm (numerator) and about 718 nm (denominator). Thus, an exemplary spectral characteristic identifiable with this set of blood-obscured "outlier" data includes the ratio of the reflectance spectral data at about 595 nm and the reflectance spectral data about 718 nm. This embodiment uses reflectance spectral data. Other embodiments may use other types of spectral data, including fluorescence data.

Figure 60:
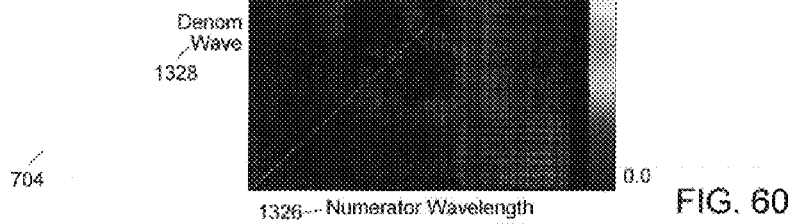
FIG. 60 shows a graph depicting a ratio of the weighted differences between the mean reflectance values of mucus-obscured regions and unobscured regions of tissue at two wavelengths, used in determining metrics for application in the arbitration step in FIG. 1 according to an illustrative embodiment of the invention.

FIG. 60 shows a graph 1327 depicting a ratio of the weighted differences 1324 between the mean reflectance values of mucus-obscured regions and unobscured regions of tissue at two wavelengths, a numerator wavelength 1326 and a denominator wavelength 1328, according to an illustrative embodiment of the invention. The weighted difference is as given in Equation 84. For the data sets used in FIG. 60, the two wavelengths providing the maximum value of D in Equation 84 are about 545 nm (numerator) and about 533 nm (denominator). Thus, an exemplary spectral characteristic identifiable with this set of mucus-obscured "outlier" data includes the ratio of the reflectance spectral data at about 545 nm and the reflectance spectral data at about 533 nm. This embodiment uses reflectance spectral data. Other embodiments may use other types of spectral data, including fluorescence data.

Another type of lighting artifact which may obscure spectral data is shadow, which may be caused, for example, by an obstruction blocking part of the light from an illumination source on the optical probe 142 of the embodiment apparatus. It may be important to differentiate between glare and shadow, so that spectral data representing unobstructed tissue can be properly identified. In an embodiment, broadband reflectance is expressed as the intensity of light diffusely reflected from a region of the tissue, $I_t$ over the intensity of incident light, $I_o$, at the region. When glare is measured in addition to light diffusely reflected from the tissue, a percentage of the original intensity of incident light is included in the tissue reflectance measurement, so that the "reflectance" reading of a region of a sample experiencing glare, $R_g(\lambda)$, may be expressed as in Equation 85:

$$R_g(\lambda) = (I_t(\lambda) + \alpha I_o(\lambda))/I_o(\lambda), \quad (85)$$

where $\alpha$ is a real number between 0.0 and 1.0; $I_t(\lambda)$ is the intensity of light diffusely reflected from the region of tissue at wavelength $\lambda$, and $I_o(\lambda)$ is the intensity of light incident on the region of the sample at wavelength $\lambda$. The intensity of the specularly-reflected light is $\alpha I_o(\lambda)$. When the region of the sample is shadowed, only a portion of the incident intensity reaches the region. Thus, the "reflectance" reading of a region of a sample experiencing shadow, $R_s(\lambda)$, may be expressed as in Equation 86:

$$R_s(\lambda) = \beta I_t(\lambda)/I_o(\lambda). \quad (86)$$

where $\beta$ is a real number between 0.0 and 1.0; $I_t(\lambda)$ is the intensity of light at wavelength $\lambda$ diffusely reflected from the region of tissue with an incident light intensity of $I_o(\lambda)$ and $I_o(\lambda)$ is the intensity of light at wavelength $\lambda$ that would be incident on the region of the sample if unshadowed.

In one embodiment, the arbitration in step 128 of FIG. 1 comprises determining if only one set of a pair of sets of spectral data is affected by a lighting artifact, such as glare or shadow, each set having been obtained using light incident on the sample at a unique angle. If it is determined that only one set of a pair of sets of spectral data is affected by the artifact, then the other set of spectral data may be used in the determination of a characteristic of the region of the sample, for example. In one embodiment, it is determined that there is evidence of a lighting artifact in the spectral data. Such evidence may be a large difference between the reflectance measurements of the two sets of spectral data. If such evidence exists, then one of the reflectance measurements will either be $R_g$ or $R_s$, as given by Equation 85 and Equation 86. In cases where members of only one set are affected by a lighting artifact, the remaining set of reflectance measurements may be expressed as R, the intensity of light diffusely reflected from the region of the tissue, $I_r$, divided by the intensity of light incident on the region of the tissue, $I_o$. In an embodiment method, the larger of the two reflectance measurements corresponding to a given wavelength is divided by the smaller. In cases where only one of the sets is affected by a lighting artifact, the resulting quotient will be either $R_g/R$, which is equal to $1+\alpha I_o(\lambda)/I_r(\lambda)$, or $R/R_s$, which is equal to the constant, $1/\beta$. If glare is present, the value of the quotient will depend on wavelength and the plot of the quotient as a function of wavelength should look like an inverted unobstructed tissue broadband signal because of the $\alpha I_o(\lambda)/I_r(\lambda)$ term. If shadow is present, the plot of the quotient should be constant across the spectrum.

Figure 61:
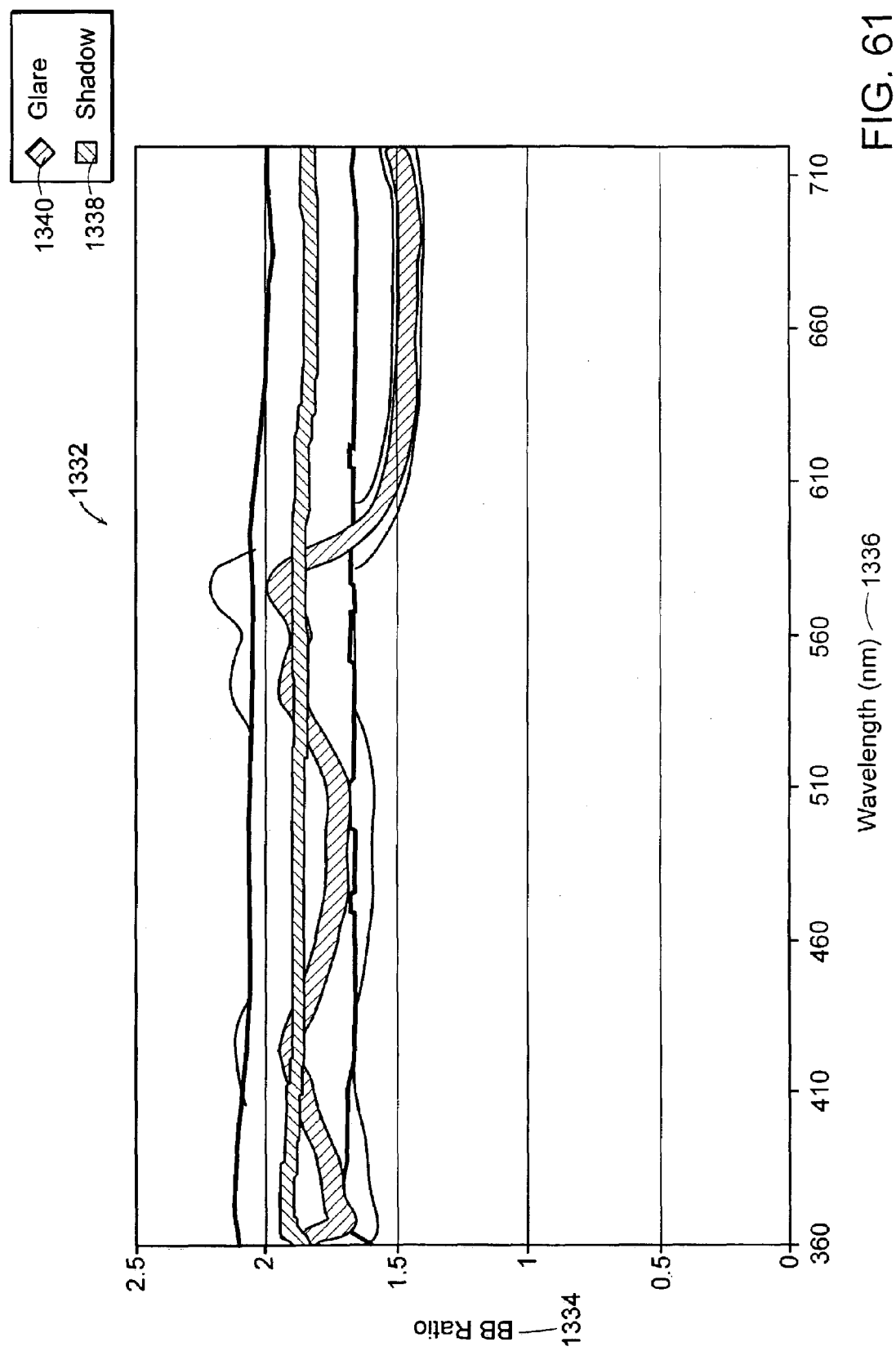
FIG. 61 shows a graph depicting as a function of wavelength mean values and confidence intervals of a ratio of BB1 and BB2 broadband reflectance spectral values for regions confirmed as being either glare-obscured or shadow-obscured tissue, used in determining metrics for application in the arbitration step in FIG. 1 according to an illustrative embodiment of the invention.

FIG. 61 shows a graph 1332 depicting as a function of wavelength 1336 mean values and confidence intervals of a ratio 1334 of BB1 and BB2 broadband reflectance spectral values (larger value divided by smaller value) for regions confirmed as being either glare-obscured or shadow-obscured tissue, according to an illustrative embodiment of the invention. The shadow points 1338 yield a nearly constant value, while the glare points 1340 vary over the range of wavelength 1336 in a manner that resembles the inverse of unobstructed tissue reflectance. Thus, FIG. 61 illustrates an embodiment in which it is determined whether only one set of a pair of sets of spectral data is affected by either glare or shadow, such that the other set is unaffected by glare or shadow and may be used to determine a characteristic of the tissue, for example. In an embodiment, the method comprises differentiating between glare and shadow by observing the steep slope of glare-affected reflectance spectral measurements between about 577 nm and 599 nm, for example, compared to the nearly flat slope of shadow-affected reflectance spectral measurements at those wavelengths, as seen in FIG. 61.

In one embodiment, the arbitration in step 128 of FIG. 1 includes applying and/or developing spectral artifact classification rules (metrics) using spectral data, including one or more sets of fluorescence and broadband reflectance data obtained using light at one or more angles. In one embodiment, one set of fluorescence data and two sets of reflectance data are obtained from a given region of a tissue sample (interrogation point), where each of the two sets of reflectance data are obtained using light incident on the region at a different angle. These metrics determine what data is representative of a given region of tissue. By varying the metrics, desired levels of sensitivity and selectivity of a resulting tissue characterization using tissue-representative data may be achieved.

The following metrics are applied in one embodiment of the arbitration in step 128 of FIG. 1 and were determined using the embodiments discussed above. These metrics were developed using one set of fluorescence data and two sets of reflectance data, BB1 and BB2, for samples of cervical tissue. Other embodiments use other combinations of spectral data sets. Each of the two sets of reflectance data used in the following metrics were obtained using light incident to a region of a sample at different angles. An embodiment of the invention uses any or all of the metrics listed below to determine if any set of data should be eliminated from use in determining a characteristic of a region of tissue, due to the presence of a spectral artifact. In an embodiment of the invention, wavelengths within a range of the wavelengths shown below are used. In one embodiment, this range about the wavelengths is about ±10 nm. In an embodiment of the invention, only certain parts of the metrics shown below are used. In one embodiment, only a portion of a given set of spectral data are eliminated, not the entire set. In one embodiment, BB1 and BB2 reflectance data are obtained, but fluorescence data is not. Here, "eliminate data" means to eliminate data from consideration in an analysis, for example, an analysis to determine a condition of a region. It is possible to change sensitivity and selectivity of a tissue diagnostic algorithm by varying the metrics below, for instance by changing one or more of the threshold constants. Such variations are within an embodiment of this invention. The metrics for one exemplary embodiment are as follows:

Glare Metric #1: Eliminate BB1 data IF:
I. {BB1(419)>0.25 AND BB1(699)>0.51} OR BB1(529)/BB1(543)<1.0;
OR II. Max{|ΔBB|/avgBB}(370-710)>0.25 AND BB1(419)>0.18 AND BB1(699)>0.51 AND {BB1(576)/BB2(576)}/{BB1(599)/BB2(599)}>1.1;
OR III. Max{|ΔBB|/avgBB}(370-710)>0.4 AND {BB1(576)/BB2(576)}/{BB1(599)/BB2(599)}>1.1 AND BB2(699)>0.3.

Glare Metric #2: Eliminate BB2 data IF:
I. {BB2(419)>0.25 AND BB2(699)>0.51} OR BB2(529)/BB2(543)<1.0;
OR II. Max{|ΔBB|/avgBB}(370-710)>0.25 AND BB2(419)>0.18 AND BB2(699)>0.51 AND {BB2(576)/BB1(576)}/{BB2(599)/BB1(599)}>1.1;
OR III. Max{|ΔBB|/avgBB}(370-710)>0.4 AND {BB2(576)/BB1(576)}/{BB2(599)/BB1(599)}>1.1 AND BB1(699)>0.3.

Shadow Metric #1: Eliminate BB1 data IF:
I. BB2(499)>BB1(499) AND Max{|ΔBB|/avgBB}(370-710)>0.25 AND BB1(499)<0.05;
OR II. Max{|ΔBB|/avgBB}(370-710)>0.5 AND {BB1(576)/BB2(576)}/{BB1(599)/BB2(599)}<1.1 AND BB2(576)>BB1(576) AND BB1(419)<0.2.

Shadow Metric #2: Eliminate BB2 data IF:
I. BB1(499)>BB2(499) AND Max{|ΔBB|/avgBB}(370-710)>0.25 AND BB2(499)<0.05;
OR II. Max{|ΔBB|/avgBB}(370-710)>0.5 AND {BB2(576)/BB1(576)}/{BB2(599)/BB1(599)}<1.1 AND BB1(576)>BB2(576) AND BB2(419)<0.2.

Low Signal: Eliminate BB1, BB2, and Fl data IF:
I. Fl(479)<3.5 counts/μJ (where mean fluorescent intensity of normal squamous tissue is about 70 counts/μJ at about 450 nm);
OR II. BB1(499)<0.035 & BB2(499)<0.035.

where BB1(X) is the BB1 reflectance spectrum measurement at wavelength X, BB2(X) is the BB2 reflectance spectrum measurement at wavelength X, Max{|ΔBB|/avgBB}(370-710) indicates the maximum of {the absolute value of the difference between the BB1 and BB2 reflectance spectrum measurements divided by the average of the BB1 and BB2 measurements at a given wavelength} over the range of about 370 to 710 nm, and Fl(X) is the fluorescence spectrum measurement at wavelength X. The following are notes regarding the Metrics listed above and apply to a preferred embodiment, subject to the variations described above:

Glare Metric #1 and Glare Metric #2:
Level I: Broadband measurements are generally greater than about 0.25 at about 419 nm and greater than about 0.51 at about 699 nm only when there is glare in the channel (i.e. BB1 or BB2). The lack of a downward slope between about 499 and about 543 nm is also a strong indication that the broadband measurements are affected by glare.
Level II: Large percentage differences in the broadband measurements combined with higher than average reflectance at about 419 nm and about 699 nm also indicates the presence of glare. The presence of a slope when the broadband measurements at about 576 nm and about 599 nm are divided is further confirmation that glare is present.
Level III: A maximum broadband percent difference that is larger than about 0.4 indicates that there is a lighting artifact present. The presence of a slope when the broadband measurements at about 576 and about 599 nm are divided and an off-channel broadband greater than about 0.3 at about 699 nm reveals that the lighting artifact is due to glare instead of shadow.
If a point is identified as glare in one channel, then subsequently identified as glare in both channels, both broadband measurements should be eliminated.

Shadow Metric #1 and Shadow Metric #2:
Level I: Broadband measurements that are shadowed generally will have a large percent difference between BB1 and BB2 and a low reflectance at about 499 nm.
Level II: A maximum broadband percent difference that is larger than about 0.5 indicates that there is a lighting artifact present. Lacking a large slope when the broadband measurements at about 576 and about 599 nm are divided and an off-channel broadband less than about 0.2 at about 419 nm reveals that the point is shadow instead of glare.

Cases where both BB and Fl measurements should be eliminated:
Low Signal:
Broadband measurements lower than about 0.035 at about 449 nm or fluorescence measurements lower than about 3.5 at about 479 nm indicate that the measurements are not coming from tissue, but rather from blood, the os, smoke tube, speculum, or another obstruction. Sites with significant shadowing in both broadband channels are also identified with this metric. Because of the uncertainty of the tissue being measured, the reflectance and fluorescence data from that point are assumed invalid, regardless of whether it was identified by fluorescence or the broadband channels.
The low signal metric acts as a hard mask because it eliminates a qualifying interrogation point from consideration by the classifier or the other masks, such as the spectral masks in step 130 of FIG. 1. The low signal metric acts as a hard mask, for example, for points that have shadowing in both BB1 and BB2.

The metrics used in this embodiment of step 128 of FIG. 1 include a low signal metric, which detects spectral data affected by obstruction artifacts such as blood, a speculum, a smoke tube, or other obstruction. This metric also identifies regions where both sets of broadband reflectance data are affected by shadow. These were combined into one low signal metric in this embodiment, since regions affected by these artifacts exhibit similar characteristics, such as low fluorescence and low broadband reflectance measurements.

Figure 62:
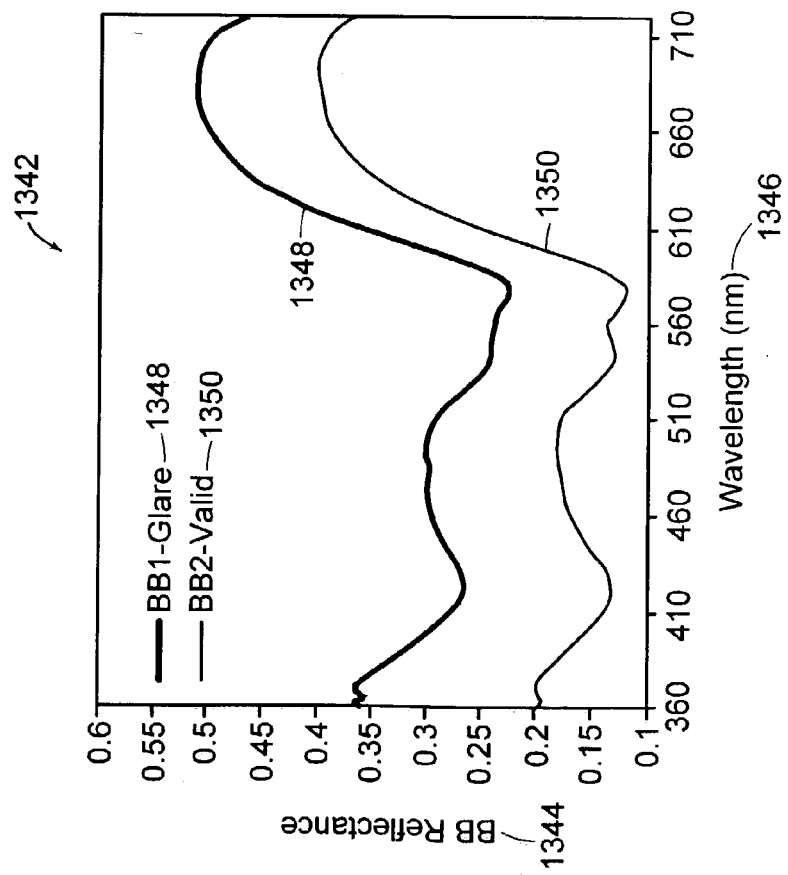
FIG. 62 shows a graph depicting BB1 and BB2 broadband reflectance spectral data for a region of tissue where the BB1 data is affected by glare but the BB2 data is not, according to an illustrative embodiment of the invention.

FIG. 62 shows a graph 1342 depicting broadband reflectance 1344 as a function of wavelength 1346 for the BB1 channel 1348 and the BB2 channel 1350 measurements for a region of tissue where the BB1 data is affected by glare but the BB2 data is not, according to an illustrative embodiment of the invention. The glare leads to a higher value of reflectance 1344 than that of surrounding unaffected tissue. By applying the metrics listed above in step 128 of FIG. 1, it is determined that the exemplary BB1 set of spectral data shown in FIG. 62 is affected by glare and is thus not suitably representative of this region of the tissue sample. Applying the metrics of step 128 also determines that the BB2 set of spectral data is potentially representative of this region of the sample (unaffected by an artifact), since it is not eliminated. One embodiment comprises using this representative data in step 132 of FIG. 1 to determine a condition of this region of the sample, for example, the state of health.

Figure 63:
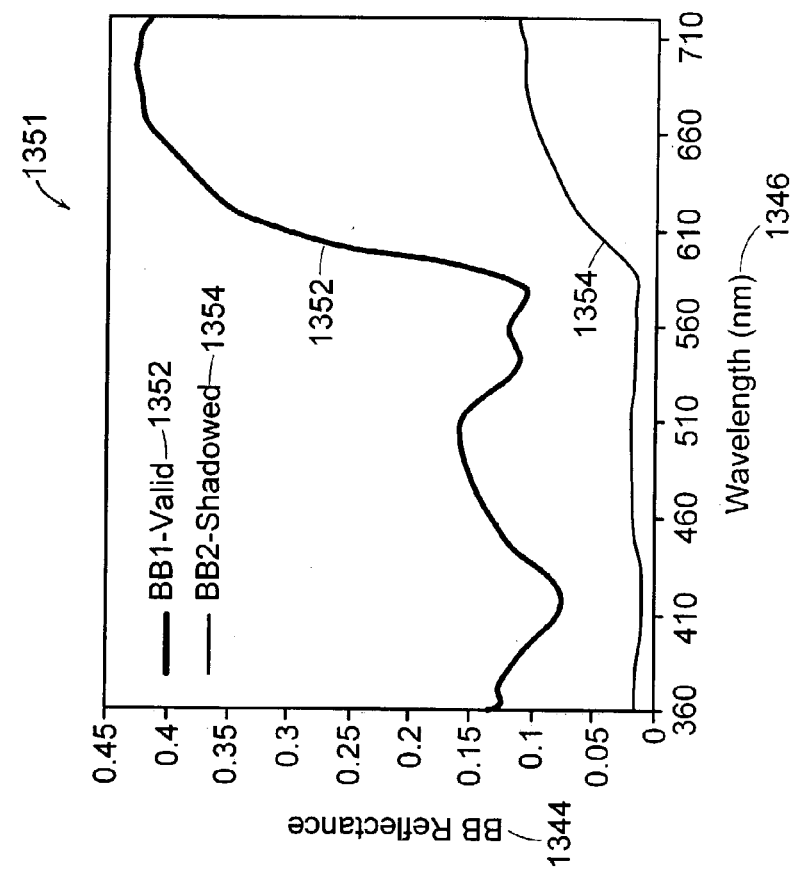
FIG. 63 shows a graph depicting BB1 and BB2 broadband reflectance spectral data for a region of tissue where the BB2 data is affected by shadow but the BB1 data is not, according to an illustrative embodiment of the invention.

FIG. 63 shows a graph 1351 depicting broadband reflectance 1344 as a function of wavelength 1346 for the BB1 channel 1352 and the BB2 channel 1354 broadband reflectance spectral data for a region of tissue where the BB2 data is affected by shadow but the BB1 data is not, according to an illustrative embodiment of the invention. The shadow leads to a lower value of reflectance 1344 than that of surrounding unaffected tissue. By applying the metrics listed above in step 128 of FIG. 1, it is determined that the exemplary BB2 set of spectral data shown in FIG. 63 is affected by shadow and is therefore not suitably representative of this region of the tissue sample. Applying the metrics of step 128 also leads to the determination that the BB1 set of spectral data is potentially representative of this region of the sample, since the BB1 set of data is not eliminated. One embodiment comprises using this representative data in step 132 of FIG. 1 to determine a condition of this region of the sample, for example, the state of health.

Figure 64:
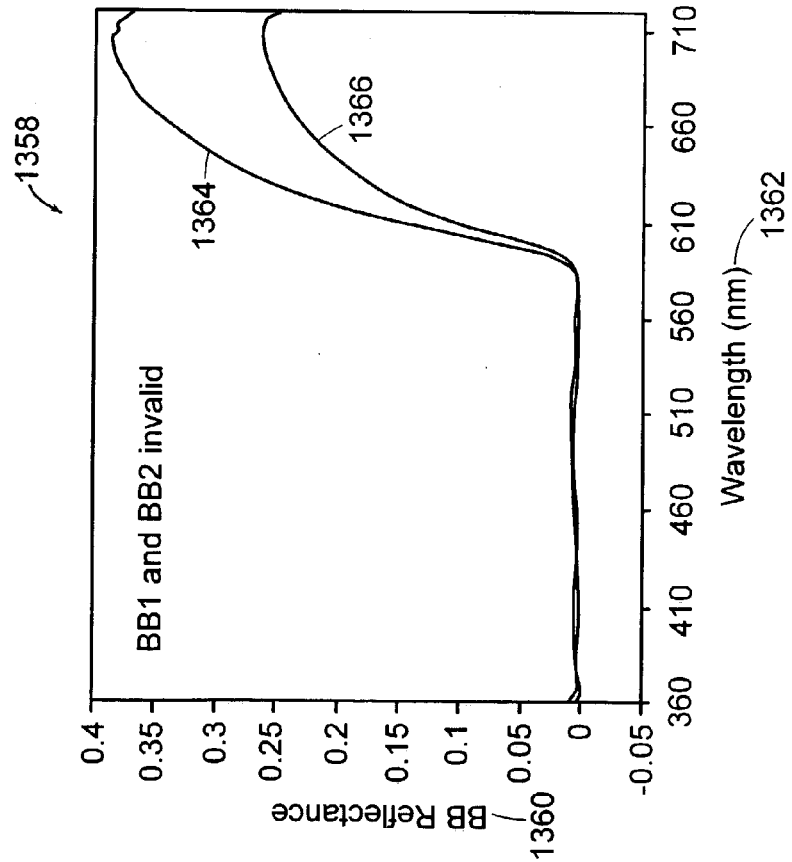
FIG. 64 shows a graph depicting BB1 and BB2 broadband reflectance spectral data for a region of tissue that is obscured by blood, according to an illustrative embodiment of the invention.

FIG. 64 shows a graph 1358 depicting broadband reflectance 1360 as a function of wavelength 1362 for the BB1 channel 1364 and the BB2 channel 1366 measurements for a region of tissue that is obscured by blood, according to an illustrative embodiment of the invention. By applying the metrics listed above, it is determined that blood is present, and that both the BB1 and the BB2 sets of spectral data are considered unrepresentative of this region of the tissue sample.

Figure 65:
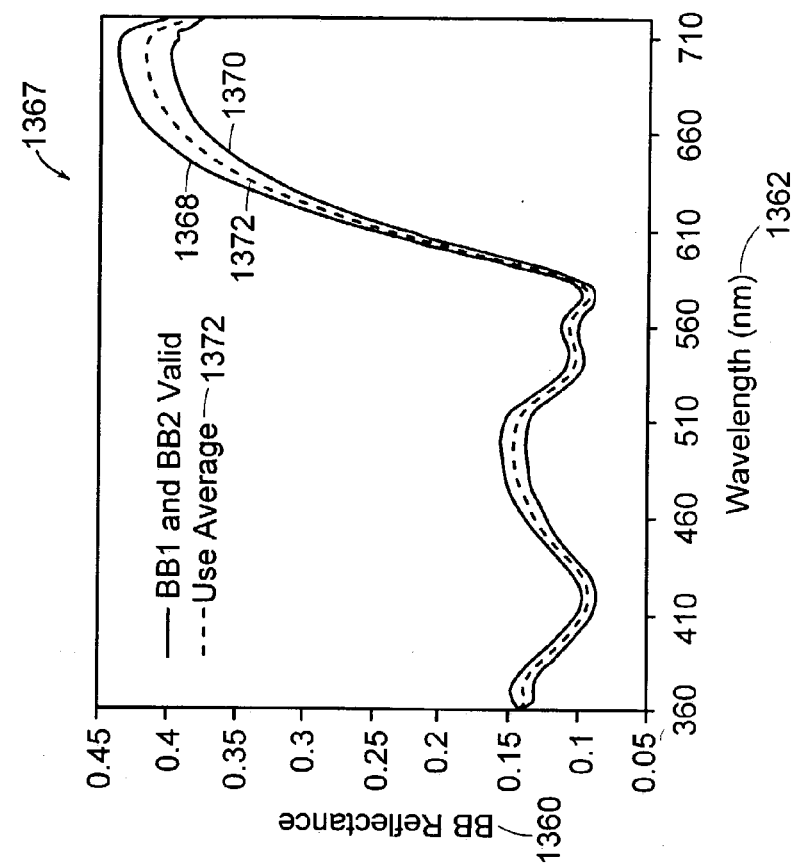
FIG. 65 shows a graph depicting BB1 and BB2 broadband reflectance spectral data for a region of tissue that is unobscured, according to an illustrative embodiment of the invention.

FIG. 65 shows a graph 1367 depicting broadband reflectance 1360 as a function of wavelength 1362 for the BB1 channel 1368 and the BB2 channel 1370 measurements for a region of tissue that is unobscured, according to an illustrative embodiment of the invention. Applying this method determines that neither set of spectral data is affected by an artifact, and, therefore, either is representative of the tissue sample. One embodiment comprises using an average value 1372 of the BB1 and BB2 measurements at each wavelength to represent the region of the tissue sample in determining a condition of this region, for example, the state of health of the region, in step 132 of FIG. 1.

Application of the metrics listed above was performed using various tissue types to verify the sensitivity and specificity of the metrics. While, in one embodiment, it is undesirable to eliminate good spectral data of normal tissue, it is worse to eliminate good spectral data of diseased tissue, particularly if it is desired to use the data in the classification of the state of health of a region of tissue. The following tissue types were used in the verification: tt-132 (metaplasia by impression), tt-155 (normal by impression), tt-117 (blood), NEDpath (no evidence of disease confirmed by pathology), and cin23all (CIN 2/3 diseased tissue). Table 5 shows the number of points (regions) corresponding to each of these tissue types, the determinations from the metrics listed above for these points, and the number of points where one set of broadband reflectance spectral data were eliminated, where both sets of broadband reflectance spectral data were eliminated, and where both reflectance and fluorescence spectral data were eliminated.

TABLE 5

Verification of Metrics

| Tissue Type | cin23all | nedpath | tt-117 | tt-132a | tt-155 |
|---|---|---|---|---|---|
| Total pts. | 477 | 919 | 175 | 5000 | 2016 |
| Low Signal | 2 | 14 | 126 | 2 | 0 |
| Glare in BB1 | 7 | 30 | 4 | 122 | 26 |
| Glare in BB2 | 9 | 40 | 9 | 134 | 16 |
| Glare in both | 3 | 5 | 1 | 15 | 5 |
| Shadow in BB1 | 47 | 35 | 4 | 165 | 132 |
| Shadow in BB2 | 16 | 37 | 24 | 359 | 32 |
| One BB Removed (%) | 16.6 | 15.5 | 23.4 | 15.6 | 10.2 |
| Both BB Removed (%) | 1.05% | 2.07% | 72.57% | 0.34% | 0.25% |
| FI Removed (%) | 0.42 | 1.52 | 72.00 | 0.04 | 0.00 |

For the regions (points) corresponding to CIN 2/3 diseased tissue, no broadband reflectance measurements were unnecessarily eliminated from the set using the above metrics. The points identified as being low signal were all located on the os. All points that were identified by the metric as shadow were verified as being correct, and only one point identified as glare was incorrect.

For the nedpath points (no evidence of disease), only two tissue points were unnecessarily eliminated after being misidentified as mucus. A point that was actually dark red tissue with glare was incorrectly identified as shadow in BB2. The points that were identified as glare were verified as being correct.

Out of the 175 blood points, 126 were identified as being low signal. The glare points and shadow points were accurate.

Out of the 5000 points in the metaplasia by impression group, there were no valid tissue points lost. The data set was improved by eliminating about 800 readings of points affected by either glare or shadow.

Out of the 2016 normal by impression points, no measurements were unnecessarily removed from the set.

Figure 66:
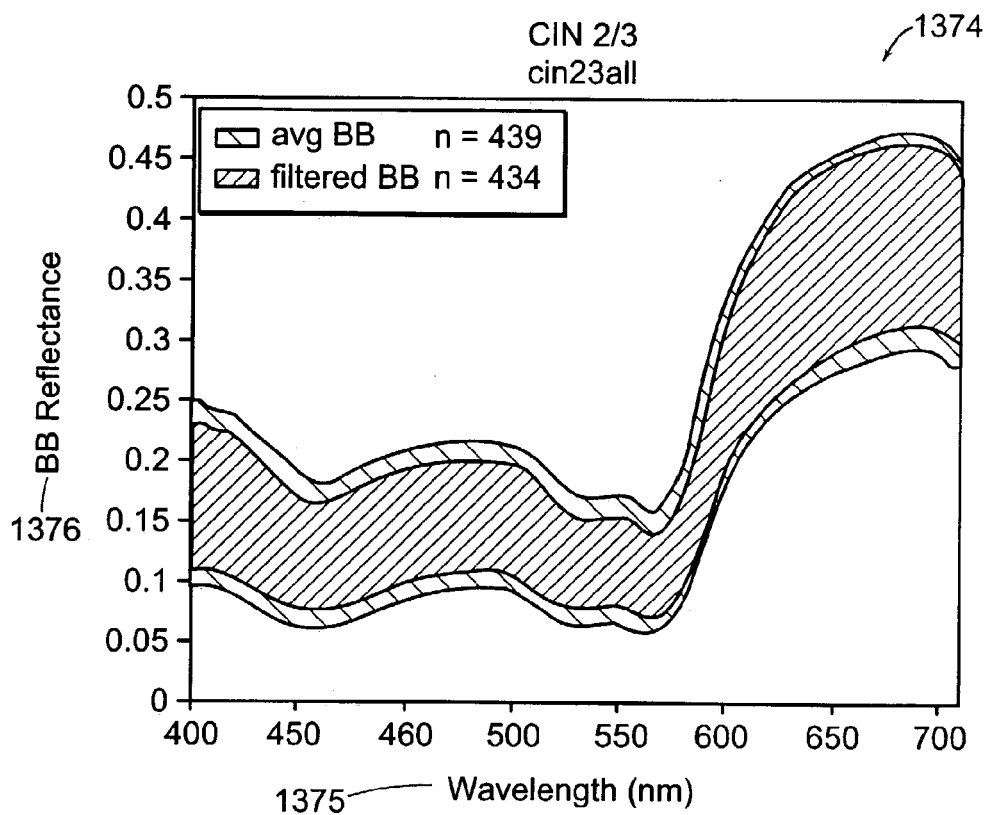
FIG. 66 shows a graph depicting the reduction in the variability of broadband reflectance measurements of CIN 2/3-confirmed tissue produced by applying the metrics in the arbitration step 128 of FIG. 1 to remove data affected by an artifact, according to an illustrative embodiment of the invention.

FIG. 66 shows a graph 1374 depicting the reduction in the variability of broadband reflectance measurements 1376 of CIN 2/3-confirmed tissue produced by filtering (eliminating non-representative spectral data) using the metrics of step 128 in FIG. 1 described above, according to an illustrative embodiment of the invention. The graph 1374 depicts mean values and standard deviations of broadband reflectance spectral data before and after filtering.

Figure 67:
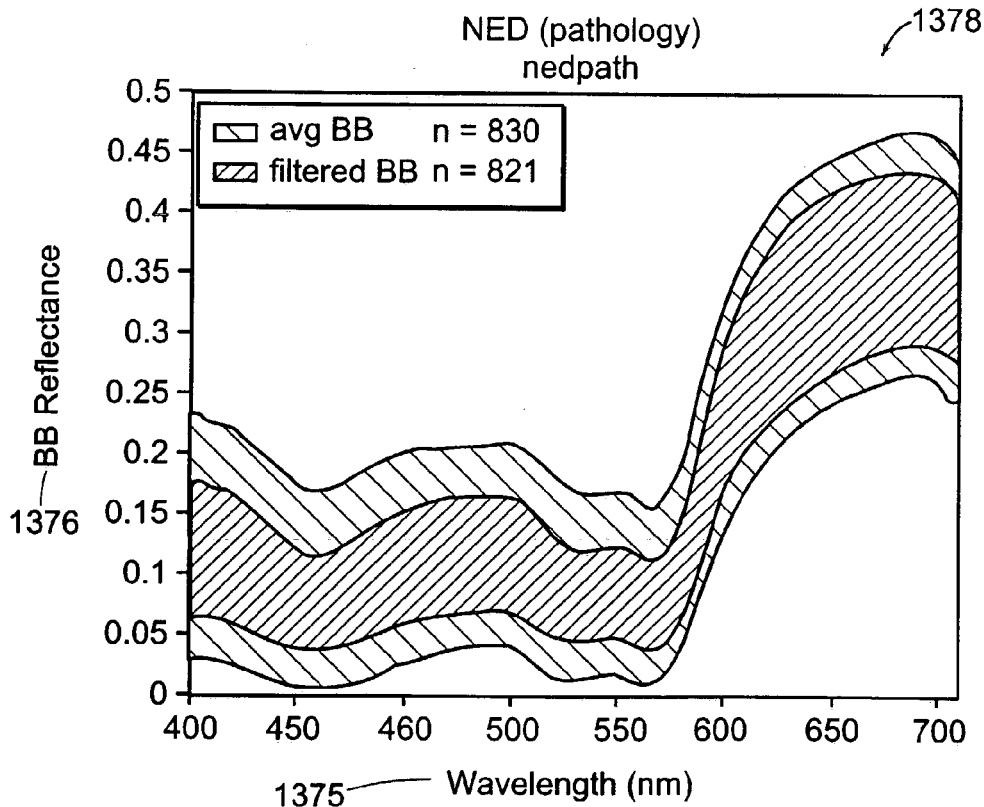
FIG. 67 shows a graph depicting the reduction in the variability of broadband reflectance measurements of tissue classified as "no evidence of disease confirmed by pathology" produced by applying the metrics in the arbitration step 128 of FIG. 1 to remove data affected by an artifact, according to an illustrative embodiment of the invention.

FIG. 67 shows a graph 1378 depicting the reduction in the variability of broadband reflectance measurements 1376 of tissue classified as "no evidence of disease confirmed by pathology" produced by filtering using the metrics described above, according to an illustrative embodiment of the invention. The graph 1378 depicts mean values and standard deviations of broadband reflectance spectral data before and after filtering.

Figure 68:
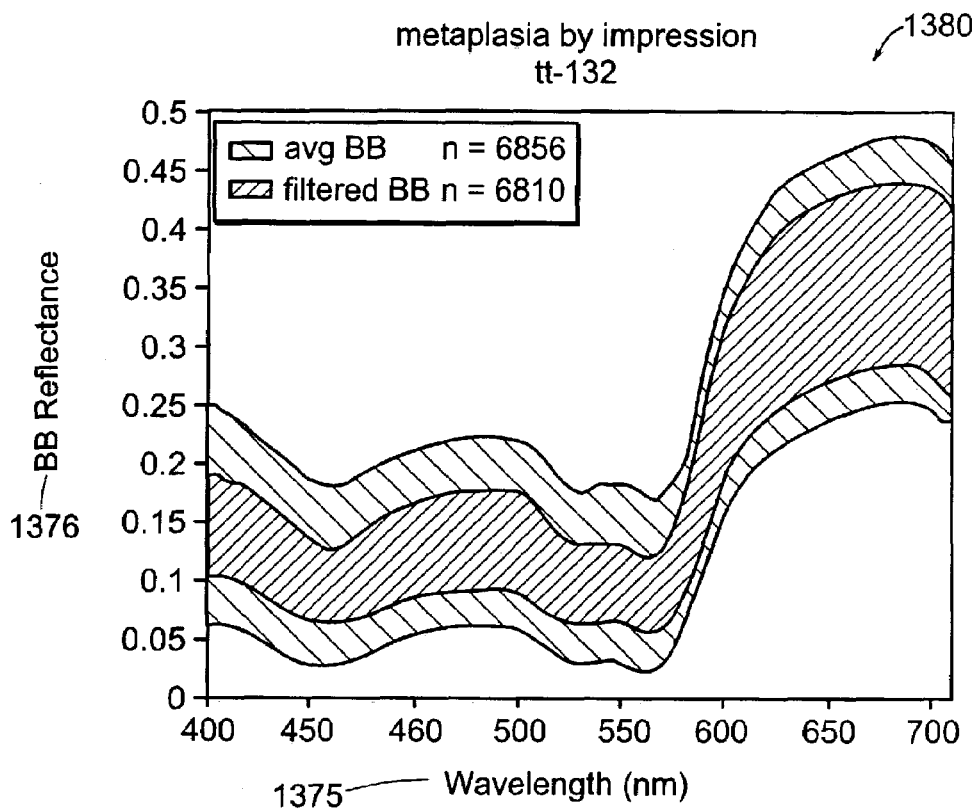
FIG. 68 shows a graph depicting the reduction in the variability of broadband reflectance measurements of tissue classified as "metaplasia by impression" produced by applying the metrics in the arbitration step 128 of FIG. 1 to remove data affected by an artifact, according to an illustrative embodiment of the invention.

FIG. 68 shows a graph 1380 depicting the reduction in the variability of broadband reflectance measurements 1376 of tissue classified as "metaplasia by impression" produced by filtering using the metrics described above, according to an illustrative embodiment of the invention. The graph 1380 depicts mean values and standard deviations of broadband reflectance spectral data before and after filtering.

Figure 69:
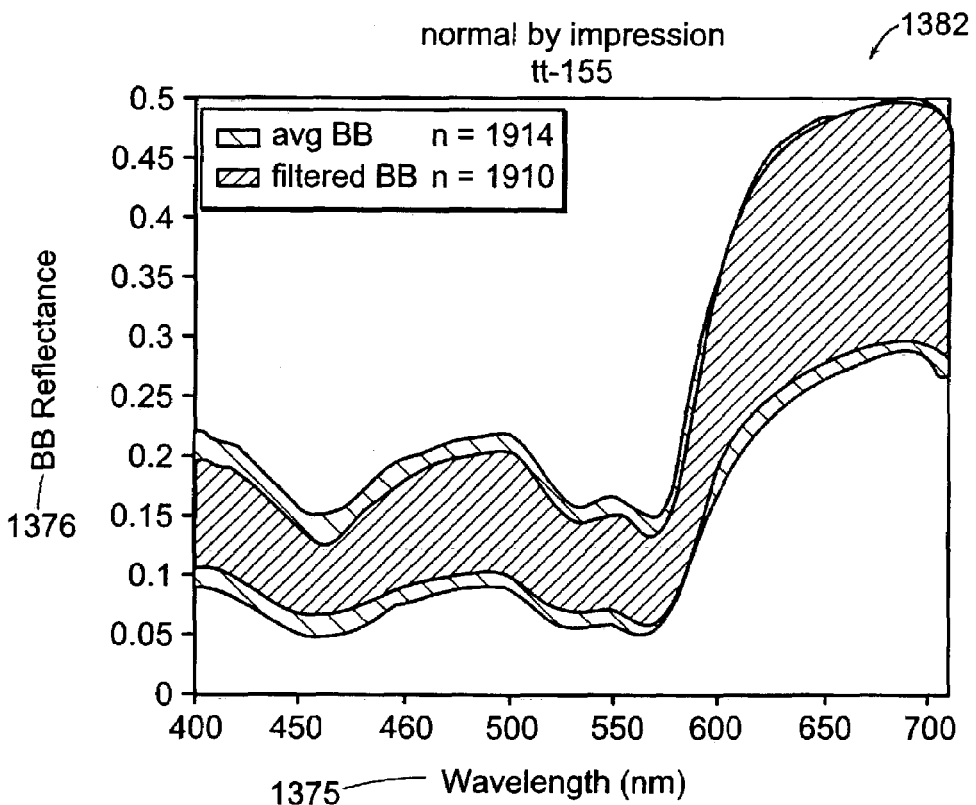
FIG. 69 shows a graph depicting the reduction in the variability of broadband reflectance measurements of tissue classified as "normal by impression" produced by applying the metrics in the arbitration step 128 of FIG. 1 to remove data affected by an artifact, according to an illustrative embodiment of the invention.

FIG. 69 shows a graph 1382 depicting the reduction in the variability of broadband reflectance measurements 1376 of tissue classified as "normal by impression" produced by filtering using the metrics described above, according to an illustrative embodiment of the invention. The graph 1382 depicts mean values and standard deviations of broadband reflectance spectral data before and after filtering.

FIG. 70A depicts an exemplary image of cervical tissue 1388 divided into regions for which two types of reflectance spectral data and one type of fluorescence spectral data are obtained, according to one embodiment of the invention. FIG. 70B is a representation 1398 of the regions depicted in FIG. 70A and shows the categorization of each region using the metrics in step 128 of FIG. 1. The black-highlighted sections 1390 of the image 1388 in FIG. 70A correspond to points (regions) that had both reflectance measurements eliminated by application of the embodiment method. Many of the lower points 1392, as seen in both FIGS. 70A and 70B, are in shadow because the speculum obstructs the view of one of the channels. Glare is correctly identified prominently at the upper one o'clock position 1394. Since there are blood points on the shadowed section, some are labeled blood (low signal) and others are treated as shadow.

FIG. 71A depicts an exemplary image of cervical tissue 1402 divided into regions for which two types of reflectance spectral data and one type of fluorescence spectral data are obtained, according to one embodiment of the invention. FIG. 71B is a representation 1406 of the regions depicted in FIG. 71A and shows the categorization of each region using the metrics in step 128 of FIG. 1. FIGS. 71A and 71B show an example of a cervix that has a large portion of the lower half 1404 affected by shadow. However, only one of the sets of reflectance spectral data (BB2) is affected by the shadow artifact. The BB1 reflectance spectral data is not affected by shadow. Applying the metrics above, the BB1 data are used to describe, these regions, while the BB2 data are eliminated from consideration. The accuracy of tissue characterization using the reflectance measurements should be improved significantly for this patient using the arbitration metrics of step 128 of FIG. 1, since the more accurate broadband measurements will be used in later characterization steps instead of simply averaging the two broadband measurements, which would skew the measurements due to a lighting artifact.

Figures 72A, 72B:
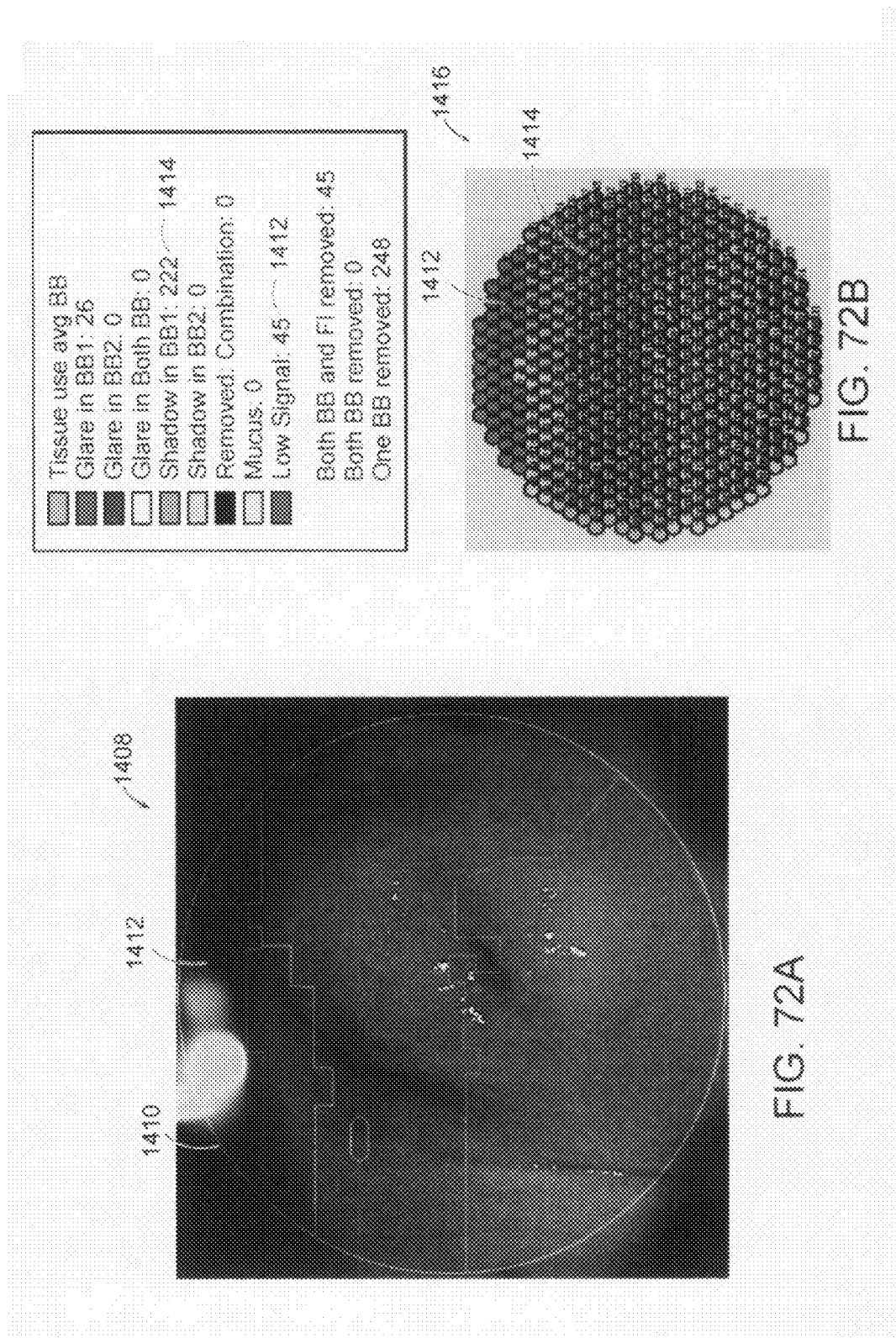
FIG. 72A depicts an exemplary image of cervical tissue divided into regions for which two types of reflectance spectral data and one type of fluorescence spectral data are obtained, according to an illustrative embodiment of the invention.
FIG. 72B is a representation of the regions depicted in FIG. 72A and shows the categorization of each region using the metrics in the arbitration step 128 of FIG. 1, according to an illustrative embodiment of the invention.

FIG. 72A depicts an exemplary image of cervical tissue 1410 divided into regions for which two types of reflectance spectral data and one type of fluorescence spectral data are obtained, according to an illustrative embodiment of the invention. FIG. 72B is a representation 1416 of the regions depicted in FIG. 72A and shows the categorization of each region using the metrics in step 128 of FIG. 1. FIGS. 72A and 72B show an image with a portion 1412 that is shadowed and off of the cervix. Due to an obstruction from the smoke tube in the upper part of the image, there are many low signals. Even though much of the cervix is shadowed in BB1 1414, there are still some BB2 and fluorescence readings usable in later tissue classification steps.

Classification System Overview

The tissue characterization system 100 of FIG. 1 combines spectral data and image data obtained by the instrument 102 to characterize states of health of regions of a tissue sample. In one embodiment, the spectral data are first motion-tracked 106, preprocessed 114, and arbitrated 128 before being combined with image data in step 132 of FIG. 1. Likewise, in one embodiment, the image data are first focused 122 and calibrated 124 before being combined with spectral data in step 132 of FIG. 1. Each of these steps are discussed in more detail herein.

Figure 73:
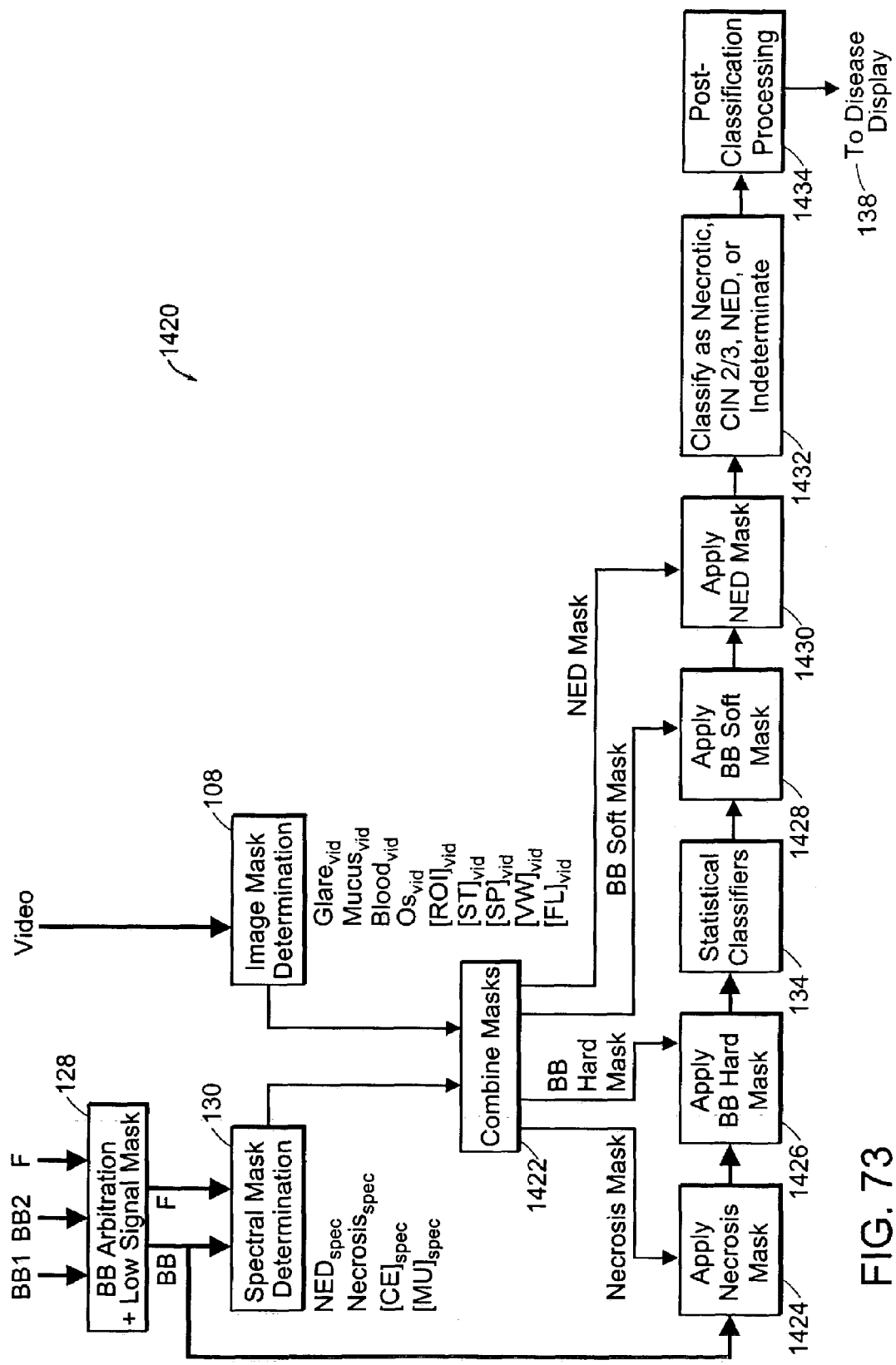
FIG. 73 is a block diagram depicting steps in a method of processing and combining spectral data and image data obtained in the tissue characterization system of FIG. 1 to determine states of health of regions of a tissue sample, according to an illustrative embodiment of the invention.

FIG. 73 shows how spectral data and image data are combined in the tissue characterization system of FIG. 1, according to one embodiment. The block diagram 1420 of FIG. 73 depicts steps in processing and combining motion-tracked 106, preprocessed 114, and arbitrated 128 spectral data with focused 122, calibrated 124 image data to determine states of health of regions of a tissue sample. After preprocessing 114, spectral data from each of the interrogation points (regions) of the tissue sample are arbitrated in step 128 of FIG. 73. In the embodiment shown, a fluorescence spectrum, F, and two broadband reflectance spectra, BB1 and BB2, are used to determine one representative reflectance spectrum, BB, used along with the fluorescence spectrum, F, for each interrogation point. This is depicted in FIG. 73 as three heavy arrows representing the three spectra—BB1, BB2, and F—entering arbitration block 128 and emerging as two spectra—BB and F. Block 128 of FIG. 73 also applies an initial low-signal mask as a first pass at identifying obscured interrogation points, discussed previously herein.

In the embodiment of FIG. 73, the arbitrated broadband reflectance spectrum, BB, is used in the statistical classification algorithm 134, while both the broadband reflectance spectrum, BB, and the fluorescence spectrum, F, as well as the image data, are used to determine heuristic-based and/or statistics-based metrics, or "masks", for classifying the state of health of tissue at interrogation points. Masking can be a means of identifying data that are potentially non-representative of the tissue sample. Potentially non-representative data includes data that may be affected by an artifact or obstruction such as blood, mucus, fluid, glare, or a speculum. Such data is either hard-masked or soft-masked. Hard-masking of data includes identifying interrogation points at which the data is not representative of unobscured, classifiable tissue. This results in a characterization of "Indeterminate" at such an interrogation point, and no further computations are necessary for that point. Soft-masking includes applying a weighting function or weighting factor to identified, potentially non-representative data. The weighting is taken into account during calculation of disease probability and may or may not result in an indeterminate diagnosis at the corresponding tissue region. Soft-masking provides a means of weighting spectral and/or image data according to the likelihood that the data is representative of clear, unobstructed tissue in a region of interest. In the embodiment shown in FIG. 73, both hard masks and soft masks are determined using a combination of spectral data and image data. Furthermore, the masks of FIG. 73 use spectral and image data to identify interrogation points that are not particularly of interest in the exam, such as the vaginal wall, smoke tube tissue, the os, or tissue outside the region of interest.

In addition to determining data that are potentially non-representative of regions of interest, the masks shown in FIG. 73 also include masks that determine where the data is highly indicative of necrotic tissue or disease-free (NED) tissue. It has been discovered that necrotic tissue and disease-free tissue are often more predictably determined by using a heuristic metric instead of or in combination with a statistical classifier than by using a statistical classifier alone. For example, one embodiment uses certain values from fluorescence spectra to determine necrotic regions, since fluorescence spectra can indicate the FAD/NADH component and porphyrin component of necrotic tissue. Also, an embodiment uses prominent features of fluorescence spectra indicative of normal squamous tissues to classify tissue as "NED" (no evidence of disease) in the spectral mask.

Identifying necrotic and NED regions at least partially by using heuristic metrics allows for the development of statistical classifiers 134 that concentrate on differentiating tissue less conducive to heuristic classification—for example, statistical classifiers that differentiate high grade cervical intraepithelial neoplasia (i.e. CIN 2/3) from low grade neoplasia (i.e. CIN 1) and healthy tissue.

In FIG. 73, step 130 uses the arbitrated spectra, BB and F, to determine four spectral masks—$NED_{spec}$ (no evidence of disease), $Necrosis_{spec}$, $[CE]_{spec}$ (cervical edge/vaginal wall), and $[MU]_{spec}$ (mucus/fluid). The focused, calibrated video data is used to determine nine image masks—$Glare_{vid}$, $Mucus_{vid}$, $Blood_{vid}$, $Os_{vid}$, $[ROI]_{vid}$ (region of interest), $[ST]_{vid}$ (smoke tube), $[SP]_{vid}$ (speculum), $[VW]_{vid}$ (vaginal wall), and $[FL]_{vid}$ (fluid and foam). Step 1422 of FIG. 73 combines these masks to produce a hard "indeterminate" mask, a soft "indeterminate" mask, a mask identifying necrotic regions, and a mask identifying healthy (NED) regions. In the embodiment of FIG. 73, steps 1424 and 1426 apply the necrotic mask and hard "indeterminate" mask, respectively, prior to using the broadband spectral data in the statistical classifiers 134, while steps 1428 and 1430 apply the soft "indeterminate" mask and the NED mask after the statistical classification step 134.

The embodiment shown in FIG. 73 can classify each interrogation point in step 1432 as necrotic, CIN 2/3, NED, or Indeterminate. There may be some post-classification processing in step 1434, for example, for interrogation points having a valid fluorescence signal but having both broadband signals, BB1 and BB2, eliminated by application of the arbitration metrics in step 128. The embodiment in FIG. 73 then uses the final result to create a disease display overlay of a reference image of the tissue sample in step 138. Each of the masking and classification steps summarized above are discussed in more detail herein.

In one alternative embodiment, the statistical classifiers in step 134 of FIG. 73 additionally include the use of fluorescence, image, and/or kinetic data. One alternative embodiment includes using different sets of spectral and/or image masks than those in FIG. 73. Also, one alternative embodiment includes using a different order of application of heuristic masks in relation to one or more statistical classifiers. In one alternative embodiment, kinetic data is determined by obtaining intensity data from a plurality of images captured during a tissue scan, determining a relationship between corresponding areas of the images to reflect how they change with time, and segmenting the images based on the relationship. For example, an average kinetic whitening curve may be derived for tissue areas exhibiting similar whitening behavior. Whitening kinetics representative of a given area may be compared to reference whitening kinetics indicative of known states of health, thereby indicating a state of health of the given area. In one alternative embodiment, the kinetic image-based data may be combined with spectral data to determine states of health of regions of a tissue sample.

Figure 74:
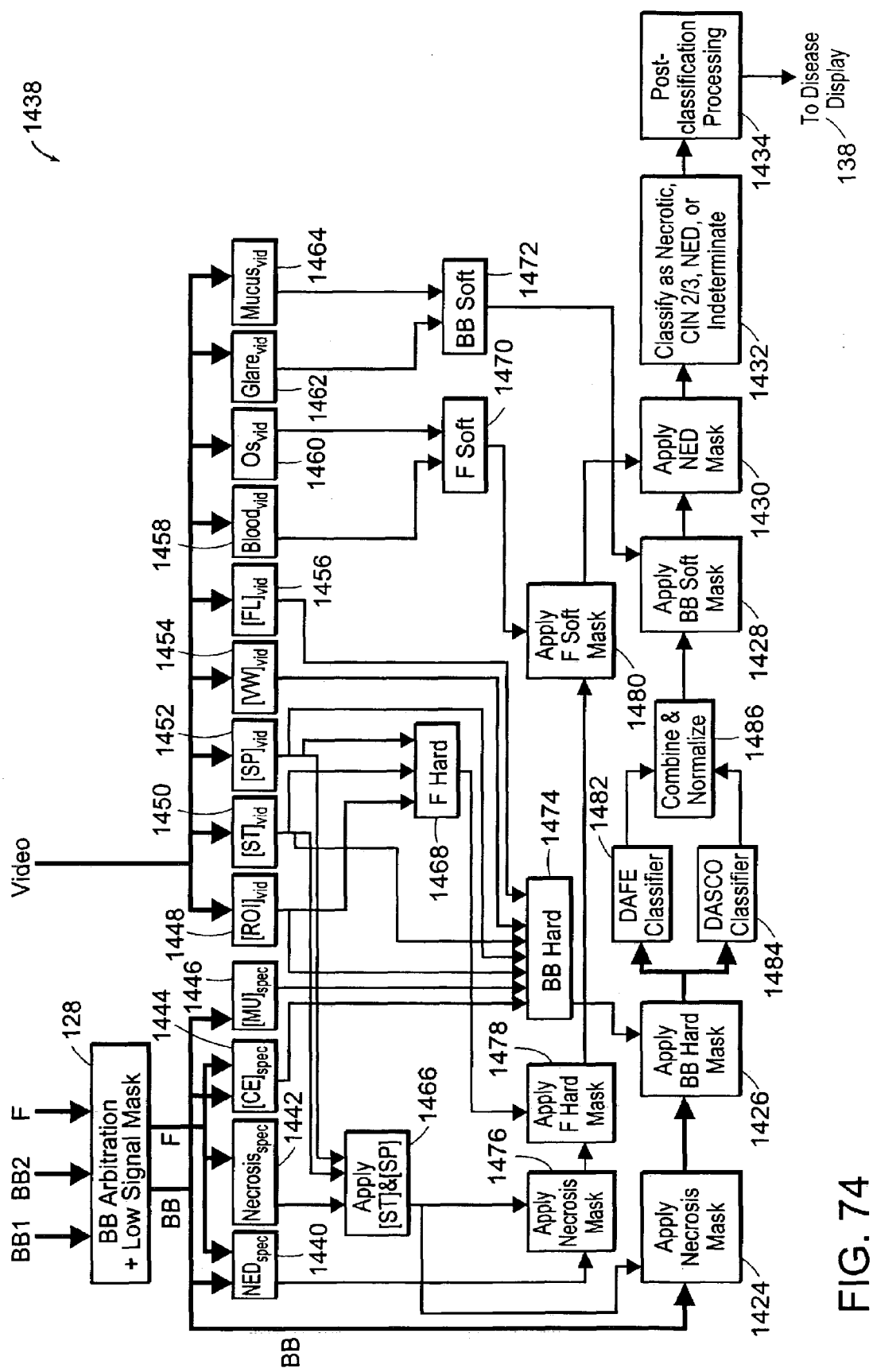
FIG. 74 is a block diagram depicting steps in the method of FIG. 73 in further detail, according to an illustrative embodiment of the invention.

FIG. 74 shows a block diagram 1438 depicting steps in the method of FIG. 73 in further detail. The steps of FIG. 74 are summarized below and are discussed in detail elsewhere herein. Steps 1440, 1442, 1444, and 1446 in FIG. 74 depict determination of the spectral masks from the arbitrated broadband reflectance and fluorescence signals, as seen in step 130 of FIG. 73. Steps 1448, 1450, 1452, 1454, 1456, 1458, 1460, 1462, and 1464 in FIG. 74 depict determination of the image masks from the focused, calibrated video data, as seen in step 108 of FIG. 73. The lines extending below these mask determination steps in FIG. 74 show how (in one embodiment) the masks are combined together, as indicated in step 1422 of FIG. 73. Steps 1466, 1468, 1470, 1472, 1474, 1476, 1478, and 1480 of FIG. 74 shows which masks are combined. Also important is the manner in which the masks are combined, disclosed in the detailed step explanations herein.

The statistical classification step 134 from FIG. 73 is shown in FIG. 74 as steps 1482, 1484, and 1486. Here, the pictured embodiment applies a necrosis mask 1424 and a hard "indeterminate" mask 1426 to the arbitrated broadband spectral data to eliminate the need to further process certain necrotic and indeterminate interrogation points in the classification step. Classification includes processing of broadband spectral data via wavelength region truncation, wavelength subsampling, and/or mean-centering. The processed data is then used in two different feature extraction methods. These include a principal component analysis (PCA) method used in the DASCO classifier step 1484 (Discriminant Analysis with Shrunken Covariances) and a feature coordinate extraction (FCE) method used in the DAFE classifier step 1482 (Discriminant Analysis Feature Extraction). Each of steps 1484 and 1482 extract a lower dimensional set of features from the spectral data that is then used in a Bayes' classifier to determine probabilities of classification in one or more tissue-class/state-of-health categories. The classification probabilities determined in steps 1482 and 1484 are combined in step 1486. Each of the classifiers in steps 1482 and 1484 are specified by a set of parameters that have been determined by training on known reference data. One embodiment includes updating the classifier parameters, as additional reference data becomes available.

Spectral Masking

The invention comprises determining spectral masks. Spectral masks identify data from a patient scan that are potentially non-representative of regions of interest of the tissue sample. Spectral masks also identify data that are highly indicative of necrotic tissue or normal squamous (NED) tissue. In one embodiment, the spectral masks are combined as indicated in the block flow diagram 1438 of FIG. 74, in order to account for the identification of spectrally-masked interrogation points in the tissue-class/state-of-health classification step 1432. Steps 1440, 1442, 1444, and 1446 in FIG. 74 depict the determination of spectral masks from the arbitrated broadband reflectance and fluorescence spectra obtained during a patient scan and are discussed in more detail below.

Step 1440 in FIG. 74 depicts the determination of an $NED_{spec}$ (no evidence of disease) spectral mask using data from the fluorescence spectrum, F, and the broadband reflectance spectrum, BB, at each of the interrogation points of the scan pattern, following the arbitration and low-signal masking step 128. Applying the $NED_{spec}$ mask reduces false positive diagnoses of CIN 2/3 resulting from the tissue-class/state-of-health classification step 134 in FIG. 1 (and FIG. 89). The $NED_{spec}$ mask identifies tissue having optical properties distinctly different from those of CIN 2/3 tissue. More specifically, in one embodiment, the $NED_{spec}$ mask uses differences between the fluorescence signals seen in normal squamous tissue and CIN 2/3 tissue. These differences are not accounted for by tissue-class/state-of-health classifiers based on broadband reflectance data alone. For example, the $NED_{spec}$ mask uses the collagen peak seen in the fluorescence spectra of normal squamous tissue at about 410 nm to distinguish normal squamous tissue from CIN 2/3 tissue.

Figure 75:
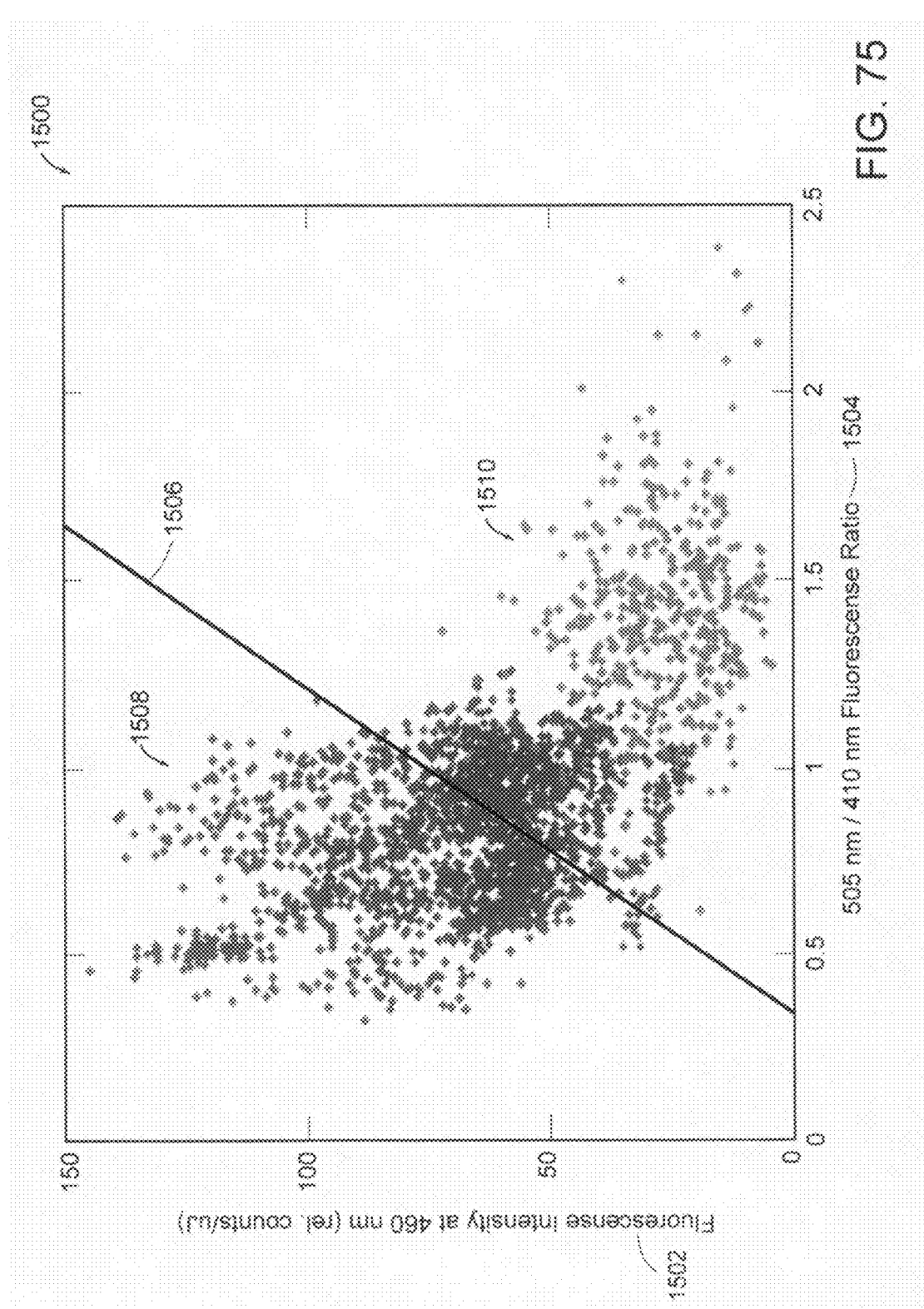
FIG. 75 shows a scatter plot depicting discrimination between regions of normal squamous tissue and CIN 2/3 tissue for known reference data, obtained by comparing fluorescence intensity at about 460 nm to a ratio of fluorescence intensities at about 505 nm and about 410 nm, used in determining an NED spectral mask ($NED_{spec}$) according to an illustrative embodiment of the invention.

FIG. 75 shows a scatter plot 1500 depicting discrimination between regions of normal squamous tissue and CIN 2/3 tissue for a set of known reference data, according to one embodiment. Plotting fluorescence intensity at 460 nm (y-axis, 1502) against a ratio of fluorescence intensity, F(505 nm)/F(410 nm), (x-axis, 1504) provides good discrimination between regions known to be normal squamous tissue (blue points in FIG. 75) and regions known to be CIN 2/3 tissue (red points in FIG. 75). One component of the $NED_{spec}$ discrimination metric is shown by line 1506 in FIG. 75, which divides a region of the plot that is predominately representative of normal squamous tissue (1508) from a region of the plot that is predominately representative of CIN 2/3 tissue (1510). The divider 1506 can be adjusted, for example, to further reduce false positives or to allow detection of more true positives at the expense of increased false positives.

In one embodiment, the fluorescence over reflectance ratio at about 430 nm is also included in the $NED_{spec}$ metric to determine normal columnar tissue sites that may not be identified by the component of the metric illustrated in FIG. 75 (i.e. blue points on the right of line 1506). It is found that fluorescence of CIN 2/3 tissue at about 430 nm is lower relative to normal tissue, while CIN 2/3 reflectance at about 430 nm is higher relative to normal tissue, after application of a contrast agent such as acetic acid.

Figure 76:
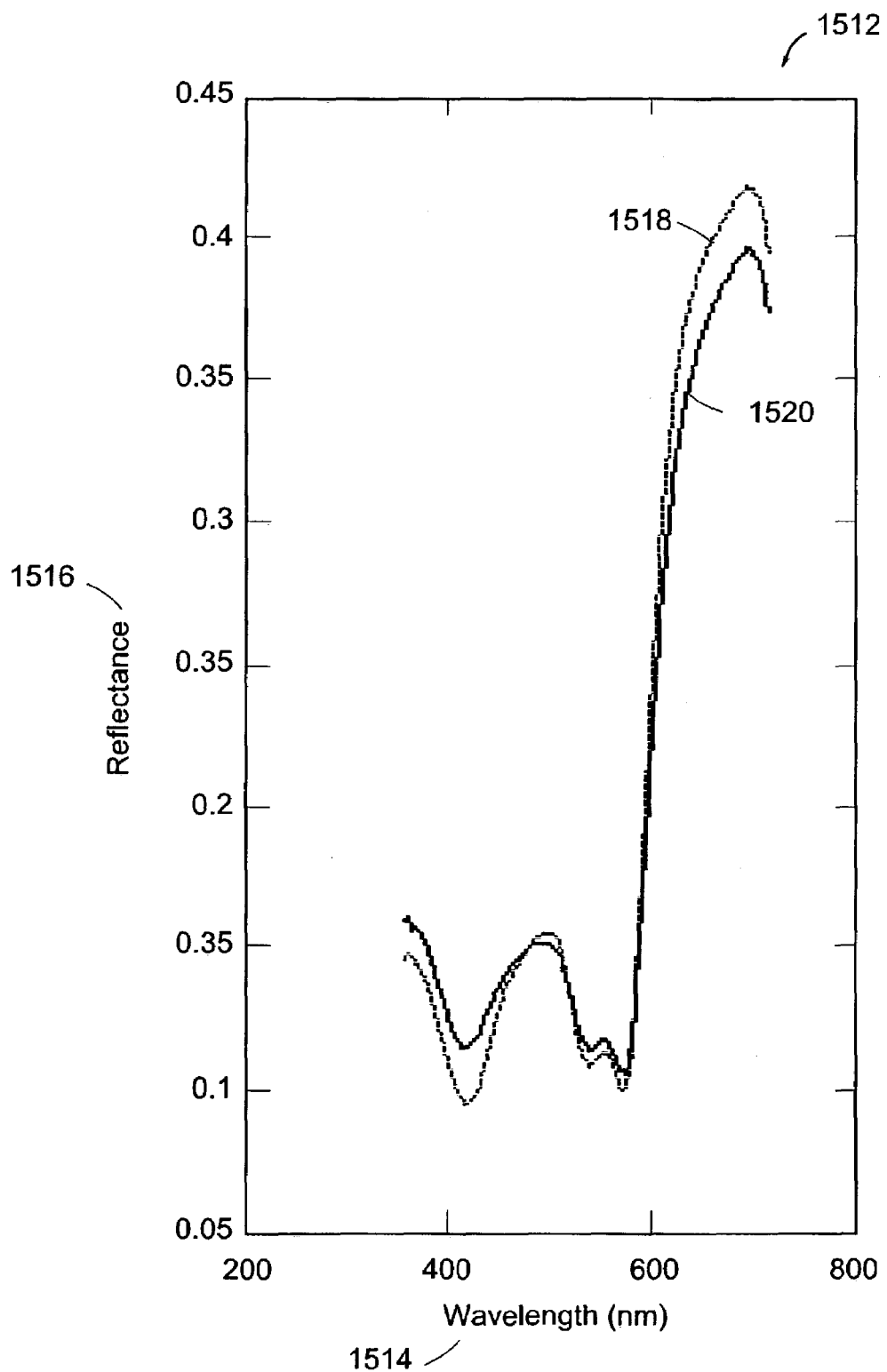
FIG. 76 shows a graph depicting as a function of wavelength mean broadband reflectance values for known normal squamous tissue regions and known CIN 2/3 tissue regions, used in determining an NED spectral mask ($NED_{spec}$) according to an illustrative embodiment of the invention.
Figure 77:
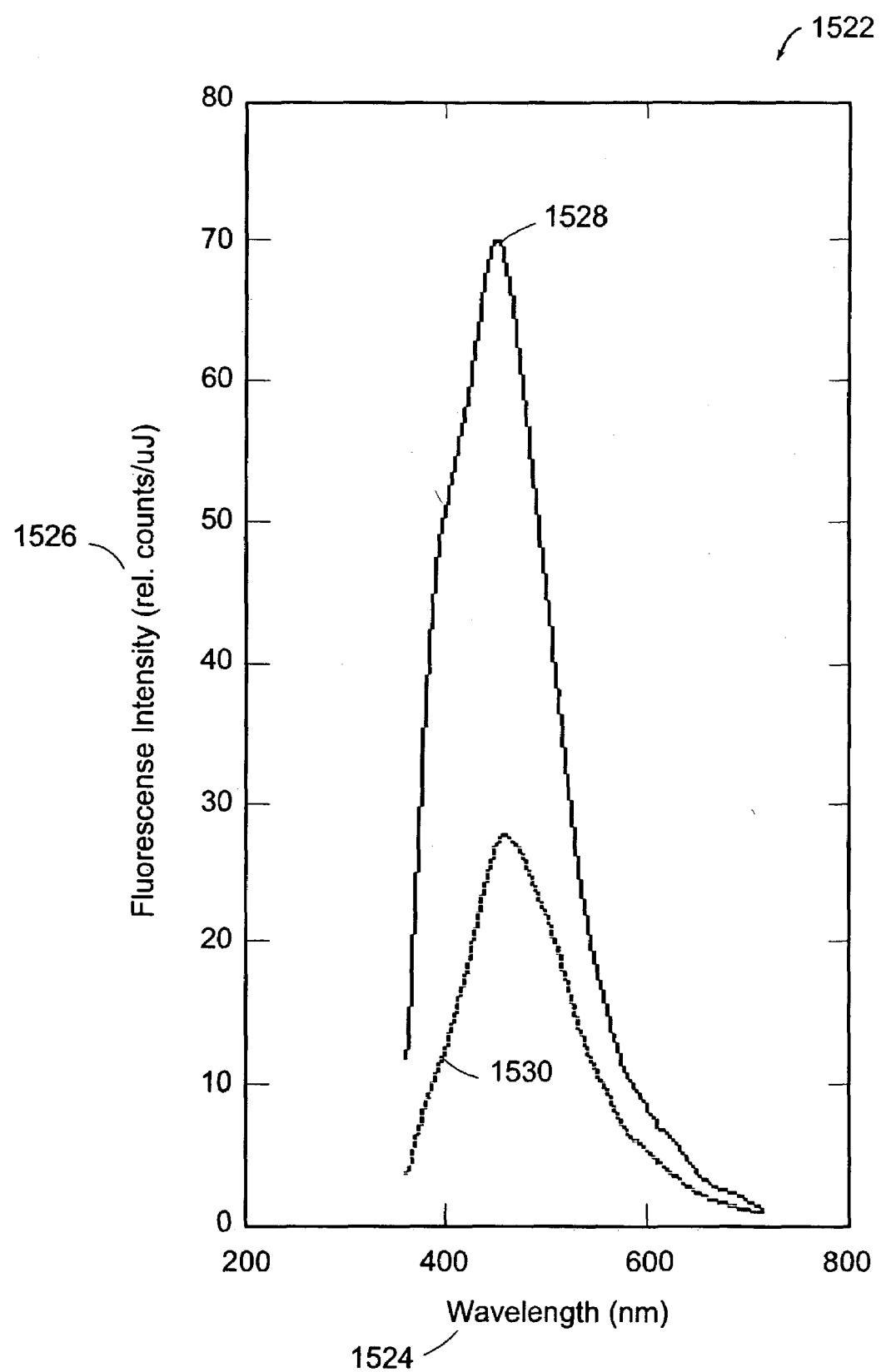
FIG. 77 shows a graph depicting as a function of wavelength mean fluorescence intensity values for known squamous tissue regions and known CIN 2/3 tissue regions, used in determining an NED spectral mask ($NED_{spec}$) according to an illustrative embodiment of the invention.
Figure 78:
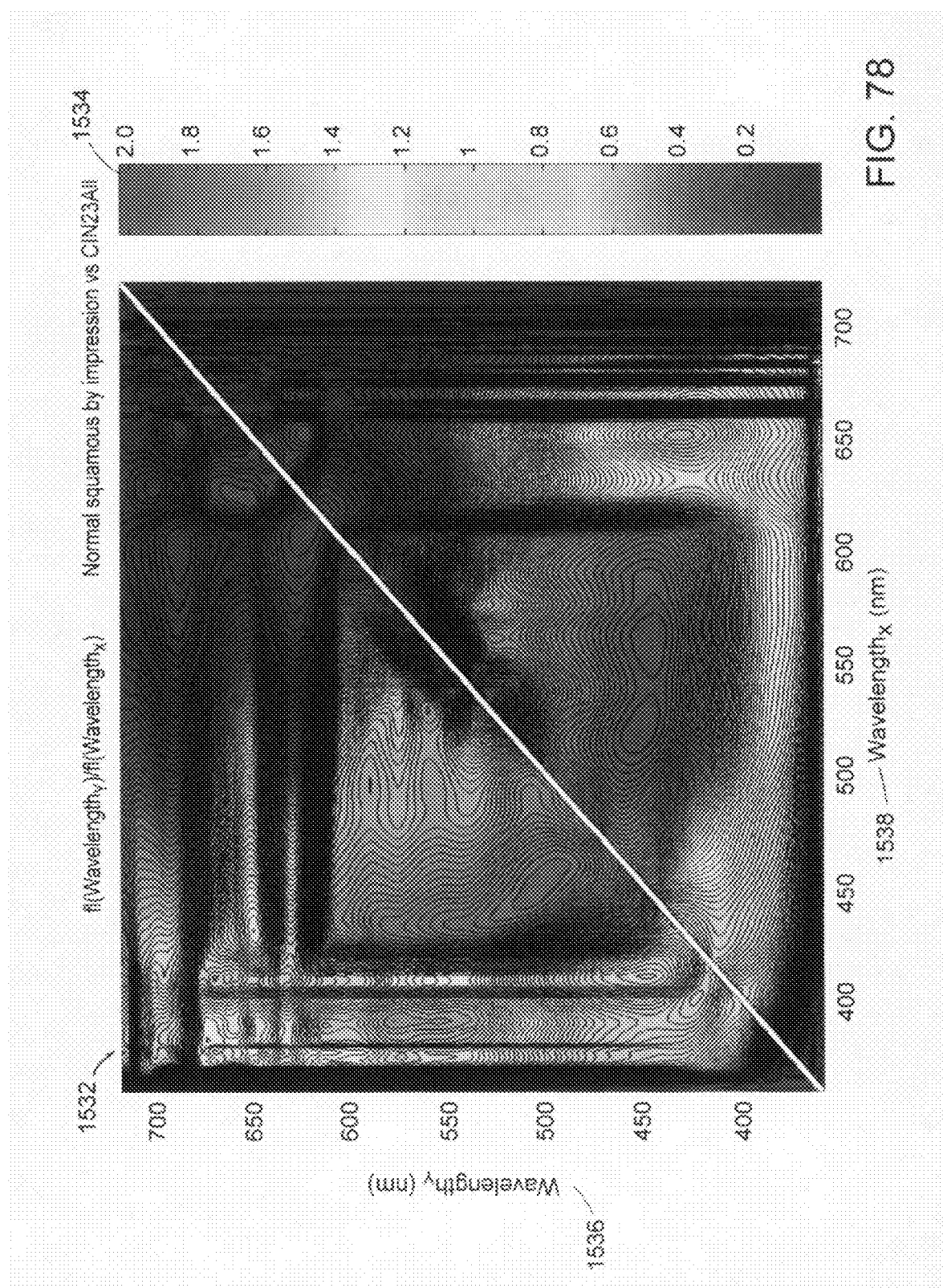
FIG. 78 shows a graph depicting values of a discrimination function using a range of numerator wavelengths and denominator wavelengths in the discrimination analysis between known normal squamous tissue regions and known CIN 2/3 tissue regions, used in determining an NED spectral mask ($NED_{spec}$) according to an illustrative embodiment of the invention.

FIG. 76 shows a graph 1512 depicting as a function of wavelength 1514 the mean broadband reflectance values 1516 for a set of known normal squamous tissue regions 1518 and a set of known CIN 2/3 tissue regions 1520, used in one embodiment to determine an additional component of the $NED_{spec}$ spectral mask. FIG. 77 shows a graph 1522 depicting as a function of wavelength 1524 the mean fluorescence intensity values 1526 for the set of known squamous tissue regions 1528 and the set of known CIN 2/3 tissue regions 1530. The difference between curves 1528 and 1530 in FIG. 77 is pronounced. Thus, a term is included in the $NED_{spec}$ metric based on the best ratio of wavelengths found to maximize values of D in the discrimination equation, Equation 87, below:

$$D = \frac{|\mu(F(\lambda)/F(\lambda'))_{Outlier} - \mu(F(\lambda)/F(\lambda'))_{Tissue}|}{\sqrt{\sigma^2(F(\lambda)/F(\lambda'))_{Outlier} + \sigma^2(F(\lambda)/F(\lambda'))_{Tissue}}} \quad (87)$$

where μ indicates mean and σ indicates standard deviation. FIG. 78 shows a graph 1532 depicting values of D in Equation 87 using a range of numerator wavelengths 1536 and denominator wavelengths 1538. According to the graph 1532 in FIG. 78, values of D are maximized using the fluorescence ratio F(450 nm)/F(566 nm). Alternately, other combinations of numerator wavelength and denominator wavelength may be chosen.

A scatter plot depicting discrimination between regions of normal squamous tissue and CIN 2/3 tissue for a set of known reference data are produced by comparing the ratio F(450 nm)/F(566 nm) to a threshold constant. Then, a graph of true positive ratio (TPR) versus false positive ratio (FPR) in the discrimination between regions of normal squamous tissue and CIN 2/3 tissue are obtained using a threshold constant. For example, a TPR of 65% and an FPR of 0.9% is obtained using a threshold constant of 4.51. The ratio of false positives may be reduced by adjusting the threshold.

Therefore, in one embodiment, the $NED_{spec}$ mask combines the following three metrics:

$$F(430)/BB(430) > x_1 \quad (88)$$

$$F(450)/F(566) > x_2 \quad (89)$$

$$F(460) > x_3 \cdot F(505)/F(410) - x_4 \quad (90)$$

where $x_1$, $x_2$, $x_3$, and $x_4$ are constants chosen based on the desired aggressiveness of the metric. Equations 88-90 account for the distinguishing features of spectra obtained from regions of normal squamous tissue versus spectra from CIN 2/3 tissue regions, as discussed above.

Figure 79A:
FIG. 79A depicts an exemplary reference image of cervical tissue from a patient scan in which spectral data is used in arbitration, NED spectral masking, and statistical classification of interrogation points of the tissue sample, according to an illustrative embodiment of the invention.
Figure 79B:
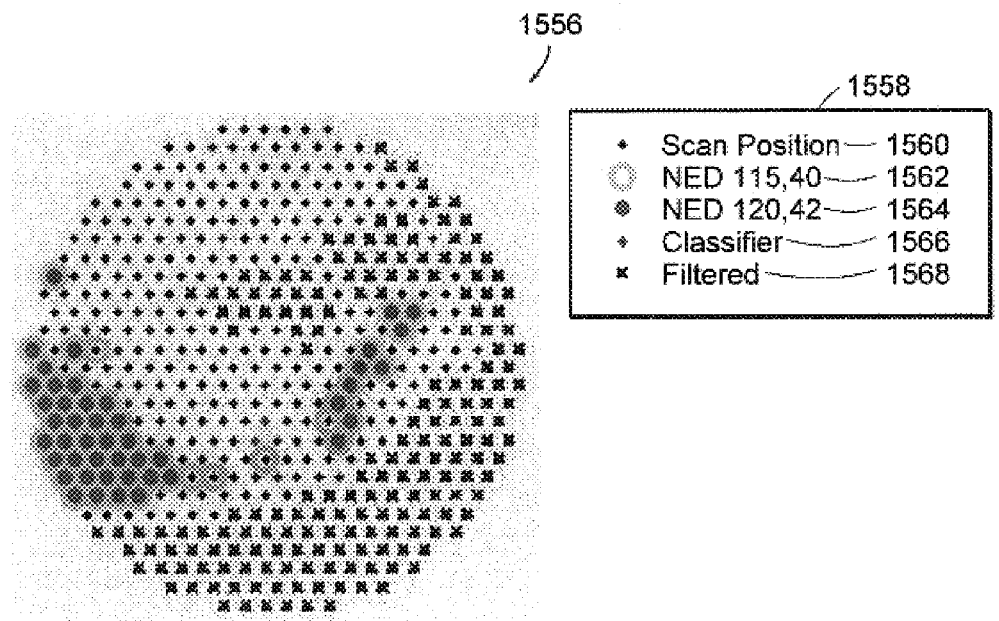
FIG. 79B is a representation (obgram) of the interrogation points (regions) of the tissue sample depicted in FIG. 79A and shows points classified as "filtered" following arbitration, "masked" following NED spectral masking with two different sets of parameters, and "CIN 2/3" following statistical classification, according to an illustrative embodiment of the invention.
Figure 79C:
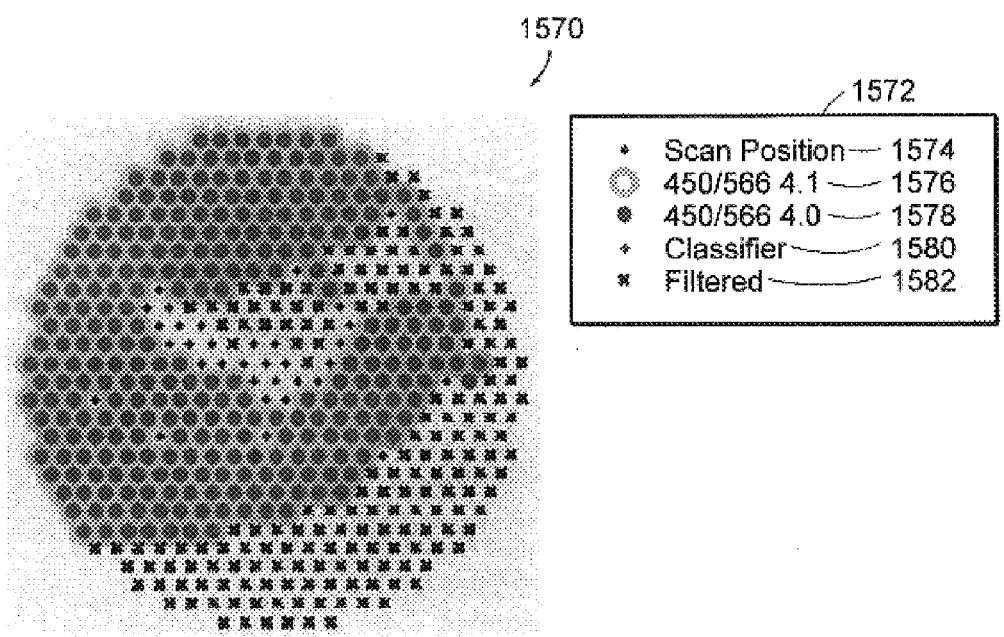
FIG. 79C is a representation (obgram) of the interrogation points (regions) of the tissue sample depicted in FIG. 79A and shows points classified as "filtered" following arbitration, "masked" following NED spectral masking with two different sets of parameters, and "CIN 2/3" following statistical classification, according to an illustrative embodiment of the invention.
Figure 79D:
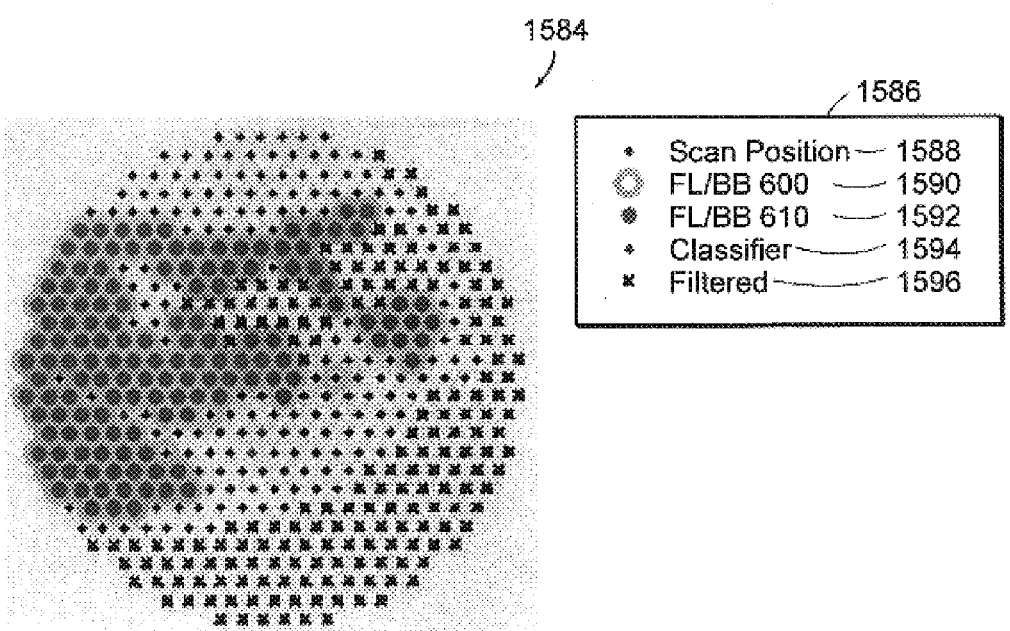
FIG. 79D is a representation (obgram) of the interrogation points (regions) of the tissue sample depicted in FIG. 79A and shows points classified as "filtered" following arbitration, "masked" following NED spectral masking with two different sets of parameters, and "CIN 2/3" following statistical classification, according to an illustrative embodiment of the invention.

FIGS. 79A-D illustrate adjustment of the components of the $NED_{spec}$ mask metric shown in Equations 88, 89, and 90. FIG. 79A depicts a reference image of cervical tissue 1554 from a patient scan in which spectral data is used in arbitration step 128, in $NED_{spec}$ spectral masking, and in statistical classification of interrogation points of the tissue sample. FIG. 79B is a representation (obgram) 1556 of the interrogation points (regions) of the tissue sample depicted in the reference image 1554 of FIG. 79A and shows points that are "masked" following application of Equation 90. The obgram 1556 of FIG. 79B shows that some additional interrogation points are masked as NED tissue by adjusting values of $x_3$ and $x_4$ in Equation 90 from $\{x_3=120, x_4=42\}$ to $\{x_3=115, x_4=40\}$. FIG. 79C shows interrogation points that are "masked" following application of Equation 89. The obgram 1570 of FIG. 79C shows that a few additional points are masked as NED tissue by adjusting the value of $X_2$ from 4.0 to 4.1. FIG. 79D shows interrogation points that are masked following application of Equation 88. The obgram 1584 of FIG. 79D shows that a few additional points are masked as NED tissue by adjusting the value of $x_1$ from 610 to 600.

In one embodiment values of $x_1$, $x_2$, $x_3$, and $x_4$ in Equations 88, 89, and 90 are determined using multidimensional unconstrained nonlinear minimization. In one embodiment, the overall $NED_{spec}$ metric that results is as follows:

$$F(430)/BB(430) > 600 \text{ ct/}\mu J \text{ OR}$$

$$F(450)/F(566) > 4.1 \text{ OR}$$

$$F(460) > 115 \cdot F(505)/F(410) - 40$$

where the mean fluorescent intensity of normal squamous tissue is about 70 counts/$\mu$J at about 450 nm.

Step 1442 in FIG. 74 depicts the determination of $Necrosis_{spec}$, a necrotic tissue spectral mask, using data from the fluorescence spectrum, F, at each of the interrogation points of the scan pattern, following the arbitration and low-signal masking step 128. Unlike the other spectral masks (steps 1440, 1442, and 1446 in FIG. 74), which are designed to reduce false positive diagnoses of CIN 2/3, the $Necrosis_{spec}$ mask identifies areas of necrotic tissue, thereby identifying patients with fairly advanced stages of invasive carcinoma.

Figure 80:
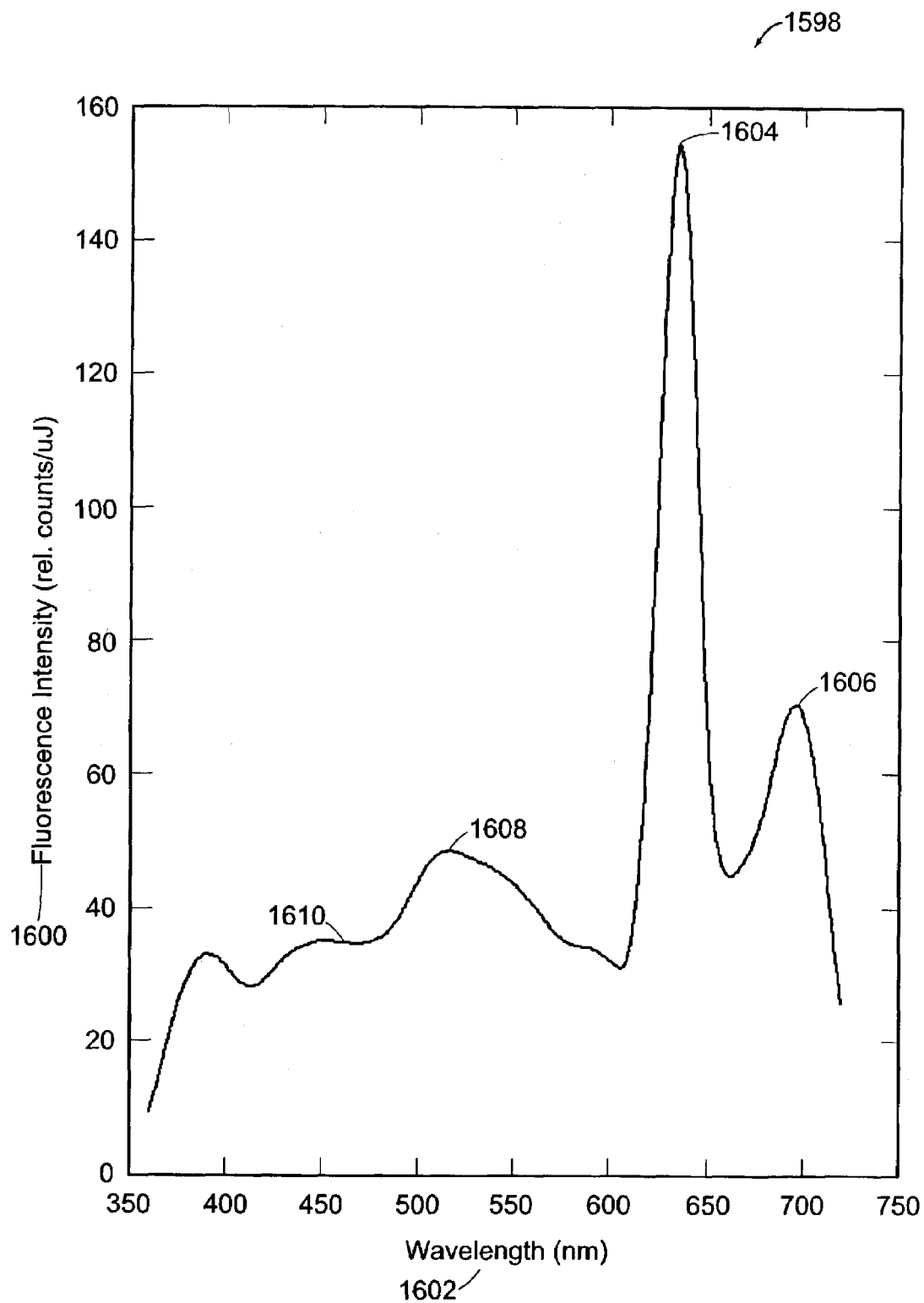
FIG. 80 shows a graph depicting fluorescence intensity as a function of wavelength from an interrogation point confirmed as invasive carcinoma by pathology and necrotic tissue by impression, used in determining a Necrosis spectral mask according to an illustrative embodiment of the invention.
Figure 81:
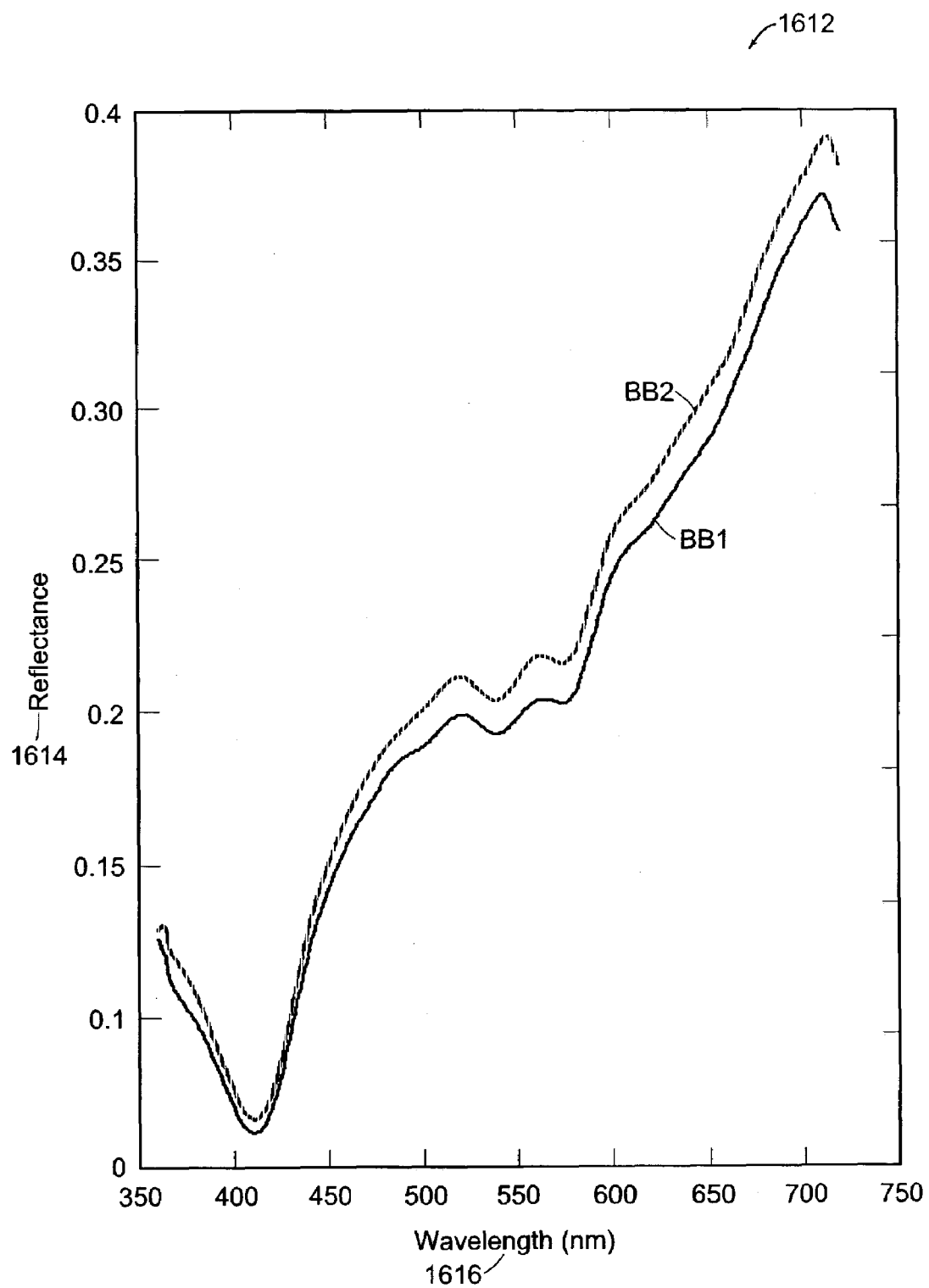
FIG. 81 shows a graph depicting broadband reflectance BB1 and BB2 as functions of wavelength from an interrogation point confirmed as invasive carcinoma by pathology and necrotic tissue by impression, used in determining a Necrosis spectral mask according to an illustrative embodiment of the invention.

In one embodiment, the $Necrosis_{spec}$ mask uses prominent features of the fluorescence spectra from a set of known necrotic regions to identify necrotic tissue. For example, in one embodiment, the $Necrosis_{spec}$ mask uses the large porphyrin peaks of necrotic tissue at about 635 nm and/or at about 695 nm in identifying necrotic tissue. FIG. 80 shows a graph 1598 depicting fluorescence intensity 1600 as a function of wavelength 1602 from an interrogation point confirmed as invasive carcinoma by pathology and necrotic tissue by impression, while FIG. 81 shows a graph 1612 depicting broadband reflectance spectra BB1 and BB2 for the same point.

The graph 1598 of FIG. 80 shows the distinctive porphyrin peaks at reference numbers 1604 and 1606. Concurrent with high porphyrin fluorescence at necrotic regions is a smaller peak at about 510 nm (label 1608), possibly due to flavin adenine dinucleotide (FAD), with an intensity greater than or equal to that of nicotinamide adenine dinucleotide (NADH) at about 450 nm (label 1610). The FAD/NADH ratio is a measure of ischemia and/or hypoxia indicative of advanced stages of cancer.

Thus, in one embodiment, the overall $Necrosis_{spec}$ metric has one or more components indicative of FAD/NADH and one or more components indicative of porphyrin. In one embodiment, the $Necrosis_{spec}$ metric is as follows:

$$F(510 \text{ nm})/F(450 \text{ nm}) > 1.0 \text{ AND}$$

$$F(635 \text{ nm})/F(605 \text{ nm}) > 1.3 \text{ AND}$$

$$F(635 \text{ nm})/F(660 \text{ nm}) > 1.3 \text{ AND}$$

$$F(635 \text{ nm}) > 20 \text{ ct/}\mu J$$

where mean fluorescent intensity of normal squamous tissue is about 70 counts/$\mu$J at about 450 nm, and where the first line of the metric indicates FAD/NADH (FAD) and the remainder of the metric indicates porphyrin. This metric requires all components to be satisfied in order for a region of tissue to be classified as necrotic. In one embodiment, the combination is needed to reduce false necrosis diagnoses in patients. The presence of porphyrin does not always indicate necrosis, and necrosis masking based solely on the detection of porphyrin may produce an unacceptable number of false positives. For example, porphyrin may be present due to hemoglobin breakdown products following menses or due to systemic porphyrin resulting from medications, bacterial infection, or porphyria. Thus, the presence of both porphyrin and the indication of FAD must both be determined in order for a region to be identified as necrotic by the $Necrosis_{spec}$ metric in the embodiment described above.

Figure 82A:
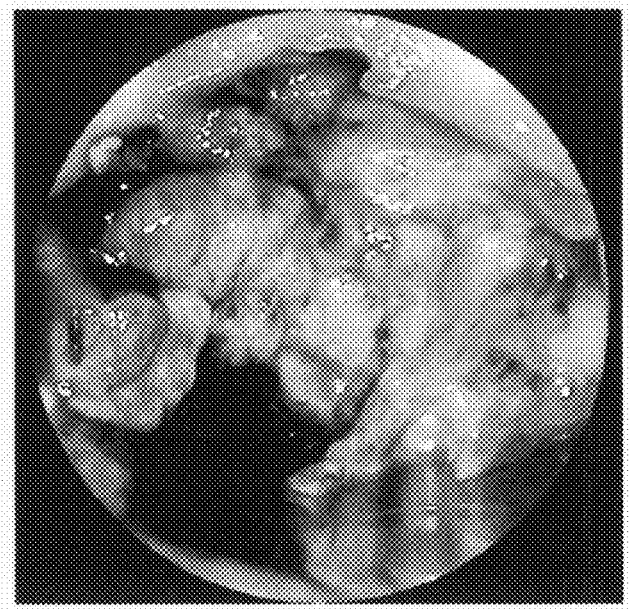
FIG. 82A depicts an exemplary reference image of cervical tissue from the scan of a patient confirmed as having advanced invasive cancer in which spectral data is used in arbitration, Necrosis spectral masking, and statistical classification of interrogation points of the tissue sample, according to an illustrative embodiment of the invention.
Figure 82B:
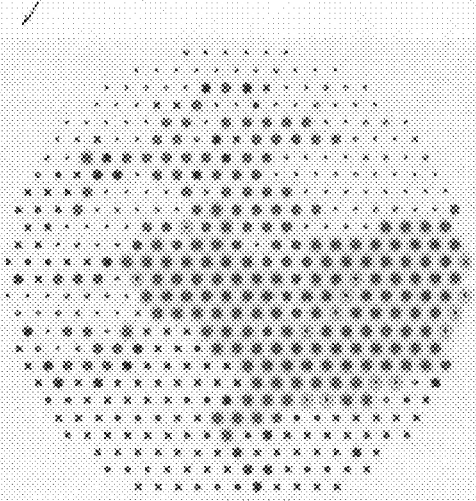
FIG. 82B is a representation (obgram) of the interrogation points (regions) of the tissue sample depicted in FIG. 82A and shows points classified as "filtered" following arbitration, "masked" following application of the "Porphyrin" and "FAD" portions of the Necrosis spectral mask, and "CIN 2/3" following statistical classification, according to an illustrative embodiment of the invention.

FIG. 82A depicts a reference image 1618 of cervical tissue from the scan of a patient confirmed as having advanced invasive cancer, in which spectral data is used in arbitration step 128, in $Necrosis_{spec}$ spectral masking, and in statistical classification 134 of interrogation points of the tissue sample. FIG. 82B is an obgram 1620 of the interrogation points (regions) of the tissue sample depicted in FIG. 82A and shows points that are identified by application of the FAD component of the $Necrosis_{spec}$ metric above (1628), as well as points that are identified by application of the porphyrin component of the $Necrosis_{spec}$ metric above (1626). The overall $Necrosis_{spec}$ mask above identifies points as necrotic only when both FAD and porphyrin are identified. In FIG. 82B, interrogation points that are marked by both a blue dot (FAD 1626) and a green ring (porphyrin 1626) are identified as necrotic tissue by application of the $Necrosis_{spec}$ metric above.

Step 1444 in FIG. 74 depicts the determination of a cervical edge/vaginal wall spectral mask ($[CE]_{spec}$) using data from the fluorescence spectrum, F, and the broadband reflectance spectrum, BB, of each interrogation point of a scan, following the arbitration and low-signal masking step 128. The [CE]$_{spec}$ mask identifies low-signal outliers corresponding to the cervical edge, os, and vaginal wall, which, in one embodiment, are regions outside an area of diagnostic interest for purposes of the tissue characterization system 100 of FIG. 1.

Figure 83:
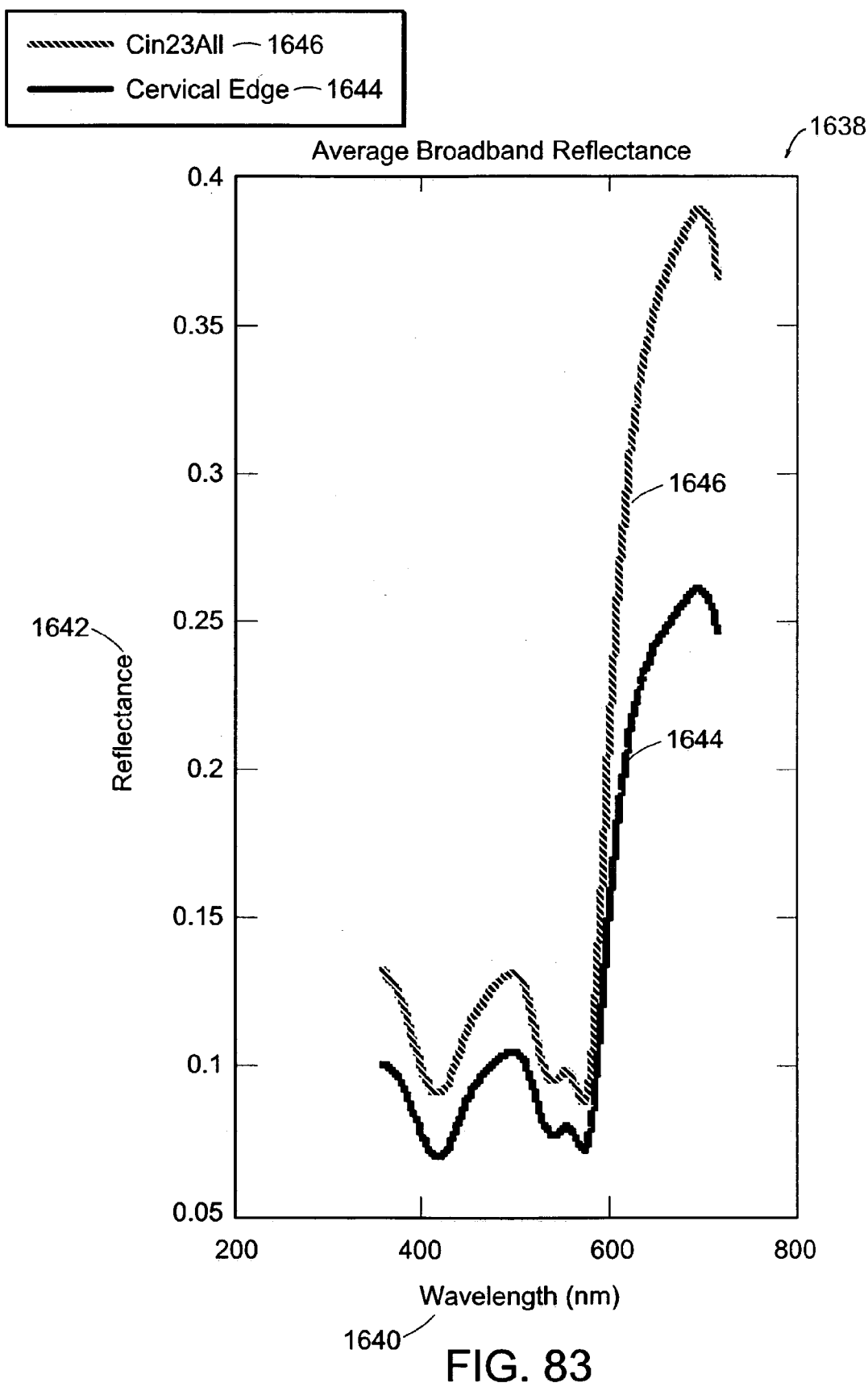
FIG. 83 shows a graph depicting as a function of wavelength mean broadband reflectance values for known cervical edge regions and known CIN 2/3 tissue regions, used in a discrimination analysis to determine a cervical edge/vaginal wall ($[CE]_{spec}$) spectral mask according to an illustrative embodiment of the invention.
Figure 84:
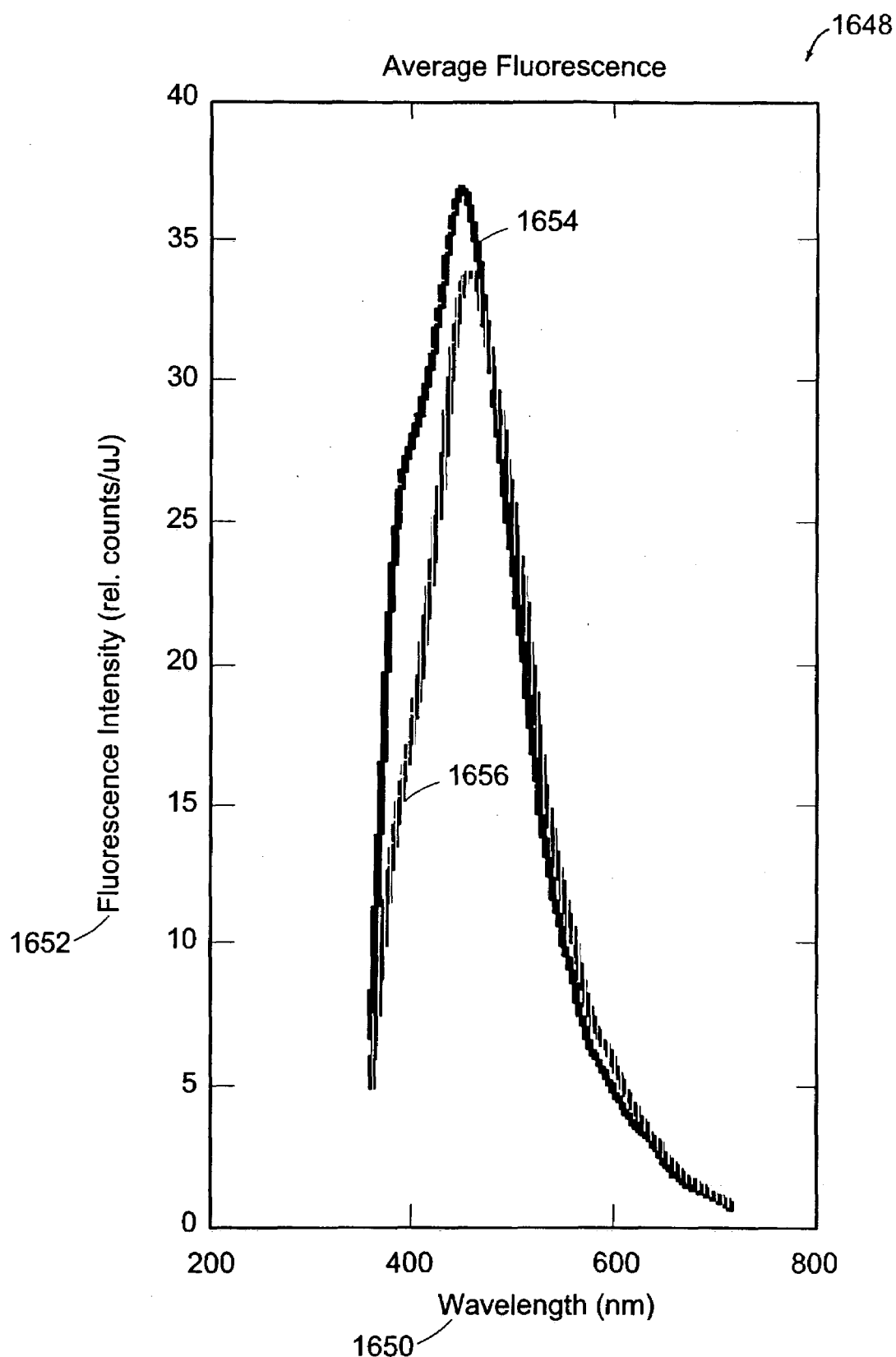
FIG. 84 shows a graph depicting as a function of wavelength mean fluorescence intensity values for known cervical edge regions and known CIN 2/3 tissue regions, used in a discrimination analysis to determine a cervical edge/vaginal wall ($[CE]_{spec}$) spectral mask according to an illustrative embodiment of the invention.
Figure 85:
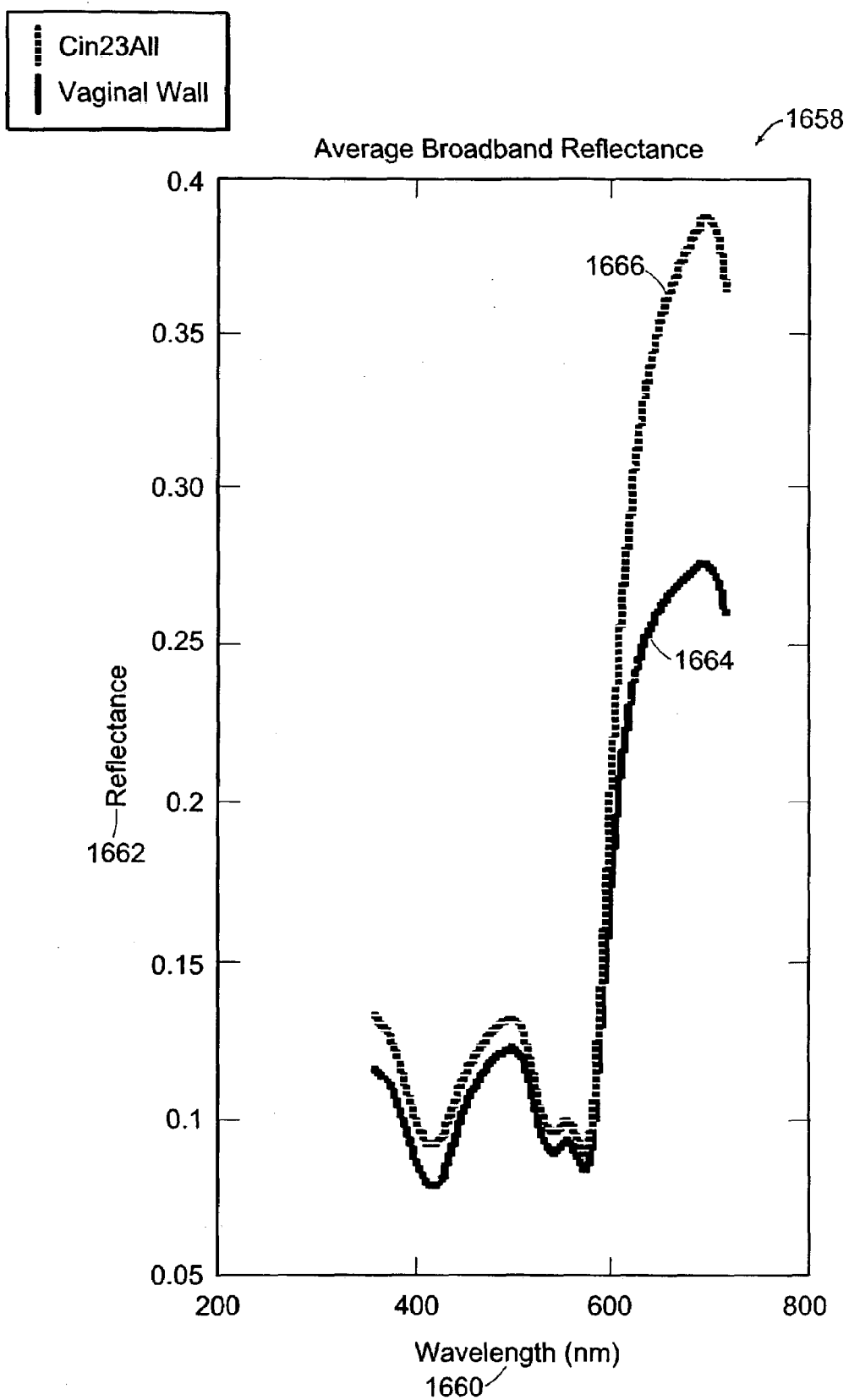
FIG. 85 shows a graph depicting as a function of wavelength mean broadband reflectance values for known vaginal wall regions and known CIN 2/3 tissue regions, used in a discrimination analysis to determine a cervical edge/vaginal wall ($[CE]_{spec}$) spectral mask according to an illustrative embodiment of the invention.
Figure 86:
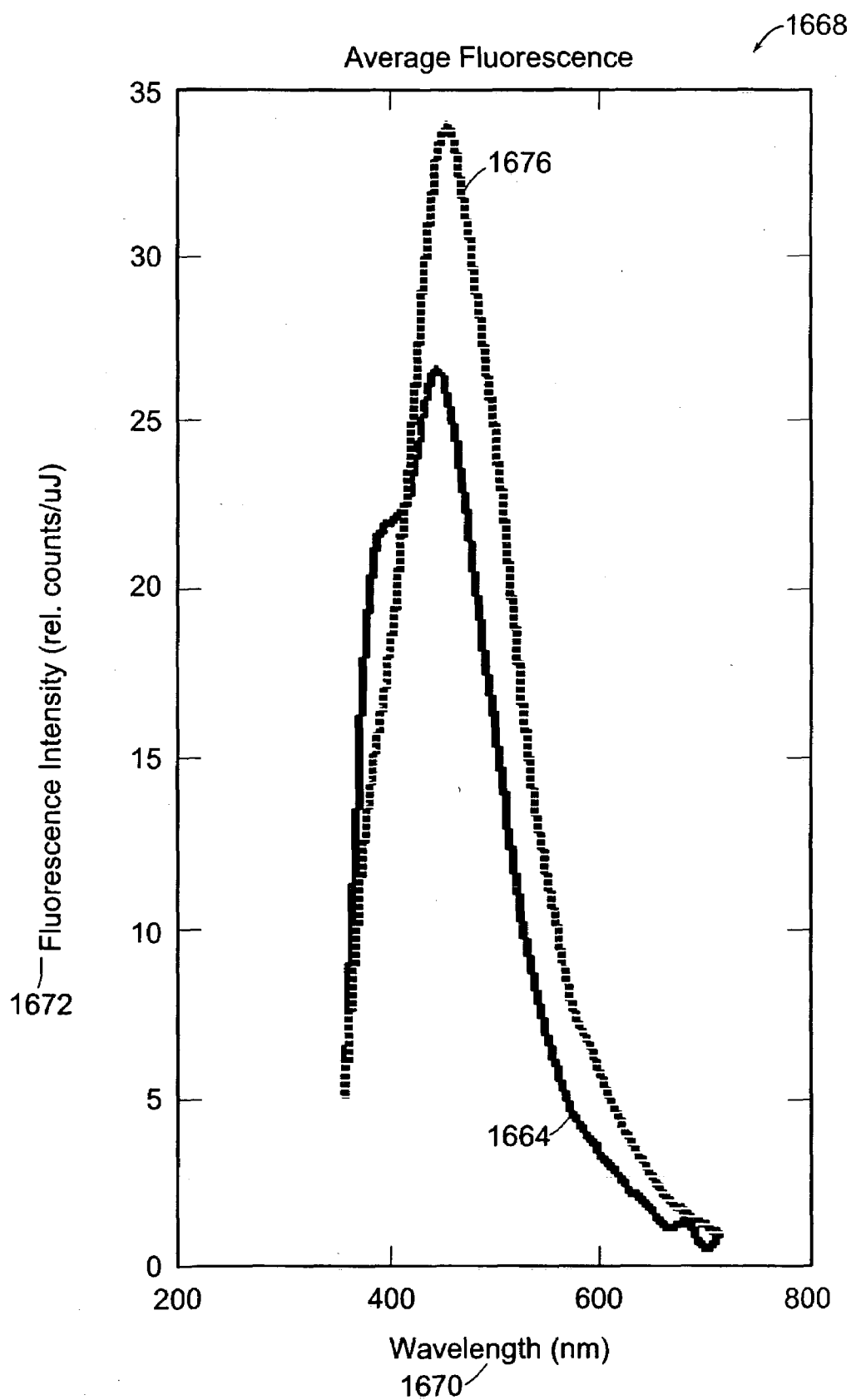
FIG. 86 shows a graph depicting as a function of wavelength mean fluorescence intensity values for known vaginal wall regions and known CIN 2/3 tissue regions, used in a discrimination analysis to determine a cervical edge/vaginal wall ($[CE]_{spec}$) spectral mask according to an illustrative embodiment of the invention.

FIGS. 83, 84, 85, and 86 compare broadband reflectance and fluorescence spectra of cervical edge and vaginal wall regions to spectra of CIN 2/3 tissue. In one embodiment, these comparisons are used in a discrimination analysis to determine a [CE]$_{spec}$ spectral mask. FIG. 83 shows a graph 1638 depicting as a function of wavelength 1640 the mean broadband reflectance values 1642 for a set of known cervical edge regions 1644 and a set of known CIN 2/3 tissue regions 1646. FIG. 84 shows a graph 1648 depicting as a function of wavelength 1650 the mean fluorescence intensity values 1652 for the set of known cervical edge regions 1654 and the set of known CIN 2/3 tissue regions 1656. FIG. 85 shows a graph 1658 depicting as a function of wavelength 1660 the mean broadband reflectance values 1662 for a set of known vaginal wall regions 1664 and a set of known CIN 2/3 tissue regions 1666. FIG. 86 shows a graph 1668 depicting as a function of wavelength 1670 the mean fluorescence intensity values 1672 for the set of known vaginal wall regions 1674 and the set of known CIN 2/3 tissue regions 1676.

In one embodiment, features of the curves in FIGS. 83, 84, 85, and 86 are used in determining the [CE]$_{spec}$ spectral mask metric. For example, from FIGS. 84 and 86, it is seen that reflectance values for cervical edge/vaginal wall regions are lower than CIN 2/3 reflectance, particularly at about 450 nm and at about 700 nm. From FIGS. 84 and 86, it is seen that there is a "hump" in the fluorescence curves for cervical edge regions 1654 and vaginal wall regions 1674 at about 400 nm, where there is no such hump in the CIN 2/3 curve (1656/1676). This causes the ratio of fluorescence intensity, F(530 nm)/F(410 nm), to be low at cervical edge/vaginal wall regions, relative to that of CIN 2/3 regions. From FIG. 86, the mean fluorescence intensity of vaginal wall regions 1674 is lower than that of CIN 2/3 regions at least from about 500 nm to about 540 nm. In one embodiment, these observations are combined to determine the overall [CE]$_{spec}$ mask metric as follows:

BB(450 nm)·BB(700 nm)/BB(540 nm)<0.30 OR

F²(530 nm)/F(410 nm)<4.75.

The top line of the metric above reflects the observation that the mean reflectance of cervical edge/vaginal wall tissue is comparable to that of CIN 2/3 tissue at about 540 nm and lower than that of CIN 2/3 tissue at about 450 nm and about 700 nm. The bottom line of the metric above reflects the observation that the fluorescence of a cervical edge/vaginal wall region may have a lower fluorescence at 530 nm than CIN 2/3 tissue and that the cervical edge/vaginal wall region may have a lower F(530 nm)/F(410 nm) ratio than CIN 2/3 tissue.

Figure 87A:
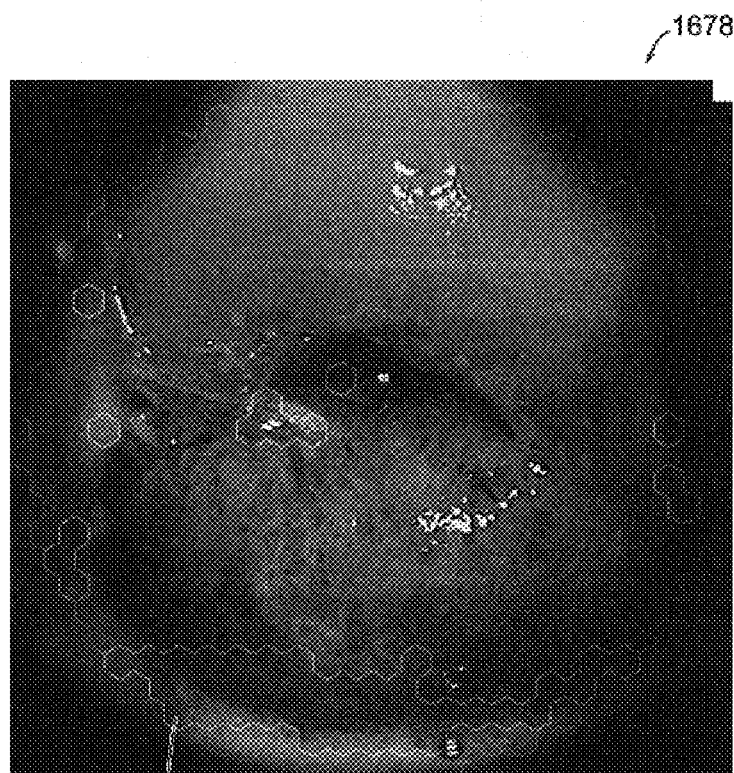
FIG. 87A depicts an exemplary reference image of cervical tissue from a patient scan in which spectral data is used in arbitration and cervical edge/vaginal wall ($[CE]_{spec}$) spectral masking, according to an illustrative embodiment of the invention.
Figure 87B:
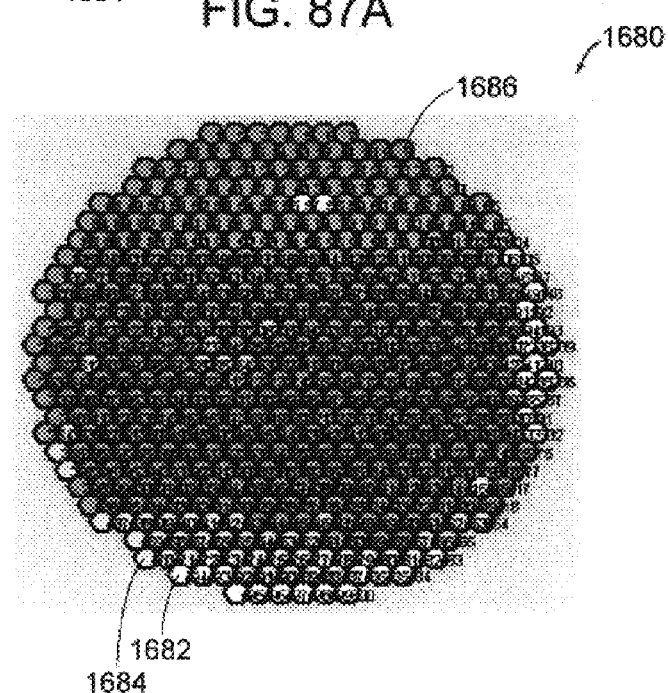
FIG. 87B is a representation (obgram) of the interrogation points (regions) of the tissue sample depicted in FIG. 87A and shows points classified as "filtered" following arbitration and "masked" following cervical edge/vaginal wall ($[CE]_{spec}$) spectral masking, according to an illustrative embodiment of the invention.

FIG. 87A depicts a reference image 1678 of cervical tissue from a patient scan in which spectral data is used in arbitration and [CE]$_{spec}$ spectral masking. FIG. 87B is an obgram 1680 of the interrogation points (regions) of the tissue sample depicted in FIG. 87A and shows, in yellow (1684), the points that are "masked" by application of the [CE]$_{spec}$ metric above. White points (1682) in FIG. 87B indicate regions that are filtered out by the arbitration and low-signal mask of step 128, while pink points (1686) indicate regions remaining after application of both the arbitration/low-signal mask of step 128 as well as the [CE]$_{spec}$ spectral mask.

Step 1446 in FIG. 74 depicts the determination of a fluids/mucus ([MU]$_{spec}$) spectral mask using data from the broadband reflectance spectrum, BB, at each interrogation point of the tissue sample following the arbitration and low-signal masking step 128. In one alternate embodiment, the fluorescence spectrum is used in place of or in addition to the broadband reflectance spectrum. The [MU]$_{spec}$ mask identifies tissue sites covered with thick, opaque, and light-colored mucus, as well as fluid that is pooling in the os or on top of the speculum during a patient scan.

Figure 88:
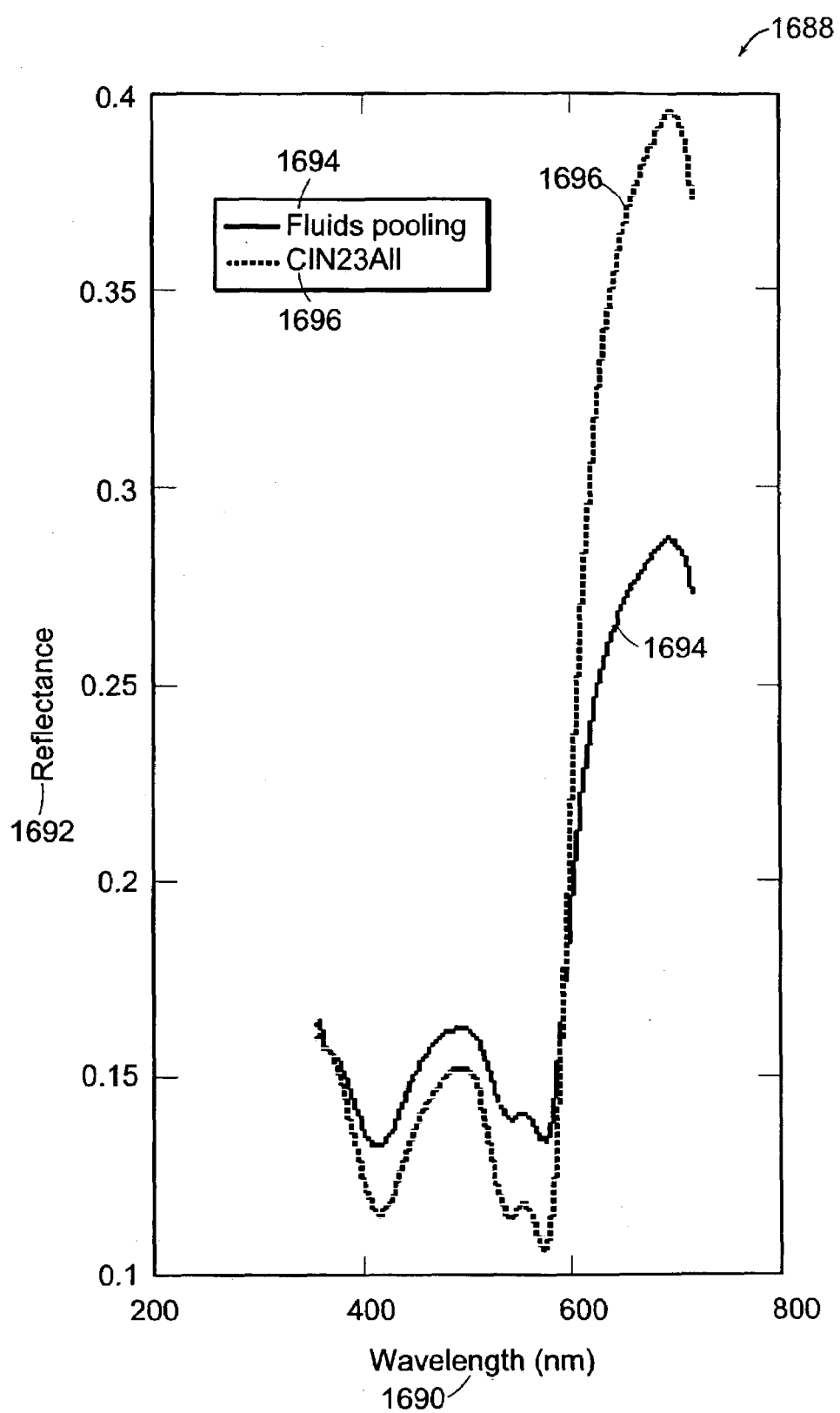
FIG. 88 shows a graph depicting as a function of wavelength mean broadband reflectance values for known pooling fluids regions and known CIN 2/3 tissue regions, used in a discrimination analysis to determine a fluids/mucus ($[MU]_{spec}$) spectral mask according to an illustrative embodiment of the invention.
Figure 89:
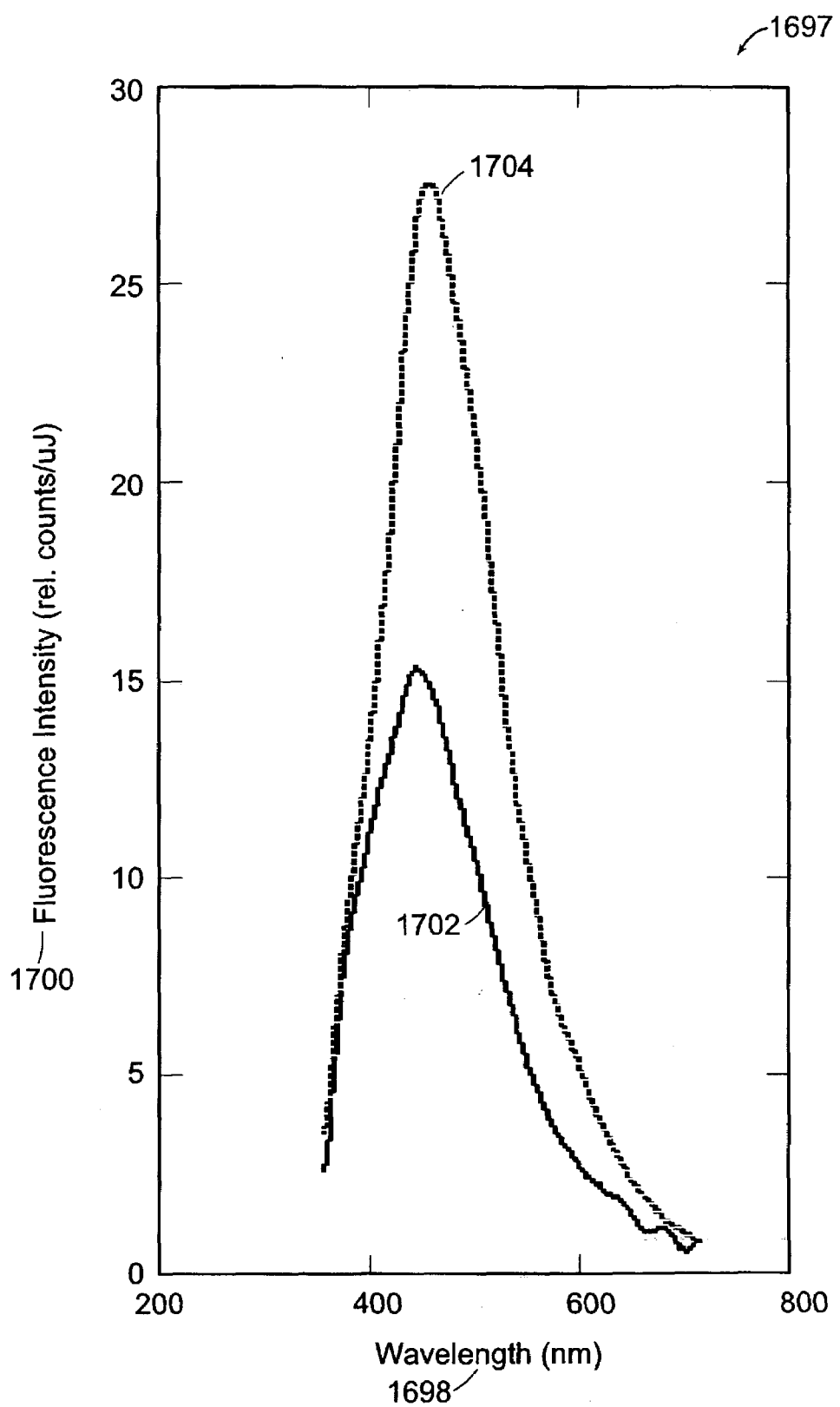
FIG. 89 shows a graph depicting as a function of wavelength mean fluorescence intensity values for known pooling fluids regions and known CIN 2/3 tissue regions, used in a discrimination analysis to determine a fluids/mucus ($[MU]_{spec}$) spectral mask according to an illustrative embodiment of the invention.
Figure 106:
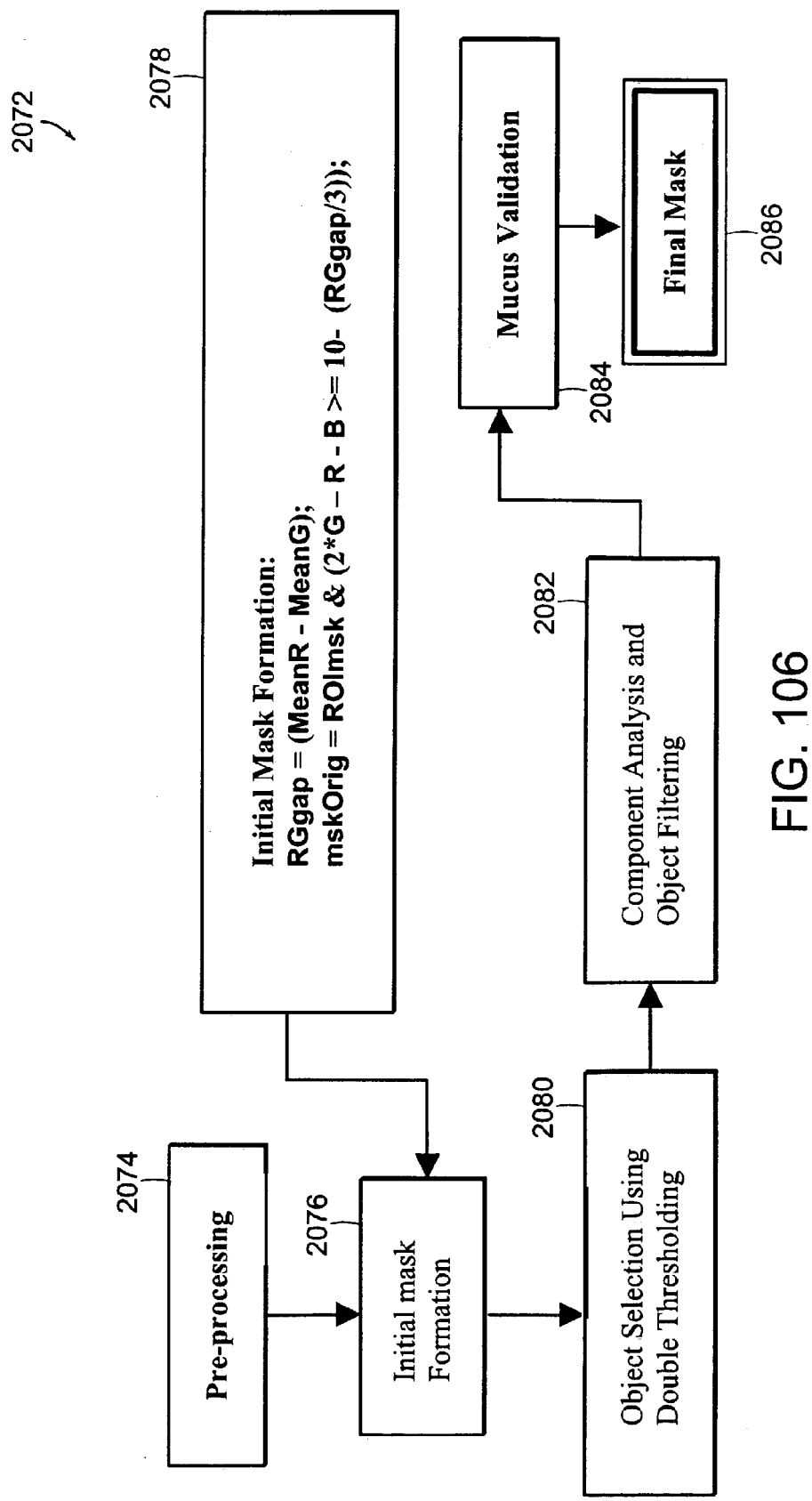

FIGS. 88, 89, 90, and 91 show steps in an exemplary discrimination analysis to determine a [MU]$_{spec}$ spectral mask. FIG. 106 shows a graph 1688 depicting as a function of wavelength 1690 the mean broadband reflectance values 1692 for a set of known pooling-fluids regions 1694 and a set of known CIN 2/3 tissue regions 1696. FIG. 89 shows a graph 1697 depicting as a function of wavelength 1698 the mean fluorescence intensity values 1700 for the set of known pooling fluids regions 1702 and the set of known CIN 2/3 tissue regions 1704. The difference between curves 1694 and 1696 in FIG. 88 is pronounced. Thus, in one embodiment, a term is included in the [MU]$_{spec}$ mask metric based on the best ratio of wavelength found to maximize values of D in the discrimination equation, Equation 91, as follows:

$$D = \frac{|\mu(BB(\lambda)/BB(\lambda'))_{Outlier} - \mu(BB(\lambda)/BB(\lambda'))_{Tissue}|}{\sqrt{\sigma^2(BB(\lambda)/BB(\lambda'))_{Outlier} + \sigma^2(BB(\lambda)/BB(\lambda'))_{Tissue}}} \quad (91)$$

In one embodiment, values of D above are maximized using the broadband reflectance ratio BB(594 nm)/BB(610 nm).

A scatter plot depicting discrimination between pooling fluids regions and CIN 2/3 tissue regions for a set of known reference data are obtained by comparing the ratio of arbitrated broadband intensity, BB(594 nm)/BB(610 nm) to a threshold constant. Then, a graph of true positive ratio (TPR) versus false positive ratio (FPR) in the discrimination between pooling fluids regions and CIN 2/3 tissue regions are obtained using a threshold constant. For example, a TPR of 56.3% and an FPR of 0.9% is obtained using a threshold constant of 0.74. The ratio of false positives may be reduced by adjusting the threshold.

Figure 90:
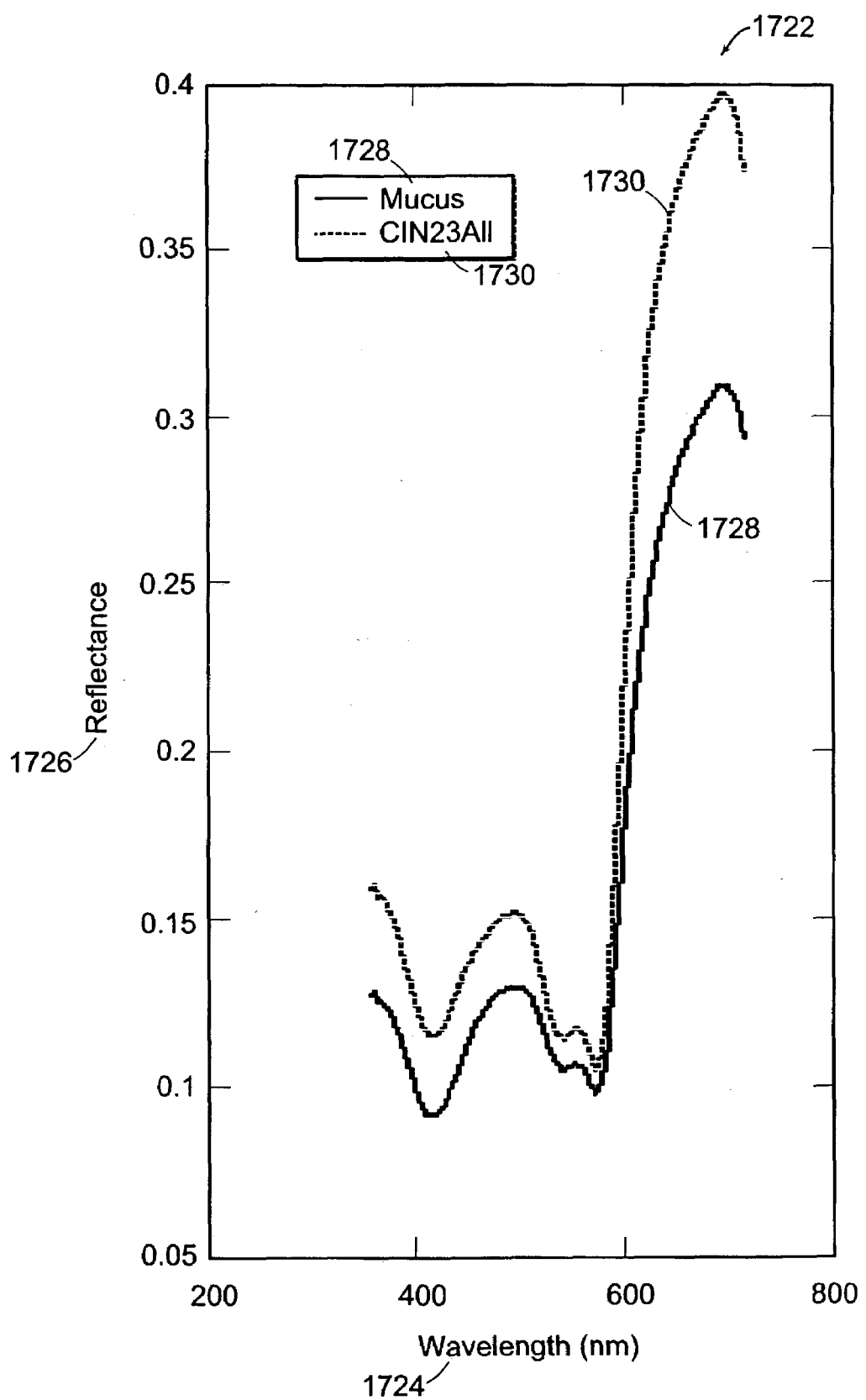
FIG. 90 shows a graph depicting as a function of wavelength mean broadband reflectance values for known mucus regions and known CIN 2/3 tissue regions, used in a discrimination analysis to determine a fluids/mucus ($[MU]_{spec}$) spectral mask according to an illustrative embodiment of the invention.
Figure 91:
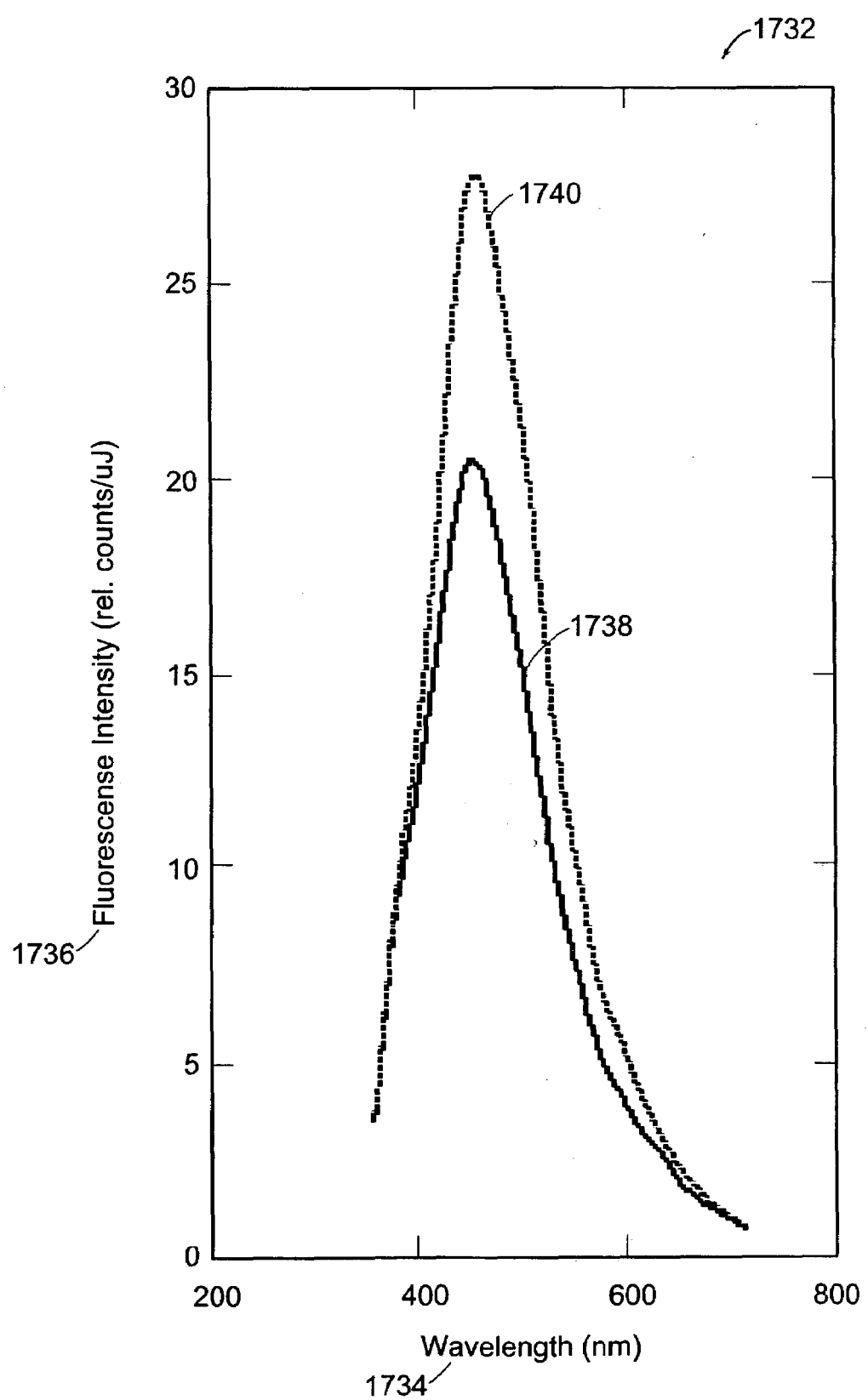
FIG. 91 shows a graph depicting as a function of wavelength mean fluorescence intensity values for known mucus regions and known CIN 2/3 tissue regions, used in a discrimination analysis to determine a fluids/mucus ($[MU]_{spec}$) spectral mask according to an illustrative embodiment of the invention.

FIG. 90 shows a graph 1722 depicting as a function of wavelength 1724 the mean broadband reflectance values 1726 for a set of known mucus regions 1728 and a set of known CIN 2/3 tissue regions 1730. FIG. 91 shows a graph 1732 depicting as a function of wavelength 1734 the mean fluorescence intensity values 1736 for the set of known mucus regions 1738 and the set of known CIN 2/3 tissue regions 1740. The difference between curves 1728 and 1730 in FIG. 90 is pronounced. Thus, in one embodiment, a term is included in the [MU]$_{spec}$ metric based on the best ratio of wavelength found to maximize values of D in the discrimination equation, Equation 91 above. In one embodiment, this ratio is BB(456 nm)/BB(542 nm).

A scatter plot depicting discrimination between mucus regions and CIN 2/3 tissue regions for a set of known reference data may be obtained by comparing the ratio of arbitrated broadband intensity, BB(456 nm)/BB(542 nm) to a threshold constant. Then, a graph of true positive ratio (TPR) 1752 versus false positive ratio (FPR) 1754 in the discrimination between mucus regions and CIN 2/3 tissue regions are obtained using a threshold constant. For example, a TPR of 30.4% and an FPR of 0.8% is obtained using a threshold constant of 1.06. The ratio of false positives may be reduced by adjusting the threshold.

In one embodiment, the discrimination analysis illustrated in FIGS. 88, 89, 90, and 91 lead to the overall $[MU]_{spec}$ mask metric as follows:

BB(456 nm)/BB(542 nm)<1.06 OR

BB(594 nm)/BB(610 nm)>0.74.

The metric above combines the sites identified by the pooled fluids mask, as indicated by the bottom line of the metric above, with the sites identified by the mucus mask, as indicated by the top line of the metric above.

FIG. 92A depicts a reference image 1758 of cervical tissue from a patient scan in which spectral data is used in arbitration and $[MU]_{spec}$ spectral masking. FIG. 92B is an obgram 1770 of the interrogation points (regions) of the tissue sample depicted in FIG. 92A and shows, in yellow (1768), the points that are "masked" by application of the $[MU]_{spec}$ metric above. White points (1766) in FIG. 92B indicate regions that are filtered out by the arbitration and initial low-signal mask of step 128, while pink points (1770) indicate regions remaining after application of both the arbitration/low-signal mask of step 128 as well as the $[MU]_{spec}$ spectral mask.

Image Masking

The invention also comprises an image masking feature. Image masks identify data from one or more images obtained during patient examination that are potentially non-representative of regions of interest of the tissue sample. Potentially non-representative data includes data that are affected by the presence of an obstruction, such as blood, mucus, a speculum, pooled fluid, or foam, for example. In one embodiment, a reference image of an in-situ cervical tissue sample is obtained just prior to a spectral scan, and image masks are determined from the reference image to reveal where there may be an obstruction or other area that is not of diagnostic interest. Areas that are not of diagnostic interest include regions affected by glare, regions of the os, vaginal wall tissue, or regions that are otherwise outside the area of interest of the tissue sample. These areas may then be "masked" from the analysis of spectral data obtained from tissue regions that coincide with the obstruction, for example. The image masks are combined with each other and/or with the spectral masks, as shown in block 1422 of FIG. 73 and as shown in FIG. 74. The resultant masks include "hard" masks and "soft" masks, described in more detail herein. Hard masks result in a characterization (or diagnosis) of "Indeterminate" at affected regions, while soft masking provides a means of weighting spectral data according to the likelihood that the data is representative of clear, unobstructed tissue in a region of interest.

In one embodiment, image masks are combined and applied as indicated in the block diagram 1438 of FIG. 74, in order to account for the identification of image-masked interrogation points in the tissue-class/state-of-health classification step 1432. Steps 1448, 1450, 1452, 1454, 1456, 1458, 1460, 1462, and 1464 in FIG. 74 depict the determination of image masks from the image data obtained around the time of the patient spectral scan. These image masks are discussed in more detail below.

Figure 93:
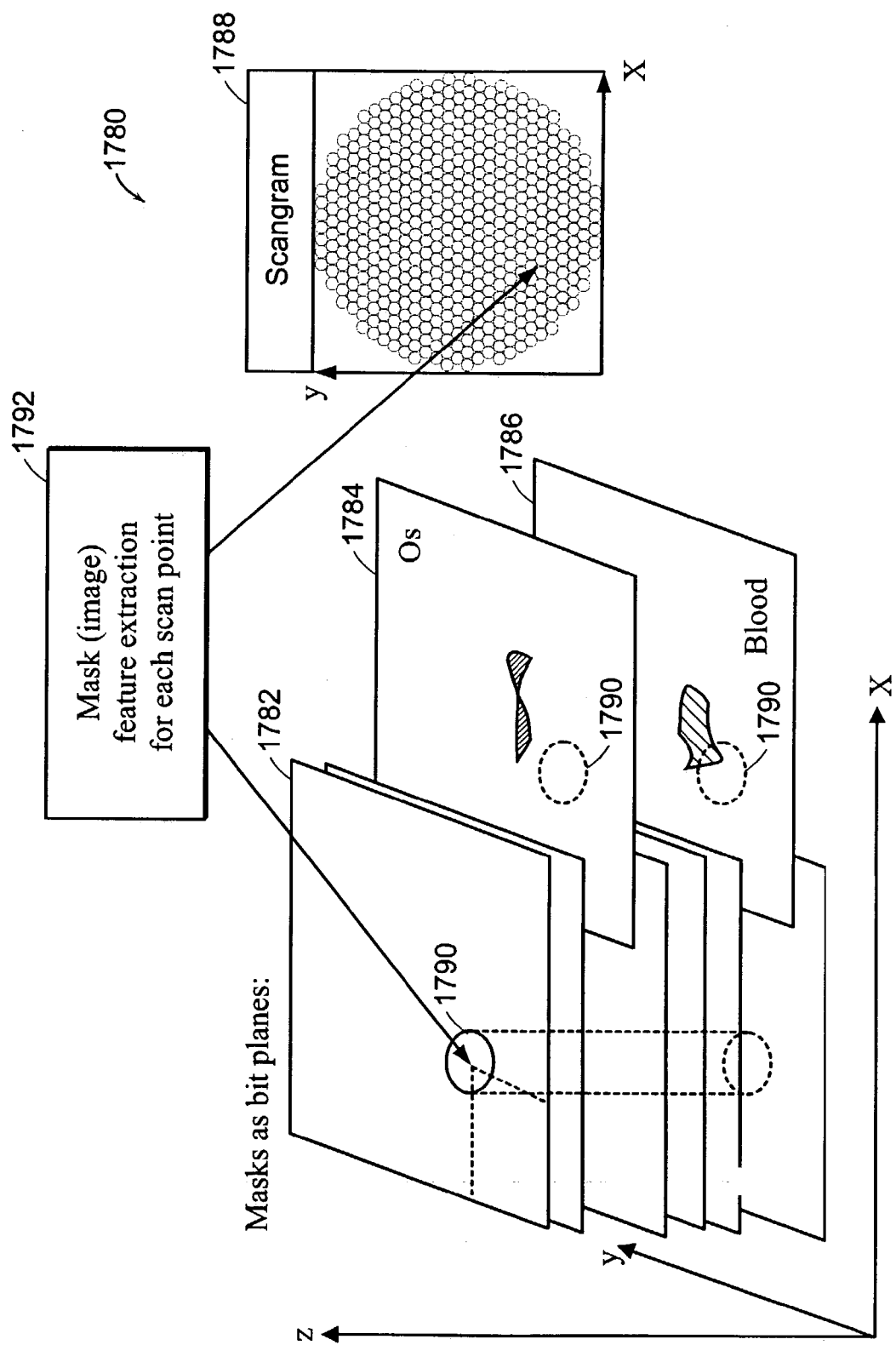
FIG. 93 depicts image masks determined from an image of a tissue sample and shows how the image masks are combined with respect to each spectral interrogation point (region) of the tissue sample, according to an illustrative embodiment of the invention.

FIG. 93 depicts image masks 1782, 1784, 1786 determined from a reference image of a tissue sample and conceptually shows how the image masks are combined with respect to each interrogation point (region) 1790 of the tissue sample, according to one embodiment. Generally, for a given interrogation point 1790 in the scan pattern 1788, the system determines whether any of the features detected by the image masks, such as the os image mask 1784 and the blood image mask 1786, intersects that interrogation point (region) 1790. For certain image masks, a percent coverage is determined for regions they intersect. For some image masks, if any of the mask intersects a region, the region is flagged as "masked".

In one embodiment, a backend process determines the coverage of one or more masks for each interrogation point of the scanning pattern. Given a known correspondence between image pixels and interrogation points, a given point is assigned a percentage coverage value for a feature determined by a given image mask, such as blood detected by the $Blood_{vid}$ image mask 1458 in FIG. 74. The percentage coverage value corresponds to the number of pixels for the given interrogation point coinciding with the selected image mask feature, divided by the total number of pixels for that interrogation point. For example, if the blood mask for a given interrogation point coincides with 12 out of 283 pixels that cover the point, then the percentage coverage for lo that interrogation point is 12/283, or 4.2%.

Steps 1468, 1470, 1472, and 1474 in FIG. 74 demonstrate how the image masks are combined in one embodiment, and steps 1466, 1476, 1424, 1478, 1480, 1424, 1426, 1428, and 1430 in FIG. 74 demonstrate how the combined masks are applied with respect to the tissue-class/state-of-health classifications at the spectral interrogation points, in one embodiment. These steps are discussed in more detail herein.

The image masks in FIG. 74 are determined using image processing methods. These methods include color representation, spatial filtering, image thresholding, morphological processing, histogram processing, and component labeling methods, for example.

In one embodiment, images are obtained in 24-bit RGB format. There are a number of ways to quantify image intensity and other image characteristics at each pixel. Most of the image masks in FIG. 74 use values of luminance (grayscale intensity) at each pixel. In one embodiment, luminance, Y, at a given pixel is defined as follows:

$$Y = 0.299R + 0.587G + 0.114B \qquad (92)$$

where Y is expressed in terms of red (R), green (G), and blue (B) intensities; and where R, G, and B range from 0 to 255 for a 24-bit RGB image. Some of the image masks in FIG. 74 use one or more of the following quantities:

$$\text{redness} = \frac{R-G}{R+G} + \frac{R-B}{R+B} \qquad (93)$$

$$\text{greenness} = \frac{G-R}{G+R} + \frac{G-B}{G+B} \qquad (94)$$

$$\text{blueness} = \frac{B-R}{B+R} + \frac{B-G}{B+G} \qquad (95)$$

where R, G, and B are as defined above.

Determination of the image masks in FIG. 74 includes the use of one-dimensional (1-D) and two-dimensional (2-D) filters. The types of filters used includes low-pass, smoothing filters and gradient, edge detection filters. The 1-D filters generally range in size from 3 to 21 pixels and the 2-D filters generally range from 3×3 to 15×35 pixels, although other filter sizes may be used. In one embodiment, box car filters are the preferred type of low-pass (smoothing) filters. Box car filters replace the value at the center of the filter support with an equally-weighted average of all pixels within the filter support. In one embodiment, the preferred types of gradient filters are Sobel and Laplacian of Gaussian filters.

In one embodiment, the image masks in FIG. 74 are determined using image thresholding, a subclass of image segmentation in which the image is divided into two segments. The criterion for assigning a pixel to one of the two segments is whether its value is less than, larger than, or equal to a prescribed threshold value. A binary image may be obtained by marking pixels having values less than the threshold with zeros and the remaining pixels with ones. Some image masks are determined using multiple thresholding and/or dynamic thresholding, where the threshold for each pixel or group of pixels is computed dynamically from image statistics, for example.

In one embodiment, the determination of the image masks in FIG. 74 includes binary morphological processing. Binary morphological processing is performed on a binarized (thresholded) image to smooth object boundaries, change the size of objects, fill holes within objects, remove small objects, and/or separate nearby objects. Morphological operators used herein include dilation, erosion, opening, and closing. An operator may be defined by (1) a binary mask or structuring element, (2) the mask origin, and (3) a mathematical operation that defines the value of the origin of the mask. In one embodiment, a 3×3 square structuring element is used, and is generally preferred unless otherwise specified.

In one embodiment, dilation increases the size of a binary object by half the size of the operator mask/structuring element. Erosion is the inverse of dilation and decreases the size of a binary object. For example, an erosion of a binary object is equivalent to the dilation of the background (non-objects). Opening is an erosion followed by a dilation, and closing is a dilation followed by an erosion. As used herein, dil(Img, n) denotes performing n dilation steps on image Img with a 3×3 square structuring element, and erod(Img, n) denotes performing n erosion steps on image Img with a 3×3 square structuring element.

In one embodiment, the determination of the image masks in FIG. 74 includes the use of histograms. Here, a histogram relates intervals of pixel luminance values (or other quantification) to the number of pixels that fall within those intervals. In one embodiment, histogram processing includes smoothing a histogram using a 1-D low-pass filter, detecting one or more peaks and/or valleys (maxima and minima), and/or computing thresholds based on the peaks and/or valleys.

In one embodiment, the determination of the image masks in FIG. 74 includes component labeling. Component labeling is used to join neighboring pixels into connected regions that comprise the components (objects) in an image. Extracting and labeling of various disjoint and connected components (objects) in an image allows separate analysis for each object.

In component labeling of a binary image using 8-connectivity, a connected components labeling operator scans the image by moving along the row until coming to a pixel p with a value V=1, then the operator examines the four neighbors of p that have already been encountered in the scan. For example, the four neighbors of p are (1) the pixel to the left of p, (2) the pixel directly above p, and (3,4) the two pixels in the row above pixel p that are diagonal to pixel p. Based on this information, p is labeled as follows:

If all four neighbors have V=0, assign a new label to p, ELSE
If only one neighbor has V=0, assign its label to p, ELSE
If one or more neighbors have a value of 1, assign one of the labels to p and note the equivalences.

After completing the scan, the equivalent label pairs are sorted into equivalence classes and a unique label is assigned to each class. A second scan is made through the image, and each label is replaced by the label assigned to its equivalence class. Component labeling of a binary image with 4-connectivity may be performed similarly.

In one embodiment, an image mask is determined using data from a representative image of a tissue sample obtained near to the time of a spectral scan of the tissue (just before, during, and/or just after the spectral scan). In one embodiment, the representative image is obtained within about 30 seconds of the beginning or ending of the spectral scan; in another embodiment, the representative image is obtained within about 1 minute of the beginning or ending of the spectral scan; and in another embodiment, the representative image is obtained within about 2 minutes of the beginning or ending of the spectral scan. Other ranges of time in relation to the spectral scan are possible. In one embodiment, there is only one reference image from which all the image masks are determined.

$Glare_{vid}$

Figure 94A:
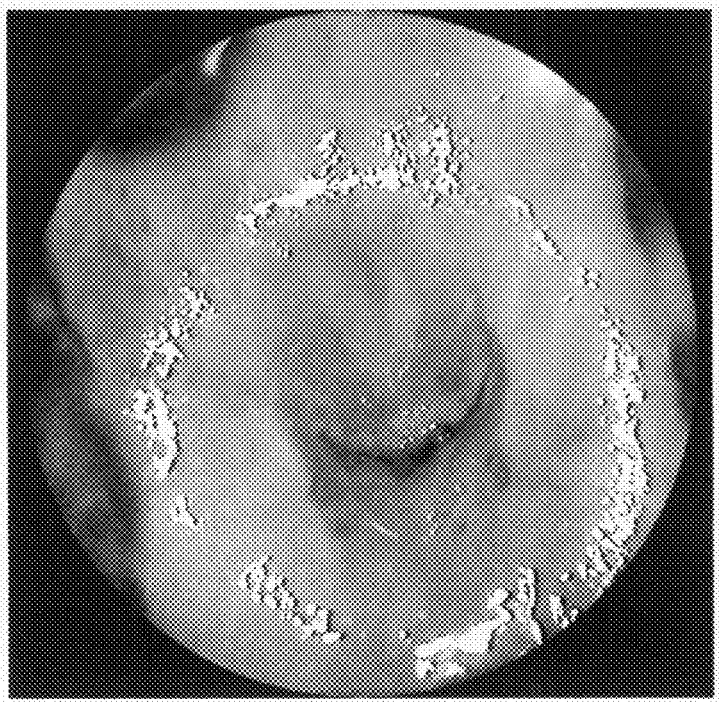
FIG. 94A depicts an exemplary image of cervical tissue obtained during a patient examination and used in determining a corresponding glare image mask, $Glare_{vid}$, according to an illustrative embodiment of the invention.
Figure 94B:
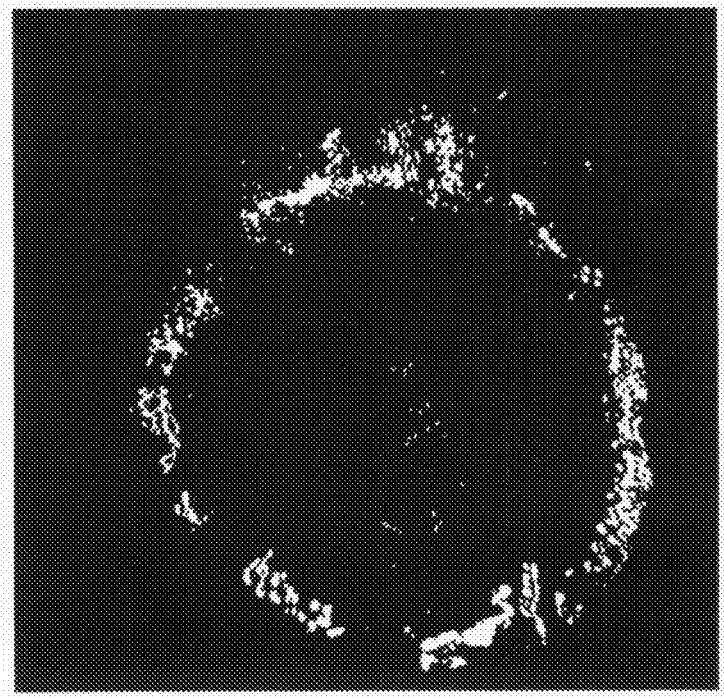
FIG. 94B represents a glare image mask, $Glare_{vid}$, corresponding to the exemplary image in FIG. 94A, according to an illustrative embodiment of the invention.

Step 1462 in FIG. 74 depicts the determination of a glare mask, $Glare_{vid}$, for an image of a tissue sample. $Glare_{vid}$ indicates regions of glare in a tissue image. $Glare_{vid}$ is also used in the computation of other image masks. FIG. 94A depicts an exemplary image 1794 of cervical tissue used to determine a corresponding glare image mask, $Glare_{vid}$. FIG. 94B represents a binary glare image mask, $Glare_{vid}$, 1796 corresponding to the tissue image 1794 in FIG. 94A.

The white specks of glare in the tissue image 1794 in FIG. 94A are identified by the image mask 1796. The image mask is determined using an adaptive thresholding image processing procedure. Different thresholds are applied in different areas of the image, since the amount of illumination may vary over the image, and a threshold luminance indicative of glare in one area of the image may not indicate glare in another, lighter area of the image. In one embodiment, for example, an image of a tissue sample is divided into a 4 by 4 grid of equally-sized, non-overlapping blocks. A suitable glare threshold is computed for each block, and the subimage within that block is binarized with the computed threshold to yield a portion of the output glare segmentation mask, $Glare_{vid}$. Each block computation is independent, and blocks are serially processed until the complete binary glare mask, $Glare_{vid}$, is completely calculated. For each block, multiple thresholds based on luminance value and/or histogram shape are computed and are used to detect and process bimodal distributions.

Figure 95:
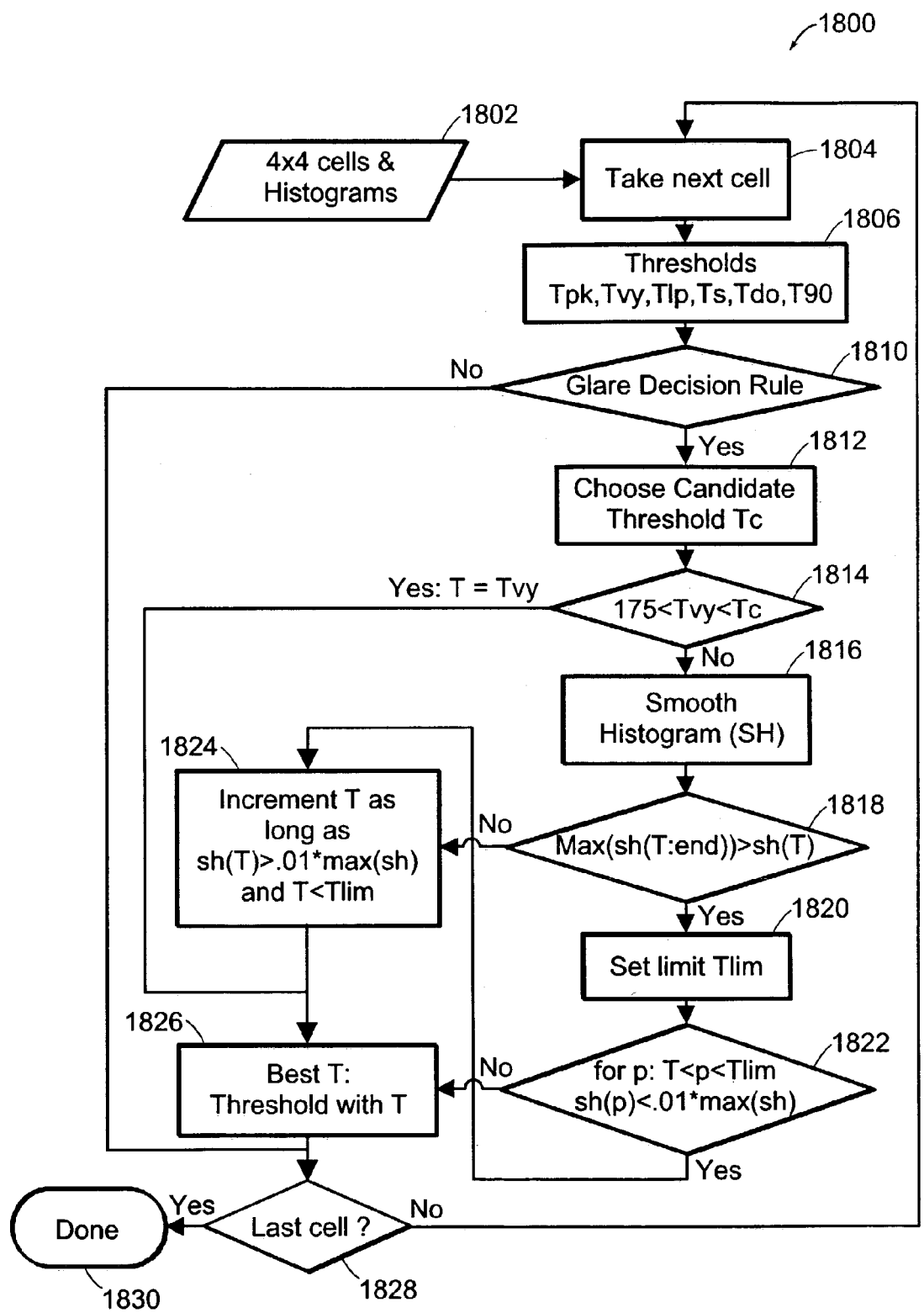
FIG. 95 is a block diagram depicting steps in a method of determining a glare image mask, $Glare_{vid}$, for an image of cervical tissue, according to an illustrative embodiment of the invention.

FIG. 95 is a block diagram depicting steps in a method of determining a glare image mask, $Glare_{vid}$, for an image of cervical tissue. Step 1802 in FIG. 95 indicates dividing an image into a 4×4 grid of cells (blocks) 1804 and computing a histogram for each cell that is then used to determine thresholds 1806 applicable to that block. Each histogram correlates intervals of luminance values, Y, (Y ranging from 0 to 255) to the number of pixels in the cell (subimage) having luminance values within those intervals.

Figure 96:
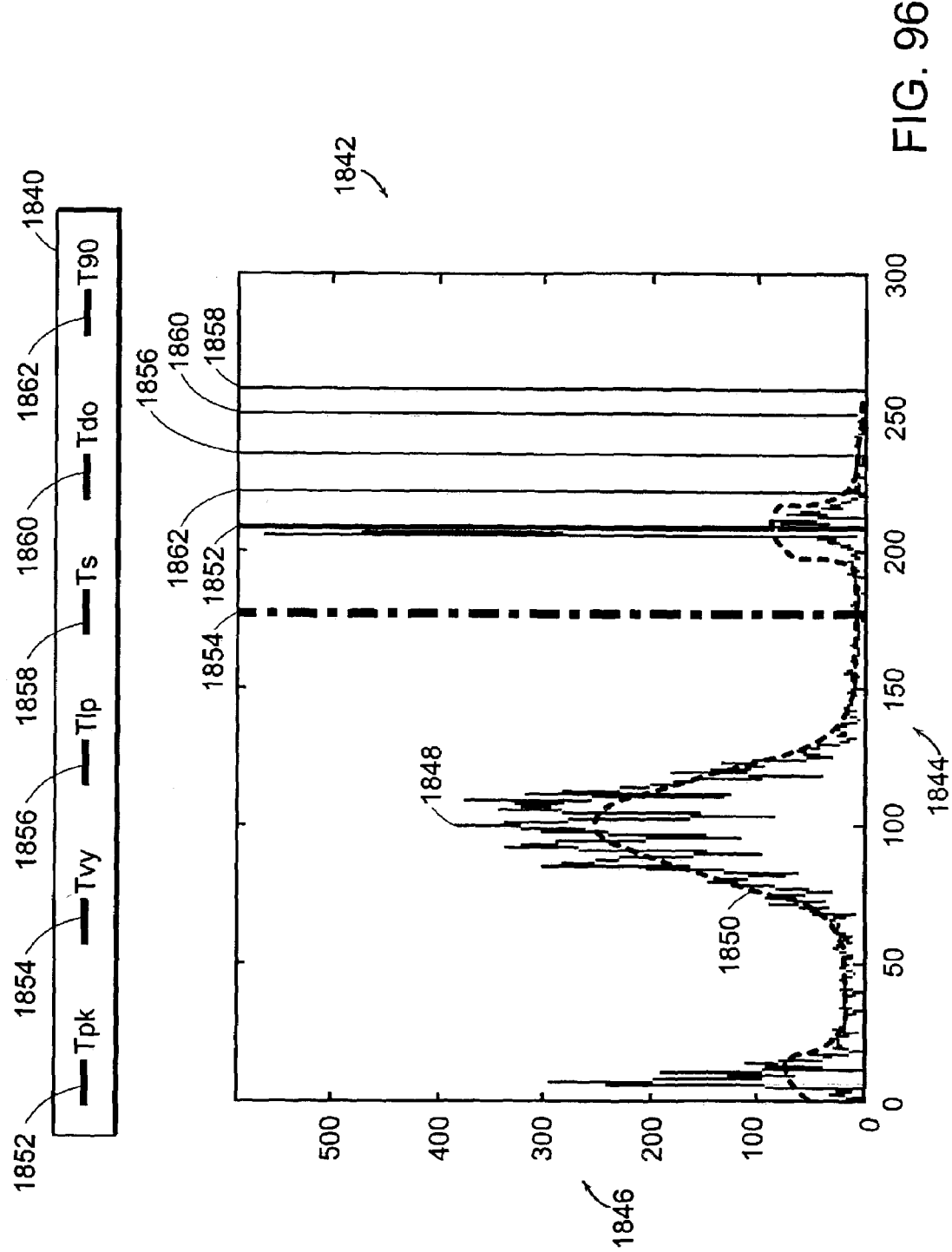
FIG. 96 shows a detail of a histogram used in a method of determining a glare image mask, $Glare_{vid}$, for an image of cervical tissue, according to an illustrative embodiment of the invention.

Step 1806 in FIG. 95 indicates determining thresholds applicable to a given cell of the image. For example, FIG. 96 shows a histogram 1842 for one cell of an exemplary image. Curve 1848 indicates a raw histogram plot for the cell (subimage), and curve 1850 indicates the curve after 1-D filtering using a 21-point box car filter. Quantities 1840 related to thresholding that are calculated from each histogram 1842 include $T_{pk}$ (peak), $T_{vy}$ (valley), $T_{lp}$, $T_s$, $T_{do}$, and $T_{90}$, all of which are described below. The exemplary histogram 1842 in FIG. 96 shows bars indicating values of $T_{pk}$ (1852), $T_{vy}$ (1854), $T_{lp}$ (1856), $T_s$ (1858), $T_{do}$ (1860), and T90 (1862) for the cell histogram curve. The heavy dashed line (1854) indicates the final threshold chosen for the cell according to the method of FIG. 95.

The following describes the steps of the method 1800 shown in FIG. 95, according to one embodiment.

The method 1800 in FIG. 95 comprises calculating intended thresholds in step 1806. Four thresholds are computed to decide whether the block (cell) contains glare:

1. Ts=mean+3*std where mean is the average intensity of the block and std its standard deviation.
2. Tlp=last peak of smoothed histogram. Smoothing is performed using a width 5 maximum order statistic filter.
3. Tdo=Lmax+2 (Ldo−Lmax) where Lmax is the index (gray level) at which the 21-point boxcar filtered histogram, sHist, reaches it maximum value sHistMax, and Ldo is the first point after Lmax at which the filtered histogram value falls below 0.1*sHistMax.
4. T90 is defined so that 90% of the graylevels greater than 210 are greater than T90.

Next, the method 1800 in FIG. 95 includes a block (cell) glare detector in step 1810. The block (cell) glare detector assesses whether glare is present in the block and selects the next block if no glare is detected. The block is assumed to have no glare if the following condition is met:

((Tlp<Ts) AND (Ts<T90)) OR
((Tlp<Tdo) AND (Tdo<T90)) OR
((Tlp<Tdo) AND (Tlp<Ts) AND (Tlp<T90)) OR
((Tlp<0.8*T90) AND (no valid glare mode as described in the bimodal histogram detection section below)).

Next, the method 1800 in FIG. 95 comprises selecting a candidate threshold, Tc, in step 1812. A candidate threshold Tc is chosen based upon the values of the intermediate thresholds Ts, Tlp, Tdo and T90 according to the following rules:

1. if (Tlp<T90):
   a. if (Tdo<Tlp/2):
      i. if (Ts<Tlp): Tc=(Ts+Tlp)/2
      ii. else Tc=Tlp
   b. else Tc=min (Tdo, Tlp)
2. (Tlp>=T90) High intensity glare
   a. if(Ts<=T90):
      i. if ((Ts<=100) AND (Tdo<=100)): Tc=max (Ts, Tdo)
      ii. else if ((Ts<=100) and (Tdo>100): Tc=min (Tdo, Tlp)
      iii. else Tc=min (Ts, Tdo)
   b. else
      i. if(Tdo<100): Tc=T90
      ii. else Tc=min (Tdo, T90).

Next, the method 1800 in FIG. 95 includes detecting a bimodal histogram in step 1806. Step 1806 detects bimodal histograms that are likely to segment glare from non-glare and uses the 21 point boxcar filtered histogram sHist to determine Tvy after computing Tpk and Tcross, as described herein. To compute Tpk, sHist is searched backwards from the end until point Tpk where the value is greater than the mean and maximum of its 5 closest right and left neigbors and where Tpk is greater or equal to 10. Tcross is the point after Tpk (in backwards search) where the histogram value crosses over the value it has at Tpk. If the histogram is unimodal, Tpk is equal to Lmax, the graylevel where sHist attains its max value, and Tcross is 0. Tvy is the minimum point on sHist between Tpk and Tcross if the following glare condition, called valid glare mode, is met:

(Tpk>175) AND (Tpk>Lmax) AND
(sHist[tPk]<0.6*sHist[Lmax]) AND
((Tpk−Tcross>20) OR (Tpk>T90)) AND
((Tpk>(mean+(1.5*std))) OR (Tpk>T90)).

Next, the method 1800 in FIG. 95 includes selecting a final threshold in steps 1814, 1816, 1818, 1820, 1822, 1824, and 1826. The final threshold selected depends on whether the histogram is bimodal or unimodal. For a bimodal histogram with a valid glare mode, the final threshold T is Tvy if 175<Tvy<Tc. In all other cases (i.e. for unimodal histograms with a candidate threshold Tc and for bimodal histograms with a valley threshold Tvy outside the range 175 to Tc), Tc is chosen as the final threshold unless it can be incremented until sHist[Tc]<0.01*Shist[Lmax] or Tc>Tlim under the following two conditions. First, if a value L exists in the range [Tc,255] where sHist[L] >sHist[Tc], define Lmin to be the gray value where sHist reaches its minimum in the range [Tc,L]. Then, Tc should not be incremented beyond Lmin, and the limit threshold TLim=Lmin. If L<150, then Tlim=210. Secondly, if L does not exist, Tlim=210.

$$[ROI]_{vid}$$

Figure 97A:
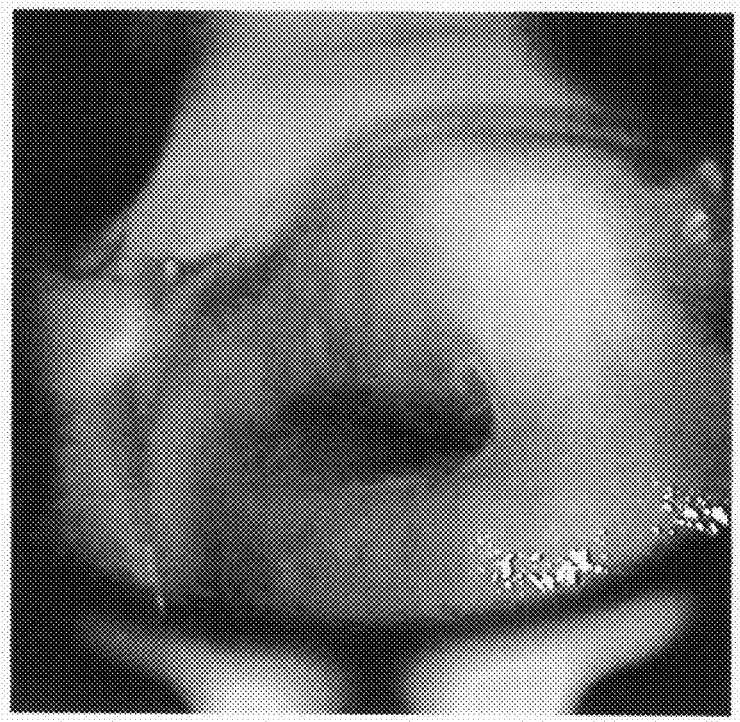
FIG. 97A depicts an exemplary image of cervical tissue obtained during a patient examination and used in determining a corresponding region-of-interest image mask, $[ROI]_{vid}$, according to an illustrative embodiment of the invention.
Figure 97B:
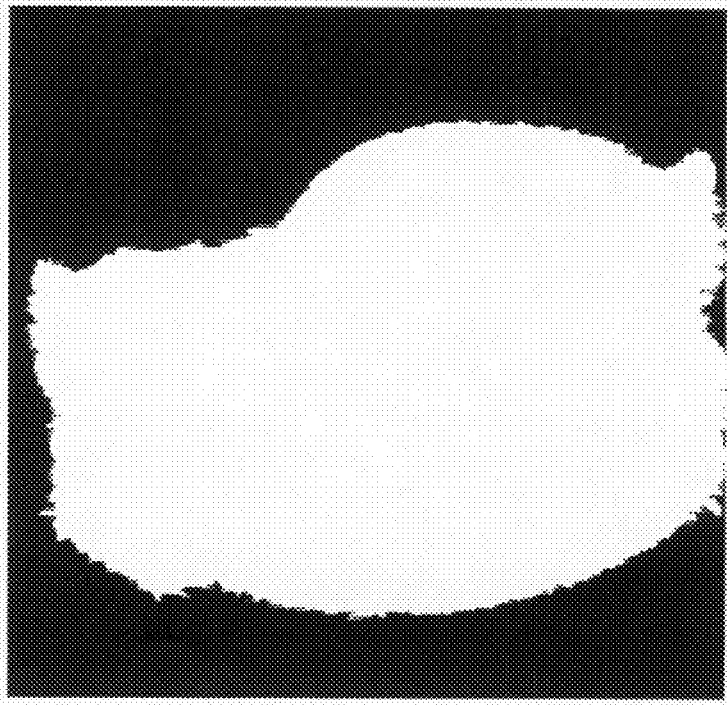
FIG. 97B represents a region-of-interest image mask, $[ROI]_{vid}$, corresponding to the exemplary image in FIG. 120A, according to an illustrative embodiment of the invention.

Step 1448 in FIG. 74 depicts the determination of a general region-of-interest mask, $[ROI]_{vid}$, for an image of a tissue sample. The general region-of-interest mask determines where there is tissue in an image, and removes the non-tissue background. $[ROI]_{vid}$ is also used in the computation of other image masks. FIG. 97A depicts an exemplary image 1894 of cervical tissue used to determine a corresponding region-of-interest mask, $[ROI]_{vid}$, 1896 corresponding to the tissue image 1894 in FIG. 97A. The mask 1896 excludes the non-tissue pixels in image 1894.

The $[ROI]_{vid}$ mask detects the general areas of the image indicative of tissue, and is determined by thresholding a pre-processed red channel image of the tissue and by performing additional processing steps to remove unwanted minor regions from the thresholded image, explained in more detail below.

Figure 98:
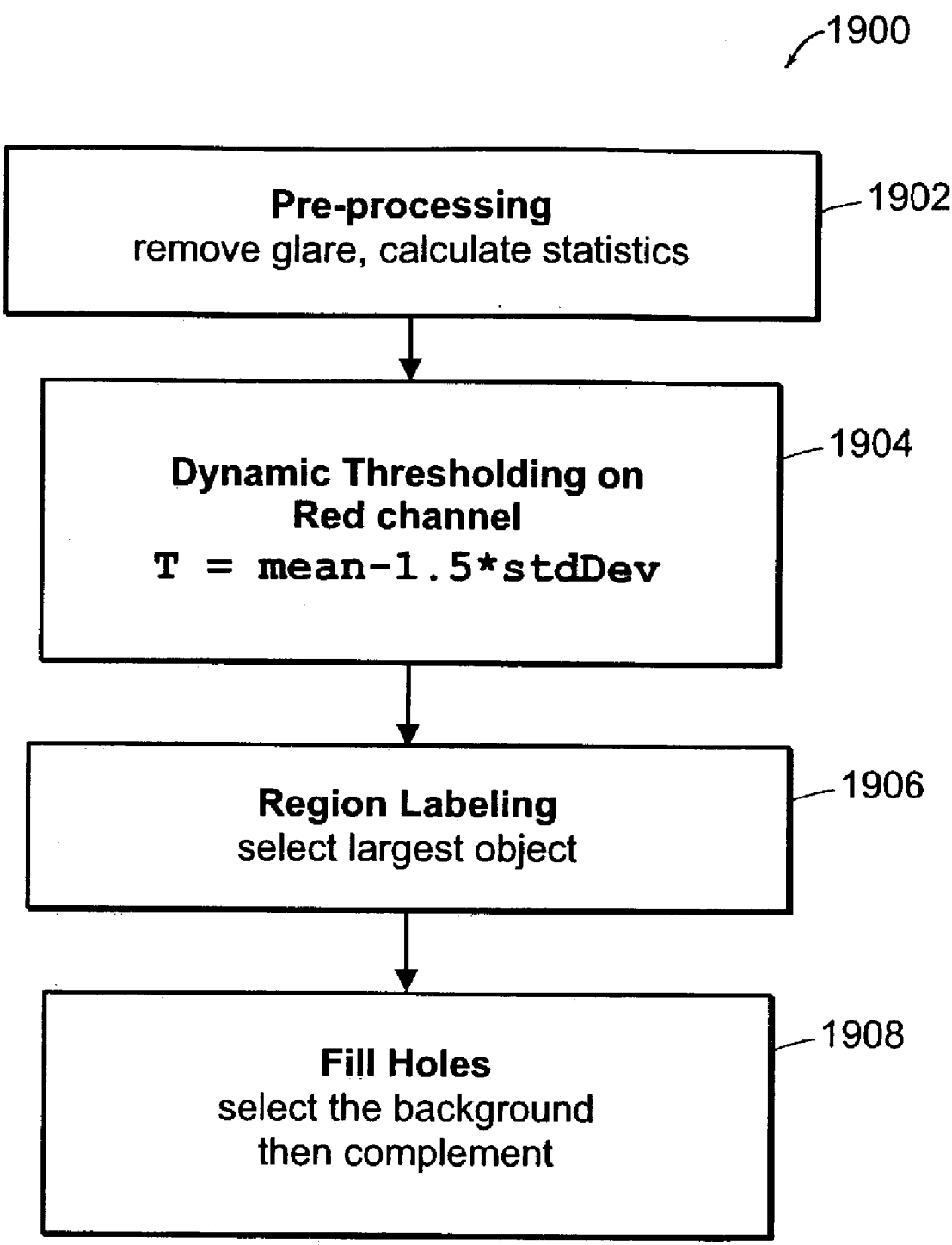
FIG. 98 is a block diagram depicting steps in a method of determining a region-of-interest image mask, $[ROI]_{vid}$, for an image of cervical tissue, according to an illustrative embodiment of the invention.

FIG. 98 is a block diagram 1900 depicting steps in a method of determining a region-of-interest image mask, $[ROI]_{vid}$, for an image of cervical tissue. The following describes the steps of the method shown in FIG. 98 (1900), according to one embodiment.

The method 1900 includes pre-processing in step 1902. First, smooth the red channel image by twice applying a 5×5 box car filter. The filtered image is sRed. Next, compute a best dynamic threshold for sRed as follows. Create a foreground binary image of sRed using a threshold of 15. Create a glare mask binary image, glareMsk, using glare mask process Glare$_{vid}$ above. Create a valid cervix pixel image, validPix, by binary AND-ing foreground and glareMsk inverse. Binary erode validPix, evalidPix=erod (validPix, 3). In evalidPix, find the top row containing the first valid pixel, topR; find the bottom row containing the last valid pixel, botR; the middle row is expressed as midR=(topR+botR)/2; then, set all evalidPix pixels above midR to 0. Compute mean, mean, and standard deviation, stdDev, of sRed on the region defined by evalidPix. The best dynamic threshold is then T=max(10, min (mean−1.5*stdDev, 80)). Threshold sRed using T in step 1904.

Next, the method 1900 in FIG. 98 includes thresholding sRed using T in step 1904. Then, step 1906 is performing a binary component labeling using 4-way connectivity. Finally, step 1908 is computing the area of each object obtained in the previous step and selecting the largest object. Flood fill the background of the object selected in the previous step to fill holes. The result is the $[ROI]_{vid}$ mask.

$$[ST]_{vid}$$

Figure 99A:
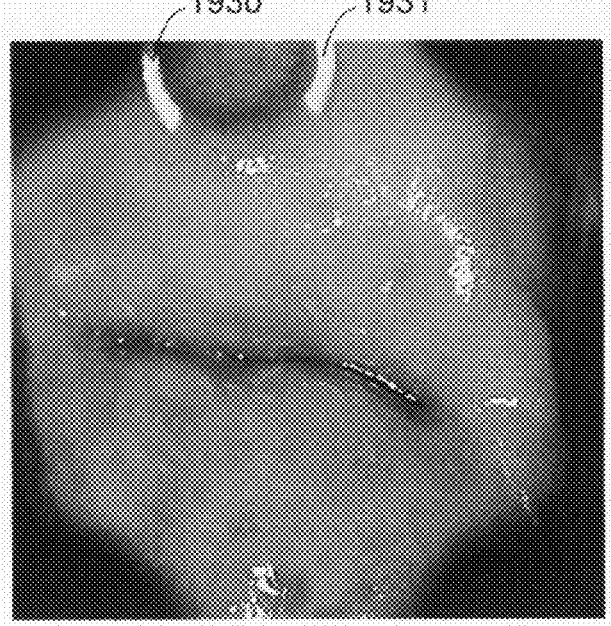
FIG. 99A depicts an exemplary image of cervical tissue obtained during a patient examination and used in determining a corresponding smoke tube image mask, $[ST]_{vid}$, according to an illustrative embodiment of the invention.
Figure 99B:
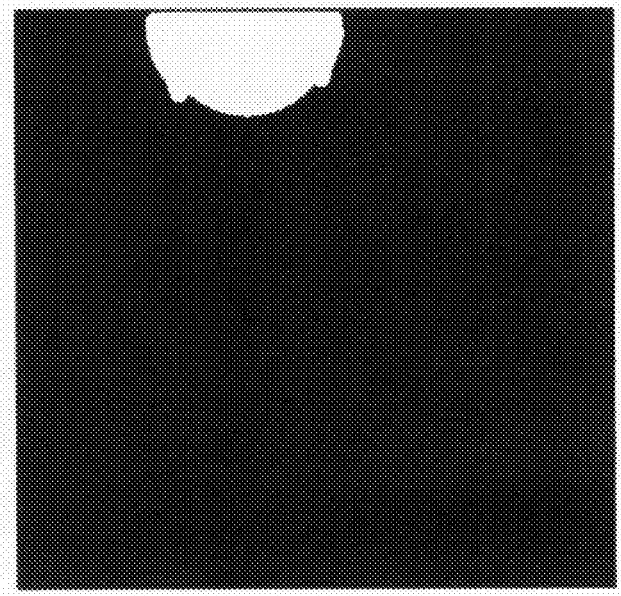

Step 1450 in FIG. 74 depicts the determination of a smoke tube mask, $[ST]_{vid}$, for an image of a tissue sample. The smoke tube mask determines whether the smoke tube portion of the speculum used in the procedure is showing in the image of the tissue sample. The smoke tube mask also identifies a portion of tissue lying over the smoke tube (which may also be referred to as "smoke tube" tissue) whose optical properties are thereby affected, possibly leading to erroneous tissue-class/state-of-health characterization. FIG. 99A depicts an exemplary image 1932 of cervical tissue used to determine a corresponding smoke tube mask, $[ST]_{vid}$, 1934 shown in FIG. 99B. The smoke tube mask is determined in part by isolating the two "prongs" holding the smoke tube tissue. The two prongs are visible in the image 1932 of FIG. 99A at reference numbers 1930 and 1931. In some images, the prongs are not visible. However, the smoke tube tissue in these images (without visible prongs) is generally either a blue or blue-green color with almost no red component; and the smoke tube in these images is identified (and removed from consideration) by the general region-of-interest image mask, $[ROI]_{vid}$.

Figure 100:
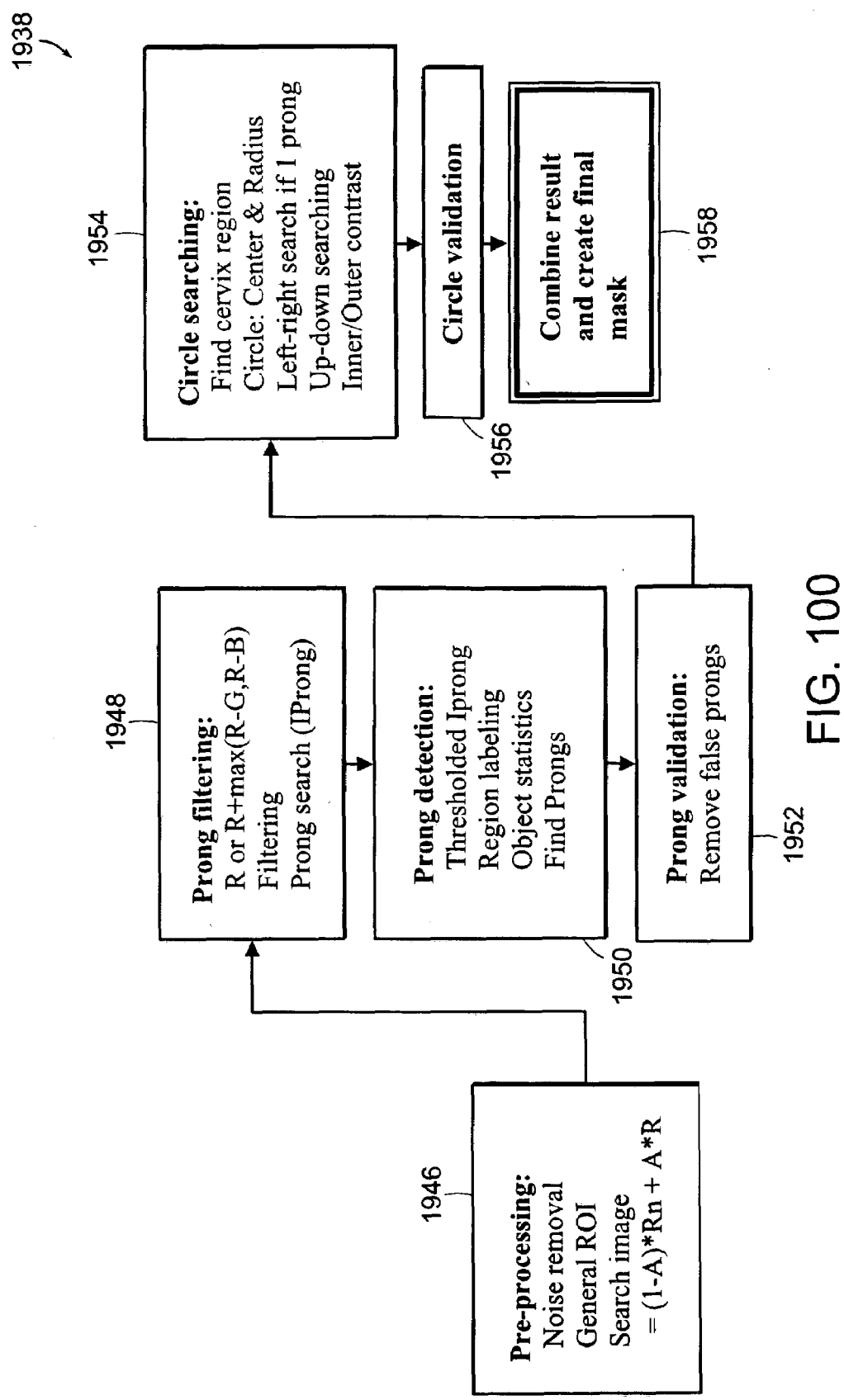

FIG. 100 is a block diagram 1938 depicting steps in a method of determining a smoke tube mask, $[ST]_{vid}$, for an image of cervical tissue. Image 1944 is an exemplary input image for which a corresponding smoke tube mask 1960 is computed. Image 1944 shows a circle 1945 used in steps 1954 and 1956 of the method in FIG. 100.

The following describes the steps of the method shown in FIG. 100, according to one embodiment.

The method 1938 in FIG. 100 comprises step 1946, pre-processing the image. Pre-processing includes processing each RGB input channel with a 3×3 median filter followed by a 3×3 boxcar filter to reduce noise. Step 1946 also includes calculating or retrieving the general ROI mask ROImsk ($[ROI]_{vid}$, described above) and the glare mask glareMsk ($Glare_{vid}$, described above), and computing the search image, srcImg, as follows. First, compute the redness image Rn. Set to zero all values in Rn that are oustide ROImsk. Autoscale the redness image to the [0,1] range. Then, compute srchImg, which will be used at the final stages of the algorithm to compute a rough correlation to find the best circle location. SrchImg is a linear combination of the redness and red images: srchImg=(1−A)*Rn+A*R. The linear weight factor A is in the range [0.2, 0.8]. Form validPix=ROImsk AND not(dil (glareMsk, 3). Compute mean, meanR, meanG, meanB of the RGB channels on the region defined by validPix. The weight A is initially computed as: A=max (0.5, min ((2*meanR)/(meanG+meanB), 1.5)). Remap the value of A into the range [0.2, 0.8], A=0.2+(0.6*(A−0.5)). SrchImg is computed using the A factor determined above.

Next, the method 1938 in FIG. 100 comprises a prong detector filter in step 1948. The prong detector is applied to the red image, R and to an enhanced red image, RE to produce 2 different prong images that will be arbitrated later. First, calculate the red-enhanced image, RE=R+max(R−G, R−B). Next, set up the prong detector filter. The filter is designed to be sensitive to smoke-tube prongs and to reject glare, edges and other features. The filter is a rectangular 35 by 15 separable filter. The horizontal filter H is defined by H=[−1.5 −1.5 −1.5 −1.5 −1.5 0 0 0 0 0 1 1 1 1 1 1 1 1 1 1 1 1 1 1 1 0 0 0 0 0 −1.5 −1.5 −1.5 −1.5 −1.5]. The vertical filter V is a box car filter of length 15. Next, apply the prong filter to R and RE images yielding Rprong and Reprong. Clip filtered images to 0 and autoscale to the range [0, 1]. Set the bottom half of each filtered image as well as the first 20 and the last 20 columns to 0 (there are no prongs in these sections of images). Then, find a maximum value for each of the first 125 rows of the 2 filtered images. Find the constant Rfact and REfact for each filtered image. These constants are defined as the mean of the maxima of the first 125 rows divided by mean of the first 125 rows. If (Rfact>Refact) use Rprong as the prong search image, iProng, otherwise use REprong.

Next, the method 1938 in FIG. 100 comprises thresholding, component analysis, and prong selection in step 1950. Step 1950 is used to select prongs. First, threshold iProng image with a threshold of 0.2. Perform binary component labelling to obtain all regions (objects). Compute regions (objects) statistics, including area, centroid, and major and minor axis length. Filter prong regions (objects). Discard each region (object) that statisfies any of the following criteria:

1. Region size<300.
2. iProng maximum on object<0.4.
3. Region does not extend above row 100.
4. Minor axis length>=30.
5. Region does not overlap with ROImsk.
6. Region centroid is below row 140.
7. Centroid y-value>40 and object thinness=(major axis length/minor axis length)<=2.

Choose as the main prong the brightest remaining region (i.e where the region maximum value is greater than the maxima from all other remaining regions). Filter all other prong regions based upon the distance from the main prong by calculating the distance from each region's centroid to the centroid of the main prong, and discarding the region if the intra-centroid distance>160 or if the intra-centroid distance<110.

Next, method 1938 in FIG. 100 comprises validation of the selected prongs in step 1952. For each retained prong object in step 1950, the following computations are peformed to validate the selected prongs. Define pad, the rough distance from an object to its perimeter. Here, pad is set to 8. Form images of the dimension of the bounding box of the object plus pad pixels on each side (OBJ). Crop the original object of the prong search image IOrig, from the original unsmoothed red channel image, Rorig, and form the binarized image BWProng. Compute internal region, intReg=erod (dil (OBJ, 2), 1). Compute object perimeter region, perObj=dil ((dil (OBJ, 2) AND not (OBJ)), 2). Compute mean and standard deviation, mean and std, of the object on the interior region, intReg, and the mean, pmean, on the perimeter region perObj. Compute left/right bias by computing locations of the center points of the object top row and bottom row, drawing a line connecting those 2 points to divide the perimeter region, perObj, into 2 sections, calculating the mean value of iProng on each of the half perimeter sections, LperMean, RperMean, and using the means to compute left/right biases, LRBias using LRBias=max (LperMean/RperMean, RperMean/LperMean). Discard any objects where the following holds: (mean/pmean<1.4) OR (std>0.55) OR ((LRBias>1.45) AND (mean/pmean<1.48)). If more than 2 prong candidates are remaining, keep the one closest to the main prong. If no prong candidates are left, the smoke tube mask is empty.

Next, method 1938 in FIG. 100 comprises template searching using circles in step 1954. Step 1954 is used to qualify regions as smoke tube candidates. First, construct a binary mask, validCervix, of valid cervix pixel locations: by Computing or retrieving blood mask, bloodMsk, ($Blood_{vid}$, described below); Computing or retrieving glare mask, glareMsk, ($Glare_{vid}$, described above), then compute the bloodMsk using validCervix=ROImsk AND not(BWProng) AND not(dil (glareMsk, 3)) AND not(bloodMsk). Then, determine an x-coordinate value for the center, xCent, of the circle and radius, rad. For 2 prongs xCent is the half point between centroids of 2 prongs and rad is the half distance bewteen prongs+5. For 1 prong, choose a default rad of 85 and do a left-right search to decide wether the smoke tube is on the left or right. The x-coordinate values, xCent, for each of the 2 search circles is the x-coordinate of the prong centroid ±rad. The y-coordinate, yCent, is the y-coordinate of the prong centroid. For each circle center (xCent, yCent), find all points within rad that are in validCervix and compute the regional mean from the redness image. Then, find all points outside rad that are in validCervix and compute the regional mean from the redness image. Compute the contrast as the ratio of inner mean redness to outer mean redness and select the circle with minimum contrast. Discard the previous circle if xCent is within rad/4 from the left or right edge of the image, since it cannot be a smoke tube. Then, use the search image, srchImg, to perform an up-down search on the y-coordinate, yCent, to determine the actual smoke tube location using the x-coordinate xCent computed named above in section 2. Repeat the search with the redness image Rn if the results are unsatisfactory. A minimum and maximum value for yCent, yCentMin and yCentMax are chosen as follows:

1. yCentMin=-rad+yProngBot; where yProngBot is the mean of the bottom-most points of the prong(s), or the bottom-most point for a single prong.
2. For two prongs, yCentMax=yProngBot-(0.75*rad) i.e. the circle cannot extend beyond ¼ rad below the bottom of the prongs.
3. For one prong, yCentMax=min(yProngBot+rad/3, 150) i.e. the circle can go quite past the end of the prong, but not below the 150th row of the image.

Three more points spaced (yCentMax-yCentMin)/4 apart are computed between yCentMax and yCentMin. The search algorithm uses a total of yCent candidate points. For each yCent candidate, the inner/outer contrast for circles centered at (xCent, yCent) are computed using srchImg as follows:

1. Find all points within rad that are in validCervix and compute the regional mean from srchImg.
2. Find all points outside rad that are in validCervix and compute the regional mean from srchImg.
3. Compute the contrast as the ratio of the inner mean value of srchImg to the outer mean value of srchImg and select the circle with minimum contrast.

Check to see that at least one of the 5 contrast numbers is less than 1. If not, break out of the loop and proceed no further with this search. If at least one circle has contrast less than 1, choose the minimum and select a new set of five points centered around this one using the following steps:

1. If the top or bottom point was the minimum, choose that point, the one below/above it, and three points evenly spaced in between them.
2. If one of the three central points was the minimum, choose that point with the ones immediately below and above it, and two additional ones centered in the two spaces that divide those three.

Using the new set of five points, go back to the computation of the inner/outer contrast for circles using srchImg, discussed herein above, and proceed in this way until the distance between the five points is less than 3 pixels. When the distance between the points is less than 2 pixels, exit the loop and choose the yCent with the current minimum contrast number as the final value of yCent for the circle. The contrast for the final circle must be less than 0.92 in order for the algorithm to find a valid circle. If that is not the case, then the search-algorithm is repeated with the pure redness-image, Rn instead of srchImg, which was a mixture of R and Rn. If the Rn search produces an acceptable result with contrast less than 0.92, then this value of yCent is used and we can proceed. Otherwise, there is no suitable circle and the segmentation mask will contain prongs but no circle.

Finally, method 1938 in FIG. 100 comprises producing the final smoke tube segmentation mask in step 1958. First, set the values of all pixels above the horizontal line inside the circle which is bisected by the center to 1. This effectively casts a "shadow" straight upward from the bottom of the image, and creates the effect that the smoke tube is coming straight down from outside of the image. The shadowed circle and prong images are combined to yield the final segmentation mask. Clean up any stray non-prongs by performing a flood-fill of "on" valued regions with seeds in the first or thirtieth row of the image to select only objects that touch the first or thirtieth row of the image.

$Os_{vid}$

Figure 101A:
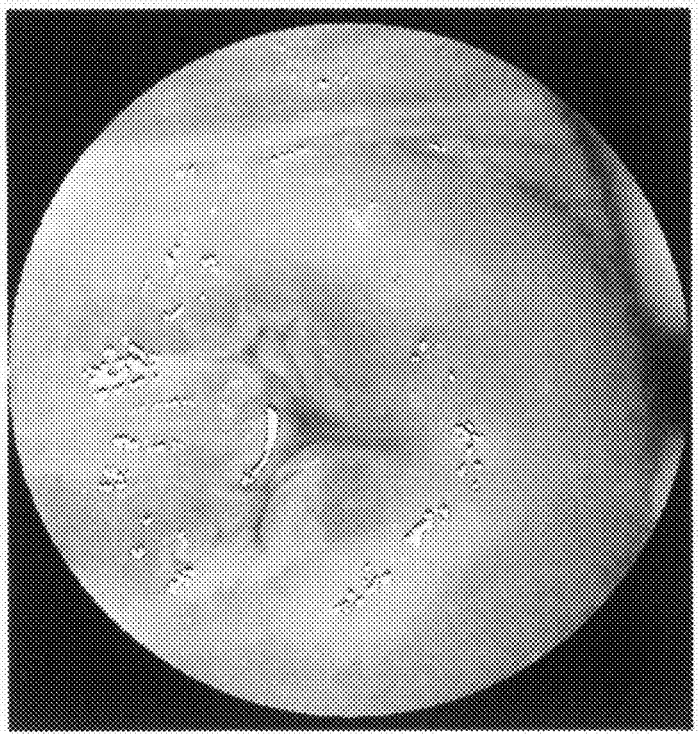
Figure 101B:
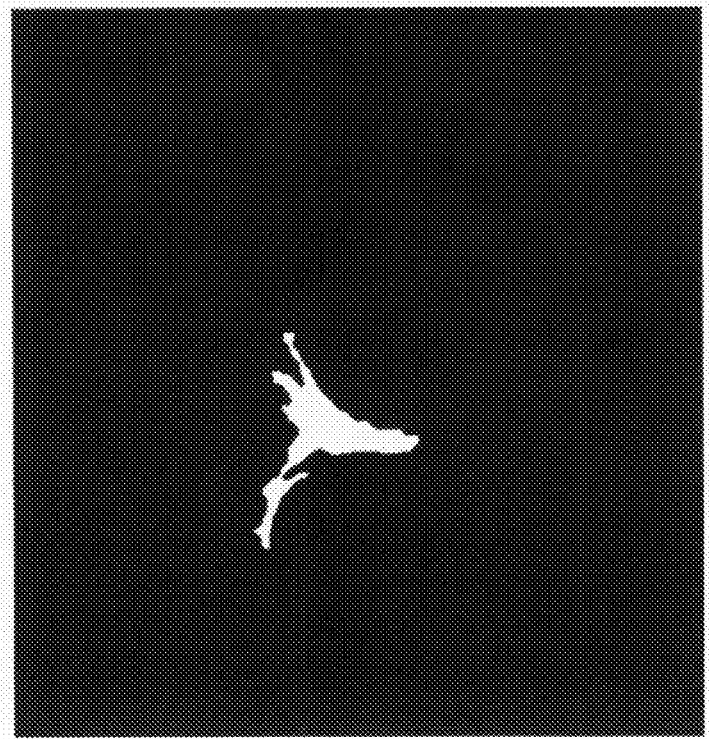

Step 1460 in FIG. 74 depicts the determination of an os image mask, $OS_{vid}$, for an image of a tissue sample. The optical properties of the os region may differ from optical properties of the surrounding tissue. In the method 1438 of FIG. 74, the os image mask is used in soft masking to penalize data from interrogation points that intersect or lie entirely within the os region. FIGS. 101A depicts an exemplary image 1964 of cervical tissue used to determine a corresponding os image mask, $OS_{vid}$, 1968, shown in FIG. 101B.

The $OS_{vid}$ image mask is determined using a combination of thresholds from different color channels and using a binary component analysis scheme. An initial mask is formulated from a logical combination of masks computed from each color channel, R, G, B, and luminance, Y (equation 94). The four individual masks are computed using a thresholding method in which the threshold is set relative to the statistics of the colorplane values on the image region-of-interest (ROI). A component analysis scheme uses the initial mask to detect an os candidate area (object), which is validated.

Figure 102:
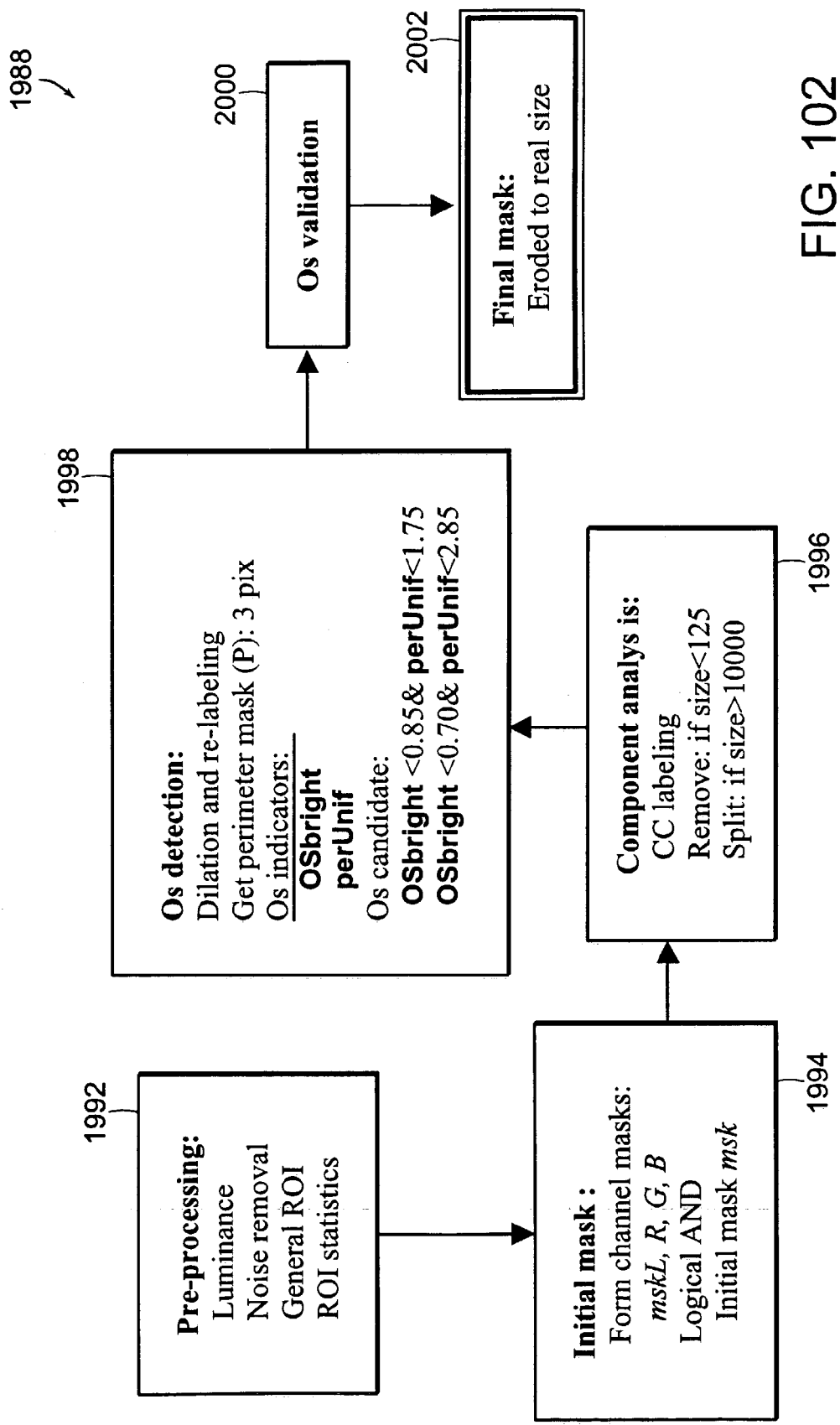

FIG. 102 is a block diagram 1988 depicting steps in a method of determining an os mask, $Os_{vid}$, for an image of cervical tissue. Image 1990 is an exemplary input image for which a corresponding os mask 2004 is computed. The following describes the steps of the method 1988 shown in FIG. 102, according to one embodiment.

The method 1988 in FIG. 102 includes image preprocessing in step 1992. Preprocessing includes computing luminance Y from RGB components Y=0.299*R+0.587*G+ 0.114*B; smoothing RGB channels using 2 iterations of a 3×3 box car filter; and computing a ROI mask, ROImsk, ([ROI]$_{vid}$) using the method described herein above. Next, process the ROI mask by eroding ROImsk 14 times to obtain eROImsk=erod (ROImsk, 14). Compute annulus perimeter, annMsk: annMsk=dil ((eROImsk AND not erod (eROImsk, 1)), 4). This is a thick closed binary image which traces the edge of the ROI, useful in closing the boundary around any os which might extend to the background. Remove glare in ROImsk by logically AND-ing ROImsk with the complement of the glare mask (obtain as described above) to obtain centerROImsk. Then, compute a mean and standard deviation of each color channel (meanR, stdR, meanG, stdG, meanB, stdB, meanY, stdY) in the region specified by the centerROImsk.

Next, the method 1988 in FIG. 102 includes thresholding to produce an initial segmentation mask in step 1994. First, cut-off centerROImsk around the annulus: centerROImsk=centerROImsk AND not (annMsk). Next, form a binary mask for each of the RGBY channels that represents pixels that exist in centerROImsk and that satisfy the following conditions:

1. mskR=(R pixels such that R<(meanR−.0.40*stdR));
2. mskG=(G pixels such that G<(meanG−.0.65*stdG));
3. mskB=(B pixels such that B<(meanB−.0.75*stdB));
4. mskY=(Y pixels such that Y<(meanY−.0.75*stdY)).

The resulting "initial" segmentation mask, msk, is then defined by:
msk=centerROImsk AND mskR AND mskG AND mskB AND mskY.

Next, the method 1988 in FIG. 102 includes performing a binary component analysis in step 1996. This step breaks up the segmentation mask into multiple objects. First, perform binary component labeling on segmentation msk. Remove all objects with size less than 125. Break apart all objects with size greater than 10000. For each object greater than 10000 (thisObjMsk), do the following:

1. Compute mean value meanR and meanY for the area selected by thisObjMsk in the red and luminance channels.
2. Set a new threshold for red and Y as follows:
   a. redT=0.90*meanR
   b. lumT=meanY
3. Break the object apart, or make it smaller to yield newObj, then complement thisObjMsk with the region that is not part of the newly broken-up region:
   newObj=thisObjMsk AND (R pixels such as R>=redT) AND (Y pixels such as Y>=lumT).
   thisObjMsk=thisOBjMsk AND (not(newObj)).
4. Keep track of the original large image mask (thisObjMsk) that produces the smaller objects in step c. Create a large object mask lgObMsk for each thisObjMsk that is set to on for each large object which was found.

Next, the method 1988 in FIG. 102 includes performing dilation, binary component analysis, and candidate selection in step 1998. Step 1998 is performed to find os candidates from the multiple binary objects produced in step 1996. First, dilate segMsk produced in step 1996 twice to obtain bMsk=dil (segMsk, 2). Perform a component labeling on bMsk. Discard objects of size less than 125 or greater than 23,000. For each remaining object, thisObjMsk, apply the following procedure to select candidates:

1. Compute mean, intMeanR, intMeanY, and standard deviation, intStdR, intStdY for red and luminance channel pixel values in thisObjMsk.
2. Dilate thisObjMsk 7 times to yield dThisObjMsk=dil (thisObjMsk, 7).
3. Compute perimeter mask:
   a. thisObjPerim=dil ((thisObjMsk AND not(erod (dThisObjMsk, 1))), 3).
4. Compute mean, perMeanR, perMeanY, and standard deviation, perStdR, perStdY, for red and luminance channel pixel values in thisObjPerim.
5. Compute the following indicators:
   a. os brightness (osBright)=intMeanY/perMeanY.
   b. Perimeter uniformity (perUnif)=perStdR/intStdR.
6. An object is an os candidate if:
   ((osBright<0.85) AND (perUnif<1.75)) OR
   ((osBright<0.7) AND (perUnif<2.85) AND (part of object came from large object as recorded in IgObjMsk).

Next, the method 1988 in FIG. 102 includes performing candidate filtering and final selection in step 2000. The remaining os candidates are processed as follows. First, discard large non-os objects at the periphery of the cervix using the following algorithm:

1. Define a binary image with a centered circular area of radius 150.
2. Discard the object if more than half of it is outside the circle and if perunif>0.9. This step is done by performing a logical AND of the object with the circular mask, counting pixels and comparing to the original size of object.

If the number of remaining objects is greater than 1, perform the following loop for each object:

1. Compute the centroid of the object, and compute the distance to the image center
2. Exit if either:
   a. The distance to the center is less than 100 for all objects.
   b. No object lies within 100 pixels of center and a single object remains.

Discard the object with the highest perUnif, and go back to step b. Finally, step 2002 of the method 1988 in FIG. 102 determines the final os mask by twice eroding the final mask obtained in step 2000.

Blood$_{vid}$

Figure 103:
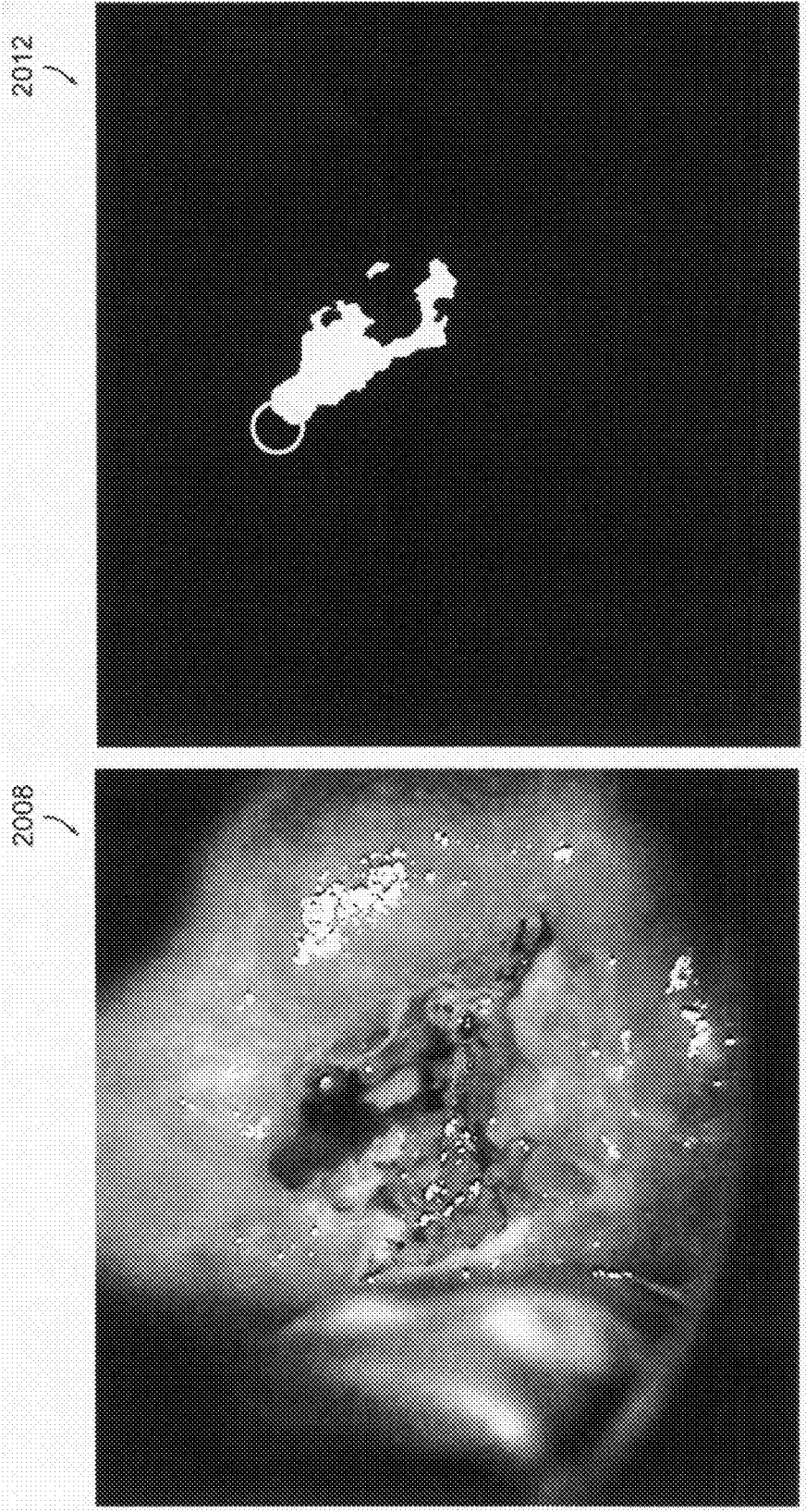

Step 1458 in FIG. 74 depicts the determination of a blood image mask, Blood$_{vid}$, for an image of a tissue sample. The presence of blood may adversely affect the optical properties of the underlying tissue. In the method of FIG. 74, the blood image mask is used in soft masking to penalize data from interrogation points that intersect or lie entirely within the blood regions. FIG. 103A depicts an exemplary image 2008 of cervical tissue used to determine corresponding blood image mask, Blood$_{vid}$, 2012, shown in FIG. 103B.

In one embodiment, the Blood$_{vid}$ image mask is similar to the Os$_{vid}$ image mask in that it is determined using an initial mask formulated from a logical combination of masks computed from each color channel R, G, B and luminance, Y. However, the initial Blood$_{vid}$ image mask is formed as a logical "OR" (not "AND") combination of the four different masks, each designed to capture blood with different color characteristics. Blood may be almost entirely red, in which case the Red channel is nearly saturated and the green and blue channels are nearly zero. In other cases, blood is almost completely black and devoid of color. In still other cases, there is a mix of color where the red channel dominates over green and blue. In one embodiment, the Blood$_{vid}$ mask identifies relatively large regions of blood, not in scattered isolated pixels that may be blood. The logical OR allows combination of regions of different color characteristics into larger, more significant areas that represent blood. As with the $Os_{vid}$ mask, the $Blood_{vid}$ mask is formulated by thresholding the initial mask and by performing component analysis.

Figure 104:
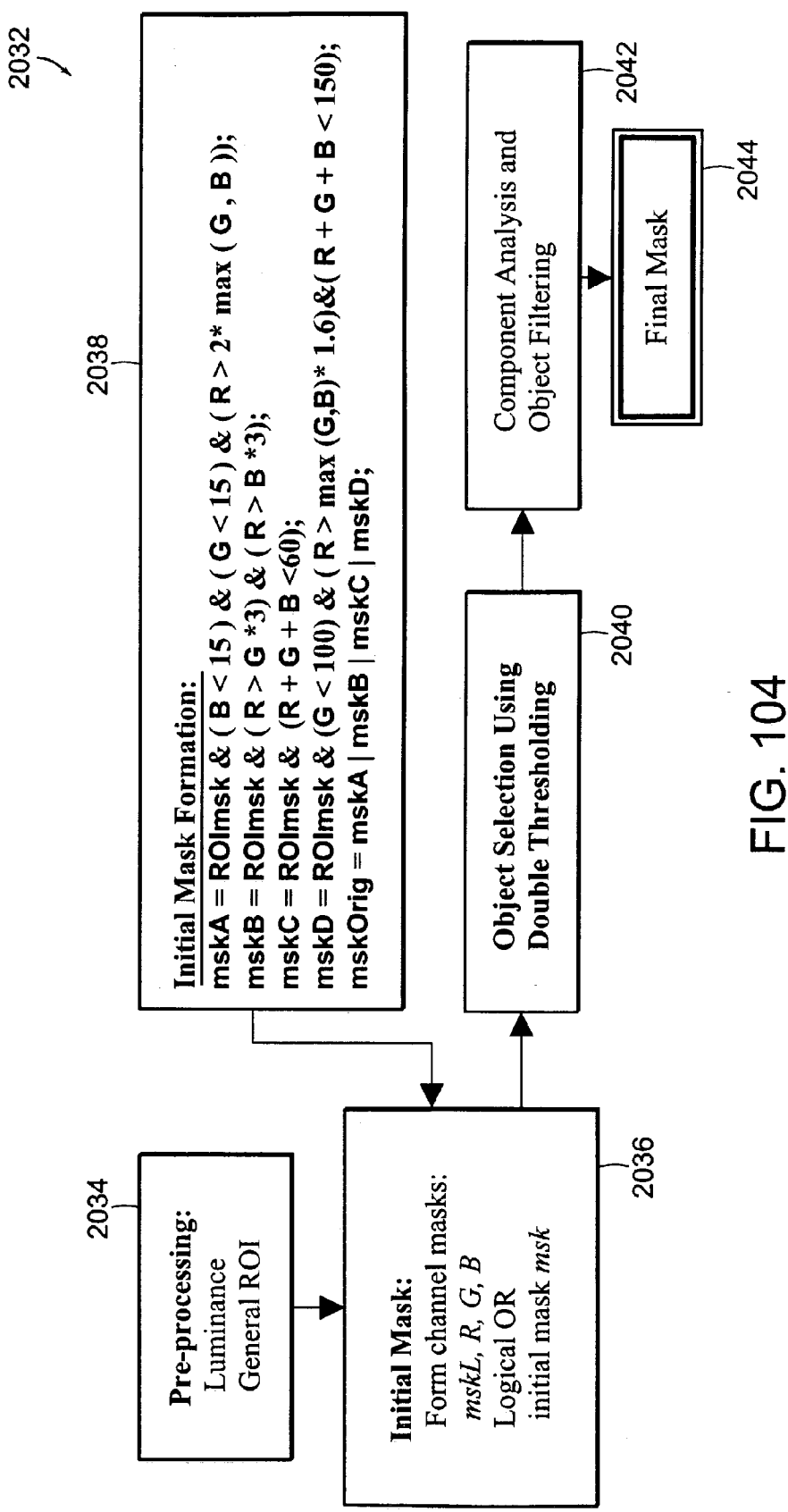

FIG. 104 is a block diagram 2032 depicting steps in a method of determining a blood image mask, $Blood_{vid}$, for an image of cervical tissue. The following describes the steps of the method 2032 shown in FIG. 104, according to one embodiment.

The method 2032 in FIG. 104 includes image preprocessing in step 2034. Peprocessing includes computing luminance Y from RGB components Y=0.299*R+0.587*G+ 0.114*B, and computing the ROI mask, ROImsk, ($[ROI]_{vid}$) using the method described hereinabove.

Next, the method 2032 in FIG. 104 includes mask formation via thresholding in step 2036. The following steps are used to produce an initial segmentation mask. First, four preliminary masks are generated to detect "likely" regions of blood, as follows:
1. To catch blood which is almost completely red, mskA
   mskA=ROImsk AND (B pixels such as B<15) AND (G pixels such as G<15) AND (R pixels such as R>2*max (G,B)).
2. To catch areas where red dominates over green and blue, mskB:
   mskB=ROImsk AND (R pixels such as R>G*3) AND (R pixels such as R>B*3).
3. To catch really dark, almost black blood, mskC:
   mskC=ROImsk AND (R, G, B pixels such as R+G+B<60).
4. To catch dark, but not completely black blood, mskD:
   mskD=ROImsk AND (R, G, B pixels such as R+G+B<150) AND (R pixels such as R<100) AND (R pixels such as R>max(G, B)*1.6).

The final candidate segmentation mask, mskOrig, is computed as follows: mskOrig=mskA OR mskB OR mskC OR mskD.

Next, the method 2032 in FIG. 104 includes object selection using double thresholding in step 2040. The following steps are used to select regions that are blood candidate regions. First, a seed mask, seedMsk, is made by eroding mskOrig twice. Then, to connect neighboring pixels, dilate mskOrig once, then erode the result once to obtain cIMskOrig. Finally, to eliminate spurious pixels and regions that are not connected to larger features, compute mask, msk, by performing a flood fill of "on" valued regions of cIMskOrig with seeds in seedMsk.

Next, the method 2032 in FIG. 104 includes binary component analysis and object filtering in step 2042. Binary component labeling is performed on msk to select blood regions. For each labeled object the following steps are performed:
1. The Object mask is set to 0. Upon validation, the object mask is turned ON.
2. An interior object is found by shrinking it once (1 erosion step) unless it disappears, in which case the algorithm reverts to the original object prior to erosion.
3. Dilate the object OBJ 5 times, compute its perimeter and dilate the perimeter 5 times:
   ObjPer=dil ((OBJ AND not(erod (dil (OBJ,5), 1))), 3).
4. For both the interior and perimeter objects, the mean and standard deviation is found for the Red, Green, and Blue color-planes within the objects. The interior and perimeter mean luminance is found as the average of the Red, Green and Blue means.
5. Two indicators are calculated which will help in the decision step:
   a. DarkBloodIndicator=(Perimeter Red mean)/(Interior Red mean). This number is high for dark or black blood because there is more red in the perimeter than in the interior.
   b. BrightBloodIndicator=((Perimeter Green Mean+Perimeter Blue Bean)/Perimeter Red Mean)/((Interior Green Mean+Interior Blue Bean)/Interior Red Mean). This number is large when the interior region has a much higher red content than green and blue as compared to the perimeter.
6. If the following three conditions are met, the region is considered to be a "noisy" feature which is most likely near the edge of the cervix. This determination affects the decision rules to follow:
   a. Interior mean Red<40
   b. (Interior standard deviation of Red>Interior mean Red) OR (Interior standard deviation of Green>Interior mean Green) OR (Interior standard deviation of Blue>Interior mean Blue)
   c. DarkBloodIndicator<5.
7. The decision rules: If any of the following three rules are satisfied, then this object is Blood. Otherwise it is not.
   a. DarkBloodIndicator>2.5 AND not "noisy";
   b. BrightBloodIndicator>2.25 AND not "noisy";
   c. BrightBloodIndicator>2.25 AND DarkBloodIndicator>2.5 (in this case it doesn't matter if it's a "noisy").
8. If the object is blood, it is turned ON in the final segmentation mask.

Finally, the method 2032 in FIG. 104 includes determining the final blood mask in step 2044. Step 2044 includes performing a flood-fill of all objects in which the seed objects were found to be blood. This yields the final blood segmentation.

$Mucus_{vid}$

Figure 105B:
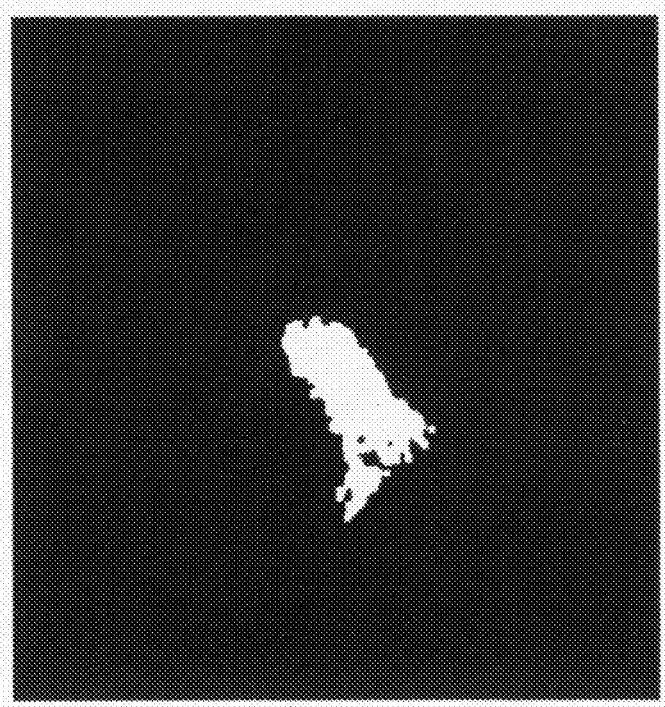
Figure 105A:
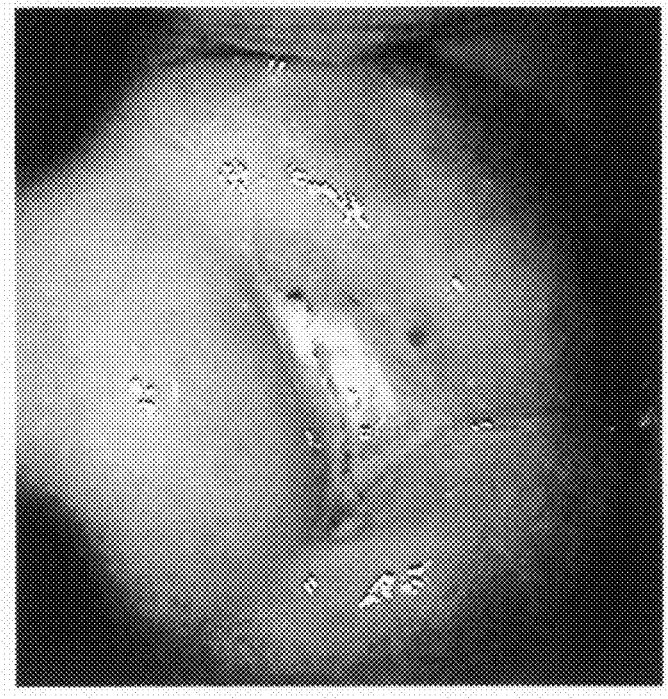

Step 1464 in FIG. 74 depicts the determination of a mucus image mask, $Mucus_{vid}$, for an image of a tissue sample. The presence of mucus may affect the optical properties of the underlying tissue, possibly causing the tissue-class/state-of-health characterization in those regions to be erroneous. In the method 1438 of FIG. 74, the mucus mask is used in soft masking to penalize data from interrogation points that intersect or lie entirely within the mucus regions. FIG. 105A depicts an exemplary image 2064 of cervical tissue used to determine a corresponding mucus image mask, $Mucus_{vid}$, 2068 shown in FIG. 105B.

In one embodiment, the $Mucus_{vid}$ image mask is a modified blood image mask, tuned to search for greenish or bright bluish objects. FIG. 106 is a block diagram 2072 depicting steps in a method of determining a mucus mask, $Mucus_{vid}$, for an image of cervical tissue. The following describes steps of the method 2072 shown in FIG. 106, according to one embodiment.

The method 2072 in FIG. 106 includes preprocessing in step 2074. Preprocessing includes processing each RGB input channel with a 3×3 median filter followed by a 3×3 boxcar filter to reduce noise. Then, calculate or retrieve the following masks:

1. Glare mask (Glare$_{vid}$): dilate glare mask once to yield glareMsk
2. ROI mask ([ROI]$_{vid}$): ROImsk
3. Blood mask (Blood$_{vid}$): bloodMsk
4. os mask (Os$_{vid}$): osMsk Compute a valid cervix pixels mask, validCervix, by ANDing the ROImsk with the complement of the other masks as follows: validCervix=ROImsk AND not(glareMsk) AND not(bloodMsk) AND not(osMsk).

Next, the method 2072 in FIG. 106 includes mask formation via thresholding and morphological processing in step 2076. The following steps are used to produce an initial mucus segmentation mask. First, calculate the means, meanR, meanG and meanB, for the RGB channels on the validCervix region. Compute the difference, RGgap between the red and green mean: RGgap=meanR−meanG. Create a binary mask, mskOrig, according to the following rule: mskOrig=ROImsk AND (R,G,B pixels such as ((2*G−R−B)>=(10−RGgap/3))). This rule selects regions where green is somewhat higher than either red or blue relative to the gap. Finally, process the binary mask with an opening morphological operator to obtain opMsk, as follows:

1. Perform two erosions with a 3-by-3 disk structuring element.
2. Perform one dilation with a 3-by-3 square structuring element.
3. Perform one dilation with a 3-by-3 disk structuring element.

Next, the method 2072 in FIG. 106 includes object selection using double thresholding in step 2080. The followings steps are used to select objects from the initial segmentation mask by computation of seed points. First, a seed image, seedMsk, is computed by eroding opMsk 3 times. Then, opMsk is dilated twice then eroded once. Objects in opMsk are selected using seedMsk. For example, object I is selected at points where opMsk and seedMsk intersect, then selMsk is defined as the resulting object selection mask.

Then, the method 2072 in FIG. 106 includes binary component analysis and object filtering in step 2082. The following steps are applied to all objects selected in step 2080:

1. Perform binary component labelling on all selected objects in selMsk.
2. Set final segmentation mask to all 0's.
3. Compute area for each object in selMsk and discard any object with an area less than 1000 pixels, update selMsk by removing discarded objects
4. Process all remaining objects in selMsk as follows (steps 2084, 2086):
   a. Compute mean and standard deviations of the red, green and blue smoothed images, meanR, meanG, meanB, stdR, stdG, stdB, for each object.
   b. Compute the object perimeter for each object:
      i. Binary object, binObj, is dilated 15 times dilBinObj=dil(binObj, 15).
      ii. Object perimeter is computed and then dilated: perBinObj=dil((dilBinObj AND not(erod (dilBinObj, 1)), 4).
   c. Compute mean and standard deviations on each color channel, pmeanR, pmeanG, pmeanB, pstdR, pstdG, pstdB for each region's perimeter.
   d. Compute six decision rule indicators:
      i. Mucus Indicator 1: mucInd1=(meanG/pmeanG)*(pmeanR/meanR)
      ii. Mucus Indicator 2: mucInd2=(meanG/pmeanG)*(pmeanR/meanR)*(meanB/pmeanB)
      iii. Green bright indicator: gBrightInd=3*meanG−meanR−meanB
      iv. Local variation quotient: locVarQuo=(stdR+stdG+stdB)/(psdfR+pstdG+pstdB)
      v. Target laser Indicator: targLasInd=(meanG*(pmeanR+pmeanB))/(pmeanG*(meanR+meanB))
      vi. Blue not too bright indicator: bNotBrightInd
         if ((meanB>meanR) AND (meanB>meanG))
         bNotBrightInd=(meanG−meanR)/(2*abs (meanB−meanG)
         else
         bNotBrightInd=10.
   e. Object is not mucus object if the following holds: (mucInd1<1.25) OR (mucInd2<1.5) OR (gBrightInd<100) OR (bNotBrighInd<1) OR (targLasInd>1.5) OR (locVarQuo>1.75).
   f. If the object is selected as a mucus object, it is added to the final mucus mask.

[SP]$_{vid}$

Step 1452 in FIG. 74 depicts the determination of a speculum image mask, [SP]$_{vid}$, for an image of a tissue sample. [SP]$_{vid}$ is used in hard masking in the tissue characterization method 1438 of FIG. 74. Here, data from the interrogation points that intersect the speculum are removed from consideration in the tissue-class/state-of-health classification steps. FIG. 107A depicts an exemplary image, 2098, of cervical tissue used to determine the corresponding speculum image mask, [SP]$_{vid}$, 2100, shown in FIG. 107B.

In one embodiment, the speculum image mask is determined by finding circles near the bottom of the image. Projections of a number of different types of speculums resemble circles of different radii. In one embodiment, two types of circle searches are used: an outer bottom search and an inner bottom search. The outer bottom search finds points near the bottom edge of the general region-of-interest and infers circles from these points. If multiple circles result, they are evaluated to find the one that best models the curvature at the bottom of the region-of-interest. A circle that models this curvature well enough is used to form the speculum segmentation mask, [SP]$_{vid}$.

If the outer bottom search does not produce a circle that models the ROI curvature well enough, then another search is performed to find a circle that models the curvature of a speculum within the ROI. This is the inner bottom search, and may be necessary where there is significant reflection of light from the speculum. In the inner bottom search, a set of angular projections is formed based on a best guess of the center of curvature from the outer circle search. The projections are then analyzed to find a significant intensity trough near the end of the projections that agrees with the general expected location of a speculum at the bottom of the image. The projection analysis provides new points with which to model circles, and the resulting circles are evaluated using the image data to detect the presence of a speculum.

FIG. 108 is a block diagram 2112 depicting steps in a method of determining a speculum image mask, [SP]$_{vid}$, for an image of cervical tissue. The following describes the steps of the method 2112 shown in FIG. 108, according to one embodiment.

The method 2112 in FIG. 108 includes image preprocessing in steps 2114 and 2116. The following steps are used to preprocess the image used in speculum mask computation. First, remove glare from the RGB image by performing the following:
1. Calculate or retrieve glare mask, glareMsk ($Glare_{vid}$).
2. Dilate glareMsk 4 times to obtain dilGlareMsk.
3. Filter the RGB values using dilGlareMsk to perform run-length boundary interpolation as follows:
   a. Raster scan each row of dilGlareMsk to find all beginnings and ends of pixel runs.
   b. For each pixel P(x,y) in a given run specified by beginning point P(xb, y) and end point P(xe,y) in the intensity image, replace P(x,y) by half the linearly interpolated value at P(x,y) from P(xb,y) and P(xe, y).
   c. Raster scan each column of dilGlareMsk to find all beginnings and ends of pixel runs.
   d. For each pixel P(x,y) in a given run specified by beginning point P(x, yb) and end point P(x,ye) in the intensity image, add to P(x,y) half the linearly interpolated value at P(x,y) from P(x,yb) and P(x,ye).

Then, smooth the RGB channels by filtering twice with a 5×5 box car filter. Finally, calculate or retrieve the ROI mask, ROImsk ($[ROI]_{vid}$). Next, the method 2112 in FIG. 108 includes outer bottom circle detection in step 2120. The outer bottom circle detection is designed to find the best circular segmentation matching the bottom of ROImsk. Step 2120 includes the following:
1. Where width specifies the image width, compute the x-location of 7 columns (defined by none the intervals $C_i$=i width/10, where i=1 to 9). The x-locations are used to determine y-values. The resultant (x,y) pairs are used to find different candidate circles.
2. Four candidate circles—narrow, wide, left, and right—are calculated from the x values using the following matrix:
   a. Narrow circle: C3 C5 C7
   b. Wide circle: C2 C5 C8
   c. Left circle: C2 C4 C6
   d. Right circle: C4 C6 C8
3. The y-values are determined by scanning the y-axis, at a given x-position, starting at the bottom, until an "on" pixel is encountered in ROImsk. The same process is performed for 5 adjacent pixels to the right and left of the given x-position. The resulting 11 y-values are averaged to obtain the y-value used for calculating circles at the given x-position.
4. For each set of x values defined by the rows in the matrix above, the y values are computed as described above, and the resulting three pairs of coordinates are used to determine a unique circle intersecting these 3 points.
5. A candidate circle is retained if:
   a. Radius R>250 AND
   b. R<700 AND
   c. The circle's center lies at a y value less than 240 (half the image height).

Next, the method 2112 in FIG. 108 includes validation of the outer circle in step 2122. The following steps are used to validate the outer circle:
1. If circles remain after the previous pruning, perform the following evaluation procedure:
   a. Compute candidate circle center, draw perimeter at given radius and construct 2 offset regions from the drawn perimeter.
   b. The average intensity values, meanTop and meanBot, are calculated for each region on the red image.
   c. The BotTopRatio is calculated as the ratio of meanTop to meanBot.
      i. The top region is centered 10 pixels above the perimeter of the circle, and is 7 pixels in height. For example, for a given (x0,y0) point on the perimeter, the vertical region at x0 comprises the pixels in the range (x0, y0+10) to (x0, y0+10−7).
      ii. Similarly, the bottom region is centered 10 pixels below the perimeter of the circle, and is 7 pixels in height.
   d. The average intensity values, meanTop and meanBot, are calculated for each region on the red image.
   e. The BotTopRatio is calculated as the ratio of meanTop to meanBot.
2. The circle with the best fit to the actual speculum should minimize this ratio. If there is more than one circle remaining, the circle with minimum BotTopRatio is chosen.
3. If BotTopRatio>0.55, the circle is rejected, and it is concluded that the outer bottom circle detection found no valid circle.

If BotTopRatio<0.55, the circle is kept as the initial result for the speculum segmentation. If the outer circle detection produces a circle with a strong enough representation of the speculum, then this is taken as the result and an inner speculum search is not done. Otherwise the inner speculum search is done. If no circle is found using the outer algorithm, perform the inner bottom speculum search. If the outer search finds a circle, look at the BotTopRatio to determine whether it qualifies:
1. If BotTopRatio<0.275, take the outer circle as the final segmentation mask and stop.
2. If BotTopRatio>=0.275, try the inner speculum search to see if it yields a satisfactory result.

Next, the method 2112 in FIG. 108 includes inner bottom circle detection in step 2126. The Inner bottom circle detection algorithm looks for circles within the ROI mask by calculating angular projections and looking for "valleys" in the projections to determine points that can be used to infer circles. The resulting circles are evaluated with a scheme similar to the one for outer bottom circle detection. Step 2126 includes the following:
1. Angular projection center point selection:
   a. If an outer circle was detected, use the center point of the outer circle.
   b. Else, use the point (n/2,1), where n is the width of the image.
2. The inner speculum search is done on the red colorplane R and a redness-enhanced red image ERn. The search results from the two images R and ERn are evaluated as a group and the best result is taken from the entire set. The redness enhanced red image is given by ERn=(2*R+Rn)/3, where Rn is the redness image defined in Equation 95. If no inner speculum is found from the redness enhanced red image, then the inner speculum search has determined that there is no identifiable inner speculum. The inner speculum search algorithm is described in the subsequent steps.
3. Calculate angular projections as follows:
   a. Five x-values give the center of each projection as it crosses the bottom row of the image: [C0 C2 C4 C6 C8].
   b. From these x-values, the angle thetaCtr, the central angle for the projection, is computed.

c. For each angle thetaCtr, a projection sweeping out 10 degrees (5 degrees on each side of thetaCtr) is calculated.
d. For each 10 degree span, 50 equidistant line profiles (10/50 degrees) are used to calculate the projection. The profiles extend from the center point to the point where the line at each angle crosses the bottom row of the image.
e. The 50 profiles are averaged to yield the projection for each of the angles thetaCtr.
f. Each projection profile is filtered with a 15 sample long boxcar moving window averager.
4. Each projection is searched backward to find the first "peak" in the projection, then search backwards again until the valley beyond that peak is found. This valley usually occurs near the boundary between the speculum and the cervix. Not every projection will yield a good valley point V. The criteria for finding the valley V of a projection P are as follows:
   a. P (V)<=mean(P (V+k) for all k in [1:12] (12 samples after V);
   b. P (V)<=mean(P (V+k) for all k in [−12:−1] (12 samples before V);
   c. P (V)<=P (V+k) for all k in [−12:12];
   d. P (V)<P (V+k)−4 for some k in [V:length(P)] (peak-valley is >=4);
   e. For valley V, find the y coordinate value $y_V$ and check that $y_V$>300.
5. After V is located, search backwards to find the point VMin where the first derivative of the projection is less than K*minSlope, where minSlope is the minimum slope between the valley V and the maximum of P(n) for n in [1:V], and K is a constant parameter set to 0.3. VMin becomes the final point used for inferring circles from this projection.
6. If the number of points to infer circles (calculated from the valleys as described above) is greater than 3, then as many circles as possible can be identified from these points and evaluated. The circles are chosen from the following matrix:
   CircleIDX=[1 3 5; % X-X-X
     2 3 4; % -XXX--
     1 2 3; % XXX--
     3 4 5; % --XXX
     1 2 4; % XX-X-
     2 4 5; % -X-XX
     1 3 4; % X-XX-
     2 3 5; % -XX-X
     1 2 5; % X-X--X
     1 4 5;]; % X--XX where the elements of the matrix correspond to the five projections computed above. If a specific projection j fails to yield an acceptable valley point, then all rows of the CircleIDX matrix which contain j are removed.
7. All remaining rows in CircleIDX are used to select projections for inferring circles. The circles are calculated by first getting (x, y) coordinates for the 3 points defined in the steps above, using the center of projection and the radius along the projection. A unique circle is fitted through the 3 points, unless points are collinear, and circle center (xCent, yCent) and radius rad are computed.

Next, the method 2112 in FIG. 108 includes validation of the inner bottom circle in step 2128. The following steps are used to validate the inner bottom circle:

1. For each circle, the circle is discarded if any of the following conditions applies:
   a. rad<250 (the circle is too small to be a speculum)
   b. yCent>(image height)/2 (center of circle in lower half of image or beyond).
2. Each remaining circle is evaluated with the following technique:
   a. A temporary image is defined for identifying three different regions specific to the circle. It is an 8-bit image with the following values:
      i. 1 for the "inner" region, which is the region between the circle and another circle whose center is 12 pixels below the original one.
      ii. 2 for the "bottom" region, which is a 12 pixel wide circle drawn centered at 20 pixels below the original circle.
      iii. 3 for the "top" region, which is a 12 pixel wide circle drawn centered at 20 pixels above the original circle.
      iv. 0 for all other points in the image.
   b. Five sets of pixels are calculated on the temporary image. The average pixel value is calculated from the search image (Red or Redness enhanced Red) for each set of pixels:
      i. Top pixels, used to calculate AvgTop;
      ii. Bottom Pixels, used to calculate AvgBot;
      iii. Inner pixels, used to calculate AvgIn;
      iv. Outer pixels (top and bottom), used to calculate AvgOut;
      v. Inner-bottom pixels (inner and bottom), used to calculate AvgInBot.
   c. Two ratios are calculated from these sets of pixels:
      v. InOutRatio=AvgIn/AvgOut;
      vi. BotTopRatio=min([AvgBot/AvgTop, AvgIn/AvgTop, AvgInBot/AvgTop]).
   d. The InOutRatio gives an estimate of how closely the circle conforms to a low-intensity cervix-speculum boundary, and the BotTopRatio helps to evaluate how well the circle matches an intensity difference.
   e. To be a valid speculum representation, a circle should satisfy the following criterion:
      (InOutRatio<0.70) OR (InOutRatio<0.92 AND BotTopRatio<0.83 ).
      If no circles meet this criterion, then the algorithm detects NO inner speculum.
   f. The inner circle representing the speculum is the circle from step e that has the minimum value of InOutRatio.
   g. If there is a resulting circle that has passed the validation procedure, evaluate to verify it is not a false positive by comparing the mean luminance on two portions of the ROI, above the speculum and below the speculum.
      vii. Glare, blood and os are removed from ROI to obtain dROI, where
         dROI=ROI AND not(glareMsk) AND not (bloodMsk) AND not(osMsk).
      viii. Compute mean luminance, meanLTop, on dROI region above circle.
      ix. Compute mean luminance, meanLBot, on dROI region below circle.
      x. If meanLBot>0.8*meanLTop and the bottom-most point on the inner circle is less than ¾ of the image height, then the candidate is a false positive and is discarded.

Finally, the method 2112 in FIG. 108 includes final determination of the specular segmentation mask in step 2128. The final segmentation mask is computed from the results of the inner and outer speculum searches. If the outer search produces a satisfactory result and no inner search is done, the final mask is the one computed by the outer speculum search. If the outer search produces a satisfactory result and an inner search is performed which also produces a result, the final segmentation mask is the logical OR of the inner and outer masks. If the outer search produces no result but the inner search produces a result, the final mask is the mask from the inner search. If neither search produces a result, the final segmentation is empty, indicating that the algorithm has determined that no speculum is present.

$[VW]_{vid}$

Step 1454 in FIG. 74 depicts the determination of a vaginal wall image mask, $[VW]_{vid}$, for an image of a tissue sample. $[VW]_{vid}$ is used in hard-masking in the tissue characterization method 1438 of FIG. 74. FIG. 109A depicts an exemplary image 2190 of cervical tissue used to determine the corresponding vaginal wall image mask, $[VW]_{vid}$, 2194 shown in FIG. 109B.

In one embodiment, the vaginal wall mask detects vaginal walls and cervical edges, including fornices and speculum blades. Here, the mask is determined using a filter shaped like a notch to emphasize the vaginal wall. This is similar to template matching in which the template is present along one dimension and the filter is constant along the other dimension. This achieves a projection-like averaging.

After application of the filter in horizontal and vertical orientations, the resultant gradient images are thresholded and skeletonized. A heuristic graph searching method connects disconnected edges, and the edges are extended to the bounds of the image to form a full mask. Once the edges are extended, the edge lines are shadowed outward from the center of the image to form the final vaginal wall segmentation mask, $[VW]_{vid}$.

FIG. 110 is a block diagram 2218 depicting steps in a method of determining a vaginal wall image mask, $[VW]_{vid}$, for an image of cervical tissue. The following describes the steps of the method 2218 shown in FIG. 110, according to one embodiment.

The method 2218 in FIG. 110 includes preprocessing in step 2220. First, calculate or retrieve the glare, glareMsk, ROI, ROIMsk, and os, osMsk, segmentation masks. Calculate the luminance L from the RGB signal using the formula: L=0.299*R+0.587*G+0.114*B. Dilate glareMsk 4 times to obtain dilGlareMsk. Then, filter the RGB image using dilGlareMsk to perform run-length boundary interpolation as follows:

1. Raster scan each row of dilGlareMsk to find all beginnings and ends of pixel runs.
2. For each pixel P(x,y) in a given run specified by beginning point P(xb, y) and end point P(xe,y) in the intensity image, replace P(x,y) by half the linearly interpolated value at P(x,y) from P(xb,y) and P(xe,y).
3. Raster scan each column of dilGlareMsk to find all beginnings and ends of pixel runs.
4. For each pixel P(x,y) in a given run specified by beginning point P(x, yb) and end point P(x,ye) in the intensity image, add to P(x,y) half the linearly interpolated value at P(x,y) from P(x,yb) and P(x,ye).
5. Perform a 11×11 box car filter smoothing on dilGlareMsk regions only.

Finally, smooth the filled RGB channels by filtering once with a 3×3 box car filter.

Next, the method 2218 in FIG. 110 includes gradient image processing in steps 2222, and 2224. First, create a notch filter for detecting the vaginal wall. The filter of length 22 is defined by the following coefficients: [1 1 1 1 2/3 1/3 0 −1/3 −2/3 −1 −1 −1 −1 −2/3 −1/3 0 1/3 2/3 1 1 1 1]. Then, normalize the filter: The average of the filter coefficients is subtracted from the filter in order to make it a zero-gain convolution kernel. Replicate rows 24 times to create a 22 by 24 filter. Filter the luminance image L with the vaginal wall notch filter to produce the vertical gradient image vGradImg. Filter the luminance image with the transpose of the notch filter to produce the horizontal gradient image hGradImg. Clip gradient images to 0. Finally, perform the following thresholding and clean-up operations on each of the gradient images hGradImg and vGradImg:

1. Threshold the images at 975 to yield a binary object image.
2. Perform a binary component labeling using 4-way connectivity.
3. Compute regions statistics: area, centroid, major and minor axis length.
4. Discard any object whose size is less than 1000 pixels.
5. Discard any object which is within 80 pixels of distance from the center of the image.
6. Dynamically calculate the minimum allowable length, MinAllowedLength, for each object based upon the distance of its centroid (xCentroid, yCentroid) from the center of the image (Cx, Cy) defined by Cx=(image width)/2 and Cy=(image height)/2. Let x be the distance of the centroid to the center of the image, $x=sqrt((xCentroid-Cx)^2+(yCentroid-Cy)^2)$. MinAllowedLength scales the minimum allowed distance from 250 (at the image center) to 100 at the left or rightmost edge of the image and is defined by: MinAllowedLength=250−(15*x/25).
7. Discard any object with a major axis length less than MinAllowedLength.
8. Discard any object that is more than 50% outside of the image's ROI.
9. Discard any object that covers more than 5% of the os.

Next, the method 2218 in FIG. 110 includes skeletonization in step 2226. The binary images resulting from step 2224 are processed with a skeletonization algorithm that approximates the medial axis transform. The skeletonization algorithm works for either horizontal or vertical edges. For vertical edges, each row is scanned from left to right. Each time the pixel values transition from OFF to ON, the index of the ON pixel is remembered. If the first pixel in the row is ON, this qualifies as a transition. When there is a transition from ON back to OFF, the index of the last ON pixel is averaged with the index from the previous step to give the center pixel in the ON region. If an ON region extends to the last pixel in the row, then this last pixel is treated as a transition point. All pixels between and including the first and last ON pixels are turned off except the center pixel. For horizontal edges, each column is scanned from top to bottom. The same steps described hereinabove are repeated for the columns instead of the rows.

Next, the method 2218 in FIG. 110 includes edge linking and extension in steps 2226, and 2228. The skeletonizations are processed with a heuristic graph-searching method which connects slight gaps in the skeletonized images and extends the edges to the image boundary. The following images and parameters are used by the edge linking algorithm:

Horizontal and vertical skeletonized edge image, vSkelImg, hSkelImg

Input label matrix, LblMat. This is found by labeling matrix output from the connected components analysis, where discarded regions have been removed from the label matrix by setting their pixel values back to 0.

Horizontal and vertical edge orientation, vEdgeOrient, hEdgeOrient.

Skeletonized input label matrix, skLblMat. This is a copy of LblMat where all the pixels which are OFF in the skeletonized image are set to 0 in skLblMat.

Gap=16.0, the maximum allowable gap to fill in for a disconnected edge.

The following are searching methods that are implemented.
1. Search for Edge Pixels: For both the horizontal and vertical edge images, the images are raster searched to locate edges within them.
    a. The vertical edge image, vSkelImg, is searched by row raster scanning to ensure that the first point in an edge is encountered.
    b. The horizontal edge image, hSkelImg, is searched by column raster scanning to ensure that the first point in an edge is encountered.
    c. When a point is encountered, the algorithm references skLblMat to see if that point has a positive label, indicating that this edge has not yet been processed. If so, the edge connection and edge extension routines described in the steps below are executed starting from this point.
2. Edge Connection. The edge connection routine starts from the point from which it is called. The routine keeps a list of the points encountered in the edge. The search is executed only for points with the same label in dilGlareMsk.
    a. Create Label matrix skLblMat as described above.
    b. Find second point:
        i. Starting from the first point, do a search in a rectangular region of size 2*(Gap+1.5)+1 centered about the first point.
        ii. The second point will be the point which is ON in the edge image which is closest to the first point, and which is not already part of any other linked edge (must have same label value as the first point).
        iii. Fill in the gap between the first point and the second point. The Gap filling algorithm is described below in step 3.
        iv. If this edge begins at a point "sufficiently close" (with respect to Gap) to another edge, set a flag to prevent extension of the beginning of this edge.
        v. If no second point is found, or if the second point is part of another edge which has already been linked, erase this edge in the output edge image (see Edge Erasing description below) and in skLblMat, stop processing this edge, and continue the loop to look for the next edge.
    c. Find the third point:
        i. Starting from the second point, do a search in a rectangular region of size 2*(Gap+1.5)+1 centered about the second point.
        ii. The third point will be the point which is ON in the edge image which is closest to the second point, and which is not already part of this or any other linked edge (must have same label value as the first point).
        iii. Fill in the gap between the second point and the third point.
        iv. If no third point is found, or if the third point is part of another edge which has already been linked, erase this edge in the output edge image, stop processing this edge, and continue the loop to look for the next edge.
    d. After three points in this edge are discovered, there is enough information to infer a search direction, and from here on out all searches in the Edge Connection are directional. Steps for computing the search location are listed below.
    e. Starting with the search for the fourth point, the following steps are iteratively performed until no further pixels in this edge can be found:
        i. The search direction: North (N), South (S), East (E), West (W), NorthEast (SE), NorthWest (NW), SouthEast (SE) or SouthWest (SW) is computed by the steps described below.
        ii. Check the edge length, if it is greater than 2048, break out of the loop because this edge must have looped back upon itself.
        iii. Find the next point in the given search direction: If no further points were found, check to see if the edge length is less than 120.
            1. If edge length <120, erase edge and break out of this loop to continue the processing to find other edges (back to step 1).
            2. If edge length >=120, keep edge end break out of loop and continue with step f).
        iv. Fill in the gap between the current point and the new point.
        v. If the new point belongs to an edge which was already linked by this algorithm, do the following:
            1. If the current edge is less than 40 pixels in length, erase this edge. Break out of the loop and continue searching for further edges (back to step 1).
            2. Otherwise, the edge will be kept, but a flag is set so that the end of this edge is not extended. Break out of the loop and continue with step f.
        vi. Increment the edge length so that the new point becomes the current point for the next iteration.
        vii. Continue with step i) to continue processing.
    f. At this point, a valid edge has been detected. This edge will then be extended in the both directions to the boundary of the image unless either edge (or both) is flagged for not extending. The edge extension steps are described below in step 5.
    g. Check to see if an extension passed through the center of the image (defined by a circle of radius 80 centered at the geometrical center of the image).
        i. If an extension did pass through the center of the image, erase this edge and all of its extensions.
        ii. Otherwise, relabel this edge in the Label matrix to have value −1, and draw the extensions on the output edge image, simultaneously labeling the corresponding pixels in the Label matrix with value −2.
3. Gap Filling method:
    a. Check to see if there is no gap, i.e. if the edge is already connected. Where (x1,y1) and (x2,y2) are the new point and the current point, if abs(x1−x2)<2 and abs(y1−y2)<2, then there is no gap to fill, and the Gap Filling processing stops.
    b. Remove the "New pixel" from the edge vectors so that it can be replaced with a set of filled-in pixels.

c. Check for special cases where x1=x2 or y1=y2. In either of those two cases, the Gap Filling is accomplished by simply turning on every pixel which lies between the two pixels in the output Edge image.
d. For the case where x1 is not equal to x2 and y1 not equal to y2, a diagonal line needs to be drawn to fill the gap.
   i. This is done first by computing an equation for the line which connects the two points.
   ii. If the slope is greater than 1, iterate from y=y1 to y2, and compute the x value for each y value. For each (x,y) turn on the corresponding pixel in the output Edge image and in skLabMat.
   iii. If the slope is less than 1, iterate from x=x1 to x2, and compute the y value for each x value. For each (x,y) turn on the corresponding pixel in the output Edge image and in skLabMat.
e. Finally, all of the new pixels are added to the edge vectors in order from the current pixel to the new one. The corresponding pixels in skLabMat are set to the label value −2.

4. Computing Search Direction:
   a. Two pixel locations are used to infer a search direction.
      i. The first point is the geometric average of the two most current pixels in the edge.
      ii. If there are less than 6 pixels in the edge, the second point is the average of the first and second pixels in the edge.
      iii. If there are more than 6 pixels in the edge, the second point is the average of the fifth and sixth most current pixels in the edge.
   b. For the two pixels (x1,y1) and (x2,y2), the search direction is computed as follows:
      i. Compute the angle formed by the two points using the ATAN2 function:
         angle=atan2(y1 −y0,x1 −x0)*180/π;
      ii. If angle is in the interval [−22.5, 22.5], the search direction is E.
      iii. If angle is in the interval [22.5, 67.5], the search direction is SE.
      iv. If angle is in the interval [67.5, 112.5], the search direction is S.
      v. If angle is in the interval [112.5, 157.5], the search direction is SW.
      vi. If angle is in the interval [−67.5, −22.5], the search direction is NE.
      vii. If angle is in the interval [−112.5, −67.5], the search direction is N.
      viii. If angle is in the interval [−157.5, −112.5], the search direction is E.
      ix. Otherwise, the search direction is W.

5. Edge Extension:
   a. It is the default to extend both the beginning and end of the edge. However, during the edge connection steps, if it is discovered that the edge originates close to a different edge, the edge is connected to the different edge and is not extended. If an edge ends by merging with another edge, the end of the edge is not extended.
   b. For both the beginning and the end of the edge:
      i. For Vertically oriented edge images (vEdgeOrient):
         1. If the y-coordinate for the first/last point of the edge is less than the image height/6 or greater than 5*height/6, extend the beginning/end of the edge using the local slope method (described below).
         2. Otherwise, extend the beginning/end of the edge using the global slope method (described below).
      ii. For Horizontally oriented edge images (HEdgeOrient):
         1. If the x-coordinate for the first/last point of the edge is less than the image width/6 or greater than 5*width/6, extend the beginning/end of the edge using the local slope method (described below).
         2. Otherwise, extend the beginning/end of the edge using the global slope method (described below).
   c. Local Slope Extension: This method uses the slope of the edge near its beginning/end to determine the slope of the extending line.
      i. Compute two points for slope computation:
         1. the average of the four pixels from the beginning/end of the edge; and
         2. the average of the 6th through 9th pixels from the beginning/end of the edge.
      ii. Using the two computed points, the edge is extended from its beginning/end point using a line of the computed slope until it reaches the edge of the image.
   d. Global Slope Extension: this method uses pixel values between 20% and 80% of the length along the edge to guess the "average" slope of this edge. Then the beginning/end of the edge is extended using this slope.
      i. If the edge has edgeLen pixels in it, select the points in the edge with the following indices:
         1. begIDX=round(edgeLen*0.2); pointA=edge (begIDX);
         2. endIDX=round(edgeLen*0.8); pointB=edge (endIDX).
      ii. Compute the slope using pointA and pointB, and use a line of this slope to extend from the beginning/end of this edge.
   e. After the extension is computed, the extended pixels are turned ON in the output edge image, and the corresponding pixels in skLabMat are assigned value −2.

6. Edge Erasing.
   When an edge is to be erased check to verify that for each pixel in the edge and its extension the label for the pixel is >0. If so, set the value in the output Edge image and the label matrix to 0. This method assures that pixels in another edge that has already been linked are not erased (the two edges might have crossed).

Finally, the method 2218 in FIG. 110 includes mask computation in step 2230. The output of the Edge Linking algorithm is used to generate the vaginal wall mask in the following way:

1. Vertical connected-edge image: VConnImg, a cumulative sum, is calculated for each row, starting from the center and extending both to the left and to the right.
2. Horizontal connected-edge image: HConnImg, a cumulative sum, is calculated for each column, starting from the center and extending both upward and downward.
3. The two cumulative sums are thresholded at >=1 and OR-ed together to yield the final vaginal wall mask.

$[FL]_{vid}$

Step 1454 in FIG. 74 depicts the determination of a fluid-and-foam mask, $[FL]_{vid}$, for an image of a tissue sample. This mask identifies fluid and foam regions appearing on tissue samples and is used in hard masking in the tissue characterization method 1438 of FIG. 74. FIG. 111A depicts an exemplary image 2234 of cervical tissue used to determine the corresponding fluid-and-foam image mask, $[FL]_{vid}$, 2238 shown in FIG. 111B.

In one embodiment, the fluid-and-foam image mask identifies regions where excess fluids and/or foam collect on cervical-tissue. Excess fluid or foam can collect near the speculum, around or in the os, and/or in the folds between the vaginal walls and the cervix, for example. One embodiment of the fluid-and-foam image mask, $[FL]_{vid}$, uses a measure of whiteness and a measure of blue-greenness to identify regions of fluid/foam. After extracting white and blue-green color features, thresholding and validation is performed to produce the final fluid-and-foam image mask, $[FL]_{vid}$.

FIG. 112 is a block diagram 2258 depicting steps in a method of determining a fluid-and-foam image mask, $[FL]_{vid}$, for an image of cervical tissue. The following describes the steps of the method 2258 shown in FIG. 112, according to one embodiment.

The method 2258 in FIG. 112 includes preprocessing in step 2260. First, remove glare from the RGB image. Retrieve or compute glare mask, glareMsk. Dilate glareMsk 4 times to obtain dilGlareMsk. Next, retrieve or compute ROI mask, ROIMsk. Finally, smooth each of the RGB channel using a 3×3 box car filter to remove noise.

Next, the method 2258 in FIG. 112 includes image color feature calculation in step 2262. This step computes a "whiteness" image, Wimg, and a "green-blueness" image, GBImg. First, calculate the luminance L from the RGB signal using the formula: $L=0.299*R+0.587*G+0.114*B$. Next, compute, normalize and threshold Wimg as follows:
1. $WImg=abs((R-G)/(R+G))+abs((R-B)/(R+B))+abs((G-B)/(G+B))$.
   This operation is a pixel-wise operation and is performed on each pixel sequentially.
2. Normalize Wimg: WImg=3−Wimg.
3. Set low luminance:pixels to 0 (low luminance pixels are unlikely to be in the fluid and foam regions):
   If L<mean(L), WImg=0.

Finally, compute, normalize and threshold BGImg as follows:
1. $BGImg=(abs((R+30-G)/(R+30+G))+abs((R+30-B)/(R+30+B))+abs((G-B)/(G+B)))$.
   This operation is a pixel-wise operation and is performed on each pixel sequentially.
2. Normalize BGImg, BGImg=3−BGImg.
3. Set low luminance pixels to 0 (low luminance pixels are unlikely to be in the fluid and foam regions):
   If L<0.65*mean(L), BGImg=0.

Next, the method 2258 in FIG. 112 includes processing and segmenting bright green-bluish regions in steps 2264, 2266, 2268, 2270, 2272, 2274, and 2276. These steps are performed as follows:
1. Retrieve or compute glare mask, glareMsk.
2. Fill glare regions of BGImg using glareMsk to perform run-length boundary interpolation as follows:
   a. Raster scan each row of glareMsk to find all beginnings and endsof pixel runs.
   b. For each pixel P(x,y) in a given run specified by beginning point P(xb, y) and end point P(xe,y) in the intensity image, replace P(x,y) by half the linearly interpolated value at P(x,y) from P(xb,y) and P(xe, y).
   c. Raster scan each column of glareMsk to find all beginnings and ends of pixel runs.
   d. For each pixel P(x,y) in a given run specified by beginning point P(x, yb) and end point P(x,ye) in the intensity image, add to P(x,y) half the linearly interpolated value at P(x,y) from P(x,yb) and P(x,ye).
3. Eliminate low intensity areas using a threshold of 1.5:
   If BGImg<1.5, BGImg=1.5.
4. Rescale the BGImg to [0, 1]:
   BGImg=BGImg−min(BGImg))/(3−min(BGImg).
5. Compute thresholds from image statistics and perform thresholding.
   a. Compute image mean intensity, Imean, for BGImg>0.
   b. Compute image standard deviation of intensity, IstdDev, for BGImg>0. Compute threshold thGB, thGB=Imean+1.63*IstdDev.
   c. Apply threshold limits:
      if thGB<0.80, thGB=0.80;
      if thGB>0.92, thGB=0.92.
   d. Threshold to get the initial green-bluish fluid and foam mask GBMask if BGImg>thGB, then
      GBMask=1; else
      GBMask=0.
6. Perform morphological processing to fill small holes and smooth boundaries of the found regions in GBMask:
   a. Dilate the segmentation mask GBMask twice, GBMask=dil(GBMask, 2).
   b. Erode the resultant mask three times, GBMask=erode(GBMask, 3).
   c. Dilate the resultant mask once, GBMask=dil(GBMask, 1).
7. Perform binary region labeling and small region removal:
   a. Perform a connected components labeling, described above, to label all found regions.
   b. Compute each region area, area, and eccentricity, ecc.
   c. Remove small and round regions and small line segments that are not likely to be the fluid and foam regions:
      If ((area<1000) AND (ecc<0.70)) OR ((area<300) AND (ecc>0.70)) OR (area<1000), remove region.
8. Green-Bluish feature validation for each found region is based on the original RGB values:
   a. For each found region, retrieve the mask, Imsk, and compute the mean intensities within the region for each of the red, green and blue channels as MRed, MGreen and Mblue.
   b. If the found region is tissue-like, remove the region:
      if [(MGreen−MRed)+(MBlue−MRed)]<−5 remove region.
   c. If the found region is too blue, remove the region:
      if (MBlue>MGreen+15) remove region.
9. The final green-bluish fluid and foam mask, FGBMask, is calculated by performing a flood-fill of "on" valued regions of GBMask from step 5 with seeds in the validated regions from step 6 and step 7.

Next, the method 2258 in FIG. 112 includes processing and segmenting pure white regions in steps 2278, 2280, 2282, 2284, 2286, 2288, and 2290. These steps are performed as follows:

1. Retrieve glare mask, glareMsk and ROI mask, ROIMsk.
2. Fill glare regions of WImg using glareMsk to perform run-length boundary interpolation as follows:
   a. Raster scan each row of glareMsk to find all beginnings and ends of pixel runs.
   b. For each pixel P(x,y) in a given run specified by beginning point P(xb, y) and end point P(xe,y) in the intensity image, replace P(x,y) by half the linearly interpolated value at P(x,y) from P(xb,y) and P(xe, y).
   c. Raster scan each column of glareMsk to find all beginnings and ends of pixel runs.
   d. For each pixel P(x,y) in a given run specified by beginning point P(x, yb) and end point P(x,ye) in the intensity image, add to P(x,y) half the linearly interpolated value at P(x,y) from P(x,yb) and P(x,ye).
3. Compute WImg mean, mWImg, and standard deviation, stdWImg.
4. Eliminate low intensity areas:
   if WImg<mWImg−0.1*stdWImg, WImg mWImg− 0.1*stdWImg.
5. Rescale the WImg to [0, 1]:
   WImg=WImg−min(WImg))/(3−min(WImg).
6. Compute thresholds from image statistics and perform thresholding:
   a. Compute image mean intensity, Imean, for WImg>0.
   b. Compute image standard deviation of intensity, IstdDev, for WImg>0.
   c. Compute threshold thW,
      thW=Imean+1.10*IstdDev.
   d. Threshold to get the initial green-bluish fluid and foam mask WMask:
      if ((WImg>thW) AND (pixel is included in ROIMsk)), then WMask=1; else
      WMask=0.
7. Perform morphological processing to fill small holes and smooth boundaries of the found regions in WMask:
   a. Erode the segmentation mask WMask twice, WMask=erode(WMask, 2).
   b. Dilate the resultant mask three times, WMask=dilate (WMask, 3).
8. Perform binary region labeling and small region removal:
   a. Perform a connected components labeling, as described, to label all found regions.
   b. Compute each region area, area.
   c. Remove small regions that are not likely to the fluid and foam regions:
      If (area<300) remove the region from the region list.
9. Whiteness feature validation for each found region based on the original RGB values:
   a. For each found region, retrieve the mask, iMsk, and compute the mean intensities within the region for each of the red, green and blue channels as iMRed, iMGreen and iMBlue.
   a. Dilate iMsk five times to obtain iD1Msk=dilate (iMsk, 5).
   b. Compute the perimeter pixels iPeriMsk from iD1Msk:
      iPeriMsk=not (erod (iD1Msk, 1)) AND (iD1Msk), 1).
   c. Dilate iPeriMsk three times to get the outer mask: iD2Msk=dilate (iPeriMsk, 3).
   d. Compute mean intensities on iD2Msk for each of the R, G and B channels as perimeter (Outer) means: pMRed, pMGreen and pMBlue.
   e. Compute the Inner region green-blueness:
      innerGB=(iMGreen−iMRed)+(iMBlue−iMRed).
   f. Compute the Inner region whiteness:
      innerW=3.0−(abs((iMRed−iMGreen)/(iMRed+iMGreen))+abs((iMGreen−iMBlue)/(iMGreen+iMBlue))+abs((iMBlue−iMRed)/(iMBlue+iMRed))).
   g. Compute the Outer region whiteness:
      outerW=3.0−(abs((pMRed−pMGreen)/(pMRed+pMGreen))+abs((pMGreen−pMBlue)/(pMGreen+pMBlue))+abs((pMBlue−pMRed)/(pMBlue+pMRed))).
   h. Compute the Outer region redness:
      outerRed=(pMRed−pMGreen)+(pMRed−pMBlue).
   i. Apply general whiteness validation rule:
      if (((innerGB<10) AND (outerRed>25)) OR (outerW>(innerW −0.1)), then:
      set isFluid to 0, since it is not likely to be a fluid and foam region; else,
      Set isFluid to 1.
   j. Very white fluid-foam validation rule:
      If ((innerW>(outerW+0.16)) set isFluid to 1.
   k. Very high inner green bluish fluid-foam validation rule:
      If (innerGB>10) set isFluid to 1.
10. The final white fluid-foam mask fWMask is calculated by performing a flood-fill of "on" valued regions of Mask from step 8 with seeds in the validated regions (isFluid=1) from step 9.

Finally, the method 2258 in FIG. 112 includes constructing the final fluid-foam mask. The final fluid-foam mask is a logical "OR" of the two segmented and validated masks as follows: FluidFoamMask=fBGMask OR fWMask.

Classifiers

In one embodiment, the tissue characterization system 100 of FIG. 1 comprises using broadband reflectance data obtained during a spectral scan of regions (interrogation points) of a tissue sample to determine probabilities that a given region belongs in one or more tissue-class/state-of-health categories. In one embodiment, probabilities of classification are determined as a combination of probabilities computed by two different statistical classifiers. The two classifiers are a DASCO classifier (discriminant analysis with shrunken covariances), and a DAFE classifier (discriminant analysis feature extraction). The DASCO classifier (step 1484, FIG. 74) uses a principal component analysis technique, and the DAFE classifier (step 1482, FIG. 74) uses a feature coordinate extraction technique to determine probabilities of classification.

The embodiment shown in FIG. 74 applies a necrosis mask 1424 and a hard "indeterminate" mask 1426 to a set of arbitrated broadband spectral data to eliminate the need to further process certain necrotic and indeterminate interrogation points in the classification steps 1482, 1484, 1486. After determining statistical classification probabilities in step 1486, the embodiment of FIG. 74 applies a soft "indeterminate" mask 1428 as well as the NED (no evidence of disease) classification result 1430 in order to obtain a final characterization 1432 of each interrogation point on the tissue sample as Necrotic, CIN 2/3, NED, or Indeterminate.

The statistical classifiers in steps 1482 and 1484 of FIG. 74 each determine respective probabilities that a given region belongs to one of the following five tissue-class/state-of-health categories: (1) Normal squamous ($N_s$), (2) CIN 1 ($C_1$), (3) CIN 2/3 ($C_{23}$), (4) Metaplasia (M), and (5) Normal columnar ($C_{o1}$) tissue. Other embodiments use one or more of the following tissue classes instead of or in addition to the categories above: CIN 2, CIN 3, NED (no evidence of disease), and cancer. The category with the highest computed probability is the category that best characterizes a given region according to the classifier used. In one alternative embodiment, other categories and/or another number of categories are used. The results of the two statistical classifiers are combined with the NED mask classification, along with the hard and soft "indeterminate" masks, to obtain a final characterization for each interrogation point 1432.

In one embodiment, statistical classification includes comparing test spectral data to sets of reference spectral data (training data) representative of each of a number of classes. A collection of reference spectra from the same tissue class is a class data matrix. For example, a class data matrix $T_j$ comprising reference spectra (training data) from samples having known class j is expressed as in Equation 96 as follows:

$$T_j = \begin{bmatrix} S_1(\lambda_1) & S_1(\lambda_2) & \cdots & S_1(\lambda_p) \\ S_2(\lambda_1) & S_2(\lambda_2) & \cdots & S_2(\lambda_p) \\ \vdots & \vdots & \cdots & \vdots \\ S_{n_j}(\lambda_1) & S_{n_j}(\lambda_2) & \cdots & S_{n_j}(\lambda_p) \end{bmatrix} \equiv \begin{bmatrix} S_1(\lambda) \\ S_2(\lambda) \\ \vdots \\ S_{n_j}(\lambda) \end{bmatrix} \quad (96)$$

where class j contains $n_j$ reference spectra, $S(\lambda)$, and each reference spectra, $S(\lambda)=[S(\lambda_1), S(\lambda_2), \ldots, S(\lambda_p)]$, is a p-dimensional vector where p is the number of wavelengths in a measured spectrum. The class data matrix $T_j$ has associated with it a class mean vector $\mu_j$ (a 1-by-p vector) and a class covariance matrix $C_j$ (a p-by-p matrix) as shown in Equations 97-99 as follows:

$$\mu_j(\lambda) \equiv \mu_j = \left[\frac{1}{n_j}\sum_{k=1}^{n_j} S_k(\lambda_1) \frac{1}{n_j}\sum_{k=1}^{n_j} S_k(\lambda_2) \cdots \frac{1}{n_j}\sum_{k=1}^{n_j} S_k(\lambda_p)\right] \quad (97)$$

$$C_j = \frac{1}{n_j - 1}\sum_{k=1}^{n_j}(S_k(\lambda) - \mu_j)^T(S_k(\lambda) - \mu_j) \quad (98)$$

$$\equiv \frac{1}{n_j - 1}(T_j - M_j)^T(T_j - M_j)$$

$$M_j = \begin{bmatrix} \mu_j \\ \mu_j \\ \vdots \\ \mu_j \end{bmatrix}_{n_j \times p} \quad (99)$$

Statistical tissue classification uses reference data to determine for a given test spectrum to which class(es) and with what probabilit(ies) that test spectrum can be assigned.

The broadband data used in the statistical classifiers in steps 1482 and 1484 are wavelength truncated. For the DASCO classifier (step 1484), only training data and testing data that corresponds to wavelengths between about 400 nm and about 600 nm are used. For the DAFE classifier (step 1482), only training data and testing data that correspond to wavelengths between about 370 nm and about 650 nm are used. One alternative embodiment uses different wavelength ranges. The training data include reference broadband reflectance data from interrogation points having a known classification in one of the five states of health, and the testing data include broadband reflectance data from a region having an unknown classification.

The discriminant analysis feature extraction (DAFE) method of step 1482 in FIG. 74 transforms a measurement of high dimension into a feature space of lower dimension. Here, the feature space is the orthogonal projection in the direction of maximal data discrimination. The DAFE method includes constructing feature coordinates by computing the feature space projection matrix. The projection matrix requires the inversion of the pooled within-groups covariance matrix, $C_{pool}$. Where $T_1, T_2, \ldots, T_g$ are training matrices for classes 1 through g (here, for example, g=5), the number of reference spectra in a given class, $n_j$, may be less than the number of wavelengths in a measured spectrum, p; and $C_{pool}$ is therefore singular and cannot be inverted.

Thus, in one embodiment of the DAFE method of step 1482, the spectral measurements are subsampled so that a covariance matrix can be computed. In one embodiment, a subsampling rate, $n_z$, is determined according to Equation 100:

$$n_z = \max\left(\left\lfloor\frac{p}{n_1}, \frac{p}{n_2}, \ldots, \frac{p}{n_g}\right\rfloor\right) + 1 \quad (100)$$

where p is the number of wavelengths in a measured spectrum; $n_1, n_2, \ldots, n_g$ represent the numbers of reference spectra in each of classes 1, 2, ..., g, respectively; and $\lfloor \; \rfloor$ indicates the "nearest integer" function. Typically, $n_z=2$ or 3, but values up to about 10 do not generally remove too much information from a measured reflectance spectrum, and may also be considered. After subsampling, the non-singular pooled covariance matrix, $C_{pool}$, is computed according to Equation 101 as follows:

$$C_{pool} = \frac{1}{n-g}\sum_{k=1}^{g}(n_k - 1) \cdot C_k \quad (101)$$

$$n = \sum_{k=1}^{g} n_k$$

where $n_k$ is the number of reference spectra in class k; and $C_k$ is the covariance matrix for class k. Then, the between-groups covariance, $C_{btwn}$, is computed according to Equation 102:

$$C_{btwn} = \frac{1}{g}\sum_{k=1}^{g} n_k \cdot (\mu_k - \bar{\mu})^T(\mu_k - \bar{\mu}) \quad (102)$$

$$\bar{\mu} = \frac{1}{n}\sum_{k=1}^{g} n_k \cdot \mu_k$$

$$n = \sum_{k=1}^{g} n_k$$

Next, the maxtrix $$P = C_{pool}^{-1} \cdot C_{bwtn}$$

is formed and singular value decomposition is applied to obtain the following:

$$P = U\ D\ V^T \tag{103}$$

Let $U_{g-1}$ equal the first $g-1$ columns of the orthogonal matrix of singular values U as follows:

$$U = \begin{bmatrix} u_{11} & u_{12} & \cdots & u_{1,g-1} & \cdots & u_{1p} \\ u_{21} & u_{22} & \cdots & u_{2,g-1} & \cdots & u_{2p} \\ \vdots & \vdots & \cdots & \vdots & \cdots & \vdots \\ u_{p,1} & u_{p,2} & \cdots & u_{p,g-1} & \cdots & u_{p,p} \end{bmatrix} \Rightarrow U_{g-1} = \begin{bmatrix} u_{11} & u_{12} & \cdots & u_{1,g-1} \\ u_{21} & u_{22} & \cdots & u_{1,g-1} \\ \vdots & \vdots & \cdots & \vdots \\ u_{p,1} & u_{p,2} & \cdots & u_{p,g-1} \end{bmatrix} \tag{104}$$

Then, the feature projection, mapping measured space into feature space, is obtained via right-multiplication by $U_{g-1}$.

The DAFE classification algorithm (step 1482 of FIG. 74) proceeds as follows. Let $\hat{T}_1, \hat{T}_2, \ldots, \hat{T}_g$ be the wavelength reduced, subsampled training (class data) matrices and $\hat{S}(\lambda)$ be the corresponding wavelength reduced, subsampled test spectrum. The matrices $\hat{T}_j$ and $\hat{S}(\lambda)$ are projected into feature space as follows:

$$\hat{T}_j \mapsto \hat{T}_j \cdot U_{g-1} \equiv V_j \tag{105}$$

$$\hat{S}(\lambda) \mapsto \hat{S}(\lambda) \cdot U_{g-1} \equiv x$$

Next, the group mean vectors, group covariance matrices, and pooled within-groups covariance matrix are computed using the projection matrix, $V_j$, in Equation 105, and using Equations 97, 98, and 101 as shown in Equations 106-108:

$$\mu_j = \text{mean}(V_j) \tag{106}$$

$$C_j = \text{cov}(V_j) \tag{107}$$

$$C_{pool} = \frac{1}{n-g} \sum_{j=1}^{g} (n_j - 1) \cdot C_j \tag{108}$$

Then, the Friedman matrix is calculated using the Friedman parameters $\gamma$ and $\lambda$ according to Equation 109 as follows:

$$Fr_j(\gamma, \lambda) = (1-\gamma)[(1-\lambda)C_j + \lambda C_{pool}] + \frac{\gamma}{g-1} tr[(1-\lambda)C_j + \lambda C_{pool}] \cdot I_{(g-1)\times(g-1)} \tag{109}$$

In one embodiment, $\gamma=0$ and $\lambda=0.5$. Next, the Mahalanobis distance, $d_j(x)$, is determined from the test spectrum to each data class according to Equation 110:

$$d_j^2(x) = (x-\mu_j) \cdot Fr_j^{-1}(\gamma, \lambda) \cdot (x-\mu_j)^T \tag{110}$$

The Mahalanobis distance is a (1-by-1) number. Next, the Bayes' score is computed according to Equation 111:

$$br_j(x) = d_j^2(x) - 2\ln(r_j) + \ln(|\det(Fr_j(\gamma,\lambda))|) \tag{111}$$

The index j at which the minimum Bayes' score is attained indicates the classification having the highest probability for the test point in question. The DAFE probability of classification for class j can be computed for any of the g classifications according to Equation 112:

$$\text{Prob}(x \in \text{Class } j) = \frac{\exp\left(-\frac{1}{2} br_j(x)\right)}{\sum_{k=1}^{g} \exp\left(-\frac{1}{2} br_k(x)\right)} \tag{112}$$

$$= \frac{\frac{r_j}{|\det(Fr_j(\gamma, \lambda))|} \cdot \exp\left(-\frac{1}{2} d_j^2(x)\right)}{\sum_{k=1}^{g} \frac{r_k}{|\det(Fr_k(\gamma, \lambda))|} \cdot \exp\left(-\frac{1}{2} d_k^2(x)\right)}$$

DAFE classification probabilities are computed thusly for each of the interrogation points having a test reflectance spectrum, $S(\lambda)$, that is not eliminated in the Necrosis masking step (1424) or the hard "indeterminate" masking step (1426) in the embodiment shown in FIG. 74.

Step 1484 in FIG. 74 is the DASCO (discriminant analysis with shrunken covariances) method. Like the DAFE method of step 1482, the DASCO method reduces the dimensionality of the measured space by transforming it into a lower dimensional feature space. DASCO differs from DAFE in that the feature space for the DASCO method is along orthogonal directions of maximal variance, not (necessarily) maximal discrimination. Also, DASCO uses two Mahalanobis distances, not just one. The first distance is the distance to feature centers in primary space and the second distance is the distance to feature centers in secondary space.

In one embodiment, the DASCO method (step 1484) proceeds as follows. First, a collection $\{T_1, T_2, \ldots, T_g\}$ of $n_j$-by-p training matrices is obtained from reference (training) broadband arbitrated reflectance measurements. The amount of reflectance spectral data obtained from a test region (interrogation point), as well as the amount of training data, are reduced by truncating the data sets to include only wavelengths between 400 nm and 600 nm.

Next, the training data and test data are scaled using mean scaling (mean centering) as follows:

$$T_j \mapsto (T_j - M_j) \equiv Y_j, \text{ where } M_j = \begin{bmatrix} \mu_j \\ \mu_j \\ \vdots \\ \mu_j \end{bmatrix}_{n_j \times p} \quad (113)$$

$$S(\lambda) \to S(\lambda) - \mu_j \equiv S_j \quad (114)$$

where j=1, 2, . . . , g and g is the total number of tissue-class/state-of-health classes. The number of principal components in primary space is $n_p$, and the number of principal components in secondary space is $n_s$. The total number of components is $n_t$. In one embodiment, $n_p=3$, $n_s=1$, and $n_t=4$.

Next, the first $n_t$ principal component loadings and scores are computed. This involves computing the singular value decomposition of the mean scaled training data matrix $Y_j$ from Equation 113, as follows:

$$Y_j = U_j D_j V_j^T \quad (115)$$

A similar computation was made in Equation 104. Let $V_{j,n_t}$ be the matrix comprised of the first nt columns of $V_j$. The loadings and scores for $Y_j$ are therefore indicated, respectively, in Equations 116 and 117, as follows:

$$Ld_j = V_{j,n_t} \quad (116)$$

$$sc_j = Y_j \cdot V_{j,n_t} = Y_j \cdot Ld_j \quad (117)$$

where $Ld_j$ is a p-by-$n_t$ matrix, and $sc_j$ is an $n_j$-by-$n_t$ matrix.

The next step in the DASCO method is to compute the class mean scores and covariances. First, the class mean vector in primary space, $v_{j,p}$, and the class mean vector in secondary space, $v_{j,s}$, are computed as follows:

$v_j$=mean($sc_j$) (the mean is computed analogously to $\mu_j$ in Equation 97) (118)

$$v_j = [v_{j,1}, v_{j,2}, \ldots, v_{j,n_p}, v_{j,n_p+1}, v_{j,n_p+2}, \ldots, v_{j,n_p+n_s}] = [v_{j,p}, v_{j,s}] = v_{j,p} \oplus v_{j,s} \quad (119)$$

where $v_{j,p} = [v_{j,1}, v_{j,2}, \ldots, v_{j,n_p}]$ and $v_{j,s} = [v_{j,n_p+1}, v_{j,n_p+2}, \ldots, v_{j,n_p+n_s}]$ (120)

Next, $C_j$=cov($sc_j$) is defined as the class covariance matrix analogous to that in Equation 100. In a manner similar to the computation of the primary and secondary space class mean vectors above, $C_j$ is decomposed into the primary ($C_{j,p}$) and secondary ($C_{j,s}$) space covariance matrices according to Equations 121-124 as follows:

$$C_j = C_{j,p} \oplus C_{j,s} \quad (121)$$

$$C_j = \begin{bmatrix} c_{11}(j) & c_{12}(j) & \cdots & c_{1,n_p}(j) & c_{1,n_p+1}(j) & c_{1,n_p+2}(j) & \cdots & c_{1,n_p+n_s}(j) \\ c_{21}(j) & c_{22}(j) & \cdots & c_{2,n_p}(j) & c_{2,n_p+1}(j) & c_{2,n_p+2}(j) & \cdots & c_{2,n_p+n_s}(j) \\ \vdots & \vdots & \cdots & \vdots & \vdots & \vdots & \cdots & \vdots \\ c_{n_t,1}(j) & c_{n_t,2}(j) & \cdots & c_{n_t,n_p}(j) & c_{n_t,n_p+1}(j) & c_{n_t,n_p+2}(j) & \cdots & c_{n_t,n_p+n_s}(j) \end{bmatrix} \quad (122)$$

$$C_{j,p} = \begin{bmatrix} c_{11}(j) & c_{12}(j) & \cdots & c_{1,n_p}(j) \\ c_{21}(j) & c_{22}(j) & \cdots & c_{2,n_p}(j) \\ \vdots & \vdots & \cdots & \vdots \\ c_{n_t,1}(j) & c_{n_t,2}(t) & \cdots & c_{n_t,n_p}(j) \end{bmatrix} \quad (123)$$

$$C_{j,s} = \begin{bmatrix} c_{1,n_p+1}(j) & c_{1,n_p+2}(j) & \cdots & c_{1,n_p+n_s}(j) \\ c_{2,n+1}(j) & c_{2,n_p+2}(j) & \cdots & c_{2,n_p+n_s}(j) \\ \vdots & \vdots & \cdots & \vdots \\ c_{n_t,n_p+1}(j) & c_{n_t,n_p+2}(j) & \cdots & c_{n_t,n_p+n_s}(j) \end{bmatrix} \quad (124)$$

Next, the scaled test spectrum from Equation 114 is projected into each principal component space according to Equation 125:

$$x(j) = Ld_j \cdot S_j \quad (125)$$

Then, x(j) is decomposed into primary and secondary space vectors as follows:

$$x(j) = [x_1(j), x_2(j), \ldots, x_{n_t}(j)] = x_{j,p} \oplus x_{j,s} \quad (126)$$

where $x_{j,p} = [x_1(j), x_2(j), \ldots, x_{n_p}(j)]$ is the projection of x(j) into primary space and $x_{j,s} = [x_{n_p+1}(j), x_{n_p+2}(j), \ldots, x_{n_p+n_s}(j)]$ is the projection of x(j) into secondary space.

The Mahalanobis distances in primary and secondary space are computed according to Equations 127 and 128 as follows:

$$d_{j,p}^2(x(j)) = (x_{j,p} - v_{j,p}) \cdot C_{j,p}^{-1} \cdot (x_{j,p} - v_{j,p})^T \quad (127)$$

$$d_{j,s}^2(x(j)) = (x_{j,s} - v_{j,s}) \cdot F_{j,s}^{-1} \cdot (x_{j,s} - v_{j,s})^T \quad (128)$$

where $$F_{j,s} = \frac{tr(C_{j,s})}{n_s} \cdot I_{n_s \times n_s}.$$

Then, the total distance is computed according to Equation 129 as follows:

$$d(x(j)) = \sqrt{d_{j,p}^2(x(j)) + d_{j,s}^2(x(j))} \quad (129)$$

The DASCO probability of class assignment to class j is obtained by computing the Bayes' score according to Equations 130 and 131 as follows:

$$br(x(j)) = d^2(x(j)) - 2\ln(r_j) + \ln(det(C_{j,p})) + n_s \cdot \ln(|det(Fr_{j,s})|) \quad (130)$$

$$Prob(x(j) \in \text{Class } j) = \frac{\exp\left(-\frac{1}{2}br_j(x(j))\right)}{\sum_{k=1}^{g} \exp\left(-\frac{1}{2}br_k(x(k))\right)} \quad (131)$$

Equation 131 is evaluated for all classes j=1, 2, ... g. DASCO classification probabilities are computed thusly for each of the interrogation points having a test reflectance spectrum, $S(\lambda)$, that is not eliminated in the Necrosis masking step (1424) or the hard "indeterminate" masking step (1426) in the embodiment shown in FIG. 74.

Probabilities determined using the DAFE classifier in step 1482 of FIG. 74 and probabilities determined using the DASCO classifier in step 1484 are combined and normalized in step 1486 to obtain for each interrogation point a set of statistical probabilities that the point belongs, respectively, to one of a number of tissue-class/state-of-health categories. In one embodiment, there are five classes, as described above, including the following: (1) Normal squamous ($N_s$), (2) CIN 1 ($C_1$), (3) CIN 2/3 ($C_{23}$), (4) Metaplasia (M), and (5) Columnar ($C_{o1}$) tissue.

The probability matrices $P_{DAFE}$ and $P_{DASCO}$ contain probability vectors corresponding to the interrogation points in the scan pattern and are expressed as shown in Equations 132 and 133 as follows:

$$P_{DAFE} = \begin{bmatrix} P_{DAFE,1}(1) & P_{DAFE,2}(1) & \cdots & P_{DAFE,g}(1) \\ P_{DAFE,1}(2) & P_{DAFE,2}(2) & \cdots & P_{DAFE,g}(2) \\ \vdots & \vdots & \cdots & \vdots \\ P_{DAFE,1}(nip) & P_{DAFE,2}(nip) & \cdots & P_{DAFE,g}(nip) \end{bmatrix} \quad (132)$$

$$P_{DASCO} = \begin{bmatrix} P_{DASCO,1}(1) & P_{DASCO,2}(1) & \cdots & P_{DASCO,g}(1) \\ P_{DASCO,1}(2) & P_{DASCO,2}(2) & \cdots & P_{DASCO,g}(2) \\ \vdots & \vdots & \cdots & \vdots \\ P_{DASCO,1}(nip) & P_{DASCO,2}(nip) & \cdots & P_{DASCO,g}(nip) \end{bmatrix} \quad (133)$$

where g is the total number of classes (for example, g=5); nip is the total number of interrogation points for which DAFE and DASCO probabilities are calculated (for example, nip=up to 499); $P_{DAFE,i}(j)$ represents the DAFE probability that the interrogation point j belongs to class i; and $P_{DASCO,i}(j)$ represents the DASCO probability that the interrogation point j belongs to class i.

Step 1486 of FIG. 74 represents the combination and normalization of classification probabilities determined by the DAFE and DASCO classifiers in steps 1482 and 1484, respectively. The combined/normalized probability matrix, $P_{COMB}$, is obtained by multiplying the probability matrices $P_{DAFE}$ and $P_{DASCO}$ (Equations 134 and 135) element-wise and dividing the row-wise product by the sum of each row's elements.

Combining Spectral and Image Data

The block diagram of FIG. 74 includes steps representing the combination of spectral masks and image masks (1468, 1470, 1472, 1474), as well as the application of the combined masks (1466, 1476, 1424, 1478, 1480, 1424, 1426, 1428, 1430) in a tissue characterization system, according to one embodiment. These steps are discussed in more detail below.

As discussed above, the $\text{Necrosis}_{spec}$ mask identifies interrogation points whose spectral data are indicative of necrotic tissue. Since necrosis is one of the categories in which interrogation points are classified in step 1432 of FIG. 74, the $\text{Necrosis}_{spec}$ mask is used not only to eliminate interrogation points from further processing, but also to positively identify necrotic regions. Therefore, it is necessary to filter out points affected by certain artifacts that may erroneously cause a positive identification of necrosis.

Step 1466 of FIG. 74 indicates that two image masks are applied to the necrosis spectral mask—the smoke tube mask, $[ST]_{vid}$, 1450 and the speculum mask, $[SP]_{vid}$ 1452. Regions in which a speculum or smoke tube has been identified cannot be positively identified as necrotic. Thus, interrogation points having any portion covered by pixels indicated by the smoke tube mask, $[ST]_{vid}$, 1450 and/or the speculum mask, $[SP]_{vid}$, 1452 are identified as "Indeterminate" and are eliminated from the necrosis mask.

Following this treatment, the necrosis mask is then applied in the broadband reflectance spectra classification sequence in step 1424 of FIG. 74. Each interrogation point at which the necrosis mask applies is classified as "Necrotic". The broadband spectral data at these interrogation points are then eliminated from further processing, or, alternately, the results of the statistical classifiers at these points are ignored in favor of classification of the points as "Necrotic". Similarly, the necrosis mask is applied in the NED (no evidence of disease) spectral classification sequence in step 1476 of FIG. 74. Each interrogation point at which the necrosis mask applies is classified as "Necrotic". The $\text{NED}_{spec}$ mask need not be computed for these interrogation points, or, alternately, the results of the $\text{NED}_{spec}$ mask at these points may be ignored in favor of classification of the points as "Necrotic".

Three image masks are combined to form a fluorescence hard mask, "F Hard," which is applied in the NED (no evidence of disease) spectral classification sequence in step 1478 of FIG. 74. As discussed hereinabove, hard masking results in a characterization of "Indeterminate" at affected interrogation points, and no further classification computations are necessary for such points. The combined fluorescence hard mask, "F Hard," 1468 is a combination of the three image masks shown in FIG. 74 (1448, 1450, 1452), according to Equation 134 as follows:

$$\text{F Hard} = [ROI]_{vid} \text{ OR } [ST]_{vid} \text{ OR } [SP]_{vid} \quad (134)$$

The combined "F Hard" mask is applied in the NED spectral classification sequence in step 1478 of FIG. 74. Each interrogation point at which the "F Hard" mask applies is classified as "Indeterminate". The $\text{NED}_{spec}$ mask is not computed for these interrogation points. The "F Hard" mask applies for each interrogation point having any portion covered by pixels indicated by the "F Hard" combined image mask.

Two spectral masks and five image masks are combined to form a broadband reflectance "hard" mask, which is applied in the broadband reflectance statistical classification sequence in step 1426 of FIG. 74. The combined hard mask, "BB Hard", 1474 uses the image masks $[ST]_{vid}$, $[SP]_{vid}$, $[ROI]_{vid}$, and $[VW]_{vid}$ (1450, 1452, 1448, 1454) as hard masks, and also treats them as "anchors" to qualify the sections of the two spectral masks—[CE]spec and [MU]spec (1444, 1446)—that are used as hard masks. The outer rim of interrogation points in the spectral pattern is also used as an anchor to the spectral masks. Finally, the intersection of the fluid-and-foam image mask $[FL]_{vid}$ (1456) and the mucus spectral mask $[MU]_{spec}$ (1446) is determined and used as a hard mask in "BB Hard" (1474). Each interrogation point at which the "BB Hard" mask applies is classified as "Indeterminate". The broadband spectral data at these interrogation points are then eliminated from further processing, or, alternately, the results of the statistical classifiers at these points are ignored in favor of classification of the points as "Indeterminate".

In one embodiment, the combined hard mask, "BB Hard," 1474 of FIG. 74 is determined according to the following steps.

First, form a combined image processing hard mask IPHardIPMsk using all the interrogation points (IP's) that have any portion covered by one or more of the followng image masks: $[ST]_{vid}$, $[SP]_{vid}$, $[VW]_{vid}$ and $[ROI]_{vid}$. The combined mask is expressed as: IPHardIPMsk=$[ST]_{vid}$ OR $[SP]_{vid}$ OR $[VW]_{vid}$ OR $[ROI]_{vid}$. Extend IPHardIPMsk to include the level one and level two neighbors of the interrogation points indicated above. For example, each IP that is not on an edge has 6 level one neighbors and 12 level two neighbors, as shown in the scan pattern 202 in FIG. 5. Let extIMHardIPMsk be the new mask. Add all outer rim interrogation points to extIMHardIPMsk to form anchorMsk. The rim is defined by the following interrogation points for the 499-point scan pattern 202 shown in FIG. 5: 1-9, 17-20, 31 -33, 47-48, 65-66, 84-85, 104-105, 125-126, 147-148, 170, 193, 215-216, 239, 263, 286-287, 309, 332, 354-355, 376-377, 397-398, 417-418, 436-437, 454-455, 469-471, 482-485, 493-499. Form a combined spectral mask SpecIPMsk using all the interrogation points that are marked as either $[CE]_{spec}$ or $[MU]_{spec}$ (or both). Intersect the image processing anchor mask and the combined spectral mask to obtain SPHardMsk: SPHardMsk=anchorMsk AND SpecIPMsk. Intersect the image processing mask, $[FL]_{vid}$, and spectral mucus mask, $[MU]_{spec}$, to obtain the fluid hard mask FluidHardIPMsk, FluidHardIPMsk=$[FL]_{vid}$ AND ($[MU]_{spec}$ OR $[CE]_{spec}$). Finally form the final hard mask: BBHard=IPHardIPMsk OR SPHardMsk OR FluidHardIPMsk.

Two image masks—$Blood_{vid}$ and $Os_{vid}$ (1458, 1460)—are combined to form a fluorescence "soft" mask, "F soft," 1470 which is applied in the NED spectral classification sequence in step 1480 of FIG. 74. As discussed hereinabove, soft masking involves applying a weighting function to data from points identified by the mask in order to weight the data according to the likelihood they are affected by an artifact. The mask "F soft" determines two weighting functions—$pen_{blood}(IP)$ and $pen_{os}(IP)$—for interrogation points (IP's) that are at least partially covered by the image masks $Blood_{vid}$ and $Os_{vid}$ (1458, 1460). As discussed hereinabove, a percentage coverage, α, is determined for each interrogation point according to the percentage of pixels corresponding to the interrogation point that coincide with the image mask. For the image masks $Blood_{vid}$ and $OS_{vid}$, (1458, 1460), corresponding values $\alpha_{blood}(IP)$ and $\alpha_{os}(IP)$ are determined for each affected interrogation point, and Equations 135 and 136 are used to calculate the corresponding weighting at these interrogation points:

$$pen_{blood}(IP)=1-\alpha_{blood}(IP) \quad (135)$$

$$pen_{os}(IP)=1-\alpha_{os}(IP) \quad (136)$$

The application of $pen_{blood}(IP)$ and $pen_{os}(IP)$ in the NED spectral classification sequence of step 1480 is discussed in more detail below.

Two image masks—$Glare_{vid}$ and $Mucus_{vid}$ (1462, 1464)—are combined to form a broadband reflectance "soft" mask, "BB soft", 1472 which is applied in the broadband reflectance statistical classification sequence in step 1428 of FIG. 74. As discussed hereinabove, soft masking involves applying a weighting function to data from points identified by the mask in order to weight the data according to the likelihood it is affected by an artifact. The mask "BB soft" determines two weighting functions—$pen_{glare}(IP)$ and $pen_{mucus}(IP)$—for interrogation points (IP's) that are at least partially covered by the image masks $Glare_{vid}$ and $Mucus_{vid}$ (1462, 1464). As discussed hereinabove, a percentage coverage, a, is determined for each interrogation point according to the percentage of pixels corresponding to the interrogation point that coincide with the image mask. For the image masks $Glare_{vid}$ and $Mucus_{vid}$, (1462, 1464) corresponding values $\alpha_{glare}(IP)$ and $\alpha_{mucus}(IP)$ are determined for each affected interrogation point, and Equations 137 and 138 are used to calculate the corresponding penalties at these interrogation points:

$$pen_{glare}(IP)=1-\{\alpha_{glare}(IP)\}^{1/5} \quad (137)$$

$$pen_{mucus}(IP)=1-\alpha_{mucus}(IP) \quad (138)$$

The application of $pen_{glare}(IP)$ and $pen_{mucus}(IP)$ in the broadband reflectance statistical classification sequence at step 1428 is discussed in more detail below.

The tissue-class/state-of-health classification of interrogation points includes the application of masks as determined above. These steps are shown in FIG. 74. The tissue-class/state-of-health classification method includes an NED (no evidence of disease) spectral classification sequence, as well as a broadband reflectance statistical classification sequence, that apply the combined hard masks and soft masks described above. As discussed hereinabove, the separate identification of necrotic regions and NED regions based on at least partially heuristic techniques allows for the development of a statistical classifier that concentrates on identifying tissue less conducive to heuristic classification, for example, CIN 2/3 tissue. Furthermore, by eliminating data affected by artifacts, the statistical classifiers are further improved, leading to improved sensitivity and specificity of the final classification of a tissue sample.

The Necrosis mask (1424, 1476), "BB Hard" mask (1426), and "F Hard" mask (1478) are applied as shown in FIG. 74. Interrogation points coinciding with these masks are identified as either "Necrotic" or "Indeterminate", as discussed hereinabove. In one embodiment, these regions are removed from further consideration. The NED classification sequence then applies the "F Soft" mask in step 1480. This is performed as explained below.

The $NED_{spec}$ mask identifies interrogation points that indicate normal squamous tissue, which is class (1) of the five classes used by the DAFE and DASCO classifiers discussed previously. The $NED_{spec}$ mask assigns at each indicated (masked) interrogation point a probability vector $p_s=[1, 0, \ldots, 0]$, where the normal squamous classification probability, $N_s$ (class 1), is set equal to 1 and all other class probabilities are set equal to 0. The "F Soft" mask is applied in step 1480 by multiplying the $N_s$ probability of indicated (masked) NED interrogation points by the product of the blood and os weighting functions, $pen_{blood}(IP) \cdot pen_{os}(IP)$. Hence, the normal squamous classification probability, Ns, at these points will be less than 1.0. If the product, $pen_{blood}(IP) \cdot pen_{os}(IP)$, is equal to 0, then the interrogation point IP is classified as "Indeterminate". The $NED_{spec}$ mask probability vector $p_s=0$ for all other interrogation points. It is noted that if an interrogation point is not identified by the $NED_{spec}$ mask, its $N_s$ probability calculated by the broadband reflectance statistical classification sequence is unaffected. The application of the overall $NED_{spec}$ mask is explained below in the discussion of step 1430 in FIG. 74.

The broadband reflectance statistical classification sequence applies the Necrosis mask (1424) and the "BB Hard" mask (1426) before determining statistical classification probabilities in steps 1482, 1484, and 1486. As discussed above, the output of the broadband statistical classification is the probability matrix, $P_{COMB}$, made up of probability vectors for the interrogation points, each vector indicating respective probabilities that a given interrogation point belongs to one of the five tissue-class/state-of-health categories—(1) Normal squamous ($N_s$), (2) CIN 1 ($C_1$), (3) CIN 2/3 ($C_{23}$), (4) Metaplasia (M), and (5) Columnar ($C_{o1}$) tissue. The broadband reflectance statistical classification sequence then applies the "BB Soft" mask in step 1428 by multiplying all five probabilities for each affected (masked) interrogation point by the quantity $pen_{glare}(IP) \cdot pen_{mucus}(IP)$.

Step 1432 of FIG. 74 classifies each interrogation point as Necrotic, CIN 2/3, NED, or Indeterminate. In one embodiment, the probabilities in $P_{COMB}$ that correspond to CIN 2/3 classification, $P_{COMB,C23}(IP)$ [class 3], are considered indicative of "CIN 2/3" classification in step 1432, and all other classification categories in $P_{COMB}$—classes 1, 2, 4, and 5 ($N_s$, $C_1$, M, and $C_{o1}$)—are considered indicative of "NED" tissue. In an alternative embodiment, further classification distinctions are made in step 1432.

In step 1430 of FIG. 74, the results of the $NED_{spec}$ mask are applied to the broadband reflectance-based classifications, $P_{COMB}$. The "Necrotic" interrogation points and the hard-masked "Indeterminate" points have been identified and removed before step 1430. In step 1430, the remaining interrogation points are either classified as "Indeterminate" or are assigned a value of CIN 2/3 classification probability, $p_{C23}(IP)$. Here, $p_{C23}(IP)$ is the CIN 2/3 classification probability for interrogation point IP that is set as a result of step 1430. Interrogation points that are not identified by the $NED_{spec}$ mask have been assigned $NED_{spec}$ mask probability vector $p_s=0$, and $p_{C23}(IP)=p_{COMB,C23}(IP)$ for these points. Interrogation points that are identified by the NED mask have $p_s=[1, 0, \ldots, 0]$, or $p_s=[\{pen_{blood}(IP) \cdot pen_{os}(IP)\}, 0, \ldots, 0]$, (where $p_{s,Ns}(IP)=1$ or $pen_{blood}(IP) \cdot pen_{os}(IP)$) depending on whether the point has been penalized or not by the "F Soft" mask in step 1480. The following describes how values of $p_{C23}(IP)$ are determined for interrogation pionts that are identified by the $NED_{spec}$ mask:

Due to spectral arbitration in step 128 of FIG. 74, the broadband signal may have been suppressed for some interrogation points, and only fluorescence spectra are available. For these interrogation points, the following rules are applied in step 1430 of FIG. 74:

1. IF $p_{s,Ns}(IP)>0$, THEN $p_{C23}(IP)=0$.
2. ELSE the interrogation point IP is classified as "Indeterminate".

For points having a valid arbitrated broadband signal and fluorescence signal, the following fules are applied in step 1430 of FIG. 74:

1. IF $p_{s,Ns}(IP)=1$, THEN $p_{C23}(IP)=0$.
2. IF $p_{s,Ns}(IP)=0$, THEN $p_{C23}(IP)=P_{COMB,C23}(IP)$.
3. IF $p_{s,Ns}(IP)<1$, THEN:
   IF $p_{s,Ns}(IP)<p_{COMB,Ns}(IP)$, THEN $p_{C23}(IP) \, p_{COMB,C23}(IP)$, ELSE, $p_{C23}(IP)=0$.

Step 1432 of FIG. 74 classifies each interrogation point as Necrotic, CIN 2/3, NED, or Indeterminate. Necrotic and hard-masked Indeterminate interrogation points are identified prior to step 1430, as described above. In step 1430, the remaining interrogation points are either classified as Indeterminate or are assigned a value of $p_{C23}(IP)$. For these points, if $p_{C23}(IP)=0$, the point is classified as NED. If $p_{C23}(IP)>0$, the point is considered to have a non-zero probability of high grade disease (CIN 2/3). In one embodiment, disease display (step 138 of FIG. 74) uses these non-zero $p_{C23}(IP)$ values to distinguish regions having low probability of CIN 2/3 and regions having high probability of CIN 2/3.

Step 1434 of FIG. 74 represents post-classification processing. In one embodiment, this includes a final clean-up step to remove isolated CIN 2/3-classified interrogation points on the outer rim of the spectral scan pattern (for example, the outer rim consists of the numbered interrogation points listed hereinabove. A CIN 2/3-classified interrogation point is considered isolated if it has no direct, level-1 neighbors that are classified as CIN 2/3. Such isolated points are re-classified as "Indeterminate" in step 1434 of FIG. 74.

Image Enhancement

The brightness of an acquired image of a tissue sample may change from patient to patient due to obstructions, tissue type, and other factors. As a result, some images may be too dark for adequate visual assessment. Step 126 of the tissue characterization system 100 of FIG. 1 performs an image visual enhancement method to improve the image visual quality, using an image intensity transformation method. The improved image may then be used, for example, in the disease display of step 138 of FIG. 1.

In one embodiment, the visual enhancement method of step 126 in FIG. 1 involves analyzing the histogram of the luminance values of an input image, determining luminance statistics using only portions of the image corresponding to tissue, and performing a piecewise linear transformation to produce a visually enhanced image. Step 126 involves using the image masks, as shown in step 108 of FIGS. 1 and 73 and as described previously, in order to determine which portions of the image are used to compute the image statistics. Step 126 includes performing brightness and contrast enhancement, as well as applying image feature enhancement to improve local image features such as edges, borders, and textures of different tissue types. Finally, a color balancing correction is applied to reduce the redness in certain images.

The visual enhancement method of step 126 includes determining which portions of the input tissue image correspond to tissue in the region of interest, as opposed to artifacts such as glare, mucus, a speculum, the os, blood, smoke tube, and/or areas outside the region of interest. Only the regions corresponding to tissue of interest are used in determining luminance statistics used in performing the visual enhancement. In one embodiment, the image masks of FIGS. 73 and 74 are used to determine the portion of the image corresponding to tissue of interest. In one embodiment, this image portion is $[tROI]_{vid}$, a subset of the $[ROI]_{vid}$ mask, computed in Equation 139 as follows:

$$[tROI]_{vid} = [ROI]_{vid} - \{[Glare]_{vid} + [SP]_{vid} + [os]_{vid} + Blood_{vid} + MUCUS_{vid} + [ST]_{vid}\} \quad (139)$$

where the image masks above are as shown in FIG. 74 and as described above.

FIGS. 113A-C show graphs representing a step in a method of image visual enhancement in which a piecewise linear transformation of an input image produces an output image with enhanced image brightness and contrast. A histogram 2328 is computed for the luminance values μ (2326) of pixels within $[tROI]_{vid}$ of an input image, and the histogram is used to determine parameters of a piecewise linear transformation shown in the plot 2324 of FIG. 113B. The transformation produces luminance values ν (2330) of a corresponding brightness- and contrast-enhanced output image. The transformed image generally has a wider range of luminance values, stretching from the minimum intensity (0) to the maximum intensity (255), than the input image. The luminance values from the input image are transformed so that input luminance values within a given range of the mean luminance are stretched over a wider range of the luminance spectrum than input luminance at the extremes. In one embodiment, the piecewise linear transformation is as shown in Equation 140:

$$v = \begin{cases} \alpha\mu, & L_{min} \leq \mu < \mu_a \\ \beta(\mu - \mu_a) + v_a, & \mu_a \leq \mu < \mu_b \\ \gamma(\mu - \mu_b) + v_b, & \mu_b \leq \mu < L_{max} \end{cases} \quad (140)$$

where $L_{max}$ is the maximum luminance value of a pixel within $[tROI]_{vid}$ of the input image; the parameters $\mu_a$, $\mu_b$, $v_a$, and $v_b$ are piecewise linear breakpoints; and α, β, and γ are slopes of the transformation.

In one embodiment, the image brightness and contrast enhancement is performed according to the following steps. First, calculate the luminance L from the RGB signal of the input image using the formula: L=0.299*R+0.587*G+ 0.114*B. Extract the luminance image LROI within tROI ($[tROI]_{vid}$): LROI=L AND tROI. Compute LROI mean, IMean. Compute the piecewise linear breakpoints ma, mb, na, nb ($\mu_a$, $\mu_b$, $v_a$, and $v_b$) from the LROI histogram, nHist[ ], as follows:

1. If ((IMean>38) AND (IMean<132)):
   a. Compute and normalize nHist[ ] to the range [0, 1].
   b. Compute ma and mb, the 5% and 98% histogram tails:
      ma=i, if sum(nHist [i])>0.05, i=0 to 255.
      mb=i, if sum(nHist [i])>0.98, i=0 to 255.
   c. Define the expected low and high intensity parameter na and nb:
   d. na=0 and nb=180.
2. If (IMean>38 AND (IMean<132) AND ((ma≧na AND ma<100 AND nb>20)), compute the slope or the degree of enhancement, bcDOE:

bcDOE=(nb-na)/(mb-ma).

3. If ((IMean>38) AND (IMean<132)), apply brightness and contrast enhancement transformation to input color image inRGB to obtain bcRGB (brightness and contrast enhanced color image).

In addition to producing an output image with enhanced image brightness and contrast, the visual enhancement method of step 126 (FIG. 1) also includes performing an image feature (local contrast) enhancement of the output image to emphasize high frequency components such as edges and fine features for the purposes of visual inspection. In one embodiment, image feature enhancement is performed using a spatial filtering technique according to Equations 141 and 142 as follows:

$$I_{out}(m,n) = I_{in}(m,n) + \rho G(m,n) \quad (141)$$

$$G(m,n) = I_{in}(m,n) - S(m,n) \quad (142)$$

where G(m, n) is the gradient image; ρ is the degree of the enhancement; $I_{in}$(m, n) and $I_{out}$(m, n) are the original and the resultant image of the feature enhancement operation; and S(m, n) is the smoothed (lowpass filtered) version of $I_{in}$(m, n).

In one embodiment, the image feature enhancement operation of the visual enhancement method of step 126 is performed according to the following steps:

If IMean>38:
1. Smooth bcRGB (brightness and contrast enhanced color image) with a 7×7 boxcar filter to obtain smRGB.
2. Subtract smRGB from bcRGB to obtain the gradient image, grRGB.
3. Dilate glareMsk twice to obtain dGlareMsk=dil (glareMsk, 2).
4. Remove dilated glare regions form gradient image to avoid emphasizing glare regions:
   a. Convert gray image dGlareMsk to RGB image, dGlareMskC.
   b. Remove glare image from gradient image to obtain grRGBgI:
      grRGBgI=grRGB-dGlareMskC.
5. Define the degree of feature enhancement, feDOE, from experiments, feDOE=0.8.
6. Scale grRGBgI by feDOE to obtain feRGB.
7. Add feRGB to bcRGB to produce image feature enhanced image fRGB.

In addition to producing an output image with enhanced image brightness, contrast, and image features, the visual enhancement method of step 126 (FIG. 1) also includes performing color balancing to reduce redness in certain overly-red tissue images, based on a mean-red-to-mean-blue ratio.

In one embodiment, the color balancing operation of the visual enhancement method of step 126 is performed according to the following steps:

If IMean>38:
1. Split RGB (i.e. of the image feature enhanced image fRGB) into R, G, B.
2. Extract the R image (within the tROIMsk) and compute mean tissue redness, tRed.
3. Extract the B image (within the tROIMsk) and compute mean tissue blueness tBlue.
4. Compute the red-blue ratio as RBRat=tRed/tBlue.
5. Perform color balancing:
   If RBRat<1.20, no red redection.
   Else if RBRat>=1.20 AND RBRat<1.32, R=0.95*R.
   Else if RBRat>=1.32 AND RBRat<1.55, R=0.90*R.
   Else if RBRat>=1.55, R=0.85*v.

6. Combine the R, G and B channels to form the final color image for display.

Diagnostic Display

In one embodiment, the tissue characterization system 100 of FIG. 1 comprises producing a disease probability display 138 for a reference (base) image of a test tissue sample using the interrogation point classifications in step 1432 of FIG. 74—Necrotic, CIN 2/3, NED, and Indeterminate. A method of disease probability display 138 includes producing an output overlay image with annotations for indeterminate regions, necrotic regions, and/or regions of low-to-high probability of high-grade disease, according to the classifications determined in step 1432 of FIG. 74 for a given patient scan. The annotations are shown as an overlay on top of the reference tissue image to provide easily-discernible tissue classification results, for example, indicating regions of concern for the purposes of biopsy, treatment, diagnosis, and/or further examination.

In one embodiment, indeterminate regions are indicated by a gray "see-through" crosshatch pattern that only partially obscures the underlying reference image. Necrotic regions are indicated by a green trellis pattern. Regions of tissue associated with high-grade disease (for example, CIN 2/3) are indicated by patches of contrasting color which intensify according to the likelihood of high-grade disease.

In one embodiment, the disease probability display method 138 of FIG. 74 as applied to a reference image of tissue from a patient scan includes the following steps: determining a disease display layer from the classification results of step 1432, overlaying the disease display layer on the reference image, determining an "indeterminate" mask from the classification results, overlaying the indeterminate mask on the disease display image using a gray crosshatch pattern, determining a "necrosis" mask from the classification results, and overlaying the necrosis mask on the disease display image using a green trellis pattern. The result of the disease probability display method 138 of FIG. 74 is a state-of-health "map" of the tissue sample, with annotations indicating indeterminate regions, necrotic regions, and/or regions of low-to-high probability of high-grade disease.

FIG. 114B represents an exemplary image of cervical tissue 2358 obtained during a patient examination and used as a reference (base) image in constructing an output overlay image in the disease probability display method 138 in FIG. 74. FIG. 114B shows the output overlay image 2360 produced by the disease probability display method 138 in FIG. 74 that corresponds to the reference image 2358 in FIG. 114A. The output overlay image 2360 in FIG. 114B contains annotations indicating indeterminate regions (2366), regions associated with a low probability of CIN 2/3 (2362), and regions associated with a high probability of CIN 2/3 (2364).

The disease probability display method 138 begins with the determination of a disease display layer from the CIN 2/3 classification results of step 1432 in FIG. 74. In step 1432, values of $p_{C23}(IP)$ are determined for interrogation points having a non-zero probability of high-grade disease (here, CIN 2/3). An area of tissue indicative of high-grade disease is represented on the disease display layer as an area whose color varies from yellow-to-blue, depending on values of $p_{C23}(IP)$ at corresponding interrogation points. The yellow color represents low probability of high-grade disease, and the blue color represents high probability of high-grade disease. At the low end of the probability range, the yellow color is blended into the reference image so that there is no sharp discontinuity between the high-grade disease region and the image. In one embodiment, a minimum cut-off probability, $p_{C23min}(IP)$, is set so that interrogation points with values of $p_{C23}(IP)$ lower than the minimum cut-off do not show on the disease display layer. In one embodiment, $p_{C23min}(IP)=0.2$.

FIGS. 115A and 115B represent two stages in the creation of a disease display layer, according to one embodiment. FIG. 115A shows the disease display layer 2368 wherein high-grade disease probabilities are represented by circles with intensities scaled by values of $p_{C23}(IP)$ at corresponding interrogation points. In order to more realistically represent regions of high-grade disease on the tissue sample, the circles in FIG. 115A are replaced with cones, then filtered to produce the disease display layer 2372 shown in FIG. 115B.

Finally, the grayscale intensity values are converted to a color scale so that regions of high-grade disease appear on the overlay image as patches of contrasting color that intensify according to the likelihood of disease.

In one embodiment, the disease probability display method 138 of FIG. 1 includes creating a disease display layer according to the following steps:
1. Retrieve the reference image (base image).
2. If all IPs are indeterminate, skip to creating the Indeterminate Mask.
3. Generate CIN 2/3 probability image, $I_p$, of base image size, for all non-indeterminate IPs:
    a. Generate a regular truncated cone centered at (15,15) on a square matrix of size 29-by-29, set to 0:
        i. The two truncating circles are centered around (15,15) and have a radius $R_o=14$ and $R_i=6$.
        ii. For each cone point, cone(i,j), let R be the distance from the geometric center (15,15).
            1. If $R>R_o$, cone (i,j)=0.
            2. If $R<R_i$, cone (i,j)=1.
            3. If $R_i<=R<=R_o$, cone (i,j)=$(R_o-R)/(R_o-R_i)$.
    b. Initialize $I_p$ to 0.
    c. For each IP with probability $p_{C23}(IP) \geq 0.2$:
        i. make a copy of the cone;
        ii. scale it by p;
        iii. add it to $I_p$ with the cone's center aligned with the IP location.
    d. Smooth $I_p$ using a 33 by 33 separable symmetric Hamming window filter specified by:
        i. the following coefficients (since the filter is symmetric around the origin, only 17 coefficients are specified below; the others are the mirror image around 1.0):
            (0.0800, 0.0888, 0.1150, 0.1575, 0.2147, 0.2844, 0.3640, 0.4503
            0.5400, 0.6297, 0.7160, 0.7956, 0.8653, 0.9225, 0.965, 0.9912, 1.0);
        ii. a gain of $(0.85/301.37)^{1/2}$ for the 33 point 1D filter.
    e. Linearly rescale $I_p$ from the [0.2 1] range to the [0 1] range.
    f. Clip resealed $I_p$ to range [0 1].
4. Compute an RGB colormap image and an alpha blending channel from the probability image $I_p$. The colormap defines a transformation from integer intensity values in the range [0,255] to an RGBa image.
    a. The R colormap is a piecewise linear map specified by the following breakpoints [0,255], [97,220], [179, 138] and [255,0].
    b. The G colormap is a piecewise linear map specified by the following breakpoints [0,0], [81,50], [210, 162] and [255,92].

c. The B colormap is a piecewise linear map specified by the following breakpoints [0,255], [120,225], [178,251] and [255,255].

d. The a colormap is a piecewise linear map specified by the following breakpoints [0,255], [120,225], [178,251] and [255,255].

e. Convert the floating point $I_p$ image to an 8-bit image, in the range [0,255] by rounding the product of each $I_p$ image pixel by 255.

f. Use the tissue colormap to get RGBα pixel values for the disease display layer.

FIG. 116 shows the color transformation used in overlaying the disease display layer onto the reference image, as in the overlay image 2360 of FIG. 114B. The first colorbar 2374 in FIG. 116 shows the blended colors from yellow to blue that correspond to values of disease probability $p_{C23}$ (IP), depicted on the x-axis 2375. A color corresponding to the average tissue color is determined, as shown in colorbar 2378. The average tissue color is blended into the probability-correlated yellow-to-blue colorbar 2374 so that the yellow color is blended into the reference image where the disease probability, as indicated by the filtered disease display layer, is low. This avoids a sharp discontinuity between the disease map and the tissue. In one embodiment, the disease display layer and the base (reference) image are combined by using alpha-channel blending, where the alpha channel is as shown in step #4 of the above method to create a disease display layer. The disease display layer is overlaid upon the base image with blending controlled by the computed alpha channel values according to Equation 143 as follows:

(Overlay Image Pixel)=α·(Disease Display Layer Pixel)+(1−α)·(Base Image Pixel)   (143)

Next, the disease probability display method 138 of FIG. 1 includes determining an "indeterminate" mask from the classification results in step 1432 of FIG. 74, where indeterminate regions are indicated by a gray "see-through" crosshatch pattern. For an exemplary reference image, interrogation points classified as "Indeterminate" in step 1432 of FIG. 74 indicate where the indeterminate mask is activated. The indeterminate crosshatch mask is then combined with the output overlay image, as is shown in the overlay image 2360 of FIG. 114B. Here, indeterminate regions 2366 are indicated in shadowed regions around the edge of the tissue sample.

In one embodiment, the disease probability display method 138 of FIG. 1 includes creating an indeterminate crosshatch mask according to the following steps:

1. Create image, msk, of base image size and set to 0.
2. Draw disks of radius 0.75 mm centered at the coordinate of each indeterminate interrogation point.
3. Erode mask image 3 times to obtain erodMsk=erod (msk, 3).
4. Compute image binary perimeter, perMsk, of erodMsk: perMsk=not (erod (erodMsk, 1)) AND (erodMsk)), 1).
5. Compute indeterminate crosshatch mask:
   a. Retrieve crosshatch image, xhatch, defined by a horizontal pitch of 10 pixels, a vertical pitch of 20 pixels, a crosshatch slope of 2 and a grey value of (166, 166, 166).
   b. Perform logical OR of erodMsk and xhatch to obtain xhatchMsk.
   c. Perform logical OR of xhatchMsk with perMsk.

Next, the disease probability display method 138 of FIG. 1 includes determining a "necrosis" mask from the classification results in step 1432 of FIG. 74, where necrotic regions are indicated by a green "see-through" trellis pattern. FIG. 117A depicts an exemplary reference image 2388 of cervical tissue having necrotic regions. For an exemplary reference image, interrogation points classified as "Necrotic" in step 1432 of FIG. 74 indicate where the "necrosis" mask is activated. A necrosis trellis mask is included in the overlay image, as is shown in the overlay image 2396 of FIG. 117B.

In one embodiment, the disease probability display method 138 of FIG. 1 includes creating a necrosis trellis mask according to the following steps:

1. Create image, msk, of base image size, and set it to 0.
2. Draw disks of radius 0.75 mm centered at the coordinate of each necrotic tissue interrogation point.
3. Erode mask image 3 times to obtain erodMsk=erod (msk, 3).
4. Compute image binary perimeter, perMsk, of erodMsk: perMsk=not (erod (erodMsk, 1)) AND (erodMsk)), 1).
5. Compute necrotic tissue trellis mask:
   a. Retrieve trellis image, trellis, defined by a horizontal pitch of 8 pixels, a vertical pitch of 8 pixels, a line thickness of 2 and a green value of (0, 255, 104).
   b. Perform logical OR of erodMsk and xhatch to obtain trellisMsk.
   c. Perform logical OR of trellisMsk with perMsk.

The result of the disease probability display method 138 of FIG. 74 is a state-of-health "map" of a tissue sample, with annotations indicating indeterminate regions, necrotic regions, and/or regions of low-to-high probability of high-grade disease. The disease display overlay images contain indeterminate regions and regions of low-to-high probability of CIN 2/3.

In one embodiment, the disease display overlay image is produced immediately following a patient scan in which spectral and image data are acquired and processed. This allows a physical to provide on-the-spot diagnostic review immediately following the scan.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of processing spectral data obtained from a plurality of regions of a tissue sample for use in a tissue classification scheme, the method comprising the steps of:
   (a) automatically identifying a subset of spectral data obtained from said plurality of regions of said tissue sample, said subset of data affected by one or more obstructions selected from the group consisting of glare, shadow, mucus, a smoke tube, and a speculum, and identifying one or more regions of said tissue sample from which said subset was obtained;
   (b) processing spectral data obtained from said plurality of regions in said tissue classification scheme, wherein said subset of spectral data identified in step (a) is accounted for in said tissue classification scheme by at least one of (i), (ii), (iii) as follows:
      (i) disqualifying said subset of spectral data from use in said tissue classification scheme;
      (ii) classifying said one or more identified regions from which said subset of spectral data was obtained as indeterminate; and (iii) weighting at least a portion of said subset of spectral data in said tissue classification scheme to penalize said data in favor of other spectral data determined to be unaffected by said one or more obstructions; and (c) classifying said plurality of regions of said tissue sample according to said tissue classification scheme.

2. The method of claim 1, wherein step (a) comprises:
(i) applying one or more spectral masks; and
(ii) optionally, applying one or more image masks.

3. The method of claim 2, wherein said one or more spectral masks comprises a cervical edge mask.

4. The method of claim 3, wherein said cervical edge mask is based at least in part on a ratio of a first reflectance intensity at a first wavelength to a second reflectance intensity at a second wavelength.

5. The method of claim 4, wherein said first wavelength is about 700 nm and said second wavelength is about 540 nm.

6. The method of claim 3, wherein said cervical edge mask is based at least in part on a ratio of a first fluorescence intensity at a first wavelength to a second fluorescence intensity at a second wavelength.

7. The method of claim 6, wherein said first wavelength is about 530 nm and said second wavelength is about 410 nm.

8. The method of claim 3, wherein said applying step comprises comparing F(530 nm)/F(410 nm) with a threshold of about 4.75.

9. The method of claim 3, wherein said cervical edge mask is based at least in part on (i) a ratio of a first reflectance intensity to a second reflectance intensity and (ii) a ratio of a first fluorescence intensity to a second fluorescence intensity.

10. The method of claim 3, wherein said cervical edge mask comprises a metric as follows: BB(450 nm)BB(700 nm)/BB(540 nm)<0.30 OR F(530 nm)/F(410 nm)>4.75.

11. The method of claim 2, wherein said one or more spectral masks comprises a mucus mask.

12. The method of claim 11, wherein said mucus mask is based at least in part on a ratio of a first reflectance intensityat a first wavelength to a second reflectance intensity at a second wavelength.

13. The method of claim 12, wherein said first wavelength and said second wavelength maximize a discrimination function comprising the ratio.

14. The method of claim 12, wherein said first wavelength is about 456 nm and said second wavelength is about 542 nm.

15. The method of claim 11, wherein said applying step comprises comparing BB(456 nm)/BB(542 nm) with a threshold of about 1.1.

16. The method of claim 11, wherein said applying step comprises comparing BB(594 nm)/BB(610 nm) with a threshold of about 0.74.

17. The method of claim 11, wherein said mucus mask comprises a metric as follows: BB(456 nm)/BB(542 nm)<1.06 OR BB(594 nm)/BB(610 nm)>0.74.

18. The method of claim 1, wherein said processing step comprises disqualifying said subset of spectral data from use in said tissue classification scheme.

19. The method of claim 1, wherein said subset of spectral data identified in step (a) is accounted for in said tissue classification scheme by classifying said one or more identified regions from which said subset was obtained as indeterminate.

20. The method of claim 1, wherein said processing step comprises determining an overlap between said one or more identified regions from which said subset was obtained and an area identified by one or more image masks.

21. The method of claim 20, wherein said processing step comprises classifying at least a portion of said overlap as indeterminate.

22. The method of claim 20, wherein said processing step comprises weighting spectral data from said overlap in said tissue classification scheme according to a likelihood said data are affected by an artifact.

23. The method of claim 20, wherein said one or more image masks comprise a member selected from the group consisting of a smoke tube mask, a speculum mask, a region-of-interest mask, and a vaginal wall mask.

24. The method of claim 1, wherein said spectral data comprises fluorescence spectral data and reflectance spectral data.

25. The method of claim 1, wherein step (a) comprises:
(i) applying one or more spectral masks; and
(ii) applying one or more image masks.

26. The method of claim 25, wherein step (ii) comprises automatically identifying pixels of an image of said tissue sample corresponding to said one or more obstructions.

27. The method of claim 25, wherein step (i) comprises automatically identifying one or more interrogations points at which fluorescence data, reflectance data, or both fluorescence data and reflectance data are affected by said one or more obstructions.

28. The method of claim 25, wherein said one or more spectral masks comprises a cervical edge mask, a mucus mask, an NED mask, and a necrosis mask.

29. The method of claim 25, wherein said one or more image masks comprises a glare mask, a mucus mask, a blood mask, an os mask, a region of interest mask, a smoke tube mask, a speculum mask, a vaginal wall mask, and a fluid mask.

30. The method of claim 1, wherein said subset of spectral data identified in step (a) is accounted for in said tissue classification scheme by weighting said identified subset of spectral data in said tissue classification scheme according to a likelihood said data are affected by an artifact.

31. The method of claim 1, wherein step (a) further comprises automatically identifying spectral data from a region outside a diagnostic zone of interest, said region comprising at least one member selected from the group consisting of a vaginal wall, an os, and a cervical edge.

32. The method of claim 1, wherein step (a) further comprises automatically identifying spectral data affected by at least one member selected from the group consisting of blood, fluid, and foam.

33. The method of claim 1, further comprising the step of applying a spectral mask to identify NED tissue prior to step (b).

34. The method of claim 1, further comprising the step of applying a spectral mask to identify necrotic tissue prior to step (b).

35. The method of claim 1, further comprising the step of applying a low signal mask to account for low signal data prior to step (a).

36. The method of claim 1, wherein said tissue sample comprises in vivo tissue.

37. The method of claim 1, wherein said tissue sample comprises epithelial cells.

38. The method of claim 37, wherein said tissue sample comprises at least one tissue type selected from the group consisting of colorectal, gastroesophageal, urinary bladder, lung, and skin tissue.

39. The method of claim 1, wherein said tissue sample comprises cervical tissue.

40. The method of claim 1, wherein said tissue classification scheme identifies CIN 2/3 tissue.

41. The method of claim 1, wherein said tissue classification scheme identifies a probability of CIN 2/3 associated with a portion of said tissue sample.

42. The method of claim 1, further comprising the step of:
(d) displaying results of said tissue classification scheme.

43. A method of processing spectral data obtained from a plurality of regions of a tissue sample for use in a tissue classification scheme, the method comprising the steps of:
(a) applying one or more spectral masks to automatically identify one or more regions of said tissue sample from which spectral data is non-representative of a zone of interest of said tissue sample;
(b) applying one or more image masks to automatically identify one or more regions of said tissue sample from which spectral data is non-representative of a zone of interest of said tissue sample;
(c) processing spectral data obtained from said plurality of regions in said tissue classification scheme, wherein spectral data from said one or more regions identified in steps (a) and (b) are accounted for in said tissue classification scheme by at least one of (i) (ii) (iii), as follows:
  (i) disqualifying spectral data from one or more of said identified regions from use in said tissue classification scheme;
  (ii) classifying one or more of said identified regions as indeterminate; and
  (iii) weighting spectral data from one or more of said identified regions in said tissue classification scheme to penalize said data in favor of other spectral data that is determined to be representative of said zone of interest of said tissue sample; and
(d) classifying said plurality of regions of said tissue sample according to said tissue classification scheme.

44. The method of claim 43, wherein step (a) comprises automatically identifying one or more interrogation points at which fluorescence data, reflectance data, or both fluorescence data and reflectance data are non-representative of said zone of interest of said tissue sample.

45. The method of claim 43, wherein step (b) comprises automatically identifying pixels of an image of said tissue sample corresponding to an area outside said zone of interest of said tissue sample.

46. The method of claim 43, wherein said spectral data that are non-representative of a zone of interest of said tissue sample comprise one or both of the following:
  (i) spectral data from tissue regions affected by one or more obstructions; and
  (ii) spectral data from regions lying outside a diagnostic zone of interest.

47. The method of claim 46, wherein said one or more obstructions comprises at least one of the following: mucus, fluid, foam, a medical instrument, glare, shadow, and blood.

48. The method of claim 46, wherein said regions lying outside a diagnostic zone of interest comprises at least one of the following: a tissue wall, an os, an edge surface of a tissue, and tissue in the vicinity of a smoke tube.

49. The method of claim 43, wherein said spectral data that are non-representative of a zone of interest of said tissue sample comprise:
  (i) spectral data from tissue regions affected by one or more obstructions; and
  (ii) spectral data from regions lying outside a diagnostic zone of interest.

50. The method of claim 43, wherein said one or more spectral masks comprises at least one of the following: a cervical edge mask, and a mucus mask.

51. The method of claim 43, wherein said one or more spectral masks comprise a cervical edge mask and a mucus mask.

52. The method of claim 43, wherein said one or more image masks comprises at least one of the following: a glare mask, a mucus mask, a blood mask, an os mask, a region of interest mask, a smoke tube mask, a speculum mask, a vaginal wall mask, and a fluid mask.

53. The method of claim 42, wherein said one or more image masks comprise a glare mask, a mucus mask, a blood mask, an os mask, a region of interest mask, a smoke tube mask, a speculum mask, a vaginal wall mask, and a fluid mask.

54. The method of claim 42, wherein said spectral data from said one or more regions identified in step (a), in step (b), or in both steps (a) and (b) are accounted for in said tissue classification scheme by classifying said one or more identified regions as indeterminate.

55. The method of claim 42, wherein said spectral data from said one or more regions identified in step (a), in step (b), or in both steps (a) and (b) are accounted for in said tissue classification scheme by weighting said spectral data from said one or more identified regions according to a likelihood said data are affected by an artifact.

56. The method of claim 42, further comprising at least one of the steps of:
  (i) applying a spectral mask to identify NED tissue prior to step (c);
  (ii) applying a spectral mask to identify necrotic tissue prior to step (c); and
  (iii) applying a low signal mask to account for low signal data prior to step (a).

57. The method of claim 43, wherein said tissue sample comprises in vivo tissue.

58. The method of claim 43, wherein said tissue sample comprises at least one tissue type selected from the group consisting of colorectal, gastroesophageal, urinary bladder, lung, and skin tissue.

59. The method of claim 43, wherein said tissue sample comprises cervical tissue.

60. The method of claim 43, wherein said tissue classification scheme identifies CIN 2/3 tissue.

61. The method of claim 43, wherein said tissue classification scheme identifies a probability of CIN 2/3 associated with a portion of said tissue sample.

62. The method of claim 43, further comprising the step of:
(e) displaying results of said tissue classification scheme.

63. An apparatus for processing spectral data obtained from a plurality of regions of a tissue sample for use in a tissue classification system, the apparatus comprising:
  a probe configured to obtain spectral data from said plurality of regions of said tissue sample; and
  a processor configured to:
    automatically identify a subset of spectral data obtained from said plurality of regions of said tissue sample, said subset of data affected by one or more obstructions selected from the group consisting of glare, shadow, mucus, a smoke tube, and a speculum, and identifying one or more regions of said tissue sample from which said subset was obtained; and process spectral data obtained from said plurality of regions in said tissue classification scheme, wherein said identified subset of spectral data is accounted for in said tissue classification scheme by at least one of (i), (ii), (iii) as follows:
(i) disqualifying said subset of spectral data from use in said tissue classification scheme;
(ii) classifying said one or more identified regions from which said subset of spectral data was obtained as indeterminate; and
(iii) weighting at least a portion of said subset of spectral data in said tissue classification scheme to penalize said data in favor of other spectral data determined to be unaffected by said one or more obstructions.

64. The apparatus of claim 62, wherein said processor is configured to automatically identify said subset of spectral data by:
(i) applying one or more spectral masks; and
(ii) optionally, applying one or more image masks.

65. The apparatus of claim 64, wherein said one or more spectral masks comprises a cervical edge mask.

66. The apparatus of claim 64, wherein said one or more spectral masks comprises a mucus mask.

67. The apparatus of claim 62, wherein said processor is configured to determine an overlap between said one or more identified regions from which said subset was obtained and an area identified by one or more image masks.

68. The apparatus of claim 67, wherein said processor is configured to classify at least a portion of said overlap as indeterminate.

69. The apparatus of claim 67, wherein said processor is configured to weight spectral data from said overlap in said tissue classification scheme according to a likelihood said data are affected by an artifact.

70. The apparatus of claim 67, wherein said one or more image masks comprise a member selected from the group consisting of a smoke tube mask, a speculum mask, a region-of-interest mask, and a vaginal wall mask.

71. The apparatus of claim 62, wherein said spectral data comprise fluorescence spectral data and reflectance spectral data.

72. The apparatus of claim 62, wherein said processor is configured to automatically identify said subset of spectral data by:
(i) applying one or more spectral masks; and
(ii) applying one or more image masks.

73. The apparatus of claim 72, wherein said applying one or more image masks comprises automatically identifying pixels of an image of said tissue sample corresponding to said one or more obstructions.

74. The apparatus of claim 72, wherein said applying one or more spectral masks comprises automatically identifying one or more interrogation points at which fluorescence data, reflectance data, or both fluorescence data and reflectance data are affected by said one or more obstructions.

75. The apparatus of claim 72, wherein said one or more spectral masks comprises a cervical edge mask, a mucus mask, an NED mask, and a necrosis mask.

76. The apparatus of claim 72, wherein said one or more image masks comprises a glare mask, a mucus mask, a blood mask, an os mask, a region of interest mask, a smoke tube mask, a speculum mask, a vaginal wall mask, and a fluid mask.

77. The apparatus of claim 62, wherein said tissue sample comprises in vivo tissue.

78. The apparatus of claim 62, wherein said tissue sample comprises epithelial cells.

79. The apparatus of claim 78, wherein said tissue sample comprises at least one tissue type selected from the group consisting of colorectal, gastroesophageal, urinary bladder, lung, and skin tissue.

80. The apparatus of claim 62, wherein said tissue sample comprises cervical tissue.

81. The apparatus of claim 62, wherein said tissue classification scheme identifies CIN 2/3 tissue.

82. The apparatus of claim 62, wherein said tissue classification scheme identifies a probability of CIN 2/3 associated with a portion of said tissue sample.

83. An apparatus for processing spectral data obtained from a plurality of regions of a tissue sample for use in a tissue classification system, the apparatus comprising:
a probe configured to obtain spectral data from said plurality of regions of said tissue sample; and
a processor configured to:
(i) apply one or more spectral masks to automatically identify one or more regions of said tissue sample from which spectral data is non-representative of a zone of interest of said tissue sample;
(ii) apply one or more image masks to automatically identify one or more regions of said tissue sample from which spectral data is non-representative of a zone of interest of said tissue sample; and
(iii) process spectral data obtained from said plurality of regions in said tissue classification scheme, wherein spectral data from said one or more regions identified in (i) and (ii) are accounted for in said tissue classification scheme by at least one of (A), (B), (C) as follows:
(A) disqualifying spectral data from one or more of said identified regions from use in said tissue classification scheme;
(B) classifying one or more of said identified regions as indeterminate; and
(C) weighting spectral data from one or more of said identified regions in said tissue classification scheme to penalize said data in favor of other spectral data that is determined to be representative of said zone of interest of said tissue sample.

84. The apparatus of claim 83, wherein said processor is configured to apply said one or more spectral masks to automatically identify one or more interrogation points at which fluorescence data, reflectance data, or both fluorescence data and reflectance data are non-representative of said zone of interest of said tissue sample.

85. The apparatus of claim 83, wherein said processor is configured to apply said one or more image masks to automatically identify pixels of an image of said tissue sample corresponding to an area outside said zone of interest of said tissue sample.

86. The apparatus of claim 83, wherein said spectral data that are non-representative of a zone of interest of said tissue sample comprise one or both of the following:
(A) spectral data from tissue regions affected by one or more obstructions; and
(B) spectral data from regions lying outside a diagnostic zone of interest.

87. The apparatus of claim 86, wherein said one or more obstructions comprises at least one of the following: mucus, fluid, foam, a medical instrument, glare, shadow, and blood.

88. The apparatus of claim 86, wherein said regions lying outside a diagnostic zone of interest comprises at least one of the following: a tissue wall, an os, an edge surface of a tissue, and tissue in the vicinity of a smoke tube.

89. The apparatus of claim 83, wherein said spectral data that are non-representative of a zone of interest of said tissue sample comprise:
   (A) spectral data from tissue regions affected by one or more obstructions; and
   (B) spectral data from regions lying outside a diagnostic zone of interest.

90. The apparatus of claim 83, wherein the processor is configured to perform at least one of the following:
   (A) apply a spectral mask to identify NED tissue;
   (B) apply a spectral mask to identify necrotic tissue; and
   (C) apply a low signal mask to account for low signal data.

91. The apparatus of claim 83, wherein said tissue sample comprises in vivo tissue.

92. The apparatus of claim 83, wherein said tissue sample comprises at least one tissue type selected from the group consisting of colorectal, gastroesophageal, urinary bladder, lung, and skin tissue.

93. The apparatus of claim 83, wherein said tissue sample comprises cervical tissue.

94. The apparatus of claim 83, wherein said tissue classification scheme identifies CIN 2/3 tissue.

95. The apparatus of claim 83, wherein said tissue classification scheme identifies a probability of CIN 2/3 associated with a portion of said tissue sample.

* * * * *